(12) United States Patent
Abreu

(10) Patent No.: US 8,834,020 B2
(45) Date of Patent: Sep. 16, 2014

(54) THERMAL IMAGING SYSTEM

(71) Applicant: Geelux Holdings, Ltd., Tortola (VG)

(72) Inventor: Marcio Marc Abreu, North Haven, CT (US)

(73) Assignee: Geelux Holdings, Ltd., Tortola (VG)

( * ) Notice: Subject to any disclaimer, the term of this patent is extended or adjusted under 35 U.S.C. 154(b) by 0 days.

(21) Appl. No.: 13/709,676

(22) Filed: Dec. 10, 2012

(65) Prior Publication Data

US 2013/0124039 A1    May 16, 2013

Related U.S. Application Data

(63) Continuation of application No. 11/585,344, filed on Oct. 24, 2006, now Pat. No. 8,328,420, which is a continuation-in-part of application No. 10/786,623, filed on Feb. 26, 2004, which is a continuation-in-part of application No. 10/420,295, filed on Apr. 22, 2003, now Pat. No. 7,187,960.

(60) Provisional application No. 60/729,232, filed on Oct. 24, 2005, provisional application No. 60/802,503, filed on May 23, 2006.

(51) Int. Cl.
  *G01K 1/16*  (2006.01)

(52) U.S. Cl.
  USPC .......... 374/121; 374/141; 374/45; 250/338.1; 250/341.8; 250/339.11; 250/339.15; 250/341.1; 600/474; 702/135

(58) Field of Classification Search
  USPC .......................... 374/120–132, 161, 137, 45; 702/130–136; 250/338.1, 339.06, 250/339.11, 339.15, 341.1, 341.8, 342; 600/473
  See application file for complete search history.

(56) References Cited

U.S. PATENT DOCUMENTS

| 3,545,260 A | 12/1970 | Lichtenstein et al. |
| 3,585,849 A | 6/1971 | Grolman |

(Continued)

FOREIGN PATENT DOCUMENTS

| DE | 4433104 | 5/1996 |
| EP | 0236028 | 9/1987 |

(Continued)

OTHER PUBLICATIONS

RCA Technical Notes, Contact Lens Tonometer by Robert E. Morey, RCA TN No. 602, dated Dec. 1964, 2 pages.

(Continued)

*Primary Examiner* — Gail Verbitsky
(74) *Attorney, Agent, or Firm* — Studebaker & Brackett PC

(57) ABSTRACT

Support structures for positioning sensors on a physiologic tunnel for measuring physical, chemical and biological parameters of the body and to produce an action according to the measured value of the parameters. The support structure includes a sensor fitted on the support structures using a special geometry for acquiring continuous and undisturbed data on the physiology of the body. Signals are transmitted to a remote station by wireless transmission such as by electromagnetic waves, radio waves, infrared, sound and the like or by being reported locally by audio or visual transmission. The physical and chemical parameters include brain function, metabolic function, hydrodynamic function, hydration status, levels of chemical compounds in the blood, and the like. The support structure includes patches, clips, eyeglasses, head mounted gear and the like, containing passive or active sensors positioned at the end of the tunnel with sensing systems positioned on and accessing a physiologic tunnel.

9 Claims, 181 Drawing Sheets

(56) References Cited

U.S. PATENT DOCUMENTS

| | | | |
|---|---|---|---|
| 3,626,757 A | 12/1971 | Benzinger | |
| 3,724,263 A | 4/1973 | Rose et al. | |
| 3,769,961 A | 11/1973 | Fatt | |
| 3,897,272 A | 7/1975 | Medlar | |
| 3,897,790 A | 8/1975 | Magilton et al. | |
| 3,963,019 A | 6/1976 | Quandt | |
| 4,186,184 A | 1/1980 | Zaffaroni | |
| 4,231,052 A * | 10/1980 | Day et al. | 257/442 |
| 4,305,399 A | 12/1981 | Beale | |
| 4,321,261 A | 3/1982 | Ellis et al. | |
| 4,330,299 A | 5/1982 | Cerami | |
| 4,344,315 A | 8/1982 | Moxon et al. | |
| 4,344,438 A | 8/1982 | Schultz | |
| 4,386,831 A | 6/1983 | Grounauer | |
| 4,444,990 A | 4/1984 | Villar | |
| 4,485,820 A | 12/1984 | Flower | |
| 4,597,392 A | 7/1986 | Opitz et al. | |
| 4,628,938 A | 12/1986 | Lee | |
| 4,629,424 A | 12/1986 | Lauks et al. | |
| 4,771,792 A | 9/1988 | Seale | |
| 4,784,149 A | 11/1988 | Berman et al. | |
| 4,860,755 A | 8/1989 | Erath | |
| 4,922,913 A | 5/1990 | Waters et al. | |
| 4,944,303 A | 7/1990 | Katsuragi | |
| 4,947,849 A | 8/1990 | Takahashi et al. | |
| 4,951,671 A | 8/1990 | Coan | |
| 4,979,831 A | 12/1990 | Schertz et al. | |
| 5,005,577 A | 4/1991 | Frenkel | |
| 5,046,482 A | 9/1991 | Everest | |
| 5,062,432 A | 11/1991 | James et al. | |
| 5,076,274 A | 12/1991 | Matsumoto | |
| 5,109,852 A | 5/1992 | Kaye et al. | |
| 5,115,815 A | 5/1992 | Hansen | |
| 5,148,807 A | 9/1992 | Hsu | |
| 5,165,409 A | 11/1992 | Coan | |
| 5,179,953 A | 1/1993 | Kursar | |
| 5,183,044 A | 2/1993 | Nishio et al. | |
| 5,209,231 A | 5/1993 | Cote et al. | |
| 5,217,015 A | 6/1993 | Kaye et al. | |
| 5,222,495 A | 6/1993 | Clarke et al. | |
| 5,222,809 A | 6/1993 | Ehrenkranz | |
| 5,246,867 A | 9/1993 | Lakowicz et al. | |
| 5,251,627 A | 10/1993 | Morris | |
| 5,295,495 A | 3/1994 | Maddess | |
| 5,297,554 A | 3/1994 | Glynn et al. | |
| 5,341,805 A | 8/1994 | Stavridi et al. | |
| 5,342,283 A | 8/1994 | Good | |
| 5,342,789 A | 8/1994 | Chick et al. | |
| 5,352,411 A | 10/1994 | Khuri | |
| 5,356,780 A | 10/1994 | Robinson et al. | |
| 5,375,595 A | 12/1994 | Sinha et al. | |
| 5,383,452 A | 1/1995 | Buchert | |
| 5,433,197 A | 7/1995 | Stark | |
| 5,435,307 A | 7/1995 | Friauf et al. | |
| 5,503,770 A | 4/1996 | James et al. | |
| 5,522,662 A | 6/1996 | Shiokawa | |
| 5,636,635 A | 6/1997 | Massie et al. | |
| 5,653,239 A | 8/1997 | Pompei et al. | |
| 5,664,578 A * | 9/1997 | Boczan | 600/549 |
| 5,673,692 A | 10/1997 | Schulze et al. | |
| 5,711,915 A | 1/1998 | Siegmund et al. | |
| 5,813,982 A | 9/1998 | Baratta | |
| 5,817,008 A | 10/1998 | Rafert et al. | |
| 5,820,557 A | 10/1998 | Hattori et al. | |
| 5,830,139 A | 11/1998 | Abreu | |
| 5,854,078 A | 12/1998 | Asher et al. | |
| 5,898,004 A | 4/1999 | Asher et al. | |
| 6,011,984 A | 1/2000 | Van Antwerp et al. | |
| 6,028,323 A * | 2/2000 | Liu | 257/21 |
| 6,040,194 A | 3/2000 | Chick et al. | |
| 6,042,266 A | 3/2000 | Cheslock et al. | |
| 6,072,180 A | 6/2000 | Kramer et al. | |
| 6,120,460 A | 9/2000 | Abreu | |
| 6,123,668 A | 9/2000 | Abreu | |
| 6,135,968 A | 10/2000 | Brounstein | |
| 6,152,875 A | 11/2000 | Hakamata | |
| 6,178,346 B1 | 1/2001 | Amundson et al. | |
| 6,181,957 B1 | 1/2001 | Lambert et al. | |
| 6,187,599 B1 | 2/2001 | Asher et al. | |
| 6,197,534 B1 | 3/2001 | Lakowicz et al. | |
| 6,197,928 B1 | 3/2001 | Tsien et al. | |
| 6,203,193 B1 | 3/2001 | Egawa | |
| 6,213,943 B1 | 4/2001 | Abreu | |
| 6,256,522 B1 | 7/2001 | Schultz | |
| 6,292,685 B1 | 9/2001 | Pompei | |
| 6,300,871 B1 | 10/2001 | Irwin et al. | |
| 6,312,393 B1 | 11/2001 | Abreu | |
| 6,319,540 B1 | 11/2001 | Van Antwerp et al. | |
| 6,423,001 B1 | 7/2002 | Abreu | |
| 6,470,893 B1 | 10/2002 | Boesen | |
| 6,529,617 B1 * | 3/2003 | Prokoski | 382/128 |
| 6,536,945 B2 | 3/2003 | Rolston | |
| 6,542,081 B2 | 4/2003 | Torch | |
| 6,544,193 B2 | 4/2003 | Abreu | |
| 6,681,127 B2 | 1/2004 | March | |
| 6,789,901 B1 * | 9/2004 | Kormos | 353/13 |
| 6,846,106 B1 | 1/2005 | Chen et al. | |
| 7,340,293 B2 * | 3/2008 | McQuilkin | 600/474 |
| 7,597,668 B2 | 10/2009 | Yarden | |
| 7,621,877 B2 | 11/2009 | Schnall | |
| 7,756,559 B2 | 7/2010 | Abreu | |
| 7,837,623 B2 * | 11/2010 | Aubry et al. | 600/437 |
| 2002/0035340 A1 | 3/2002 | Fraden et al. | |
| 2002/0126731 A1 * | 9/2002 | Stergiopoulos et al. | 374/122 |
| 2003/0067958 A1 | 4/2003 | Jang | |
| 2003/0108223 A1 * | 6/2003 | Prokoski | 382/115 |
| 2003/0111605 A1 | 6/2003 | Sato et al. | |
| 2003/0210146 A1 | 11/2003 | Tseng | |
| 2003/0212340 A1 | 11/2003 | Lussier et al. | |
| 2004/0076316 A1 * | 4/2004 | Fauci | 382/128 |
| 2004/0082862 A1 * | 4/2004 | Chance | 600/473 |
| 2004/0125996 A1 * | 7/2004 | Eddowes et al. | 382/128 |
| 2004/0154550 A1 | 8/2004 | McQuilkin | |
| 2004/0170216 A1 | 9/2004 | Russak et al. | |
| 2004/0210159 A1 * | 10/2004 | Kibar | 600/558 |
| 2004/0246548 A1 * | 12/2004 | Papuchon et al. | 359/196 |
| 2006/0122473 A1 | 6/2006 | Kill et al. | |
| 2006/0264726 A1 | 11/2006 | Mannheimer et al. | |
| 2007/0055171 A1 | 3/2007 | Fraden | |
| 2008/0043809 A1 | 2/2008 | Herbert | |
| 2008/0214949 A1 | 9/2008 | Stivoric et al. | |
| 2010/0204765 A1 | 8/2010 | Hall et al. | |
| 2011/0024626 A1 * | 2/2011 | O'Donnell et al. | 250/338.1 |
| 2011/0040161 A1 * | 2/2011 | Abreu | 600/321 |
| 2013/0292571 A1 * | 11/2013 | Mukherjee et al. | 250/339.11 |

FOREIGN PATENT DOCUMENTS

| | | |
|---|---|---|
| JP | 2001/031151 | 2/2001 |
| WO | 93/01745 | 2/1993 |
| WO | 97/19188 | 5/1997 |
| WO | 98/22820 | 5/1998 |
| WO | 99/51142 | 10/1999 |
| WO | 00/10007 | 2/2000 |
| WO | 00/13580 | 3/2000 |
| WO | 00/16099 | 3/2000 |
| WO | 00/18237 | 4/2000 |
| WO | 00/64492 | 11/2000 |
| WO | 02/03855 | 1/2002 |
| WO | 02/067688 | 9/2002 |

OTHER PUBLICATIONS

Ophthal. Physiol. Opt., 1989, vol. 9, April, Research Note, Multiple Applications of the NCT: An Assessment of Instrument's Effect on IOP by G.E. Russell and J.P.G. Bergmanson, pp. 212-214.

Arch Ophthalmol—vol. 97, Mar. 1979, The Pneumatonograph—A Laboratory Study, by Robert A. Moses, M.D. and Walter J. Grodzki Jr., D.D.S., pp. 547-552.

(56) References Cited

OTHER PUBLICATIONS

IEEE Transactions on bio-Medical Engineering, vol. BME-14, No. 2, Apr. 1967, Miniature Passive Pressure Transensor for Implanting in the Eye, by C.C. Collins, pp. 74-83.

Trans. Amer. Acad. of O. & O., Jan.-Feb. 1957, Tonometer Calibration, An Attempt to Remove Discrepancies Found in the 1954 Calibration Scale for Schiotz Tonometers by Jonas S. Friedenwald, M.D., pp. 108-123.

Investigative Ophthalmology, Feb. 1962, The Relationship Between Pressure and Volume Changes in Living and Dead Rabbit Eyes, by John E. Eisenlohr and Maurice E. Langham, pp. 63-77.

Investigative Ophthalmology, Sep. 1971, vol. 10, No. 9, Theory and Calibration of the Schiotz Tonometer VII. Experimental Results of Tonometric Measurements: Scale Reading Versus Indentation Volume, by Robert A. Moses and Walter J. Grodzki, pp. 716-723.

The British Journal of Ophthalmology, Jun. 1920, Communications-Tonometry, by HJ. Schiötz, pp. 249-261.

American Journal of Opthalmology, vol. 20, No. 10, Oct. 1937, Contribution to the Theory and Practice of Tonometry by Jonas S. Friedenwald, M.D., pp. 985-1024.

Ophthalmologica vol. 150, No. 5, (1965), Rheology of the Human Sclera, Unifying Formulation of Ocular Rigidity, by W.K. McEwen and Roger St. Helen, pp. 321-346.

A.M.A. Archives of Ophthalmology, vol. 57, Apr. 1957, Tonometer Calibration, by Earle H. McBain, M.D., pp. 520-531.

The Photonics Dictionary, 1996 Book 4, $42^{nd}$ Edition, pp. D-24, D153.

Manual of Skin Diseases, Fifth Edition, Gordon C. Sauer, MD., 1985, pp. 204, 373.

Fm-2 Fluorotron™ Master Ocular Fluorophotometer Specifications, 1994 OcuMetrics, Inc.

Textbook of Biochemistry With Clinical Correlations, Second Edition, Thomas M. Devlin, Ph.D., 1986, pp. 118, 139.

Physical Optics, Third Revised Edition, Robert W. Wood, 1961, pp. 650-651.

* cited by examiner

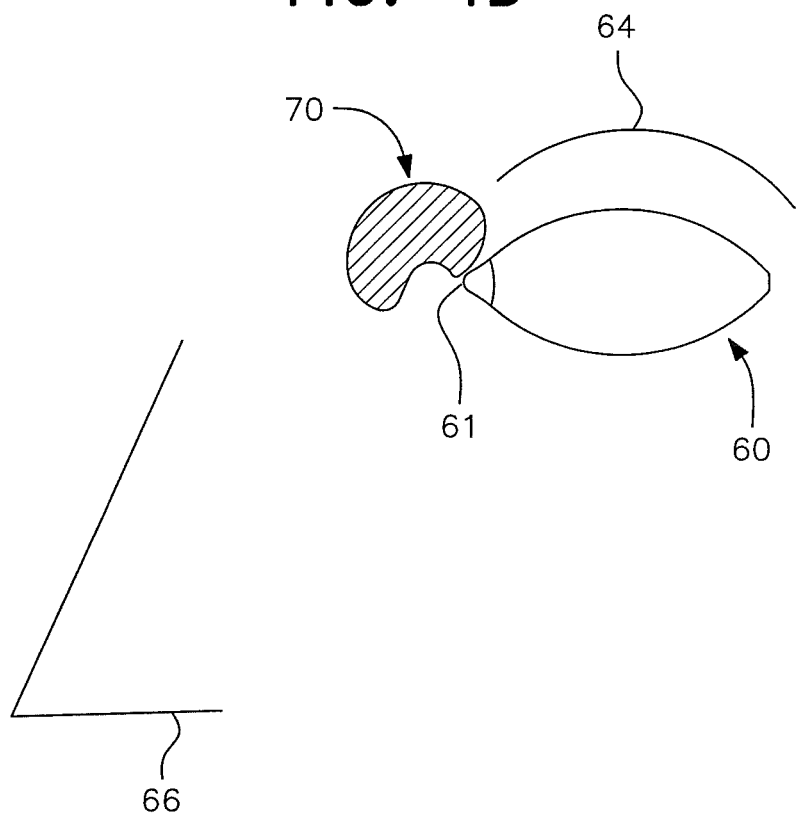
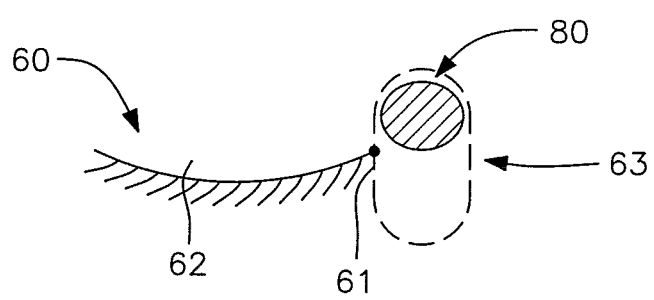

FIG. 6A
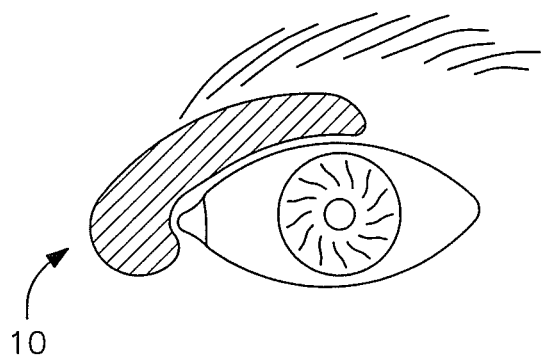
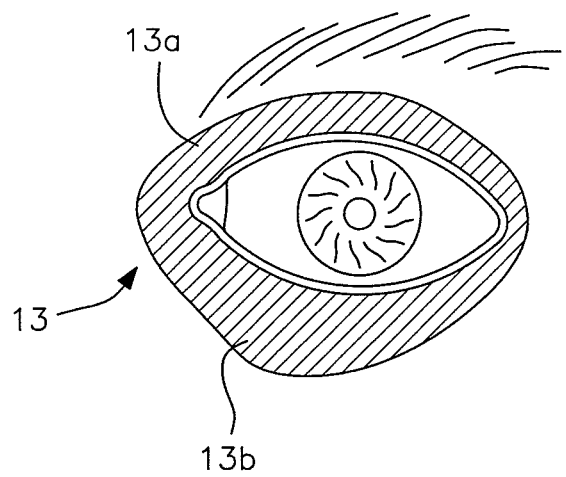

FIG. 19A1
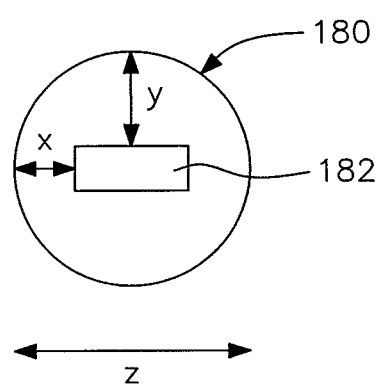
FIG. 19A2
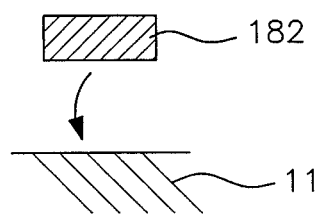
FIG. 19B
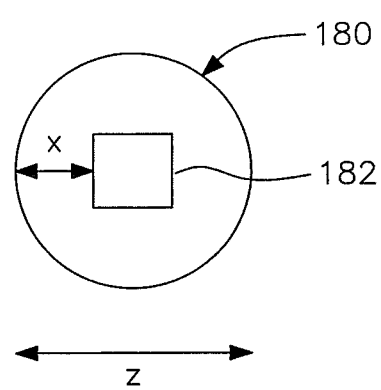
FIG. 19C
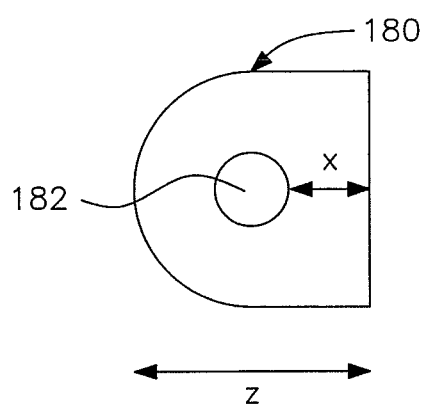
FIG. 19D
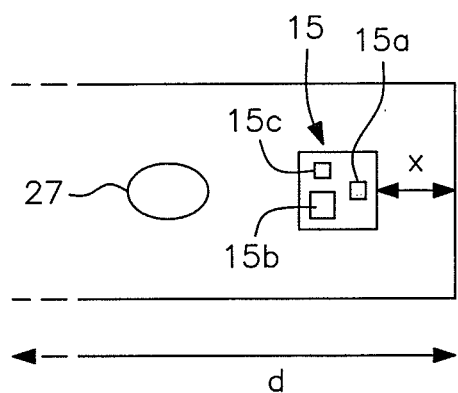

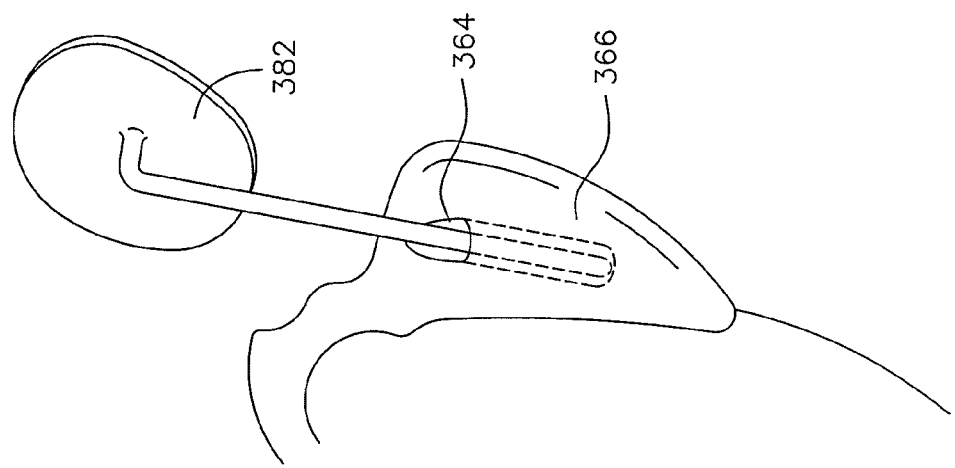
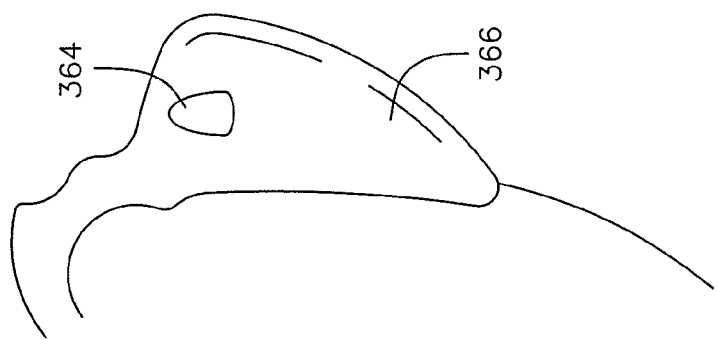

13mm

8mm

5mm

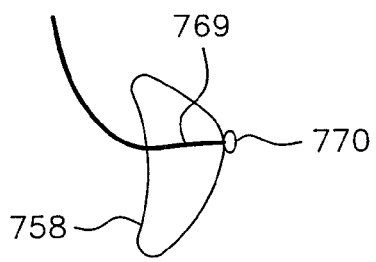
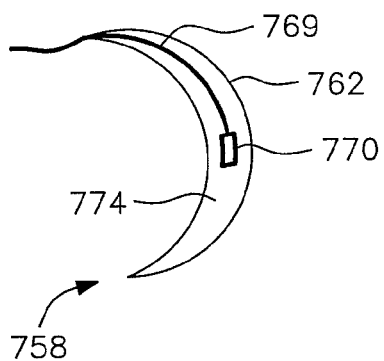
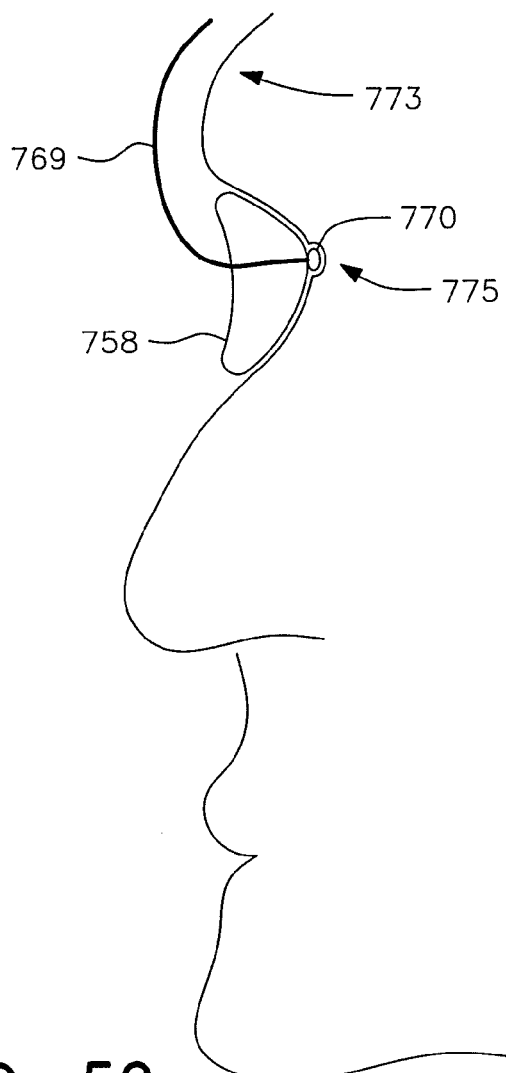
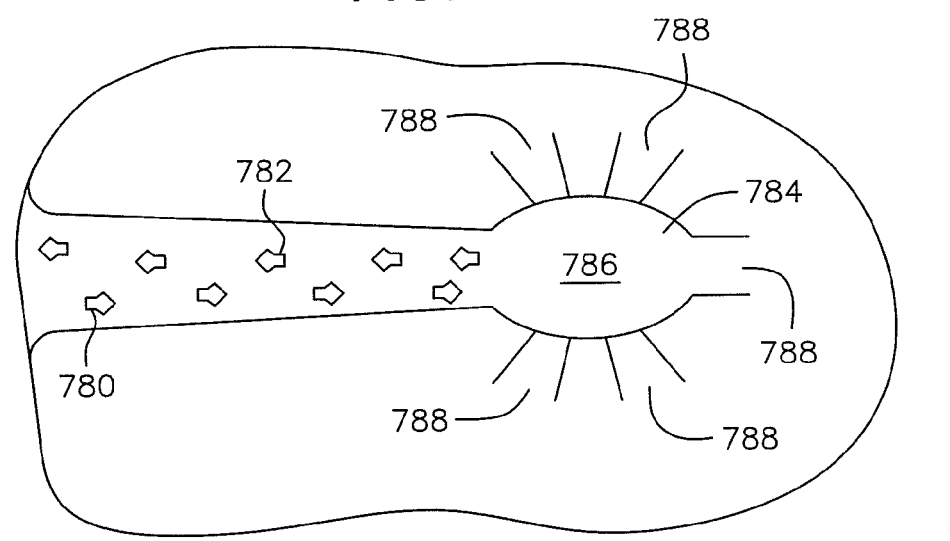

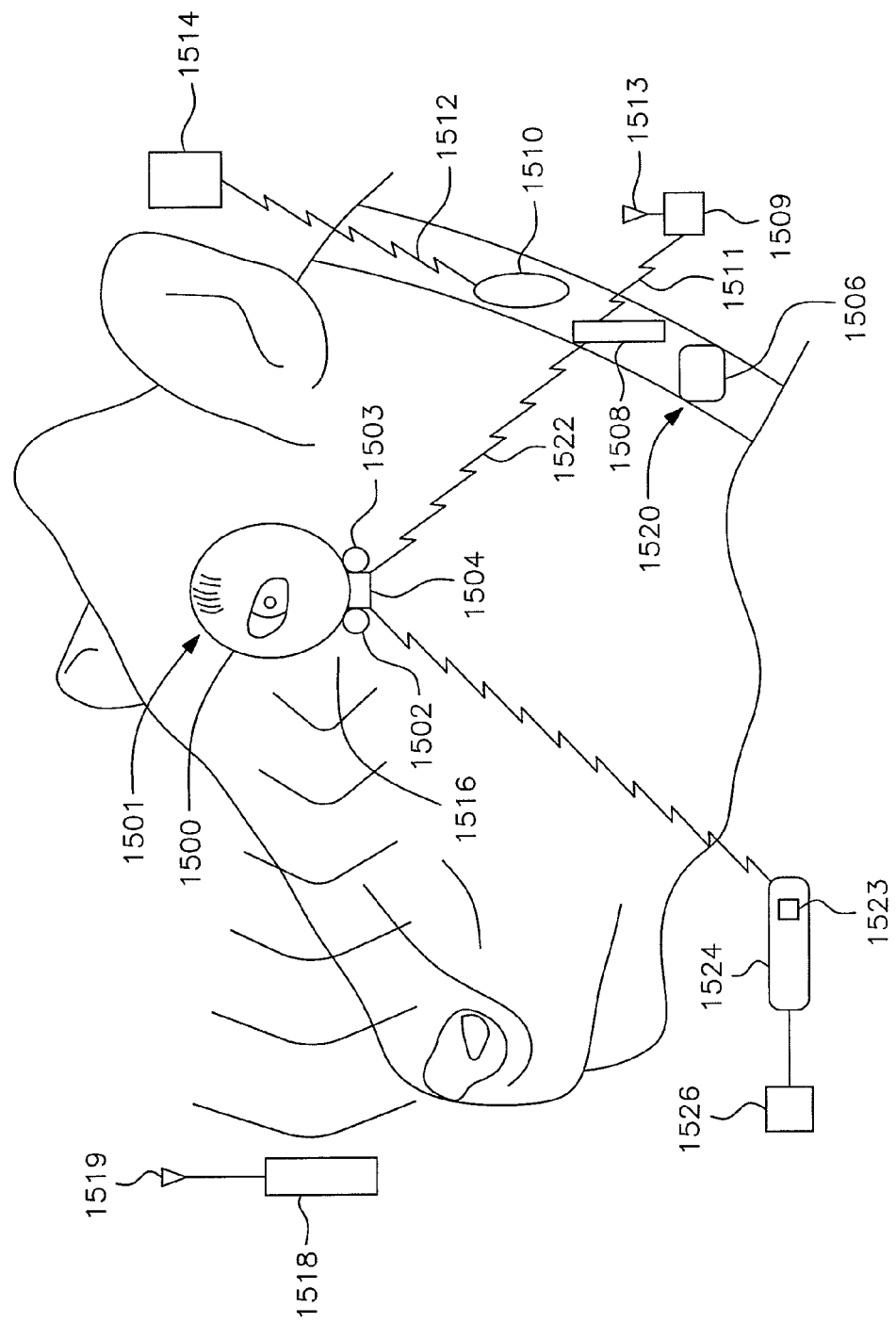

FIRST STEP: C. SCREEN

SECOND STEP:
RADIO RCV DIRECTION FINDER

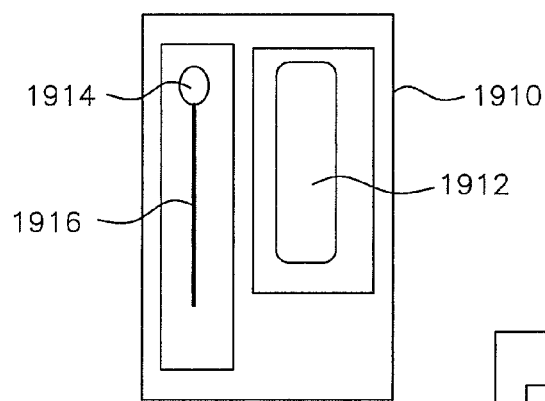
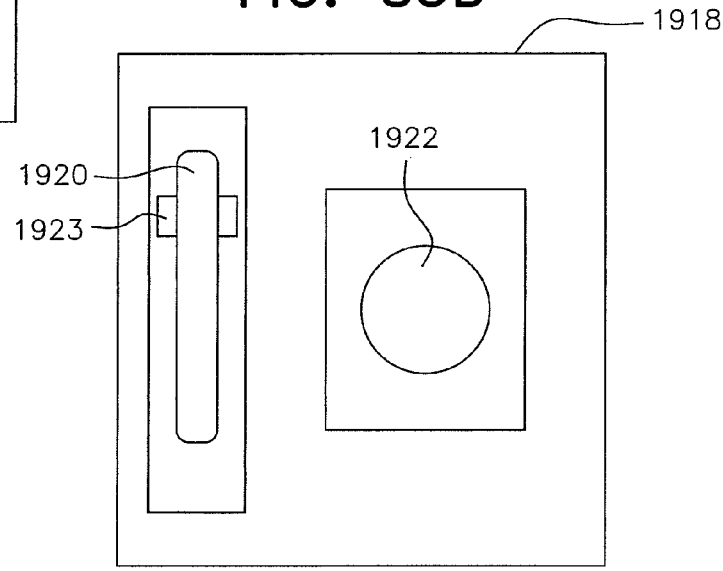
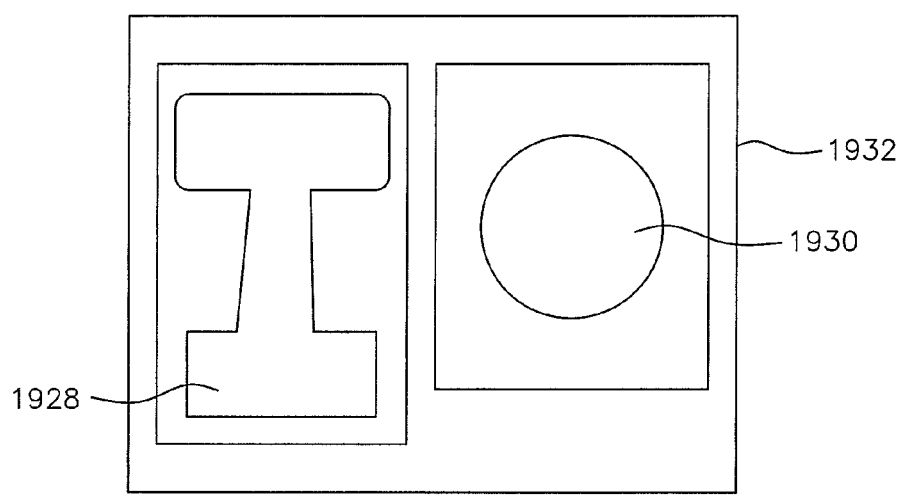

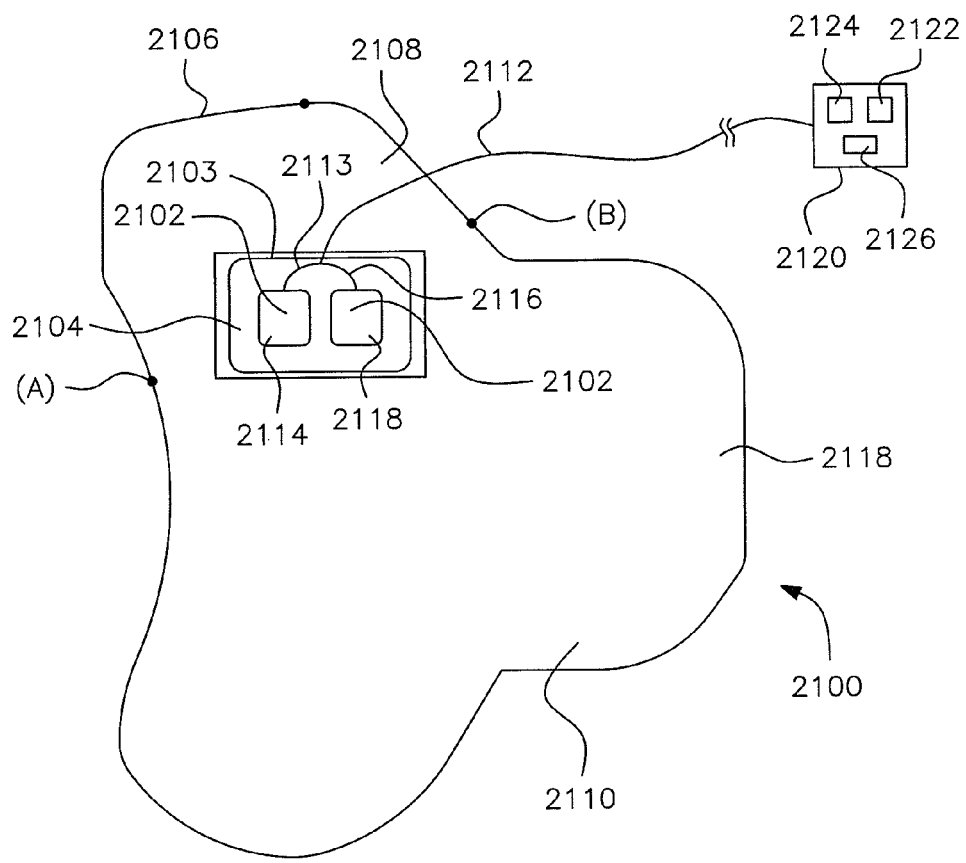
FIG. 86M
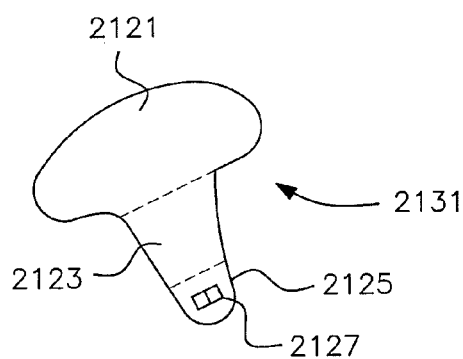
FIG. 86M(1)
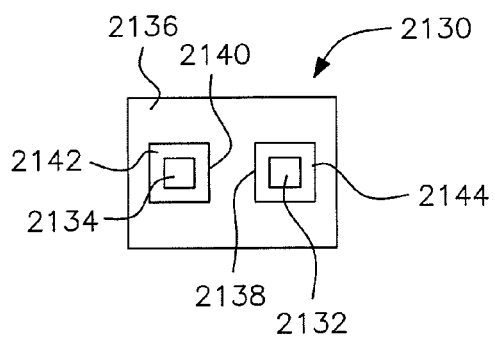
FIG. 86N

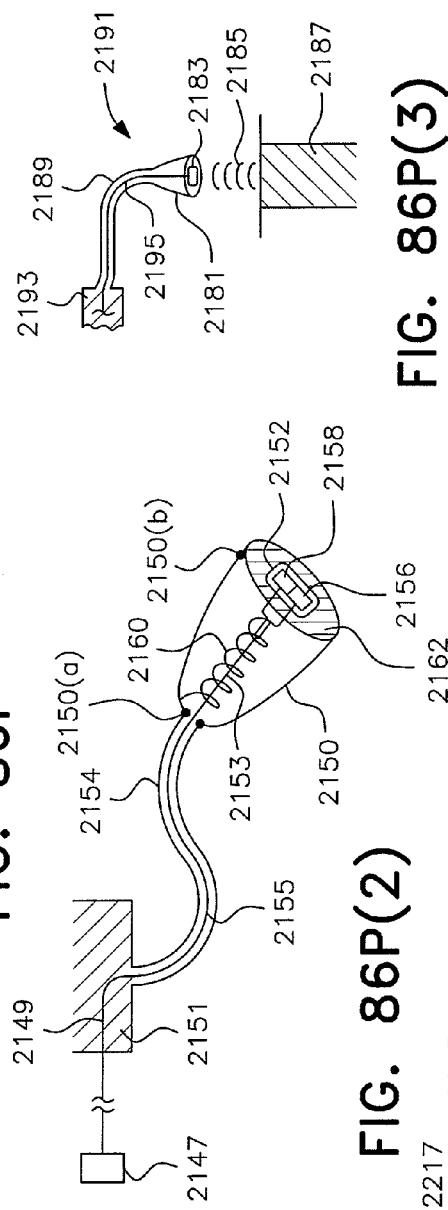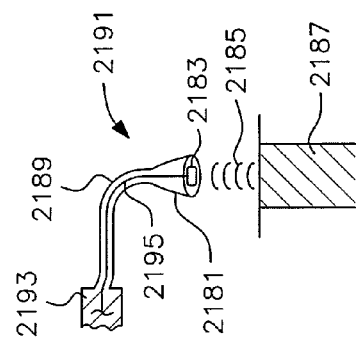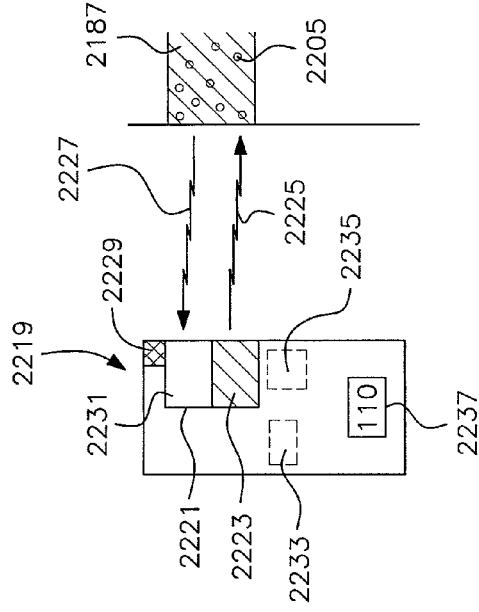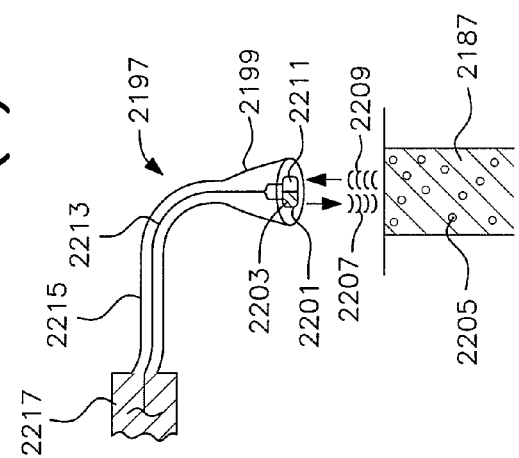

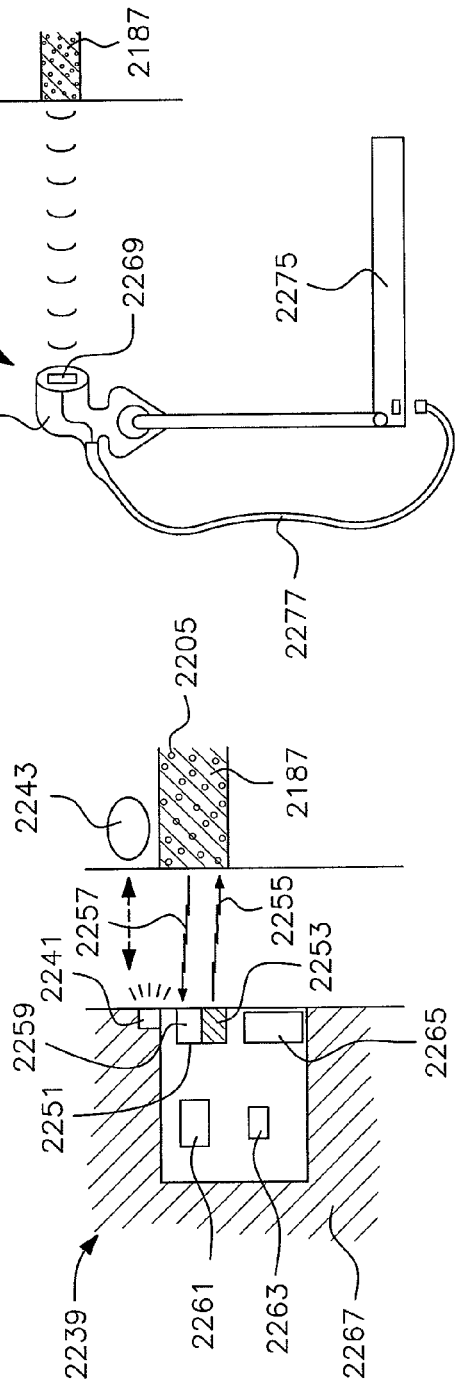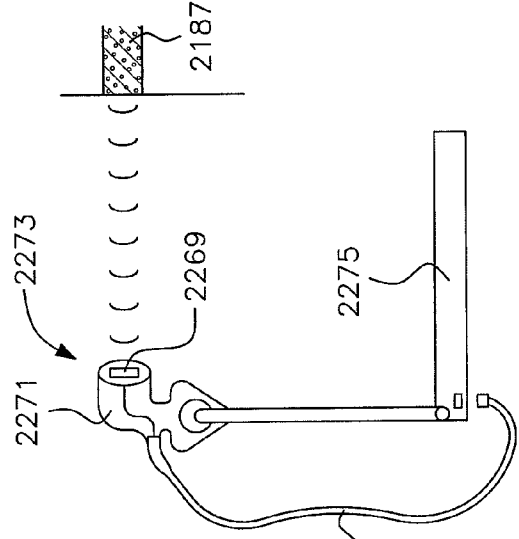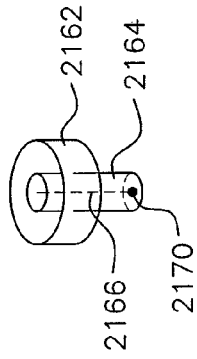

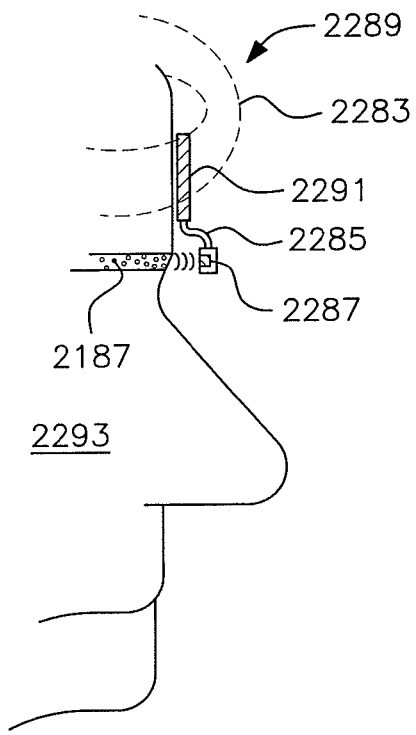
FIG. 86R(1)
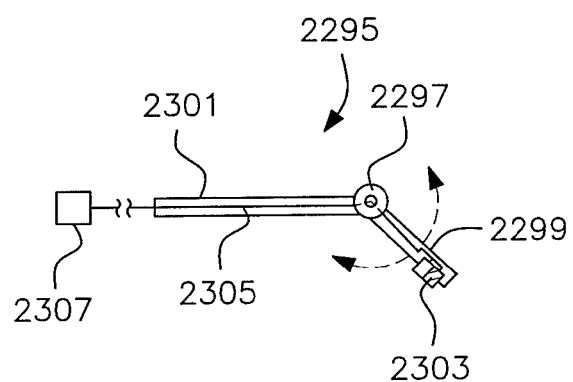
FIG. 86R(2)
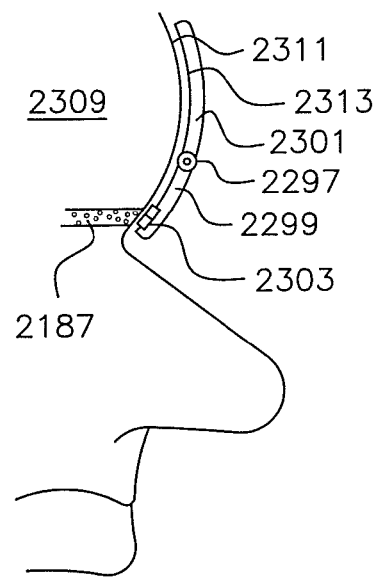
FIG. 86R(3)

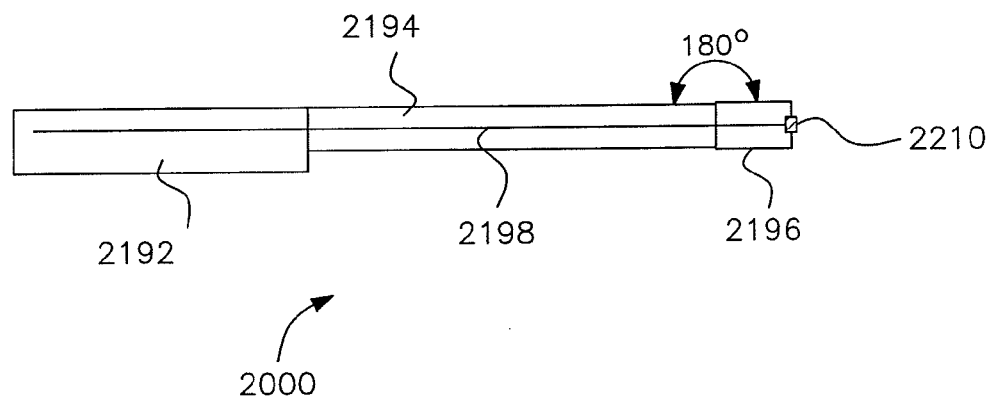
FIG. 86S(1)
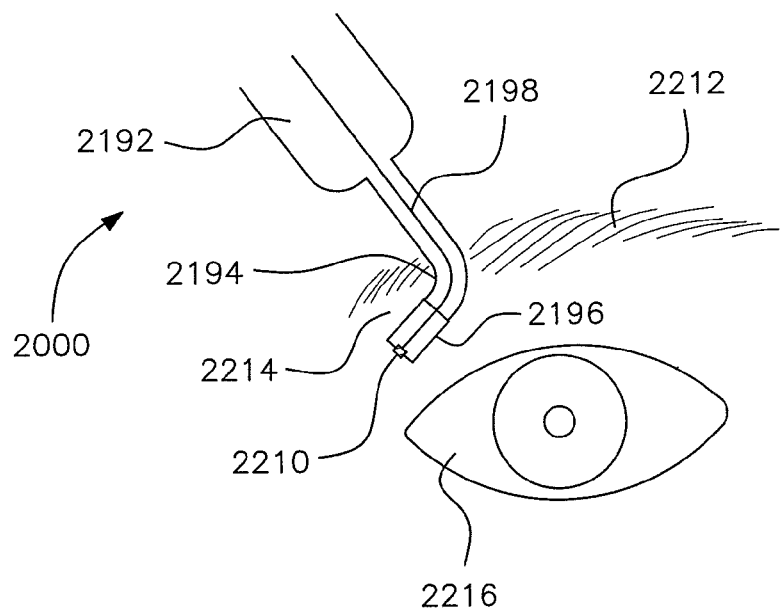
FIG. 86S(2)

FIG. 86T(1)
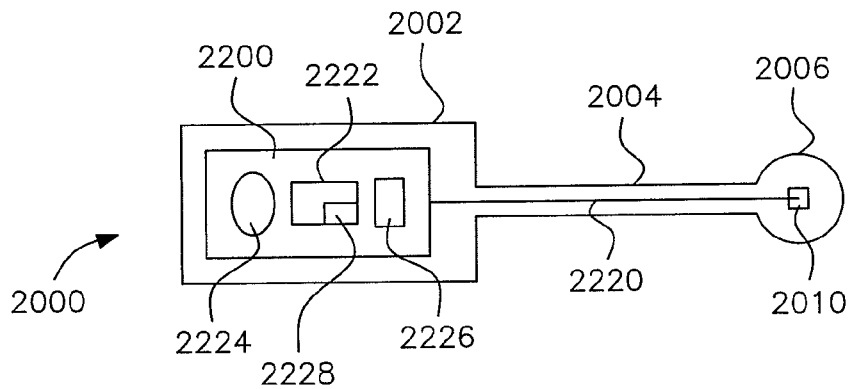
FIG. 86T(2)
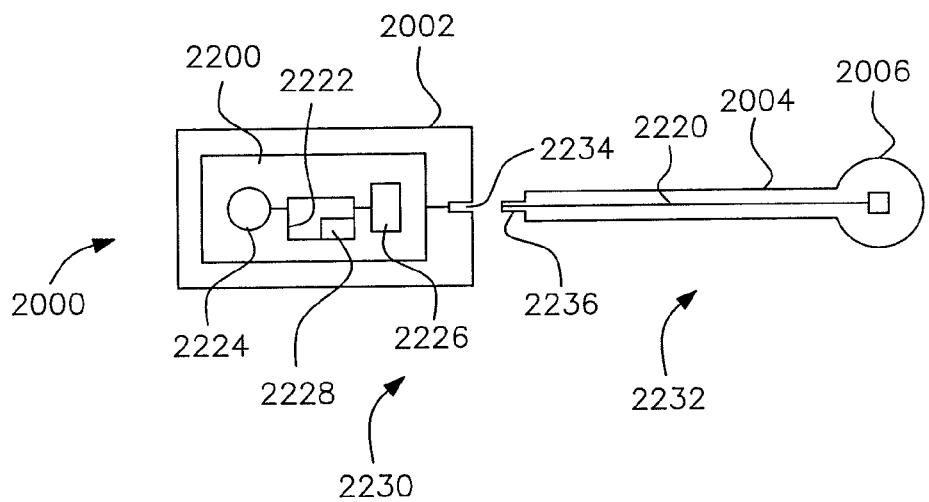
FIG. 86T(3)
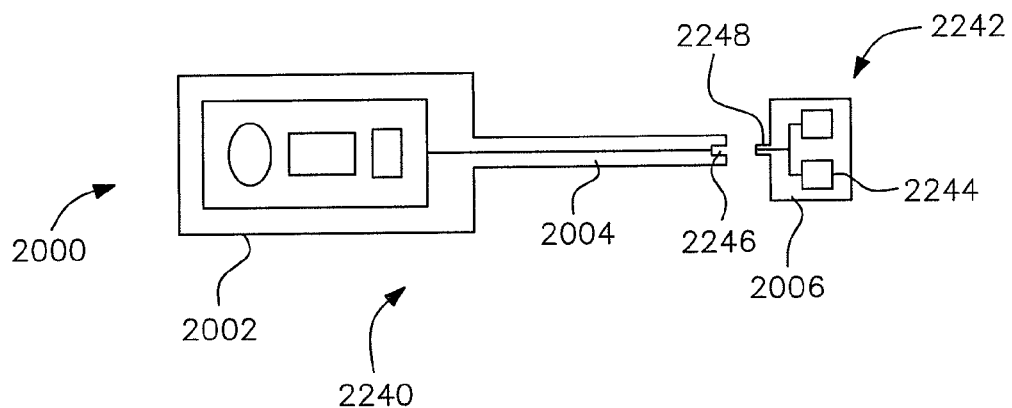

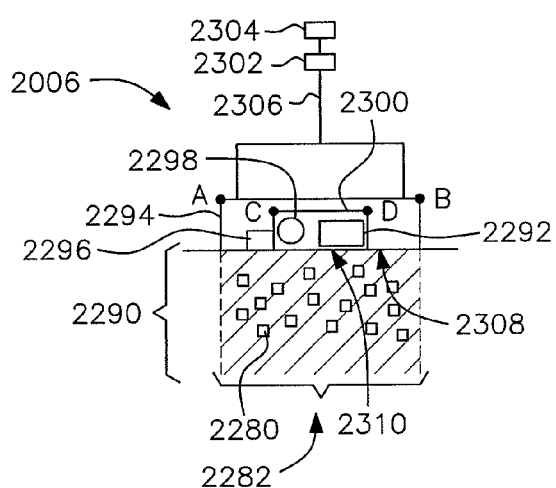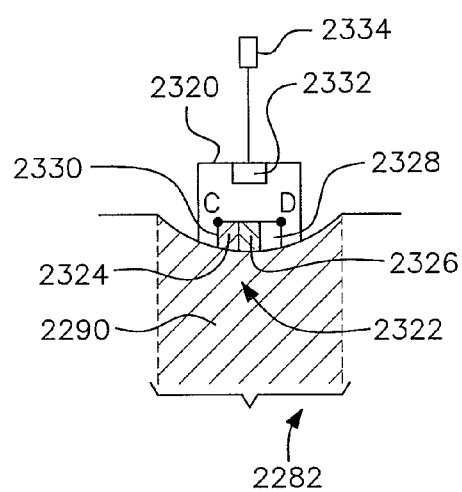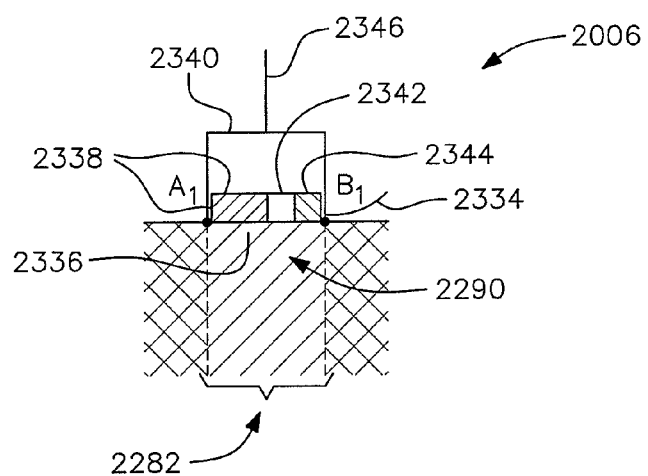

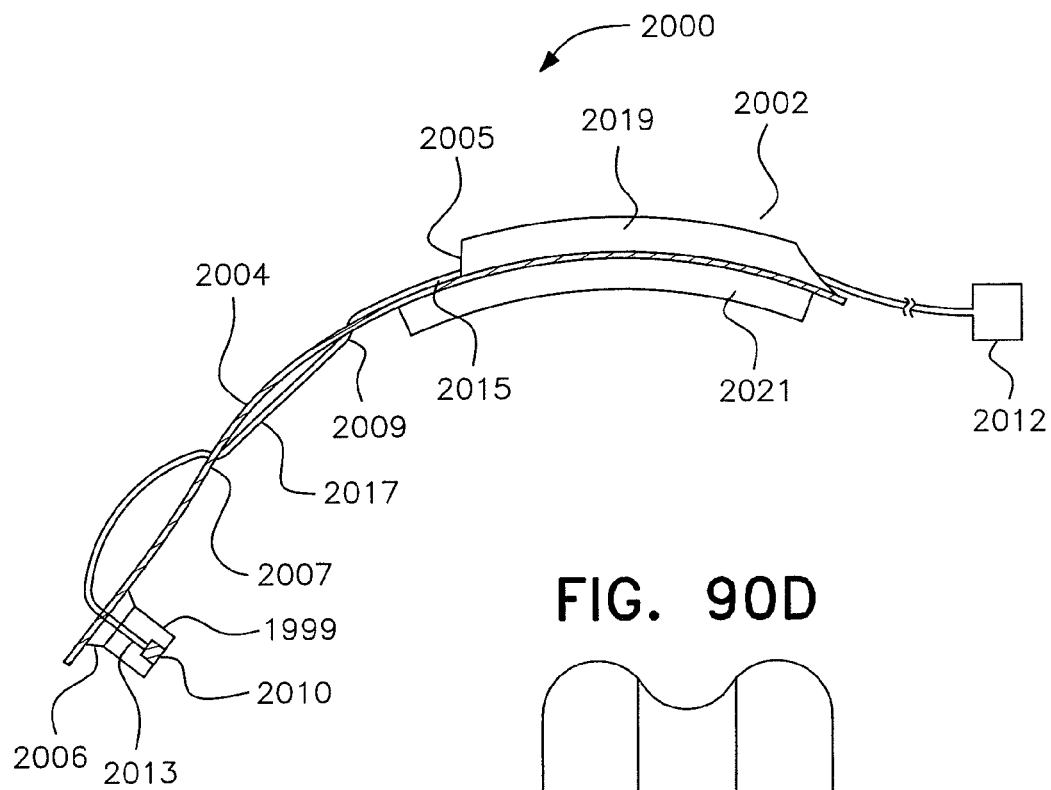
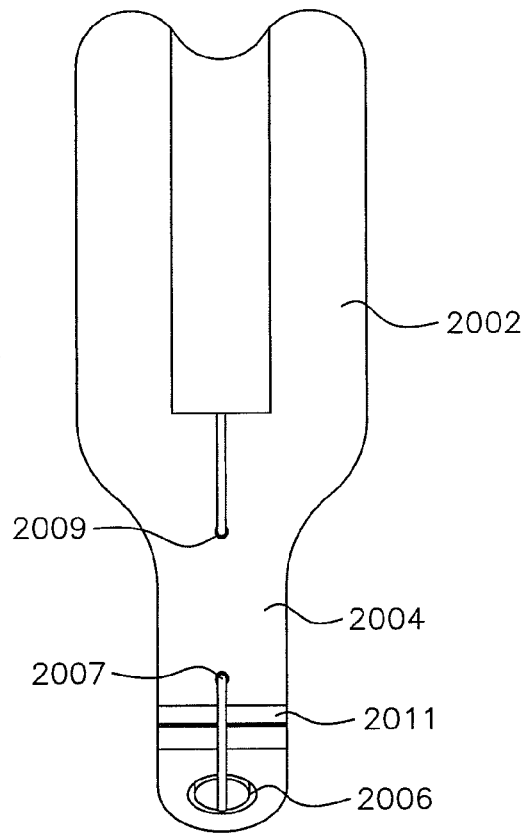

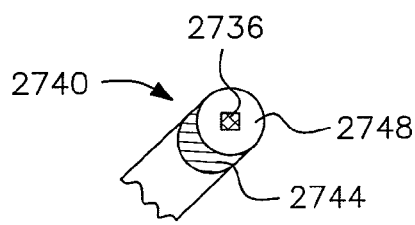
FIG. 96C
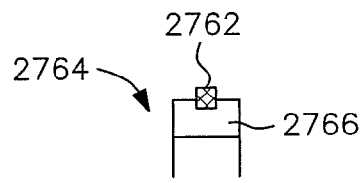
FIG. 96D
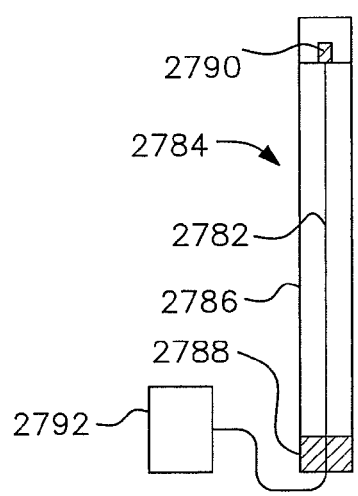
FIG. 96E
(PRIOR ART)
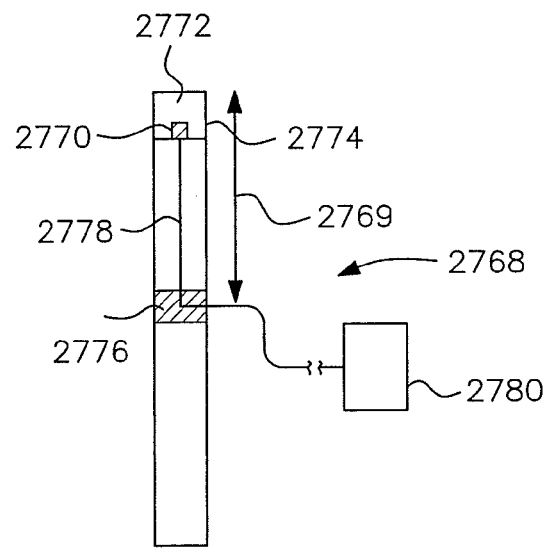
FIG. 96F
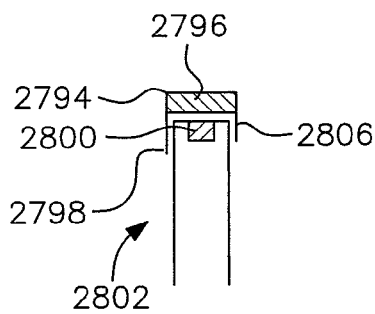
FIG. 96-G1
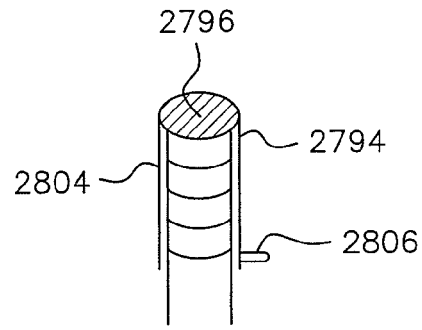
FIG. 96-G2

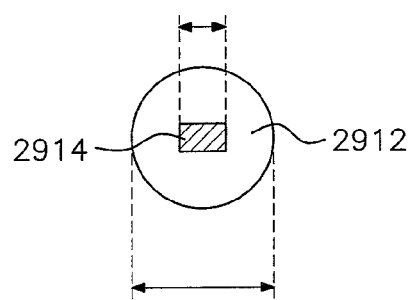
FIG. 96-Q1
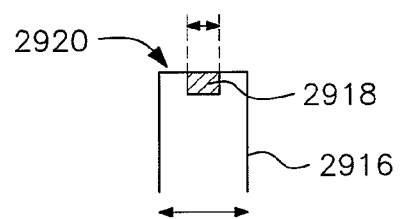
FIG. 96-Q2
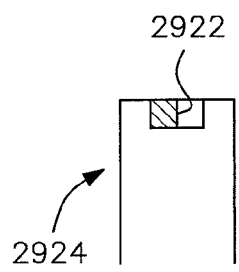
FIG. 96-Q3
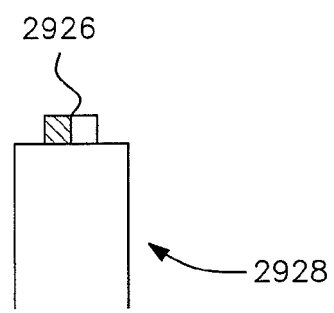
FIG. 96-Q4

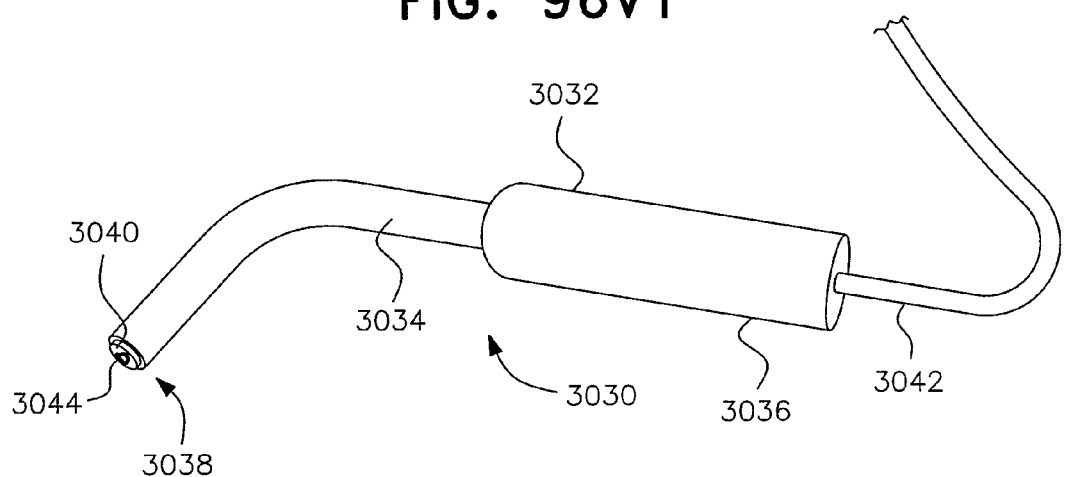
FIG. 96V1
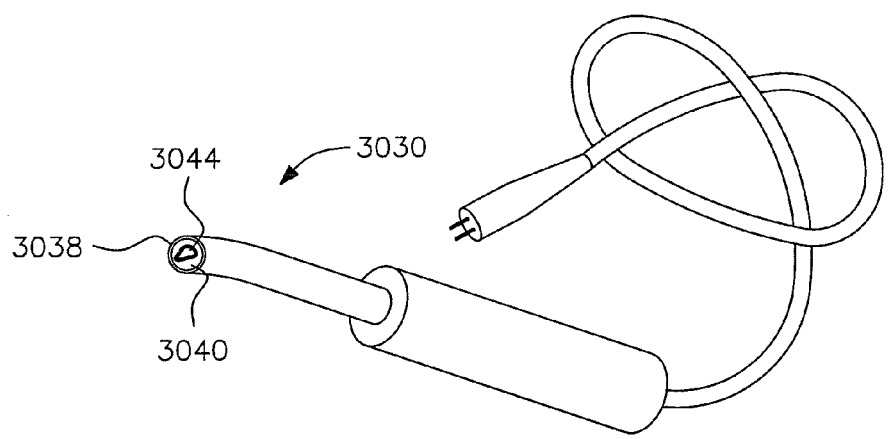
FIG. 96V2

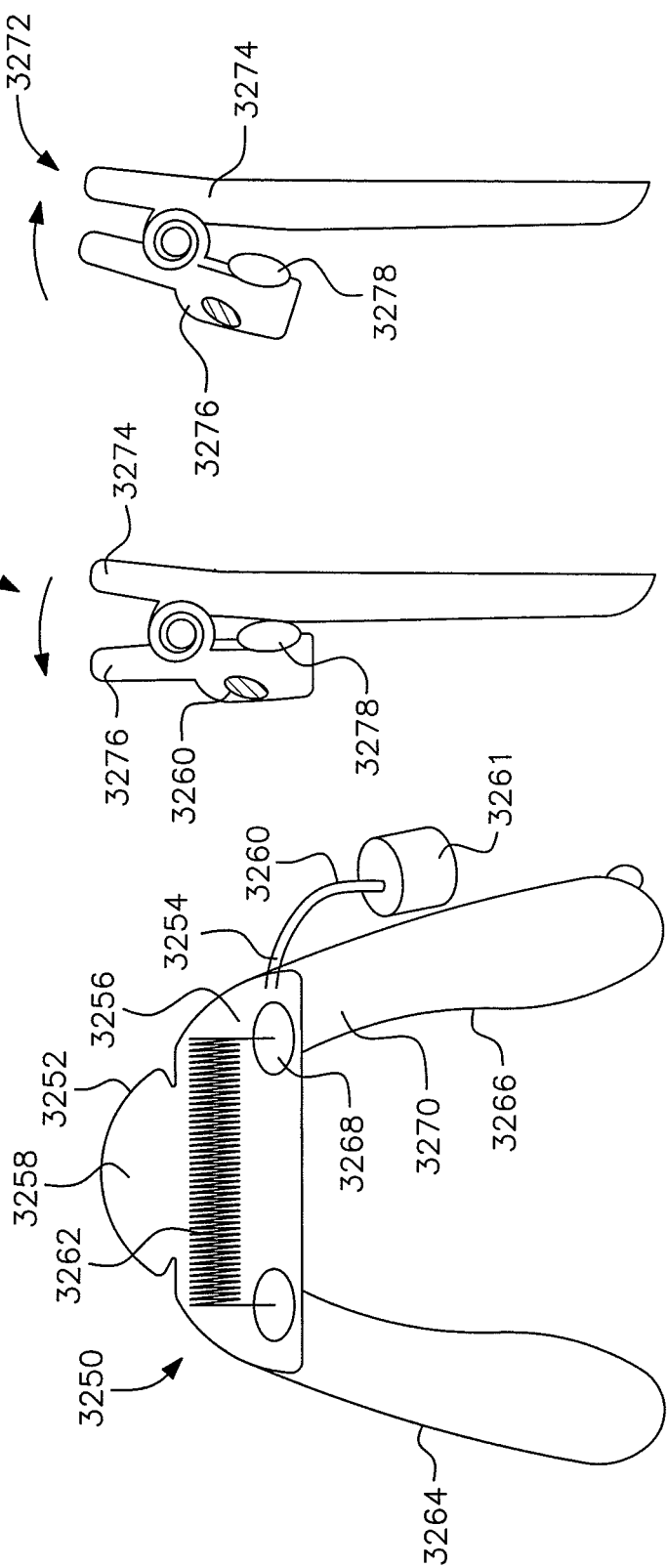

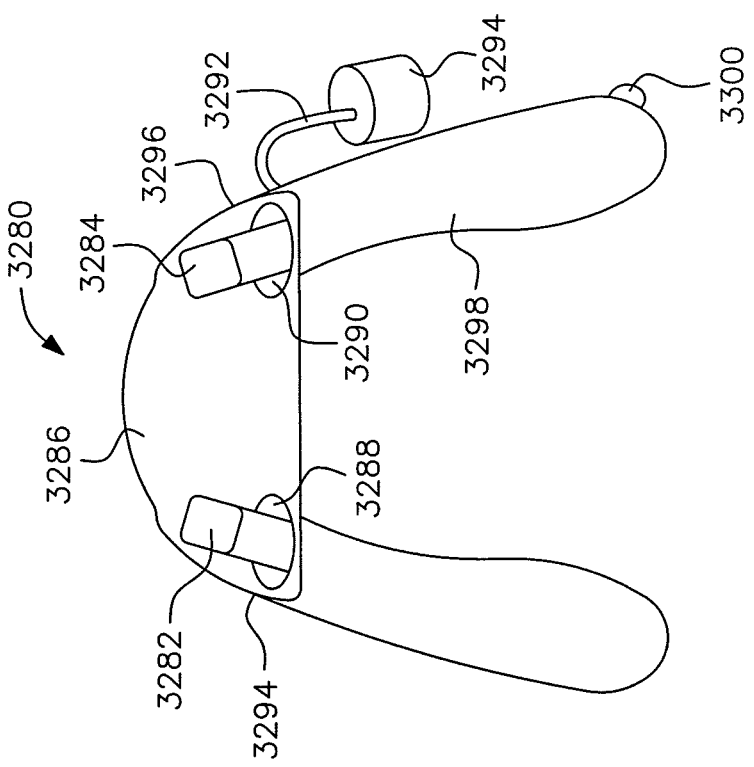
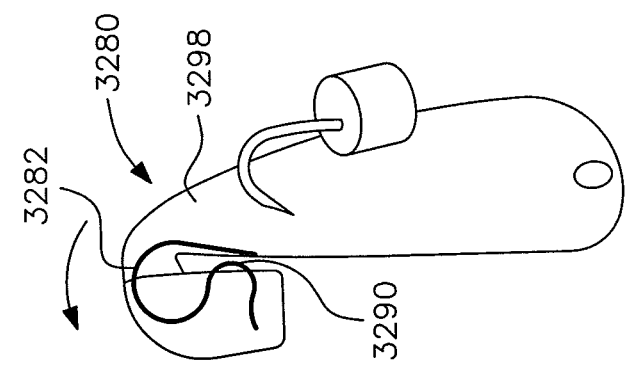
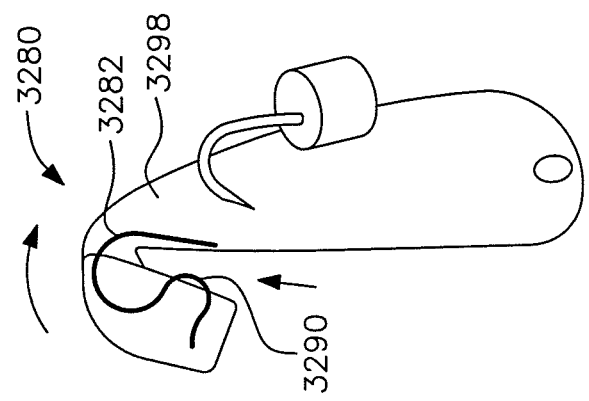

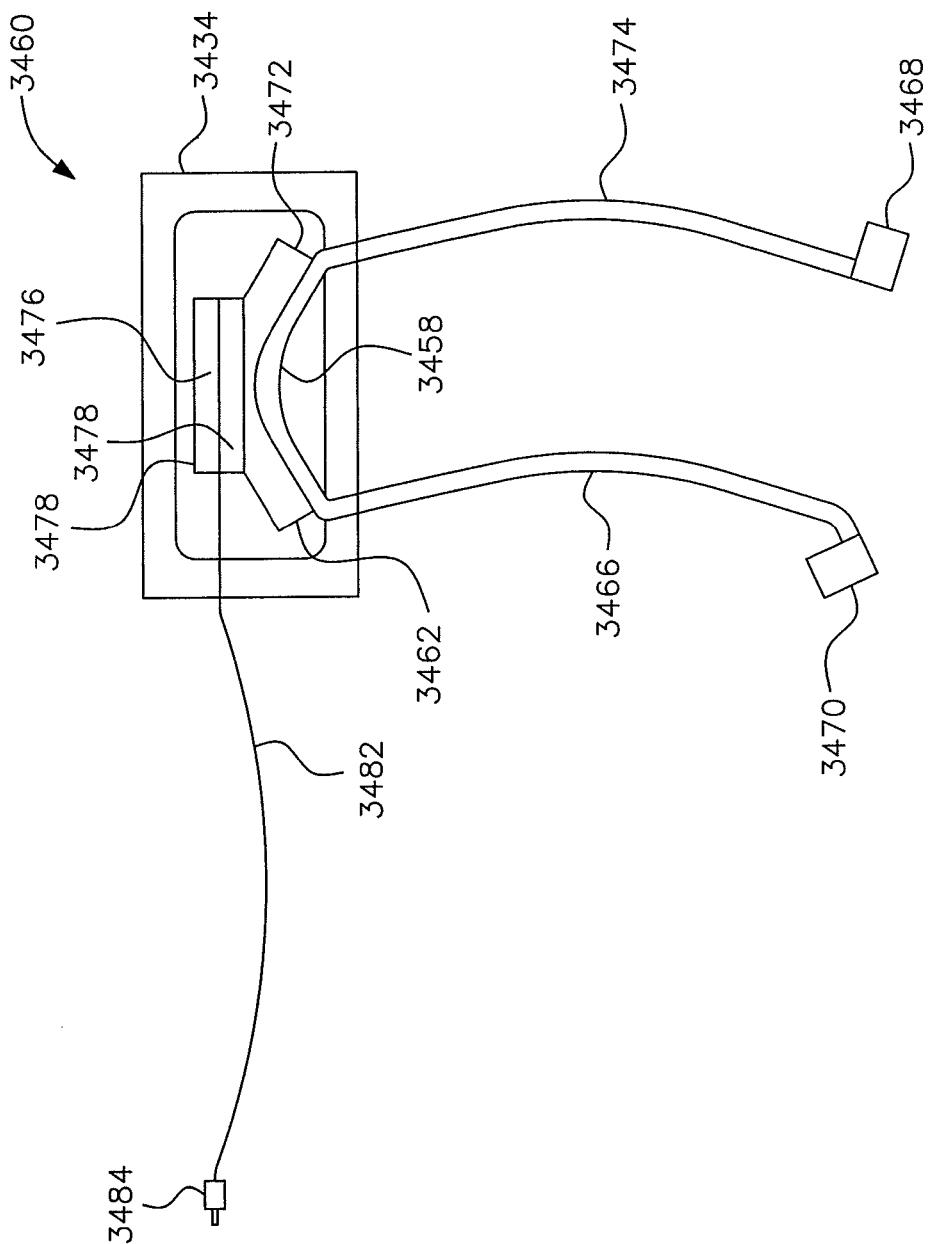

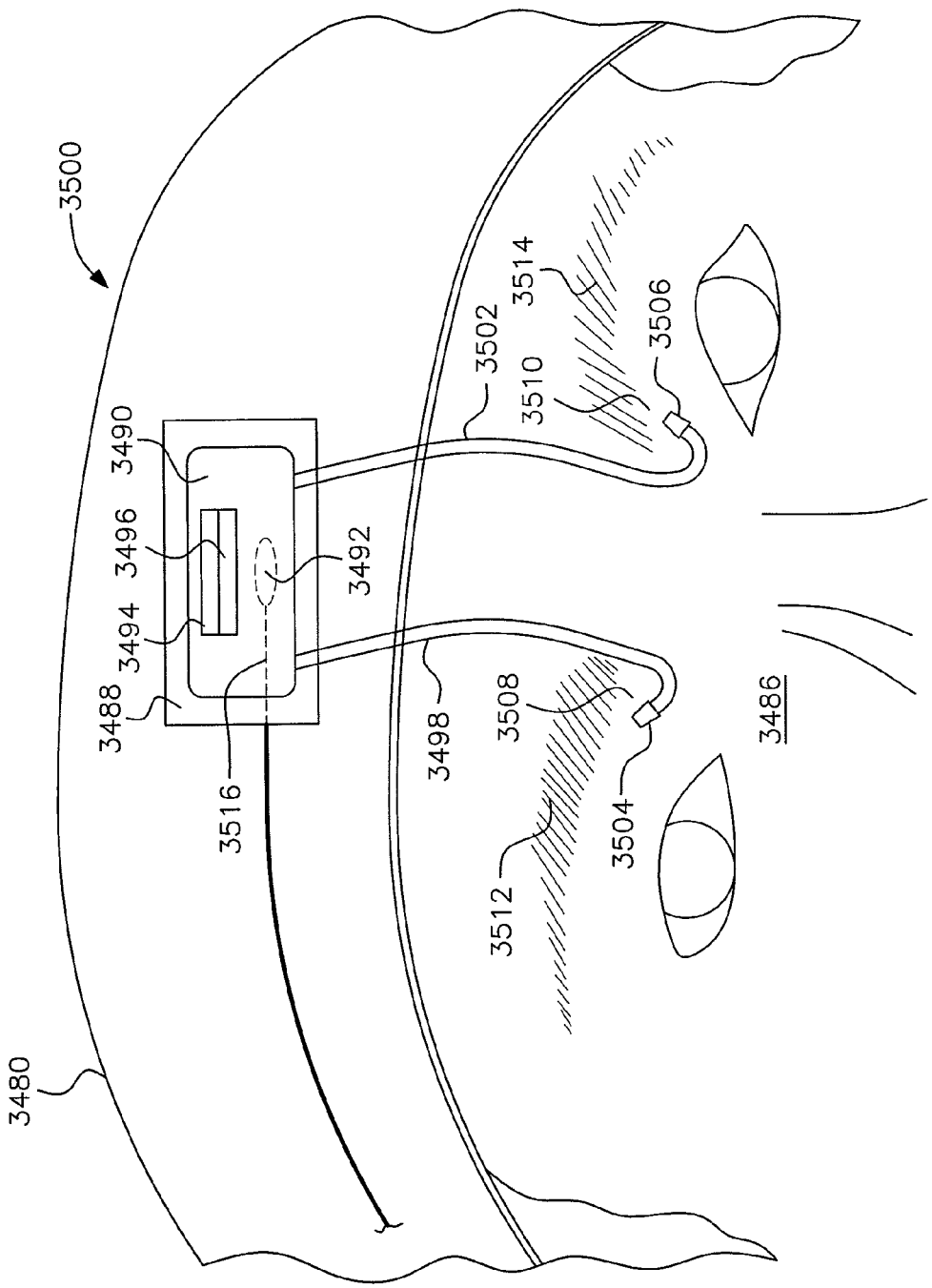

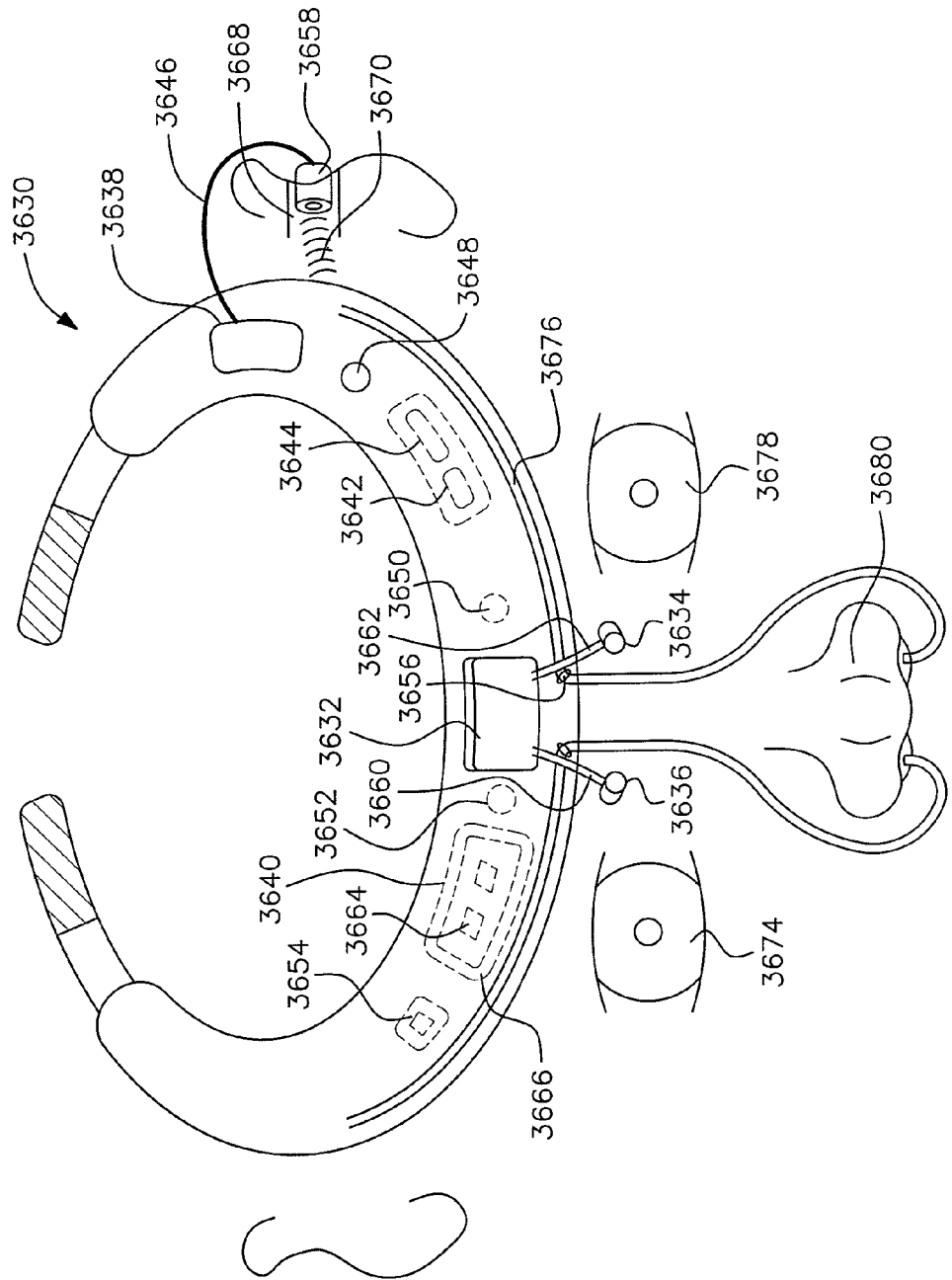

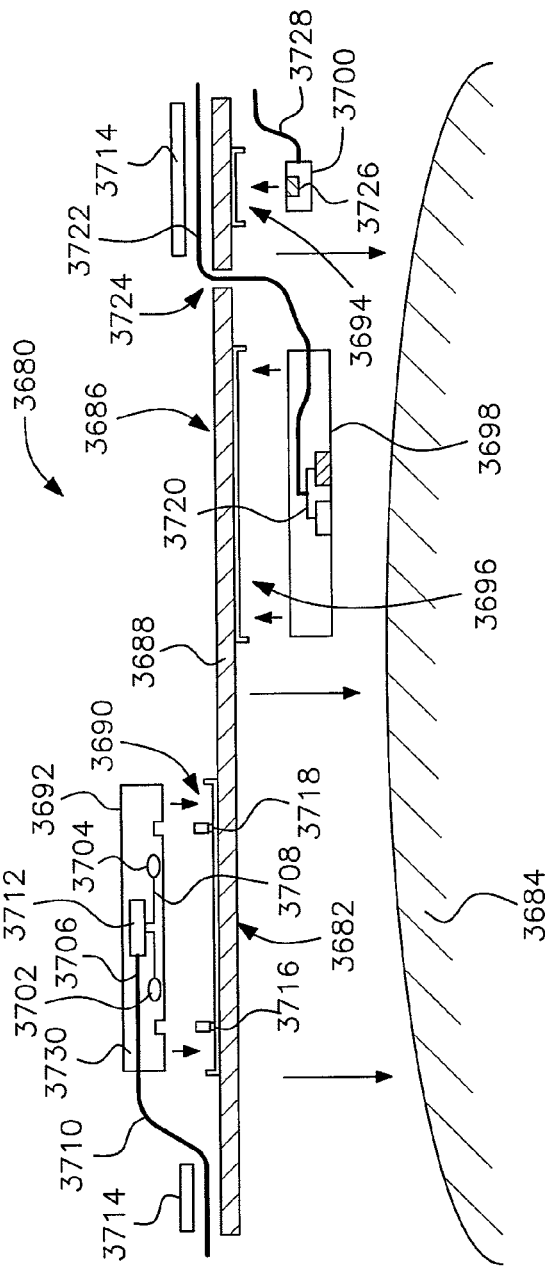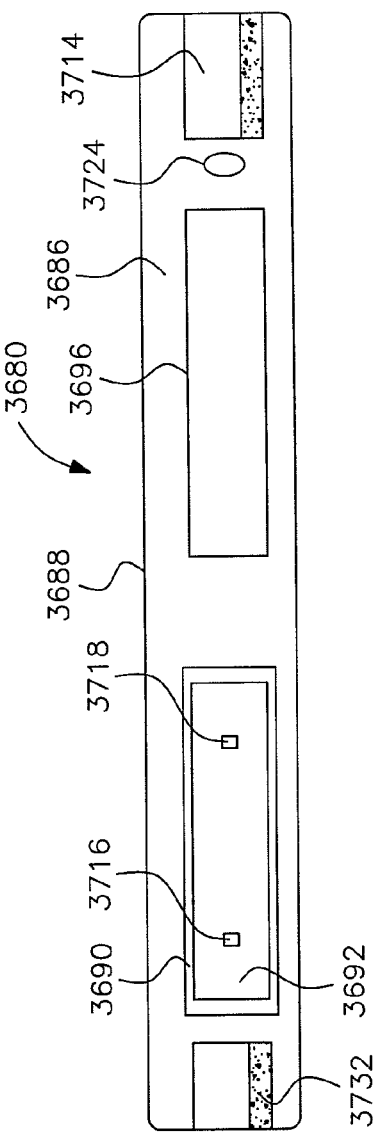

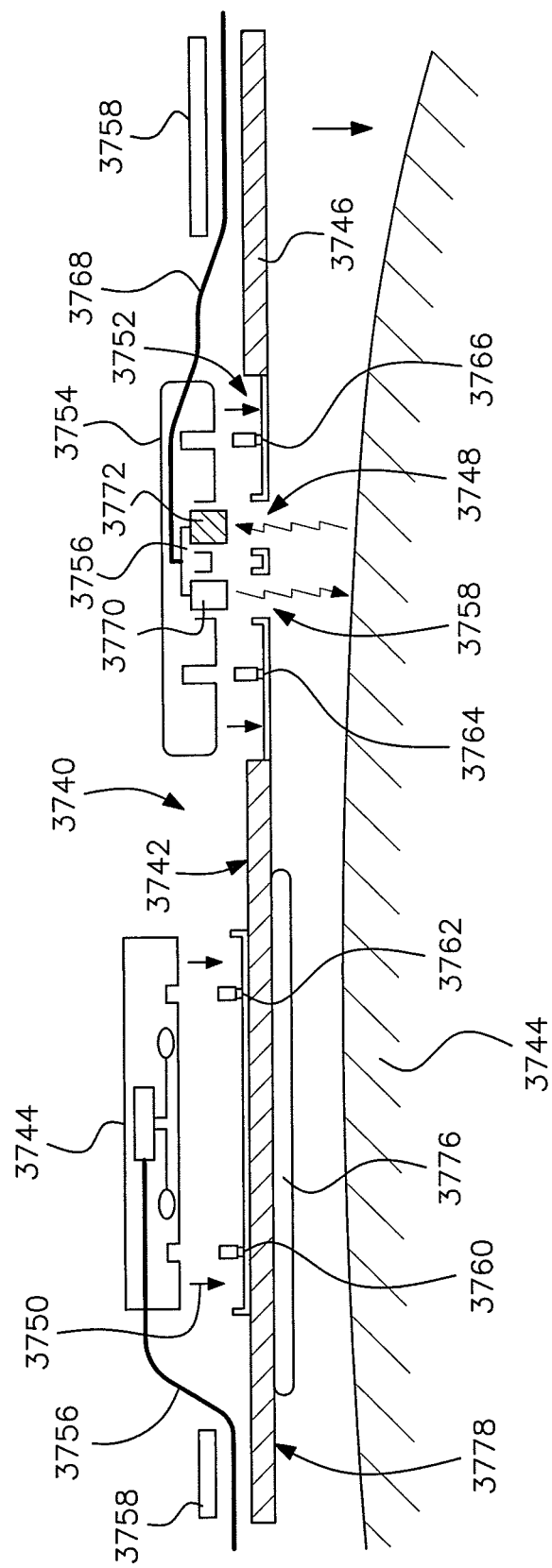

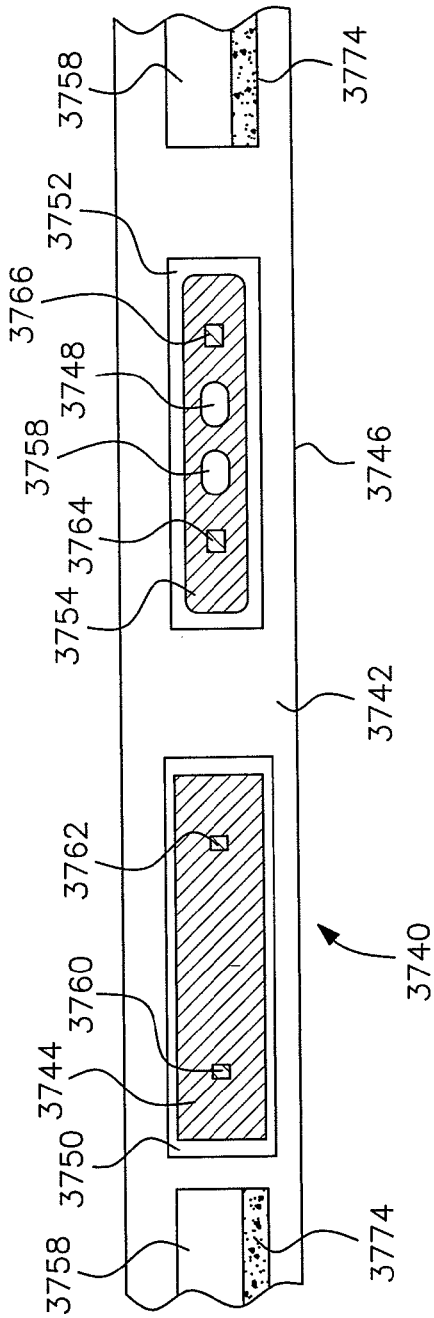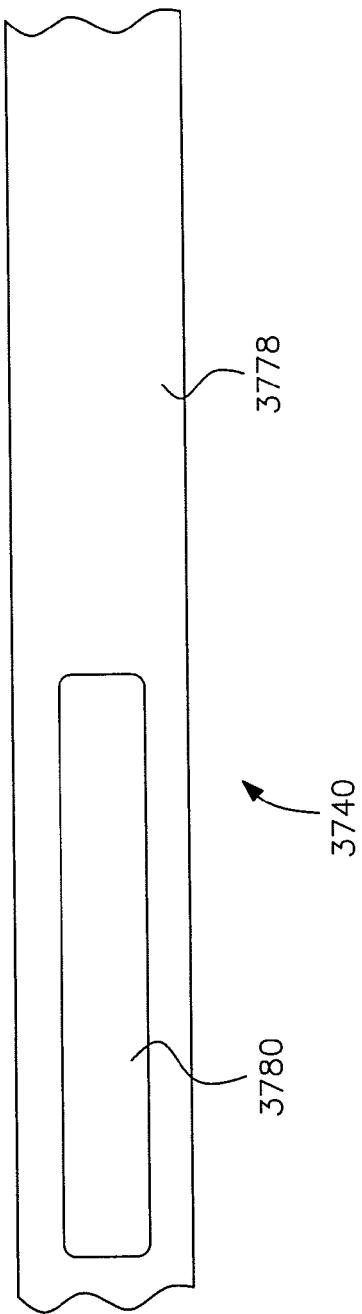

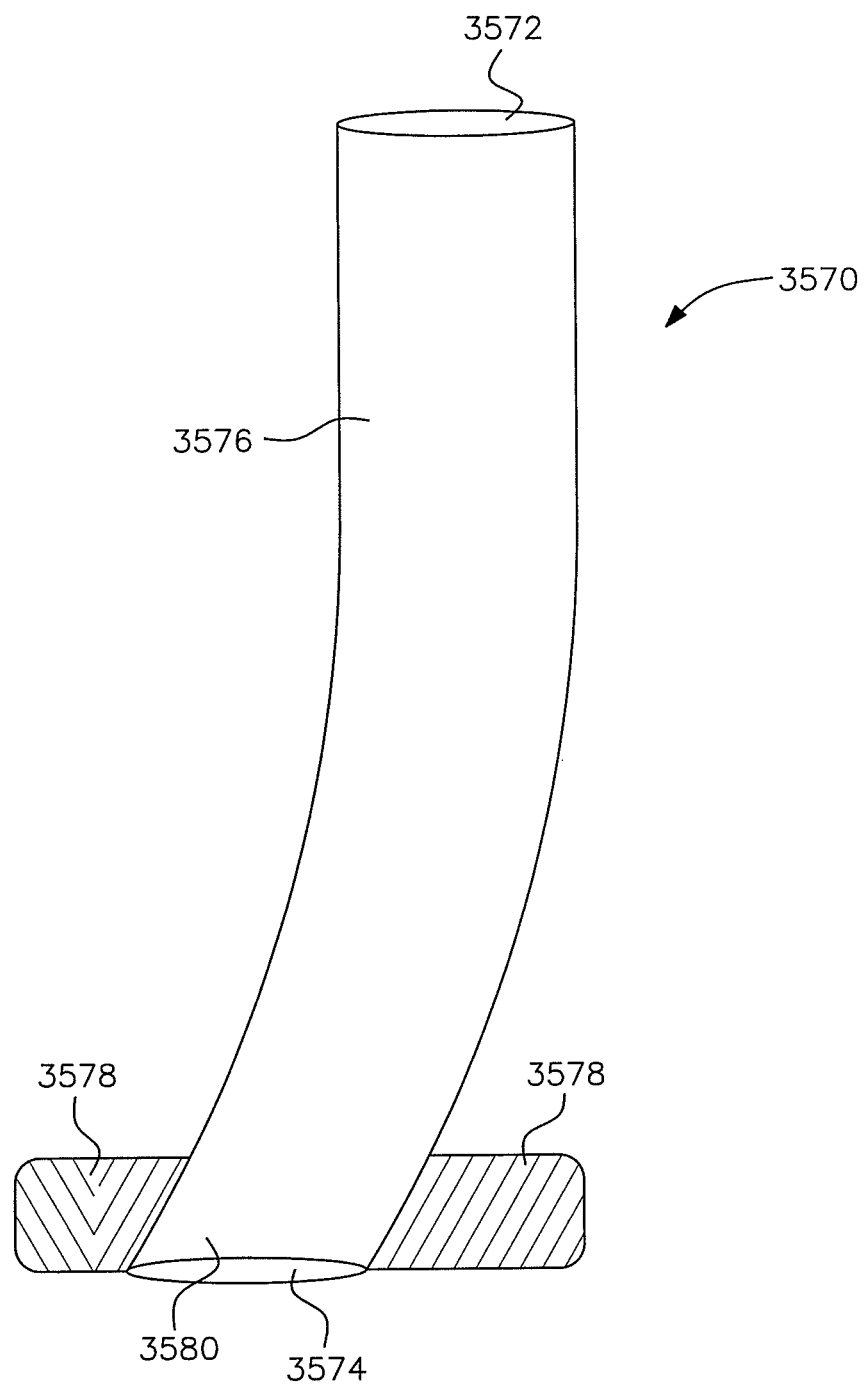

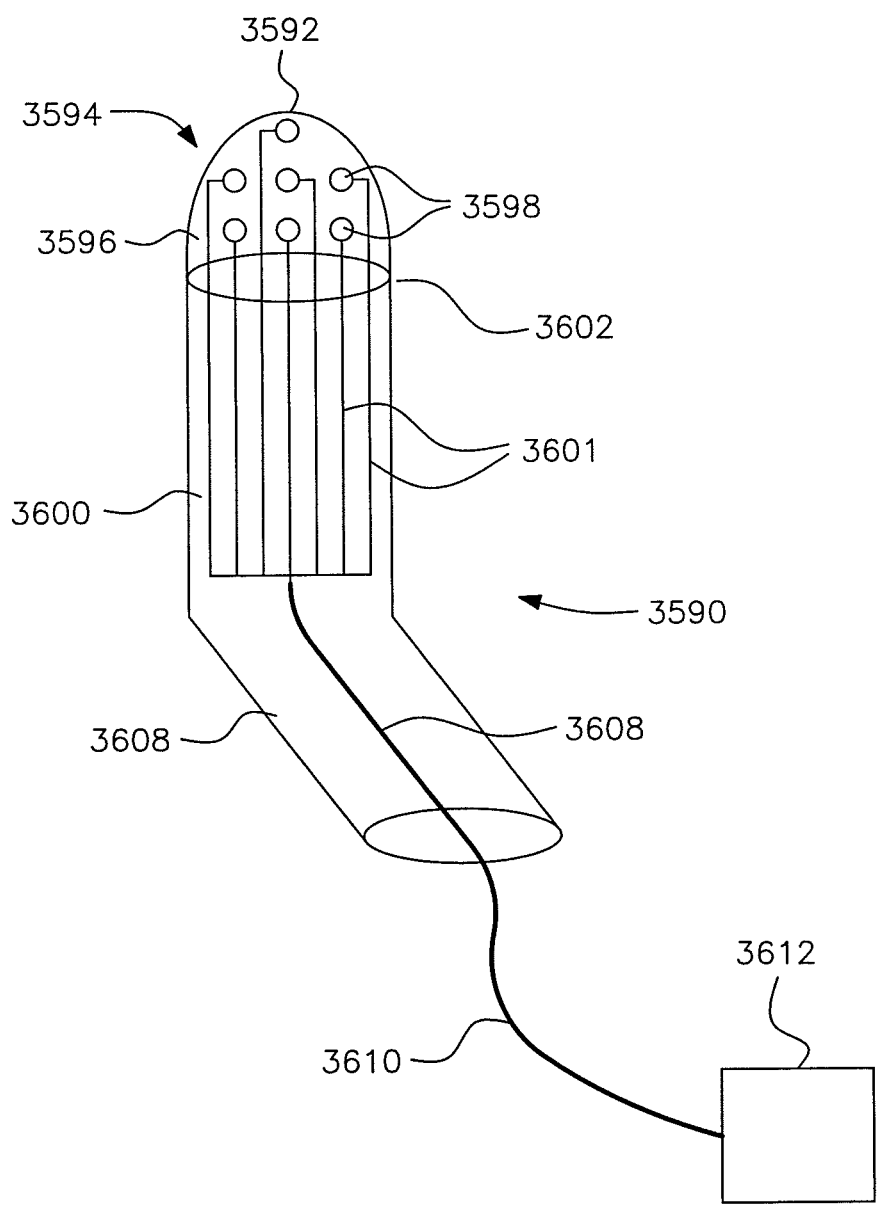
FIG. 104-A

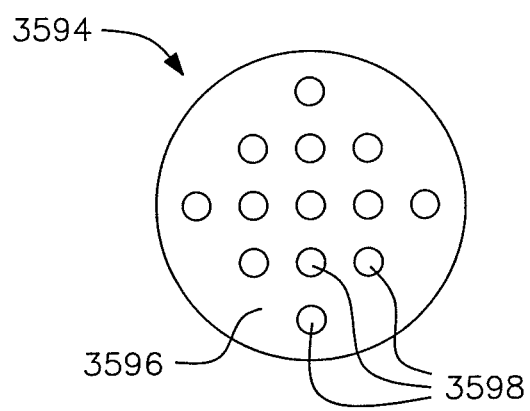
FIG. 104-B

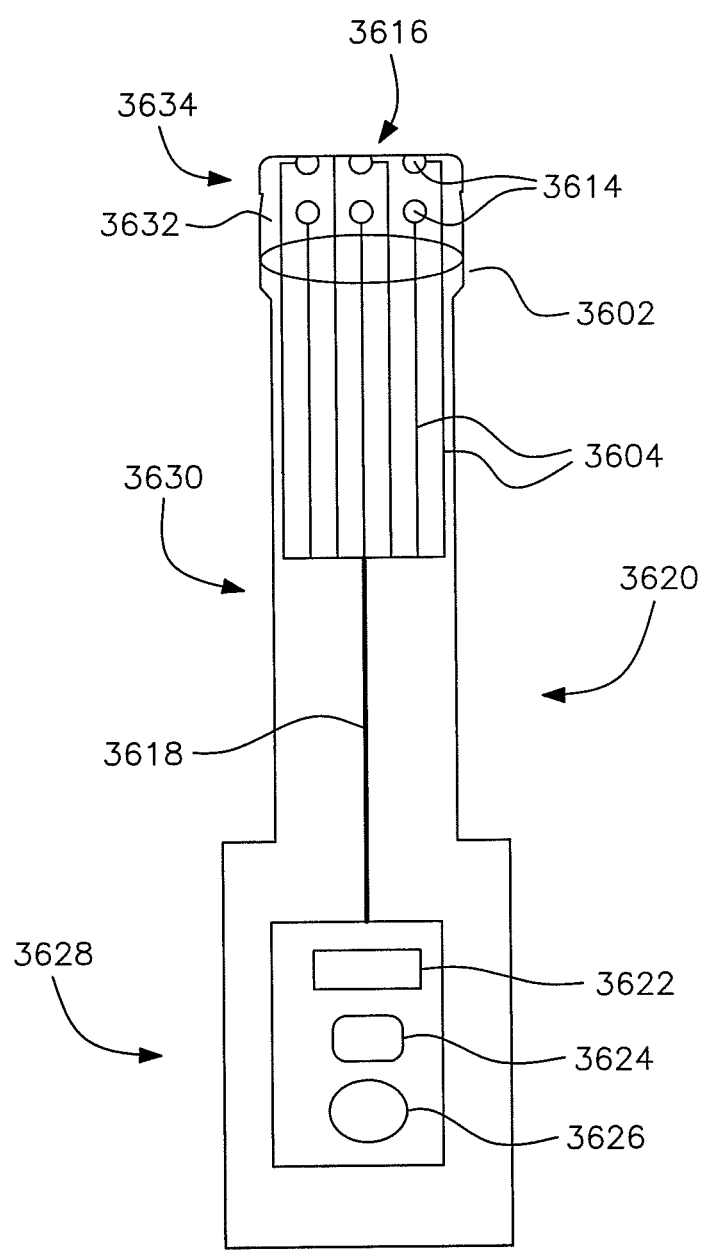
FIG. 104-C

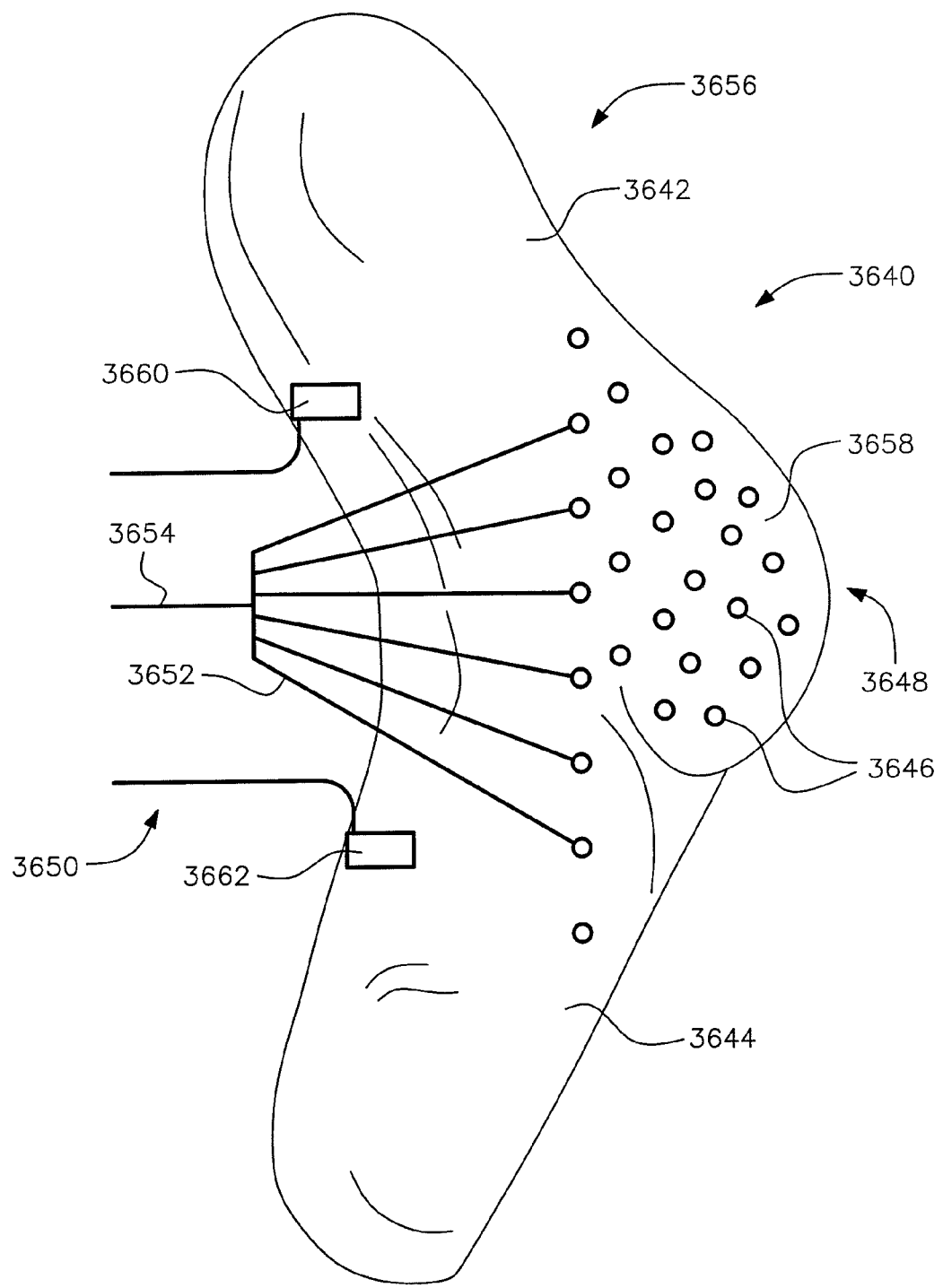
FIG. 104-D

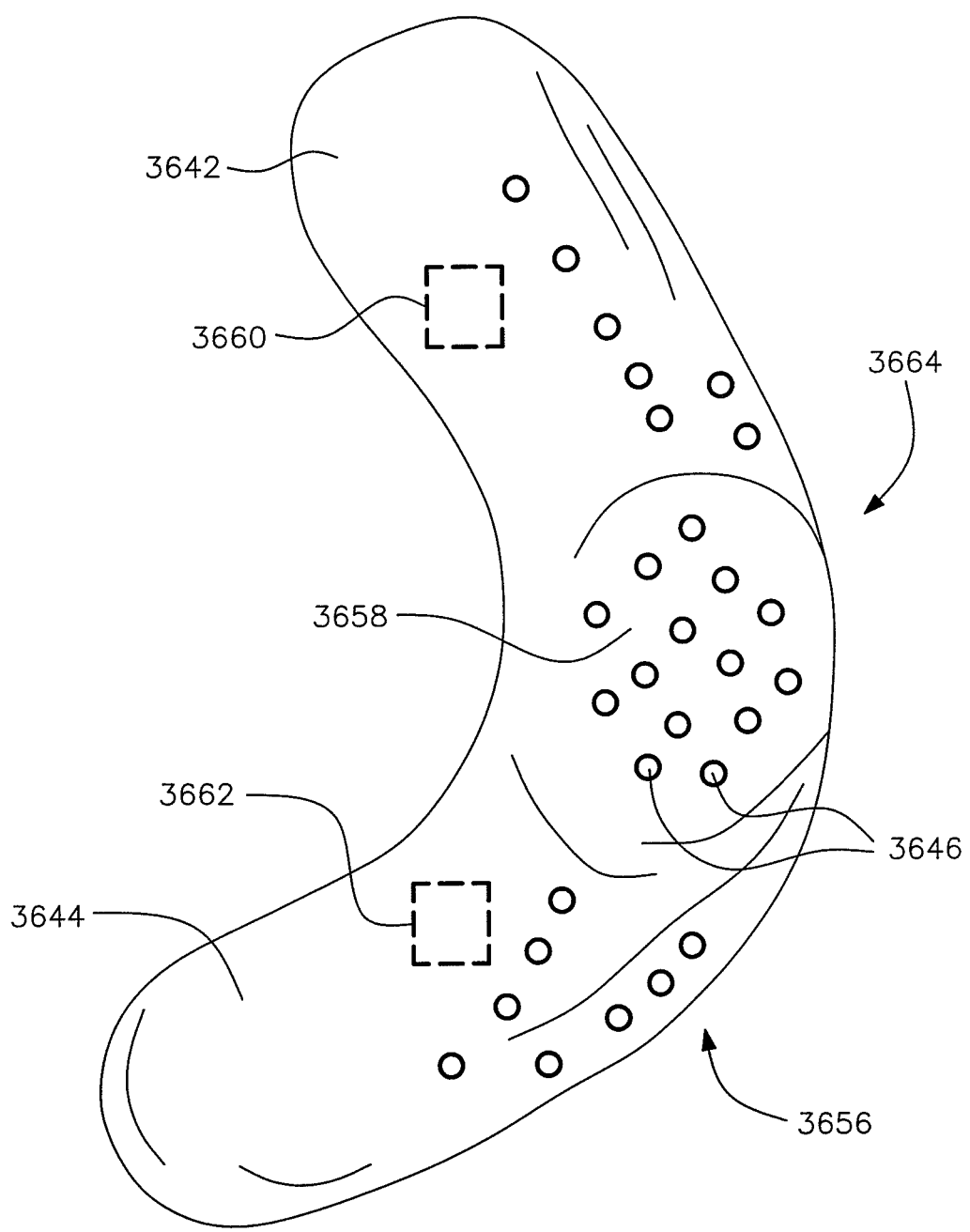
FIG. 104-E

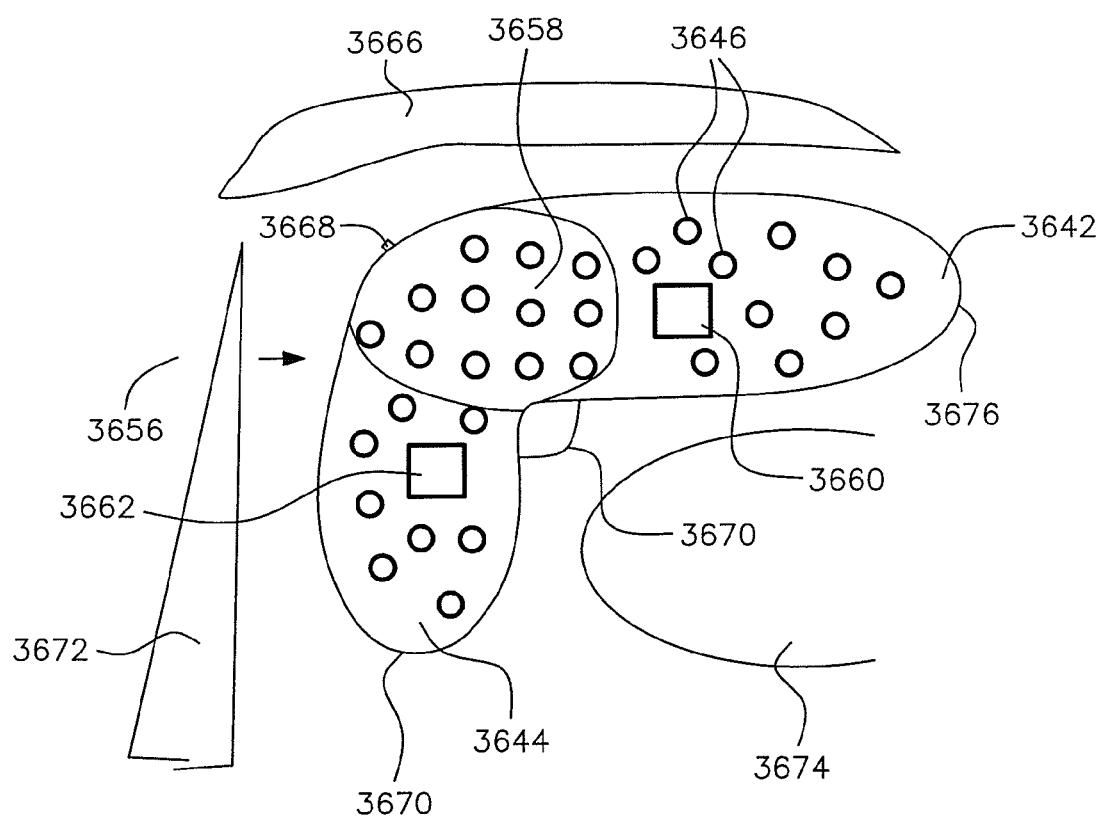
FIG. 104-F

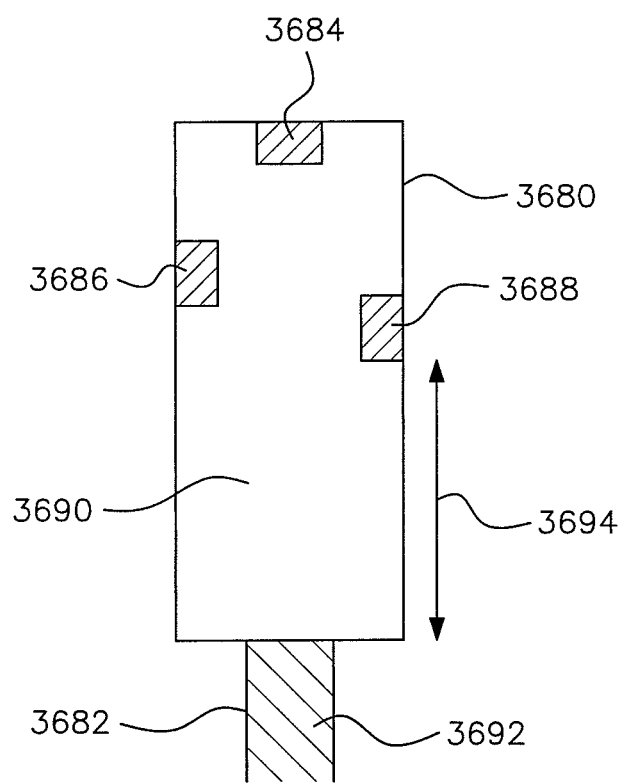
FIG. 104-G

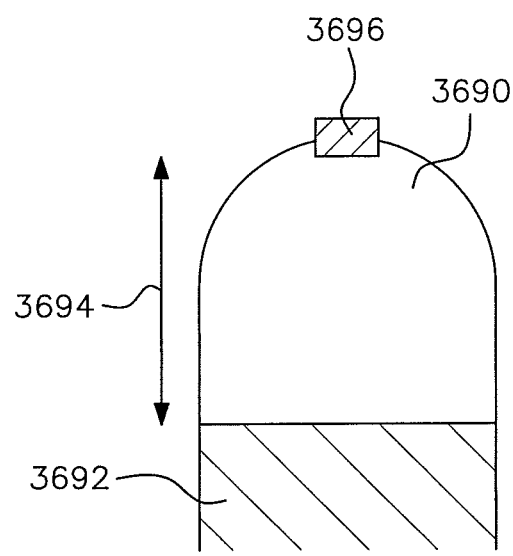
FIG. 104-H

THERMAL IMAGING SYSTEM

This application is a continuation application of U.S. patent application Ser. No. 11/585,344, filed Oct. 24, 2006, which is a complete application of provisional application Nos. 60/729,232 and 60/802,503, filed on Oct. 24, 2005 and May 23, 2006, respectively, and is a continuation-in-part of U.S. patent application Ser. No. 10/786,623, filed Feb. 26, 2004, which is a continuation-in-part of U.S. Ser. No. 10/420,295, filed Apr. 22, 2003.

FIELD OF THE INVENTION

The present invention includes support and sensing structures positioned in a physiologic tunnel for measuring bodily functions and to manage abnormal conditions indicated by the measurements.

BACKGROUND OF THE INVENTION

Interfering constituents and variables can introduce significant source of errors that prevent measured biologic parameters from being of clinical value. In order to bypass said interfering constituents and achieve undisturbed signals, invasive and semi-invasive techniques have been used. Such techniques have many drawbacks including difficulties in providing continuous monitoring for long periods of time. Non-invasive techniques also failed to deliver the clinical usefulness needed. The placement of a sensor on the skin characterized by the presence of interfering constituents do not allow obtaining clinically useful nor accurate signals due to the presence of said interfering constituents and background noise which greatly exceeds the signal related to the physiologic parameter being measured.

The most precise, accurate, and clinically useful way of evaluating thermal status of the body in humans and animals is by measuring brain temperature. Brain temperature measurement is the key and universal indicator of both disease and health equally, and is the only vital sign that cannot be artificially changed by emotional states. The other vital signs (heart rate, blood pressure, and respiratory rate) all can be influenced and artificially changed by emotional states or voluntary effort.

Body temperature is determined by the temperature of blood, which emits heat as far-infrared radiation. Adipose tissue (fat tissue) absorbs far-infrared and the body is virtually completely protected with a layer of adipose tissue adherent to the skin. Thus measurement of temperature using the skin did not achieve precision nor accuracy because previous techniques used sensors placed on skin characterized by the presence of adipose tissue.

Because it appeared to be impossible with current technology to non-invasively measure brain temperature, attempts were made to determine internal body temperature, also referred to as core temperature. An invasive, artificial, inconvenient, and costly process is currently used to measure internal (core) temperature consisting of inserting a catheter with a temperature sensor in the urinary canal, rectum or esophagus. But such methodology is not suitable for routine measurement, it is painful, and has potential fatal complications.

Semi-invasive techniques have also being tried. Abreu disclosed in U.S. Pat. No. 6,120,460 apparatus and methods for measuring core temperature continuously using a contact lens in the eyelid pocket, but the contact lens is a semi-invasive device which requires prescription by a physician and sometimes it is not easy to place the contact lens in the eye of an infant or even in adults and many people are afraid of touching their eyes.

There are several drawbacks and limitations in the prior art for continuous and/or core measurement of temperature.

Measurement of temperature today is non-continuous, non-core and nurse dependent. Nurses have to stick a thermometer in the patient's mouth, rectum or ear. To get core temperature nurses invasively place a tube inside the body which can cause infection and costly complications.

Measurement of core temperature on a routine basis in the hospital and/or continuously is very difficult and risky because it requires an invasive procedure with insertion of tubes inside the body or by ingesting a thermometer pill. The thermometer pill can cause diarrhea, measure temperature of the fluid/food ingested and not body temperature, and have fatal complications if the pill obstructs the pancreas or liver ducts. Placement of sensors on the skin do not provide clinically useful measurements because of the presence of many interfering constituents including fat tissue.

It is not possible to acquire precise and clinically useful measurements of not only brain temperature, but also metabolic parameters, physical parameters, chemical parameters, and the like by simply placing a sensor on the skin. One key element is the presence of fat tissue. Fat varies from person to person, fat varies with aging, fat content varies from time to time in the same person, fat attenuates a signal coming from a blood vessel, fat absorbs heat, fat prevents delivery of undisturbed far-infrared radiation, fat increases the distance traveled by the element being measured inside the body and an external sensor placed on the surface of the skin.

There is a need to identify a method and apparatus that can non-invasively, conveniently and continuously monitor brain temperature in a painless, simple, external and safe manner with sensors placed on the skin.

There is further a need to identify a method and apparatus that can conveniently, non-invasively, safely and precisely monitor biological parameters including metabolic parameters, physical parameters, chemical parameters, and the like.

There is a need to identify an apparatus and method capable of measuring biological parameters by positioning a sensor on a physiologic tunnel for the acquisition of undisturbed and continuous biological signals.

SUMMARY OF THE INVENTION

The present invention provides methods, apparatus and systems that effectively address the needs of the prior art.

In general, the invention provides a set of sensing systems and reporting means which may be used individually or in combination, which are designed to access a physiologic tunnel to measure biological, physical and chemical parameters. Anatomically and physiologically speaking, the tunnel discovered by the present invention is an anatomic path which conveys undisturbed physiologic signals to the exterior. The tunnel consists of a direct and undisturbed connection between the source of the function (signal) within the body and an external point at the end of the tunnel located on the skin. A physiologic tunnel conveys continuous and integral data on the physiology of the body. An undisturbed signal from within the body is delivered to an external point at the end of the tunnel. A sensor placed on the skin at the end of the tunnel allows optimal signal acquisition without interfering constituents and sources of error.

Included in the present invention are support structures for positioning a sensor on the skin at the end of the tunnel. The present invention discloses devices directed at measuring brain temperature, brain function, metabolic function, hydrodynamic function, hydration status, hemodynamic function, body chemistry and the like. The components include devices and methods for evaluating biological parameters using patches, clips, eyeglasses, head mounted gear and the like with sensing systems adapted to access physiologic tunnels to provide precise and clinically useful information about the physiologic status of the wearer and for enhancing the safety and performance of said wearer, and helping to enhance and preserve the life of said wearer by providing adequate reporting means and alert means relating to the biological parameter being monitored. Other components provide for producing direct or indirect actions, acting on another device, or adjusting another device or article of manufacture based on the biological parameter measured.

The search for a better way to measure biological parameters has resulted in long and careful research, which included the discovery of a Brain Temperature Tunnel (BTT) and other physiologic tunnels in humans and animals. The present invention was the first to recognize the physiologic tunnel in the body. The present invention was yet the first to recognize the end of the tunnel on the skin surface in which an optimal signal is acquired and measurements can be done without the presence of interfering constituents and background noise that exceeds the signal being measured. The present invention was also the first to recognize and precisely map the special geometry and location of the tunnel including the main entry point. The present invention was yet first to recognize the precise positioning of sensing systems at the main entry point for optimal signal acquisition. Careful studies have been undertaken including software development for characterizing infrared radiation to precisely determine the different aspects of the tunnel. This research has determined that the measurement of brain (core) temperature and other body parameters can be accomplished in a non-invasive and continuous manner in humans and animals with sensors positioned in a confined area of the skin at the end of a physiologic tunnel.

The key function and critical factor for life preservation and human performance is brain temperature. Brain tissue is the tissue in the body most susceptible to thermal damage, by both high and low temperature. Brain temperature is the most clinically relevant parameter to determine the thermal status of the body and the human brain is responsible for 18 to 20% of the heat produced in the body, which is an extraordinary fact considering that the brain represents only 2% of the body weight. The great amount of thermal energy generated in the brain is kept in a confined space and the scalp, skull, fat and CSF (cerebral spinal fluid) form an insulating layer. The recognition of the BTT by the present invention bypasses the insulating barriers and provides a direct connection to inside the brain physiology and physics.

Anatomically and physiologically speaking, a Brain Temperature Tunnel consists of a continuous, direct, and undisturbed connection between the heat source within the brain and an external point at the end of the tunnel. The physical and physiological events at one end of the tunnel inside the brain are reproduced at the opposite end on the skin. A BTT enables the integral and direct heat transfer through the tunnel without interference by heat absorbing elements, i.e., elements that can absorb far-infrared radiation transmitted as heat by blood within the brain. There are six characteristics needed to define a BTT. These characteristics are:

1) area without heat absorbing elements, i.e., the area must not contain adipose tissue (fat tissue). This is a key and needed characteristic for defining a temperature tunnel,
2) area must have a terminal branch of a vessel in order to deliver the integral amount of heat,
3) terminal branch has to be a direct branch of a blood vessel from the brain,
4) terminal branch has to be superficially located to avoid heat absorption by deep structures such as muscles,
5) area must have a thin and negligible interface between a sensor and the source of thermal energy to achieve high heat flow, and
6) area must not have thermoregulatory arteriovenous shunts.

All six characteristics are present on the skin on the medial canthal area adjacent to the medial corner of the eye above the medial canthal tendon and in the medial third of the upper eyelid. In more detail the end of BTT area on the skin measures about 11 mm in diameter measured from the medial corner of the eye at the medial canthal tendon and extends superiorly for about 6 mm and then extends into the upper eyelid in a horn like projection for another 22 mm.

The BTT area is the only area in the body without adipose tissue, which is in addition supplied by a terminal branch, which has a superficial blood vessel coming from the brain vasculature, and which has a thin interface and no thermoregulatory shunts. The BTT area is supplied by a terminal branch of the superior ophthalmic vein which is a direct connection to the cavernous sinus, said cavernous sinus being an endothelium-lined system of venous channels inside the brain which collects and stores thermal energy. The blood vessel supplying the BTT area is void of thermoregulatory arteriovenous shunts and it ends on the skin adjacent to the medial corner of the eye and in the superior aspect of the medial canthal area right at the beginning of the upper eyelid. The blood vessels deliver undisturbed heat to the skin on the medial canthal area and upper eyelid as can be seen in the color as well as black and white photos of infrared images shown in FIGS. 1 and 2. The undisturbed thermal radiation from the brain is delivered to the surface of the skin at the end of the tunnel. The heat is delivered to an area of skin without fat located at the end of the tunnel. The blood vessel delivering heat is located just below the skin and thus there is no absorption of infrared radiation by deep structures.

If the blood vessel is located deep, other tissues and chemical substances would absorb the heat, and that can invalidate the clinical usefulness of the measurement. There is direct heat transfer and the skin in the BTT area is the thinnest skin in the body and is void of thermoregulatory arteriovenous shunts. A very important aspect for optimal measurement of temperature is no interference by fat tissue and direct heat transfer.

The absence of fat tissue in this particular and unique area in the body at the end of the tunnel allows the undisturbed acquisition of the signal. The combination of those six elements allows the undisturbed and integral emission of infrared radiation from the brain in the form of direct heat transfer at the BTT area location, which can be seen in the infrared image photographs (FIGS. 1 to 8). The BTT and physiologic tunnels are also referred in this description as the "Target Area".

From a physical standpoint, the BTT is the equivalent of a Brain Thermal Energy tunnel with high total radiant power and high heat flow. The temperature of the brain is determined by the balance between thermal energy produced due to metabolic rate plus the thermal energy delivered by the arterial supply to the brain minus the heat that is removed by cerebral blood flow. Convection of heat between tissue and capillaries is high and the temperature of the cerebral venous blood is in equilibrium with cerebral tissue. Accordingly, parenchymal temperature and thermal energy of the brain can be evaluated by measuring the temperature and thermal energy of the cerebral venous blood. The superior ophthalmic vein has a direct and undisturbed connection to the cavernous sinus and carries cerebral venous blood with a thermal energy capacity of 3.6 J·ml$^{-1}$·(° C.)$^{-1}$ at hematocrit of 45%. Cerebral thermodynamic response, thermal energy, and brain temperature can be evaluated by placing a sensor to capture thermal energy conveyed by the cerebral venous blood at the end of the BTT.

The research concerning BTT and physiologic tunnels involved various activities and studies including: 1) In-vitro histologic analysis of mucosal and superficial body areas; 2) In-vivo studies with temperature evaluation of external areas in humans and animals; 3) In-vivo functional angiographic evaluation of heat source; 4) Morphologic studies of the histomorphometric features of the BTT area; 5) In-vivo evaluation of temperature in the BTT area using: thermocouples, thermistors, and far-infrared; 6) Comparison of the BTT area measurements with the internal eye anatomy and current standard most used (oral) for temperature measurement; 7) Cold and heat challenge to determine temperature stability of BTT; and 8) Infrared imaging and isotherm determination. Software for evaluating geometry of tunnel was also developed and used. Simultaneous measurement of a reference temperature and temperature in the BTT area were done using pre-equally calibrated thermistors. A specific circuit with multiple channels was designed for the experiments and data collection.

The measurement of temperature in the BTT area showed almost identical temperature signal between the BTT area and the internal conjunctival anatomy of the eye, which is a continuation of the central nervous system. Measurement of the temperature in the internal conjunctival anatomy of eye as used in the experiment was described by Abreu in U.S. Pat. Nos. 6,120,460 and 6,312,393. The averaged temperature levels for BTT and internal eye were within 0.1° C. (0.18° F.) with an average normothermia value equivalent of 37.1° C. (98.8° F.) for the BTT and 37° C. (98.6° F.) for the internal eye. Comparison with the standard most used, oral temperature, was also performed. The temperature voltage signal of the BTT area showed an average higher temperature level in the BTT area of an equivalent of 0.3° C. (0.5° F.) when compared to oral.

Subjects underwent cold challenge and heat challenge through exercising and heat room. The lowering and rising of temperature in the BTT area was proportional to the lowering and rising in the oral cavity. However, the rate of temperature change was faster in the BTT area than for oral by about 1.2 minutes, and temperature at the BTT site was 0.5° C. (0.9° F.) higher on few occasions. Subjects of different race, gender, and age were evaluated to determine the precise location of the BTT area across a different population and identify any anatomic variation. The location of the BTT was present at the same location in all subjects with no significant anatomic variation, which can be seen in a sample of infrared imaging of different subjects.

The tunnel is located in a crowded anatomic area and thus the positioning of the sensor requires special geometry for optimal alignment with the end of the tunnel. The clinical usefulness of the tunnel can only be achieved with the special positioning of the sensor in relation to anatomic landmarks and the support structure. The tunnel is located in a unique position with distinctive anatomic landmarks that help define the external geometry and location of the end of the tunnel. The main entry point of the tunnel, which is the preferred location for positioning the sensor, requires the sensor to be preferably placed in the outer edge of a support structure. The preferred embodiment for the measurement of biological parameters by accessing a physiologic tunnel includes sensors positioned in a particular geometric position on the support structure.

The support structure includes patches containing sensors. For the purpose of the description any structure containing an adhesive as means to secure said structure to the skin at the end of the tunnel is referred to as a patch including strips with adhesive surfaces such as a "BAND-AID" adhesive bandage. It is understood that a variety of attachment means can be used including adhesives, designs incorporating spring tension pressure attachment, and designs based on other attachment methods such as elastic, rubber, jelly-pads and the like.

The patches are adapted to position sensors at the end of the tunnel for optimal acquisition of the signal. The patch is preferably secured to the area by having an adhesive backing which lays against the skin, although a combination of adhesive and other means for creating a stable apposition of the sensor to the tunnel can be used such as fastening or pressure.

Support structures also include clips or structures that are positioned at the end of the tunnel with or without adhesive and which are secured to the area by pressure means. Any structure that uses pressure means to secure said structure to the skin at the end of the tunnel is referred as a clip.

Head-mounted structures are structures mounted on the head or neck for positioning sensors on the end of the tunnel and include headbands with accessories that are adjacent to the tunnel, visors, helmets, headphone, structures wrapping around the ear and the like. For the purpose of this description TempAlert is referred herein as a system that measures temperature in the BTT area and has means to report the measured value and that can incorporate alarm devices that are activated when certain levels are reached. Support structures yet include any article that has sensing devices in which said sensing devices are positioned at the end of the tunnel.

Support structures further include medial canthal pieces of eyeglasses. A medial canthal piece is also referred to herein as a medial canthal pad and includes a pad or a piece which positions sensing devices on the skin at the medial canthal area on top of a tunnel, with said medial canthal piece being permanently attached to or mounted to an eyeglass. Any sensing devices incorporated in an eyeglass (fixed or removable) for accessing a tunnel are referred to herein as EyEXT including devices for sensing physical and chemical parameters. Any article of manufacture that has visual function, or ocular protection, or face protection with a part in contact with the tunnel is referred herein as eyeglasses and includes conventional eyeglasses, prescription eyeglasses, reading glasses, sunglasses, goggles of any type, masks (including gas masks, surgical masks, cloth masks, diving masks, eyemask for sleeping and the like) safety glasses, and the like.

For brain temperature evaluation the tunnel area consists of the medial canthal area and the superior aspect of the medial corner of the eye. For brain function evaluation the tunnel area consists of primarily the upper eyelid area. For metabolic function evaluation the tunnel area consists of an area adjacent to the medial corner of the eye and both the upper and lower eyelids.

The measurement of metabolic function, brain function, immunogenic function, physical parameters, physico-chemical parameters and the like includes a variety of support structures with sensors accessing the physiologic tunnels. The sensors are placed in apposition to the skin immediately adjacent to the medial corner of the eye preferably in the superior aspect of the medial canthal area. The sensor can also be positioned in the medial third of the upper eyelid. The sensor is most preferably located at the main entry point of the tunnel which is located on the skin 2.5 mm medial to the corner of the eye and about 3 mm above the medial corner of the eye. The diameter of the main entry point is about 6 to 7 mm. The positioning of the sensor at the main entry point of the tunnel provides the optimum site for measuring physical and chemical parameters of the body.

Besides a sensor that makes contact with the skin at the Target Area, it is understood that sensors which do not make contact with the skin can be equally used. For instance an infrared-based temperature measuring system can be used. The measurement is based on the Stefan-Boltzman law of physics in which the total radiation is proportional to the fourth power of the absolute temperature, and the Wien Displacement law in which the product of the peak wavelength and the temperature are constant. The field of view of the non-contact infrared apparatus of the invention is adapted to match the size and geometry of the BTT area on the skin.

A variety of lenses known in the art can be used for achieving the field of view needed for the application. For example, but not by way of limitation, a thermopile can be adapted and positioned in a manner to have a field of view aimed at the main entry point of the BTT area on the skin. The signal is then amplified, converted into a voltage output and digitized by a MCU (microcontroller).

This infrared-based system can be integrated into a support structure that is in contact with the body such as any of the support structures of the present invention. In addition, it is understood that the infrared-based system of the present invention can be integrated as a portable or hand-held unit completely disconnected from the body. The apparatus of the present invention can be held by an operator that aims said apparatus at the BTT area to perform the measurement. The apparatus further includes an extension shaped to be comfortably positioned at the BTT site for measuring biological parameters without discomfort to the subject. The extension in contact with the skin at the BTT is shaped in accordance with the anatomic landmarks and the geometry and size of the BTT site. The infrared radiation sensor is positioned in the extension in contact with the skin for receiving radiation emitted from the BTT site.

The present invention provides a method for measuring biological parameters including the steps of positioning a sensing device means on the skin area at the end of a tunnel, producing a signal corresponding to the biological parameter measured and reporting the value of the parameter measured.

It is also includes a method to measure biological parameters by non-contact infrared thermometry comprising the steps of positioning an infrared detector at the BTT site with a field of view that encompasses the BTT site and producing a signal corresponding to the measured infrared radiation. The biological parameters include temperature, blood chemistry, metabolic function and the like.

Temperature and ability to do chemical analysis of blood components is proportional to blood perfusion. The present invention recognizes that the tunnel area, herein also referred as a Target Area, has the highest superficial blood perfusion in the head and has a direct communication with the brain, and that the blood vessels are direct branches of the cerebral vasculature and void of thermoregulatory arteriovenous shunts. It was also recognized that the Target Area has the highest temperature in the surface of the body as can be seen in the photographs of experiments measuring infrared emission from the body and the eye.

The Target Area discovered not only has the thinnest and most homogeneous skin in the whole body but is the only skin area without a fat layer. Since fat absorbs significant amounts of radiation, there is a significant reduction of signal. Furthermore other skin areas only provide imprecise and inaccurate signals because of the large variation of adipose tissue from person to person and also great variability of fat tissue according to age. This interference by a fat layer does not occur in the Target Area. Furthermore, the combined characteristics of the Target Area, contrary to the skin in the rest of the body, enable the acquisition of accurate signals and a good signal to noise ratio which far exceeds background noise. In addition, body temperature such as is found in the surface of the skin in other parts of the body is variable according to the environment.

Another important discovery of the present invention was the demonstration that the Target Area is not affected by changes in the environment (experiments included cold and heat challenge). The Target Area provides an optimum location for temperature measurement which has a stable temperature and which is resistant to ambient conditions. The Target Area discovered has a direct connection to the brain, is not affected by the environment and provides a natural, complete thermal seal and stable core temperature. The apparatus and methods of the present invention achieve precision and clinical usefulness needed with the non-invasive placement of a temperature sensor on the skin in direct contact with the heat source from the brain without the interference of heat absorbing elements.

The Target Area is extremely vascularized and is the only skin area in which a direct branch of the cerebral vasculature is superficially located and covered by a thin skin without a fat layer. The main trunk of the terminal branch of the ophthalmic vein is located right at the BTT area and just above the medial canthal tendon supplied by the medial palpebral artery and medial orbital vein. The BTT area on the skin supplied by a terminal and superficial blood vessel ending in a particular area without fat and void of thermoregulatory arteriovenous shunts provides a superficial source of undisturbed biological signals including brain temperature, metabolic function, physical signals, and body chemistry such as glucose level, and the like.

Infrared spectroscopy is a technique based on the absorption of infrared radiation by substances with the identification of said substances according to its unique molecular oscillatory pattern depicted as specific resonance absorption peaks in the infrared region of the electromagnetic spectrum. Each chemical substance absorbs infrared radiation in a unique manner and has its own unique absorption spectra depending on its atomic and molecular arrangement and vibrational and rotational oscillatory pattern. This unique absorption spectra allows each chemical substance to basically have its own infrared spectrum, also referred to as fingerprint or signature which can be used to identify each of such substances. Radiation containing various infrared wavelengths is emitted at the substance to be measured and the amount of absorption of radiation is dependent upon the concentration of said chemical substance being measured according to Beer-Lambert's Law.

Interfering constituents and variables such as fat, bone, muscle, ligaments and cartilage introduce significant source of errors which are particularly critical since the background noise greatly exceeds the signal of the substance of interest. Since those interfering constituents are not present on the skin at the BTT area, the sensing systems positioned at said BTT area can acquire optimal signal with minimal noise including spectroscopic-based measurements.

Spectroscopic devices integrated into support structures disclosed in the present invention can precisely non-invasively measure blood components since the main sources of variation and error, such as fat tissue, are not present in the Target Area. In addition, other key constituents which interfere with electromagnetic energy emission such as muscle, cartilage and bones, are not present in the Target Area either. The blood vessels delivering the infrared radiation are superficially located and the infrared radiation is delivered at the end of the tunnel without interacting with other structures. The only structure to be traversed by the infrared radiation is a very thin skin, which does not absorb the infrared wavelength. The present invention includes infrared spectroscopy means to provide a clinically useful measurement with the precise and accurate determination of the concentration of the blood components at the end of the tunnel.

In addition to spectroscopy in which electromagnetic energy is delivered to the Target Area, the present invention also discloses apparatus and methods for measuring substances of interest through far infrared thermal emission from the Target Area. Yet, besides near-infrared spectroscopy and thermal emission, other devices are disclosed for measurement of substances of interest at the Target Area including electroosmosis as a flux enhancement by iontophoresis or reverse iontophoresis with increased passage of fluid through the skin through application of electrical energy. Yet, transcutaneous optical devices can also be integrated into support structures including medial canthal pieces, modified nose pads, and the frame of eyeglasses, with said devices positioned to access the tunnel.

It is understood that application of current, ultrasonic waves as well as chemical enhancers of flow, electroporation and other devices can be used to increase permeation at the tunnel site such as for example increased flow of glucose with the use of alkali salts. In addition creating micro holes in the target area with a laser, or other means that penetrate the skin can be done with the subsequent placement of sensing devices on the BTT site, with said devices capable of measuring chemical compounds. Furthermore, reservoirs mounted on or disposed within support structures, such as the frame and pads of eyeglasses, can deliver substances transdermally at the BTT site by various devices including iontophoresis, sonophoresis, electrocompression, electroporation, chemical or physical permeation enhancers, hydrostatic pressure and the like.

In addition to measure the actual amount of oxygen in blood, the present invention also discloses devices to measure oxygen saturation and the amount of oxygenated hemoglobin. In this embodiment the medial canthal piece of a support structure or the modified nose pads of eyeglasses contain LEDs emitting at two wave lengths around 940 and 660 nanometers. As the blood oxygenation changes, the ratio of the light transmitted by the two frequencies changes indicating the oxygen saturation. Since the blood level is measured at the end of a physiologic brain tunnel, the amount of oxygenated hemoglobin in the arterial blood of the brain is measured, which is the most valuable and key parameter for athletic purposes and health monitoring.

The present invention also provides a method for measuring biological parameters with said method including the steps of directing electromagnetic radiation at the BTT area on the skin, producing a signal corresponding to the resulting radiation and converting the signal into a value of the biological parameter measured.

Besides using passive radio transmission or communication by cable; active radio transmission with active transmitters containing a microminiature battery mounted in the support structure can also be used. Passive transmitters act from energy supplied to it from an external source. The transensor transmits signals to remote locations using different frequencies indicative of the levels of biological parameters. Ultrasonic micro-circuits can also be mounted in the support structure and modulated by sensors which are capable of detecting chemical and physical changes at the Target Area. The signal may be transmitted using modulated sound signals particularly under water because sound is less attenuated by water than are radio waves.

One preferred embodiment comprises a support structure including a patch adapted to be worn on or attached with adhesives to the tunnel and includes structural support, a sensor for measuring biological parameters, power source, microcontroller and transmitter. The parts can be incorporated into one system or work as individual units. The sensor is located preferably within 7 mm from the outer edge of the patch. The apparatus of the invention can include a temperature sensor located in the outer edge of the patch for sensing temperature. The transmitter, power source and other components can be of any size and can be placed in any part of the patch or can be connected to the patch as long as the sensing part is placed on the edge of the patch in accordance with the principles of the invention. The sensor in the patch is positioned on the skin adjacent to the medial canthal area (medial corner of the eye) and located about 2 mm from the medial canthal tendon. The sensor can preferably include electrically-based sensors, but non-electrical systems can be used such as chemicals that respond to changes in temperature including mylar.

Besides patches, another preferred embodiment for measuring biological parameters at the physiologic tunnel includes a medial canthal pad. The medial canthal piece is a specialized structure containing sensors for accessing the tunnel and adapted to be worn on or attached to eyeglasses in apposition to the tunnel and includes structural support, a sensor for measuring biological parameters, power source, microcontroller and transmitter. The parts can be incorporated into one system or work as individual units. The sensors are positioned on the BTT area. The transmitter, power source, and other components can be placed in the medial canthal pad or in any part of the eyeglasses. A medial canthal piece or extension of nose pads of eyeglasses allow accessing the physiologic tunnel with sensing devices laying in apposition to the BTT area.

The apparatus of the invention include a temperature sensor located in the medial canthal pad. For temperature measurement the sensing system is located on a skin area that includes the medial canthal corner of the eye and upper eyelid. The sensor in the medial canthal pad is preferably positioned on the skin adjacent to the medial canthal area (medial corner of the eye). Although one of the preferred embodiments for measurement of brain temperature consists of medial canthal pads, it is understood that also included in the scope of the invention are nose pads of a geometry and size that reach the tunnel and that are equipped with temperature sensors preferably in the outer edge of said nose pads for measuring brain temperature and other functions. An oversized and modified nose pad containing sensors using a special geometry for adequate positioning at the BTT area is also included in the invention.

With the disclosure of the present invention and by using anatomic landmarks in accordance with the invention the sensor can be precisely positioned on the skin at the end of the tunnel. However, since there is no external visible indication on the skin relating to the size or geometry of the tunnel, accessory means can be used to visualize, map or measure the end of the tunnel on the skin. These accessory means may be particularly useful for fitting medial canthal pads or modified nose pads of eyeglasses.

Accordingly, an infrared detector using thermocouple or thermopiles can be used as an accessory for identifying the point of maximum thermal emission and to map the area. An infrared imaging system or thermography system may be preferably used. In this instance, an optical store selling the eyeglasses can have a thermal imaging system. The optician, technician and the like take an infrared image picture or film the area, and in real time localize the tunnel of the particular user. The medial canthal pads or modified nose pads can then be adjusted to fit the particular user based on the thermal infrared imaging. The eyeglasses are fitted based on the thermal image created. This will allow customized fitting according to the individual needs of the user. Any thermography-based system can be used including some with great visual impact and resolution as a tri-dimensional color thermal wave imaging.

It is also a feature of the invention to provide a method to be used for example in optical stores for locating the tunnel including the steps of measuring thermal infrared emission, producing an image based on the infrared emission, and detecting the area with the highest amount of infrared emission. Another step that can be included is adjusting sensors in support structures to match the area of highest infrared emission.

One of said support structures includes the medial canthal pieces or nose pads of eyeglasses. The thermal imaging method can be used for fitting a patch, but said patch can be positioned at the tunnel by having an external indicator for lining up said indicator with a permanent anatomic landmark such as the medial corner of the eye. Although medial canthal pieces of eyeglasses can have an external indicator for precise positioning, since opticians are used to fit eyeglasses according to the anatomy of the user, the thermal imaging method can be a better fit for eyeglasses than an external indicator on the medial canthal pieces or modified nose pads of eyeglasses.

The source of the signal is key for the clinical usefulness of the measurement. The brain is the key and universal indicator of the health status of the body. The signal coming from the brain or brain area provides the most clinically useful data. In accordance with another embodiment, the measurement of biological parameters will be described. The amount of sodium and other elements in sweat is a key factor for safety and performance of athletes and military, as well as health monitoring.

For instance hyponatremia (decreased amount of sodium) can lead to reduced performance and even death. Hyponatremia can occur due to excess water intake, commonly occurring with intense physical activity and military training. Sweat can be considered as an ultrafiltrate of blood. The blood vessels supplying the skin on the head are branches of the central nervous system vasculature. The amount of chemical substances present in the sweat coming from those blood vessels is indicative of the amount of chemical substances present in the cerebral vasculature. For instance, sodium concentration of sweat from blood vessels in the head changes in relation to the rates of sweating. The apparatus and methods of the present invention can prevent death or harm due to water intoxication, by providing alert signals when the levels of sodium in sweat reach a certain threshold for that particular wearer. The presence of various chemical elements, gases, electrolytes and pH of sweat and the surface of the skin can be determined by the use of suitable electrodes and suitable sensors integrated in the eyeglasses and other support structures mounted on the head or fitted on the head or face. These electrodes, preferably microelectrodes, can be sensitized by several reacting chemicals which are in the sweat or the surface of the skin. The different chemicals and substances can diffuse through suitable permeable membranes sensitizing suitable sensors.

For example but not by way of limitation, electrochemical sensors can be used to measure various analytes such as glucose using a glucose oxidase sensor and the pilocarpine iontophoresis method can be used to measure electrolytes in sweat alone or in conjunction with microfluidics system. Besides the support structures of the present invention, it is also understood that other articles such as watches, clothing, footwear and the like can be adapted to measure concentration of substances such as electrolytes present in sweat, however there is reduced clinical relevance for evaluating metabolic state of an individual outside the central nervous system.

Body abnormalities may cause a change in the pH, osmolarity, and temperature of the sweat derived from brain and neck blood vessels as well as change in the concentration of substances such as acid-lactic, glucose, lipids, hormones, gases, markers, infectious agents, antigens, antibody, enzymes, electrolytes such as sodium, potassium and chloride, and the like. Eyeglasses and any head gear can be adapted to measure the concentration of substances in sweat. Microminiature glass electrodes mounted in the end portion of the temple of eyeglasses sitting behind the ear or alternatively mounted on the lens rim against the forehead can be used to detect divalent cations such as calcium, as well as sodium and potassium ion and pH. Chloride-ion detectors can be used to detect the salt concentration in the sweat and the surface of the skin.

Many agents including biological warfare agents and HIV virus are present in sweat and could be detected with the eyeglasses or support structure on the head or face using sensors coated with antibodies against the agent which can create a photochemical reaction with appearance of colorimetric reaction and/or potential shift with subsequent change in voltage or temperature that can be detected and transmitted to a monitoring station or reported locally by audio or visual means. Electrocatalytic antibodies also can generate an electrical signal when there is an antigen-antibody interaction. It is also understood that other articles such as watches, clothing, footwear, and the like or any article capturing sweat can be adapted to identify antigens, antibody, infectious agents, markers (cancer, heart, genetic, metabolic, drugs, and the like) in accordance with the present invention. However, identification of those elements away from the central nervous system is of reduced clinical relevance.

The different amounts of fluid encountered in sweat can be easily quantified and the concentration of substances calibrated according to the amount of fluid in sweat. The relationship between the concentration of chemical substances and molecules in the blood and the amount of said chemical substances in the sweat can be described mathematically and programmed in a computer.

The present invention also includes eyeglasses or support structures in which a radio frequency transensor capable of measuring the negative resistance of nerve fibers is mounted in the eyeglasses or support structure. By measuring the electrical resistance, the effects of microorganisms, drugs, and poisons can be detected. The system also comprises eyeglasses in which a microminiature radiation-sensitive transensor is mounted in said eyeglasses or support structure.

The brain has a rich vasculature and receives about 15% of the resting cardiac output and due to the absence of fat the tunnel offers an area for optimal signal acquisition for evaluating hemodynamics. Accordingly, change in the viscosity of blood can be evaluated from a change in damping on a vibrating quartz micro-crystal mounted in the eyeglasses or support structure and the invention can be adapted to measure blood pressure and to provide instantaneous and continuous monitoring of blood pressure through an intact wall of a blood vessel from the brain and to evaluate hemodynamics and hydrodynamics. Also, by providing a contact microphone, arterial pressure can be measured using sonic devices.

Pressure can be applied to a blood vessel through a micro cuff mounted in the medial canthal pads, or alternatively by the temples of eyeglasses. Pressure can also be applied by a rigid structure, and the preferred end point is reached when sound related to blood turbulence is generated. The characteristic sound of systole (contraction of the heart) and diastole (relaxation of the heart) can be captured by the microphone. A microphone integrated into the medial canthal pad can be adapted to identify the heart sounds. Pressure transducers such as a capacitive pressure transducer with integral electronics for signal processing and a microphone can be incorporated in the same silicon structure and can be mounted in the medial canthal pad. Motion sensors and/or pressure sensors can be mounted in the medial canthal pad to measure pulse.

Reversible mechanical expansion methods, photometric, or electrochemical methods and electrodes can be mounted in the eyeglasses or support structures of the present invention and used to detect acidity, gases, analyte concentration, and the like. Oxygen gas can also be evaluated according to its magnetic properties or be analyzed by micro-polarographic sensors mounted in the eyeglasses or other support structure. A microminiature microphone mounted in the eyeglasses or other support structure can also be adapted to detect sounds from the heart, respiration, flow, vocal and the environment, which can be sensed and transmitted to a remote receiver or reported by local audio and visual means. The sensors are adapted and positioned to monitor the biological parameters at the end of the tunnel.

The eyeglasses or other support structures can also have elements which produce and radiate recognizable signals and this procedure could be used to locate and track individuals, particularly in military operations. A permanent magnet can also be mounted in the eyeglasses and used for tracking as described above. A fixed frequency transmitter can be mounted in the eyeglasses and used as a tracking device which utilizes a satellite tracking system by noting the frequency received from the fixed frequency transmitter to a passing satellite, or via Global Positioning Systems. Motion and deceleration can be detected by mounting an accelerometer in the eyeglasses. The use of eyeglasses as tracking devices can be useful for locating a kidnapped individual or for rescue operations in the military, since eyeglasses are normally unsuspecting articles.

The use of integrated circuits and advances occurring in transducer, power source, and signal processing technology allow for extreme miniaturization of the components which permits several sensors to be mounted in one unit.

The present invention provides continuous automated brain temperature monitoring without the need for a nurse. The present invention can identify a spike in temperature. Thus, proper diagnosis is made and therapy started in a timely fashion. Time is critical for identifying the temperature spike and organism causing the infection. Delay in identifying spike and starting therapy for the infection can lead to demise of the patient. The invention timely and automatically identifies the temperature spike and prevents the occurrence of complications.

The present invention also alerts the user about overheating or hypothermia to allow:
1. Proper hydration;
2. Increased performance;
3. Increased safety; and
4. Feed back control in treadmills and other exercise machines for keeping proper hydration and performance.

Annually many athletes, construction workers, college students and the general public unnecessarily die due to heatstrokes. Once the brain reaches a certain temperature level such as 40° C., an almost irreversible process ensues. Because there are no specific symptoms and after a certain point there is rapid increase in brain temperature, heatstroke has one of the highest fatality rates. The more severe and more prolonged the episode, the worse the predicted outcome, especially when cooling is delayed. Without measuring core temperature and having an alert system when the temperature falls outside safe levels it is impossible to prevent hyperthermia and heatstroke. The present invention provides a device for continuous monitoring of temperature with alert systems that can prevent dangerous levels to be reached and cooling measures applied if needed. The apparatus can be adapted to be used in an unobtrusive manner by athletes, military, workers and the general population.

All chemical reactions in the body are dependent on temperature. High temperature can lead to enzymatic changes and protein denaturation and low temperature can slow down vital chemical reactions. Hydration is dependent on brain temperature and loss of fluid leads to a rise in brain temperature. Minimal fluctuations in the body's temperature can adversely affect performance and increase risk of illness and of life threatening events. Therefore, it is essential that athletes, sports participants, military personnel, police officers, firefighters, forest rangers, factory workers, farmers, construction workers and other professionals have precise mechanisms to know exactly what is their brain temperature.

When the core temperature rises, the blood that would otherwise be available for the muscles is used for cooling via respiration and perspiration. The body will do this automatically as temperature moves out of the preferred narrow range. It is this blood shifting that ultimately impairs physical performance and thermal induced damage to brain tissue interferes with normal cognitive function. Intense exercise can increase heat production in muscles 20 fold. In order to prevent hyperthermia and death by heat stroke athletes drink water. Because the ingestion of water is done in a random fashion, many times there is water intoxication which can lead to death as occurs to many healthy people including marathon runners and military personnel. Both, excess of water (overhydration) or lack of water (dehydration) can lead to fatal events besides reducing performance. Therefore, it is essential that individuals have precise means to know exactly when and how much to drink. By monitoring brain temperature with the present invention proper hydration can be achieved and athletes and military will know precisely when and how much water to ingest.

Timely ingestion of fluids according to the core temperature allows optimization of cardiovascular function and avoidance of heat strain. Because there is a delay from the time of ingestion of fluid to absorption of said fluid by the body, the method of invention includes signaling the need for ingestion at a lower core temperature such as 38.5° C. to account for that delay, and thus avoid the onset of exhaustion. The temperature threshold can be adjusted according to each individual, the physical activity, and the ambient temperature.

In addition, software can be produced based on data acquired at the BTT site for optimizing fitness, athletic performance, and safety. The upper temperature limit of a particular athlete for maintaining optimal performance can be identified, and the data used to create software to guide said athlete during a competition. For instance, the athlete can be informed on the need to drink cold fluid to prevent reaching a certain temperature level which was identified as reduced performance for said athlete. Brain temperature level for optimal performance identified can be used to guide the effort of an athlete during competition and training. Hyperthermia also affects mental performance and software based on data from the BTT can be produced to optimize mental and physical performance of firefighters in an individual manner. People can have different thresholds for deleterious effects of hyperthermia and thus setting one level for all users may lead to underutilization of one's capabilities and putting others at risk of reduced performance. Likewise, exercise endurance and mental performance is markedly reduced by hypothermia and the same settings can be applied for low temperature situations. Determinations of brain temperature, oxygen and lactic acid levels can also be used for endurance training of athletes, fitness training, and to monitor the effects of training. The system, method, and apparatus of the invention provides a mechanism for enhancing safety and optimizing fitness for athletes and recreational sports participants.

It is a feature of the invention to provide a method for the precise and timely intake of fluids including the steps of measuring brain temperature, reporting the signal measured, and ingesting an amount of fluid based on the signal measured. Other steps can be included such as reporting devices using voice reproduction or visual devices to instruct on what beverage to drink and how much to drink to reduce core temperature. It is understood that the method of the present invention can combine measurement of temperature associated with measurement of sodium in sweat or blood, in accordance with the principles of the invention.

Children do not tolerate heat as well as adults because their bodies generate more heat relative to their size than adults do. Children are also not as quick to adjust to changes in temperatures. In addition, children have more skin surface relative to their body size which means they lose more water through evaporation from the skin. It is understood that different sizes, shapes, and designs of medial canthal pads including children size can be used in the present invention. Children eyeglasses equipped with sensors can have a booster radio transmitter that will transmit the signal to a remote receiver and alert parents about dangerous temperature levels. The eyeglasses can be incorporated with a detecting system to send a signal if the eyeglasses were removed or if the temperature sensor is not capturing signals in a proper manner. By way of illustration, but not of limitation, pressure sensing devices can be incorporated in the end of the temples to detect if the sunglasses are being worn, and an abrupt drop in the pressure signal indicates glasses were removed or misplacement of the sensor can also generate an identifiable signal. An adhesive, a double-sided adhesive tape, or other devices for increasing grip can be used in the medial canthal pads to ensure more stable position. It is understood that the eyeglasses can come equipped with sensors to detect ambient temperature and humidity, which allows for precisely alerting the wearer about any aspect affecting heat conditions.

In the current industrial, nuclear and military settings, personnel may be required to wear protective clothing. Although the protective clothing prevent harm by hazardous agents, the garments increase the rate of heat storage. It is understood that the present invention can be coupled with garments with adjustable permeability to automatically keep the core temperature within safe limits.

In addition, the present invention alerts an individual about risk of thermal damage (risk of wrinkles and cancer) at the beach or during outdoor activities. When one is at the beach, watching a game in a stadium, camping or being exposed to the sun, the radiant energy of the sun is absorbed and transformed into thermal energy. The combination of the different ways of heat transfer to the body lead to an increase in body temperature, which is reflected by the brain temperature. Convection and conduction can also lead to an increase in body temperature through heat transfer in the absence of sun light. The absorption of heat from the environment leads to a rise in the average kinetic energy of the molecules with subsequent increase in core temperature.

The levels of core temperature is related to the risk of thermal damage to the skin. After certain levels of heat there is an increased risk of denaturing protein and breaking of collagen in the skin. This can be compared with changes that occur when frying an egg. After a certain amount of thermal radiation is delivered the egg white changes from fluidic and transparent to a hard and white structure. After the egg white reaches a certain level of temperature the structural change becomes permanent. After a certain level of increase in core temperature during sun exposure, such as a level of 37.7° Celsius to 37.9° Celsius at rest (e.g.; sun bathing), thermal damage may ensue and due to the disruption of proteins and collagen there is an increased risk for wrinkle formation. The increased brain temperature correlates to the amount of thermal radiation absorbed by the body, and the duration of exposure of the temperature level times the level of temperature is an indicator of the risk of thermal damage, wrinkle formation, and skin cancer.

The present invention provides an alarm system that can be set up to alert in real time when it is time to avoid sun exposure in order to prevent further absorption of thermal radiation and reduce the risk of dermatologic changes, as can occur during outdoor activities or at the beach. In addition, thermal damage to the skin prevents the skin from adequately cooling itself and can result in increasing the risk of dehydration which further increases the temperature. The present invention helps preserve the beauty and health of people exposed to sun light and during outdoor activities while allowing full enjoyment of the sun and the benefits of sun light.

By the present invention, a method for timing sun exposure includes the steps of measuring body temperature, reporting the value measured and avoiding sun exposure for a certain period of time based on the level measured.

Hypothermia is the number one killer in outdoor activities in the U.S. and Europe. Hypothermia also decreases athletic performance and leads to injuries. It is very difficult to detect hypothermia because the symptoms are completely vague such as loss of orientation and clumsiness which are indistinguishable from general behavior. Without measuring core temperature and having an alert system when the temperature falls outside safe levels it is impossible to prevent hypothermia due to the vague symptoms. The present invention can alert an individual about hypothermia during skiing, scuba diving, mountain climbing and hiking. The present invention provides means to precisely inform when certain temperature thresholds are met, either too high or too low temperature.

The present invention continuously monitors the brain temperature and as soon as a temperature spike or fever occurs it activates diagnostics systems to detect the presence of infectious agents, which can be done locally in the BTT site, or the infectious agents can be identified in other parts of the body such as the blood stream or the eyelid pocket. The present invention can be also coupled to drug dispensing devices for the automated delivery of medications in accordance with the signal produced at the BTT site including transcutaneous devices, iontophoresis or by injection using a pump.

The invention also includes a tool for family planning. The system can detect spike and changes in basal temperature and identify moment of ovulation and phases of the menstrual cycle. This allows a woman to plan pregnancy or avoid pregnancy. This eliminates the need for invasive devices used for monitoring time for artificial insemination not only for humans but also animals. The invention can yet detect the start of uterine contractions (parturition) and allow a safer birth for animals. Support structures can be equally used in the BTT of animals.

The present invention also includes Automated Climate control according to the value measured at the BTT. The temperature of the user controls the temperature in a car. When the body starts to warm up, the signal from the apparatus of the invention automatically activates the air conditioner according to the user settings, alternatively it activates heat when the body is cold. This automation allows drivers to concentrate on the road and thus can reduce the risk for car crashes. It is understood that other articles that can affect body temperature can be controlled by the present invention including vehicle seats.

Current vehicle climate control systems are dramatically overpowered because they are designed to heat/cool the vehicle cabin air mass from an extreme initial temperature to a standard temperature within a certain period of time. Because people have different thermal needs for comfort, there is a consistent manual change of the temperature settings and said manual further increase consumption of energy. For instance, car temperature is set to remain at 73 F. Some people after 15 minutes may feel that it is too cold and some people may feel it is too hot. Subsequently the passenger changes the setting to 77 and then feels hot after another 10 minutes, and needs to manually change the set points again, and the process goes on. In addition the needs differ for people of different age, people with diabetes and other diseases, and male and female.

Manual frequent adjusting of a vehicle's climate control may increase fuel consumption 20% and increase emissions of pollutants such as carbon monoxide and nitrogen oxides. The present invention provides an automated climate control in which the brain temperature controls the air conditioner and vehicle seats which maximizes comfort and minimizes fuel consumption. The improved fuel economy provided by the present invention protects the environment due to less pollutants affecting the ozone layer; improves public health by decreasing emission of toxic fumes, and increases driver's comfort and safety by less distractions with manually controlling a car's climate control.

Thermal environment inside transportation vehicles can be adjusted according to the temperature at the BTT site including contact sensor measurement and non-contact sensor measurement such as an infrared sensor or thermal image. The temperature at the BTT adjusts any article or device in the car that changes the temperature inside the cabin including air conditioner and heater, vehicle seats, doors, windows, steering wheels, carpets on the floor of the vehicle, and the like. Exemplarily, the temperature at the BTT site adjusts the amount of thermal radiation going through a window of a vehicle, if the BTT sends a signal indicating hot sensation then the windows for instance will darken to prevent further heat from entering the car, and vice versa if cold is perceived the window changing its light transmissibility to allow more heat waves to penetrate the vehicle's cabin. Any article touching the body or in the vicinity of the body can be adapted to change its temperature to achieve thermal comfort for the occupants of the vehicle.

Besides the support structures and thermal imaging systems described in the present invention to monitor and adjust temperature of a cabin of a transportation vehicle, it is understood that a contact lens inside the eyelid pocket with a temperature sensor can also be adapted to adjust the temperature inside the cabin of the vehicle. Exemplary transportation vehicles include cars, trucks, trains, airplanes, ships, boats, and the like.

It is also understood that the sensing system can include sensors in other parts of the body working in conjunction with the temperature sensor measuring temperature and/or thermal radiation at the BTT site. Thermal energy transfer from an article to an occupant of a vehicle can occur by any of radiation, convection, and the like, and any mechanism to transfer deliver, or remove thermal energy can be adjusted based on a temperature signal measured at the BTT.

The present invention provides a more energy-efficient system to achieve thermal comfort of the passengers in any type of transportation vehicle in existence or being developed with any type of sensor alone at the BTT site or in conjunction with sensors in other parts of the body.

Likewise, automated climate control at home, work, or any confined area can be achieved by activating the thermostat directly or via BlueTooth technology based on the temperature measured at the BTT in accordance with the present invention. Besides convenience and comfort, this automation allows saving energy since gross changes manually done in the thermostat leads to great energy expenditure.

It is understood that any body temperature measuring system can provide automated climate control or adjust temperature of articles in accordance with the principles of the present invention.

The present invention yet includes methods for reducing weight. It includes monitoring of temperature during programs for weight reduction based on increasing body heat to reduce said weight. The system alerts athletes on a weight losing program to prevent injury or death by overheating. The system can monitor temperature of people in sauna, steam rooms, spas and the like as part of weight reduction programs in order to prevent injuries and enhance results.

Yet, methods to enhance memory and performance besides preserving health is achieved by providing an automated mechanism to control ambient temperature and surrounding body temperature based on the brain temperature measured by the present invention. Human beings spend about one third of their lives sleeping. Many changes in body temperature occur during sleep. All of the metabolism and enzymatic reactions in the body are dependent on adequate level of temperature. The adequate control of ambient temperature which matches the needs of body temperature such as during sleeping have a key effect on metabolism. Adequate ambient temperature and surrounding temperature of objects which matches body temperature allow not only for people to sleep better, but also to achieve improved efficiency of enzymatic reactions which leads to improved mental ability and improved immune response. A variety of devices such as blankets, clothing, hats, mattress, pillows, or any article touching the body or in the vicinity of the body can be adapted to automatically increase or decrease temperature of said articles according to the temperature signal from the present invention.

The body naturally becomes cooler during the night and many people have restless sleep and turn continuously in bed because of that temperature effect. Since the tossing and turning occurs as involuntary movements and the person is not awake, said person cannot change the stimuli such as for instance increasing room temperature or increasing temperature of an electric blanket. The present invention automatically changes the ambient temperature or temperature of articles to match the temperature needs of the person. This is particularly useful for infants, elderly, diabetics, neuro-disorders, heart disease, and a variety of other conditions, since this population has reduced neurogenic response to changes in body temperature, and said population could suffer more during the night, have increased risk of complications besides decreased productivity due to sleep deprivation. Accordingly, the temperature of an electrical blanket or the ambient temperature is adjusted automatically in accordance with the temperature at the BTT. When low temperature at the BTT is detected by the apparatus of the invention a wireless or wired signal is transmitted to the article to increase its temperature, and in the case of an electrical blanket or heating system, the thermostat is automatically adjusted to deliver more heat.

The invention also provides devices and methods to be used with bio feedback activities. A brain temperature signal from the sensor at the BTT site produces a feedback signal as an audio tone or visual display indicating temperature and a series of tones or colors identify if the brain temperature is increasing (faster frequency and red) or decreasing (lower frequency and blue). The display devices can be connected by wires to the support structure holding the sensor at the BTT site.

Head cooling does not change brain temperature. Athletes, military, firefighters, construction workers and others are at risk of heatstroke despite pouring cold water on their head or using a fan. Medically speaking that is a dangerous situation because the cool feeling sensed in the head is interpreted as internal cooling and the physical activity is maintained, when in reality the brain remains at risk of thermal induced damage and heatstroke. Other medical challenges related to temperature disturbances concern response time. The brain has a slower recovery response to temperature changes than core temperature (internal temperature measured in rectum, bladder, esophagus, and other internal mechanisms). Thus, internal measurement may indicate stable temperature while the brain temperature remains outside safe levels, with risk of induced damage to cerebral tissue, either due to hypothermia or hyperthermia. The only medically acceptable way to prevent cerebral tissue damage due to temperature disturbances is by continuous monitoring brain temperature as provided by the present invention.

The present invention utilizes a plurality of active or passive sensors incorporated in support structures for accessing a physiologic tunnel for measuring biological parameters. The present invention preferably includes all functions in a miniature semiconductor chip, which as an integrated circuit, incorporates sensor, processing and transmitting units and control circuits.

Additional embodiments include temperature measurement and mass screening for fever and temperature disturbances (hyperthermia and hypothermia) comprising a body radiation detector, herein referred as a BTT ThermoScan, which comprises a thermal imaging system acquiring a thermal image of the end of the BTT. The BTT ThermoScan of the present invention has sufficient temperature and isotherm discrimination for monitoring temperature at all times and without the possibility of the measurement to be manipulated by artificial influences.

The BTT ThermoScan detects the brain temperature and provides an image corresponding to the BTT area or an image that includes the BTT area.

The BTT ThermoScan comprises a camera that converts thermal radiation into a video image that can be displayed on a screen, such as the images seen in FIGS. 1A, 1B, 3A, 4A, 5A, 5C, 7A, 7B, 8A, 8B, 9A and 9B (for animals), and most preferably the image seen in FIG. 1B. The radiant energy emitted from the body and the BTT area is detected and imaged within the visible range.

Human skin at the BTT site has a high emissivity (e in the Stefan-Boltzman formula) in the infrared range, nearly equal to a black body. A video image of people walking by and looking at the BTT ThermoScan lens is captured and a customized software is adapted to display a colored plot of isotherm lines, as the software used to acquire the image of FIG. 1B in which any point at 99 degrees Fahrenheit is seen as yellow. For detection of SARS the software is adapted to display in yellow any point in the BTT area above 100 degrees Fahrenheit. When the yellow color appears on the screen, the software is adapted to provide an automatic alarm system. Therefore when the Brain Temperature Tunnel area appears as yellow on the screen the alarm is activated. It is understood that any color scheme can be used. For instance, the threshold temperature can be displayed as red color.

As shown in FIGS. 7A and 7B, cold challenge experiments were performed and demonstrated the stability of thermal emission in the BTT area. The cold challenge consisted of continuous capturing thermal infrared images while a subject is exposed to cold including facing a cold air generator (eg., air conditioner and fans), drinking cold liquids, body immersion in cold water, and spraying alcohol on the skin. Despite artificial means used to artificially change the body temperature the radiation from the BTT area remained intact, and can be seen as the bright white spots in the BTT area. Contrary to that, the face gradually became darker indicating cooling of the face during the exposure to cold. FIG. 7B shows a darker face compared to the face in FIG. 7A, but without any change in the thermal radiation from the BTT area.

In addition to cold challenges, hot challenges was performed in order to artificially increase body temperature and included exercise, people with sunburn, facing a heater, alcohol ingestion, cigarette smoking and body immersion in hot water. In all of those experiments the BTT area remained stable, but the remaining of the face had a change of temperature reflecting skin temperature, not internal brain temperature. As seen in FIGS. 2A to 2C the brain is completely insulated from the environment, with the exception of the end of the BTT. The current technology will have too many false positives and someone could be stopped at an airport or at customs just for drinking some alcohol or smoking a cigarette, making the devices in the prior art ineffective. Therefore, the present invention provides a system and method that eliminates or reduces both false negatives and false positives when using thermal imaging detection systems.

Many useful applications can be achieved including mass screening for fever, screening for hyperthermia in athletes at the end of a sports event (e.g., marathon), screening for hypothermia or hyperthermia for military personnel so as to select the one best fit physiologically for battle, and any other temperature disturbance in any condition in which a BTT ThermoScan can be installed.

One particular application consists of prevention of a terrorist attack by a terrorist getting infected with a disease (e.g., SARS—Severe Acute Respiratory Syndrome) and deceiving thermometers to avert detection of fever when entering the country target for the terrorist attack.

SARS could potentially become a high terrorist threat because it cannot be destroyed. By being naturally created, SARS could become a weapon of mass destruction that cannot be eliminated despite use of military force or diplomatic means. A terrorist can get the infection with the purpose of spreading the infection in the target country. With current technology any device can be deceived and current devices would measure normal temperature when indeed fever is present. Simple means can be used by a terrorist, such as washing their face with cold water or ice or by immersion in cold water, to manipulate any device in the prior art used for measuring fever including current infrared imaging systems and thermometers. The thermal physiology of the body, as it is measured and evaluated by the prior art, can be manipulated and the measurement performed can give a false negative for fever.

A terrorist with SARS could easily spread the disease by many ways including individually by shaking hands with clerks on a daily basis on a mass scale by spending time in confined environments such as movie theater, a concert, grocery store, a government building, and others, or by contaminating water or drinking fountains. All of those people infected do not know they caught the disease and start to spread SARS to family members, co-workers, friends and others, who subsequently will infect others, leading to an epidemic situation.

From a medical standpoint, intentional spread of SARS can have immeasurable devastating effects. People not knowing they have the disease may go to a hospital for routine checks or people not feeling good may go to a hospital for routine checks. Patients and others coming to the hospital can then acquire the disease. Admitted patients, who are debilitated, can easily acquire SARS. Spread of SARS in a hospital environment can be devastating and the hospital may need to shut down. Therefore, one person with SARS can lead to the shut down of a whole hospital. Considering that people infected with the disease may go to different hospitals, several hospitals could get contaminated and would have to be partially or completely shut down. This could choke the health care system of a whole area, and patients would have to be transported to other hospitals. Those patients may have acquired SARS as well as perpetuating the transmission cycle. If this is done in several areas by a concerted terrorist effort, much of the health care system of a country could be choked, besides countless doctors and nurses could become infected with SARS which would further cripple the health care system by shortage of personnel.

The key to prevent the catastrophic effects of a terrorist attack is preparedness. The apparatus and methods of the present invention can detect SARS and cannot be manipulated by artificial means. Placement of the BTT ThermoScan of the present invention at the borders, ports and airports of a country can prevent the artificial manipulation of the temperature measurement and a possible terrorist attack. The system of the present invention can identify at all times and under any circumstances the presence of SARS and other diseases associated with fever.

In addition, mass screening of athletes could be performed with a BTT ThermoScan installed at the finish line. An alert is activated for any athlete who crosses the finish line with a high level of hyperthermia. Therefore immediate care can be delivered allowing for the best clinical outcome since any delay in identifying hyperthermia could lead to heatstroke and even death. The BTT ThermoScan is adapted to view at least a portion of the BTT area. BTT ThermoScan detects the brain temperature and provides an image corresponding to or that includes the BTT area. Despite athletes pouring water on their head, the BTT ThermoScan precisely detects the thermal status of the body by detecting the temperature at the BTT.

Temperature disturbances such as hyperthermia and hypothermia can impair mental and physical function of any worker. Drivers and pilots in particular can have reduced performance and risk of accidents when affected by temperature disturbances. The BTT ThermoScan can be mounted in the visor of a vehicle or plane to monitor body temperature with the camera of the BTT ThermoScan capturing a thermal image of the BTT of the driver or pilot and providing an alert whenever a disturbance is noticed. It is understood that any thermal imaging system can be mounted in a vehicle or airplane to monitor body temperature and alert drivers and pilots.

The BTT ThermoScan also includes monitoring mass screening of children and people at risk during flu season. With the shortage of nurses an automated screening can greatly enhance the delivery of health care to the ones in need. When a student walking by the infrared camera is identified as having a temperature disturbance (e.g., fever) a conventional digital camera is activated and takes a picture of the student. The picture can be emailed to the school nurse that can identify the student in need of care or automatically by using stored digital pictures.

Hospitals, factories, homes, or any location that can benefit from automated mass or individual screening of temperature disturbances can use the thermal imaging apparatus in accordance with the present invention.

It is understood that an apparatus comprised of a radiation source emitting a wavelength around 556 nm at the BTT site can be used for determining the concentration of hemoglobin. The hemoglobin present in the red blood cells at the terminal end of the BTT strongly absorbs the 556 nm wavelength and the reflected radiation acquired by a photodetector determines the amount of hemoglobin. Blood flow can be evaluated by knowing the amount with thermal radiation, the higher amount of the thermal radiation indicating higher blood flow in accordance to a mathematical model.

Positioning of contact sensors, non-contact sensors, and thermal imaging camera are facilitated by external visible anatomic aspects that may be present. The cerebral venous blood can be seen under the skin in the medial canthal area next to the corner of the eye. Therefore a method for measuring temperature includes the step of visually detecting the blue or bluish color of the skin at the BTT area and positioning the sensor on or adjacent to the blue or bluish area. For subjects of darker skin, a distinctive feature of difference skin texture in the BTT area next to the medial corner of the eye can be used as the reference for measurement.

The present invention includes devices for collecting thermal radiation from a BTT site, devices for positioning temperature sensitive devices to receive thermal radiation from the BTT site and devices for converting said thermal radiation into the brain temperature. The present invention also provides methods for determining brain temperature with said methods including the steps of collecting the thermal emission from the BTT site, producing a signal corresponding to the thermal emission collected, processing the signal and reporting the temperature level. The invention also includes devices and methods for proper positioning of the temperature sensor in a stable position at the BTT site.

It is also an object of the present invention to provide support structures adapted to position a sensor on the end of a tunnel on the skin to measure biological parameters.

It is an object of the present invention to provide apparatus and methods to measure brain temperature including patches, adhesives strips, elastic devices, clips and the like containing sensors positioned on a physiologic tunnel.

It is an object of the present invention to provide apparatus and methods to measure brain temperature including thermal imaging systems containing infrared sensors sensing infrared radiation from the BTT.

It is an object of the present invention to provide multipurpose eyeglasses equipped with medial canthal pads containing sensors positioned on a physiologic tunnel for measuring biological parameters It is another object of the present invention to provide new methods and apparatus for measuring at least one of brain temperature, chemical function and physical function.

It is yet an object of the invention to provide apparatus that fit on both adults and children.

It is also an object of the invention to provide apparatus that report the signal produced at the tunnel by at least one of wired connection to reporting devices, wireless transmission to reporting devices and local reporting by audio, visual or tactile devices such as by vibration incorporated in support structures.

It is yet another object of the present invention to provide apparatus that allow the wearer to avoid dehydration or overhydration (water intoxication).

It is a further object of the present invention to provide methods and apparatus that allows athletes and sports participants to increase their performance and safety.

It is yet an object of the present invention to provide support structure positioned sensors on a tunnel which can be worn at least by one of athletes during practice and competition, military during training and combat, workers during labor and the general public during regular activities.

It is another object of the present invention to increase safety and comfort in vehicles by providing automated climate control and vehicle seat control based on the core temperature of the occupants of the vehicle.

It is an object of the present invention to provide methods and apparatus that act on a second device based on the level of the biological parameter measured.

It is another object of the invention to provide methods and apparatus to preserve skin health, reduce risk of wrinkles and reduce the risk of skin cancer by preventing sun damage by thermal radiation and alerting the wearer when the temperature has reached certain thresholds.

It is also an object of the invention to provide methods and apparatus for achieving controlled weight loss based on heat-based weight loss approach.

It is also an object of the invention to provide methods and apparatus to alert athletes in a weight losing program based on increasing body temperature to prevent injury or death by overheating.

It is also an object of the invention to provide methods and apparatus that allow monitoring fever and spikes of temperature.

It is also an object of the invention to provide a device for family planning by detecting time of ovulation.

It is a further object of the invention to provide methods and apparatus for the delivery of medications in accordance with the signal produced at the tunnel.

It is yet an object of the invention to provide methods and apparatus that enhance occupational safety by continually monitoring biological parameters.

It is also an object of the invention to provide an article of manufacture with a sensing apparatus positioned on a tunnel for monitoring biological parameters that can be fitted or mounted in at least one of the frame of eyeglasses, the nose pads of eyeglasses, the structure of a head mounted gear and clothing.

The invention also features transmitting the signal from the support structure to act on at least one of exercise equipment, bikes, sports gear, protective clothing, footwear and medical devices.

It is yet an object of the invention to provide support structures that transmit the signal produced at the tunnel to treadmills and other exercise machines for keeping proper hydration and preventing temperature disturbances of the user.

It is yet another object of the invention to provide apparatus and methods for monitoring biological parameters by accessing a physiologic tunnel using active or passive devices.

The invention yet features transmission of the signal from the support structures to watches, pagers, cell phones, computers, and the like.

These and other objects of the invention, as well as many of the intended advantages thereof, will become more readily apparent when reference is made to the following description taken in conjunction with the accompanying drawings.

BRIEF DESCRIPTION OF THE DRAWINGS

FIG. 6A is a schematic diagram showing the brain temperature tunnel and the metabolic tunnel.

FIGS. 19A1, 19A2, 19B, 19C and 19D are schematic diagrams of preferred geometry and dimensions of support structures and sensing devices.

FIG. 31C is a side perspective view of part of the support structure of FIG. 31B.

FIG. 31D is a side perspective view of a medial canthal piece secured at the support structure.

FIGS. 58A to 58C are schematic views showing alternative support structures in accordance with the present invention.

FIG. 59 is a schematic diagram showing bidirectional flow of thermal energy in the BTT.

FIG. 74 is a perspective diagram showing preferred BTT measuring devices for animals.

FIGS. 81C and 81D are perspective diagrams showing a support structure of FIG. 81A.

FIGS. 85A to 85C are schematic diagrams showing kits in accordance with the present invention.

FIG. 86M illustrates a cloverleaf shaped adhesive patch embodiment.

FIG. 86M(1) illustrates a rear view of an adhesive patch.

FIG. 86N illustrates the details of a light emitter-detector pair.

FIG. 86P illustrates an alternate embodiment of a sensor assembly.

FIG. 86P(1) diagrammatically illustrates the noncontact measurement of the brain tunnel.

FIG. 86P(2) schematically illustrates a light source directing radiation at the brain tunnel and measurement of reflected radiation.

FIG. 86P(3) diagrammatically illustrates a handheld sensing device for noncontact measurement at the brain tunnel.

FIG. 86P(4) illustrates a noncontact measurement at the brain tunnel.

FIG. 86P(5) illustrates a sensing device and a sensor mounted on a web-camera for measurement of radiation from the brain tunnel.

FIG. 86Q is a sectional view of a sensing device shown in detail.

FIG. 86Q(1) is a perspective diagrammatic view of a measuring portion of a sensor assembly.

Figure 86A:
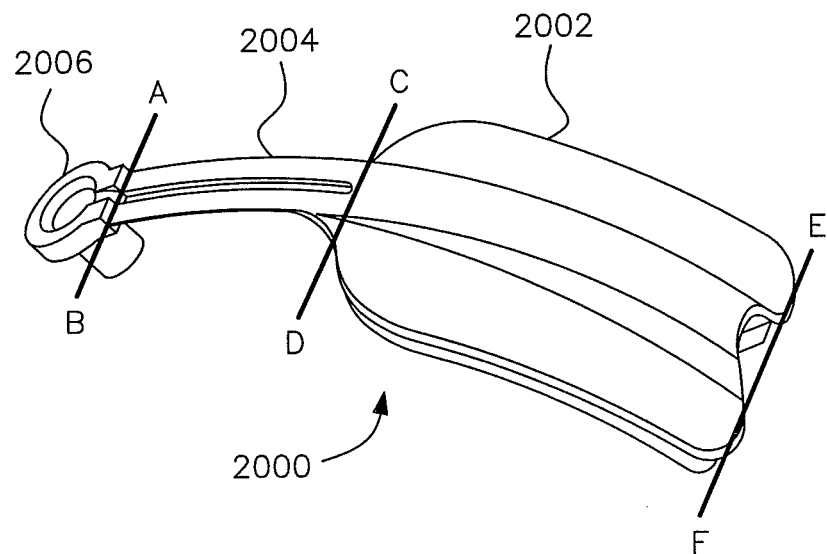
FIG. 86A is a perspective view of a support structure for the brain temperature tunnel sensor assembly of the present invention.
Figure 86B:
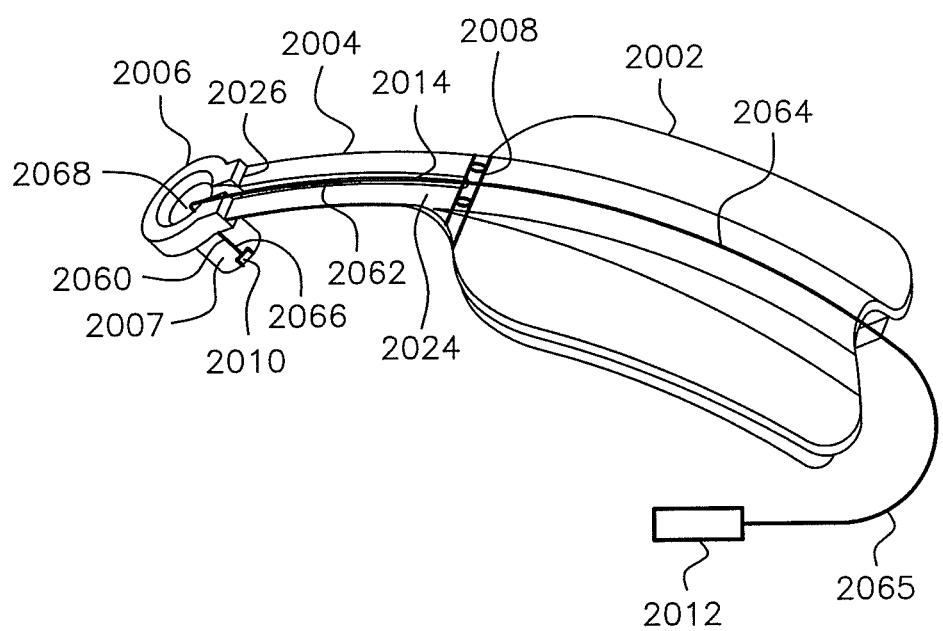
FIG. 86B illustrates an alternate embodiment with a pivotable support arm of the support structure.
Figure 86C:
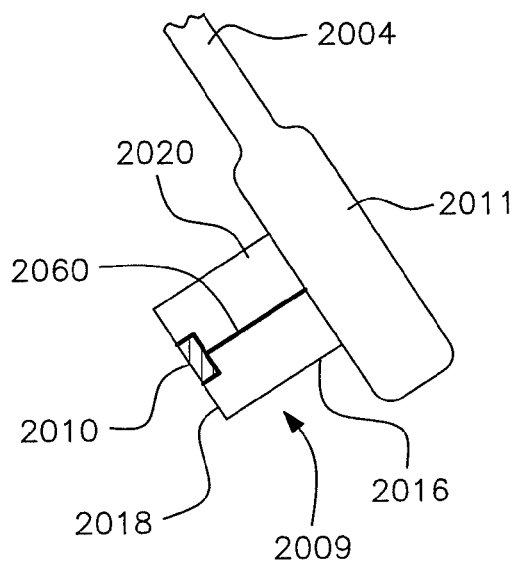
FIG. 86C is a detailed view of a sensor at one end of the support structure.
Figure 86D:
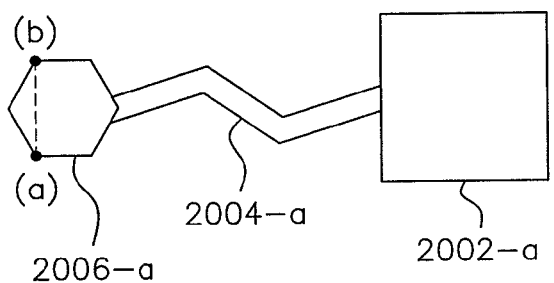
FIG. 86D is a planar diagrammatic view of an alternate embodiment of the support structure and sensor assembly.
Figure 86E:
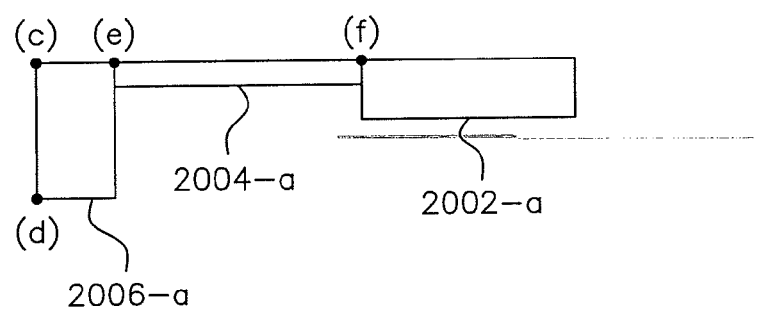
FIG. 86E is a diagrammatic side view of the embodiment of FIG. 86D.
Figure 86F:
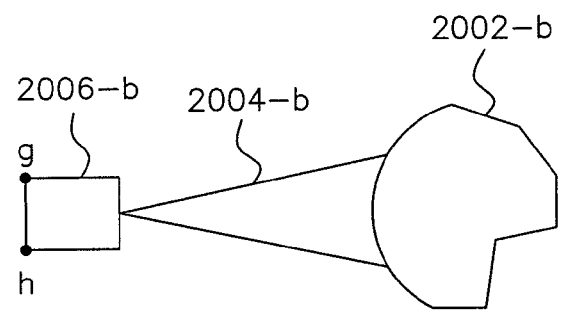
FIG. 86F illustrates an irregular geometric shape of a body portion supported by a triangular shaped arm.
Figure 86G:
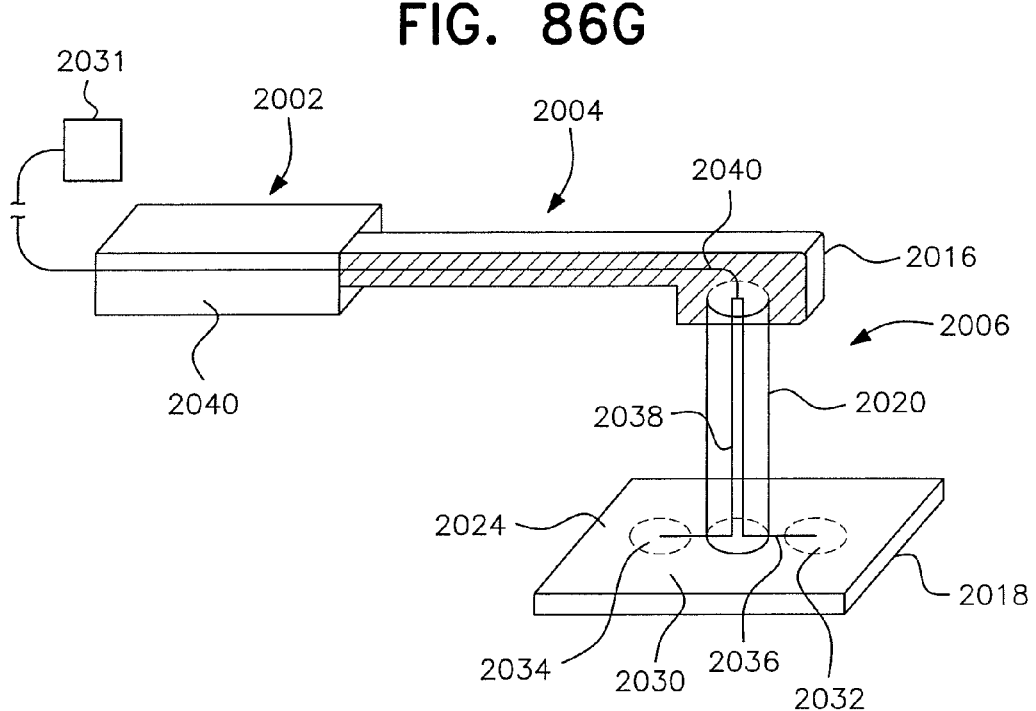
FIG. 86G is a diagrammatic perspective view of an alternate embodiment of a support structure and sensor assembly.
Figure 86H:
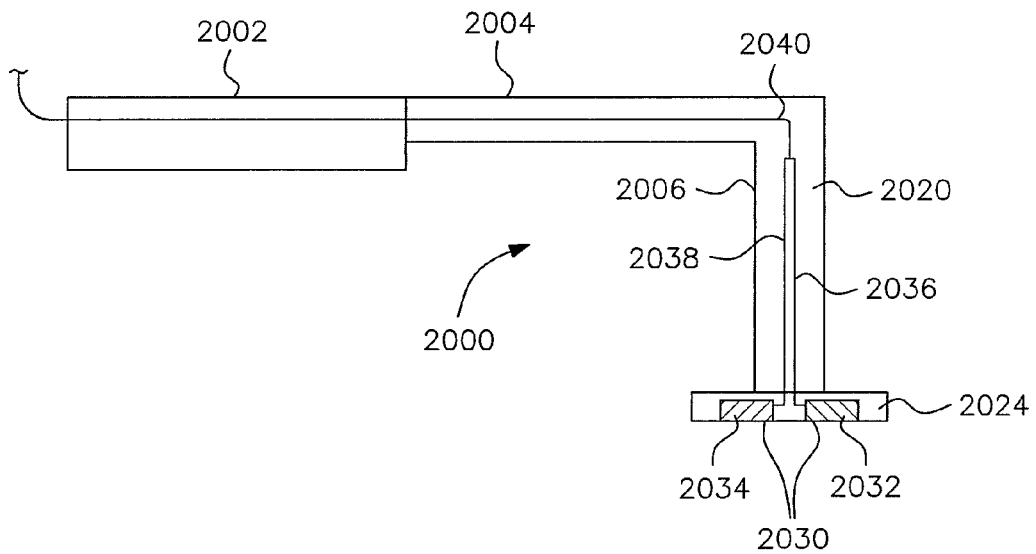
FIG. 86H is a sectional view of the embodiment shown in FIG. 86G.
Figure 86I:
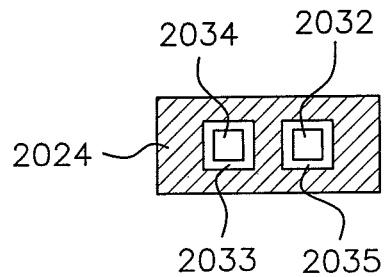
FIG. 86I is a bottom planar view of the sensor assembly illustrating the housing light emitter and light detector.
Figure 86J:
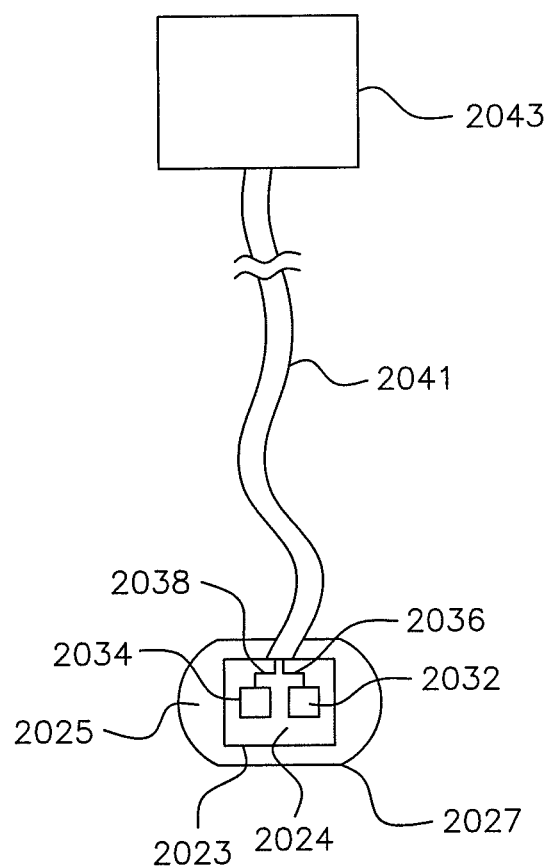
FIG. 86J is a diagrammatic planar view of an alternate embodiment of the support structure and sensor assembly.
Figure 86K:
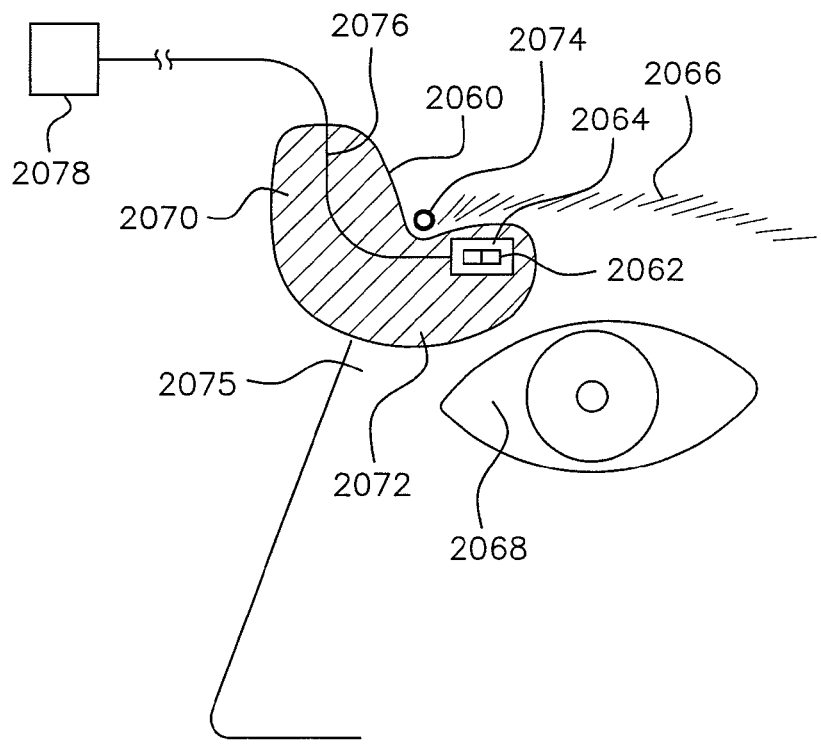
FIG. 86K illustrates an embodiment worn by a user including an adhesive patch and a light emitter-light detector pair located adjacent to the edge of the adhesive patch.
Figure 86L:
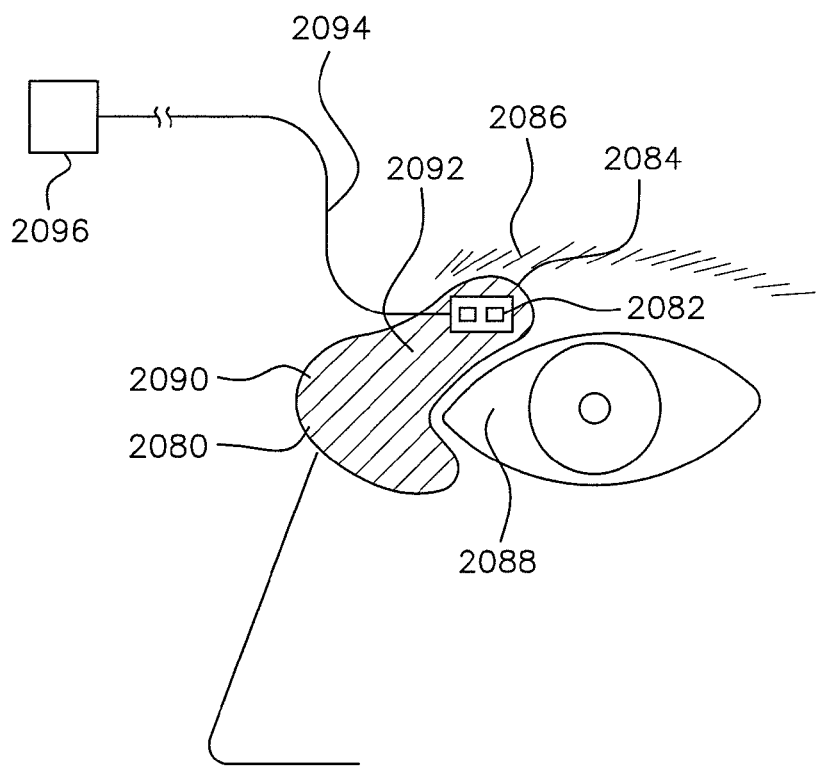
FIG. 86L illustrates an alternate embodiment of the adhesive patch.
Figure 86R:
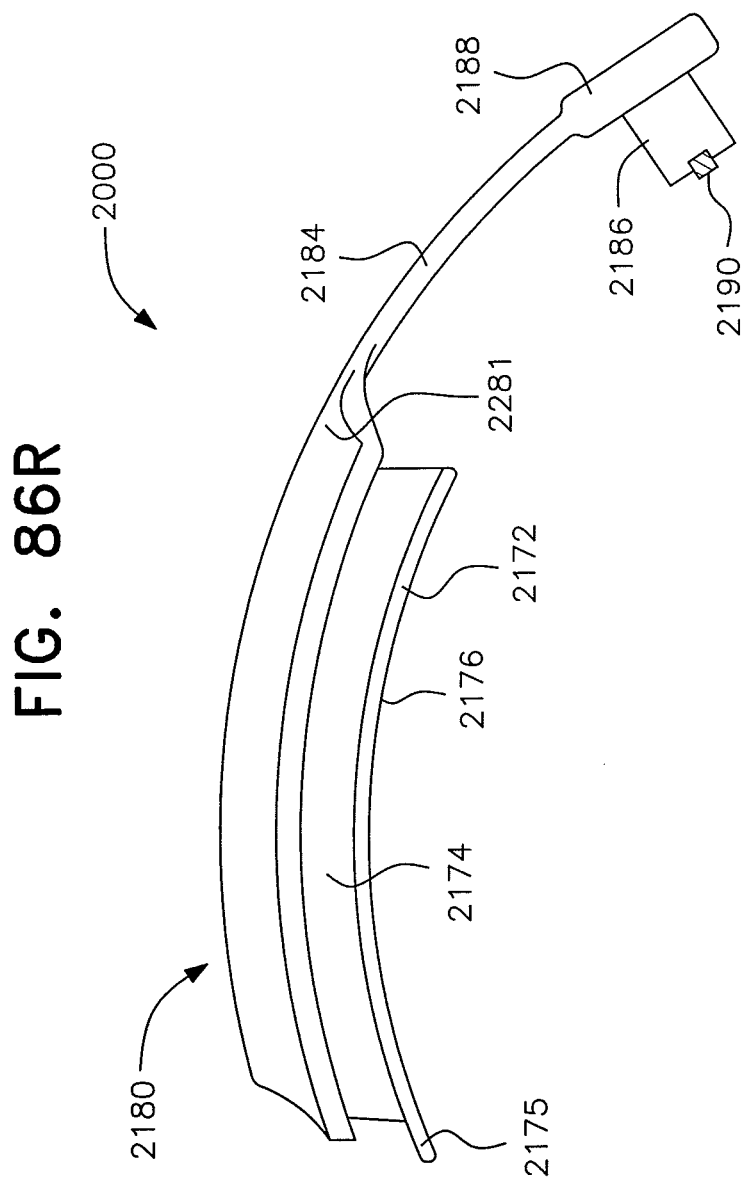

FIG. 86R illustrates a perspective view of a sensing device mounted on a support structure.

FIG. 86R(1) illustrates a sensing device worn by a user.

FIG. 86R(2) illustrates a sensing device having a swivel mechanism at the junction of an arm and a body.

FIG. 86R(3) illustrates the swivel assembly of a sensing device and support structure worn by a user.

FIG. 86S(1) is a side view of a sensing device having a straight extending wire.

FIG. 86S(2) shows a sensing device worn by a user with an arm bent into position.

FIG. 86T(1) illustrates a sensing device including an arm, measuring portion and plate.

FIG. 86T(2) shows a sensing device and support structure formed of separable pieces.

FIG. 86T(3) shows an alternate embodiment of a sensing device and support structure with different separable pieces from FIG. 86T(2).

Figure 86U:
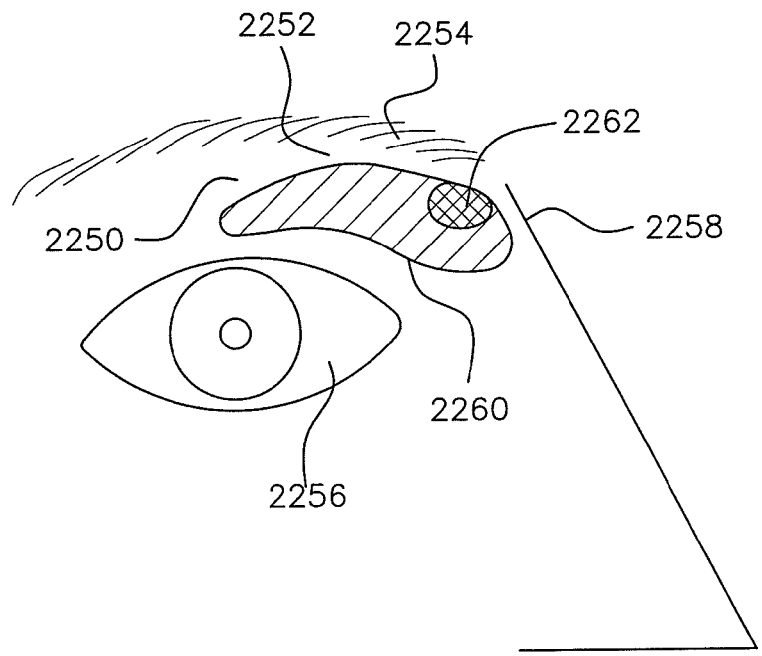

FIG. 86U illustrates the specialized skin area of the brain tunnel with a patch worn over the brain tunnel area.

Figure 87:
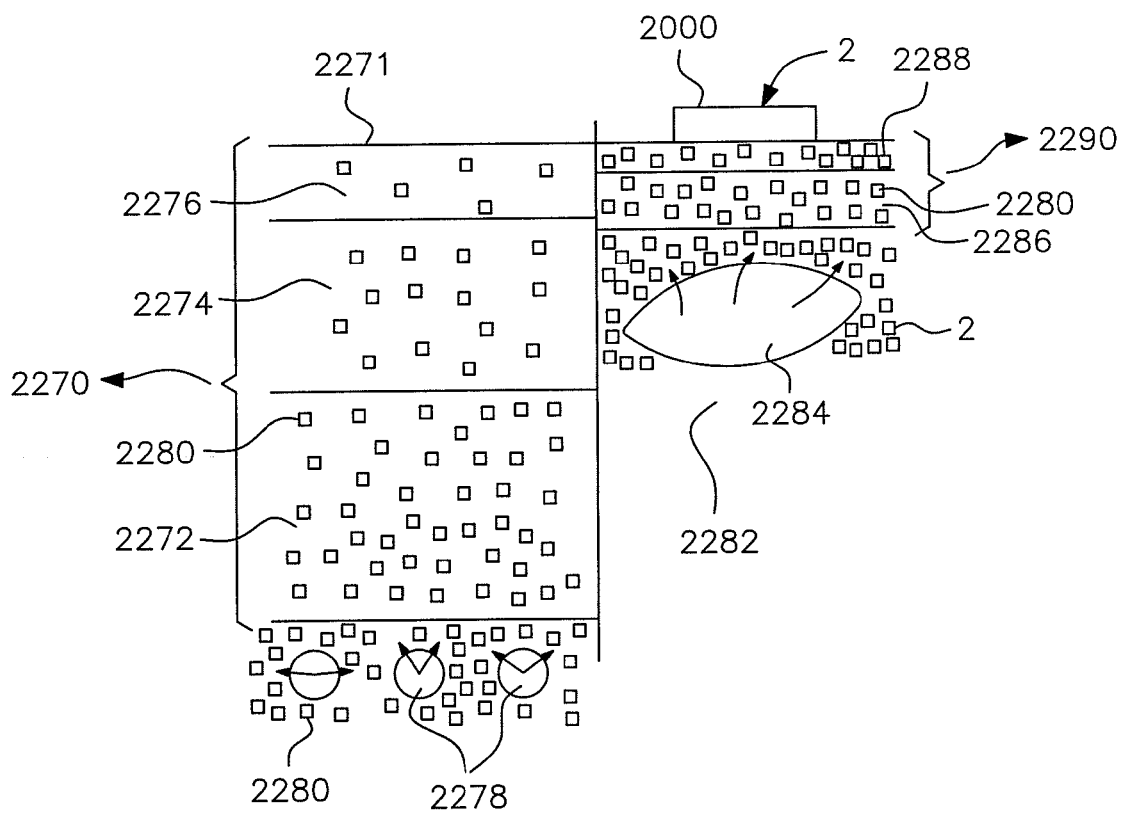

FIG. 87 schematically illustrates a comparison between trans-subcutaneous measurements of the arterial oxygen pressure as previously known and as measured by the present invention.

FIG. 87A illustrates the advantageous use of a small heating element.

FIG. 87B illustrates a convex sensing surface for a sensing system.

FIG. 87C illustrates a specialized two-plane surface including a convex surface and a flat central surface.

Figure 88:
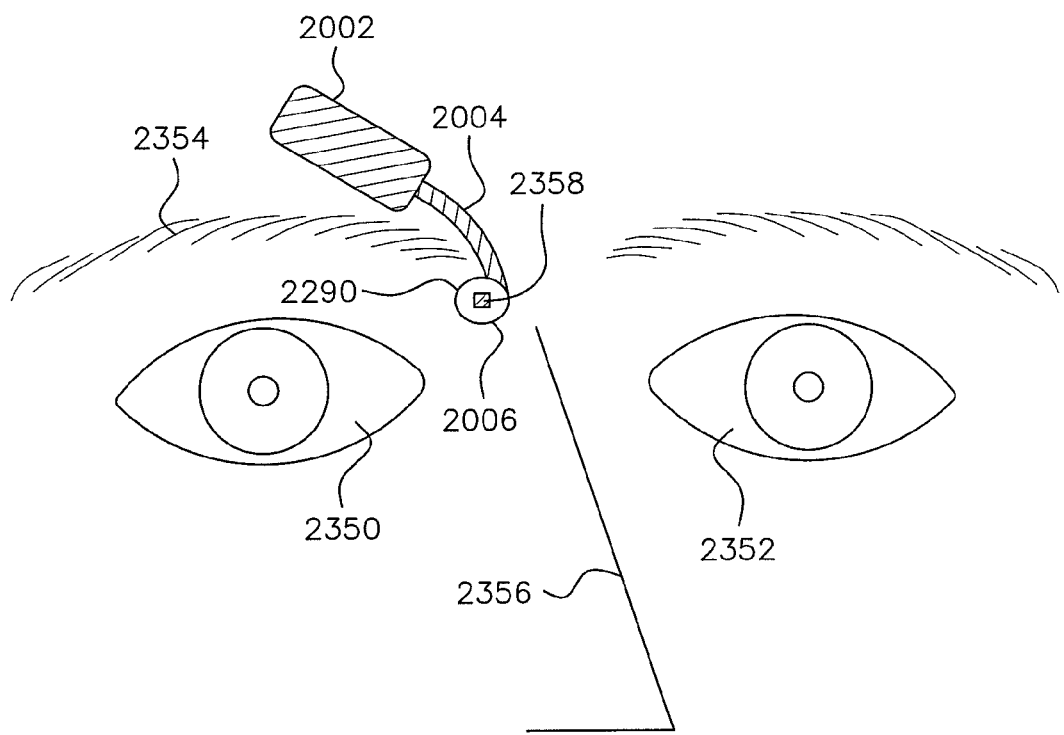

FIG. 88 schematically illustrates the placement of a sensor assembly and its support structure on the face of a wearer.

Figure 89:
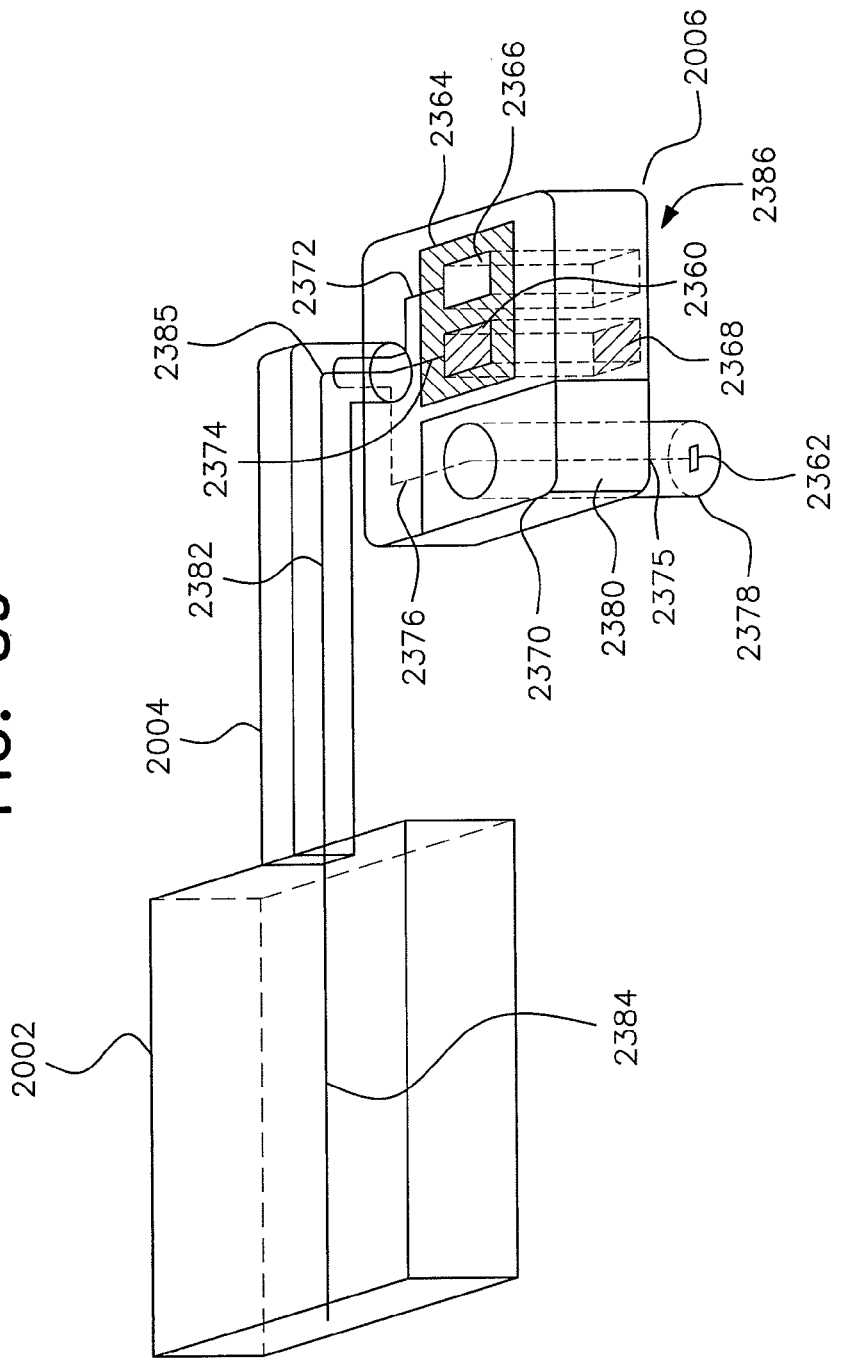

FIG. 89 is a diagrammatic perspective view of a sensor assembly measuring portion mounted on a support structure.

Figure 90A:
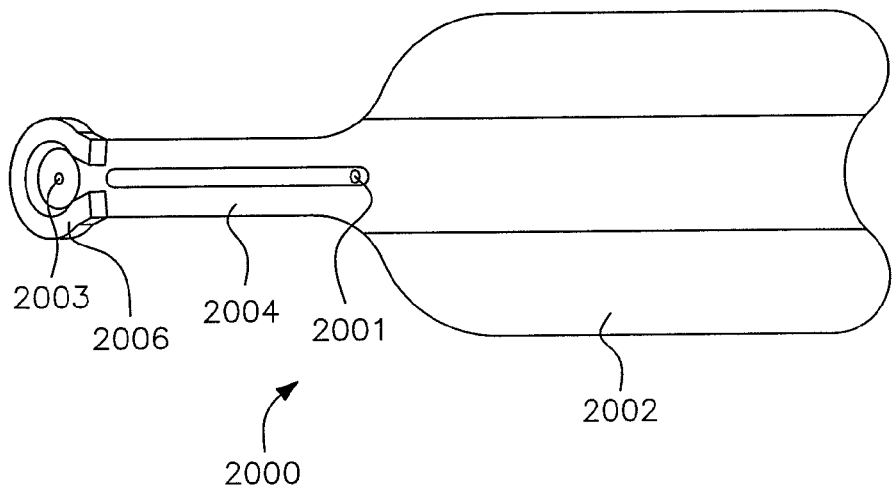

FIG. 90A illustrates a routing of a transmission wire through the support structure.

Figure 90B:
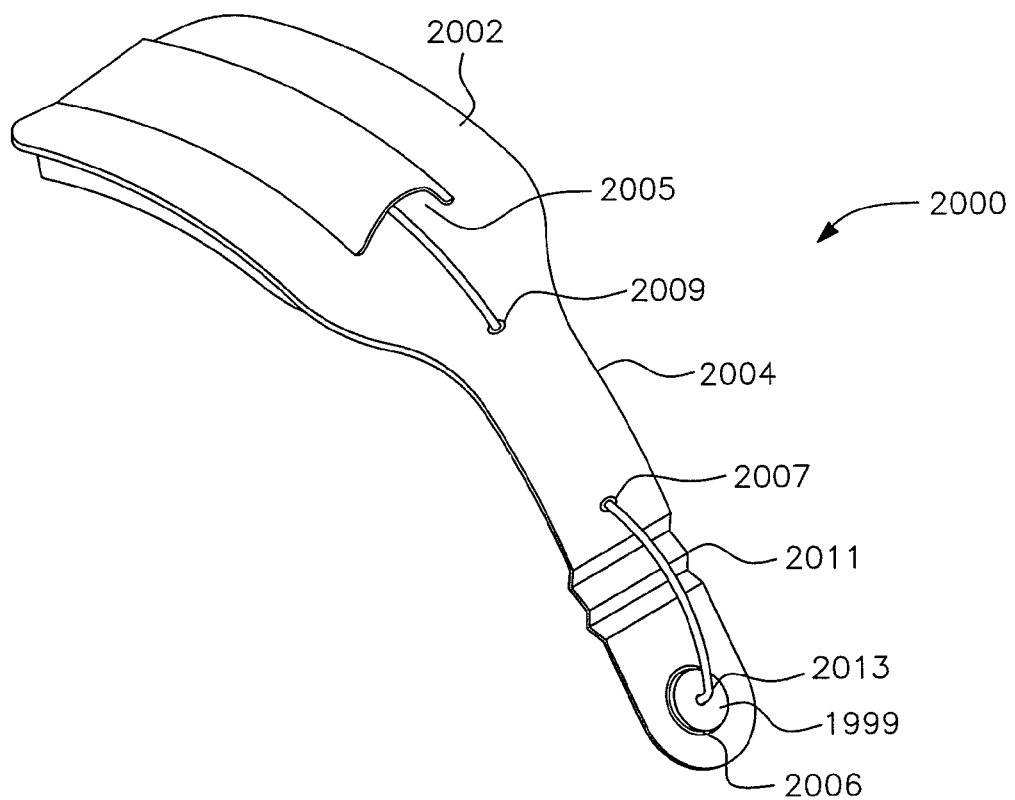

FIG. 90B is a perspective view illustrating the path of the wire through the support structure.

FIG. 90C is a side view illustrating the path of the transmission wire.

FIG. 90D is a top view illustrating the path of the transmission wire.

Figure 90E:
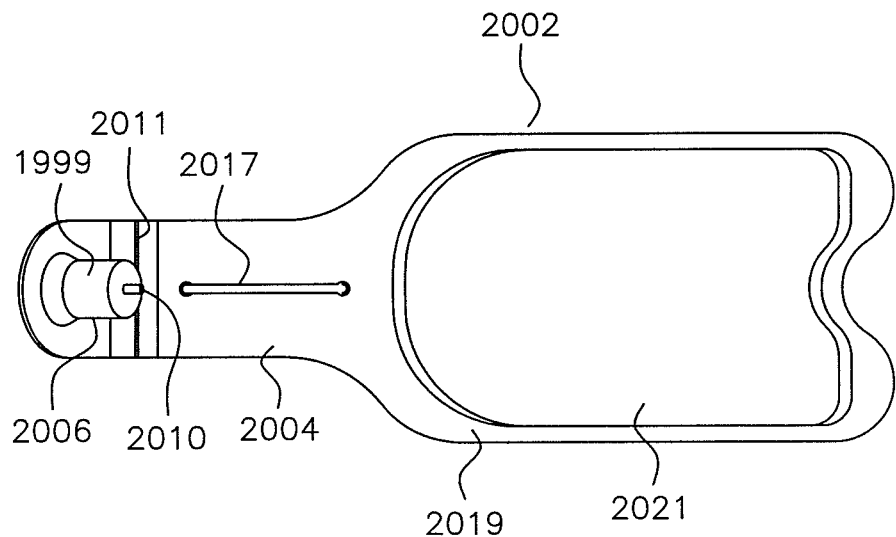

FIG. 90E illustrates a path of the transmission wire from a bottom view.

Figure 90F:
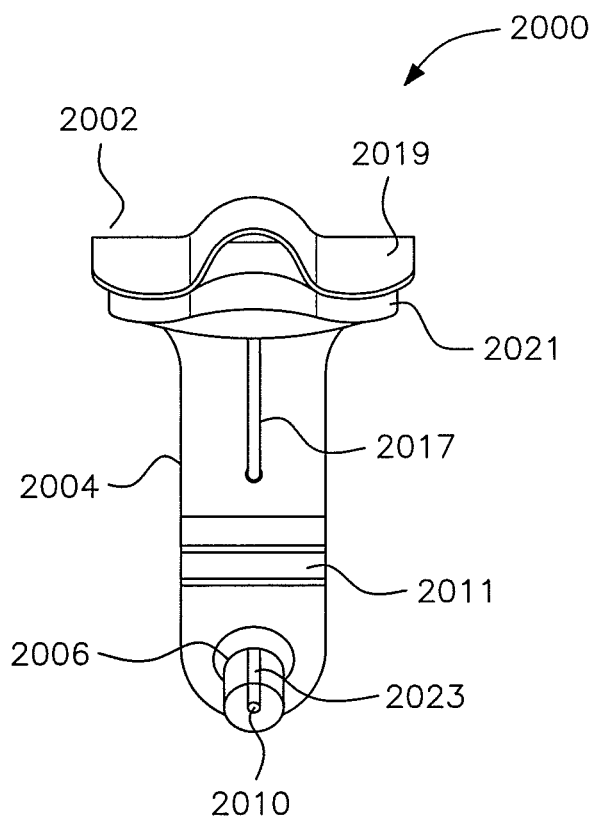

FIG. 90F illustrates the path of the wire from an end view.

Figure 90G:
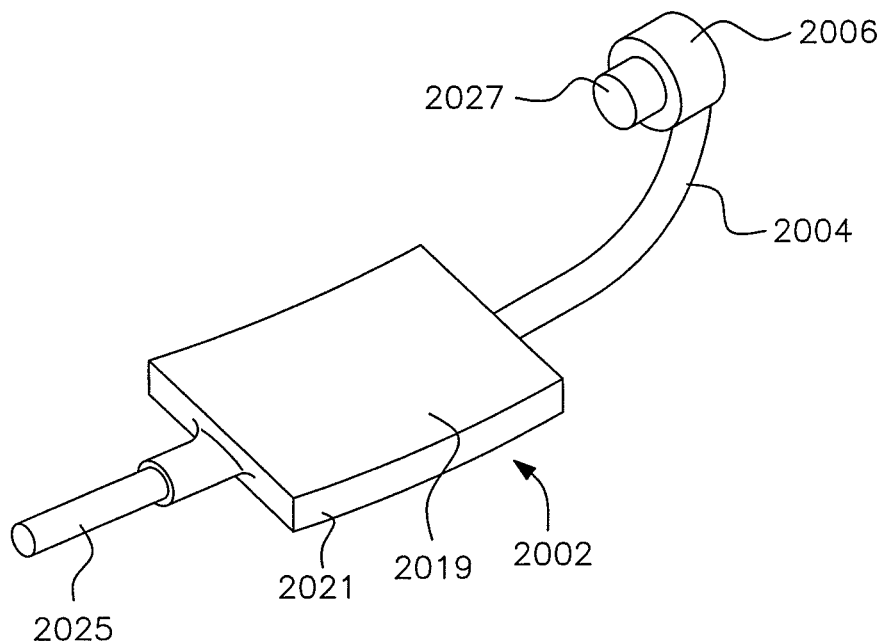

FIG. 90G illustrates a sensing device including its support body and sensor head.

Figure 90H:
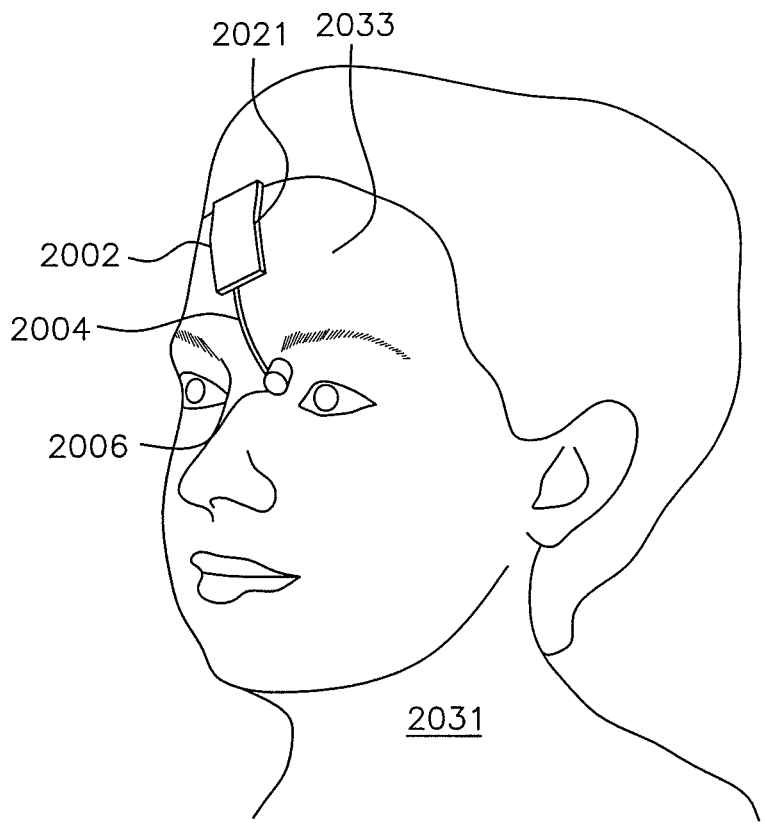

FIG. 90H illustrates the locating of the sensing assembly on the face of a wearer.

Figure 90I:
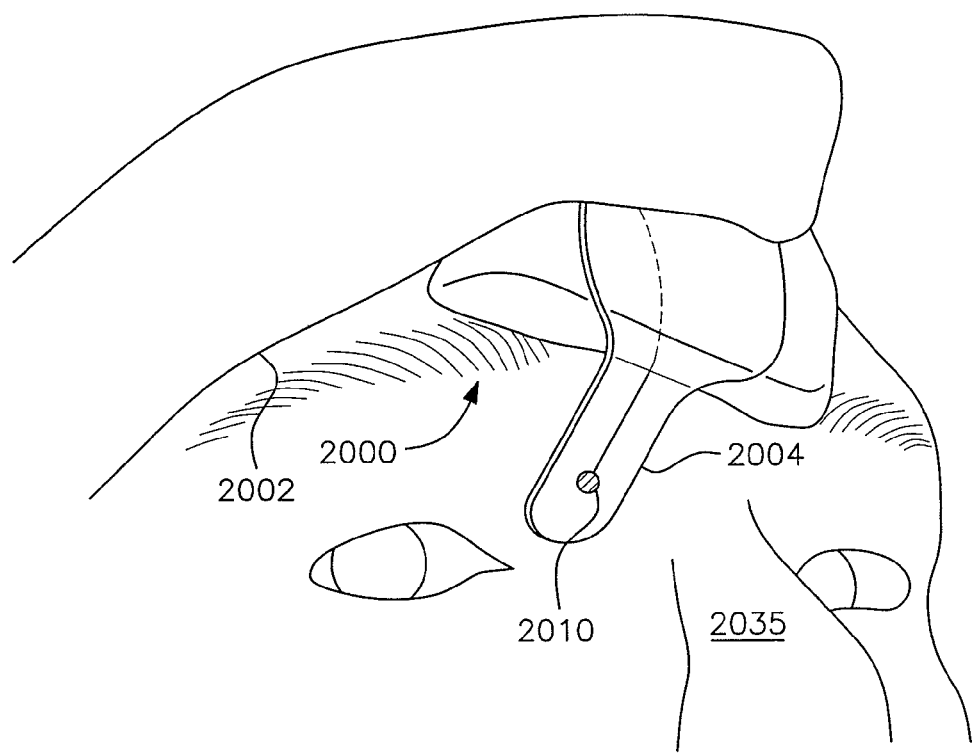

FIG. 90I illustrates a sensing device worn by a user and held in place by a headband.

Figure 90J:
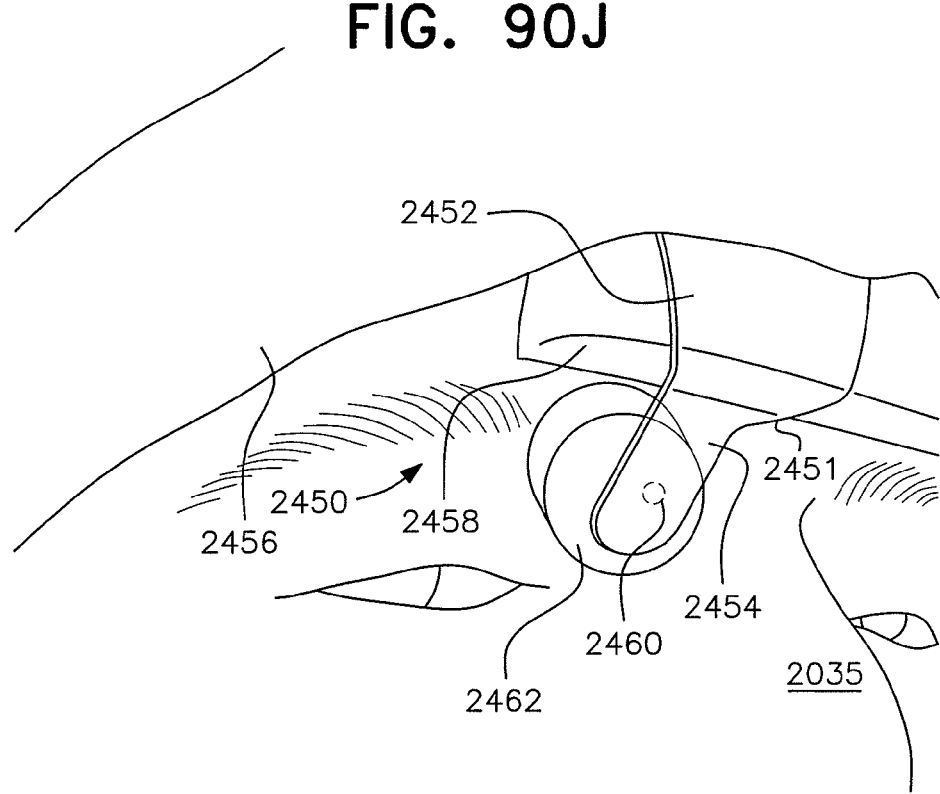

FIG. 90J illustrates a two part separable sensing device worn by a user and held in place by a headband.

Figure 91:
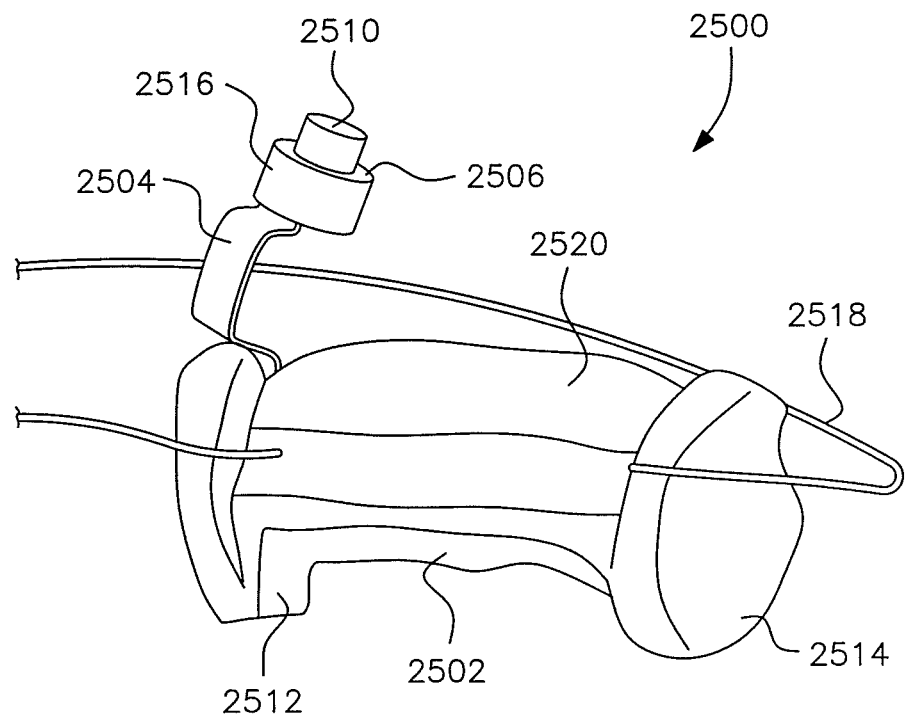

FIG. 91 illustrates a nose bridge and clip for mounting a sensing device.

Figure 92A:
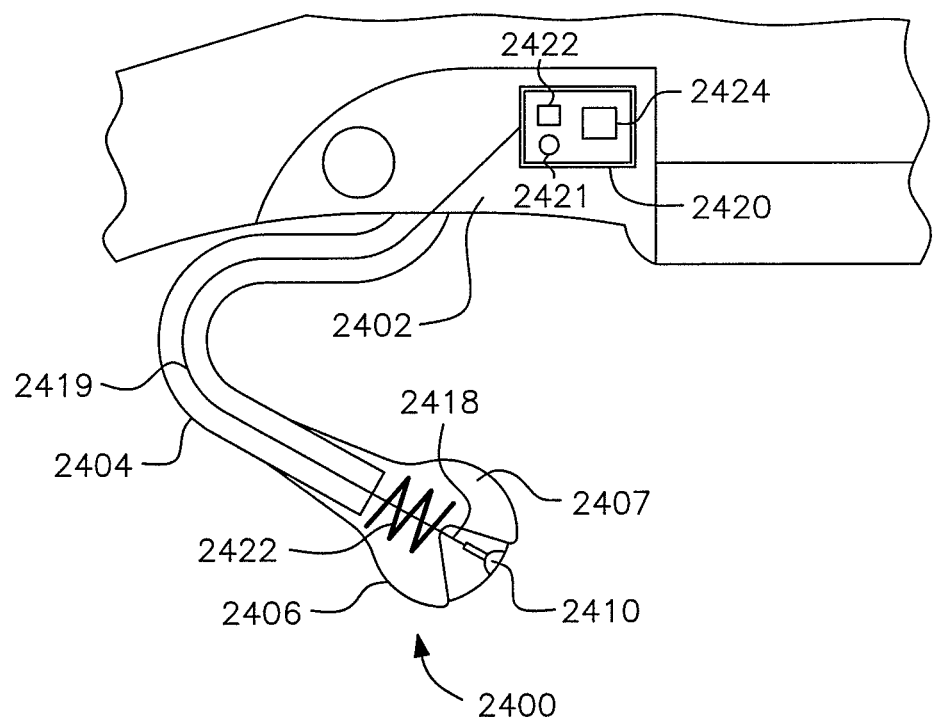

FIG. 92A illustrates a specialized support and sensing structure.

Figure 92B:
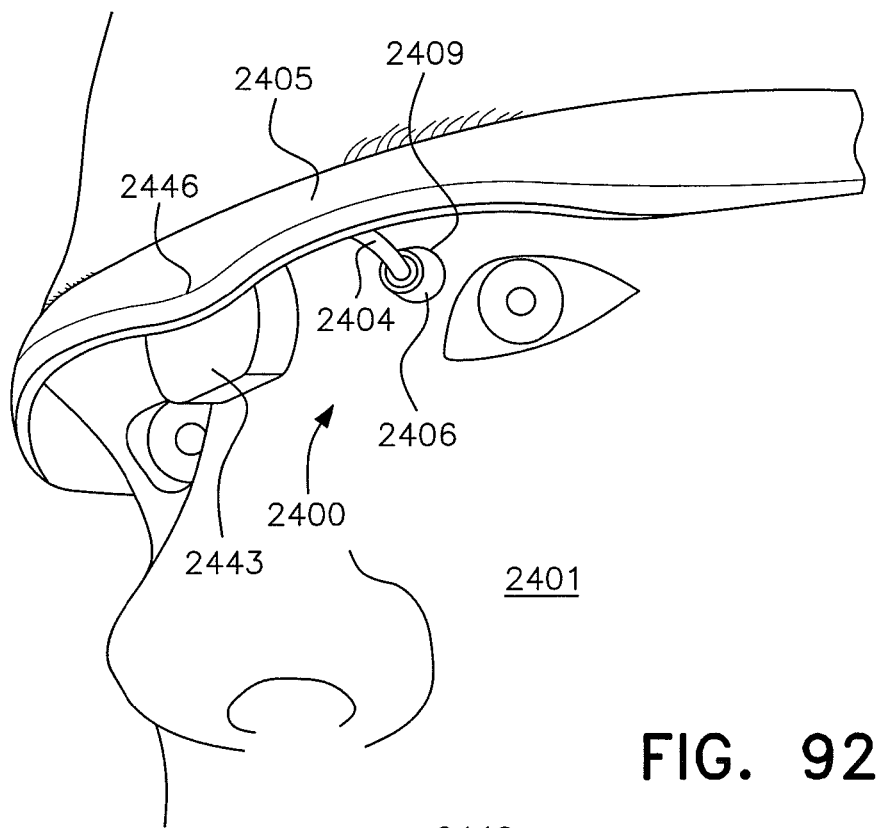

FIG. 92B illustrates a specialized support and sensing structure worn by a user.

Figure 92C:
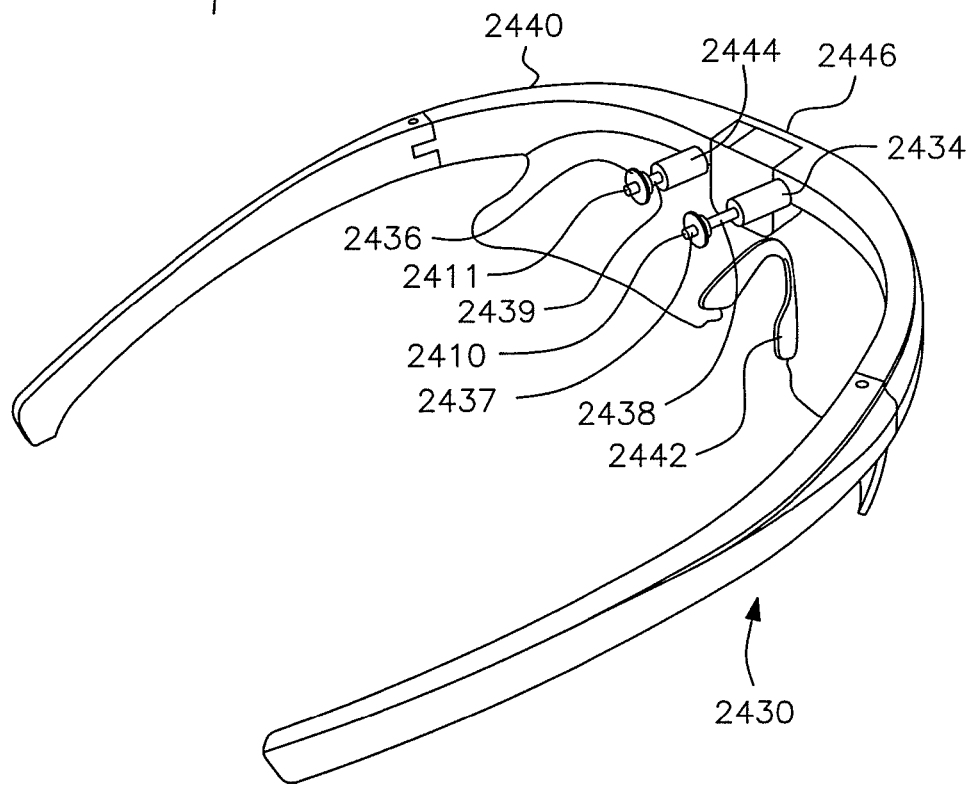

FIG. 92C illustrates the mounting of a specialized sensing device on eyeglasses.

Figure 92D:
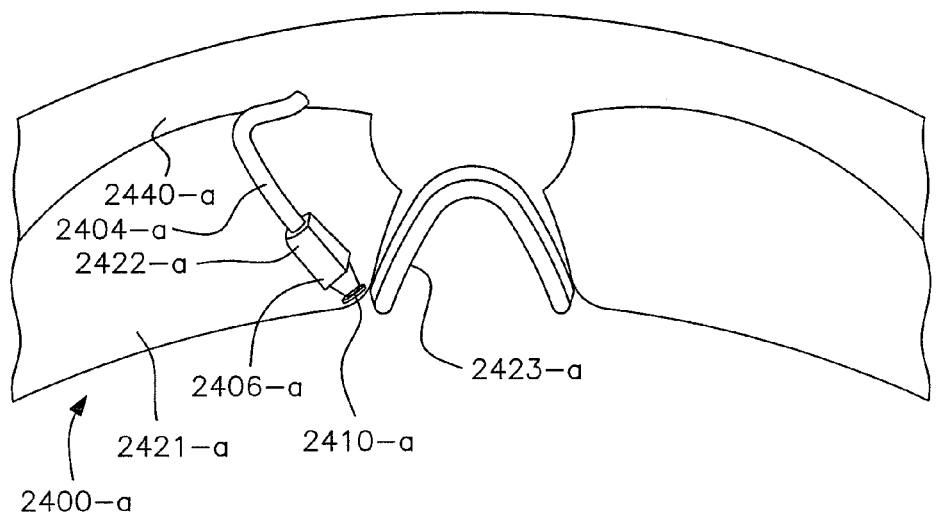

FIG. 92D illustrates the support and sensing structure mounted on a frame of eyeglasses.

Figure 92E:
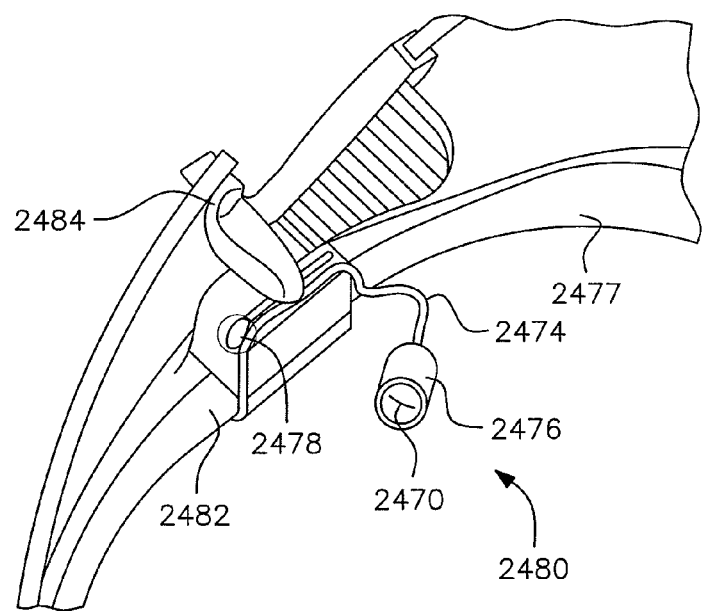

FIG. 92E illustrates a bottom view of an LED based sensing eyeglass.

Figure 92F:
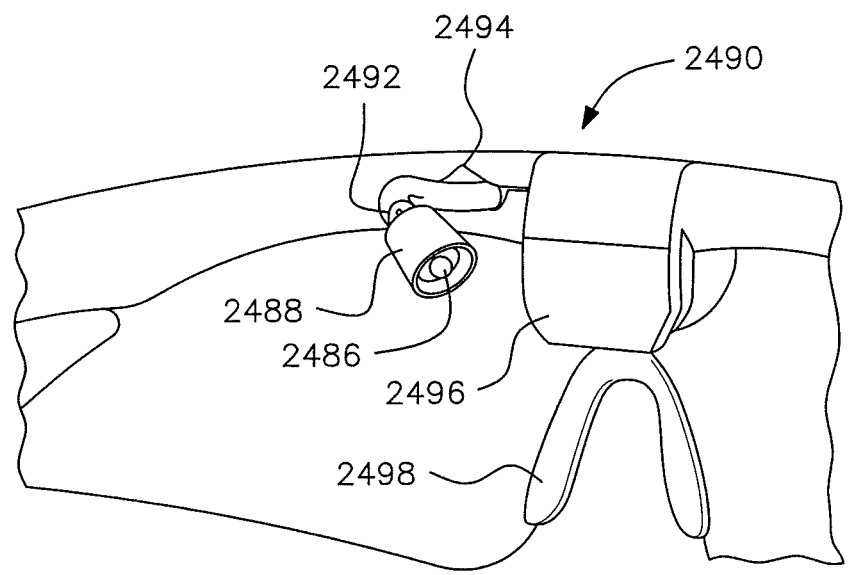

FIG. 92F illustrates a wireless based sensing pair of eyeglasses.

Figure 93A:
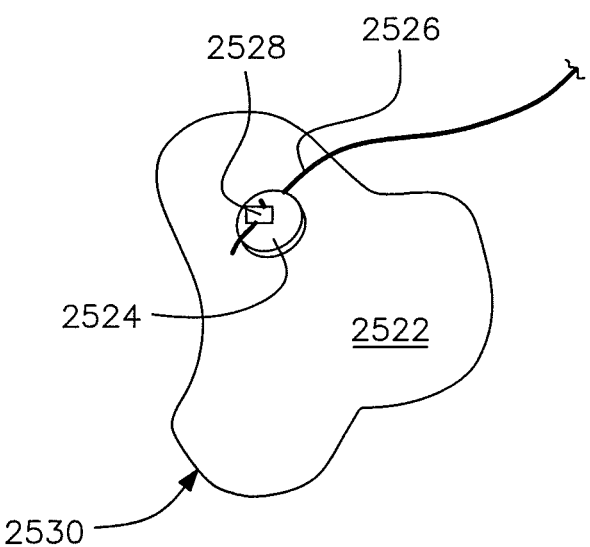

FIG. 93A illustrates a patch sensing system.

Figure 94A:
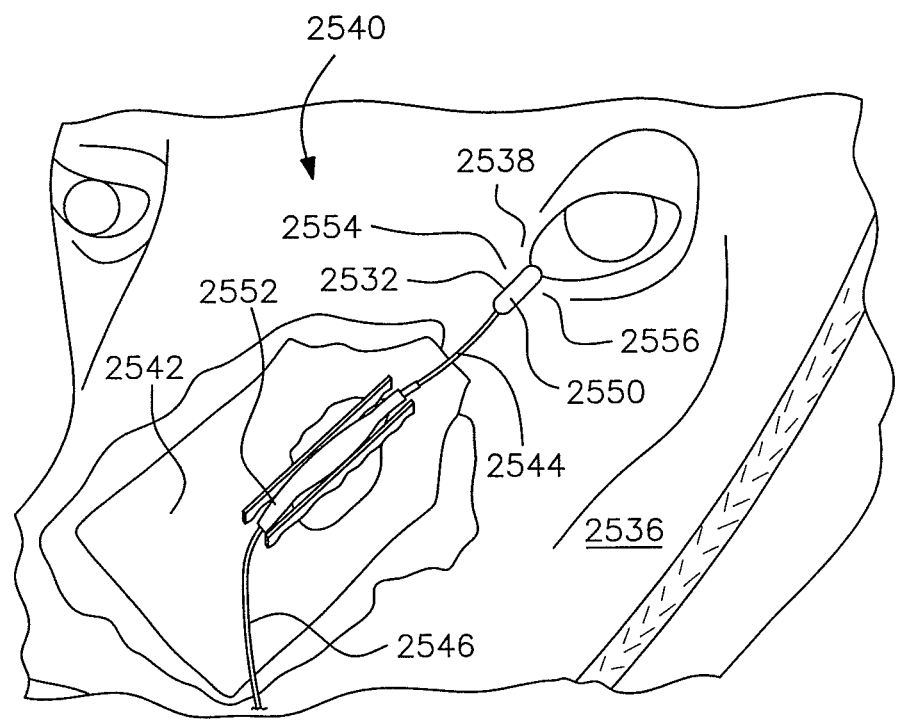

FIG. 94A illustrates a system for mounting a sensing device on an animal.

Figure 94B:
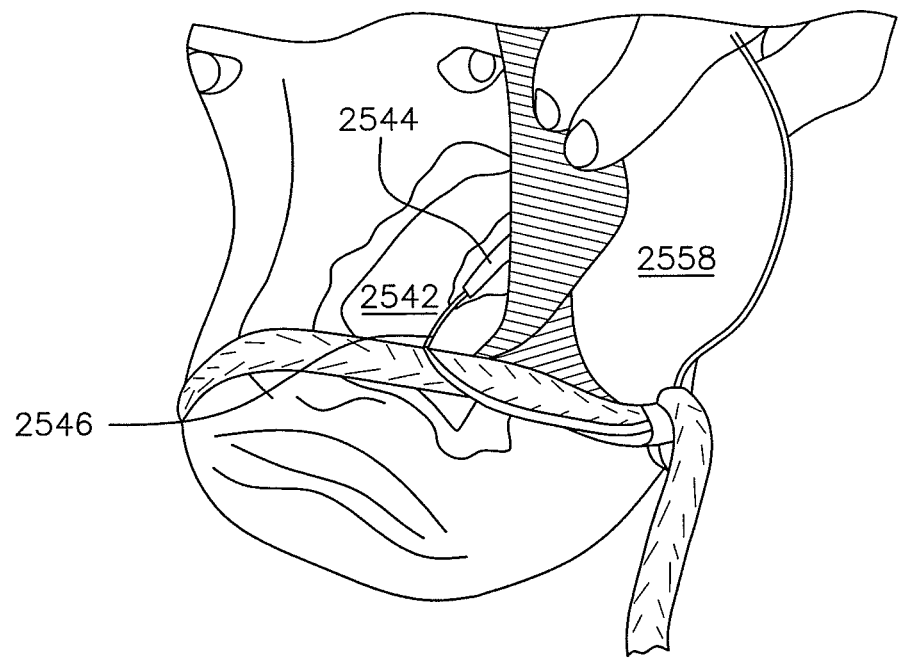

FIG. 94B illustrates a multilayer protection cover mounted on a sensing system for an animal.

Figure 95A:
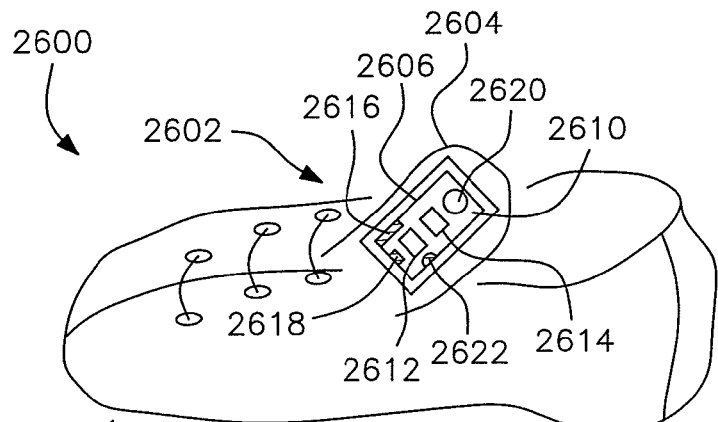

FIG. 95A illustrates a mounting of an alert device on a shoe of a user.

Figures 1, 95B:
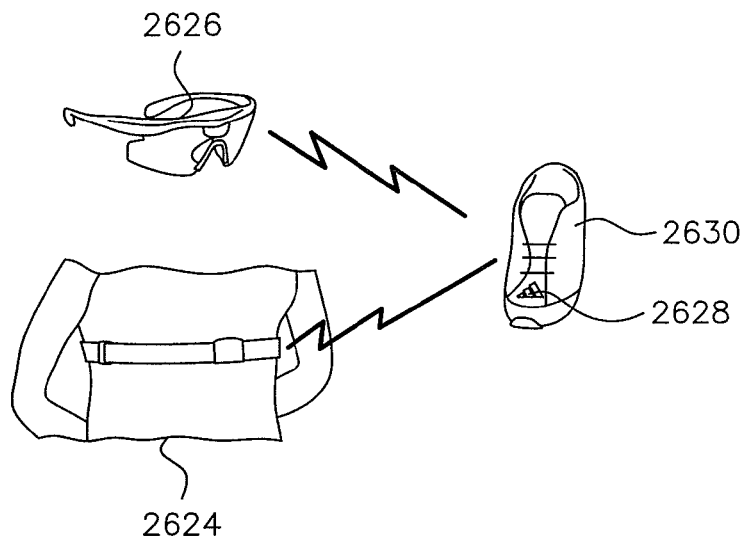

FIG. 95B-1 illustrates the transmission of signals to devices worn by a user.

Figures 2, 95B:
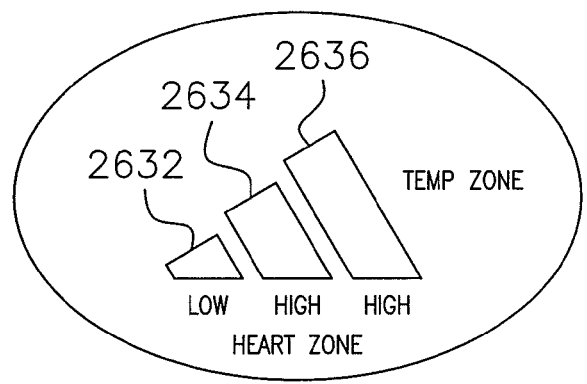

FIG. 95B-2 is an enlarged view of an alert device worn by a user.

Figures 1, 95C:
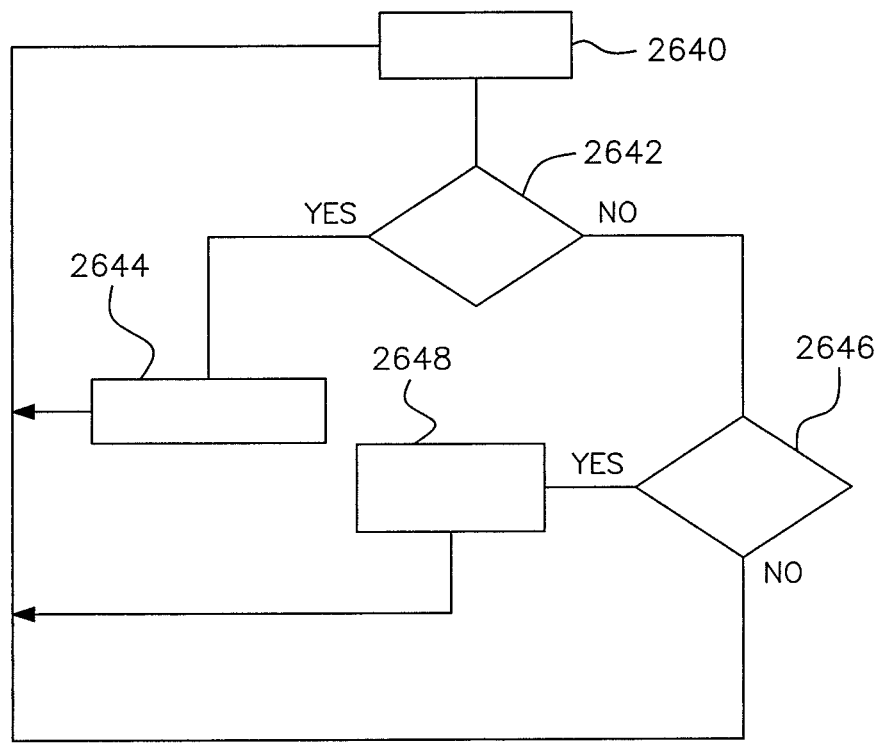
Figures 2, 95C:
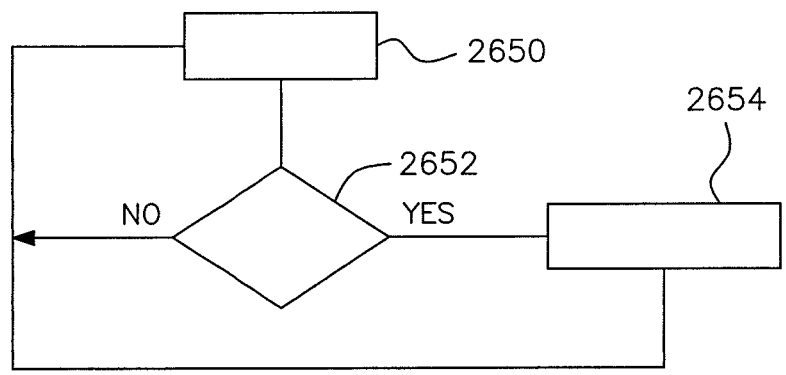

FIG. 95C-1 schematically illustrates an algorithm for heart monitoring.

FIG. 95C-2 schematically illustrates an algorithm for body temperature monitoring.

Figure 95D:
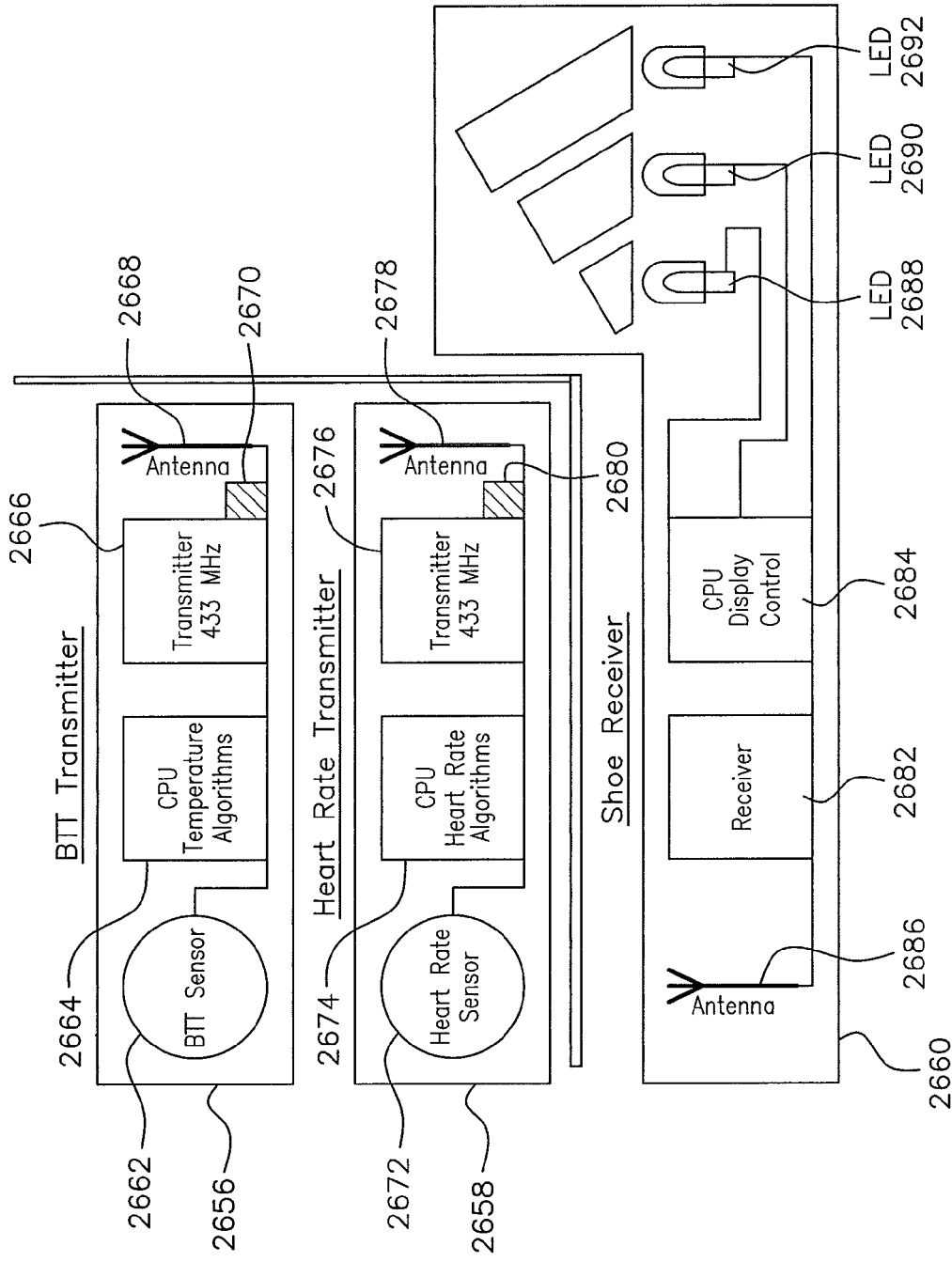

FIG. 95D schematically illustrates a brain temperature tunnel transmitting system, a heart rate transmitting system and a shoe receiving system.

Figure 96:
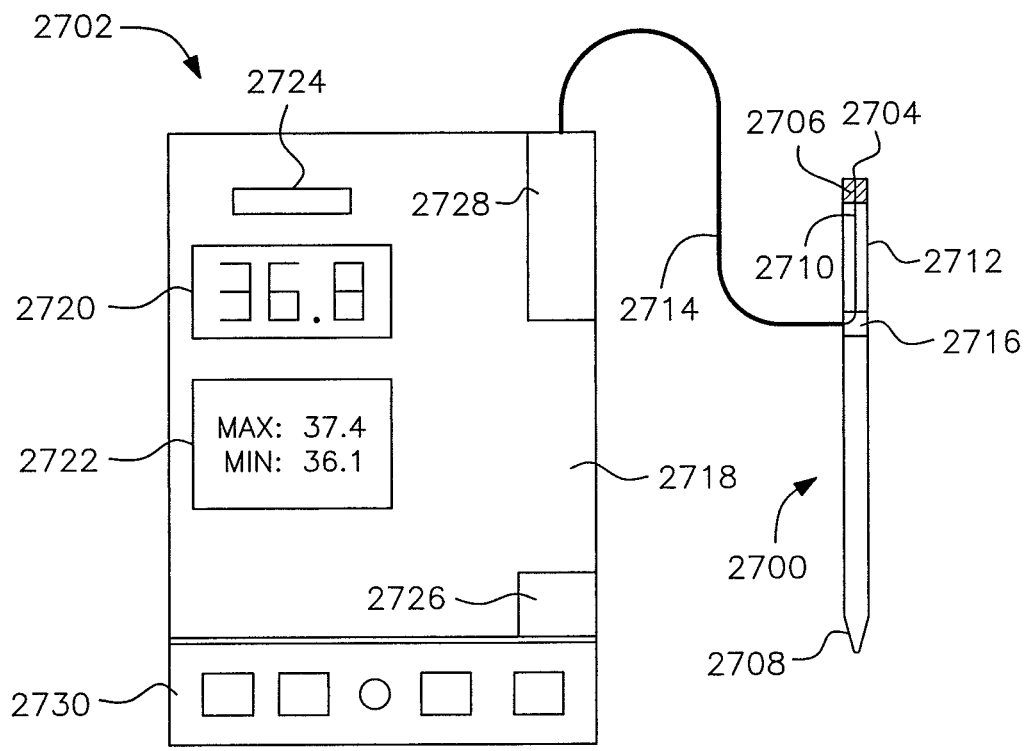

FIG. 96 illustrates an apparatus for measuring biological parameters.

Figure 96A:
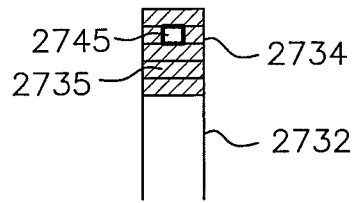

FIG. 96A illustrates a known contact sensing tip of a rod.

Figure 96B:
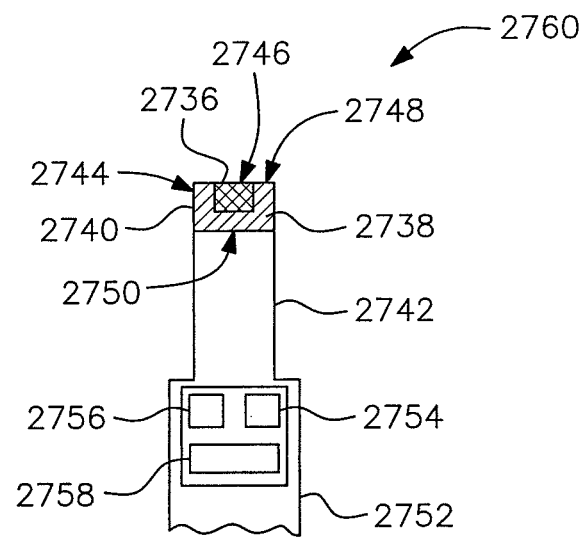

FIG. 96B illustrates a specialized temperature measuring device of the present invention.

FIG. 96C is a schematic perspective view of the tip of the rod.

FIG. 96D illustrates an alternate embodiment of a rod having a sensor.

FIG. 96E is a known thermometer.

FIG. 96F illustrates a sensor housed in an end of a stylus.

FIG. 96-G1 illustrates a glucose sensing device.

FIG. 96-G2 illustrates a specialized cap of a sensing device.

Figure 96H:
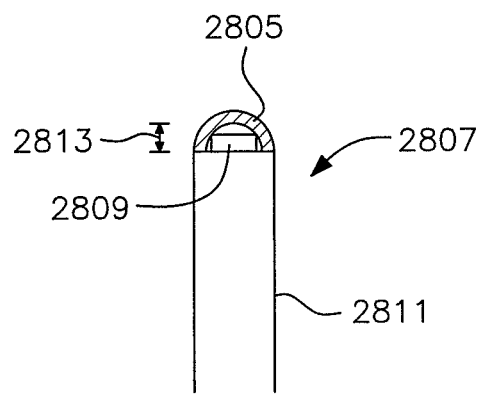

FIG. 96H illustrates a specialized end of a thermometer.

Figure 96J:
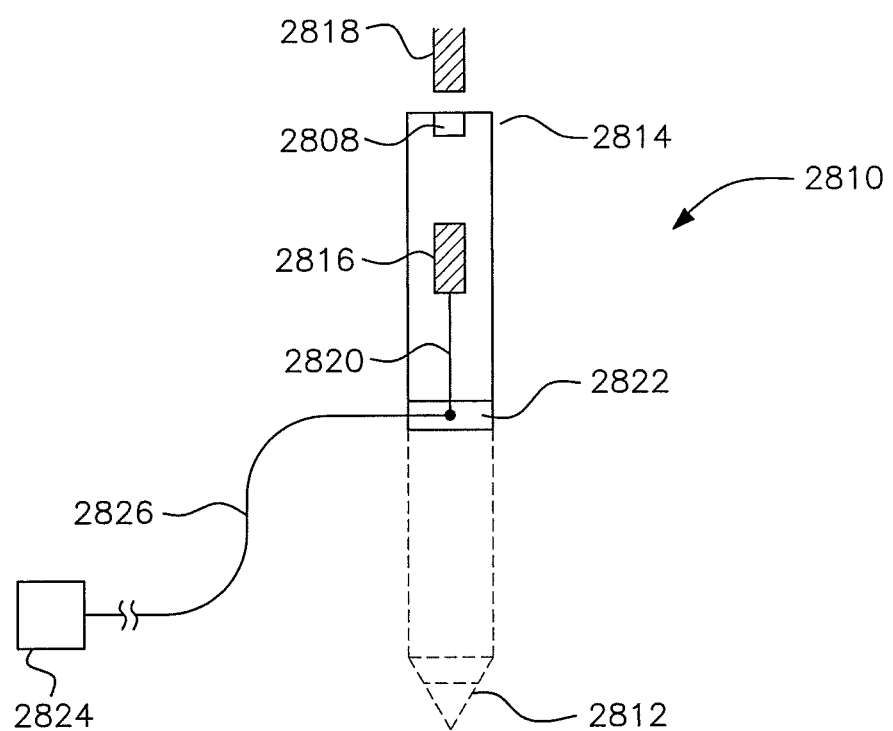

FIG. 96J illustrates a stylus having a touching end and a sensing end.

Figure 96K:
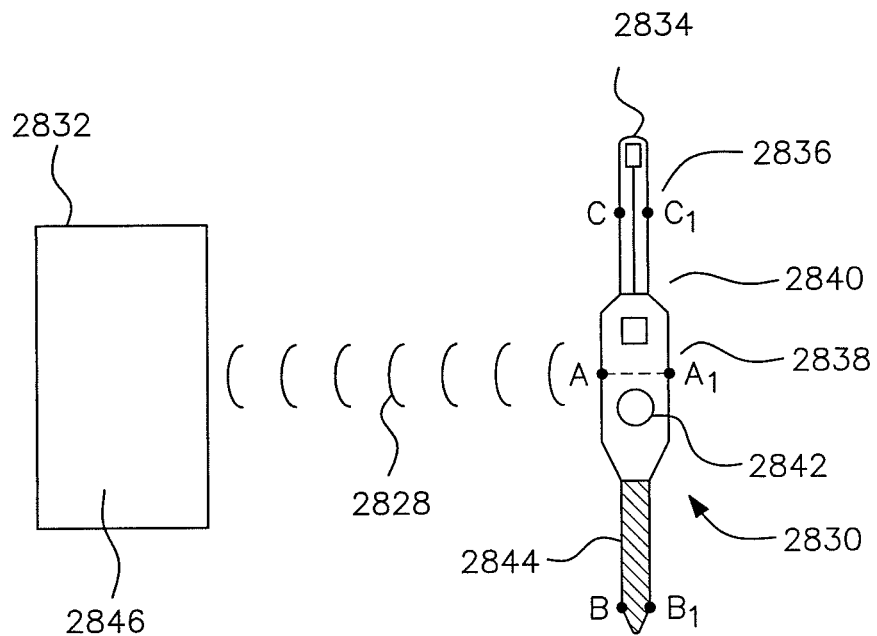

FIG. 96K illustrates a stylus connected by a wireless system with an electronic device.

Figure 96L:
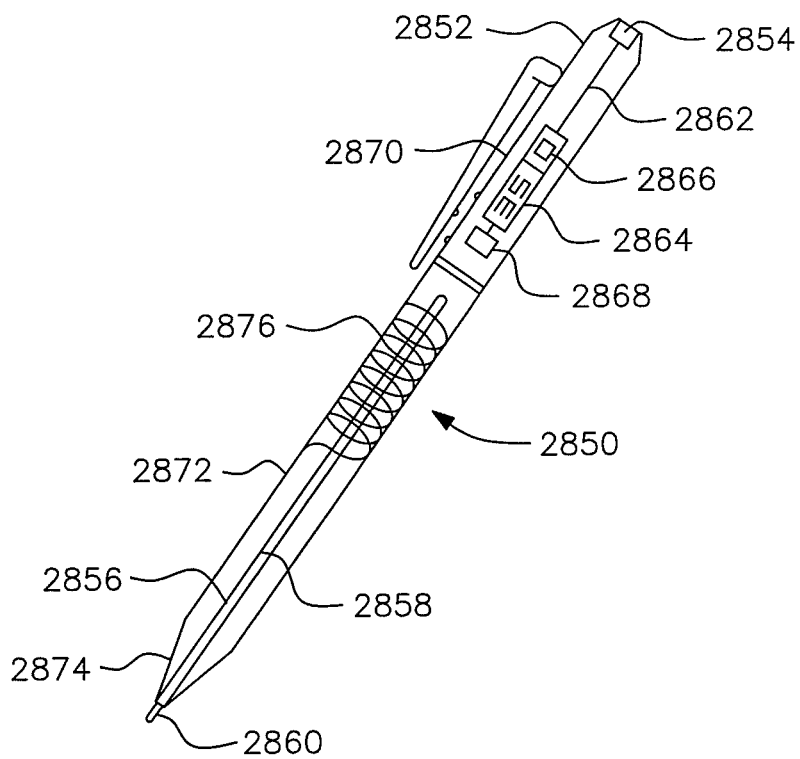

FIG. 96L illustrates a sensing-writing instrument.

Figure 96M:
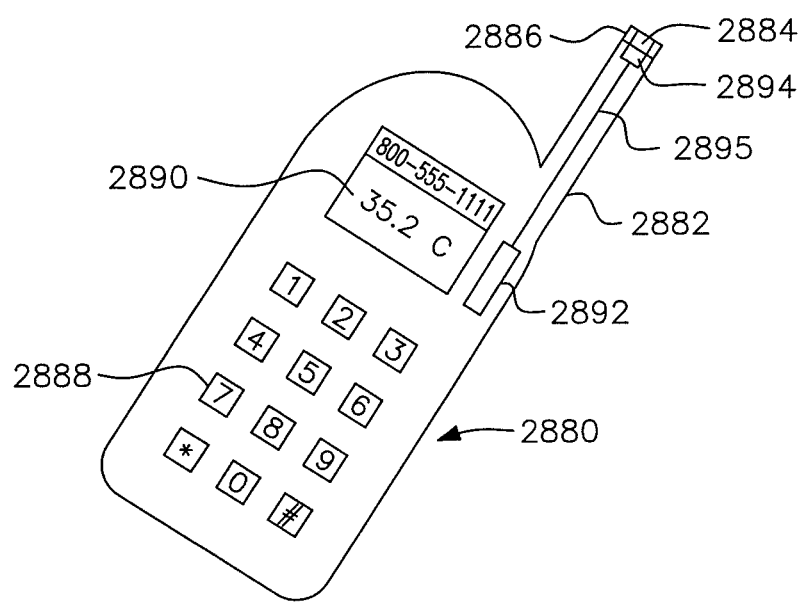

FIG. 96M illustrates a telephone having a sensing antenna.

Figure 96N:
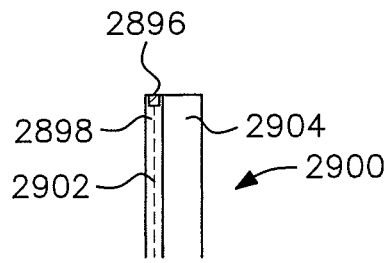

FIG. 96N illustrates a sensing antenna.

Figure 96P:
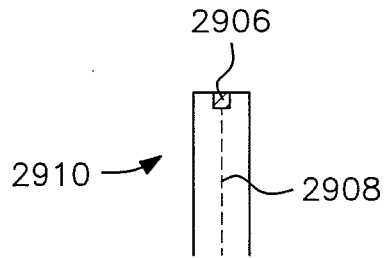

FIG. 96P illustrates a sensing antenna.

FIG. 96Q-1 is a planar view of a rod-like sensing device.

FIG. 96Q-2 is a side view of the rod-like structure.

Figures 1, 96R:
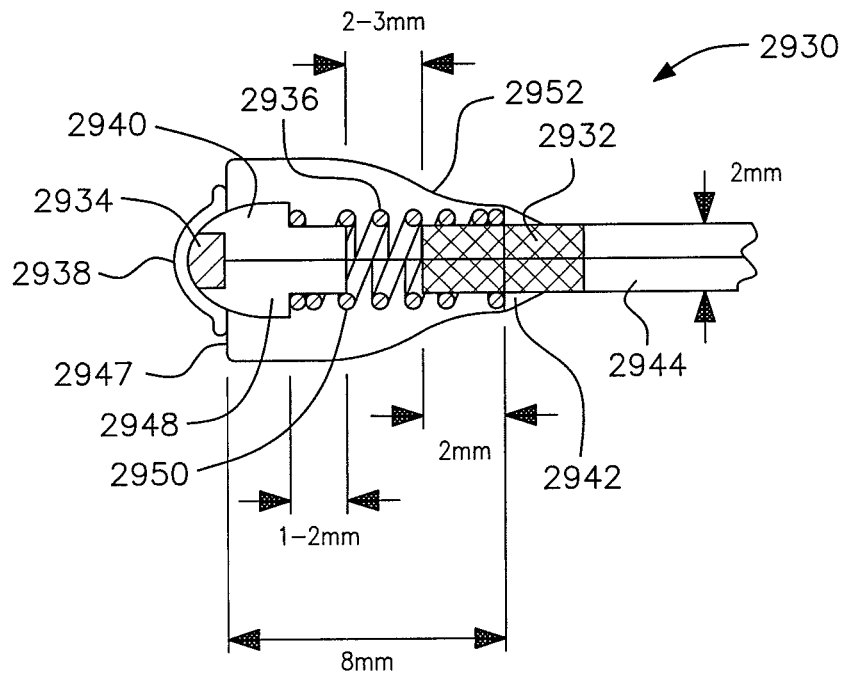
Figures 2, 96R:
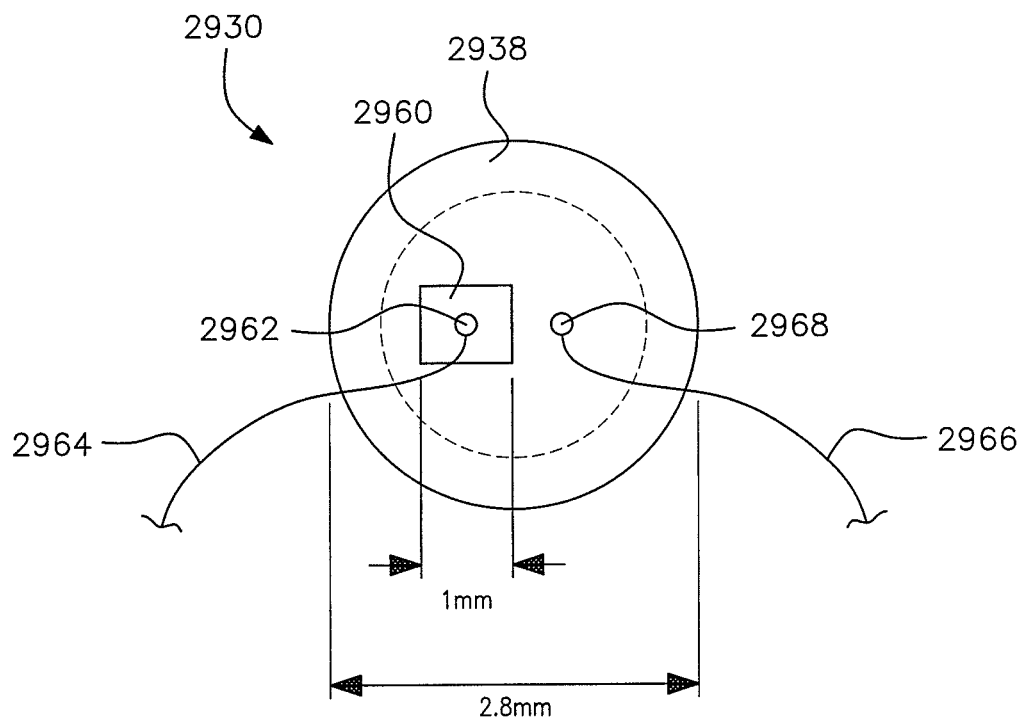
Figures 1, 96S:
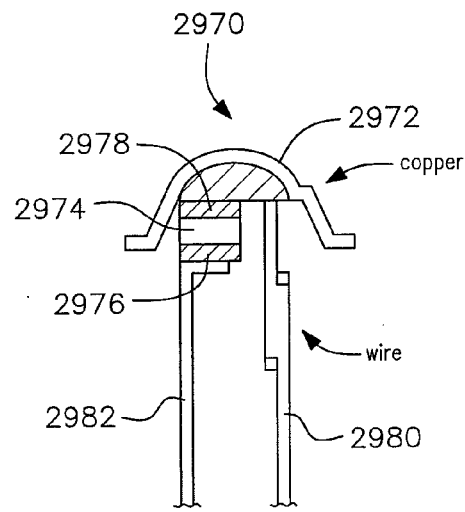
Figures 2, 96S:
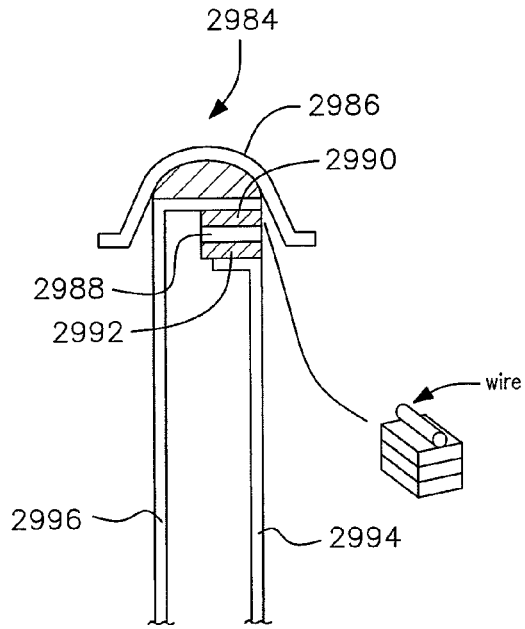
Figures 3, 96S:
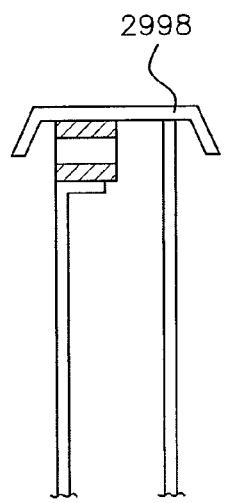

FIG. 96Q-3 illustrates a pair of light emitter-light detector sensors at the end of the rod.

Figures 4, 96S:
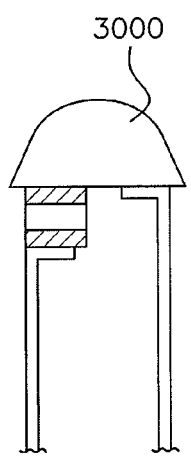
FIG. 4B is a schematic diagram of the image in FIG. 4A.

FIG. 96Q-4 illustrates a projecting light emitter-light detector pair.

FIG. 96R-1 illustrates a spring based measuring portion of a sensing rod.

FIG. 96R-2 is a planar view of the spring based measuring portion.

FIG. 96S-1 illustrates a measuring portion having a convex cap.

FIG. 96S-2 illustrates a measuring portion and a sensor arrangement.

FIG. 96S-3 illustrates a flat cap measuring portion.

FIG. 96S-4 illustrates a solid metal cap sensing portion.

Figures 1, 96T:
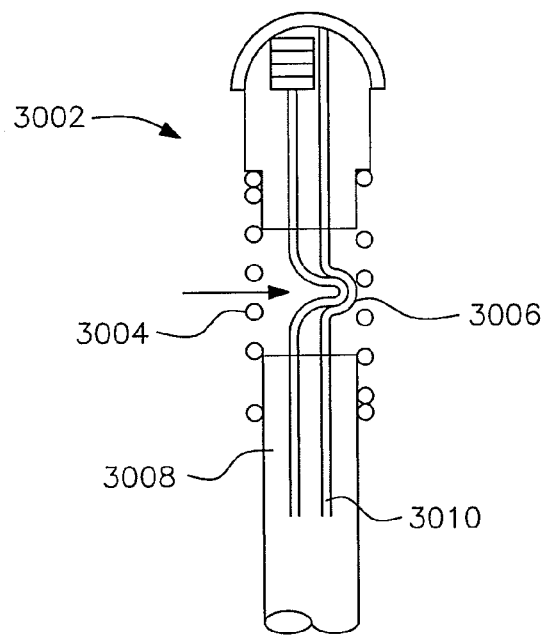
Figures 2, 96T:
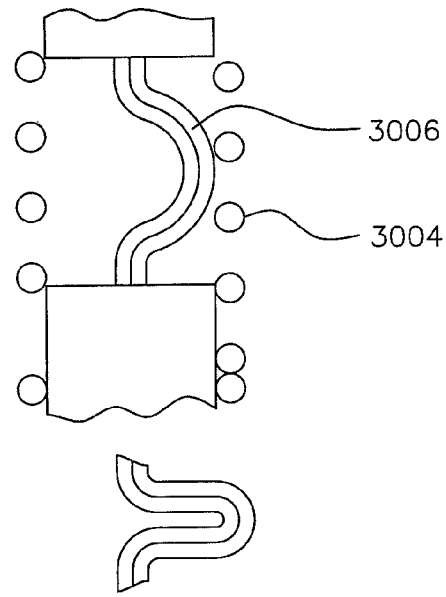

FIG. 96T-1 illustrates a sensor arrangement.

FIG. 96T-2 illustrates a detailed view of a wire portion pressing on a spring in the measuring portion.

Figure 96U:
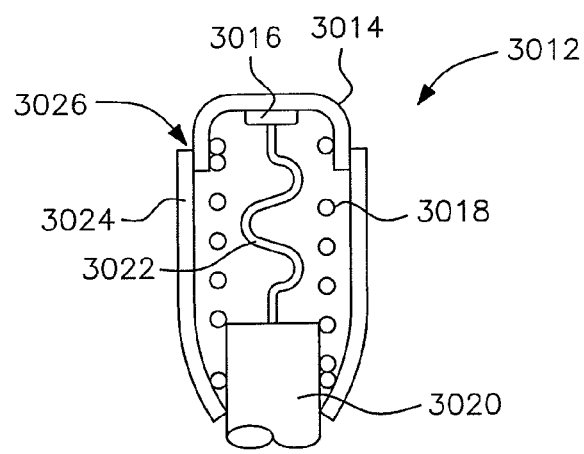

FIG. 96U is a sectional view of a measuring portion or sensing assembly.

Figures 3, 96V:
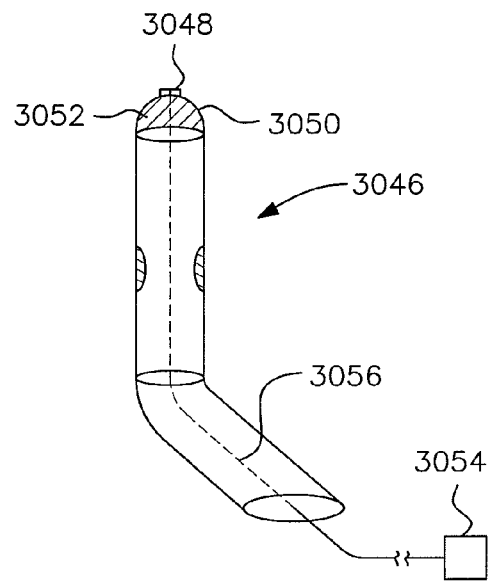
Figures 4, 96V:
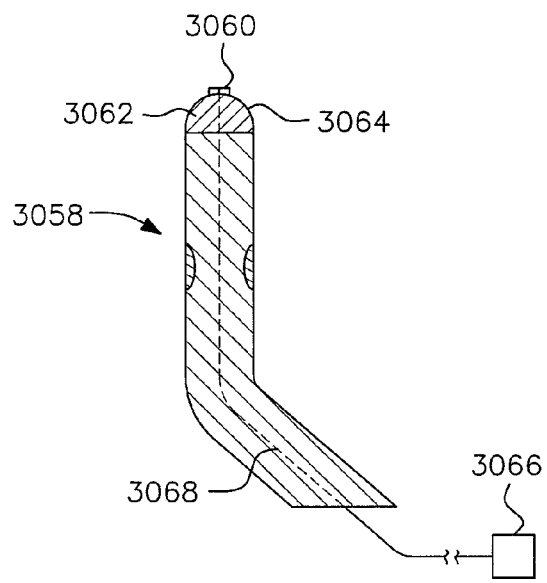

FIG. 96V-1 illustrates a handheld device for measuring biological parameters.

FIG. 96V-2 is an alternate perspective view of the handheld device

FIG. 96V-3 illustrates a handheld probe including a sensing tip.

FIG. 96V-4 illustrates a handheld probe including a barrier to infrared light.

Figures 5, 96V:
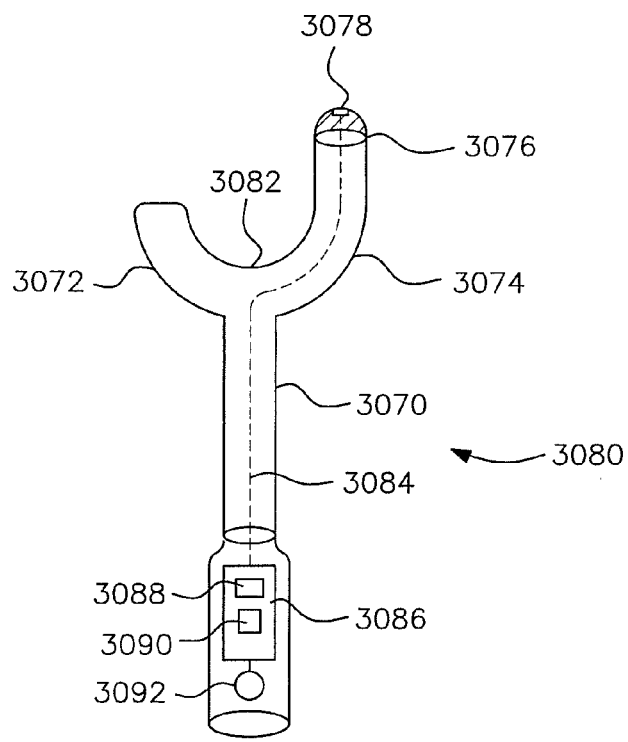
FIG. 5B is a schematic diagram of the image in FIG. 5A.

FIG. 96V-5 illustrates a J-shape configuration of the probe.

Figure 97A:
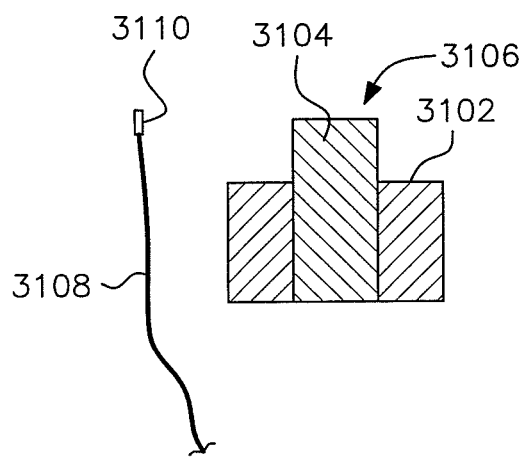

FIG. 97A illustrates a measuring portion in a sensor connected to a wire.

Figure 97B:
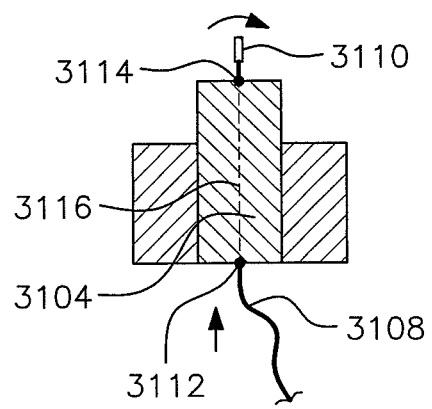

FIG. 97B illustrates a passageway for a sensor and for a wire.

Figure 97C:
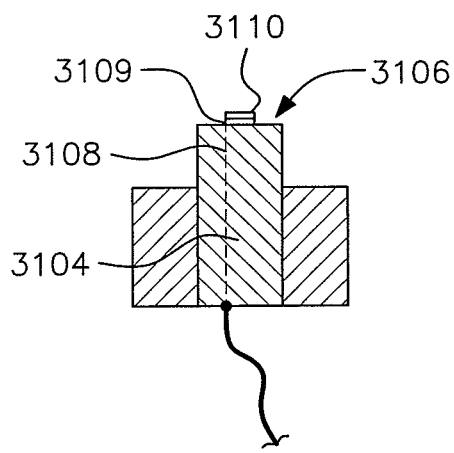

FIG. 97C illustrates a bending of the end of the wire of the sensor.

Figure 97D:
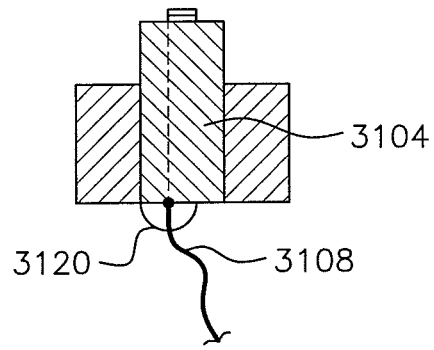

FIG. 97D illustrates securing of the wire.

Figure 97H:
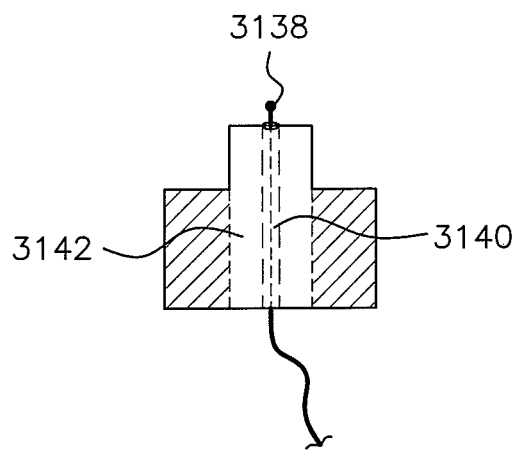
Figure 97E:
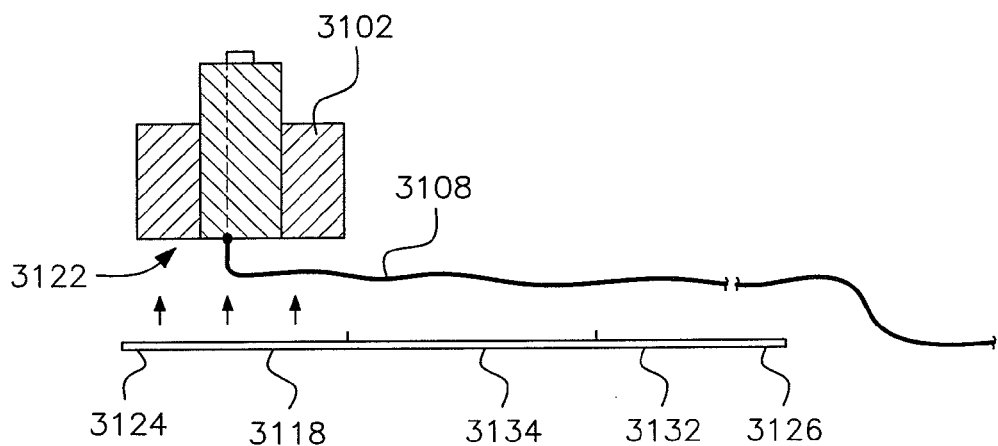

FIG. 97E illustrates a plate disposed along the lower portion of a measuring portion.

Figure 97F:
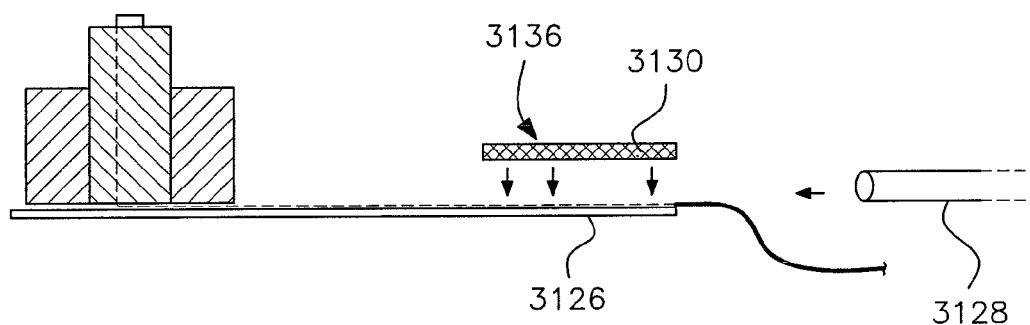

FIG. 97F illustrates insertion of a rubberized sleeve and subsequent heat shrinking of the sleeve.

Figure 97G:
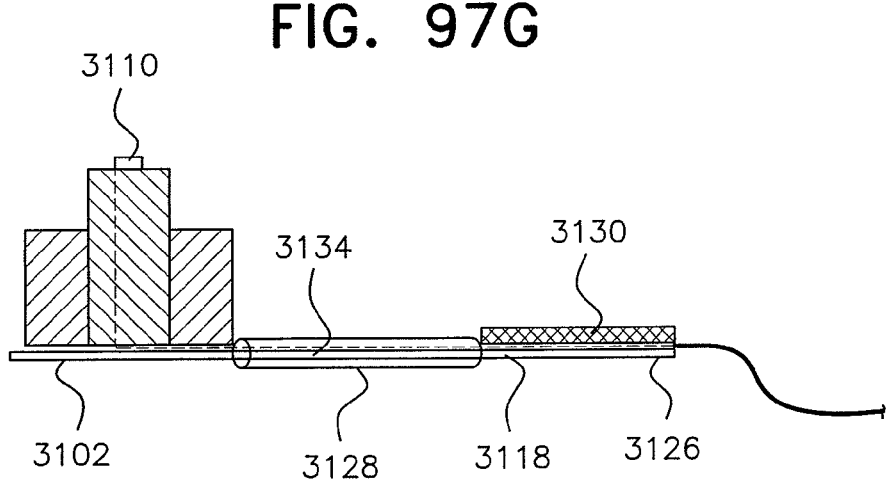

FIG. 97G illustrates a finished sensing device.

FIG. 97H shows an enlarged sensor and wire inserted through a passageway.

Figure 97J:
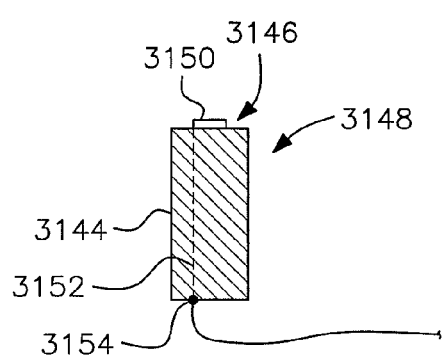

FIG. 97J illustrates a measuring portion of a sensing assembly.

Figures 1, 97K:
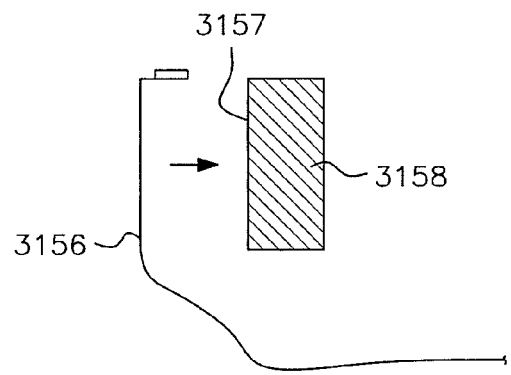
Figures 2, 97K:
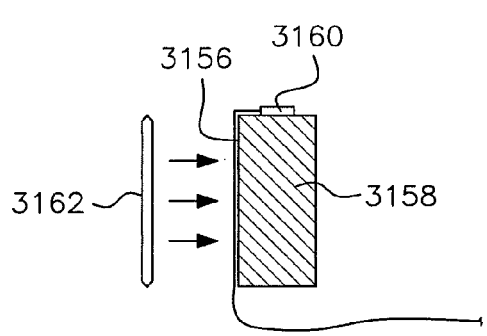

FIG. 97K-1 illustrates a wire adjacent to a support structure of a sensing assembly.

FIG. 97K-2 illustrates the manufacturing step of attaching a wire to the support structure.

Figure 97L:
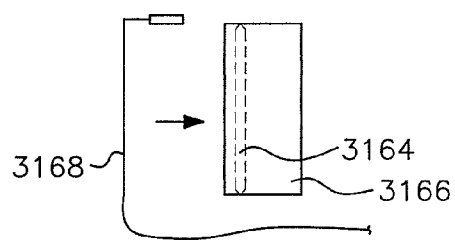

FIG. 97L illustrates passing a wire through a slit in a support structure.

Figures 1, 97M:
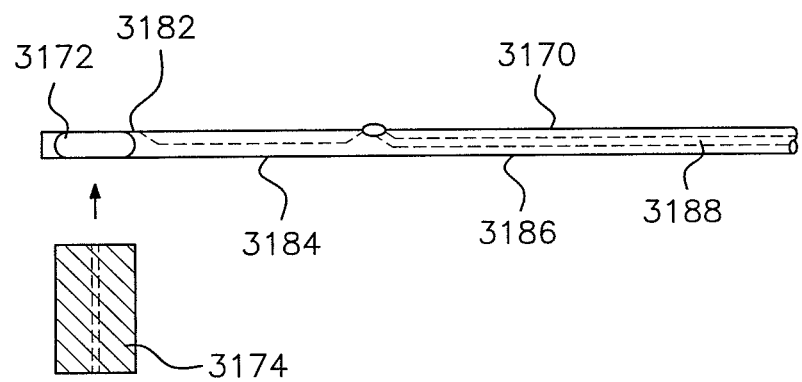
Figures 2, 97M:
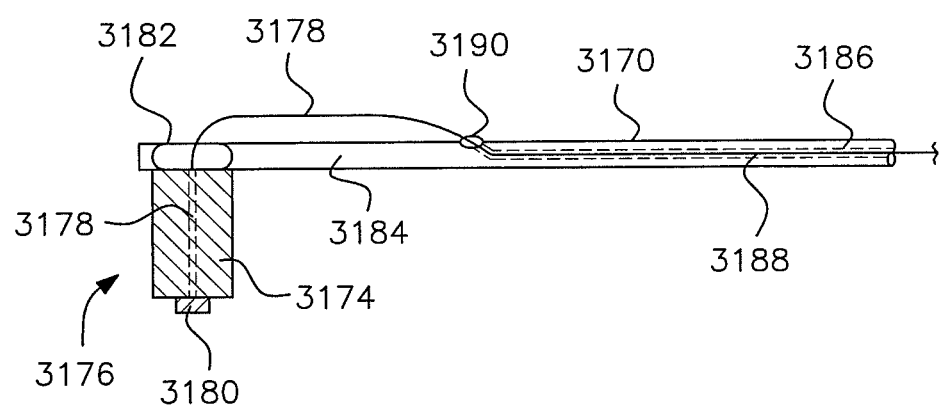

FIG. 97M-1 illustrates a perforated plate for receiving a measuring portion of a measuring assembly.

FIG. 97M-2 illustrates a measuring portion of a sensing assembly.

Figure 98A:
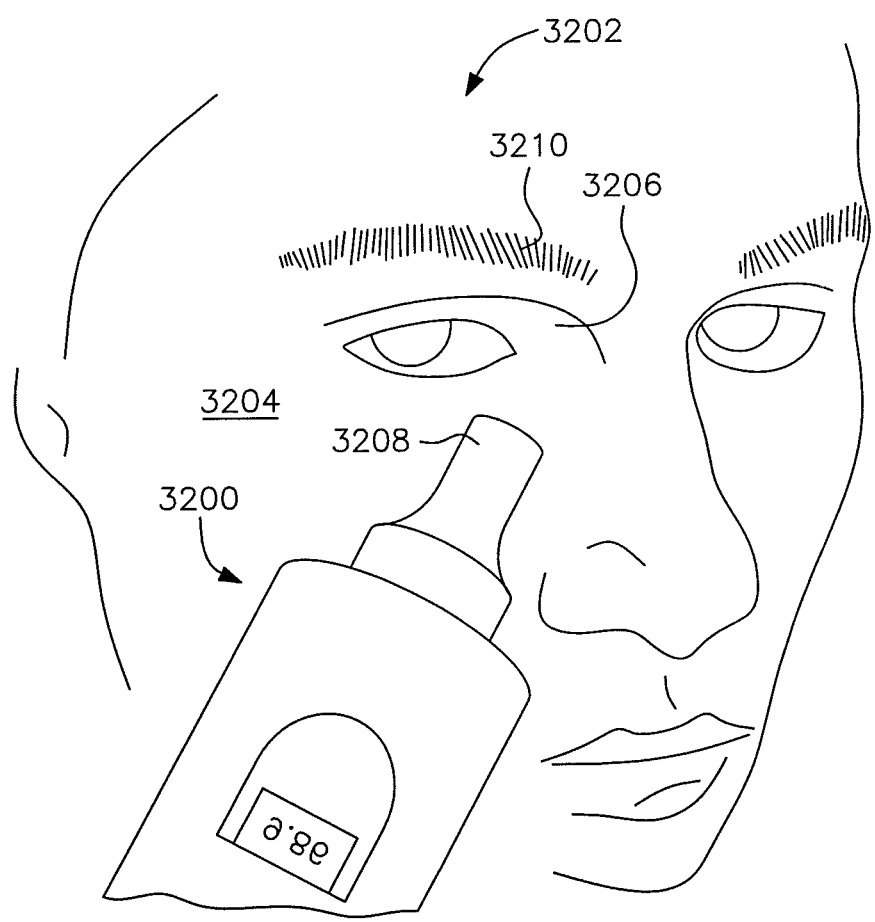

FIG. 98A illustrates a handheld radiation detector approaching the face of a user.

Figure 99A:
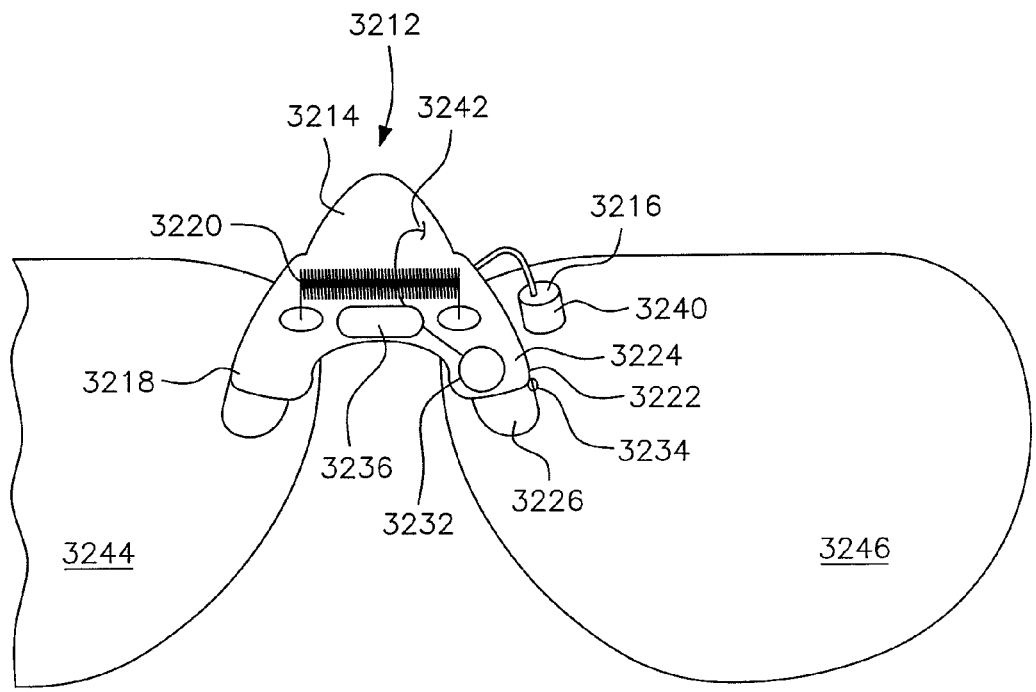

FIG. 99A illustrates a sensing clip for mounting on a pair of eyeglasses.

Figure 99B:
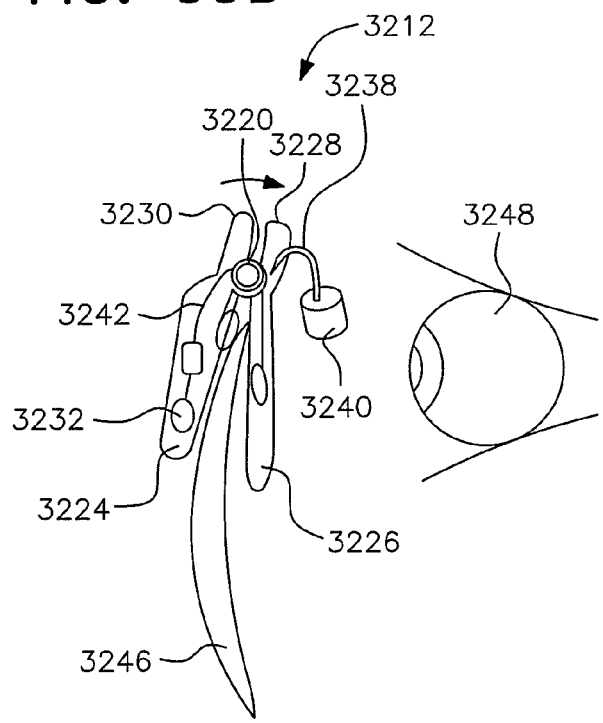

FIG. 99B is a side view of the mounting clip shown on FIG. 99A.

FIG. 99C illustrates a sensing clip including a sensor.

FIG. 99D is a side view of the sensing clip shown in FIG. 99C.

FIG. 99E illustrates the sensing clip in an open position.

FIG. 99F illustrates a tension bar in a rest position.

FIG. 99G is a side view of the sensing device shown in FIG. 99F.

FIG. 99H is a side view of the tension bar in an open position.

Figure 99J:
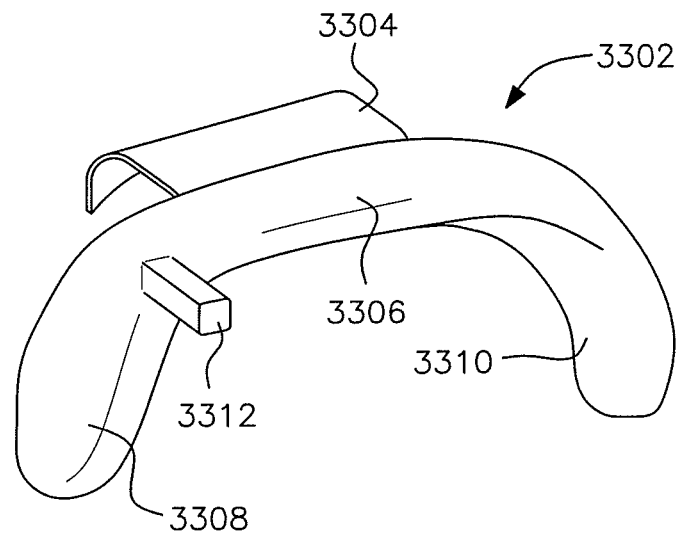

FIG. 99J illustrates a sensing device to be secured to the frame of eyeglasses.

Figure 99K:
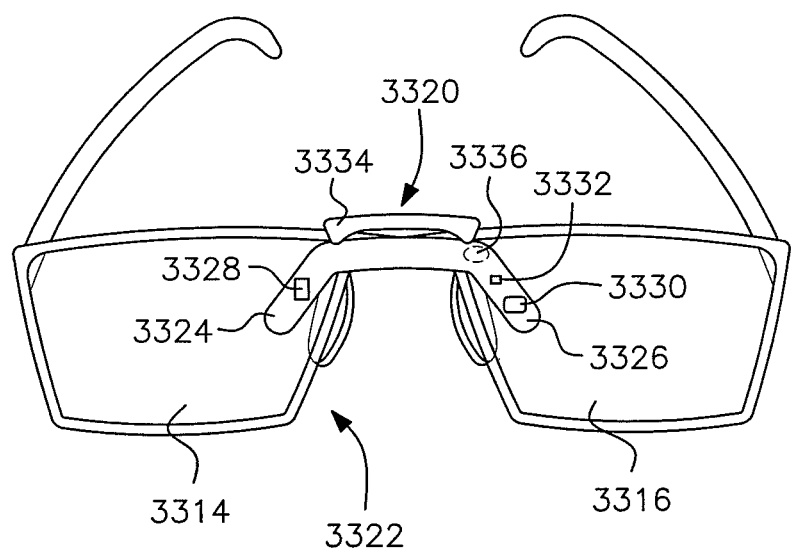

FIG. 99K illustrates a sensing device mounted on a pair of eyeglasses.

Figure 99L:
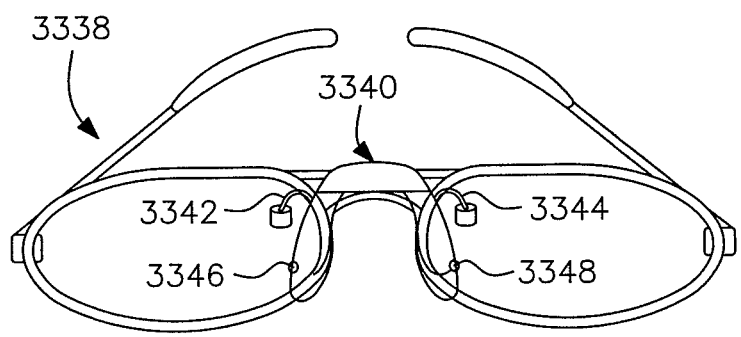

FIG. 99L illustrates a sensing device clipped to a pair of eyeglasses.

Figure 99M:
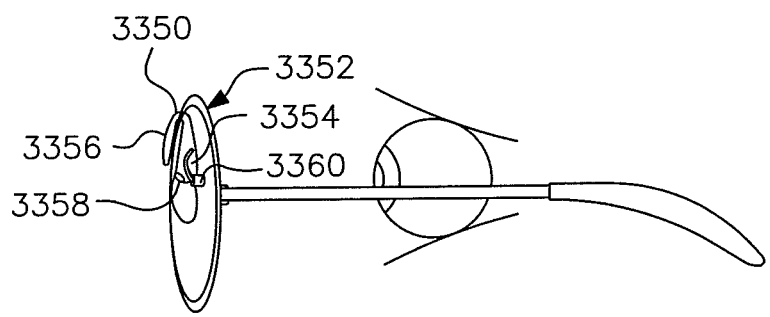

FIG. 99M illustrates a sensing device secured to the frame of a pair of eyeglasses.

Figures 1, 99N:
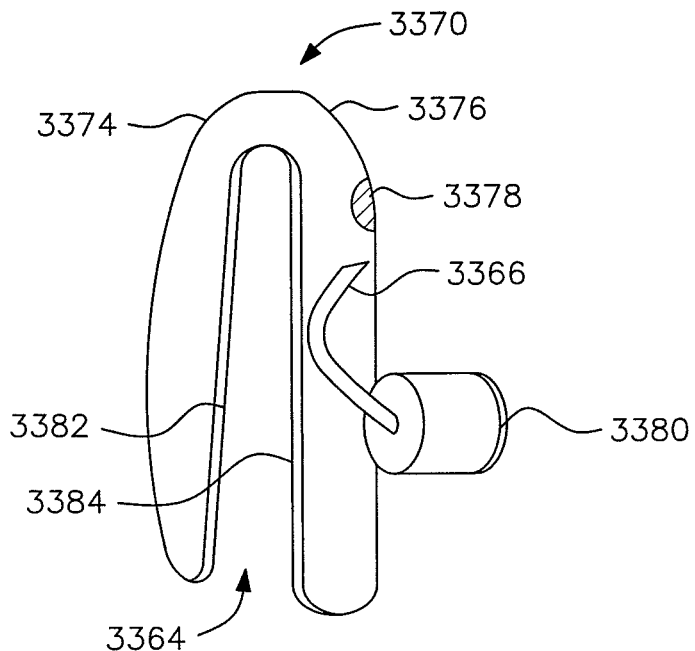
Figures 2, 99N:
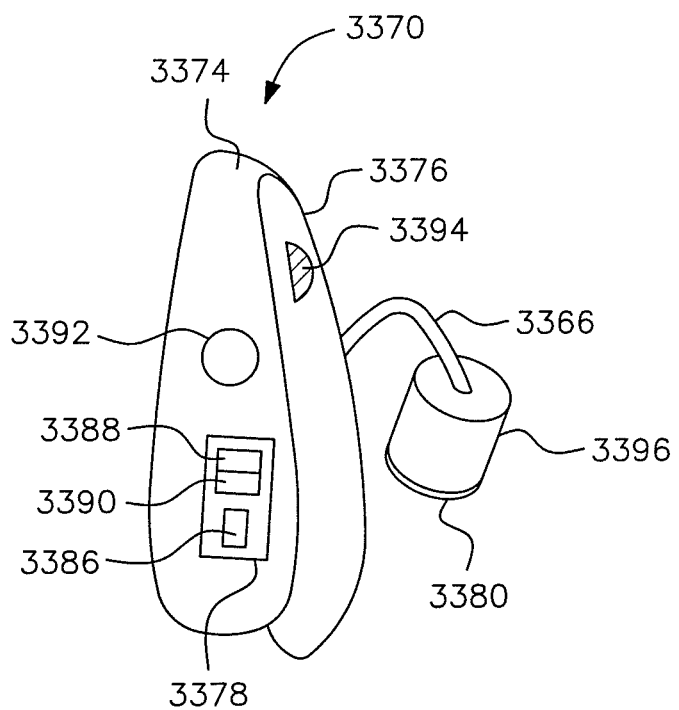
Figures 3, 99N:
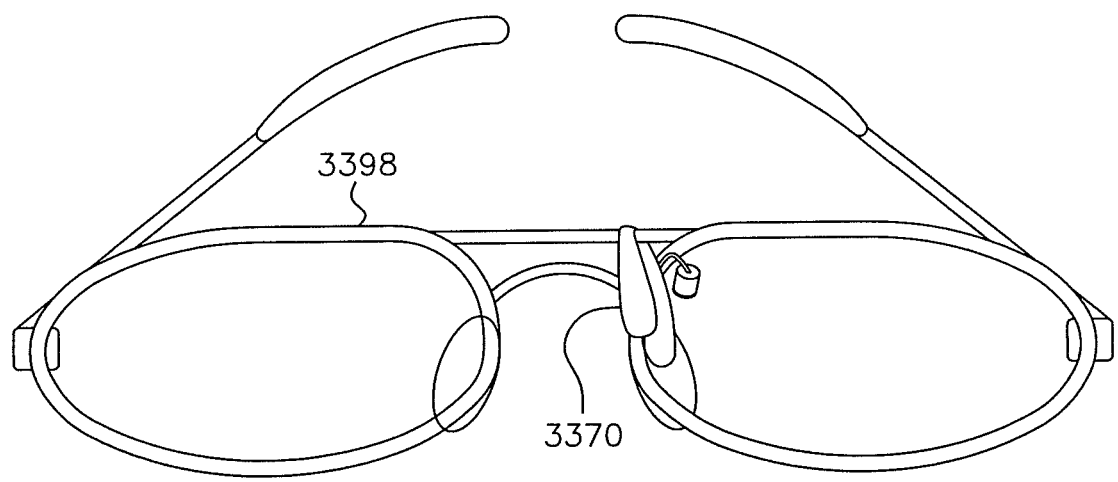

FIG. 99N-1 is a side view of a sensing device.

FIG. 99N-2 is a front view of the sensing clip device of FIG. 99N-1.

FIG. 99N-3 illustrates the mounting of the sensing clip device on a pair of eyeglasses.

Figure 99P:
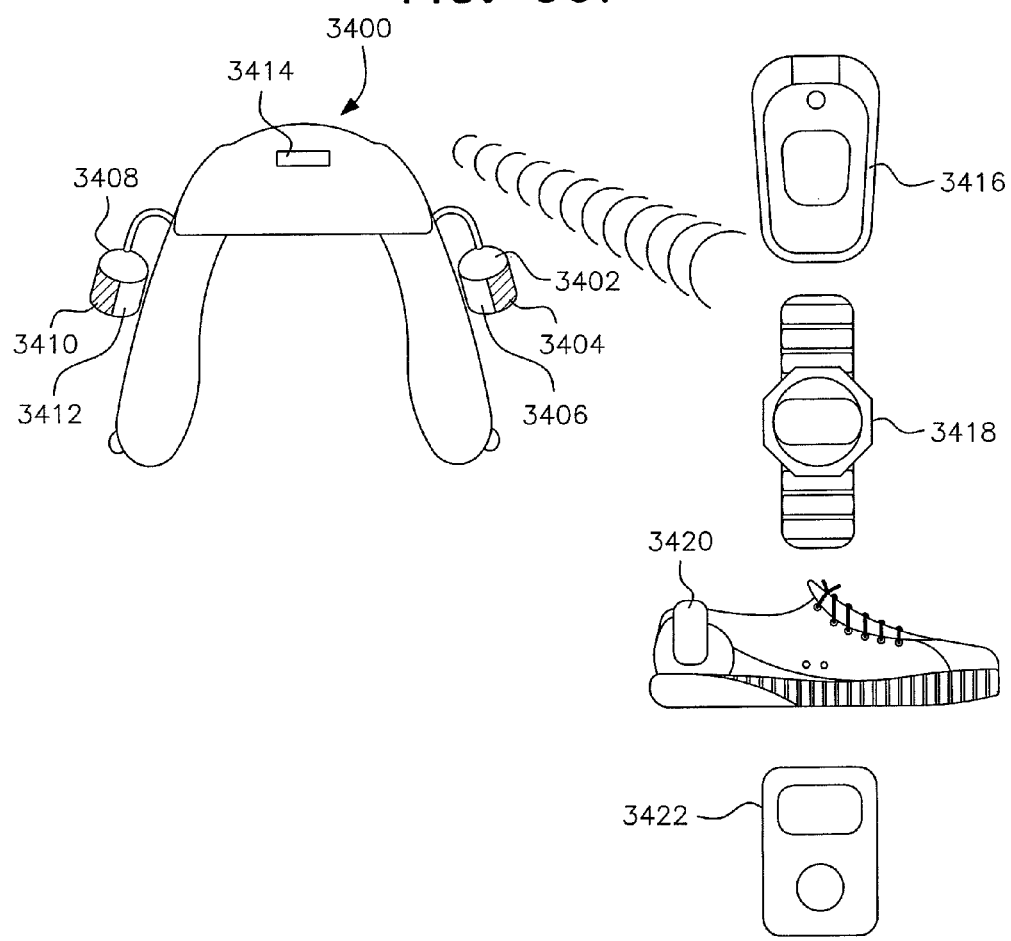

FIG. 99P is a front view of a dual sensing clip and its interaction with a plurality of devices.

Figure 100A:
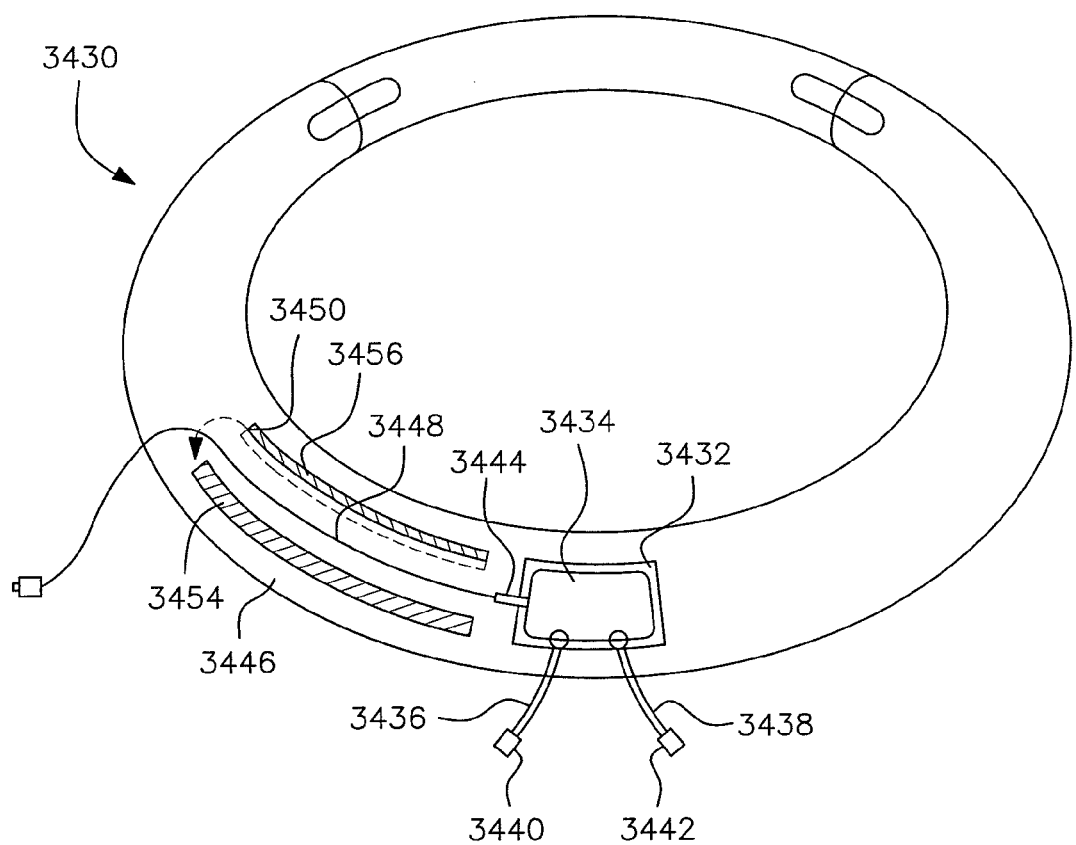

FIG. 100A illustrates a headband receiving a housing removably attached to the headband.

FIG. 100B illustrates a detailed view of a brain temperature tunnel temperature module.

FIG. 100C illustrates the wearing of a sensing modular headband.

Figure 100D:
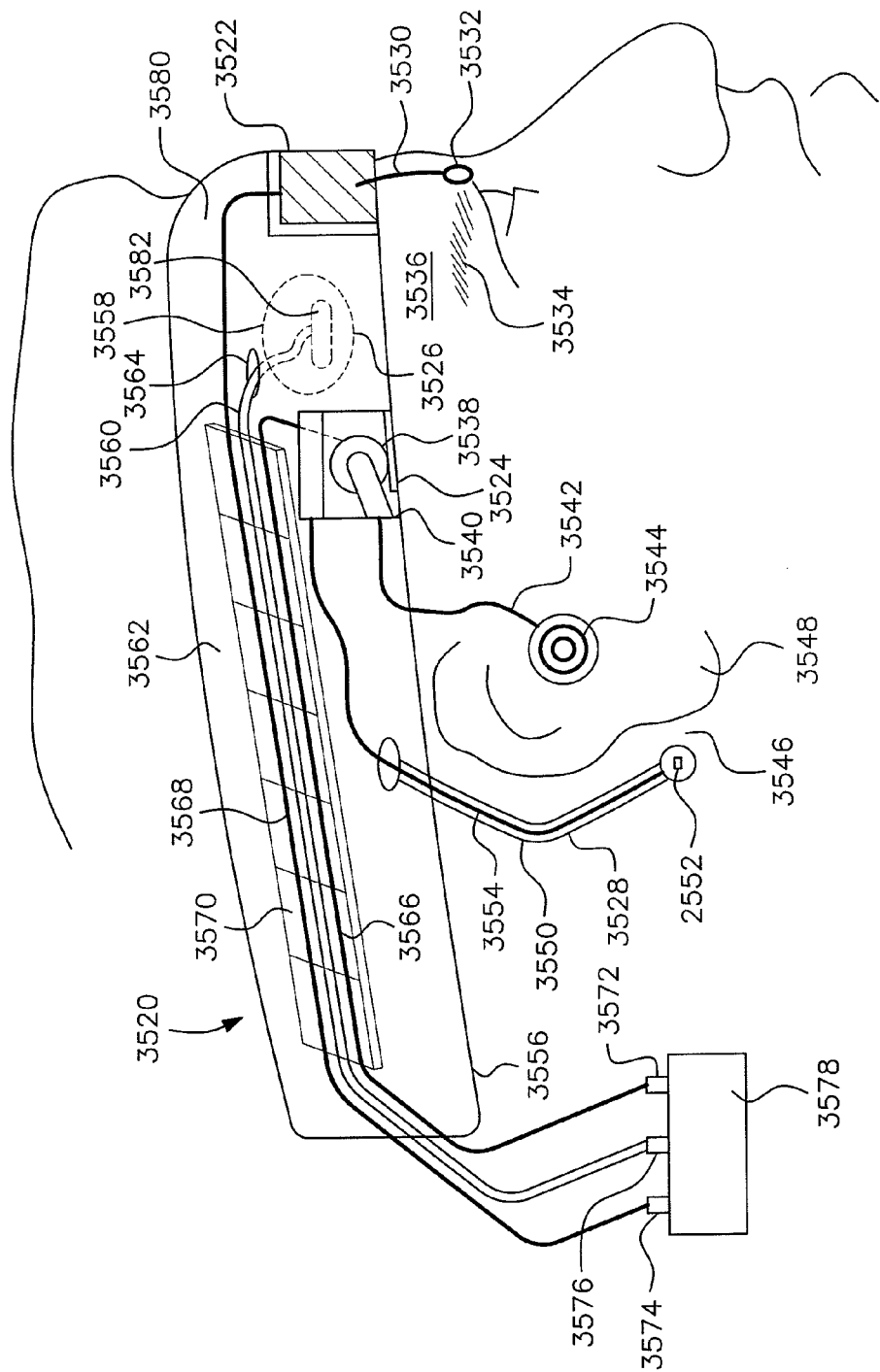

FIG. 100D illustrates an alternate embodiment of a sensing modular headband.

Figure 100E:
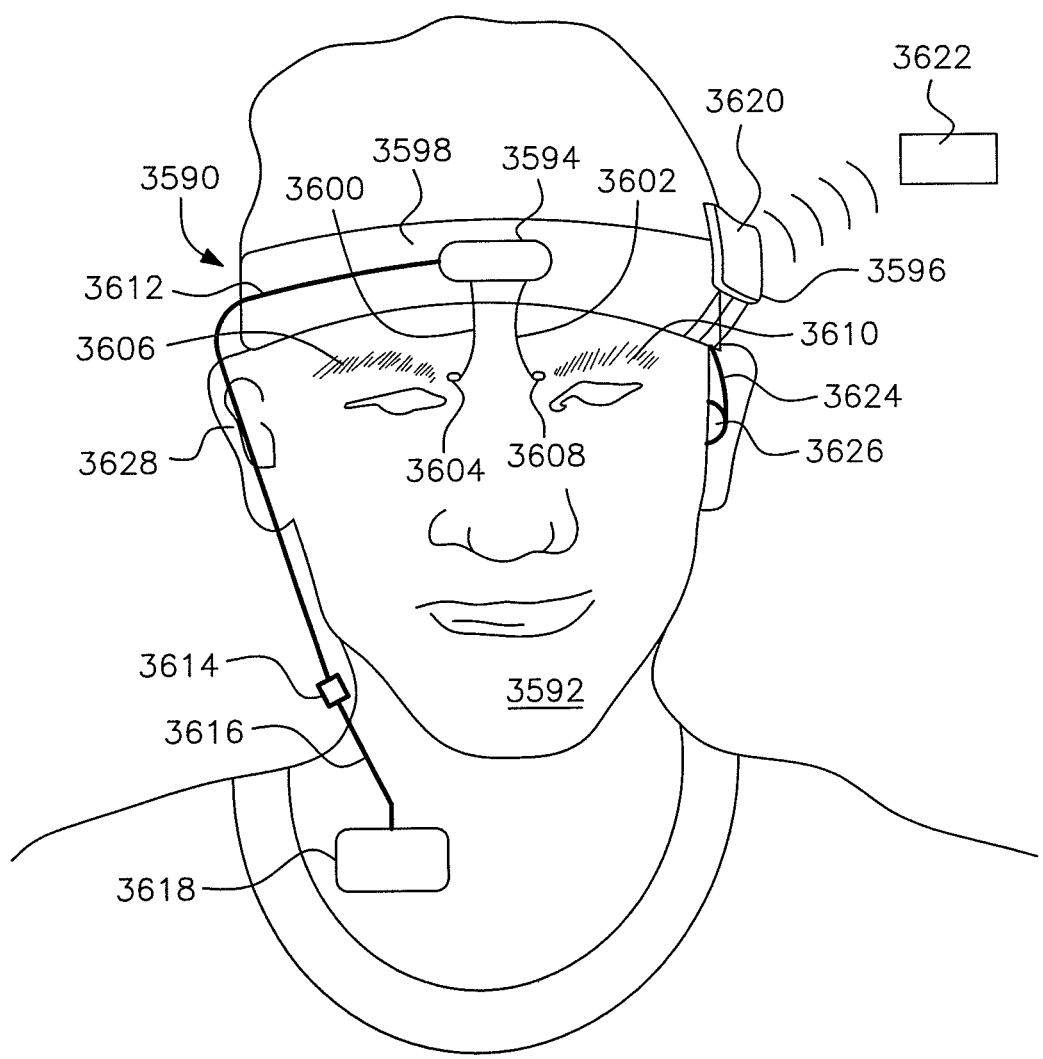

FIG. 100E illustrates another embodiment of a sensing modular headband.

FIG. 100F illustrates a sensing modular headband having eight biologic parameter modules.

FIG. 100G is a sectional view of a sensing modular headband.

FIG. 100H is a planar view of a sensing modular headband.

FIG. 100J illustrates the disposition of modules on an external surface of a sensing modular headband.

FIG. 100K is an external view of a sensing modular headband.

FIG. 100L illustrates an adhesive surface of an internal area of a sensing modular headband.

Figure 100M:
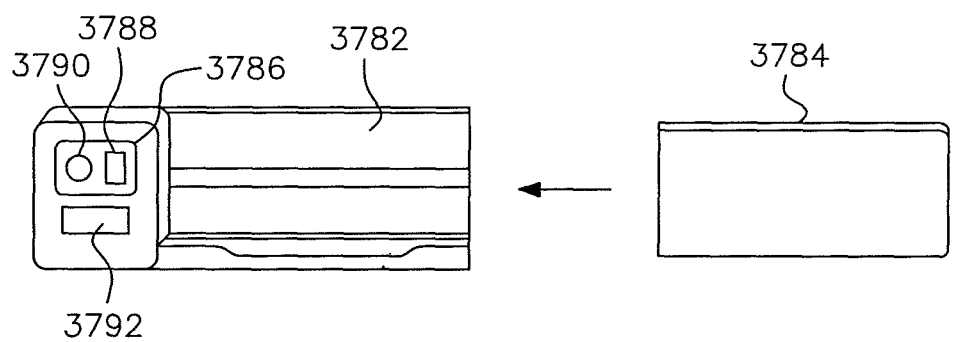

FIG. 100M illustrates a cavity for receiving a module in a sensing modular headband.

Figure 100N:
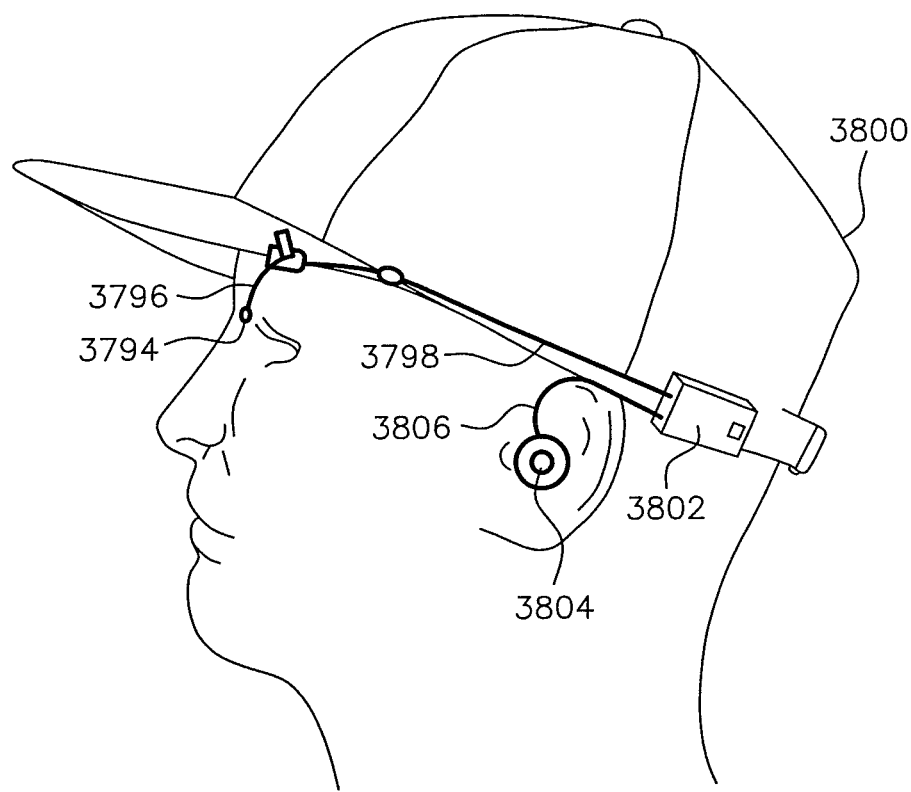

FIG. 100N illustrates a cap worn by a user including a sensing assembly.

Figure 100P:
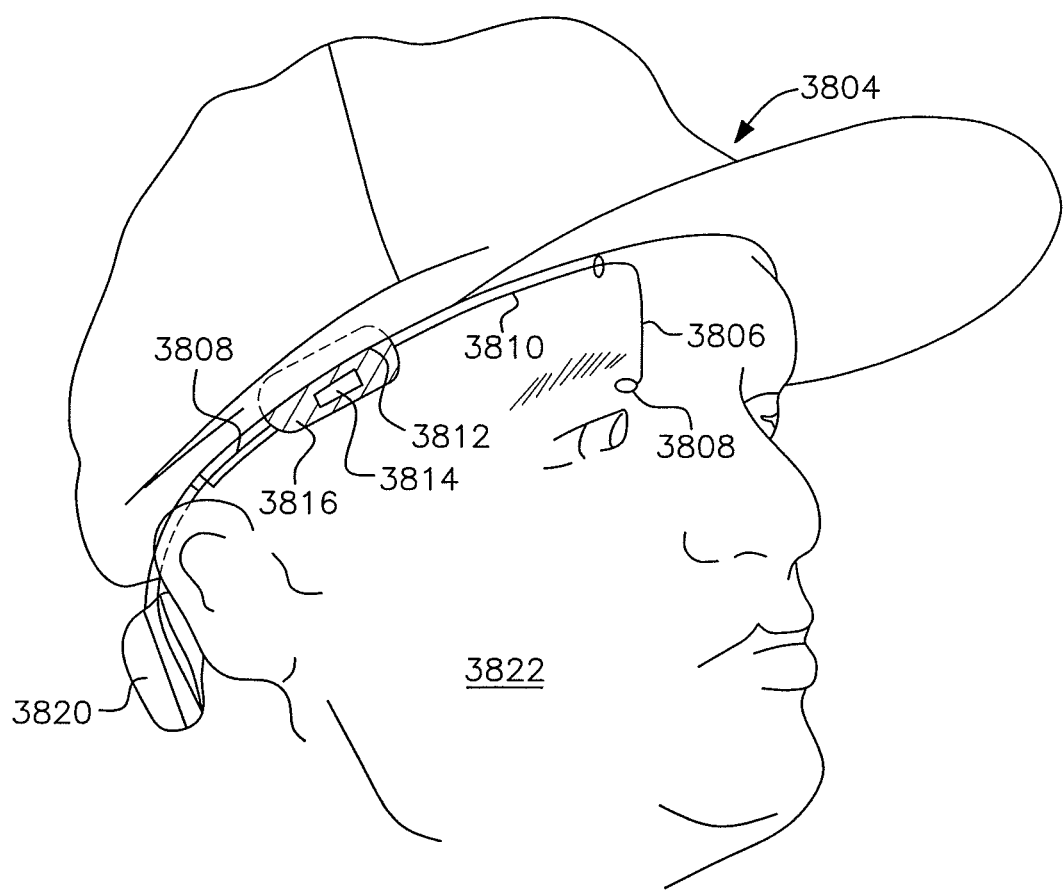

FIG. 100P illustrates a cap worn by a user including a sensing assembly.

Figure 100Q:
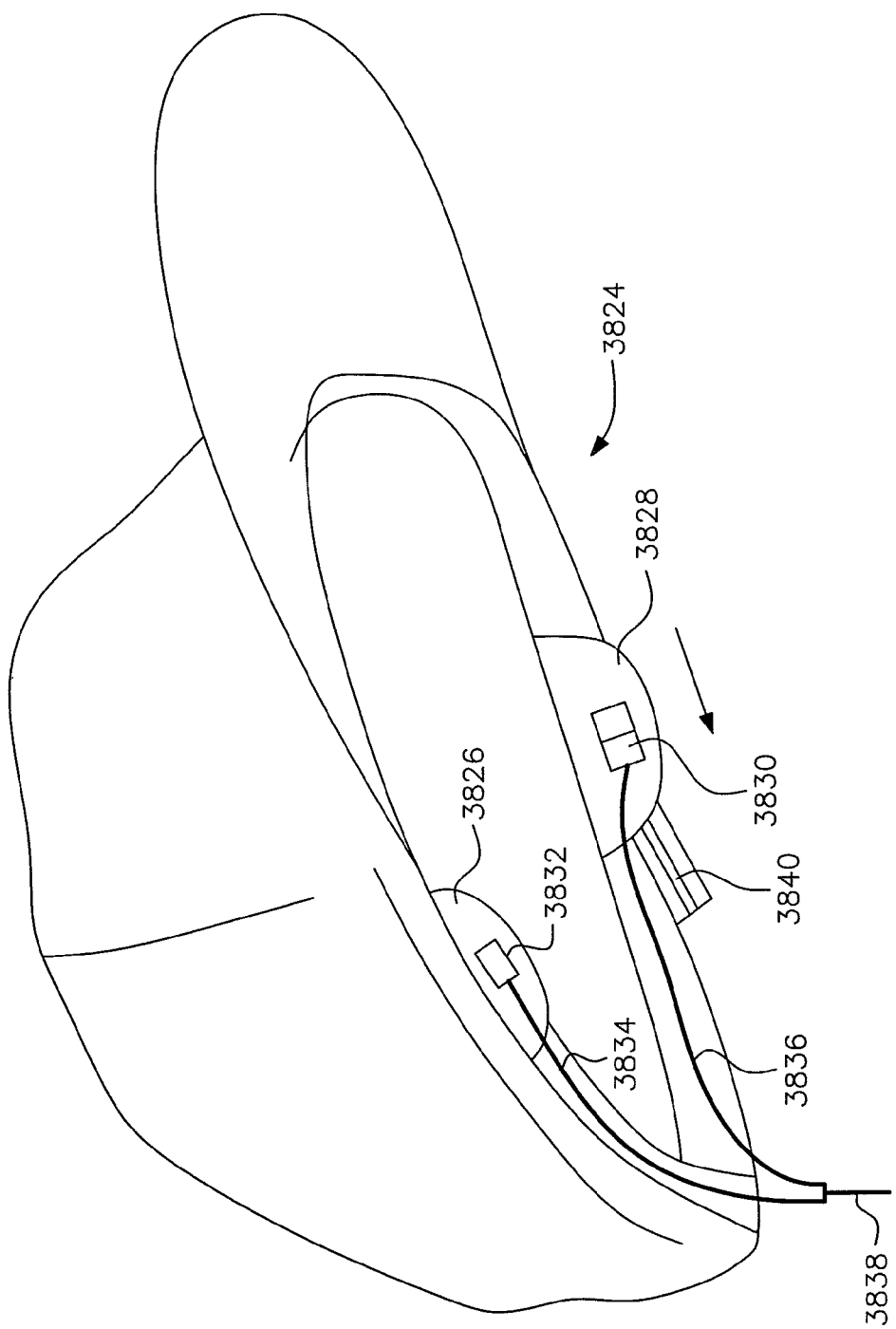

FIG. 100Q illustrates a cap worn by a user including a sensing assembly.

Figure 100R:
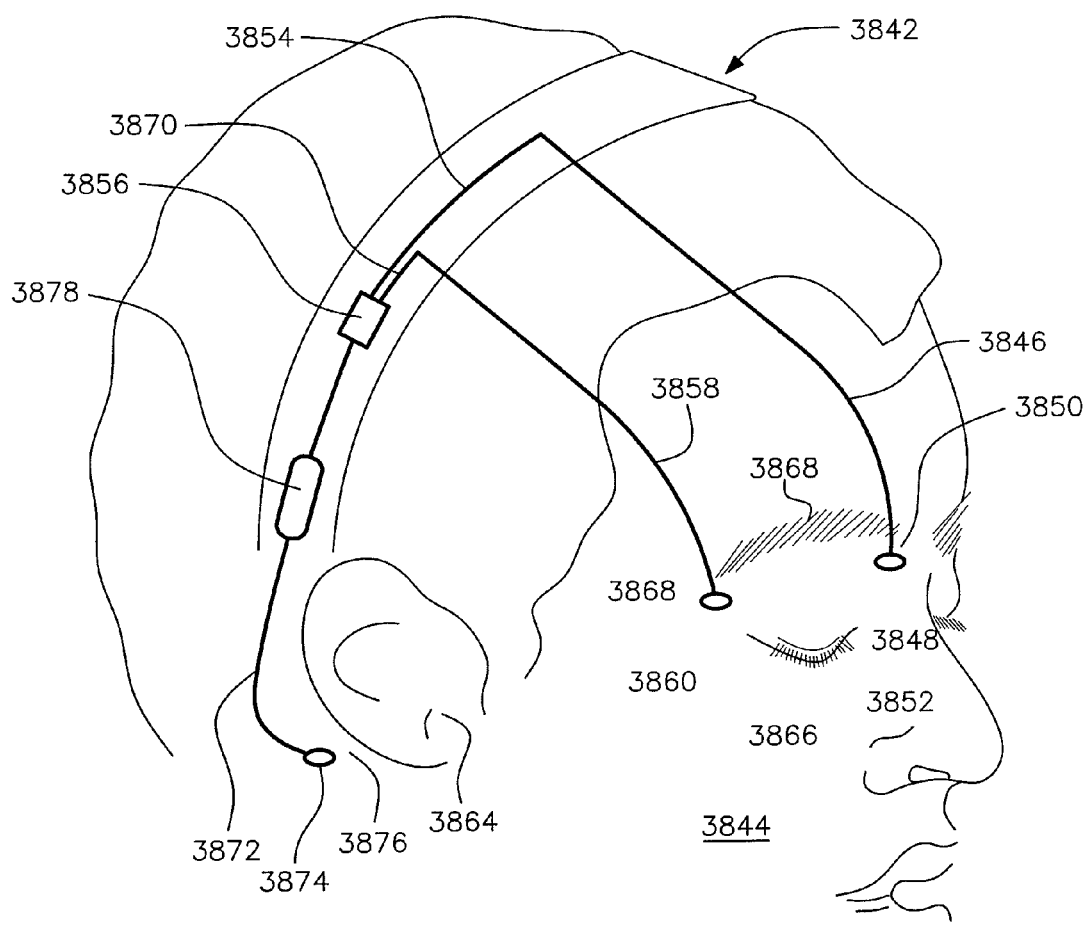

FIG. 100R illustrates head mounted gear including a sensing assembly.

Figure 100S:
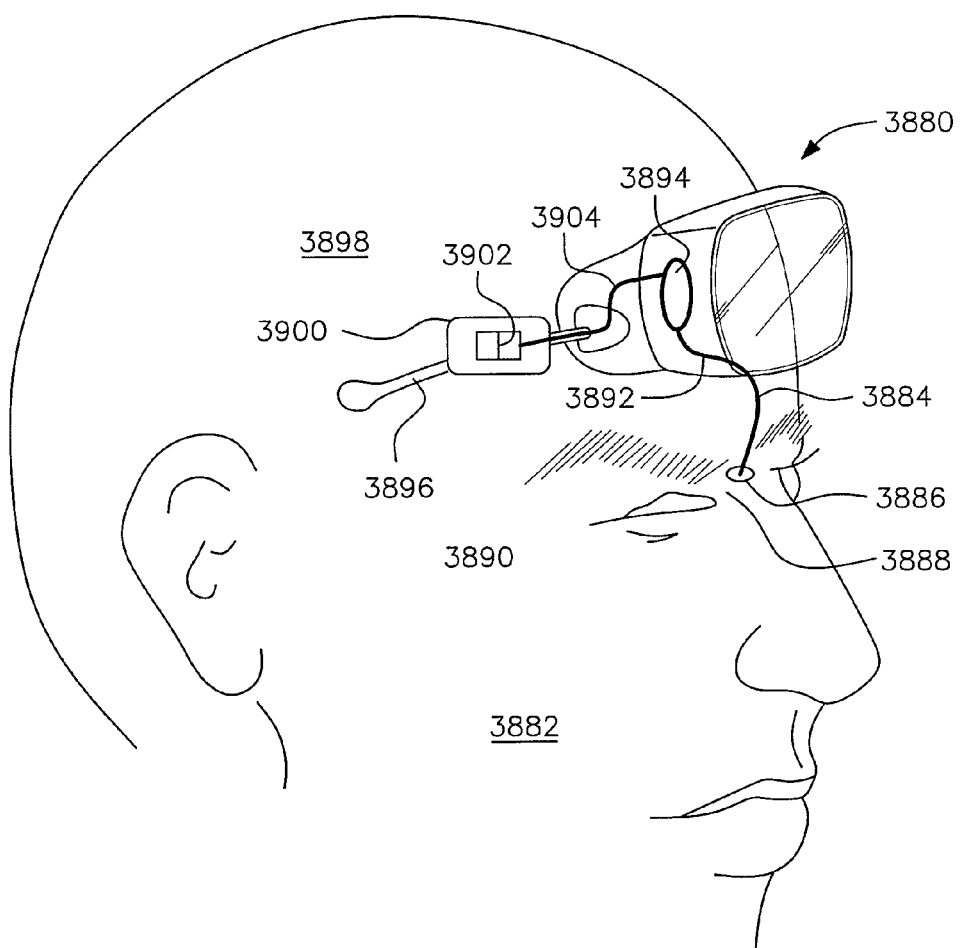

FIG. 100S illustrates head mounted gear having a light source and a sensing assembly.

Figure 100T:
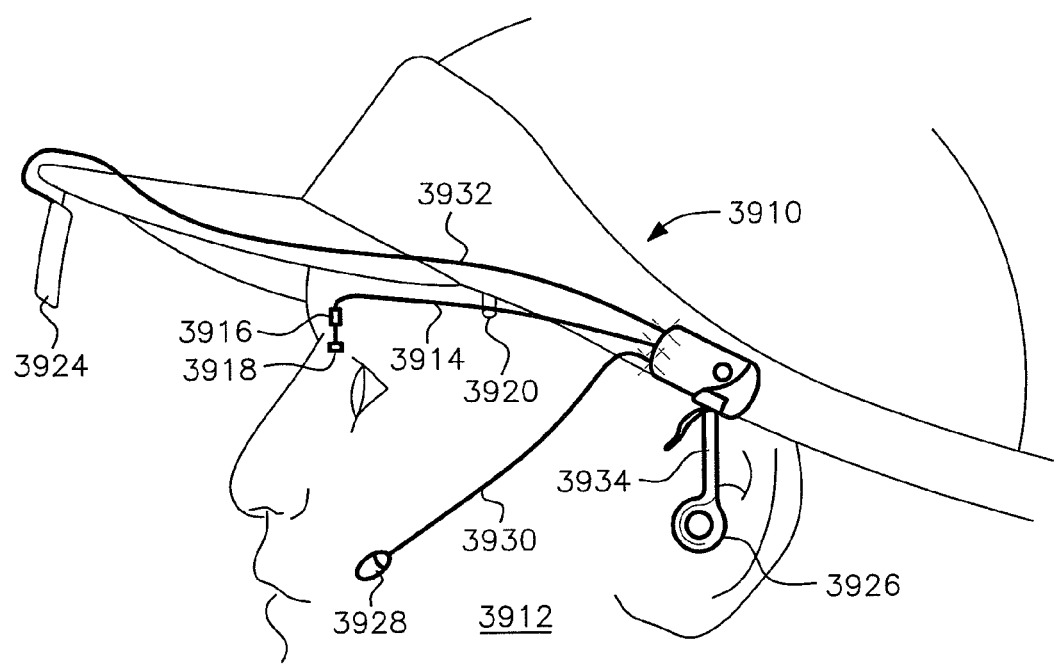

FIG. 100T illustrates head mounted gear having a sensing visor worn by a user.

Figure 100U:
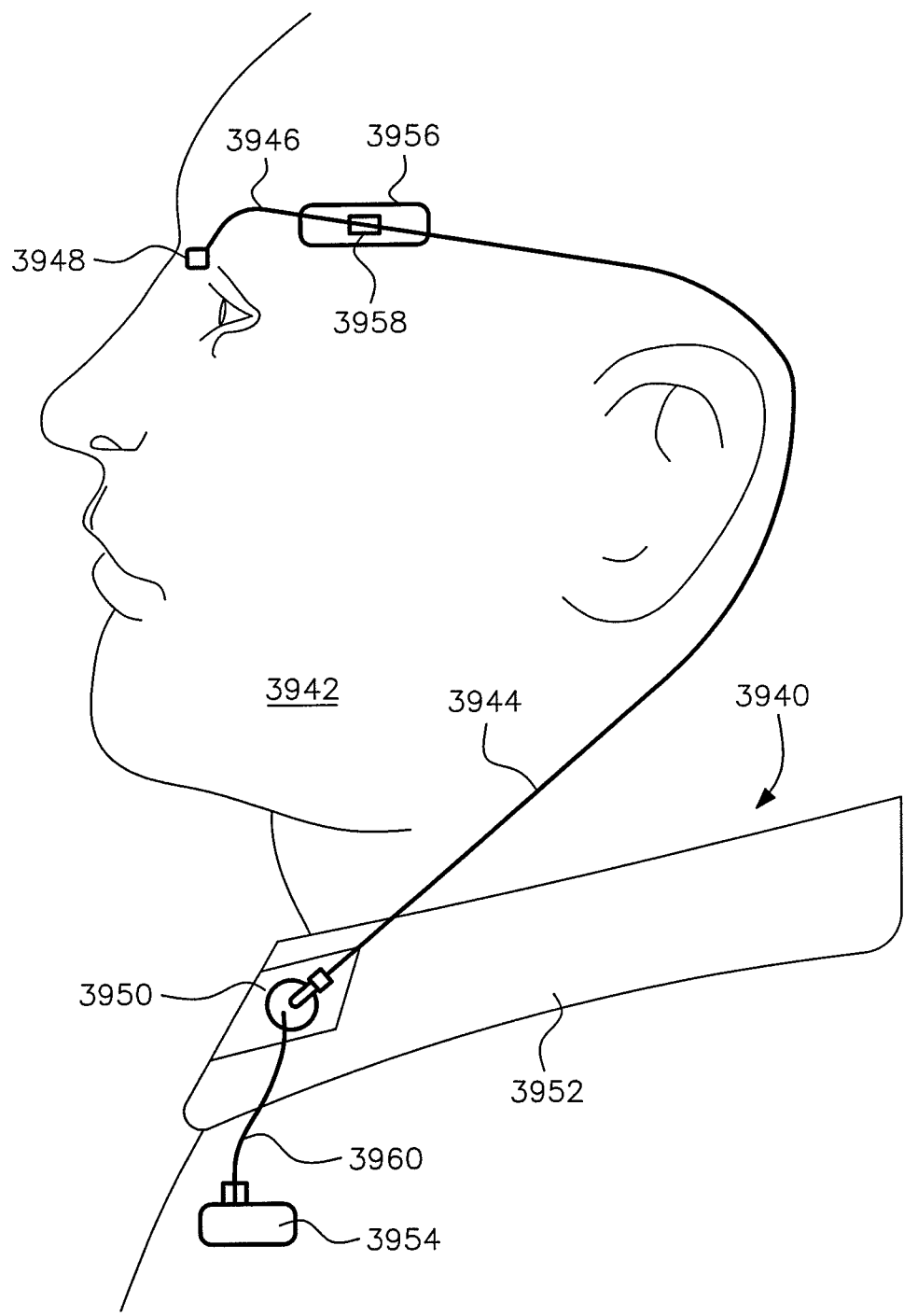

FIG. 100U illustrates a sensing enabled shirt.

Figure 100V:
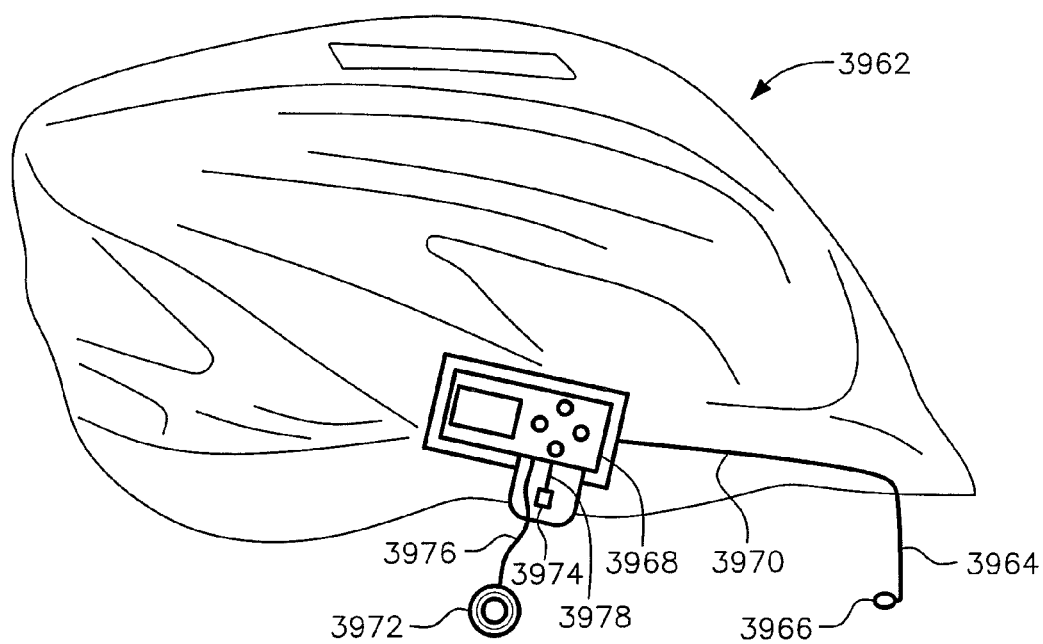

FIG. 100V illustrates a helmet including a temperature sensor.

Figure 100X:
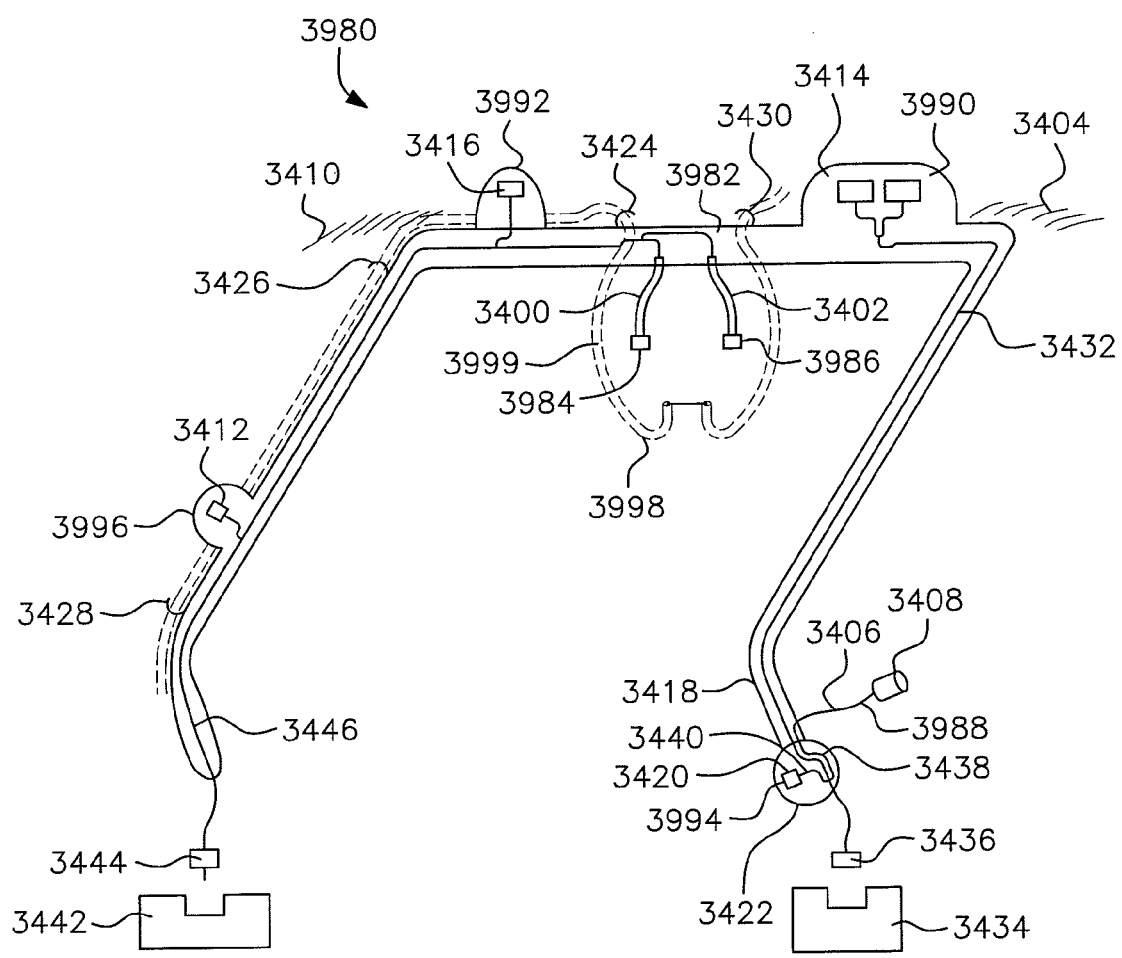

FIG. 100X is a sensing frame including seven biologic parameter modules.

Figure 100Z:
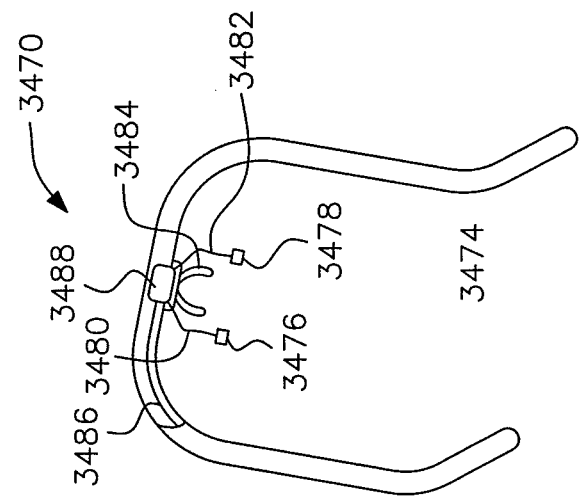
Figure 100Y:
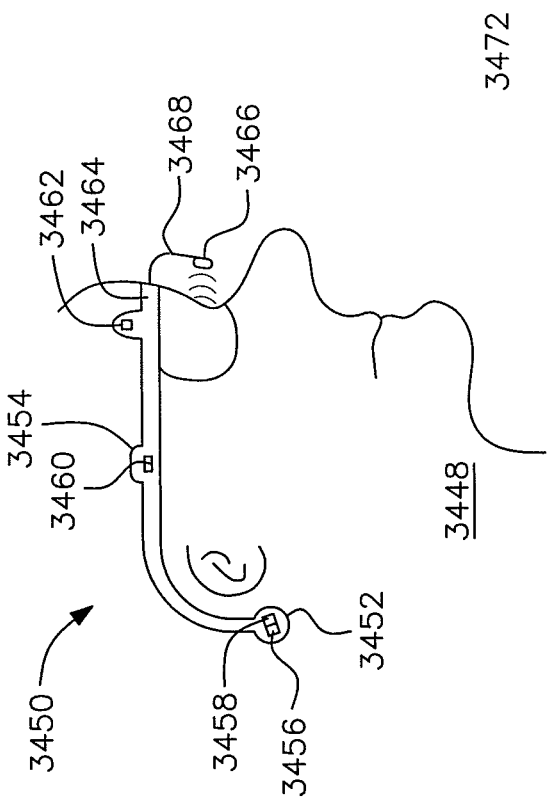

FIG. 100Y illustrates a sensing frame worn by a user.

FIG. 100Z illustrates a sensing frame having temples.

Figure 101:
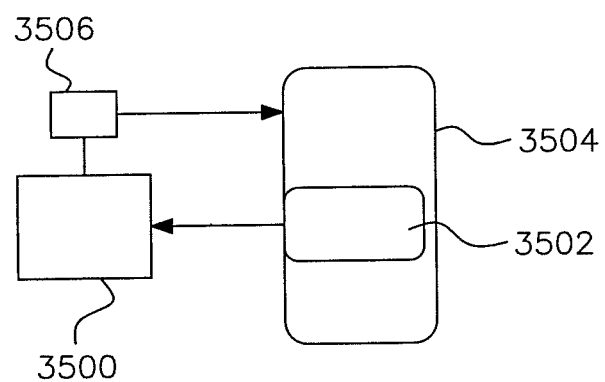

FIG. 101 illustrates an infusion pump connected to a temperature monitoring system.

Figure 102:
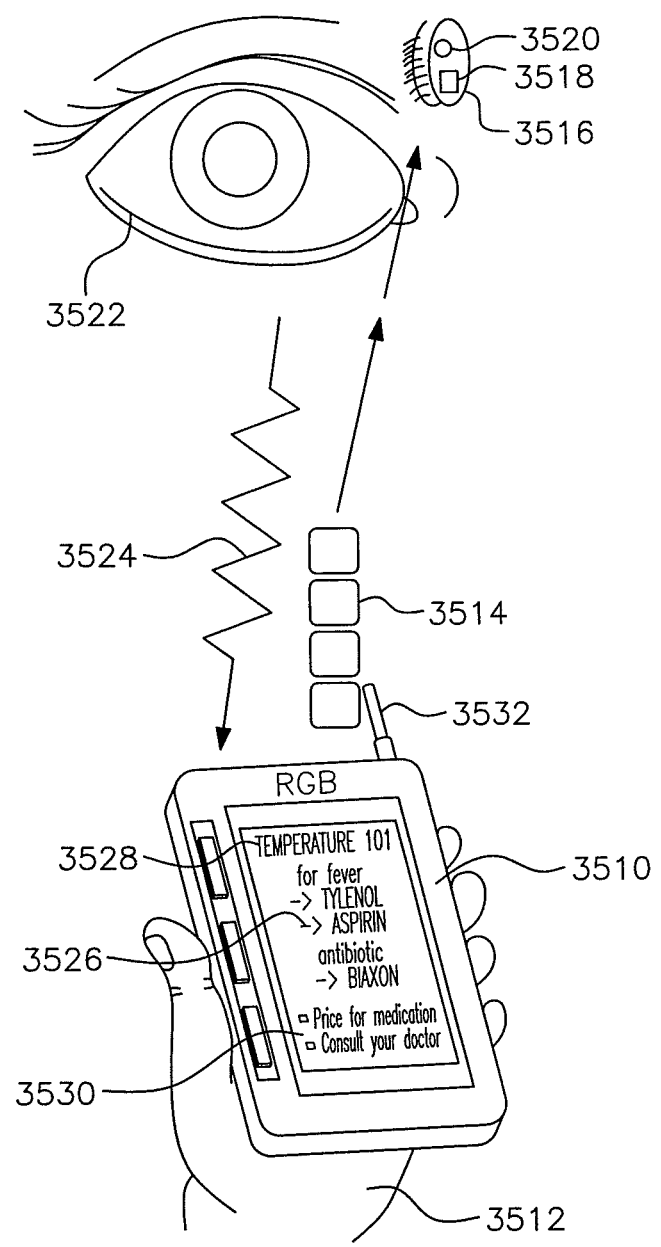

FIG. 102 illustrates a portable powering device coupled to a passive sensing device.

Figure 103A:
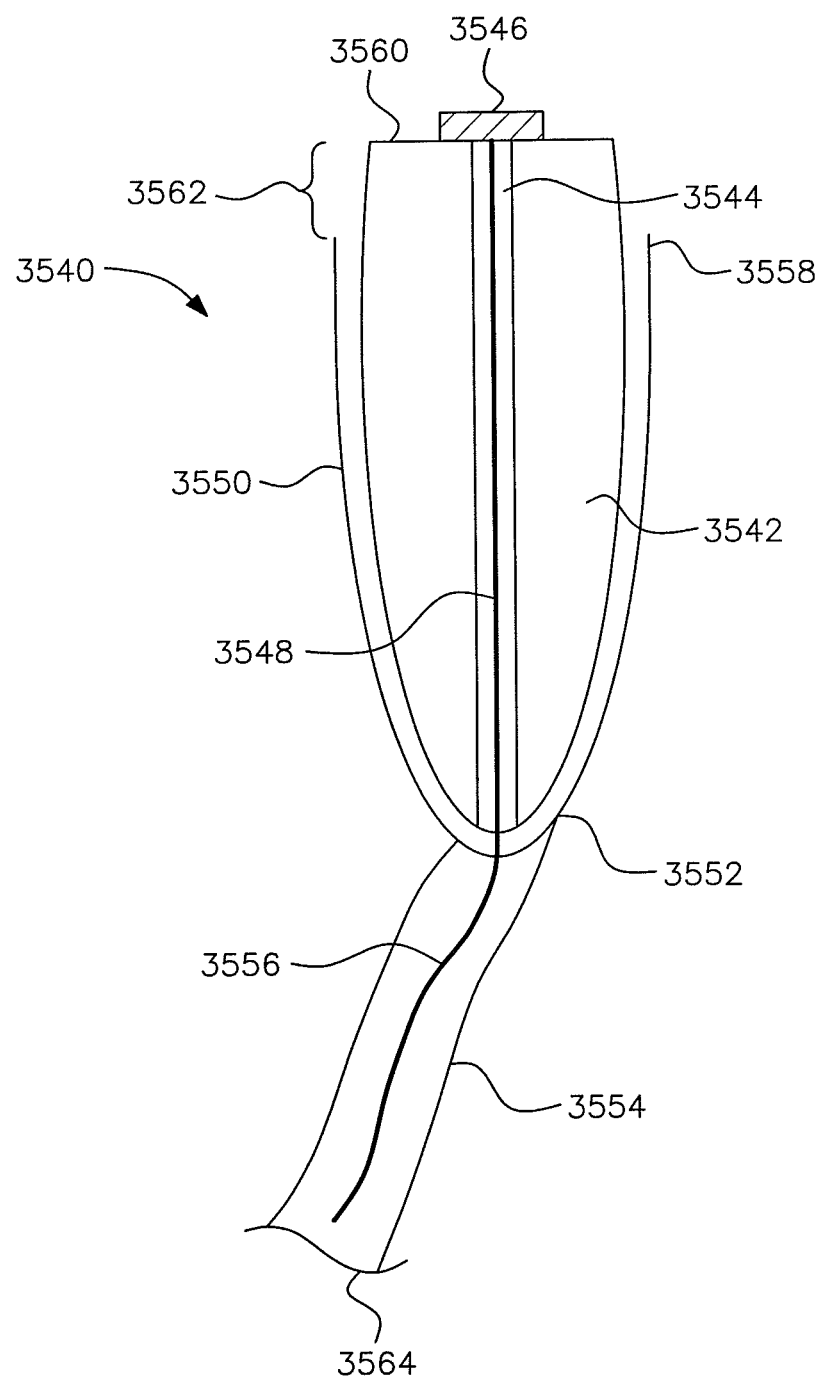

FIG. 103A illustrates a sensing device including a measuring portion and an arm.

FIG. 103B illustrates a probe covering for a measuring portion of a sensing device.

FIG. 104-A illustrates a non-invasive internal surface measurement probe.

FIG. 104-B is a planar view of a sensor head.

FIG. 104-C illustrates a handheld portable sensing probe.

FIG. 104-D illustrates a boomerang shaped sensor probe.

FIG. 104-E illustrates the boomerang shaped sensor probe showing the sensor surface of the sensor head.

FIG. 104-F illustrates the boomerang shaped sensor head and its relationship to anatomic structures.

FIG. 104-G illustrates a sensor head and handle.

FIG. 104-H illustrates a bulging sensor on the surface of an insulating material.

Figure 105:
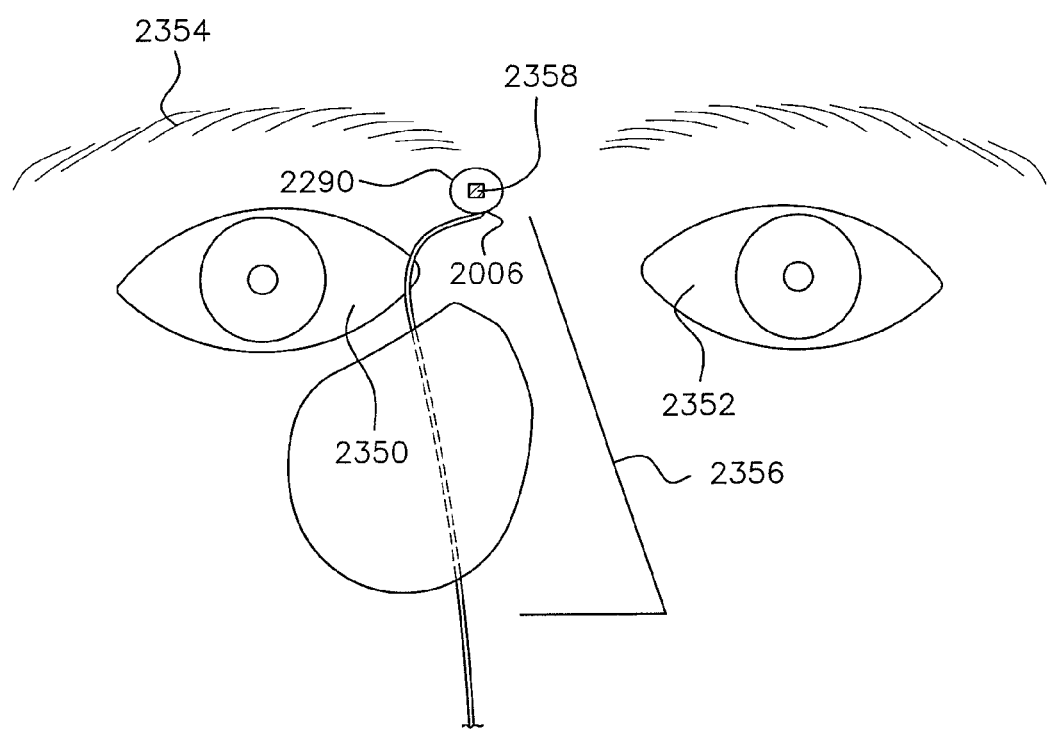

FIG. 105 illustrates an alternate embodiment of placement of a sensing assembly by securing a support structure to a cheek of the user.

DETAILED DESCRIPTION OF THE PREFERRED EMBODIMENTS

In describing a preferred embodiment of the invention illustrated in the drawings, specific terminology will be resorted to for the sake of clarity. However, the invention is not intended to be limited to the specific terms so selected, and it is to be understood that each specific term includes all technical equivalents which operate in a similar manner to accomplish a similar purpose.

Figure 1A:
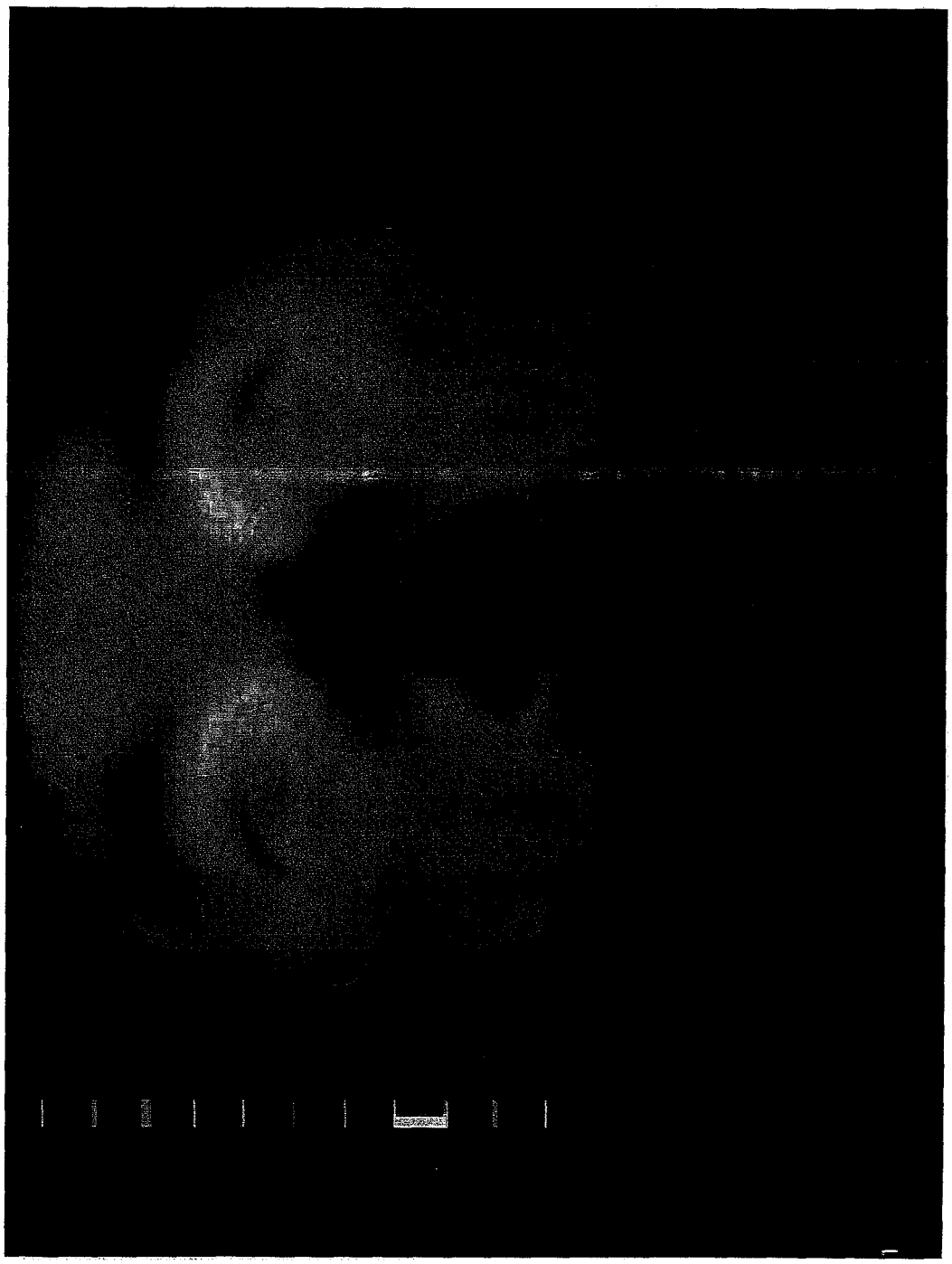
FIG. 1A is a thermal infrared image of the human face showing the brain temperature tunnel.

FIG. 1A shows a thermal infrared image of the human face showing a physiologic tunnel. The figure shows an image of the end of the brain temperature tunnel (BTT) depicted as white bright spots in the medial canthal area and the medial half of the upper eyelid. The end of the BTT on the skin has special geometry, borders, and internal areas and the main entry point is located on the supero-medial aspect of the medial canthal area diametrically in position with the inferior portion of the upper eyelid and 4 mm medial to the medial corner of the eye. From there the boundary goes down in the medial canthal area diametrically in position with the medial corner of the eye and within 5 mm down from the medial corner of the eye, and proceeding up to the upper eyelid with the lateral boundary beginning at the mid-part of the upper eyelid as a narrow area and extending laterally in a fan-like shape with the superior boundary beginning in the mid-half of the upper eyelid.

The scale indicates the range of temperature found in the human face. The hottest spots are indicated by the brightest white spots and the coldest areas are black. Temperature between the hottest and coldest areas are seen in different hues in a gray scale. The nose is cold (seen as black) since it is primarily composed of cartilage and bones, and consequently has a lower blood volume. That is the reason why frostbite is most common in the nose.

The surrounding periocular area of the upper and lower eyelids (seen as gray) is hotter because of high vascularization and the reduced amount of adipose tissue. The skin underneath the eyelids is very thin and does not have adipose tissue either. However, the other conditions necessary to define a brain temperature tunnel are not present in this area.

The BTT requirements also include the presence of a terminal branch to deliver the total amount of heat, a terminal branch that is a direct branch from a vessel from the brain, a terminal branch that is superficially located to avoid far-infrared radiation absorption by other structures, and no thermoregulatory arteriovenous shunts. Thus, the BTT, i.e., the skin area in the medial corner of the eye and upper eyelid, is the unique location that can access a brain temperature tunnel. The skin around the eyelids delivers undisturbed signals for chemical measurements using spectroscopy and is defined as a metabolic tunnel with optimal acquisition of signals for chemical evaluation, but not for evaluation of the total radiant power of the brain.

Figure 1B:
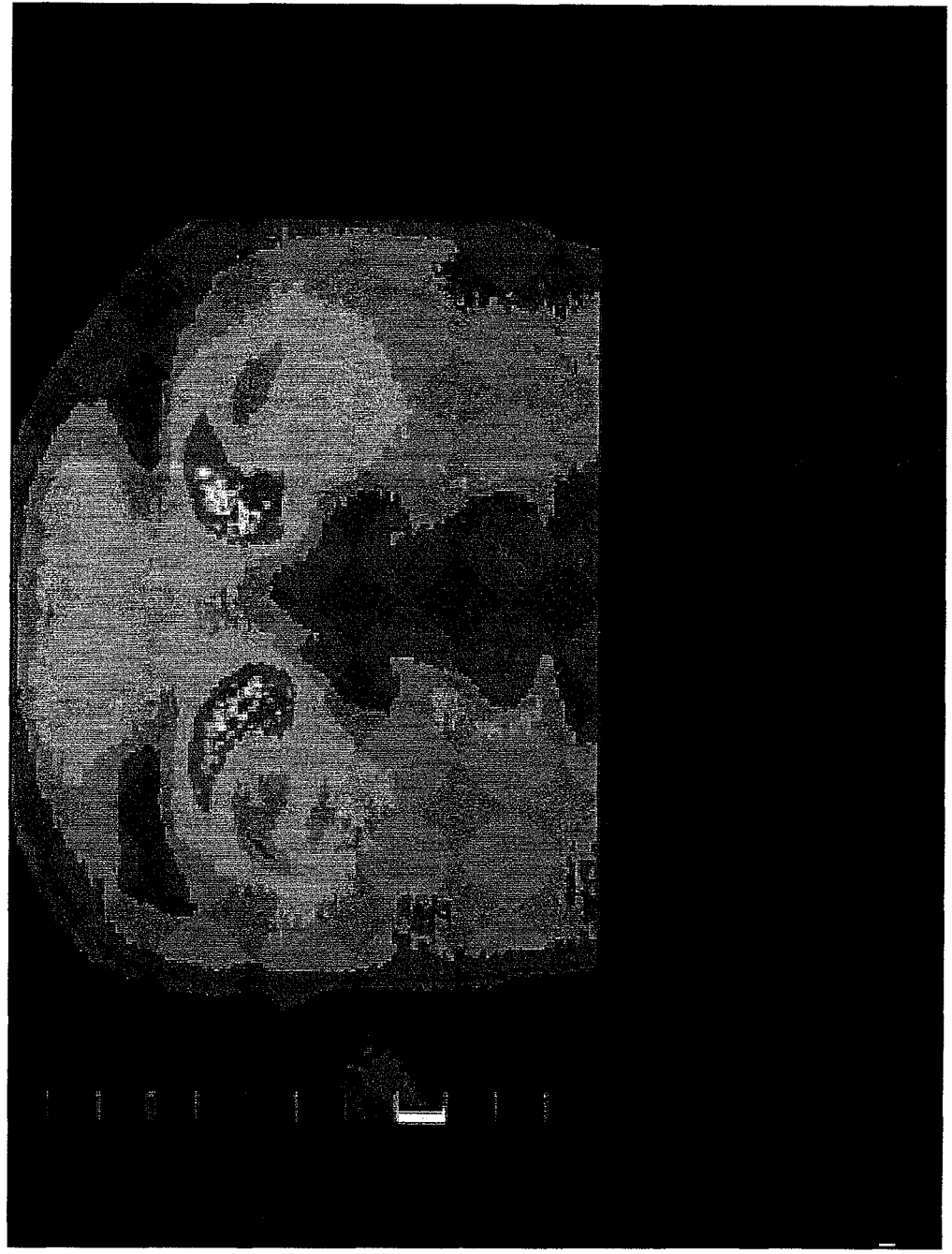
FIG. 1B is a computer generated thermal infrared color image of the human face showing the brain temperature tunnel.

FIG. 1B is a computer generated thermal infrared color plot image of the human face showing in detail the geometry and different areas of the brain temperature tunnel and surrounding areas. Only few creatures such as some beetles and rattle snakes can see this type of radiation, but not humans. The infrared images make the invisible into visible. Thus the geometry and size of the tunnel can be better quantified. The color plot of the isothermal lines show the peripheral area of the tunnel in red and the central area in yellow-white with the main entry point at the end of the BTT located in the superomedial aspect of the medial canthal area above the medial canthal tendon.

The main entry point is the area of most optimal signal acquisition. The image also shows the symmetry of thermal energy between the two BTT sites. Since other areas including the forehead do not have the aforementioned six characteristics needed to define a BTT, said areas have lower total radiant power seen as light and dark green. Thus the forehead is not suitable to measure total radiant power. The whole nose has very little radiant power seen as blue and purple areas, and the tip of the nose seen as brown has the lowest temperature of the face. Thus, the nose area is not suitable for measuring biological parameters.

Figure 2A:
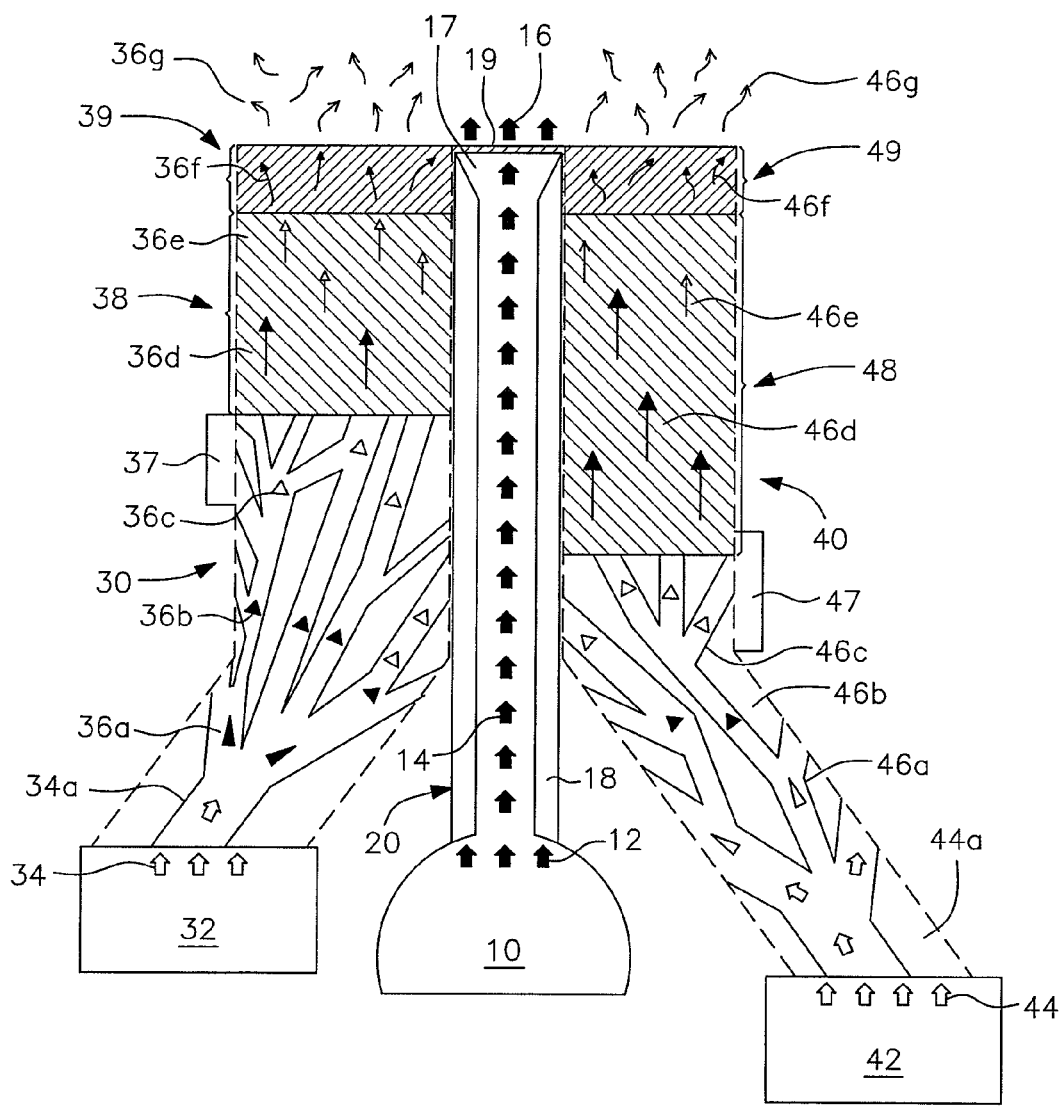
FIG. 2A is a schematic diagram showing a physiologic tunnel.

FIG. 2A is a schematic diagram of a physiologic tunnel, more particularly a Brain Temperature Tunnel. From a physical standpoint, the BTT is a brain thermal energy tunnel characterized by a high total radiant power and high heat flow and can be characterized as a Brain Thermal Energy tunnel. The tunnel stores thermal energy and provides an undisturbed path for conveying thermal energy from one end of the tunnel in the cavernous sinus inside of the brain to the opposite end on the skin with the thermal energy transferred to the surface of the skin at the end of the tunnel in the form of far-infrared radiation. High heat flow occurs at the end of tunnel which is characterized by a thin interface, and the heat flow is inversely proportional to the thickness of the interface.

The total radiated power (P) at the end of the tunnel is defined by $P=\sigma*e*A*T^4$, where $\sigma$ is the Stefan-Boltzman constant with a value $\sigma=5.67\times10^{-8}$ $W\cdot m^{-2}\cdot K^{-4}$ and e is the emissivity of the area. Since the end of the tunnel provides an optimal area for radiation, the total power radiated grows rapidly as the temperature of the brain increases because of the $T^4$ term in the equation. As demonstrated in the experiments in the present invention mentioned, the radiated power in the BTT occurred at a faster rate than the radiated power in the tongue and oral cavity.

The BTT site on the skin is a very small area measuring only less than 0.5% of the body surface area. However, this very small skin region of the body provides the area for the optimal signal acquisition for measuring both physical and chemical parameters.

FIG. 2A shows the brain 10 with the thermal energy 12 stored in its body. The BTT 20 includes the brain 10, the thermal energy 12 stored in the brain 10, the thermal energy stored in the tunnel 14 and the thermal energy 16 transferred to the exterior at the end of the tunnel. The thermal energy 12, 14, 16 is represented by dark arrows of same size and shape. The arrows have the same size indicating undisturbed thermal energy from one end of the tunnel to the other and characterized by equivalent temperature within the tunnel.

Thermal energy from the sinus cavernous in the brain 10 is transferred to the end of the tunnel 16 and a rapid rate of heat transfer occurs through the unimpeded cerebral venous blood path. The tunnel also has a wall 18 representing the wall of the vasculature storing the thermal energy with equivalent temperature and serving as a conduit from the inside of the body 10 to the exterior (skin surface) 19 which ends as a terminal vessel 17 transferring the total amount of thermal energy to said skin 19.

The skin 19 is very thin and allows high heat flow. The thickness of skin 19 is negligible compared to the skin 39, 49 in non-tunnel areas 30 and 40 respectively. Due to the characteristics of skin 19, high heat flow occurs and thermal equilibrium is achieved rapidly when a sensor is placed on the skin 19 at the end of the BTT 20.

In other areas of skin in the face and in the body in general, and in the exemplary non-tunnel areas 30 and 40 of FIG. 2 several interfering phenomena occur besides the lack of direct vasculature connection to the brain, and includes self-absorption and thermal gradient. 1. Self-absorption: This relates to the phenomena that deep layers of tissue selectively absorb wavelengths of infrared energy prior to emission at the surface. The amount and type of infrared energy self-absorbed is unknown. At the surface those preferred emissions are weak due to self-absorption by the other layers deriving disordered thermal emission and insignificant spectral characteristic of the substance being analyzed being illustratively represented by the various size, shapes and orientations of arrows 34a to 36g and 44a to 46g, of FIG. 2. Self-absorption in non-tunnel areas thus naturally prevents useful thermal emission for measurement to be delivered at the surface. 2. Thermal gradient: there is a thermal gradient with the deeper layers being warmer than the superficial layers, illustratively represented by thicker arrows 36*d* and 46*d* in the deeper layers compared to thinner arrows 36*e* and 46*e* located more superficially. There is excessive and highly variable scattering of photons when passing through various layers such as fat and other tissues such as muscles leading to thermal loss.

Contrary to that, the tunnel area 20 is homogeneous with no absorption of infrared energy and the blood vessels are located on the surface. This allows undisturbed delivery of infrared energy to the surface of the skin 19 and to a temperature detector such as an infrared detector placed in apposition to said skin 19. In the BTT area there is no thermal gradient since there is only a thin layer of skin 19 with terminal blood vessel 17 directly underneath said thin interface skin 19. The thermal energy 16 generated by the terminal blood vessel 17 exiting to the surface skin 19 corresponds to the undisturbed brain (true core) temperature of the body. The preferred path for achieving thermal equilibrium with brain tissue temperature is through the central venous system which exits the brain and enters the orbit as the superior ophthalmic vein. The arterial blood is 0.2 to 0.3 degrees Celsius lower when compared to the central venous blood, and said arterial blood is not the actual equivalent of the brain temperature. Thus although arterial blood may be of interest in certain occasions, the venous system is the preferred carrier of thermal energy for measurement of brain temperature. Arterial blood temperature may be of interest to determine possible brain cooling by the arterial blood in certain circumstances.

Non-tunnel areas 30 and 40 are characterized by the presence of heat absorbing elements. The non-tunnel areas 30 and 40 are defined by broken lines characterizing the vulnerability of interference by heat absorbing constituents and by the disorganized transferring of heat in said non-tunnel areas 30 and 40. Various layers and other constituents in non-tunnel areas 30 and 40 selectively absorb infrared energy emitted by the deeper layers before said energy reaches the surface of skin, and the different thermal energy and the different areas are represented by the different shapes and sizes of arrows and arrow heads.

Non-tunnel area 30 can be representative of measuring temperature with a sensor on top of the skin anatomically located above the heart 32. White arrows 34 represent the thermal energy in the heart 32. Non-tunnel area 30 includes the heart 32 and the various blood vessels and its branches 36*a*, 36*b*, 36*c*, 36*d* storing thermal energy.

Different amounts of heat are transferred and different temperatures measured depending on the location and anatomy of blood vessels 36*a*, 36*b*, 36*c*. The blood vessels branch out extensively from the main trunk 34*a*. The non-tunnel area 30 also includes heat absorbing structures 37 such as bone and muscles which thermal energy 34 from the heart 32 need to be traversed to reach the skin 39. The non-tunnel area 30 also includes a variable layer of fat tissue 38 which further absorbs thermal energy. The reduced amount of thermal energy reaching the skin surface due to the presence of fat 38 is represented by the arrows 36*d* and 36*e*, in which arrow 36*d* has higher temperature than arrow 36*e*. Non-tunnel area 30 also includes a thick skin 39 with low heat flow represented by arrows 36*f*.

The thick skin 39 corresponds to the skin in the chest area and fat layer 38 corresponds to the variable amount of fat present in the chest area. Arrows 36*g* represent the disordered and reduced total radiant power delivered after said thermal energy traverses the interfering constituents in the non-tunnel area including a thick interface and heat absorbing structures. In addition, BTT 20 has no fat layer as found in non-tunnel areas 30 and 40. Lack of a thick interface such as thick skin and fat, lack of thermal barriers such as fat, and lack of heat absorbing elements such as muscles allows undisturbed emission of radiation at the end of the BTT. Lack of a thick interface such as thick skin and fat, lack of thermal barriers such as fat, and lack of heat absorbing elements such as muscles allowed undisturbed emission of radiation at the end of the BTT.

Yet referring to FIG. 2, non-tunnel area 40 can be representative of measuring temperature with a sensor on top of the skin in the arm 42. The heat transfer in non-tunnel area 40 has some similarity with non-tunnel area 30 in which the end result is a disordered and reduced total radiant power not representative of the temperature at the opposite end internally. The blood vessels branch out extensively from the main trunk 44*a*. Thermal energy and temperature in blood vessels 46*a*, 46*b*, 46*c* is different than in areas 36*a*, 36*b*, 36*c*. The structures that thermal energy 44 needs to traverse to reach the skin are also different compared to non-tunnel 30. The amount of heat absorbing structures 47 is different and thus the end temperature at non-tunnel 40 is also different when compared to non-tunnel area 30. The amount of fat 48 also varies which changes the energy in areas 46*d* and 46*e*, wherein area 46*d* is deeper than area 46*e*. Thick skin 49 also reduces heat flow and the temperature of the area 46*f*. Reduction of radiant power indicated by arrow 46*g* when compared to radiant power 36*g* is usually quite different, so different skin temperature is measured depending on the area of the body. This applies to the whole skin surface of the body, with the exception of the skin at the end of the BTT.

Measurements of internal temperature such as rectal do not have the same clinical relevance as measurement in the brain. Selective brain cooling has been demonstrated in a number of mammalian species under laboratory conditions and the same process could occur in humans. For instance the temperature in bladder and rectum may be quite different than the brain. High or low temperature in the brain may not be reflected in the temperature measured in other internal organs.

Figure 2B:
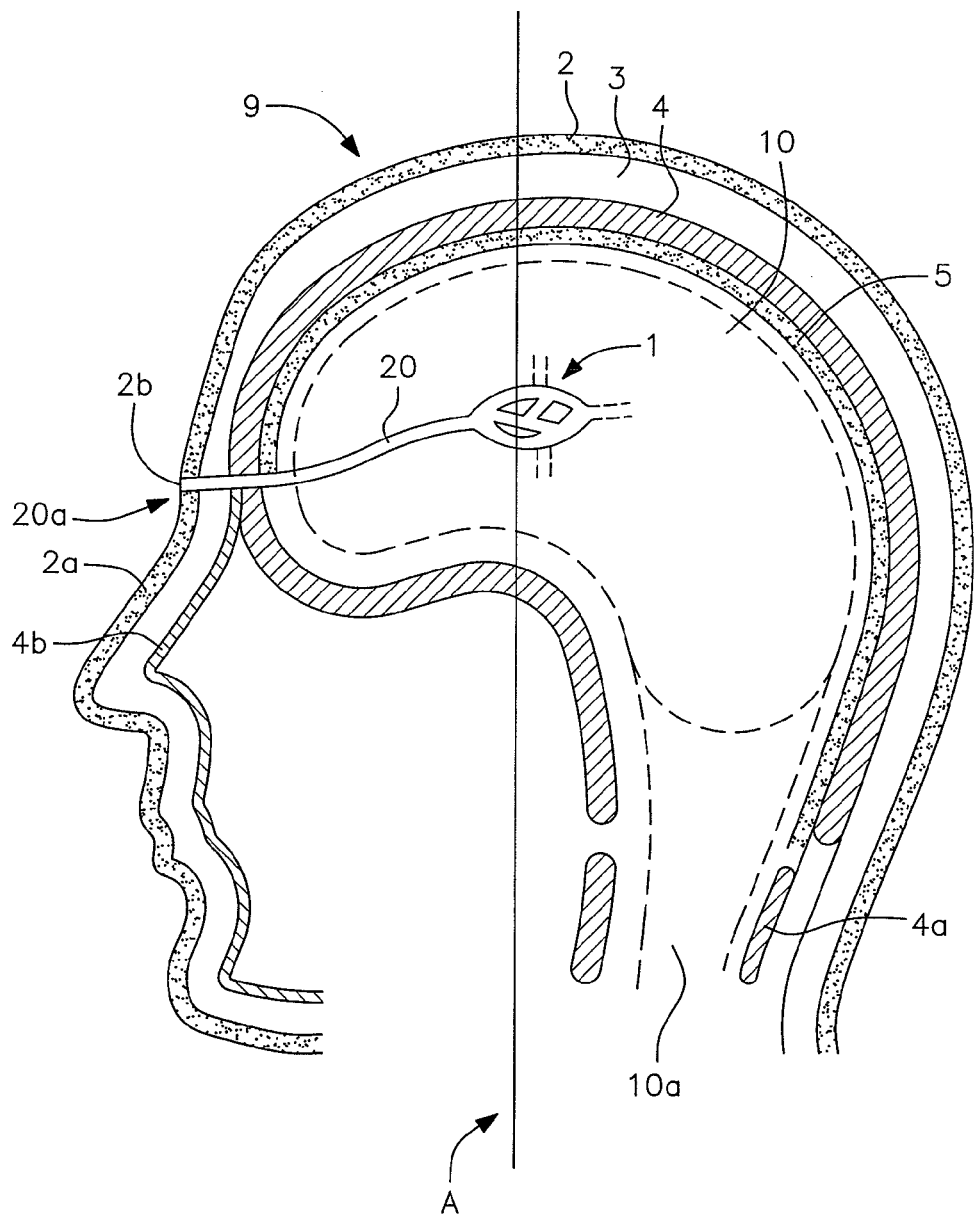
FIG. 2B is a cross-sectional schematic diagram of the human head showing the tunnel.

FIG. 2B is a cross-sectional schematic diagram of the human head 9 showing the brain 10, spinal cord 10*a*, the tunnel 20 represented by the superior ophthalmic vein, the cavernous sinus 1, which is the thermal energy storage compartment for the brain, and the various insulating barriers 2, 2*a*, 3, 4, 4*a*, 4*b*, 5 that keep the brain as a completely thermally insulated structure. Insulating barriers include skin 2 corresponding to the scalp, skin 2*a* corresponding to the skin covering the face, fat 3 covering the whole surface of the skull and face, skull bone 4, spinal bone 4*a* surrounding spinal cord 10*a*, facial bone 4*b* covering the face, and cerebral spinal fluid (CSF) 5. The combined thickness of barriers 2,3,4,5 insulating the brain can reach 1.5 cm to 2.0 cm, which is a notable thickness and the largest single barrier against the environment in the whole body. Due to this completely confined environment the brain cannot remove heat efficiently and heat loss occurs at a very low rate. Skin 2 corresponds to the scalp which is the skin and associated structure covering the skull and which has low thermal conductivity and works as an insulator. Fat tissue 3 absorbs the majority of the far-infrared wavelength and works as a thermal buffer. Skull bone 4 has low thermal conductivity and the CSF works as a physical buffer and has zero heat production.

The heat generated by metabolic rate in the brain corresponds to 20% of the total heat produced by the body and this enormous amount of heat is kept in a confined and thermally sealed space. Brain tissue is the most susceptible tissue to thermal energy induced damage, both high and low levels of thermal energy. Because of the thermal insulation and physical inability of the brain to gain heat or lose heat, both hypothermic (cold) and hyperthermic (hot) states can lead to brain damage and death can rapidly ensue, as occur to thousands of healthy people annually besides seizures and death due to high fever in sick people. Unless appropriate and timely warning is provided by continuously monitoring brain temperature anyone affected by cold or hot disturbances is at risk of thermal induced damage to the brain.

FIG. 2B also shows a notably small entry point 20*a* measuring less than 0.5% of the body surface which corresponds to the end of the tunnel 20 on the skin 2*b*. The skin 2*b* is extremely thin with a thickness of 1 mm or less compared to the skin 2 and 2*a* which are five fold or more, thicker than skin 2*b*.

The tunnel 20 starts at the cavernous sinus 1 which is a conduit for venous drainage for the brain and for heat transfer at the end of the tunnel 20 as a radiant energy. Tunnel 20 provides an unobstructed passage to the cavernous sinus 1, a structure located in the middle of the brain, and which is in direct contact with the two sources of heat to the brain: 1) thermal energy produced due to metabolic rate by the brain and carried by the venous system; and 2) thermal energy delivered by the arterial supply from the rest of the body to the brain. This direct contact arrangement is showed in detail in FIG. 2C, which is a coronal section of FIG. 2B corresponding to the line marked "A".

Figure 2C:
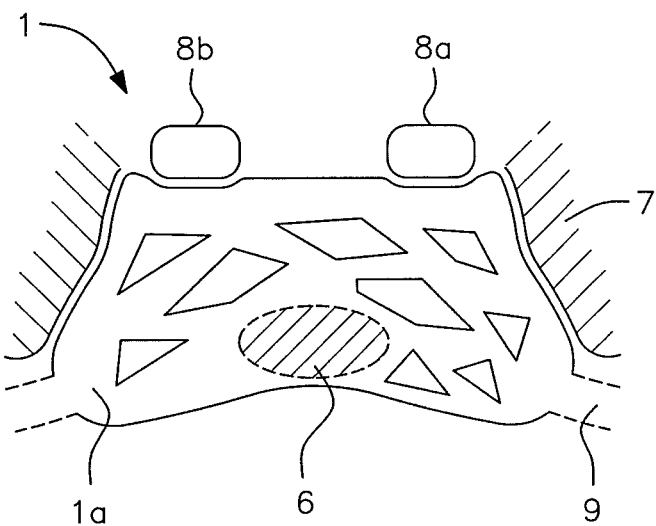
FIG. 2C is a coronal section schematic diagram showing the cavernous sinus of FIG. 2B.

FIG. 2C is a coronal section through the cavernous sinus 1 which is a cavity-like structure with multiple spaces 1*a* filled with venous blood from the veins 9 and from the superior ophthalmic vein 6. Cavernous sinus 1 collects thermal energy from brain tissue 7, from arterial blood of the right and left internal carotid arteries 8*a*, 8*b*, and from venous blood from vein 9. All of the structures 7, 8*a*, 8*b*, 9 are disposed along and in intimate contact with the cavernous sinus 1. A particular feature that makes the cavernous sinus 1 of the tunnel a very useful gauge for temperature disturbances is the intimate association with the carotid arteries 8*a*, 8*b*. The carotid arteries carry the blood from the body, and the amount of thermal energy delivered to the brain by said vessels can lead to a state of hypothermia or hyperthermia. For instance during exposure to cold, the body is cold and cold blood from the body is carried to the brain by internal carotid arteries 8*a*, 8*b*, and the cavernous sinus 1 is the entry point of those vessels 8*a*, 8*b* to the brain.

As soon as cold blood reaches the cavernous sinus 1 the corresponding thermal energy state is transferred to the tunnel and to the skin surface at the end of the tunnel, providing therefore an immediate alert even before the cold blood is distributed throughout the brain. The same applies to hot blood for instance generated during exercise which can lead to a 20 fold heat production compared to baseline. This heat carried by vessels 8*a*, 8*b* is transferred to the cavernous sinus 1 and can be measured at the end of the tunnel. In addition, the thermal energy generated by the brain is carried by cerebral venous blood and the cavernous sinus 1 is a structure filled with venous blood.

Figure 3B:
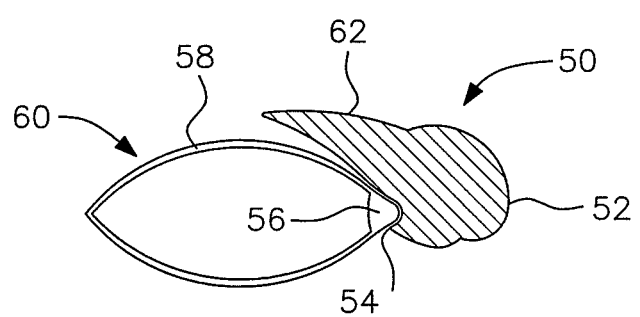
FIG. 3B is a schematic diagram of the image in FIG. 3A showing the geometry at the end of the tunnel.
Figure 3A:
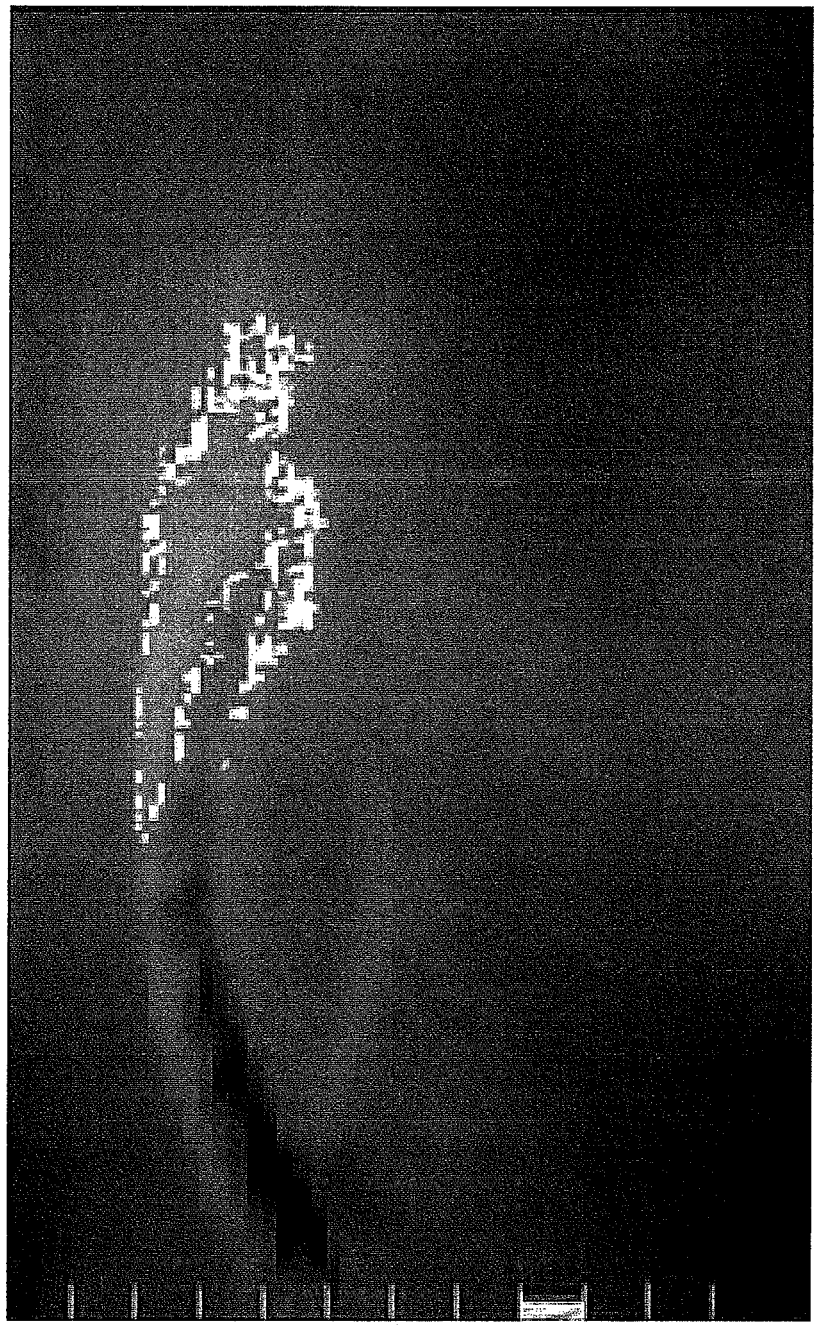
FIG. 3A is a thermal infrared image of the human face showing the tunnel.

FIG. 3A is a thermal infrared image of the human face in which the geometry of the end of the tunnel on the skin can be visualized. The white bright spots define the central area of the tunnel. FIG. 3B is a schematic diagram of an exemplary geometry on the skin surface at the end of the tunnel. The medial aspect 52 of the tunnel 50 has a round shape. The lateral aspect 54 borders the upper lid margin 58 and caruncle 56 of the eye 60. The tunnel extends from the medial canthal area 52 into the upper eyelid 62 in a horn like projection.

Figure 4A:
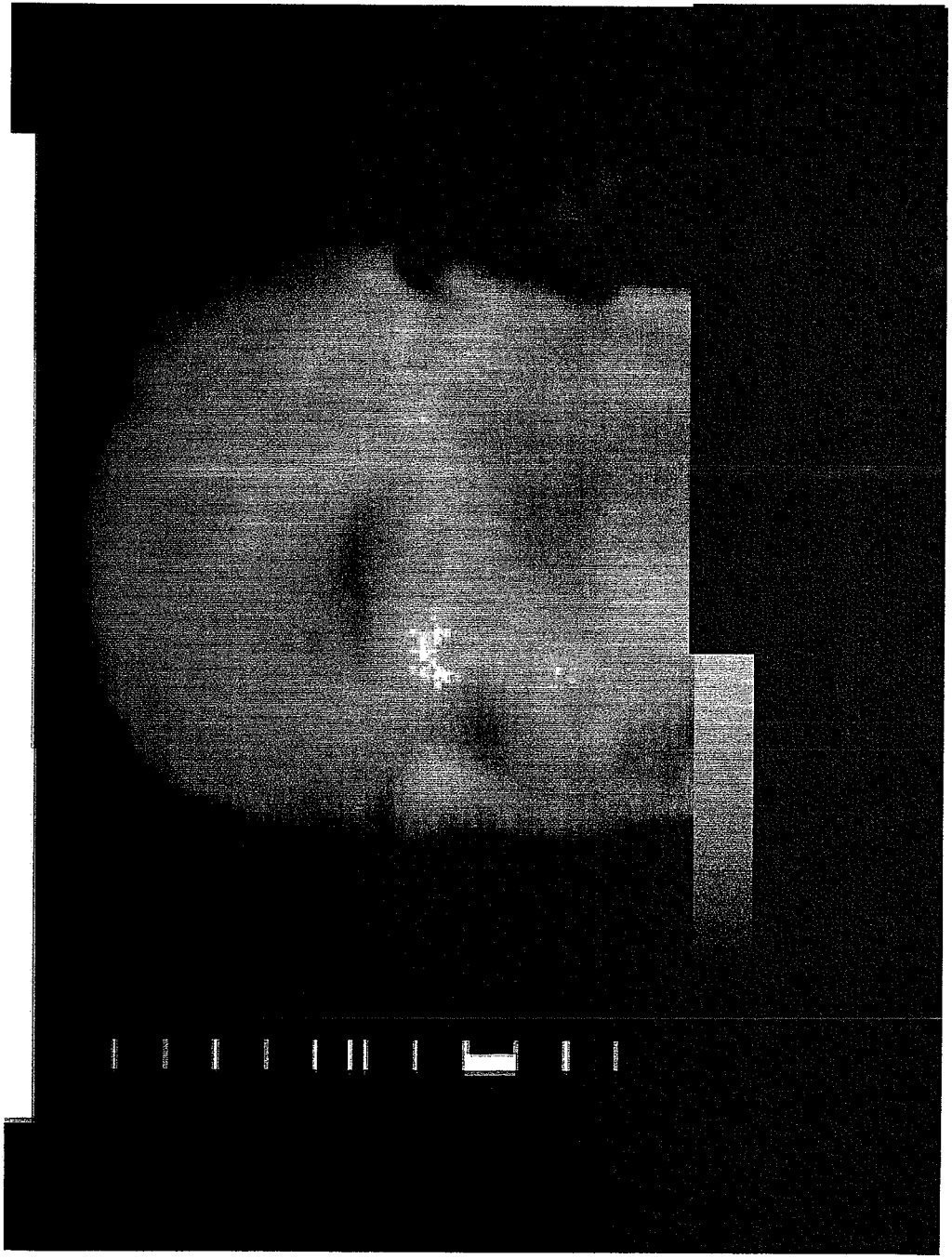
FIG. 4A is a thermal infrared image of the side of the human face showing a general view of the main entry point of the brain temperature tunnel.

The internal areas of the tunnel 50 include the general area for the main entry point and the main entry point as shown in FIGS. 4A to 5D. FIG. 4A is a thermal infrared image of the side of the human face showing a general view of the main entry point of the brain temperature tunnel, seen as white bright points located medial and above the medial canthal corner. FIG. 4B is a diagram showing the general area 70 of the main entry point and its relationship to the eye 60, medial canthal corner 61, eyebrow 64, and nose 66. The general area 70 of the main entry point provides an area with more faithful reproduction of the brain temperature since the area 70 has less interfering elements than the peripheral area of the tunnel.

Figure 5A:
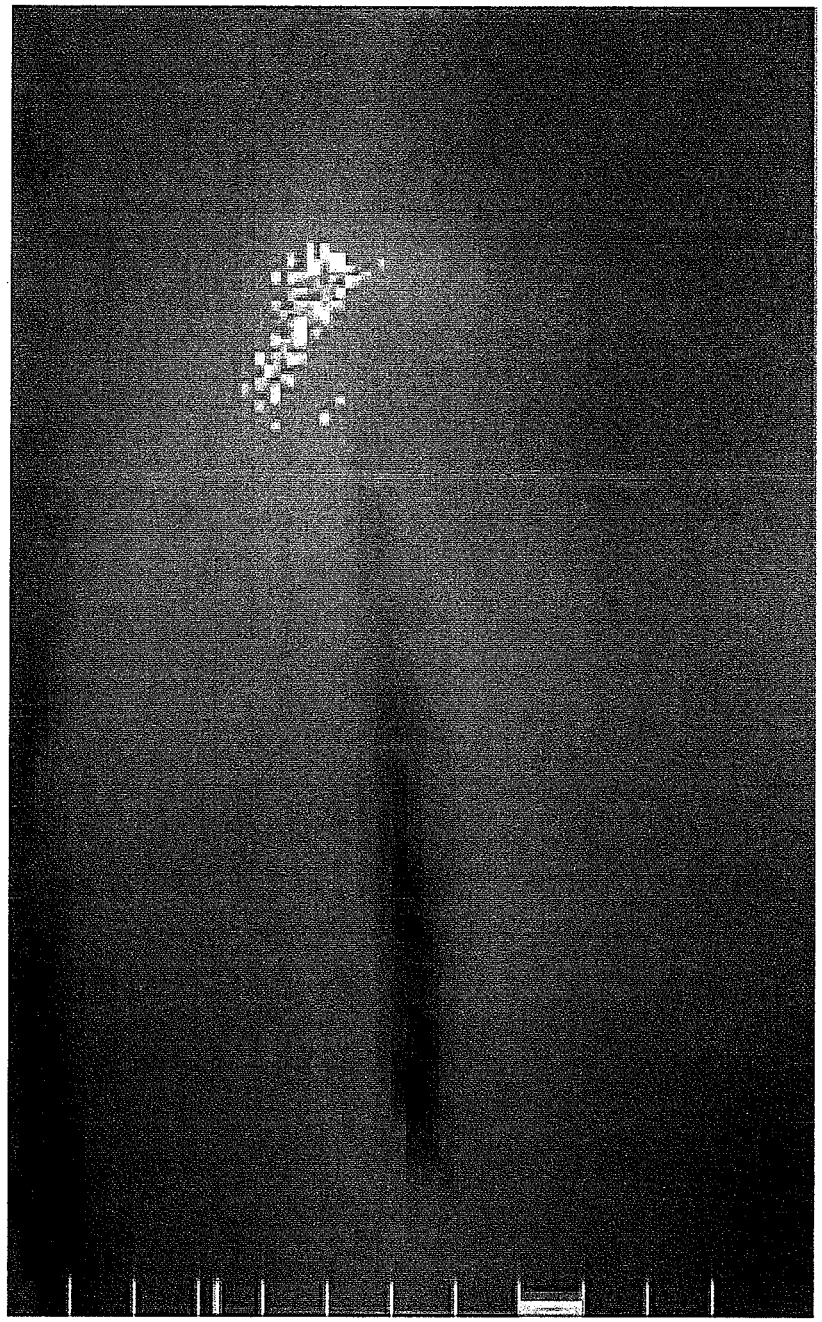
FIG. 5A is a thermal infrared image of the front of the human face showing the main entry point of the brain temperature tunnel.

FIG. 5A is a thermal infrared image of the front of the human face with the right eye closed showing the main entry point of the brain temperature tunnel seen as white bright spots above and medial to the medial canthal corner. With closed eyes it is easy to observe that the radiant power is coming solely from the skin at the end of BTT.

FIG. 5B is a diagram showing the main entry point 80 and its relationship to the medial canthal corner 61 of closed eye 60 and eyelids 62. The main entry point 80 of the tunnel provides the area with the most faithful reproduction of the brain temperature since the area 80 has the least amount of interfering elements and is universally present in all human beings at an equivalent anatomical position. The main entry point 80 has the highest total radiant power and has a surface with high emissivity. The main entry point 80 is located on the skin in the superior aspect of the medial canthal area 63, in the supero-medial aspect of the medial canthal corner 61.

Figure 5C:
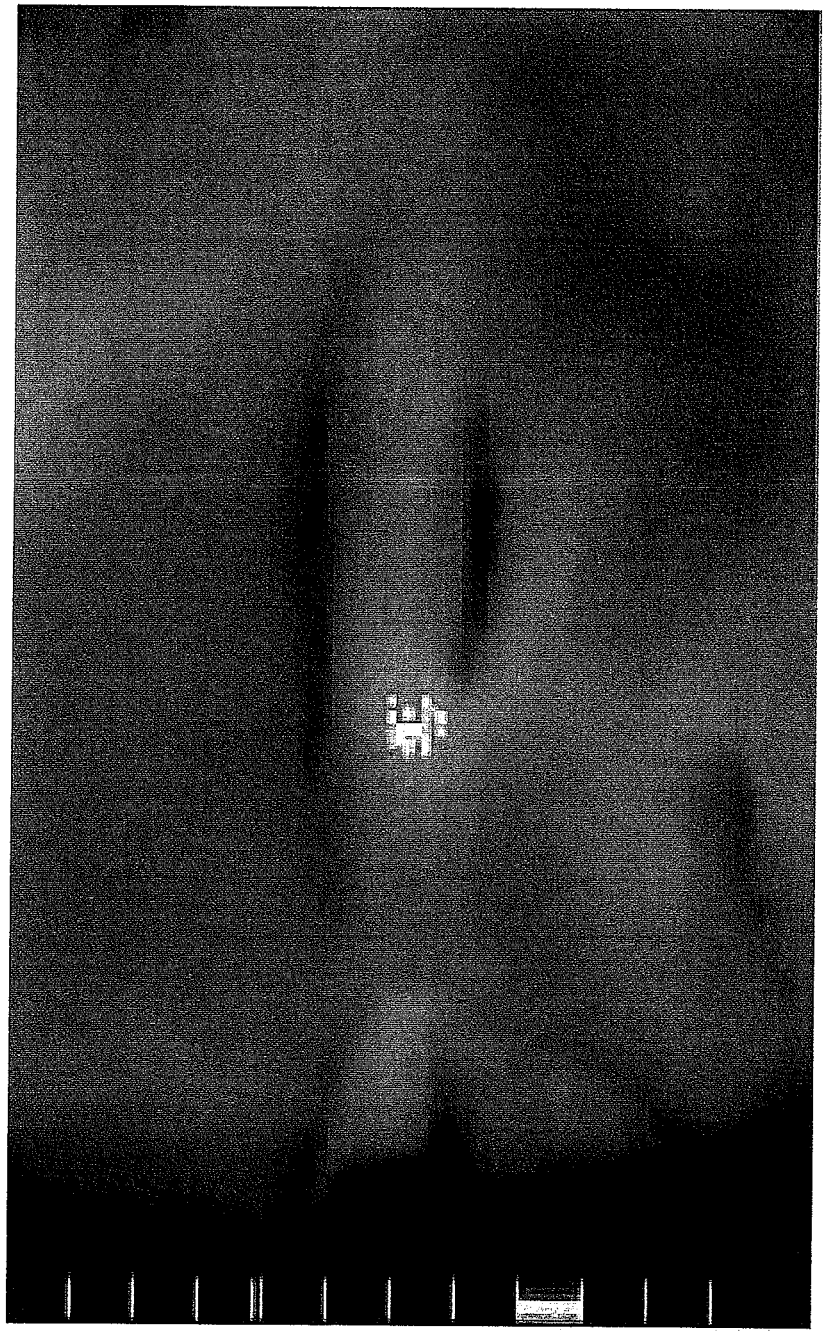
FIG. 5C is a thermal infrared image of the side of the human face in FIG. 5A showing the main entry point of the brain temperature tunnel.

FIG. 5C is a thermal infrared image of the side of the human face in FIG. 5A with the left eye closed showing a side view of the main entry point of the brain temperature tunnel, seen as bright white spots. It can be observed with closed eyes that the radiant power is coming solely from the skin at the end of BTT.

Figure 5D:
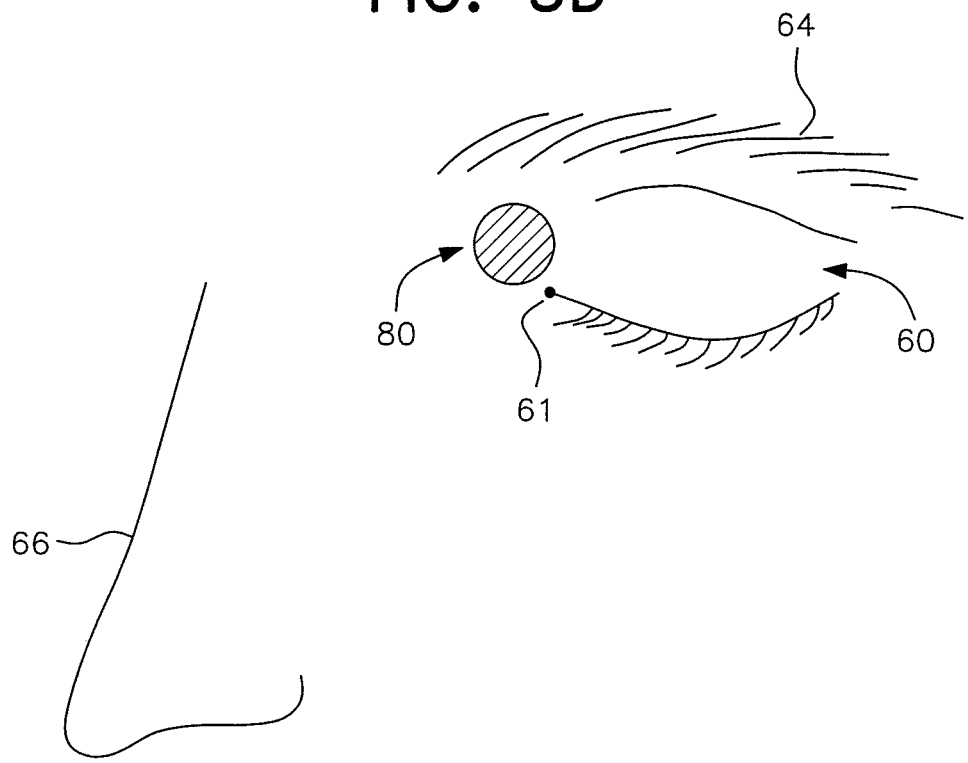
FIG. 5D is a schematic view of the image in FIG. 5C.

FIG. 5D shows the main entry point 80 in the superior aspect of the medial canthal area above the medial canthal corner 61, and also shows the position of main entry point 80 in relation to the eye 60, eyebrow 64 and nose 66. Support structures can precisely position sensing devices on top of the main entry point of the tunnel because the main entry point is completely demarcated by anatomic landmarks. In general the sensor is positioned on the medial canthal skin area above the medial canthal corner and adjacent to the eye. Although indicators can be placed on support structures to better guide the positioning of the sensor, the universal presence of the various permanent anatomic landmarks allows the precise positioning by any non-technical person.

The main entry point is the preferred location for the positioning of the sensor by the support structure, but the placement of a sensor in any part of the end of the tunnel including the general entry point area and peripheral area provides clinically useful measurements depending on the application. The degree of precision needed for the measurement will determine the positioning of the sensor. In cases of neurosurgery, cardiovascular surgery, or other surgical procedures in which the patient is at high risk of hypothermia or malignant hyperthermia, the preferred position of the sensor is at the main entry point. For recreational or professional sports, military, workers, fever detection at home, wrinkle protection in sunlight, and the like, positioning the sensor in any part of the end of the tunnel area provides the precision needed for clinical usefulness.

Figure 6:
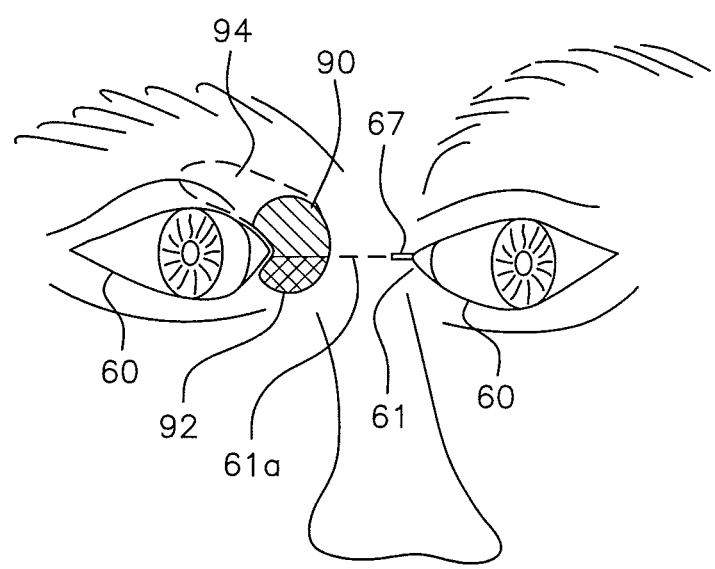
FIG. 6 is a schematic view of the face showing the general area of the main entry point of the tunnel and peripheral parts.

In accordance with the present invention, FIG. 6 is a schematic view of the face showing the general area of the main entry point of the tunnel 90 and the overall area of the end of the tunnel and its relationship to the medial canthal tendon 67. The end of the tunnel includes the general main entry point area 90 and the upper eyelid area 94. The area 90 has a peripheral portion 92. Both medial canthal areas have a medial canthal tendon and the left eye is used to facilitate the illustration. The medial canthal tendon 67 arises at the medial canthal corner 61 of eye 60. The left medial canthal tendon 67 is diametrically opposed to the right medial canthal tendon as shown by broken lines 61a which begins at the medial corner of the eye 61. Although the main entry point is above the medial canthal tendon 67, some of the peripheral area 92 of the tunnel is located below tendon 67.

FIG. 6A is a schematic diagram showing two physiologic tunnels. The upper figure shows the area corresponding to the BTT 10. The lower figure shows an area corresponding to a metabolic tunnel 13 which includes the upper eyelid area 13a and lower eyelid area 13b seen as light blue areas in FIG. 1B. For measuring the concentration of chemical substances the total radiant power is not mandatory. The key aspect for clinical useful spectroscopic measurements is signal coming from the cerebral area and the reduction or elimination of interfering constituents, and the main interfering constituent is adipose tissue. By removing adipose tissue and receiving spectral information carried by a vasculature from the brain, precise and clinical measurements can be achieved. The sensors supported by support structure are adapted to have a field of view that matches in total or in part the metabolic tunnel 13 for capturing thermal radiation from said tunnel 13.

Figure 7A:
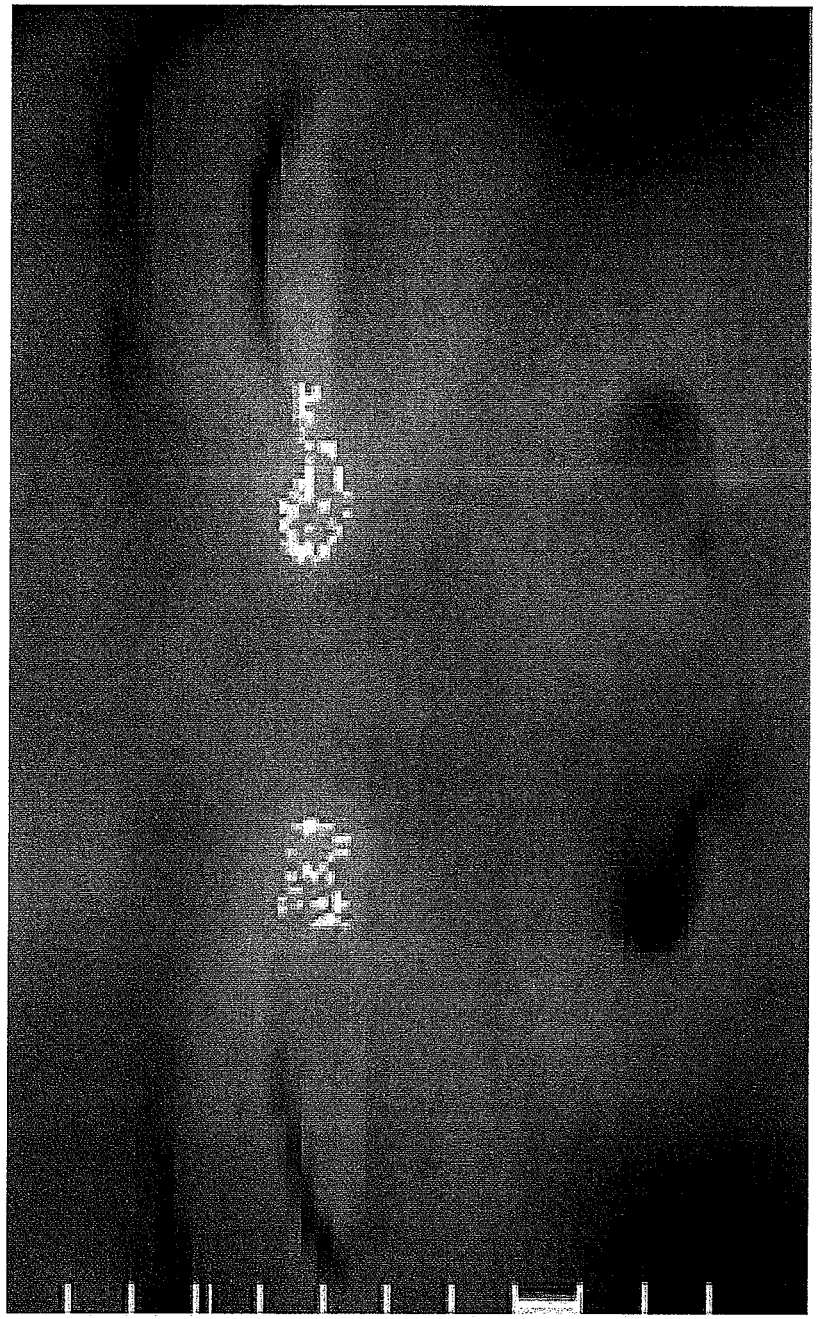
FIGS. 7A and 7B are thermal infrared images of the human face before and after cold challenge.
Figure 7B:
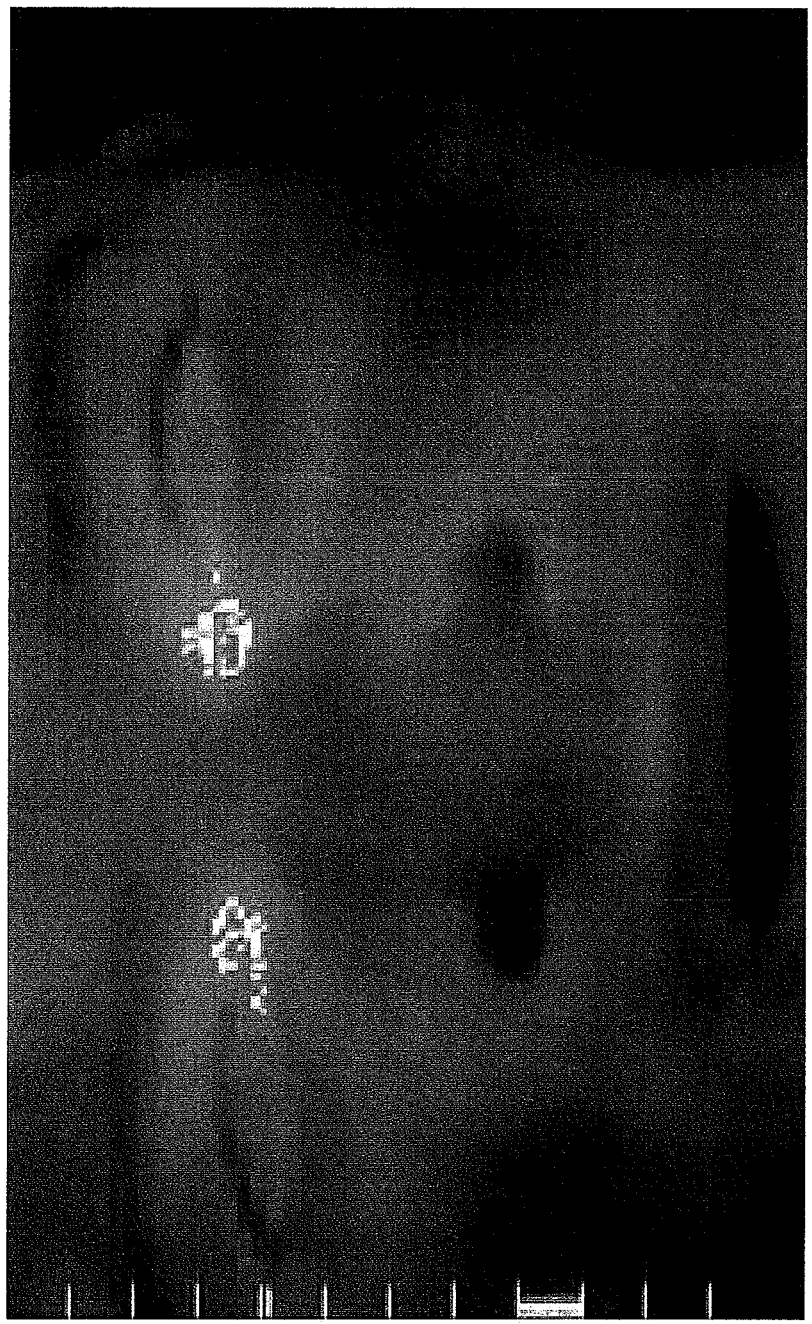

To determine the thermal stability of the tunnel area in relation to environmental changes, cold and heat challenge tests were performed. FIGS. 7A and 7B are thermal infrared images of an exemplary experiment showing the human face before and after cold challenge. In FIG. 7A the face has a lighter appearance when compared to FIG. 7B which is darker indicating a lower temperature. The nose in FIG. 7A has an overall whitish appearance as compared to the nose in FIG. 7B which has an overall darker appearance. Since the areas outside the tunnel have thermoregulatory arteriovenous shunts and interfering constituents including fat, the changes in the temperature of the environment are reflected in said areas. Thus measurements in those non-tunnel areas of the face reflect the environment instead of the actual body temperature. The non-tunnel areas of the skin in the face and body can change with the changes in ambient temperature. The radiant power of the tunnel area remains stable and there is no change in the amount of thermal energy demonstrating the stability of the thermal emission of the BTT area. Changes of thermal radiation at the tunnel area only occur when the brain temperature changes, which provides the most reliable measurement of the thermal status of the body.

Figure 8A:
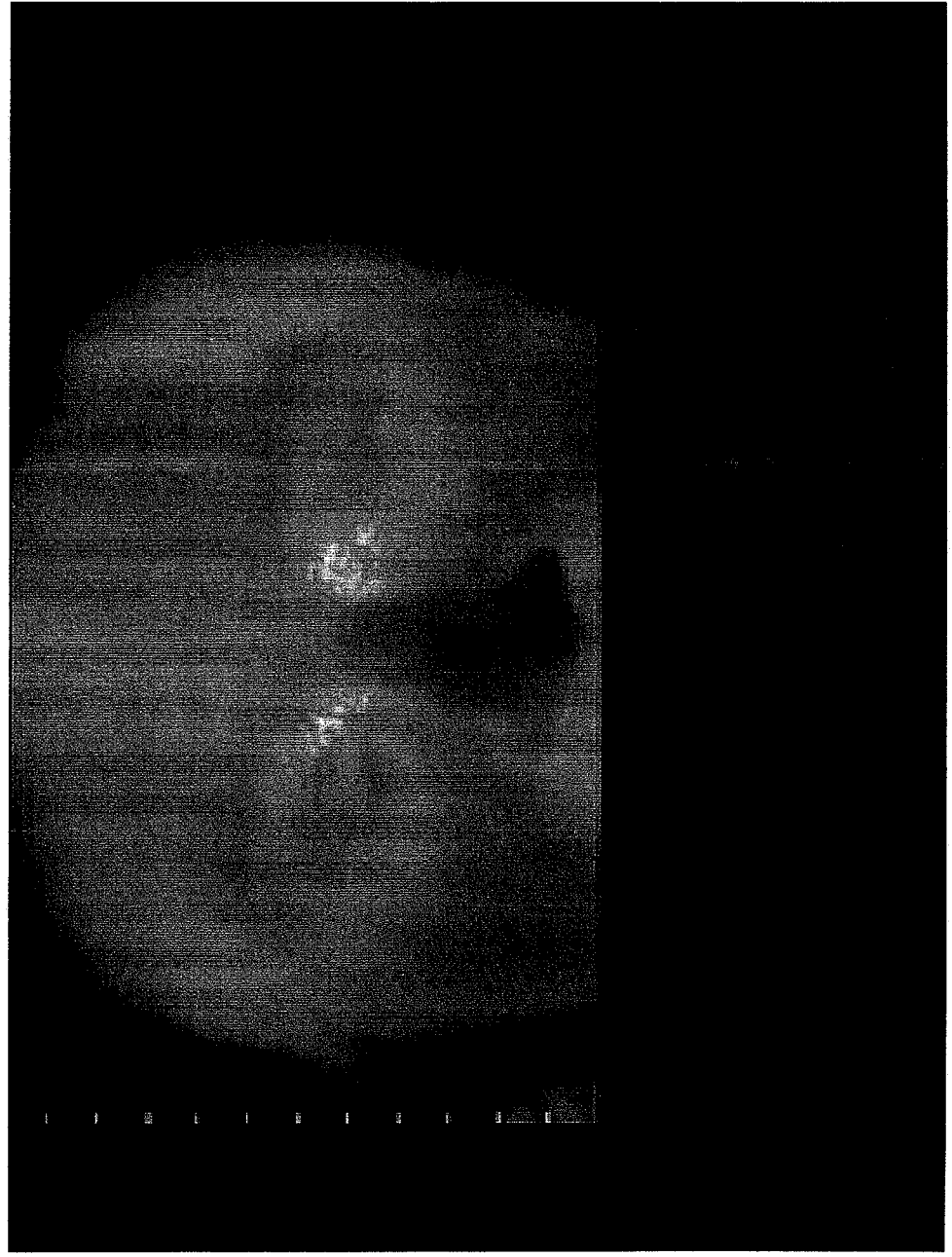
FIGS. 8A and 8B are thermal infrared images of the human face of different subjects showing the tunnel.
Figure 8B:
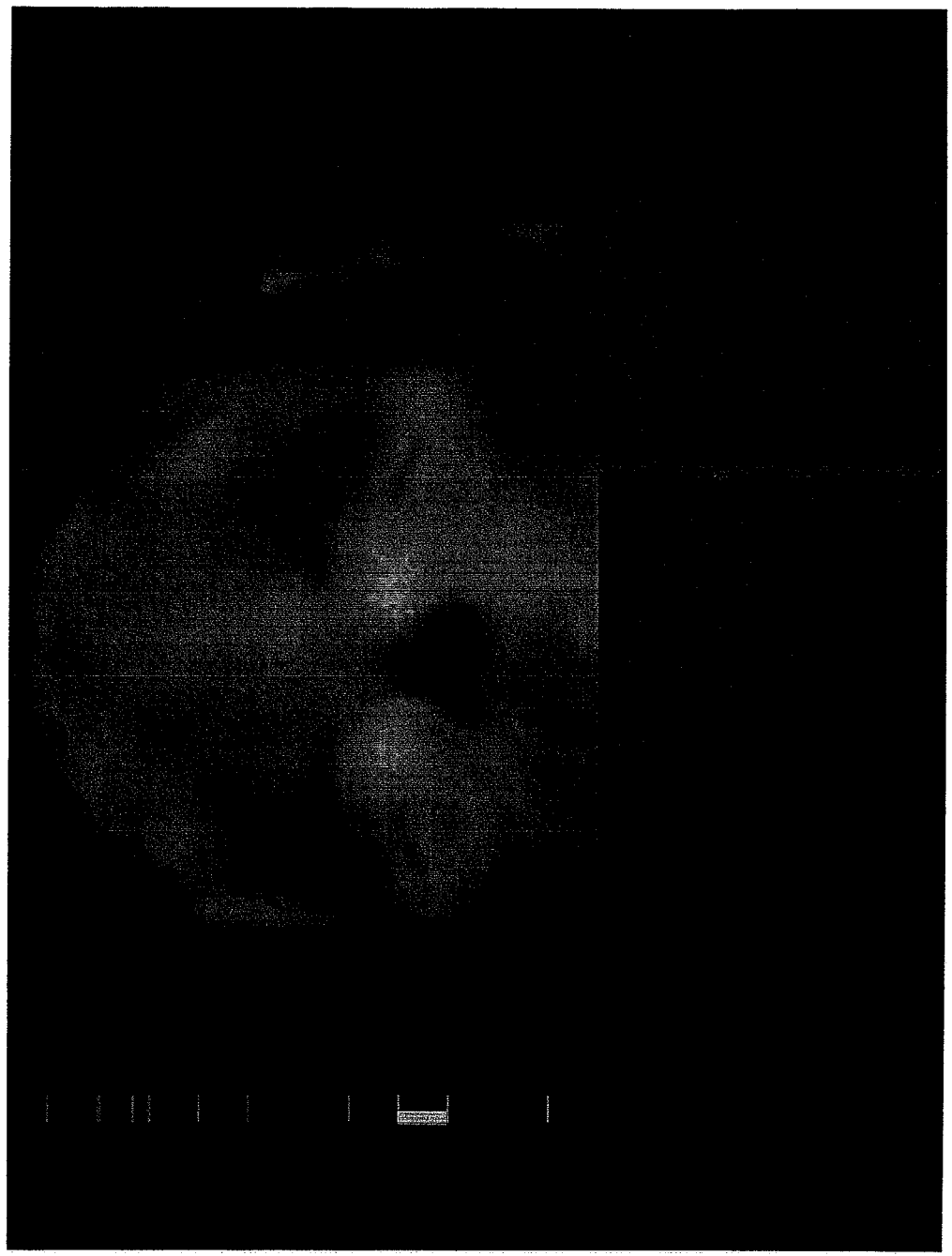
Figure 9A:
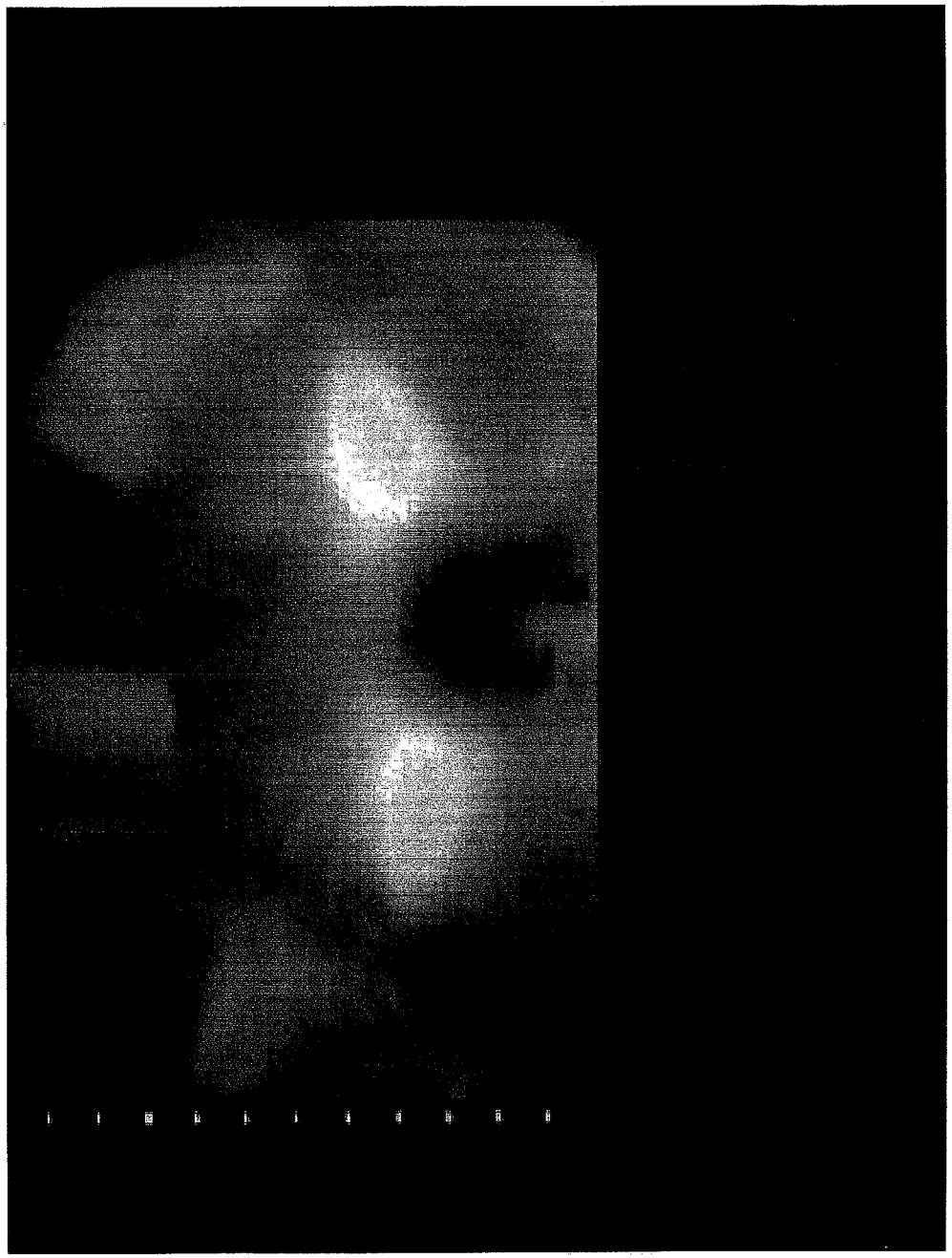
FIGS. 9A and 9B are thermal infrared images of animals showing a tunnel.
Figure 9B:
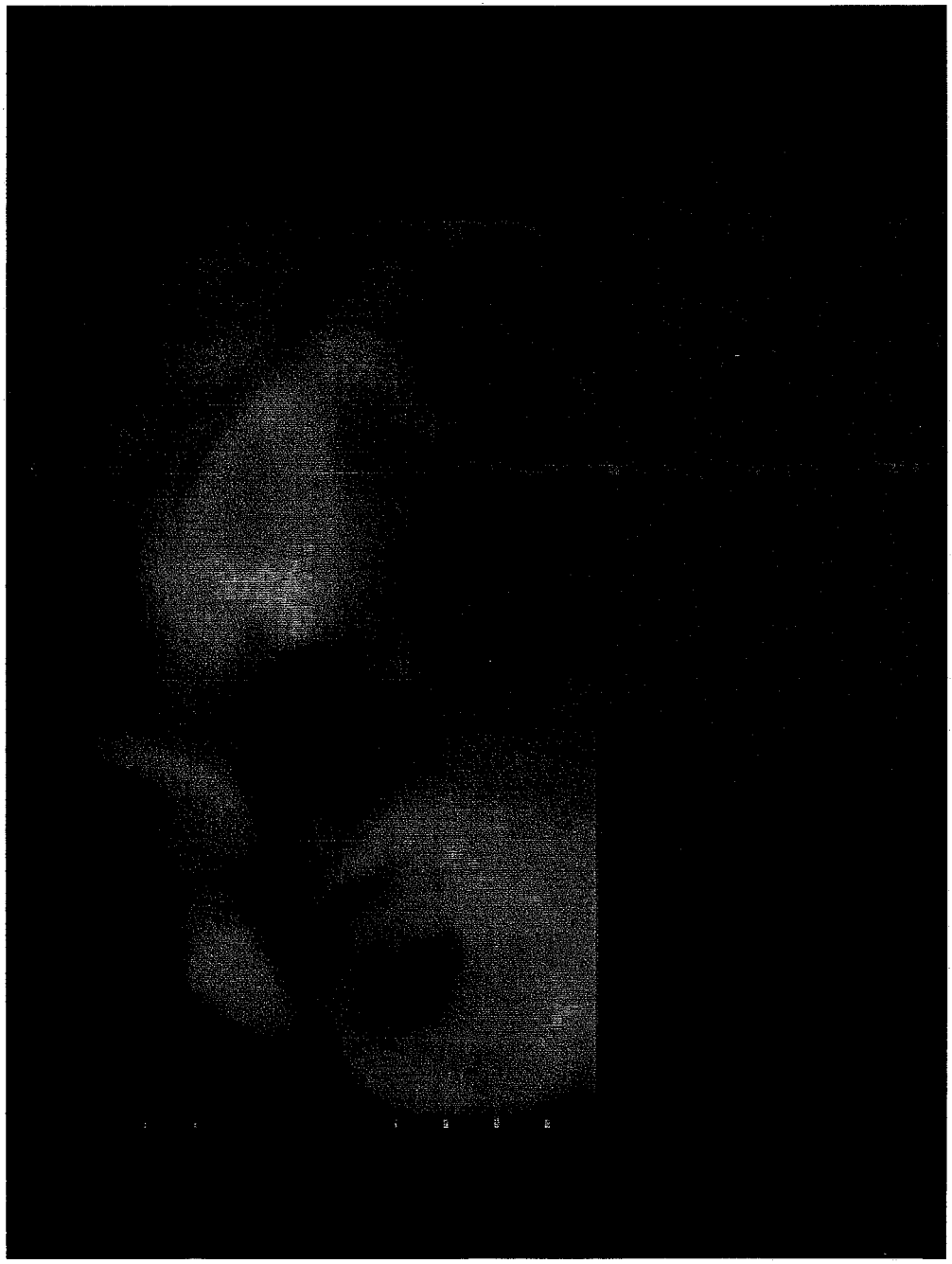

FIGS. 8A and 8B are thermal infrared images of the human face of different subjects showing the tunnel seen as bright white spots in the medial canthal area. The physiologic tunnel is universally present in all individuals despite anatomic variations and ethnic differences. FIGS. 9A and 9B are thermal infrared image showing that the tunnel seen as bright white spots are equally present in animals, illustrated here by a cat (FIG. 9A) and a dog (FIG. 9B).

Figure 10:
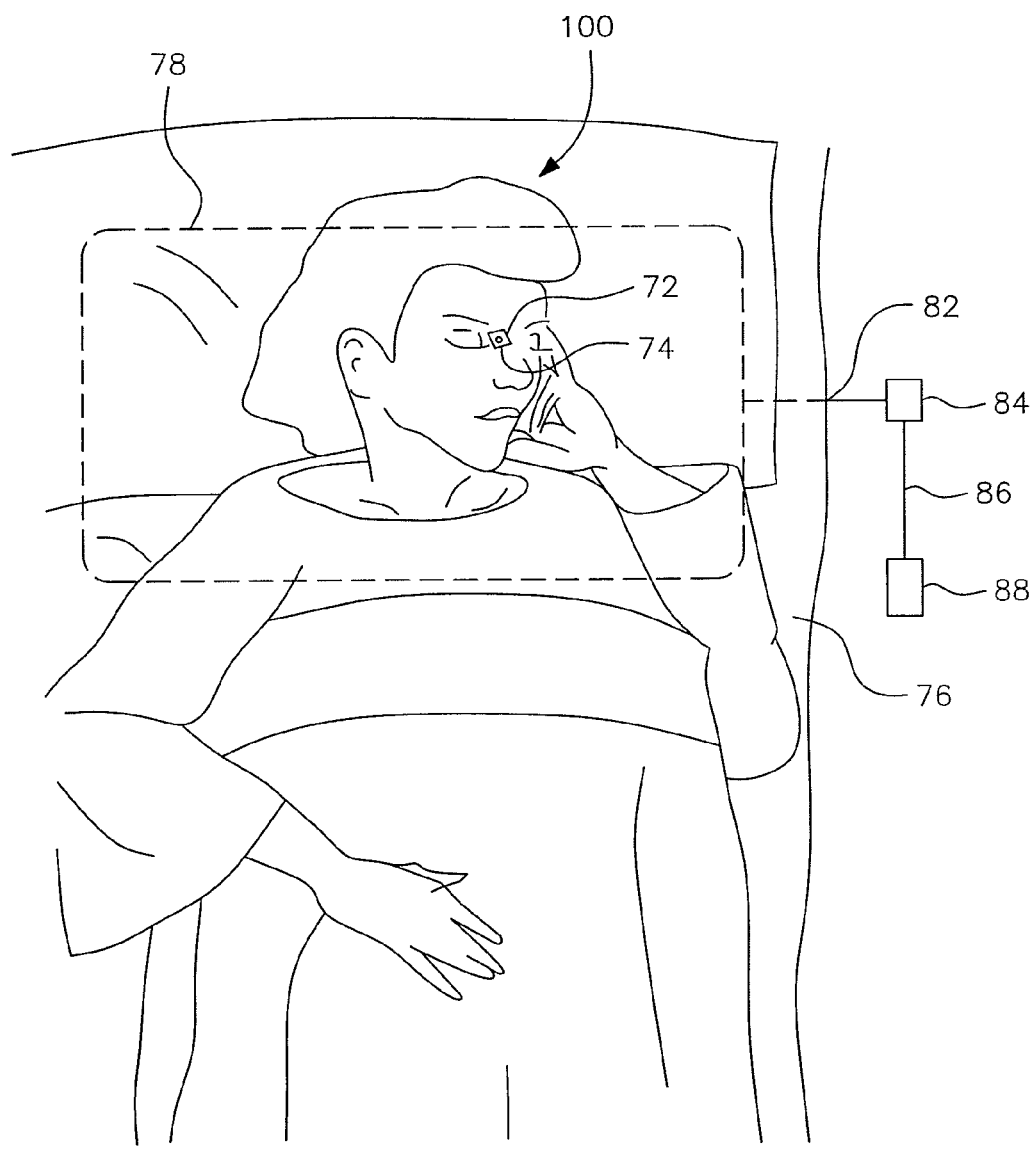
FIG. 10 is a perspective view of a preferred embodiment showing a person wearing a support structure comprised of a patch with a passive sensor positioned on the skin at the end of the tunnel in accordance with the present invention.

A preferred embodiment includes a temperature sensor with measurement processing electronics housed in a patch-like support structure which positions a passive sensor directly in contact with the skin over the brain temperature tunnel site. Accordingly, FIG. 10 is a perspective view of a preferred embodiment showing a person 100 wearing a support structure comprised of a patch 72 with a passive sensor 74 positioned on the skin at the end of the tunnel. Person 100 is laying on a mattress 76 which contains antenna 78. Wire 82 extends from antenna 78 to controller unit 84 with said controller 84 communicating with device 88 by communication line 86. Exemplary device 88 includes a decoding and display unit at the bedside or at the nursing station. It is understood that controller unit 84 besides communicating by cable 86, can also contain a wireless transmission device to wirelessly transmit the signal acquired to a remote station. This inductive radio frequency powered telemetry system can use the same antenna 78 to transfer energy and to receive the signal.

The antenna 78 can be secured to a mattress, pillow, frame of a bed, and the like in a removable or permanent manner. The preferred embodiment includes a thin flat antenna encapsulated by a flexible polymer that is secured to a mattress and is not visible to the user. Alternatively an antenna can be placed in any area surrounding the patient, such as on a night stand.

The antenna 78 and controller unit 84 works as a receiver/interrogator. A receiver/interrogator antenna 78 causes RF energy to radiate to the microcircuit in the patch 72. This energy would be stored and converted for use in the temperature measurement process and in the transmission of the data from the patch 72 to the antenna 78. Once sufficient energy has been transferred, the microcircuit makes the measurement and transmits that data to the receiver/interrogator antenna 78 with said data being processed at controller 84 and further communicated to device 88 for display or further transmission. The switching elements involved in the acquisition of the sensor data (measurement of the energy) is done in a sequence so that the quantitized answer is available and stored prior to the activation of the noise-rich transmission signal. Thus the two inherently incompatible processes successfully coexist because they are not active simultaneously.

The capability of the RF link to communicate in the presence of noise is accomplished by "spreading" the spectral content of the transmitted energy in a way that would inherently add redundancy to the transmission while reducing the probability that the transmission can ever be interpreted by the receiver/interrogator 78 as another transmission or noise that would cause the receiver/interrogator 78 to transmit and display incorrect information. This wireless transmission scheme can be implemented with very few active elements. The modulation purposely spreads the transmission energy across the spectrum and thus provides noise immunity and the system can be ultimately produced via batch processing and thus at a very low cost.

Since the energy to operate sensor 74 in patch 72 comes from the antenna 78, the microcircuit in said patch 72 can be very small and ultra-thin. Size of the patch 72 would be further minimized to extremely small dimensions by the design approach that places all the processing function of the RF link in the controller unit 84 working as a receiver. RF messaging protocol and the control of the sensor 74 resides in the receiver/interrogator controller powered by commercially available batteries or by AC current. Thus the RF messaging protocol and the control of the sensor 74 is directly controlled by the MCU of controller 84. The circuit resident in the patch 72 is preferably completely self-contained. The sensing system 74 in the patch 72 is preferably a silicon microcircuit containing the circuits needed to support the sensor, quantatize the data from the sensor, encode the data for radio frequency transmission, and transmit the data, besides power conditioning circuits and digital state control. Sensor, support circuitry, RF power and communications are all deposited on a micro-chip die allowing the circuit to be built in large quantities and at very low cost. This scheme is preferably used for both passive and active devices.

The operational process can consist of two modes, manual or automated. In the manual mode, an operator such as a nurse activates the system and RF energy radiated to the microcircuit in the patch 72 would be stored and converted for use in the temperature measurement process and in the transmission of the data from the end of the BTT to the antenna 78. Once sufficient energy has been transferred (less than 1 second) the microcircuit would make the measurement and transmit the data to the antenna 78 receiver and controller 84 to be displayed for example on a back-lit LCD display at the nursing station. An audio "beep" will signal that the data had been received and is ready for view. In the automated mode, the process is done automatically and continuously by interrogation at preset frequency and an alarm being activated when the reading is outside the specified range. A tri-dimensional antenna can also be used and the controller 84 set up to search the three dimensions of the antenna to assure continued and proper connection between antenna 78 and sensing means 74. It is also understood that the sensor can modulate reflected RF energy. Accordingly, the energy will trigger the unit to acquire a temperature measurement, and then the unit will modulate the reflected energy. This reflected energy and information will be received at the interrogator and displayed as above.

The present invention also provides a method for monitoring biological parameters, which comprises the steps of: securing a passive sensor to the body; generating electromagnetic radiation from a device secured to at least one of a mattress, a pillow and the frame of a bed; generating a signal from said passive sensor; receiving said signal by a device secured to at least one of a mattress, a pillow and the frame of a bed; and determining the value of the biological parameter based on said signal.

It is understood that a variety of external power sources such as electromagnetic coupling can be used including an ultra-capacitor charged externally through electromagnetic induction coupling and cells that can be recharged by an external oscillator. It is also understood that the sensing system can be remotely driven by ultrasonic waves.

Figure 11:
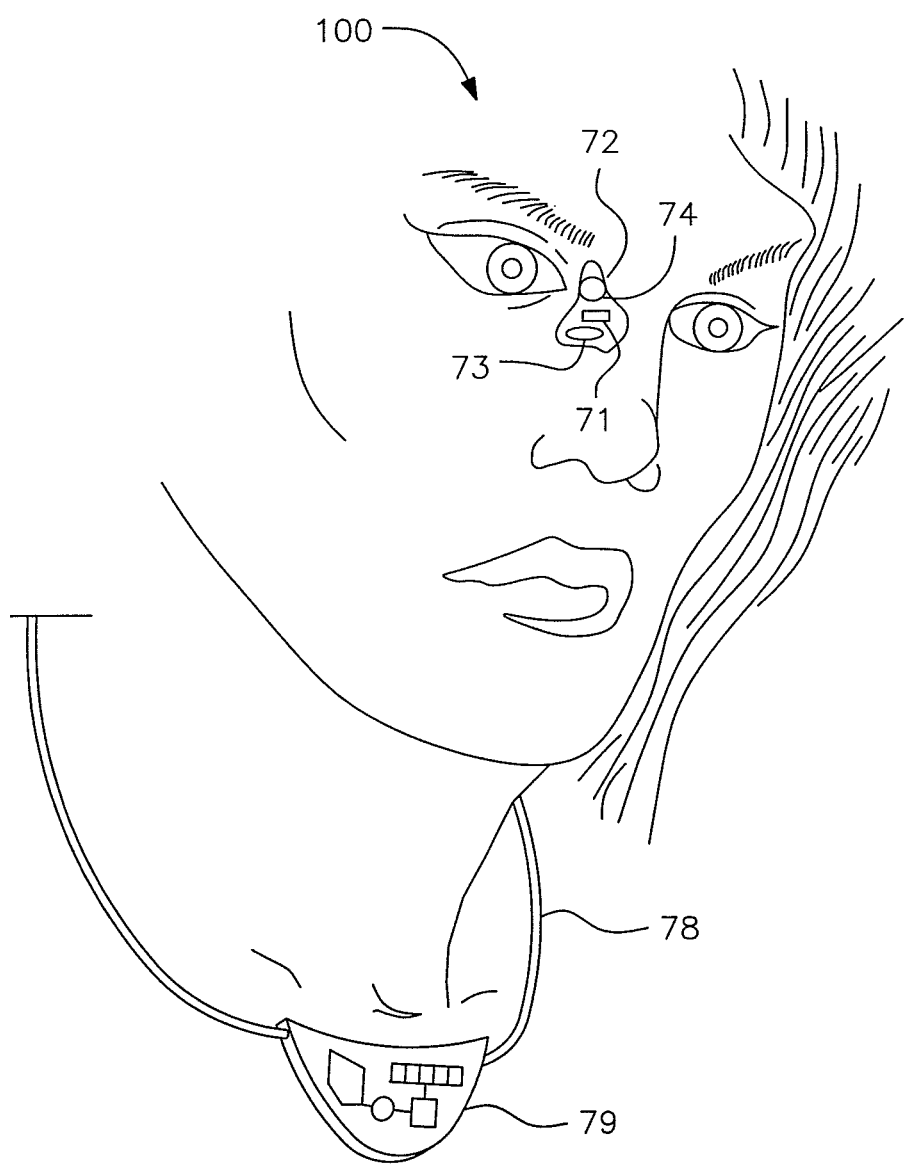
FIG. 11 is a perspective view of another preferred embodiment showing a person wearing a support structure comprised of a patch with a passive sensor positioned on the skin at the end of the tunnel in accordance with the present invention.

FIG. 11 is a perspective view of another preferred embodiment showing in closer detail a person 100 wearing a support structure comprised of patch 72 with a sensor 74, transmitter 71, and digital converter and control 73 positioned on the skin at the end of the tunnel. Person 100 is wearing a necklace which works as antenna 78 and a pendant in the necklace works as the controller unit and transmitting unit 79. Solar cells and/or specialized batteries power unit 79. Patients are used to carrying Holter monitoring and cards with cords around their necks and this embodiment can fit well with those currently used systems. It is understood that, besides a necklace, a variety of articles including clothing and electric devices can be used as a receiver/interrogator and this capability can be easily incorporated into cell phones, note book computers, hand held computers, internet appliances for connecting to the internet, and the like, so a patient could use his/her cell phone or computer means to monitor his/her brain temperature.

The preferred embodiments shown in FIGS. 10 and 11 can preferably provide continuous monitoring of fever or temperature spikes for any surgery, for any patient admitted to a hospital, for nursing home patients, in ambulances, and to prevent death or harm by hospital infection. Hospital infection is an infection acquired during a hospital stay. Hospital infection is the fourth cause of death in the U.S. and kills more than 100,000 patients annually and occurs primarily due to lack of early identification of fever or temperature spikes. The present invention provides timely identification and therapy of an infection due to 24 hour automated monitoring of temperature. If there is a spike in temperature an alarm can be activated. This will allow timely identification and treatment of an infection and thus prevent death or costly complications such as septic shock that can occur due to delay in treating infectious processes. Besides, said preferred embodiments provide means for continuous fever monitoring at home including during sleeping for both children and adults.

Figure 12A:
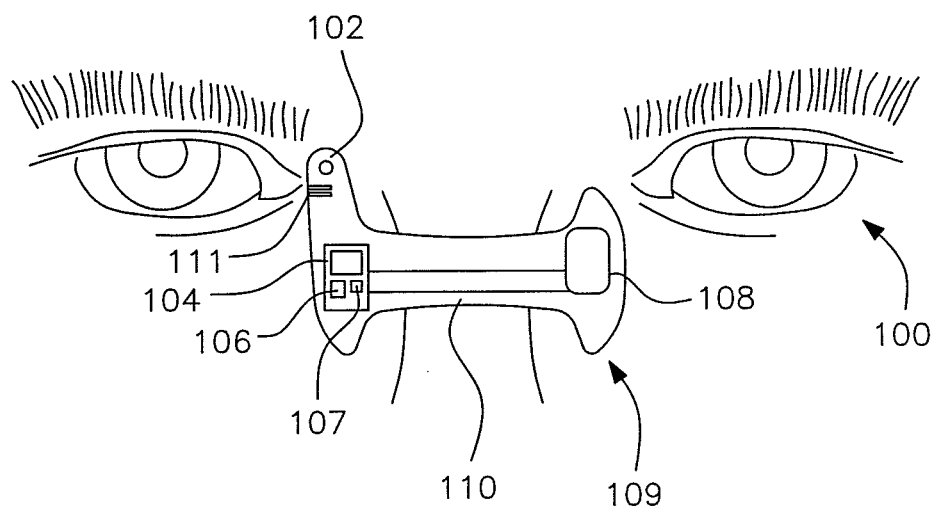
FIG. 12A is a front perspective view of a person wearing a support structure comprised of a patch with an active sensor positioned on the skin at the end of the tunnel in accordance with the present invention.
Figure 12B:
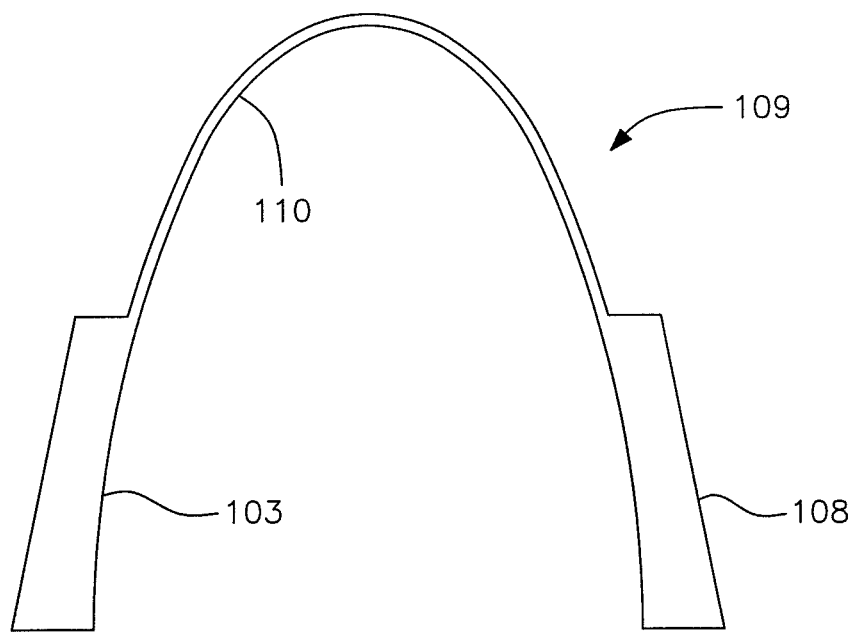
FIG. 12B is a side schematic view showing the flexible nature of the support structure shown in FIG. 12A.

FIG. 12A is a front perspective view of a preferred embodiment showing a person 100 wearing a support structure comprised of a patch 109 with indicator lines 111 and containing an active sensor 102 positioned on the skin at the end of the tunnel. The preferred embodiment shown in FIG. 12 provides a transmitting device 104, a processing device 106, AD converter 107 and a sensing device 102 connected by flexible circuit 110 to power source 108. For example the transmitting module can include RF, sound or light. FIG. 12B is a side schematic view showing the flexible nature of the support structure in FIG. 12A with flexible circuit 110 connecting microelectronic package 103 which contains a transmitting device means, a processing device and a sensing device in the right side of the patch 109 and the power source 108 in the left side of said patch 109. Exemplary embodiments will be described.

In accordance with this exemplary embodiment for temperature measurement, the thermal energy emitted by the BTT is sensed by the temperature sensor 102 such as a miniature thermistor which produces a signal representing the thermal energy sensed. The signal is then converted to digital information and processed by processor 106 using standard processing for determining the temperature. An exemplary sonic-based system for brain temperature measurement comprises a temperature sensor, input coupling circuit, signal processing circuit, output coupling circuit and output display circuit. A temperature sensor 102 (e.g., thermistor) in a patch 109 placed on the surface of the skin at the medial canthal area responds to variations in brain temperature which is manifested as a DC voltage signal.

This signal, coupled to a Signal Processor Circuit via an Input Coupling Circuit is used to modulate the output of an oscillator, e.g., a multivibrator circuit, piezoelectric systems operating in or just above the audio frequency range. The oscillator is a primary component of the Signal Processor Circuit. The output of the oscillator is input to an amplifier, which is the second primary component of the Signal Processor.

The amplifier increases the output level from the oscillator so that the output of the Signal Processor is sufficient to drive an Output Display Circuit. Depending on the nature of the Output Display Circuit, e.g., an audio speaker, a visual LED display, or other possible display embodiment, an Output Coupling Circuit is utilized to match the signal from the Signal Processor Circuit to the Output Display Circuit. For an Output Display Circuit that requires a digital input signal, the Output Coupling Circuit might include an analog to digital (A/D) converter circuit. A DC power supply circuit is the remaining primary component in the Signal Processor Module. The DC power supply is required to support the operation of the oscillator and the amplifier in the Signal Processing Circuit. Embodiments of the DC power supply can include ultra miniature DC batteries, a light sensitive DC power source, or some combination of the two, and the like. The micro transducers, signal processing electronics, transmitters and power source can be preferably constructed as an Application Specific Integrated Circuit or as a hybrid circuit alone or in combination with MEMS (micro electrical mechanical systems) technology.

The thermistor voltage is input to a microcontroller unit, i.e., a single chip microprocessor, which is pre-programmed to process the thermistor voltage into a digital signal which corresponds to the patient's measured temperature in degrees C. (or degrees F.) at the BTT site. It is understood that different programming and schemes can be used. For example, the sensor voltage can be directly fed into the microcontroller for conversion to a temperature value and then displayed on a screen as a temperature value, e.g., 98.6° F. On the other hand the voltage can be processed through an analog to digital converter (ADC) before it is input to the microcontroller.

The microcontroller output, after additional signal conditioning, serves as the driver for a piezoelectric audio frequency (ultrasonic) transmitter. The piezoelectric transmitter wirelessly sends digital pulses that can be recognized by software in a clock radio sized receiver module consisting of a microphone, low-pass audio filter, amplifier, microcontroller unit, local temperature display and pre-selected temperature level alert mechanism. The signal processing software is pre-programmed into the microcontroller unit of the receiver. Although the present invention provides means for RF transmission in the presence of noise, this particular embodiment using a microphone as the receiving unit may offer additional advantages in the hospital setting since there is zero RF interference with the many other RF devices usually present in said setting. The microcontroller unit drives a temperature display for each patient being monitored. Each transmitter is tagged with its own ID. Thus one receiver module can be used for various patients. A watch, cell phone, and the like adapted with a microphone can also work as the receiver module.

In another embodiment the output of the microcontroller is used to drive a piezo-electric buzzer. The microcontroller output drives the piezo-electric buzzer to alert the user of the health threatening situation. In this design the output of the microcontroller may be fed into a digital-to-analog converter (DAC) that transforms the digital data signal from the microcontroller to an equivalent analog signal which is used to drive the buzzer.

In yet another embodiment the output from the (DAC) is used to drive a speech synthesizer chip programmed to output an appropriate audio warning to the user, for instance an athlete at risk of heatstroke. For a sensed temperature above 39 degrees Celsius the message might be: "Your Body temperature is High. Seek shade. Drink cold liquid. Rest." For temperature below 36 degrees Celsius the message might be: "Your Body temperature is Low. Seek shelter from the Cold. Drink warm liquid. Warm up."

In another embodiment the output is used to drive a light transmitter programmed to output an appropriate light signal. The transmitter consists of an infrared light that is activated when the temperature reaches a certain level. The light signal will work as a remote control unit that activates a remote unit that sounds an alarm. This embodiment for instance can alert the parents during the night when the child is sleeping and has a temperature spike.

An exemplary embodiment of the platform for local reporting consists of three electronic modules mechanically housed in a fabric or plastic holder such as patch 109, which contain a sensor 102 positioned on the skin at the BTT site. The modules are: Temperature Sensor Module, Microcontroller Module, and Output Display Module in addition to a battery. An electronic interface is used between each module for the overall device to properly function. The configuration of this system consists of a strip such as patch 109 attached to the BTT area by a self-adhesive pad. A thermistor coupled to a microcontroller drives an audio frequency piezoelectric transmitter or LED. The system provides local reporting of temperature without a receiver. An audio tone or light will alert the user when certain thresholds are met. The tone can work as a chime or reproduction of human voice.

Another exemplary embodiment for remote reporting consists of four electronic modules: Sensor Module, Microcontroller Module, Output Transmitter Module and Receiver/Monitor Module. From a mechanical viewpoint the first three modules are virtually identical to the first embodiment. Electronically the Temperature Sensor and Microprocessor Modules are identical to the previous embodiment. In this embodiment an Output Transmitter Module replaces the previous local Output Display Module. Output Transmitter Module is designed to transmit wirelessly the temperature results determined by the Microprocessor Module to a remotely located Receiver/Monitor Module. An electronic interface is used between each module for proper function. This device can be utilized by patients in a hospital or home setting. On a continuous basis temperature levels can be obtained by accessing data provided by the Receiver/Monitor Module.

A variety of temperature sensing elements can be used as a temperature sensor including a thermistor, thermocouple, or RTD (Resistance Temperature Detector), platinum wire, surface mounted sensors, semiconductors, thermoelectric systems which measure surface temperature, optic fiber which fluoresces, bimetallic devices, liquid expansion devices, and change-of-state devices, heat flux sensor, crystal thermometry and reversible temperature indicators including liquid crystal Mylar sheets. A preferred temperature sensor includes thermistor model 104JT available from Shibaura of Japan.

Figure 13:
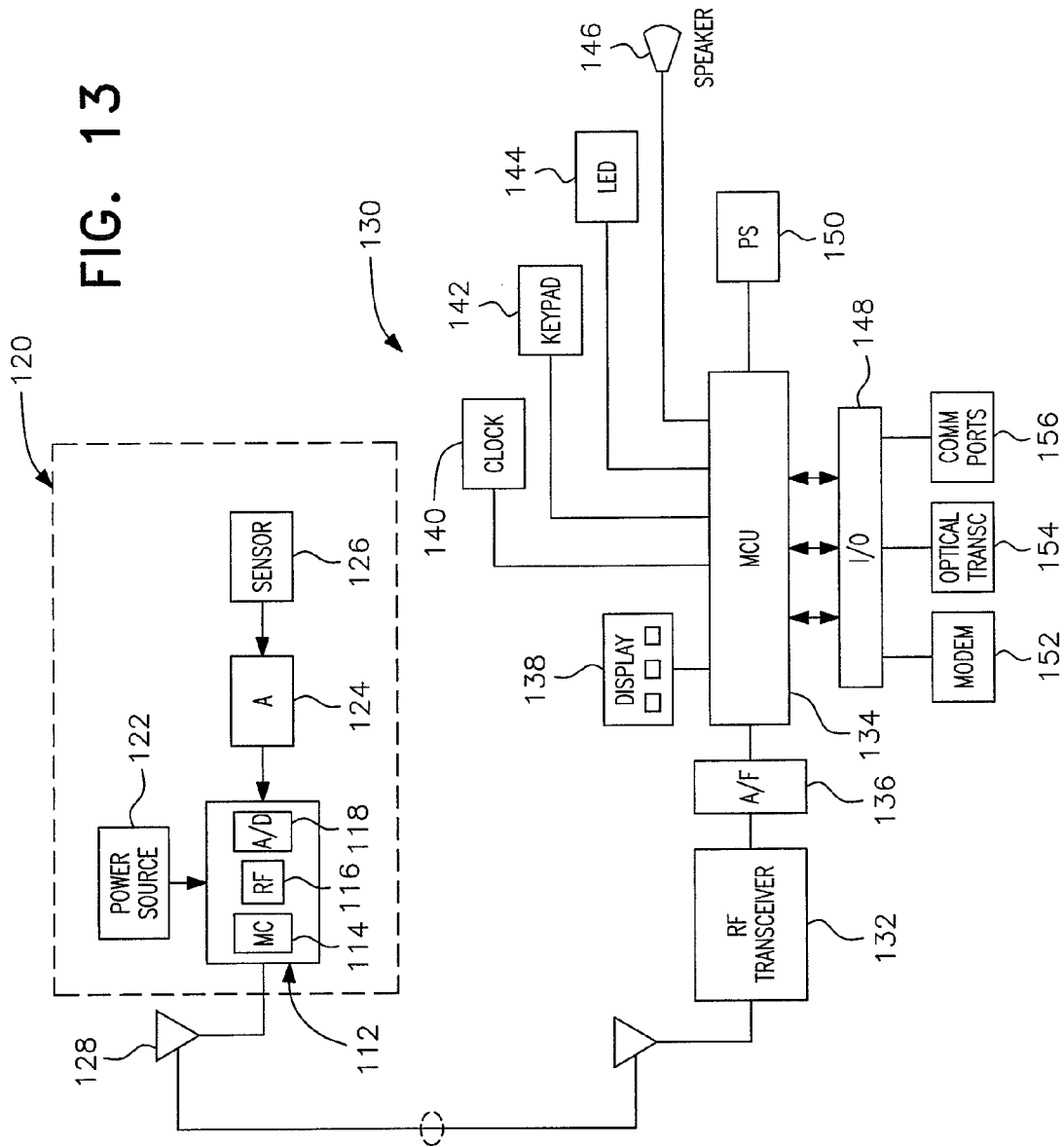
FIG. 13 is a schematic block diagram of one preferred embodiment.

FIG. 13 shows a block diagram of a preferred embodiment of the present invention linking transmitter 120 to receiver 130. Transmitter 120 preferably includes a chip 112 incorporating a microcontroller (MCU) 114, a radio frequency transmitter (RF) 116 and a A/D converter 118 in addition to a power source 122, amplifier (A) 124, sensor 126, and antenna 128, preferably built-in in the chip. Exemplary chips include: (1) rfPIC12F675F, (available from Microchip Corporation, Arizona, USA) this is a MCU+ADC+433 Mhz Transmitter (2) CC1010, available from Chipcon Corporation of Norway.

Receiver 130 preferably includes a chip RF transceiver 132 (e.g., CC1000 available from Chipcon Corporation), a microcontroller unit (MCU) 134, amplifier and filtering units (A/F) 136, display 138, clock 140, keypad 142, LED 144, speaker 146, in addition to a power source 150 and input/output units (I/O) 148 and associated modem 152, optical transceiver 154 and communication ports 156.

A variety of devices can be used for the transmission scheme besides the commercially available RF transmitter chips previously mentioned. One simple transmission devices include an apparatus with a single channel transmitter in the 916.48 MHz band that sends the temperature readings to a bed side receiver as a frequency proportional to the reading. The thermistor's resistance would control the frequency of an oscillator feeding the RF transmitter data input. If the duty cycle is less than 1%, the 318 MHz band would be usable. Rather than frequency, a period measurement technique can be used. The model uses a simple radio frequency carrier as the information transport and modulating that carrier with the brain temperature information derived from a transduction device capable of changing its electrical characteristics as a function of temperature (e.g.; thermistor). Either frequency or amplitude of the carrier would be modulated by the temperature information so that a receiver tuned to that frequency could demodulate the changing carrier and recover the slowly moving temperature data.

Another transmission technique suitable to transmit the signal from a sensor in a support structure is a chirp device. This means that when activated, the transmitter outputs a carrier that starts at a lower frequency in the ISM band and smoothly increases frequency with time until a maximum frequency is reached. The brain temperature information is used to modify the rate of change of frequency of the chirp. The receiver is designed to measure the chirp input very accurately by looking for two or more specific frequencies. When the first of the frequencies is detected, a clock measures the elapsed time until the second frequency is received. Accordingly, a third, fourth, etc., frequency could be added to aid in the rejection of noise. Since virtually all the direct sequence spread spectrum transmitters and frequency hopping transmitters are spread randomly throughout their part of the ISM band, the probability of them actually producing the "right" sequence of frequencies at exactly the right time is remote.

Once the receiver measured the timing between the target frequencies, that time is the value that would represent the brain temperature. If the expected second, third, or fourth frequency is not received by the receiver within a "known" time window, the receiver rejects the initial inputs as noise. This provides a spread spectrum system by using a wide spectrum for transmitting the information while encoding the information in a way that is unlike the expected noise from other users of the ISM band. The chirp transmitter is low cost and simple to build and the brain temperature transducer is one of the active elements that controls the rate of change of frequency.

Other preferred embodiments for local reporting include a sensor, an operational amplifier (LM358 available from National Semiconductor Corporation) and a LED in addition to a power source. It is understood that the operational amplifier (Op Amp) can be substituted by a MCU and the LED substituted by a piezoelectric component.

Figure 14:
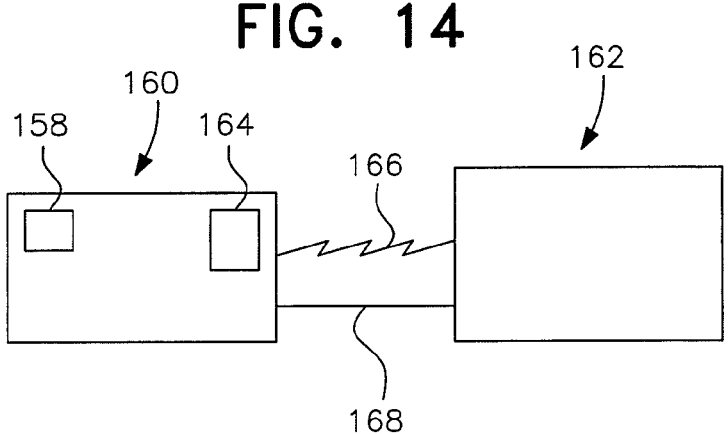
FIG. 14 is a schematic diagram of one preferred embodiment of the invention interacting with devices and articles of manufacture.

FIG. 14 is a schematic diagram showing the support structure 160 to a sensor 158, and MCU 164 controlling and/or adjusting unit 162. Communication between MCU 164 and unit 162 is achieved by wires 168 or wirelessly 166. By way of example, but not by limitation, exemplary units 162 include climate control units in cars, thermostats, vehicle seats, furniture, exercise machines, clothing, footwear, medical devices, drug pumps, and the like. For example, MCU 164 is programmed with transmit the temperature level to receiver unit 162 in the exercise machine. MCU in the exercising machine unit 162 is programmed to adjust speed or other settings in accordance with the signal generated by MCU 164.

The preferred embodiment allows precise positioning of the sensing apparatus by the support structure on the BTT site. The support structure is designed to conform to the anatomical landmarks of the BTT area which assures proper placement of the sensor at all times. The corner of the eye is considered a permanent anatomic landmark, i.e., it is present in the same location in all human beings. The BTT area is also a permanent anatomic landmark as demonstrated by the present invention. To facilitate consistent placement at the BTT site, an indicator in the support structure can be used as shown in FIGS. 15A to 15E.

Figure 15A:
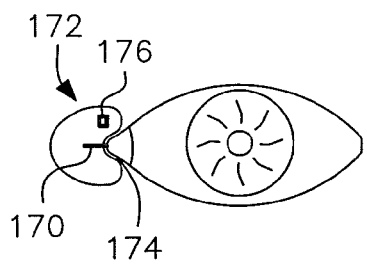
FIGS. 15A to 15E are schematic views showing preferred embodiments of the invention using indicators.

FIG. 15A shows a Guiding Line 170 placed on the outside surface of the support structure 172. The Guiding Line 170 is lined up with the medial corner of the eye 174. The sensor 176 is located above the Guiding Line 170 and on the outer edge of the support structure 172, so once the Guiding Line 170 of the support structure 172 is lined up with the medial corner of the eye 174, the sensor 176 is positioned on the main entry point of the tunnel. Thus the support structure 172 can be precisely and consistently applied in a way to allow the sensor 176 to cover the BTT area at all times.

Figure 15B:
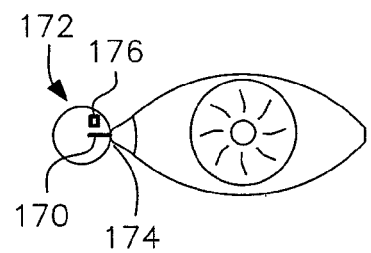

FIG. 15B shows a different design of the patch 172 but with the same Guiding Line 170 lined up with the medial corner of the eye 174, thus allowing consistent placement of sensor 176 at the BTT site despite the difference in design.

Figure 15C:
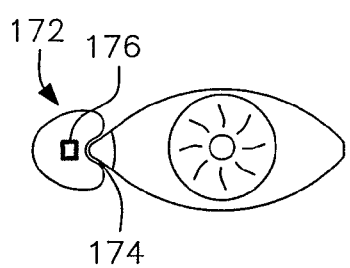

FIG. 15C is another preferred embodiment showing the sensor 176 lined up with medial corner 174. Thus in this embodiment a Guiding Line is not required and the sensor 176 itself guides the positioning.

Figure 15D:
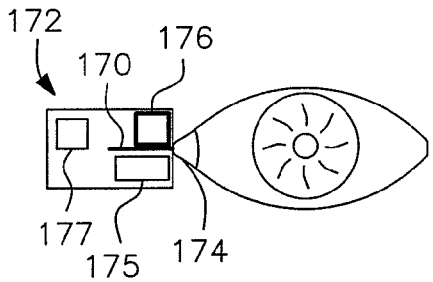

In FIG. 15D the MCU 175 and cell 177 of patch 172 are located outside of the BTT site while sensor 176 is precisely positioned at the BTT site. It is understood that any type of indicator on the support structure can be used to allow proper placement in the BTT area including external marks, leaflets, cuts in the support structure, different geometry that lines up with the corner of the eye, and the like.

Figure 15E:
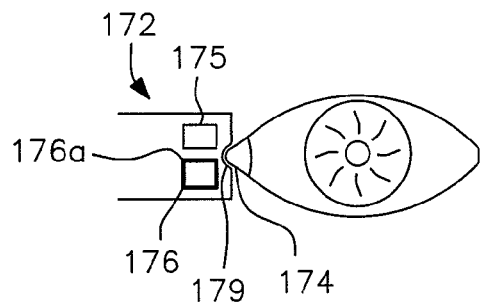

FIG. 15E is another preferred embodiment showing the superior edge 176a of sensor 176 lined up with medial corner 174 and located in the inferior aspect of the medial canthal area while microchip controller 175 is located in the superior aspect of the medial canthal area. Support structure 172 has a geometric indicator 179 comprised of a small recess on the support structure 172. It is understood that a strip working as support structure like an adhesive bandage can have the side opposite to the sensor and hardware made with tear off pieces. The sensor side is first attached to the skin and any excess strip can be easily torn off. Two sizes, adult and children cover all potential users.

The material for the support structure working as a patch can be soft and have insulating properties such as are found in polyethylene. Depending on the application a multilayer structure of the patch can include from the external side to the skin side the following: thinsulate layer; double foam adhesive (polyethylene); sensor (thermistor); and a Mylar sheet. The sensor surface can be covered by the Mylar sheet, which in turn is surrounded by the adhesive side of the foam. Any soft thin material with high thermal resistance and low thermal conductivity can be preferably used as an interface between the sensor and the exterior, such as polyurethane foam (K=0.02 W/m·C). Any support structure can incorporate the preferred insulation material.

A preferred power source for the patch includes natural thermoelectrics as disclosed by the present invention. In addition, standard lightweight thin plastic batteries using a combination of plastics such as fluorophenylthiophenes as electrodes can be used, and are flexible allowing better conformation with the anatomy of the BTT site. Another exemplary suitable power source includes a light weight ultra-thin solid state lithium battery comprised of a semisolid plastic electrolyte which are about 300 microns thick.

The system can have two modes: at room temperature the system is quiet and at body temperature the system is activated. The system can also have an on/off switch by creating a circuit using skin resistance, so only when the sensor is placed on the skin is the system activated. The patch can also have a built-in switch in which peeling off a conductive backing opens the circuit (pads) and turn the system on. In addition, when removed from the body, the patch can be placed in a case containing a magnet. The magnet in the case acts as an off switch and transmission is terminated when said patch is in the case.

Figure 16A:
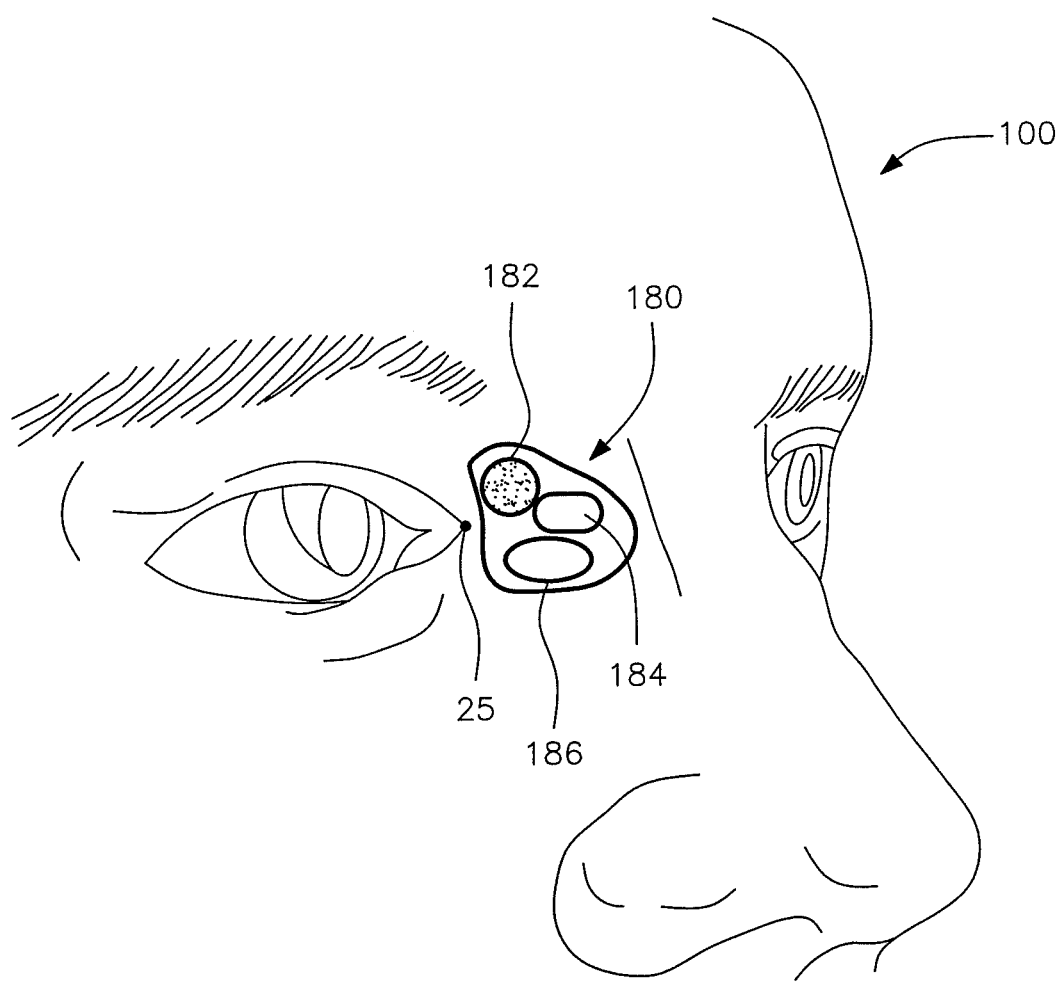
FIGS. 16A to 16C are perspective views of a preferred embodiment showing a person wearing support structures incorporated as patches.
Figure 16B:
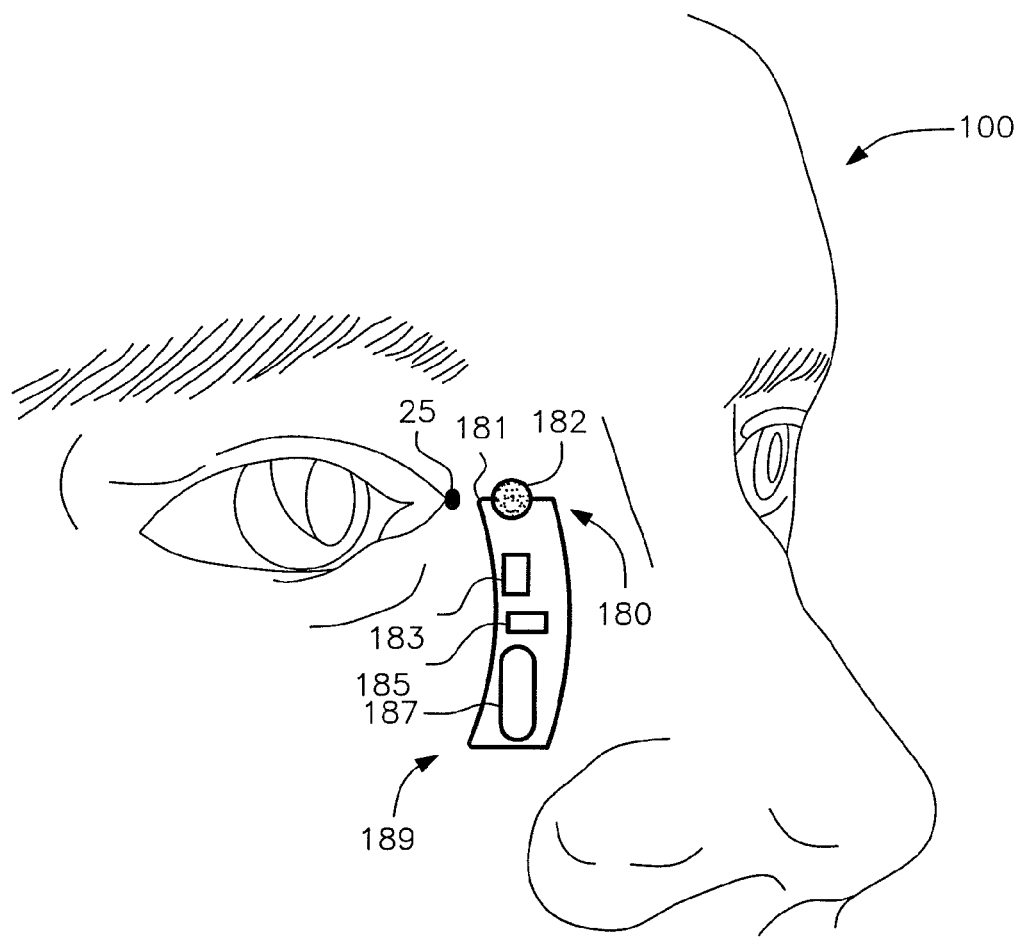
Figure 16C:
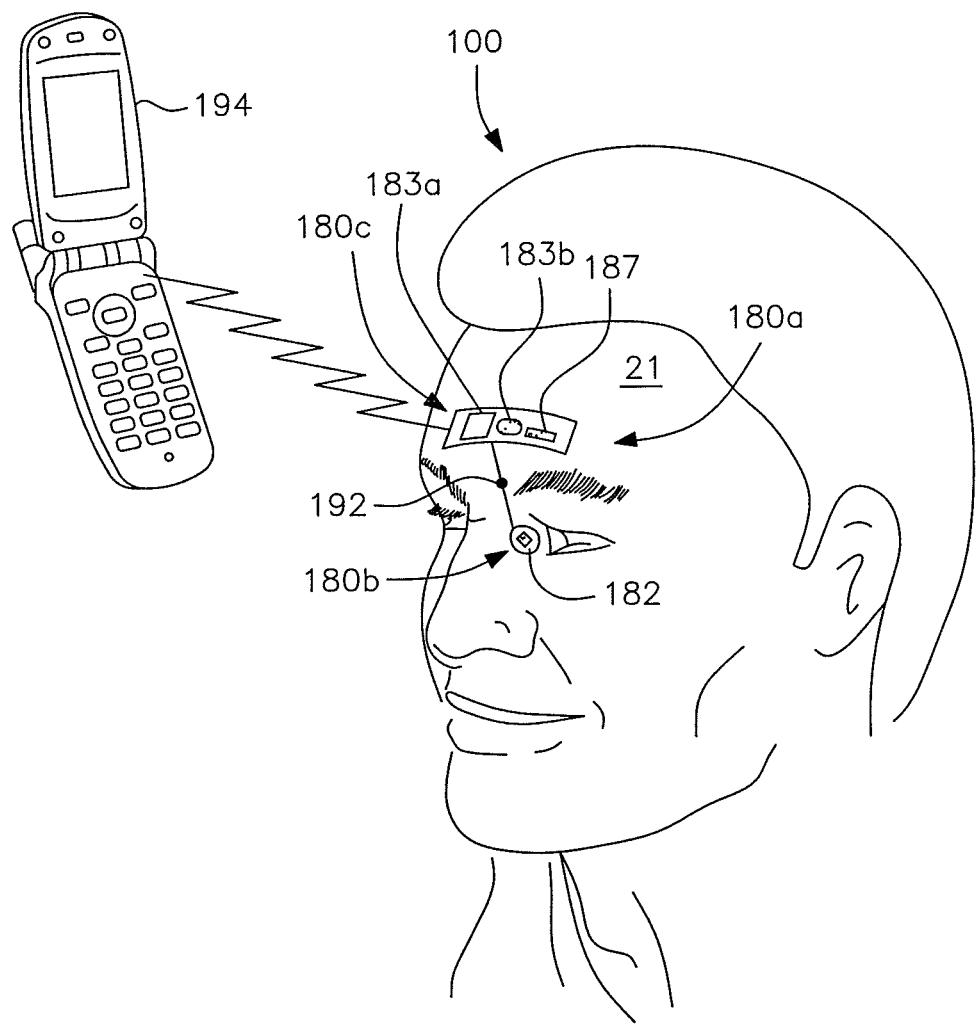

FIG. 16A to 16C are perspective views of preferred embodiments showing a person 100 wearing support structures 180 incorporated as patches. In a preferred embodiment shown in FIG. 16A, the support structure 180 contains LED 184, cell 186, and sensor 182. Sensor 182 is positioned at a main entry point on the superior aspect of the medial canthal area adjacent to the medial corner of the eye 25. LED 184 is activated when a signal reaches certain thresholds in accordance with the principles of the invention. FIG. 16B is another preferred embodiment showing a person 100 wearing support structure 180 with sensor 182 positioned at the general area of the main entry point of the tunnel with the superior edge 181 of support structure 180 being lined up with the corner of the eye 25. Support structure 180 contains an extension that rests on the cheek area 189 and houses transmitting means 183 for wireless transmission, processing means 185 and power source 187. FIG. 16C is an exemplary preferred embodiment showing person 100 wearing a two piece structure 180a comprised of support structure 180b and housing structure 180c connected by wires 192, preferably a flexible circuit. Support structure 180b contains the sensor 182 which is positioned at the BTT site. Housing structure 180c which can comprise an adhesive strip on the forehead 21 houses processing device 183a, transmitting device 183b and power source 187 for transmitting the signal to unit 194, for example a cell phone.

Figure 17:
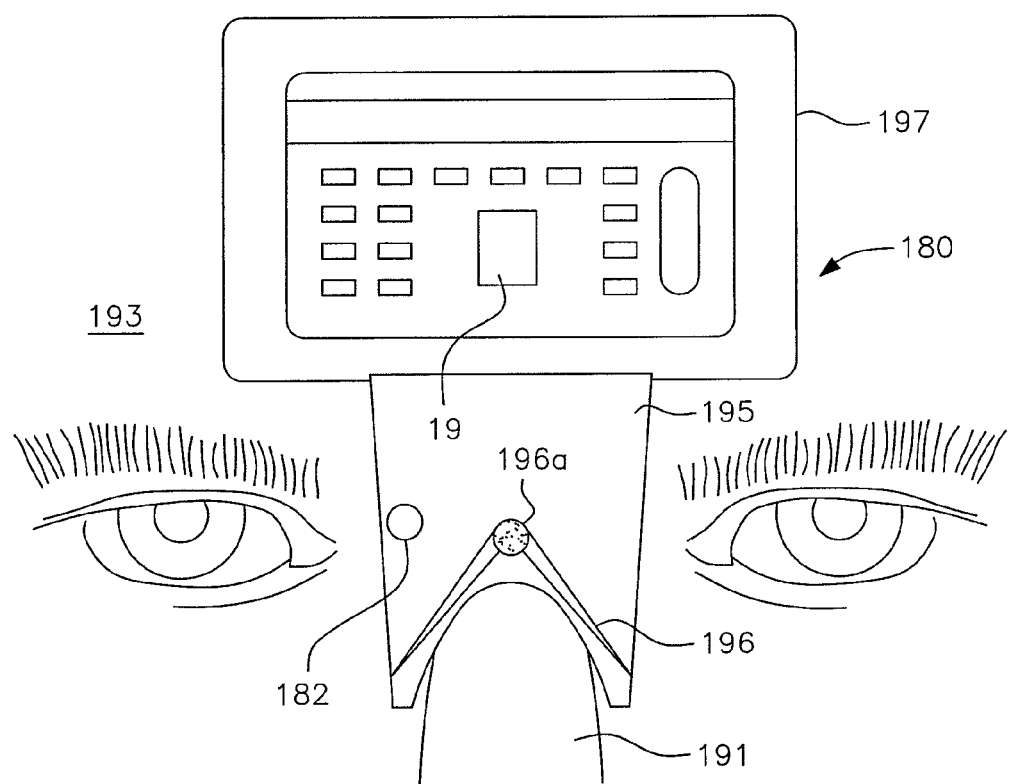
FIG. 17 is a perspective view of another preferred embodiment showing a person wearing a support structure incorporated as a clip with a sensor positioned on the skin at the end of the tunnel in accordance with the present invention.

FIG. 17 is a schematic view of another preferred embodiment showing the support structure 180 with sensor 182 being held at the nose 191 by a clip 196. Support structure 180 extends superiorly to the forehead 193. Housing 195 of support structure 180 contains pressure attachment means such as clip 196. Housing 197 on the forehead contains the transmitting device and power source. Clip 196 uses a spring based structure 196a to apply gentle pressure to secure support structure 180 and sensor 182 in a stable position. Housing 197 can also have a LCD display 19. The LCD 19 can have an inverted image to be viewed in a mirror by the user, besides LCD 19 can have a hinge or be foldable to allow proper positioning to allow the user to easily view the numerical value displayed.

Figure 18:
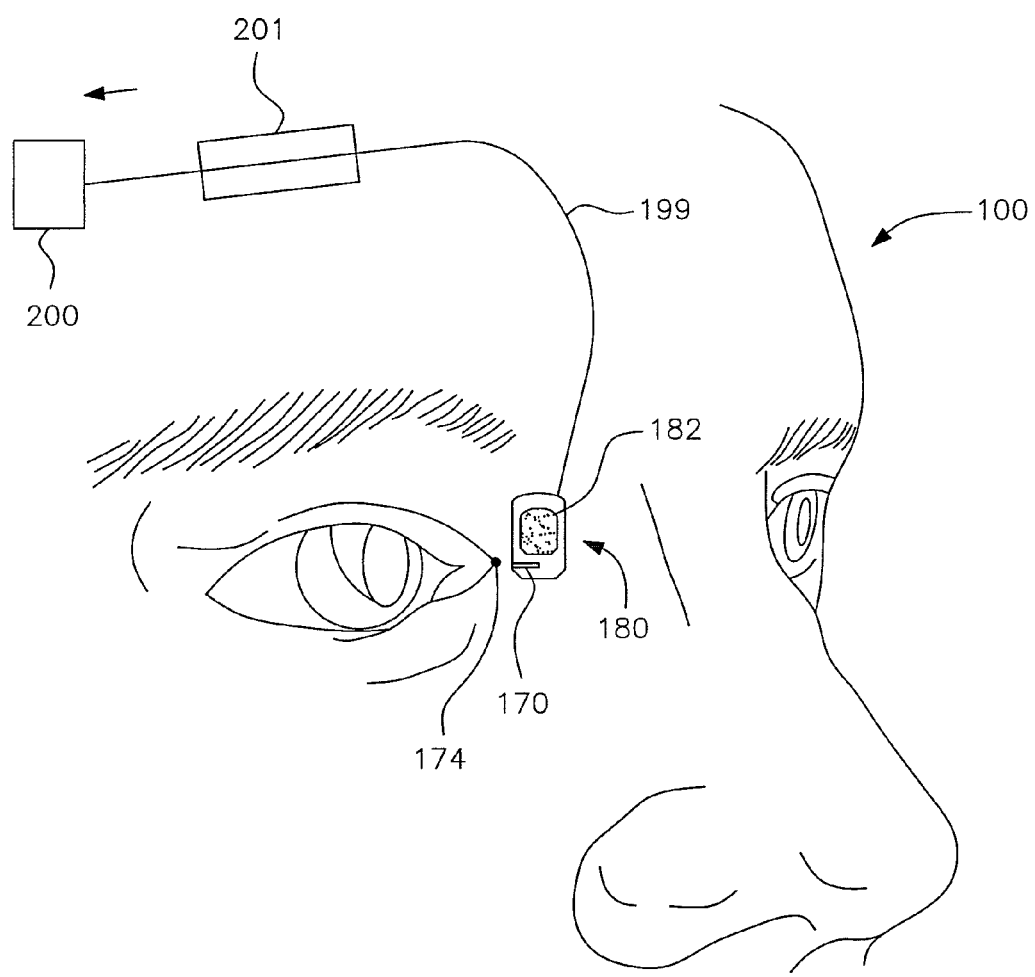
FIG. 18 is a perspective view of another preferred embodiment showing a person wearing a support structure with a sensor positioned on the skin at the end of the tunnel and connected by a wire.

FIG. 18 is a perspective view of another preferred embodiment showing a person 100 wearing a support structure 180 comprised of a patch with sensor 182 positioned on the skin at the end of the tunnel and connected by a wire 199 to a decoding and display unit 200. Support structure 180 has a visible indicator 170 lined up with the medial corner of the eye 174. Wire 199 includes an adhesive tape 201 within its first 20 cm, and most preferably adhesive tape connected to wire 199 is in the first 10 cm of wire from sensor 182.

FIGS. 19A1 to 19D are schematic views of preferred geometry and dimensions of support structures 180 and sensing device 182. Special geometry and dimension of sensors and support structure is necessary for the optimal functioning of the present invention. The dimensions and design for the support structure 180 are made in order to optimize function and in accordance with the geometry and dimensions of the different parts of the tunnel.

FIG. 19A1 shows support structure 180 working as a patch. The patch 180 contains sensor 182. The patch 180 may contain other hardware or solely the sensor 182. Exemplary sensor 182 is a flat thermistor or surface mount thermistor. The preferred longest dimension for the patch referred to as "z" is equal or less than 12 mm, preferably equal to or less than 8 mm, and most preferably equal to or less than 5 mm. The shortest distance from the outer edge of the sensor 182 to the outer edge of the patch 180 is referred to as "x". "x" is equal to or less than 11 mm, preferably equal to or less than 6 mm and most preferably equal to or less than 2.5 mm. For illustrative purposes the sensor 182 has unequal sides, and distance "y" corresponds to the longest distance from outer edge of the sensor to outer edge of the patch 180. Despite having unequal sides, the shortest distance "x" is the determining factor for the preferred embodiment. It is understood that the whole surface of the sensor 182 can be covered with an adhesive and thus there is no distance between the sensor and an outer edge of a support structure.

An exemplary embodiment for that includes a sensor in which the surface touching the skin at the BTT site is made with Mylar. The Mylar surface, which comprises the sensor itself, can have an adhesive in the surface that touches the skin. In this case, the support structure that can include a piece of glue or an adhesive may be constructed flush in relation to the sensor itself. Accordingly in FIG. 19E support structure 171 comprised of a piece of glue supports sensor 182 in position against the BTT area. Sensor 182 can include a Mylar, a thermistor, thermocouple and the like, and the sensor 182 can be preferably at the edge of the support structure 171 such as a piece of glue or any support structure, and said sensor 182 can be preferably further insulated in its outer surface with a piece of insulating material 173, such as polyethylene.

As shown in FIG. 19A2, the sensor 182 has adhesive in its surface, to be secured to skin 11. The sensor then can be applied to the BTT site in accordance with the principles of the invention. The preferred distance "x" equal to or less than 2.5 mm allows precise pinpoint placement of sensor 182 at the main entry site of the tunnel and thus allows the most optimal signal acquisition, and it should be used for applications that require greatest precision of measurements such as during monitoring surgical procedures. Although a patch was used as support structure for the description of the preferred dimensions, it is understood that the same dimensions can be applied to any support structure in accordance with the principle of the invention including clips, medial canthal pads, head mounted gear, and the like.

FIG. 19B is an exemplary embodiment of a round patch 180 with a flat sensor 182. Preferred dimensions "x" and "z" apply equally as for FIG. 19A1. FIG. 19C is an exemplary embodiment of a patch 180 with a bead-type sensor 182. Preferred dimensions "x" and "z" apply equally as for FIG. 19A1. FIG. 19D is an exemplary embodiment of a support structure 180 with a sensor-chip 15. Sensor chip 15 comprises a sensor that is integrated as part of a chip, such as an Application Specific Integrated Circuit (ASIC). For example sensor chip 15 includes sensor 15a, processor 15b, and transmitter 15c. Preferred dimension "x" apply equally as for FIG. 19A1. Other hardware such as power source 27 may be housed in the support structure 180 which can have a long dimension referred to as "d" that does not affect performance as long as the dimension is preserved.

The support structure and sensor are adapted to match the geometry and dimensions of the tunnel, for either contact measurements or non-contact measurements, in which the sensor does not touch the skin at the BTT site.

Figure 20A:
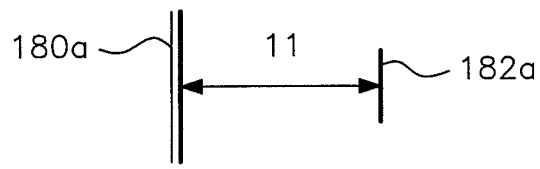
FIGS. 20A to 20C are schematic diagrams of preferred dimensions of the outer edge of support structures in relation to the outer edge of sensing devices.
Figure 20B:
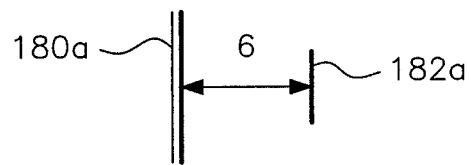
Figure 20C:
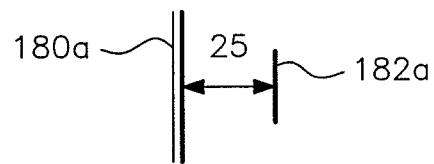

FIGS. 20A to 20C show the preferred dimensions "x" for any support structure in accordance with the present invention. The distance from the outer edge 180a of the support structure to outer edges of sensor 182a is 11 mm, as shown in FIG. 20A. Preferably, the distance from the outer edge 180a of support structure to outer edges of sensor 182a is 6 mm, as shown in FIG. 20B. Most preferably, the distance from the outer edge 180a of the support structure to outer edges of sensor 182a is 2.5 mm, as shown in FIG. 20C.

Figure 21A:
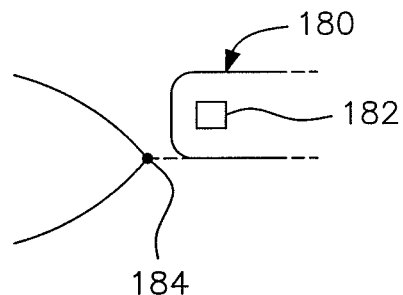
FIGS. 21A and 21B are schematic diagrams of preferred positions of sensing devices.
Figure 21B:
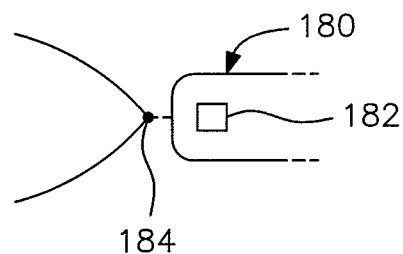

Preferred positions of sensors 182 in relation to the medial corner of the eye 184 are shown in FIGS. 21A and 21B. Support structure 180 positions sensor 182 lined up with medial corner 184 (FIG. 21B). Preferably, as shown in FIG. 21A, support structure 180 positions the sensor 182 above the medial corner 184.

The preferred embodiments of support structures incorporated as patches and clips are preferably used in the hospital setting and in the health care field including continuous monitoring of fever or temperature spikes. Support structures incorporated as medial canthal pads or head mounted gear are preferred for monitoring hyperthermia, hypothermia and hydration status of recreational athletes, professional athletes, military, firefighters, construction workers and other physically intensive occupations, occupational safety, and for preventing wrinkle formation due to thermal damage by sun light.

Figure 22A:
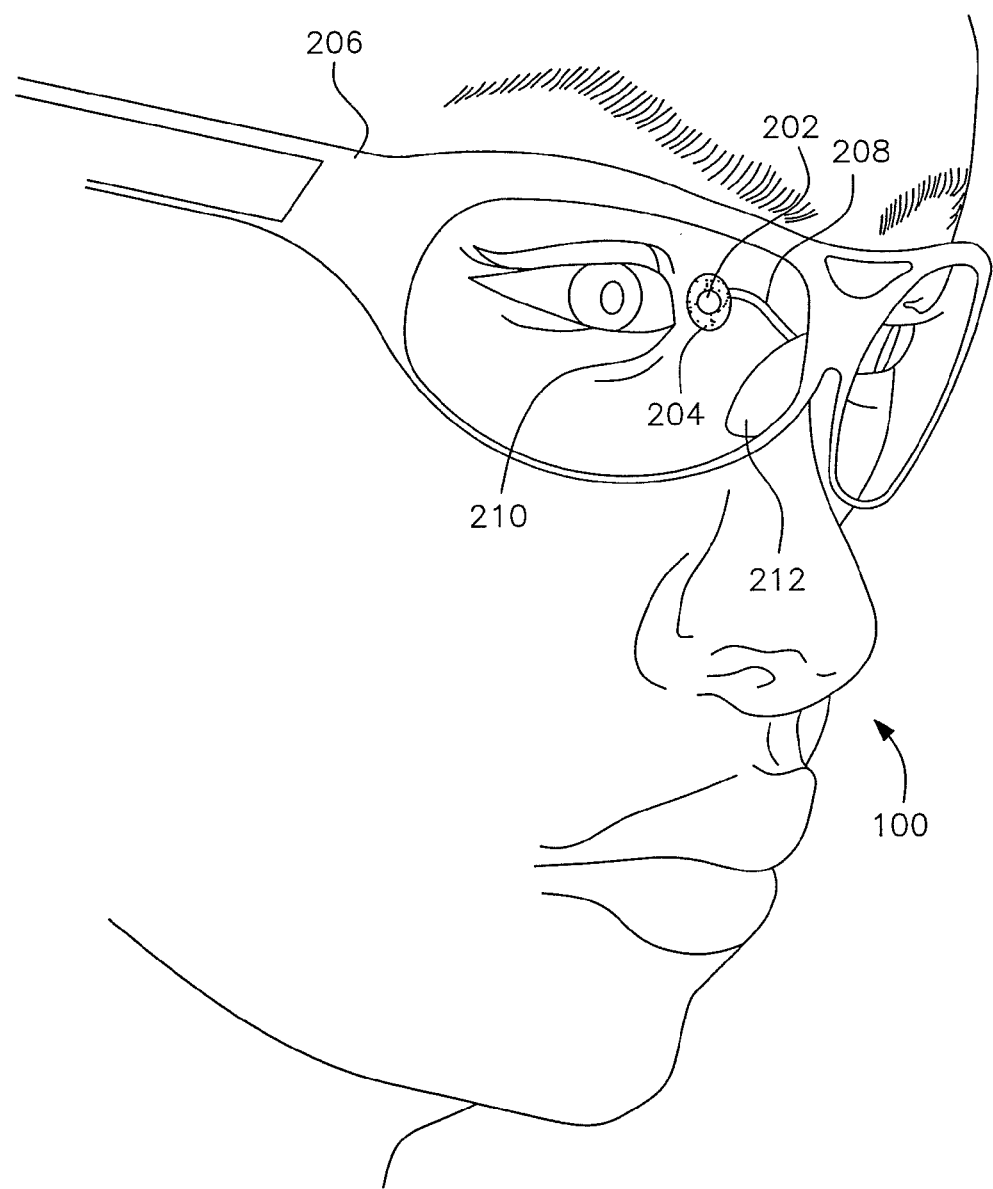
FIGS. 22A to 22C are perspective views of preferred embodiments showing a person wearing a support structure incorporated as a medial canthal pad with a sensor positioned on the skin at the end of the tunnel in accordance with the present invention.
Figure 22B:
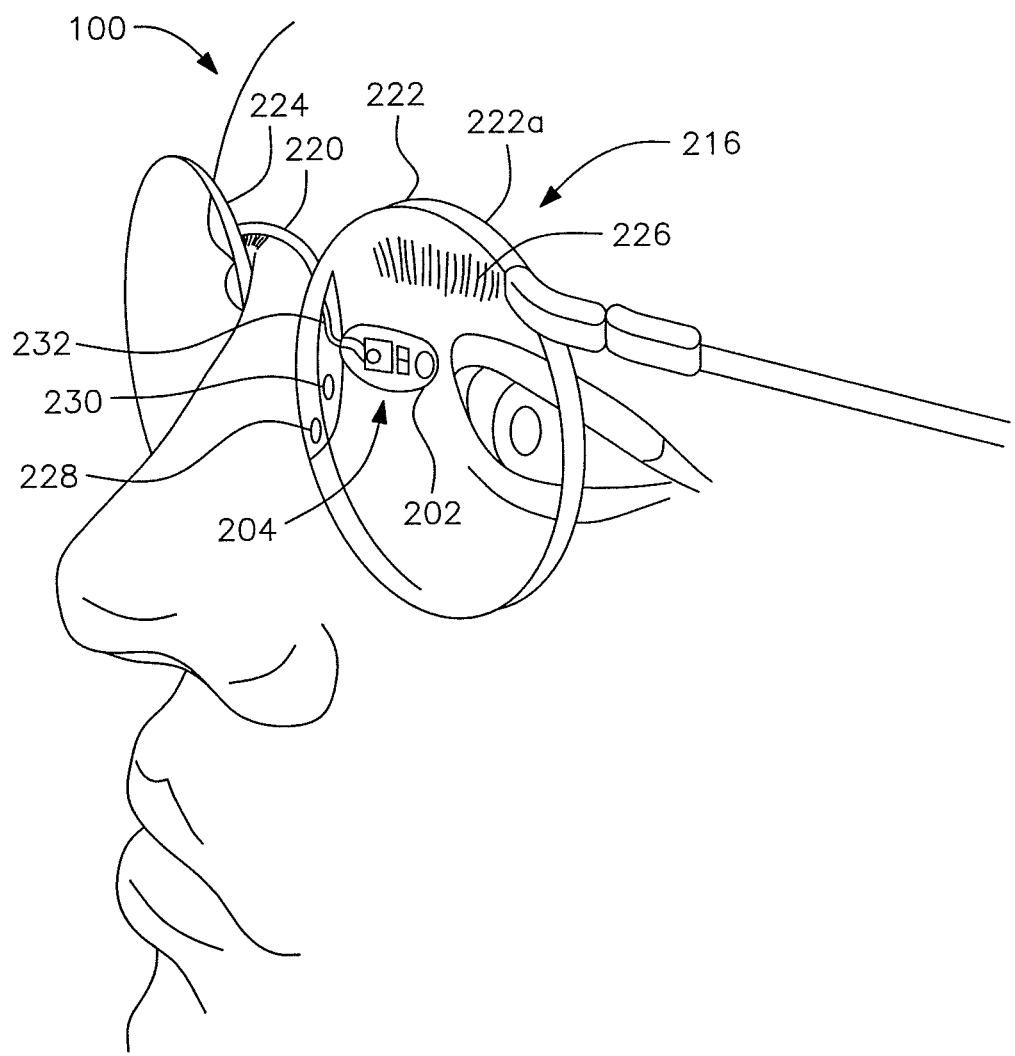
Figure 22C:
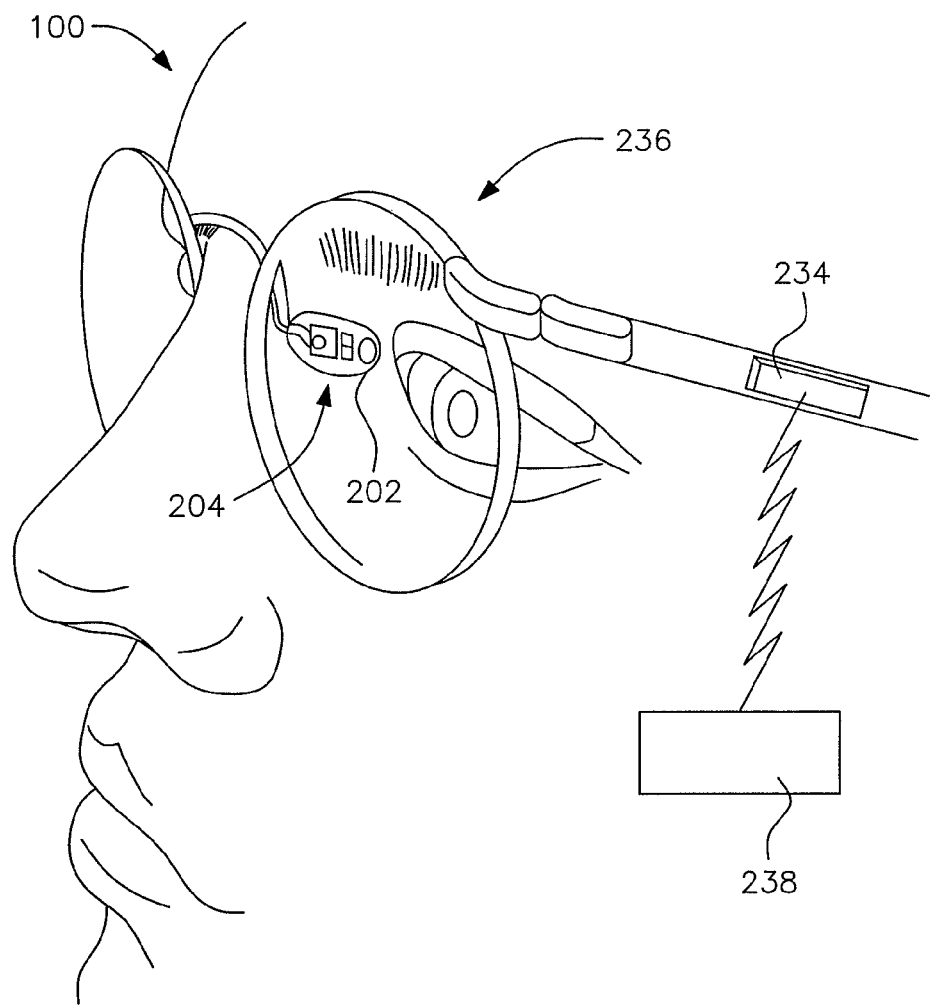

FIGS. 22A to 22C are perspective views of preferred embodiments showing a person 100 wearing support structures incorporated as a medial canthal pad 204 of eyeglasses 206. In a preferred embodiment shown in FIG. 22A, the medial canthal pad 204 contains sensor 202. Connecting arm 208 connects medial canthal pad 204 to eyeglasses frame 206 next to regular nose pads 212. Sensor 202 is positioned on the superior aspect of the medial canthal area adjacent to the medial corner of the eye 210.

FIG. 22B is an exemplary preferred embodiment showing person 100 wearing support structure incorporated as medial canthal pads 204 with sensor 202 integrated into specially constructed eyeglasses frame 216 and containing LEDs 228, 230. Connecting piece 220 which connects the left lens rim 222 and right lens rim 224 is constructed and positioned at a higher position than customary eyeglasses construction in relation to the lens rim 222, 224. Due to the higher position of connecting piece 220 and the special construction of frame 216, the upper edge 222a of left lens rim 222 is positioned slightly above the eyebrow 226. This construction allows medial canthal pad 204 to be positioned at the BTT site while LEDs 228,230 are lined up with the visual axis. Arm 232 of medial canthal pad 204 can be flexible and adjustable for proper positioning of sensor 202 on the skin at the BTT site and for moving away from the BTT site when measurement is not required. The LED 228 is green and LED 230 is red, and said LEDs 228, 230 are activated when a signal reaches certain thresholds.

FIG. 22C is an exemplary preferred embodiment showing person 100 wearing support structure incorporated as medial canthal pads 204 with sensor 202. Signal from sensor 202 is transmitted wirelessly from transmitter 234 housed in the temple of eyeglasses 236. Receiving unit 238 receives a signal from transmitter 234 for processing and displaying. Exemplary receiving units 238 include watch, cell phone, pagers, hand held computers, and the like.

Figure 23A:
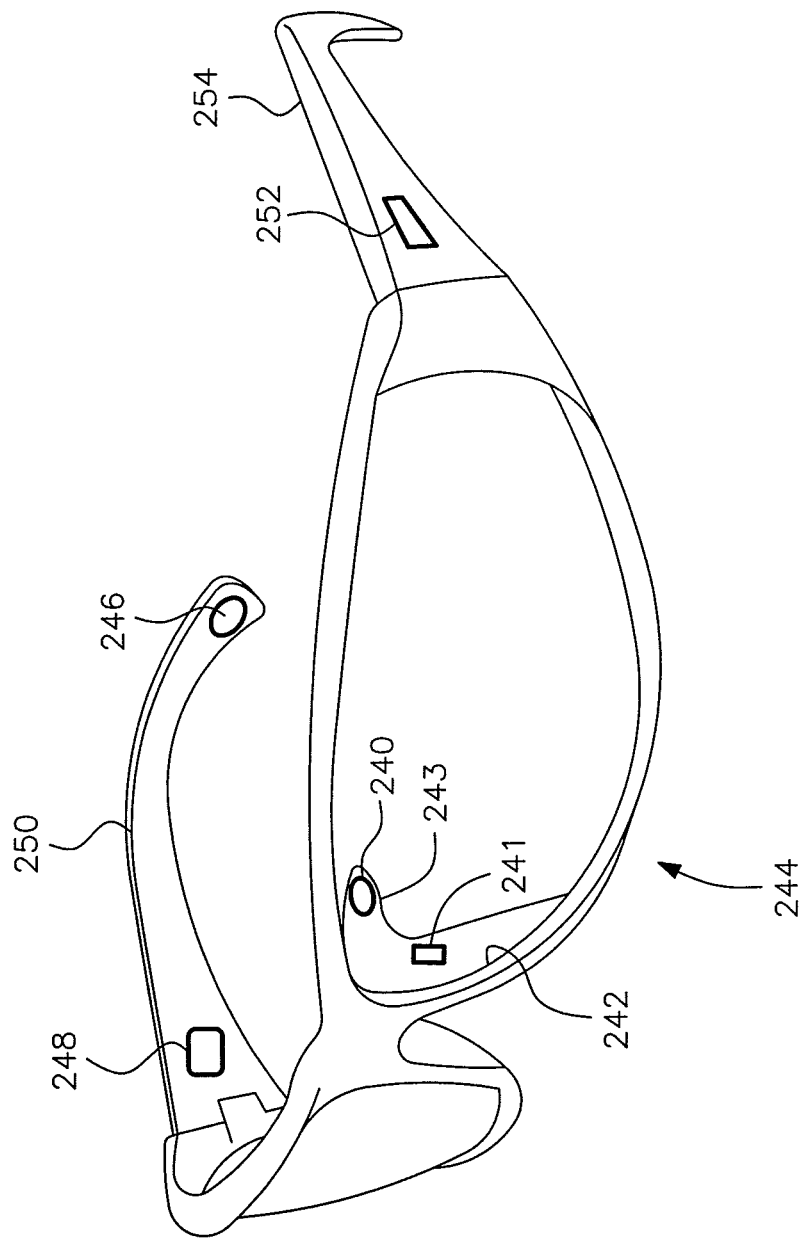
FIGS. 23A and 23B are perspective views of an alternative embodiment showing a support structure comprised of modified nose pads with a sensor positioned on the skin at the end of the tunnel in accordance with the present invention.
Figure 23B:
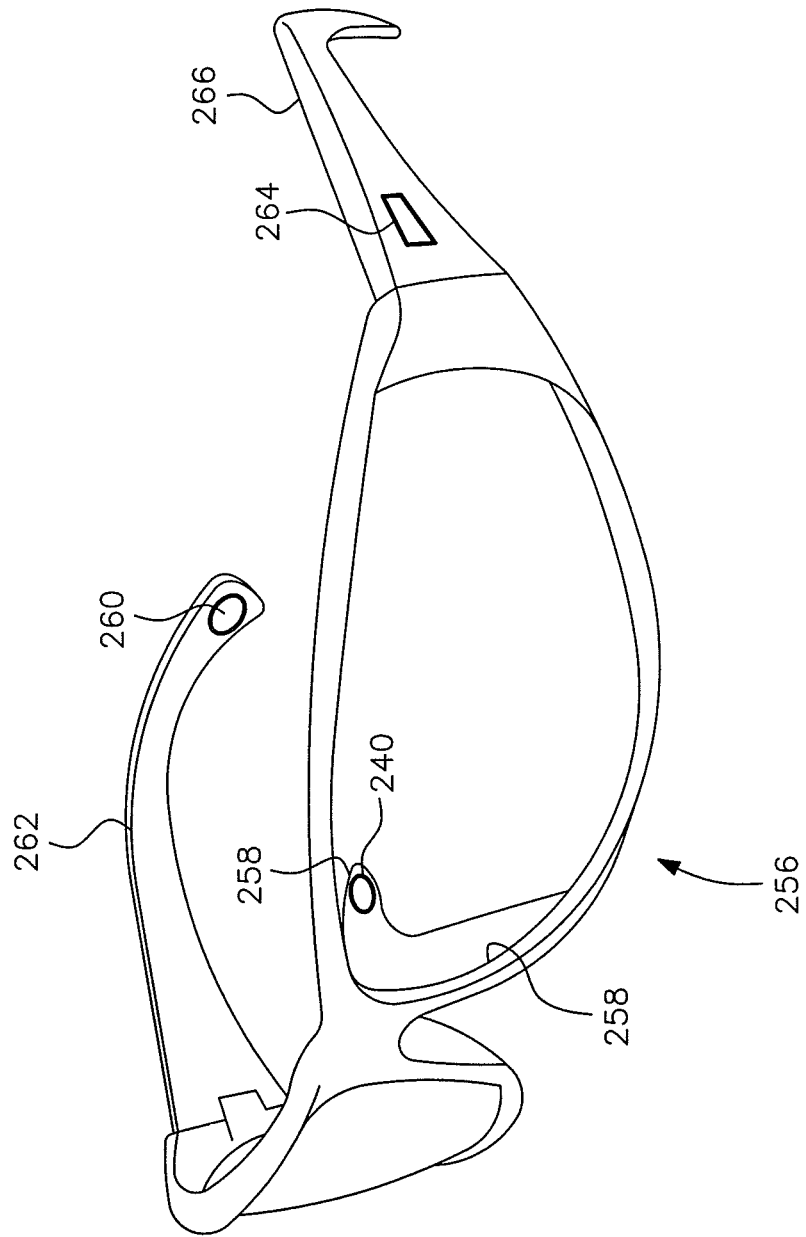

FIGS. 23A to 23B are perspective views of alternative embodiments showing support structures incorporated as a modified nose pad 242 of eyeglasses 244. FIG. 23A is a perspective view showing eyeglasses 244 containing a modified nose pad 242 with sensor 240 and processor 241, sweat sensor 246 and power source 248 supported by temple 250, and transmitter 252 supported by temple 254, all of which are electrically connected. Modified nose pads 242 are comprised of oversized nose pads with a horn like extension 243 superiorly which positions sensor 240 on top of the end of the tunnel.

FIG. 23B is a perspective view showing eyeglasses 256 containing an oversized modified nose pad 258 with sensor 240, sweat sensor 260 supported by temple 262, and transmitter 264 supported by temple 266. Modified oversized nose pad 258 measures preferably 12 mm or more in its superior aspect 258a and contains sensor 240 in its outer edge in accordance with the dimensions and principles of the present invention.

Figure 24:
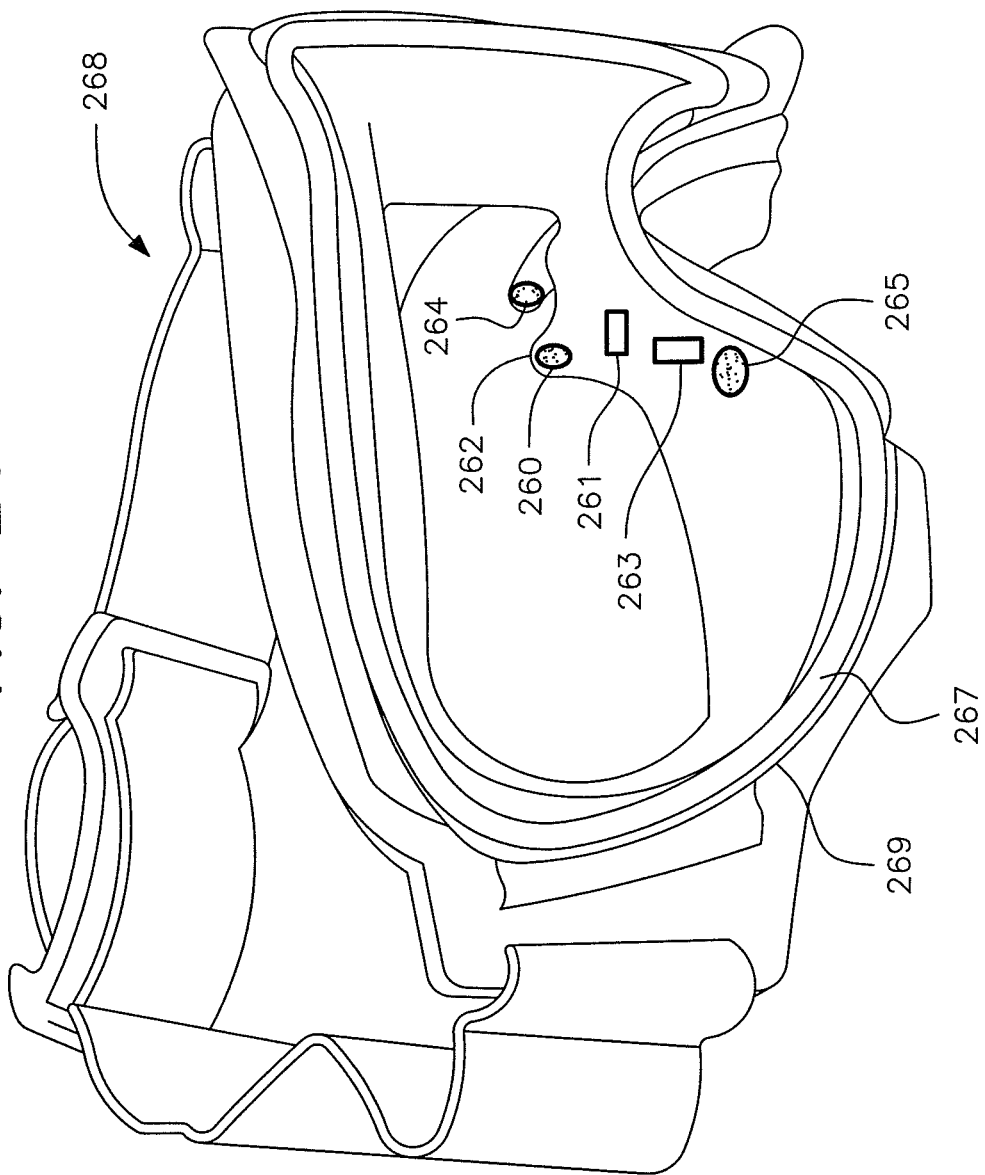
FIG. 24 is a perspective view of another preferred embodiment of support structure in accordance with the invention.

Another preferred embodiment of the invention, shown in FIG. 24, provides goggles 268 supporting medial canthal pads 260 adapted to position sensor 262, 264 at the tunnel site on the skin. As shown, goggles 268 also support transmitting device 261, power source 263, local reporting device 265 such as LED and an antenna 267 for remote reporting. Antenna 267 is preferably integrated as part of the lens rim 269 of goggles 268.

Figure 25:
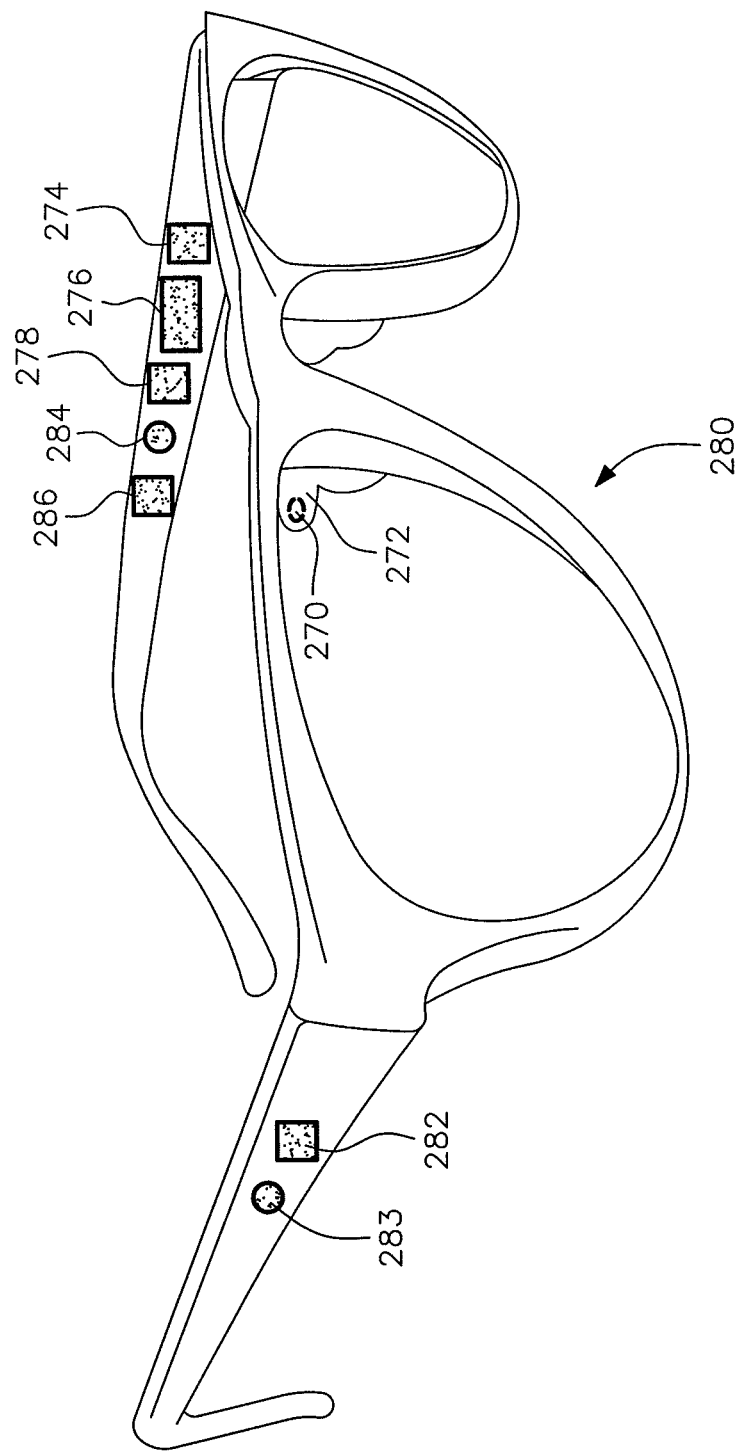
FIG. 25 is a perspective view of one preferred embodiment of support structure showing additional structures for including a sensor.

As shown in FIG. 25, additional device related to the signal generated by sensor 270 in medial canthal pad 272 include power switch 274, set switch 276 which denotes a mode selector, transmitter 278 for wireless transmission of signals, a speaker 282, piezoelectric device 283, input device 284 and processing device 286. The device 274, 276, 278, 282, 284, and 286 are preferably supported by any portion of the frame of eyeglasses 280. It is understood that a variety of devices, switches and controlling devices to allow storage of data, time and other multiple function switches can be incorporated in the apparatus in addition to wires for wired transmission of signals.

Figure 26A:
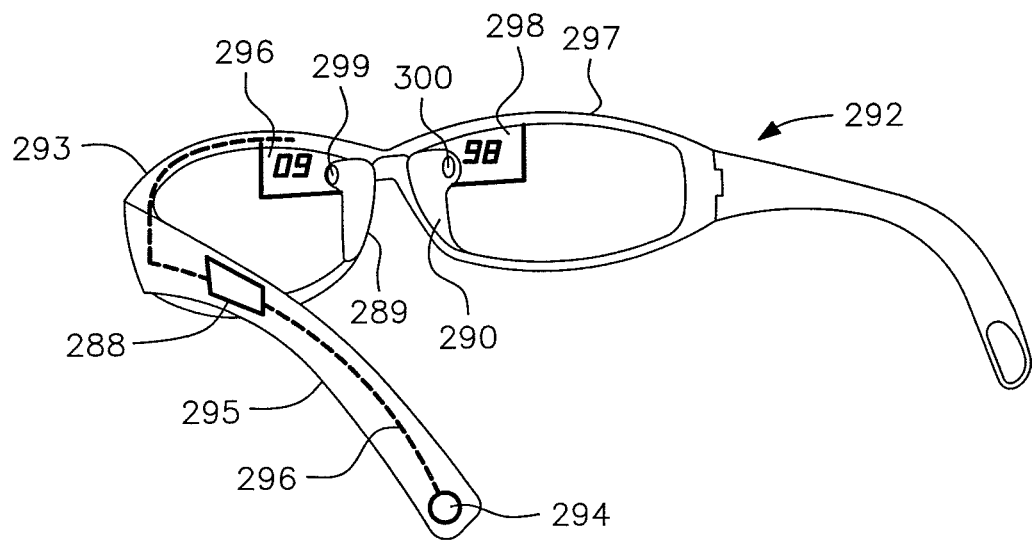
FIG. 26A is a rear perspective view of one preferred embodiment of a support structure with a display device.

FIG. 26A is a rear perspective view of one preferred embodiment showing sensors 299, 300 supported by medial canthal pads 290, 289 of eyeglasses 292 and includes lens rim 297 and display 298 in addition to transmitter 288, sweat sensor 294 and wires 296 disposed within temple 295 and lens rim 293 of said eyeglasses 292 and connected to display device 296.

Figure 26B:
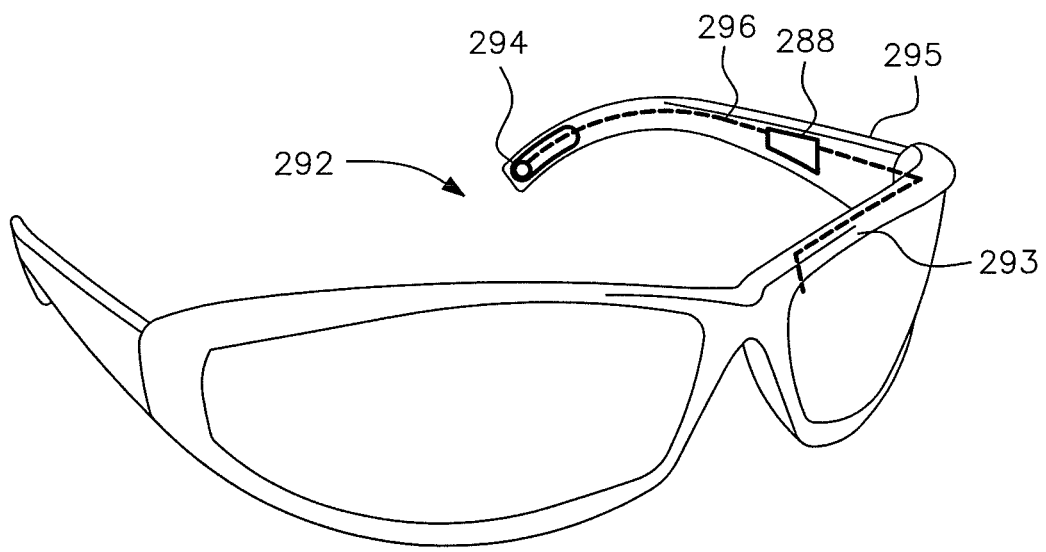
FIG. 26B is a front perspective view of one preferred embodiment of a support structure with a display device.

FIG. 26B is a front perspective view of eyeglasses 292 including sweat sensor 294, transmitter 288 and wires 296 disposed within temple 295 and lens rim 293 of eyeglasses 292 and connected to a display device. In this embodiment sweat sensor 294 produces a signal indicating the concentration of substances in sweat (e.g., sodium of 9 mmol/L) which is displayed on left side display 296 and sensor 300 supported by medial canthal pad 290 produces a signal indicative of, for example, brain temperature of 98 degrees F. which is displayed on the right side display 298. Sweat sensor can be porous or microporous in order to optimize fluid passage to sensors when measuring chemical components.

A variety of display devices and associated lenses for proper focusing can be used including liquid crystal display, LEDs, fiber optic, micro-projection, plasma devices, and the like. It is understood that a display device can be attached directly to the lens or be an integral part of the lens. It is also understood that a display device can include a separate portion contained in the lens rim or outside of the lens rim. Further, the two lenses and displays 296, 298 held within the lens rims 293, 297 can be replaced with a single unit which can be attached directly to the frame of eyeglasses 292 with or without the use of lens rim 293, 297.

Figure 27:
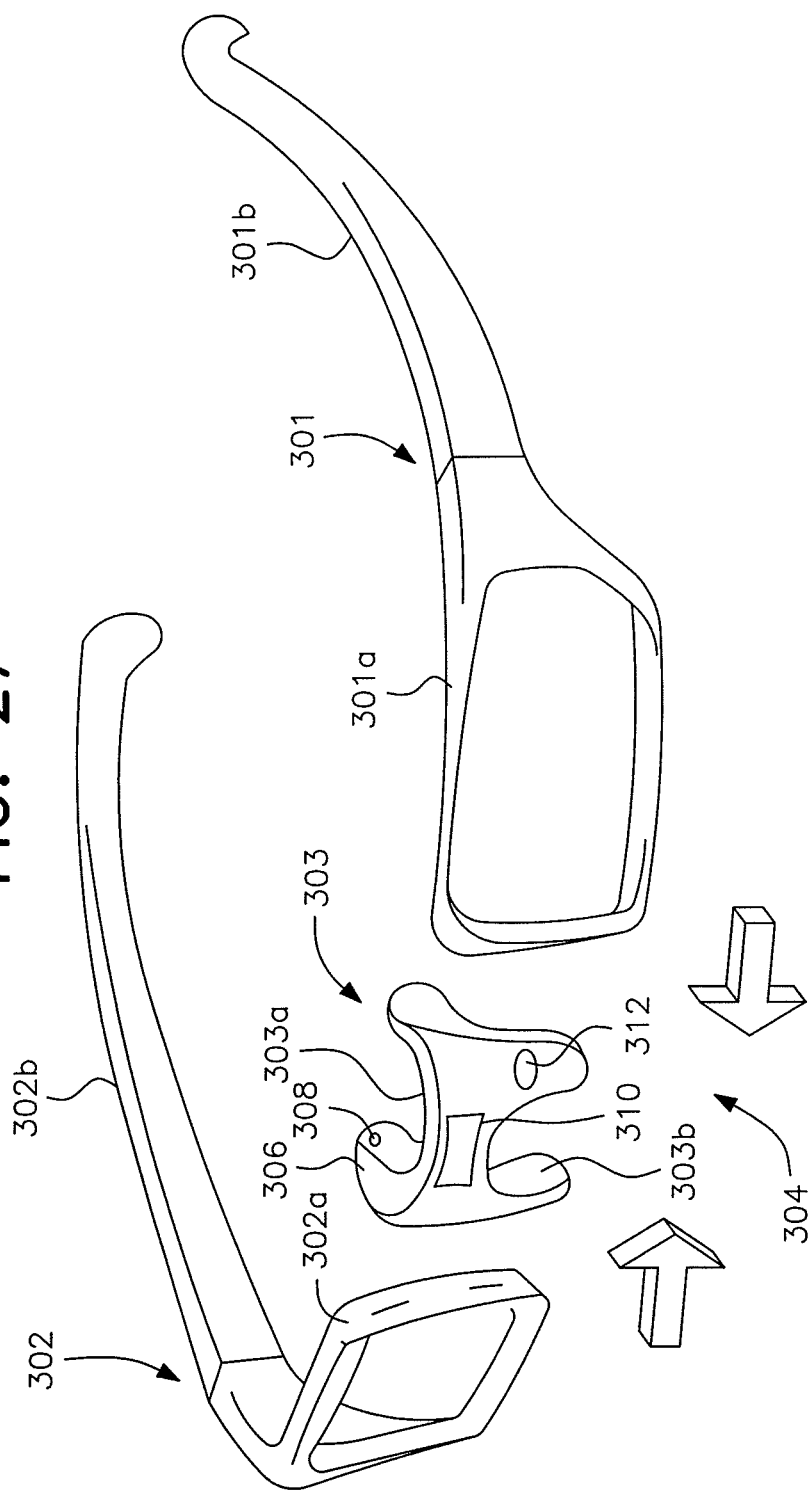
FIG. 27 is an exploded perspective view of another preferred embodiment showing a three piece support structure.

FIG. 27 is a perspective view of another preferred embodiment showing a three piece support structure 304 and preferably providing a medial canthal pad connecting piece 303 adapted as an interchangeable connecting piece. This embodiment comprises three pieces. Piece 301 comprises left lens rim 301a and left temple 301b. Piece 302 comprises right lens rim 302a and right temple 302b. Piece 303 called the medial canthal piece connector comprises the connecting bridge of eyeglasses 303a and the pad structure 303b of eyeglasses. Pad piece 303 is particularly adapted to provide medial canthal pads 306 for positioning a sensor 308 at the BTT site. In reference to this embodiment, the user can buy three piece eyeglasses in accordance with the invention in which the connector 303 has no sensing capabilities, and it is thus a lower cost. However, the three piece eyeglasses 304 offers the versatility of replacing the non-sensing connector 303 by a connector 303 with sensing capabilities. As shown in FIG. 27 connector 303 with medial canthal pads 306 and sensor 308 includes also radio frequency transmitter 310 and cell 312. Therefore, connector 303 provides all the necessary hardware including devices for sensing, transmitting, and reporting the signal. Any devices for attachment known in the art can be used including pressure devices, sliding devices, pins, and the like.

Figure 28A:
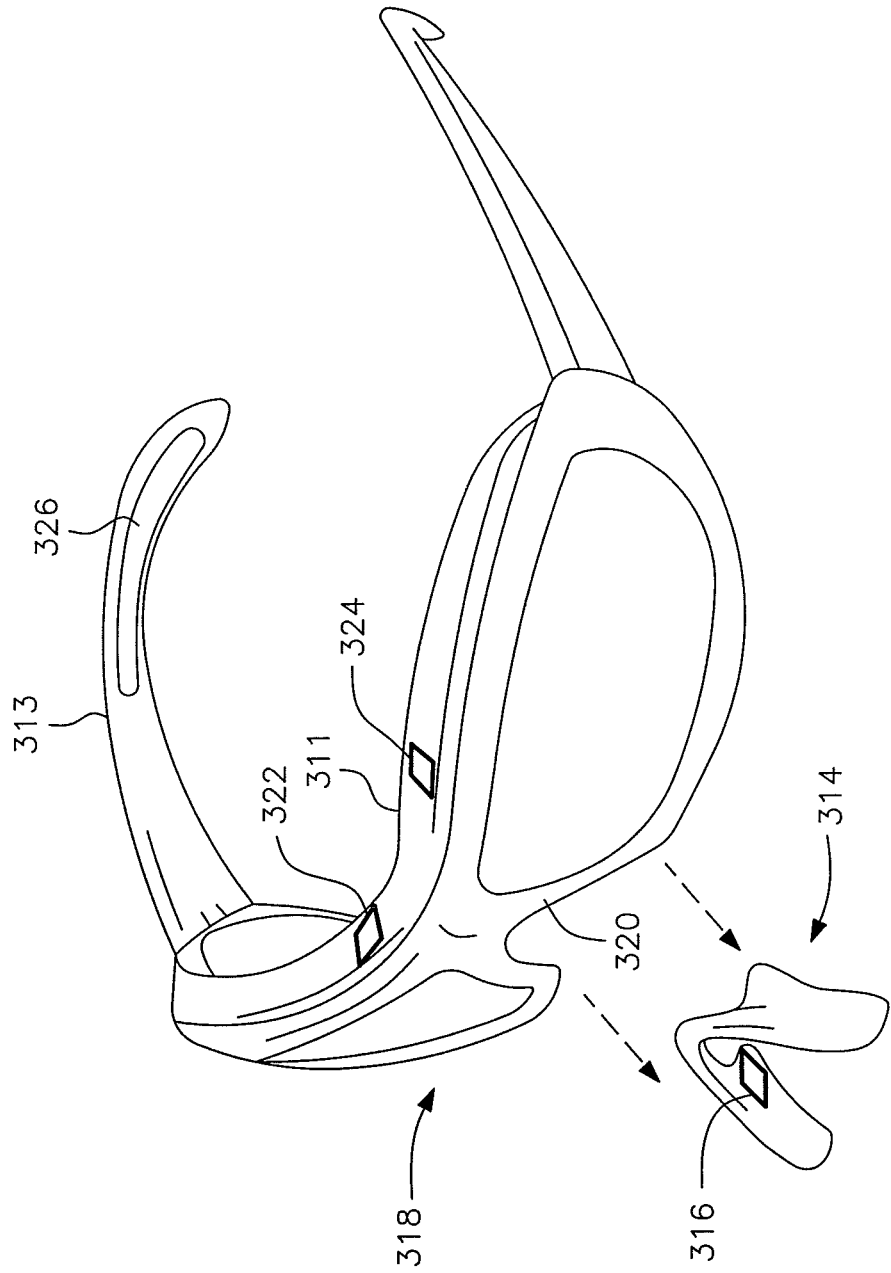
FIG. 28A is an exploded perspective view of one preferred embodiment of support structure showing a removable medial canthal piece.

Another preferred embodiment, as shown in FIG. 28A, provides a removable medial canthal piece 314 supporting sensor 316. As shown, connecting bridge 320 of eyeglasses 318 are attached to medial canthal piece 314 in a releasable manner. Eyeglasses 318 further includes sweat sensor 322, 324 supported by front part 311 and transmitting device 326 supported by temple 313. Front part 311 of eyeglasses 318 defines a front brow portion and extends across the forehead of the wearer and contains sweat sensor 322, 324. Sweat fluid goes through membranes in the sensor 322, 324 and reaches an electrode with generation of current proportional to the amount of analyte found in the sweat fluid.

Figure 28B:
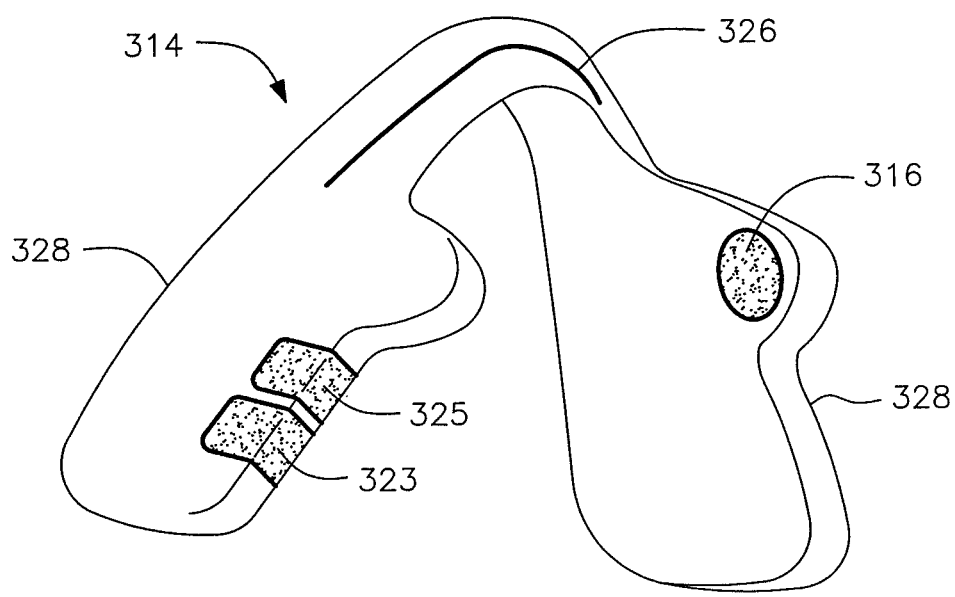
FIG. 28B is a rear perspective view of the removable medial canthal piece of FIG. 28A.
Figure 28C:
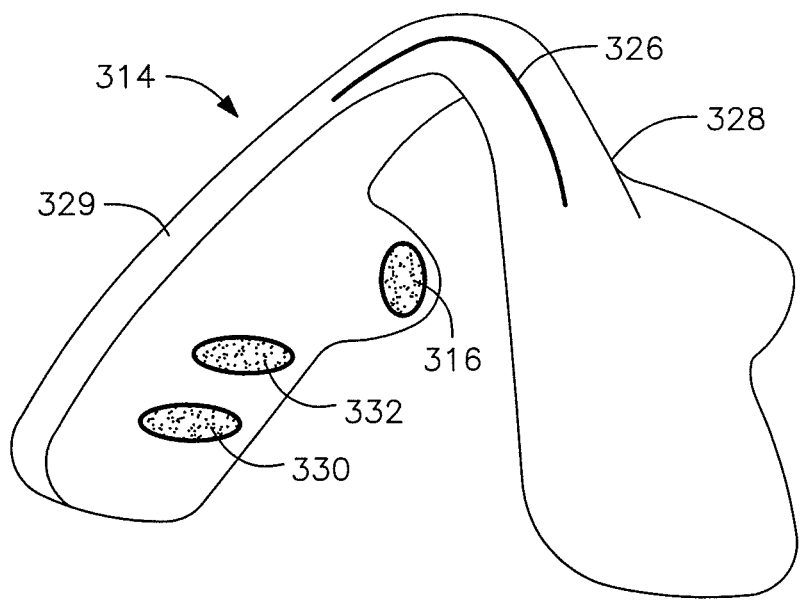
FIG. 28C is a front perspective view of the removable medial canthal piece of FIG. 28B.

FIG. 28B is a rear perspective view of the removable medial canthal piece 314 showing visual reporting devices 323, 325 such as a green LED and a red LED in left arm 328 and sensor 316 adapted to be positioned at the end of the tunnel, and wire 326 for electrically connecting right arm 329 and left arm 328 of medial canthal piece 314. FIG. 28C is a front perspective view of the removable medial canthal piece 314 showing power source 330, transmitter 332 and sensor 316 in right arm 329 and wire 326 for electrically connecting right arm 329 and left arm 328 of medial canthal piece 314. Medial canthal piece 314 can be replaced by a non-sensing regular nose pad which would have the same size and dimension as medial canthal piece 314 for adequate fitting with connecting bridge 320 of eyeglasses 318 of FIG. 28A. The removable medial canthal piece can have, besides LED, a built-in LCD display for displaying a numerical value and/or RF transmitter. Therefore, the removable medial canthal piece can have one or various reporting devices integrated as a single sensing and reporting unit.

Figure 29:
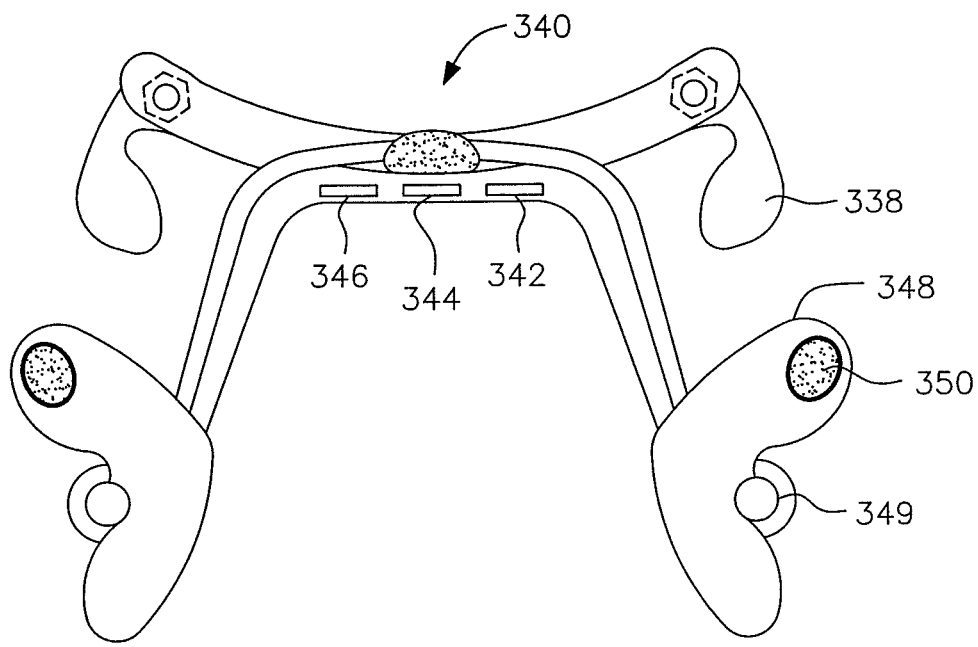
FIG. 29 is a rear perspective view of one preferred embodiment of a support structure incorporated as a clip-on for eyeglasses.

FIG. 29 is a rear perspective view of one preferred embodiment of a support structure incorporated as a clip-on 340 for eyeglasses and includes attachment device 338 such as a hook or a magnet, transmitting device 342, processing device 344, power source 346, medial canthal pad 348 mounted on a three axis rotatable structure 349 for proper positioning at the BTT site, and sensor 350. Clip-on 340 is adapted to be mounted on regular eyeglasses and to fit the medial canthal pad 348 above the regular nose pads of eyeglasses.

Figure 30:
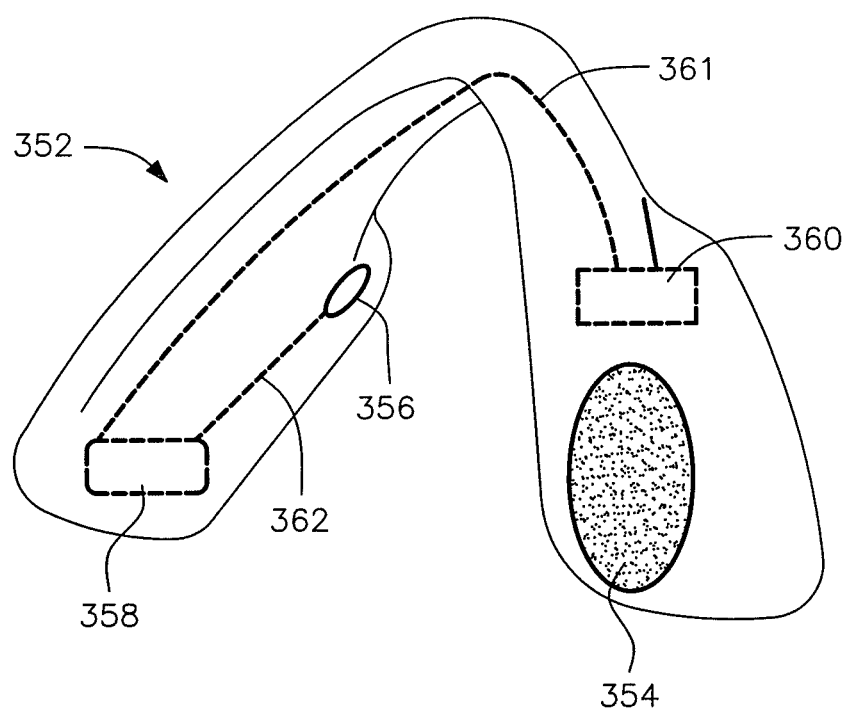
FIG. 30 is a perspective view of one alternative embodiment of a support structure with medial canthal pads that uses an adhesive backing for securing to another structure.

Sensing medial canthal pads can be preferably connected to attachment structure such as eyeglasses independent of the presence of specialized connecting or attachment devices mounted in said eyeglasses such as grooves, pins, and the like. This embodiment provides means for the universal use of sensing medial canthal pads in any type or brand of attachment structure. FIG. 30 shows a front perspective view of medial canthal pads 352 comprising an adhesive backing 354 for securing pad 352 to an attachment structure such as eyeglasses or another support structure. Adhesive surface 354 is adapted to match an area of eyeglasses that allow securing medial canthal pad 352 to said eyeglasses, such as for instance the area corresponding to regular nose pads of eyeglasses. Medial canthal pad 352 works as a completely independent unit and contains sensor 356, power source 358 and reporting device 360 electrically connected by wire 361,362. Reporting device 360 includes local reporting with visual devices (e.g., LED), audio devices (e.g., piezoelectric, voice chip or speaker) and remote reporting with wireless transmission.

Figure 31A:
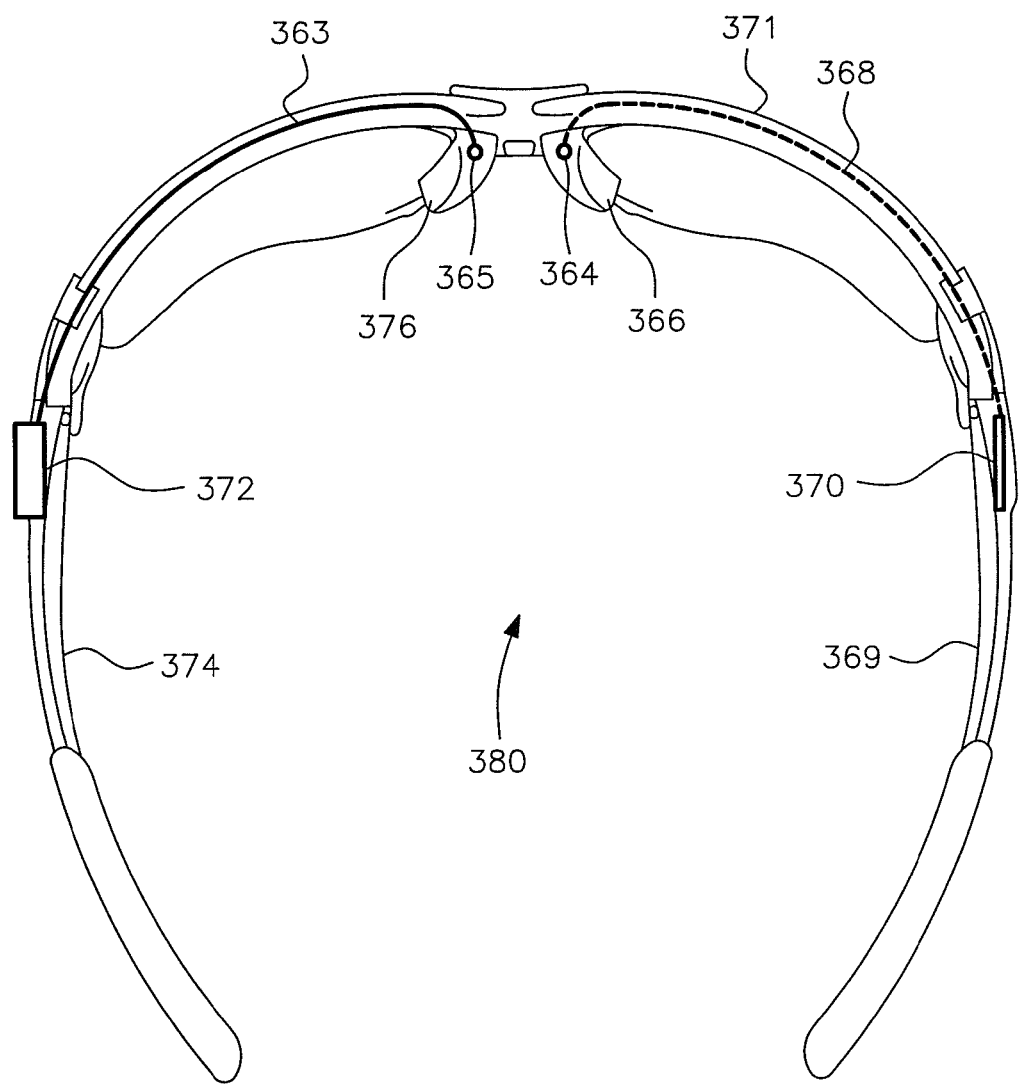
FIG. 31A is a top perspective view of one alternative embodiment of a support structure with holes for securing medial canthal pads.
Figure 31B:
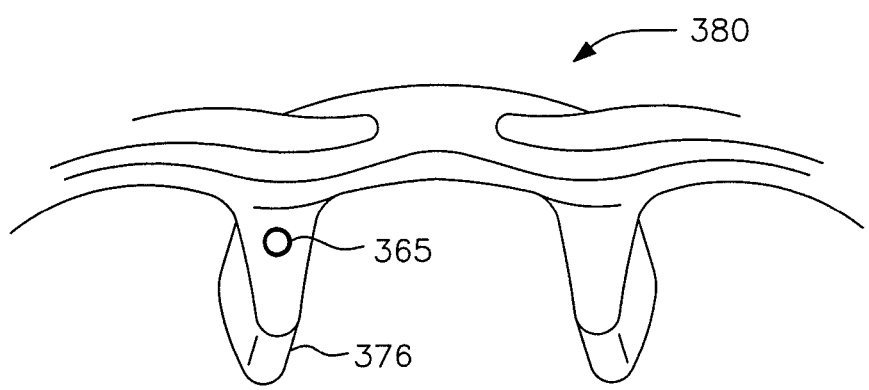
FIG. 31B is a magnified perspective view of part of the support structure of FIG. 31A.

FIG. 31A is a top perspective view of one alternative embodiment of a support structure incorporated as eyeglasses 380 with holes 364, 365 in regular nose pads 366, 376 for securing specialized medial canthal pads. Eyeglasses 380 includes wire 368 disposed within the right lens rim 371 of the frame of eyeglasses 380 with said wire 368 connecting transmitter 370 housed inside the right temple 369 to nose pad 366. Eyeglasses 380 further includes wire 363 mounted on top of left lens rim 365 with said wire 363 connecting transmitter 372 mounted on top of the left temple 374 to nose pad 376. FIG. 31B is a magnified perspective view of part of the support structure 380 with hole 365 in regular nose pad 376. FIG. 31C is a side perspective view of regular nose pad 366 with hole 364. FIG. 31D is a side perspective view of a medial canthal piece 382 secured to hole 364 of regular nose pad 366.

Figure 32A:
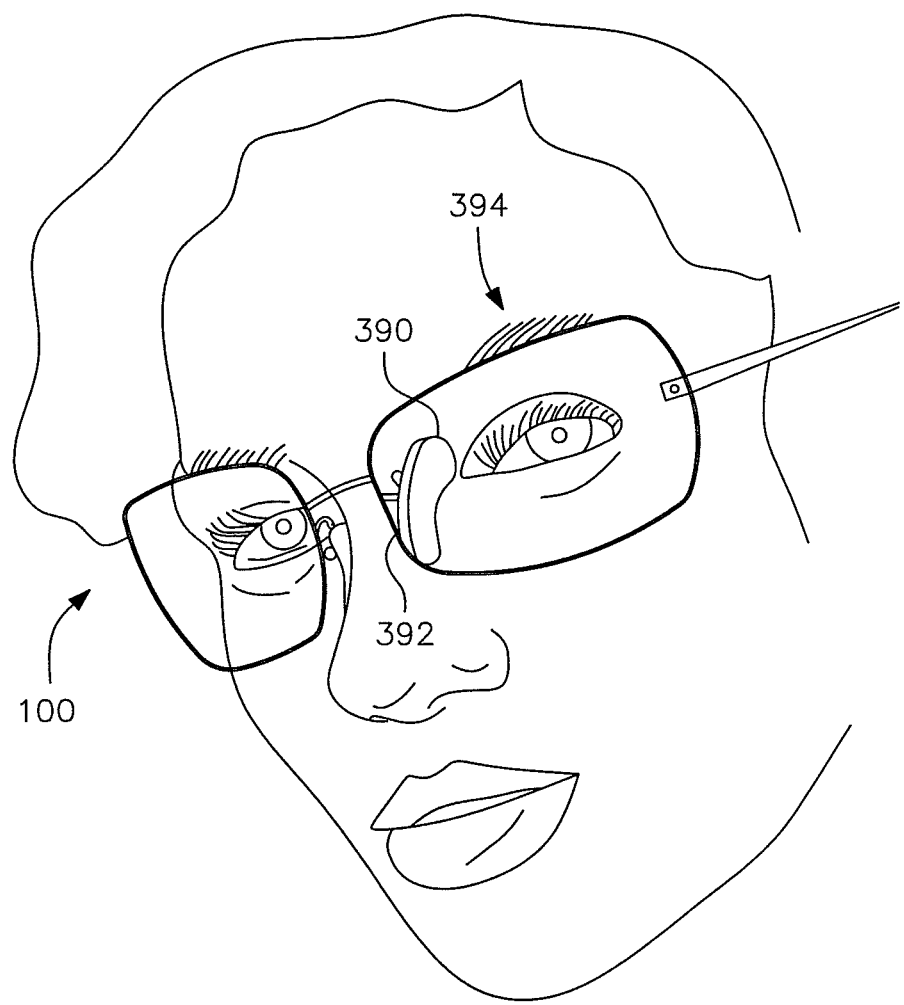
FIG. 32A is a perspective view of a person wearing a support structure comprised of medial canthal caps secured on top of a regular nose pad of eyeglasses.
Figure 32B:
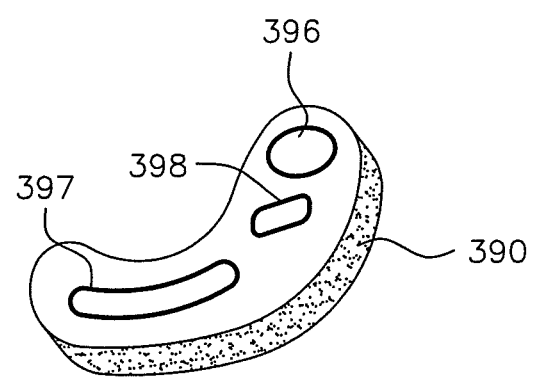
FIG. 32B is a perspective view of the medial canthal cap of FIG. 32A.

FIG. 32A is a perspective view of a person 100 wearing a support structure comprised of medial canthal caps 390 secured on top of a regular nose pad 392 of eyeglasses 394. FIG. 32B is a perspective rear view of the medial canthal cap 390 showing sensor 396, transmitter chip 398 and opening 397 for securing cap 390 to nose pads.

Figure 33A:
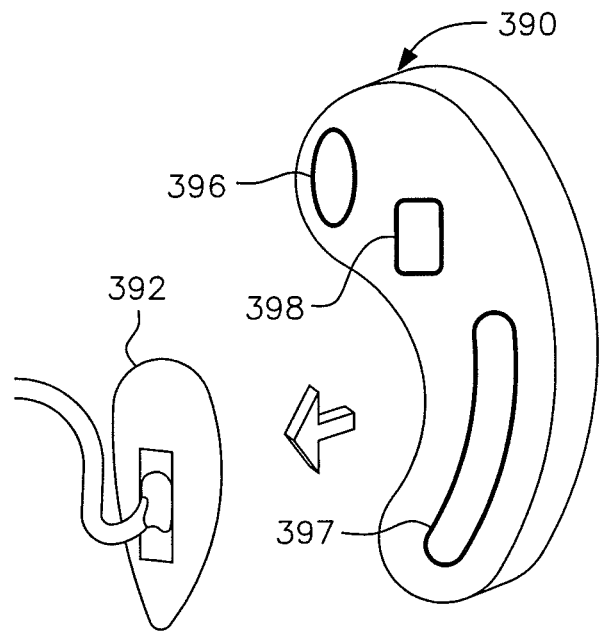
FIG. 33A is an exploded perspective view of a medial canthal cap being secured to the nose pad.
Figure 33B:
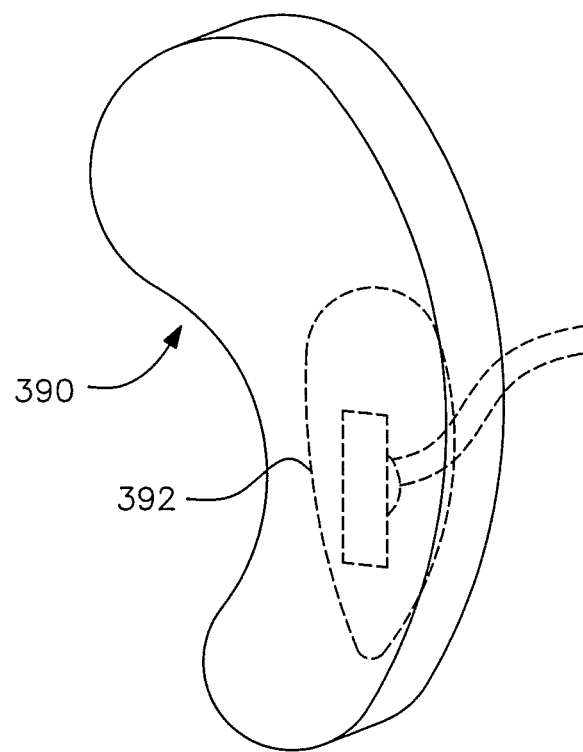
FIG. 33B is a perspective view of the end result of the medial canthal cap secured to the nose pad.

FIG. 33A is a perspective view of a medial canthal cap 390 being secured to the nose pad 392. Medial canthal cap 390 contains sensor 396, transmitter chip 398 and opening 397. FIG. 33B is a perspective view showing the end result of the medial canthal cap 390 secured to the nose pad 392.

Figure 34:
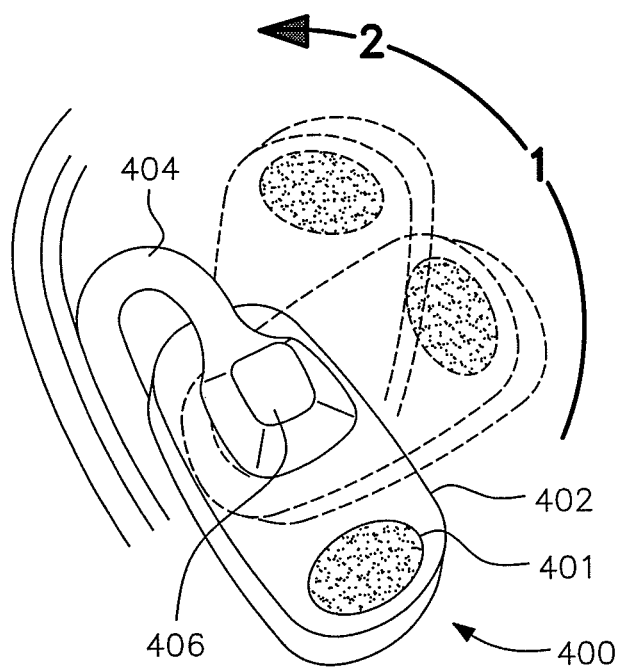
FIG. 34 is a perspective view of a modified rotatable nose pad to position a sensor on the skin at the end of the tunnel in accordance with the present invention.

Special nose pads are provided by the present invention for proper positioning a sensor at the BTT site. FIG. 34 is a perspective view of a modified left side rotatable nose pad 400 adapted to position a sensor on the skin at the end of the tunnel and includes nose pad 402 with sensor 401, arm 404, house 406 which houses a gear that allows rotation of a nose pad as a dial for positioning sensor 401 on different regions of the tunnel identified as 1 and 2. Position 1 places the sensor in line with the medial canthal corner and reaches the general area of the main entry point of the tunnel and position 2 places the sensor above the medial canthal corner right at the main entry point of the tunnel. This embodiment allows automated activation of the sensing system and takes advantage of the fact that the nose bridge is cold as seen in FIG. 1 (nose is dark) and FIG. 2 (nose is purple and blue). When the pad is in its resting position ("zero"), the sensor 401 rests in a cold place with temperature of 35.7° C. corresponding to the regular position of nose pads on the nose. In position "zero" the sensor is in Sleep Mode (temperature of 35.8° C. or less). Changing the sensor to a hot region such as the general area (position 1) or the main entry point (position 2) automatically activates the sensor which goes into Active Mode and start sensing function.

It is understood that numerous special nose pads and medial canthal pads can be used in accordance with the principles of the invention including a pivotal hinge that allows pads to be foldable in total or in part, self-adjusting pads using a spring, pivoting, sliding in a groove, and the like as well as self-adjusting mechanisms which are adaptable to anatomic variations found in different races. It is understood that the modified nose pads are preferably positioned high in the frame, most preferably by connecting to the upper part of the lens rim or within 6 mm from the upper edge of the lens rim.

A variety of materials can be used including materials with super-adherent properties to allow intimate apposition of sensing devices to the BTT site. A variety of metallic wires exhibiting super-elastic properties can be used as the hinge assembly mechanism for allowing proper positioning of a sensing device with the BTT site. Medial canthal pads can be made of a flexible synthetic resin material such as a silicon rubber, conductive plastic, conductive elastomeric material, metal, pliable material, and the like so that appropriate apposition to the BTT site at the medial canthal area and proper functioning is achieved. It is also understood that the medial canthal pads can exhibit elastic and moldable properties and include material which when stressed is able to remain in the stressed shape upon removal of the stress. Any type of rubber, silicone, and the like with shape memory can also be used in the medial canthal pads and modified nose pad.

By greatly reducing or eliminating the interfering constituents and providing a high signal to noise ratio with a sensor adapted to capture thermal radiation from the BTT, the present invention provides the devices needed for accurate and precise measurement of biological parameters including chemical components in vivo using optical devices such as infrared spectroscopy. Moreover, the apparatus and methods of the present invention by enhancing the signal allows clinical useful readings to be obtained with various techniques and using different types of electromagnetic radiation. Besides near-infrared spectroscopy, the present invention provides superior results and higher signal to noise ratio when using other forms of electromagnetic radiation such as for example mid-infrared radiation, radio wave impedance, photoacoustic spectroscopy, Raman spectroscopy, visible spectroscopy, ultraviolet spectroscopy, fluorescent spectroscopy, scattering spectroscopy and optical rotation of polarized light as well as other techniques such as fluorescent (including Maillard reaction, light induced fluorescence and induction of glucose fluorescence by ultraviolet light), colorimetric, refractive index, light reflection, thermal gradient, Attenuated Total Internal Reflection, molecular imprinting, and the like. A sensor adapted to capture thermal energy at the BTE (Brain Thermal Energy) tunnel site provides optimal means for measurement of biological parameters using electromagnetic devices. The BTE tunnel is the physical equivalent to the physiologic BTT and is used herein to characterize the physics of the tunnel. The geometry and dimension on the skin surface are the same for the BTT and BTE tunnel.

The following characteristics of the BTE tunnel allow optimal signal acquisition. Skin at the end of the BTE tunnel is thin. With a thick skin radiation may fail to penetrate and reach the substance to be measured. Skin at the BTE tunnel is homogenous with constant thickness along its entire surface. Random thickness of skin as occurs in other skin areas prevent achieving the precision needed. The BTE tunnel has no fat. The intensity of the reflected or transmitted signal can vary drastically from patient to patient depending on the individual physical characteristics such as the amount of fat. A blood vessel in the end of the BTE is superficial, terminal and void of thermoregulatory shunts. In other parts of the skin the deep blood vessels are located deep and vary greatly in position and depth from person to person. The BTE tunnel has no light scattering elements covering its end such as bone, cartilage and the like. Thermal radiation does not have to go through cartilage or bone to reach the substance to be measured. The end of the BTE tunnel on the skin has a special but fixed geometry and is well demarcated by permanent anatomic landmarks. In other skin surfaces of the body, inconsistency in the location of the source and detector can be an important source of error and variability.

Far-infrared radiation spectroscopy measures natural thermal emissions after said emissions interact and are absorbed by the substance being measured. The present invention provides a thermally stable medium, insignificant number of interfering constituents, and a thin skin is the only structure to be traversed by the thermal emissions from the BTE tunnel before reaching the detector. Thus there is high accuracy and precision when converting the thermal energy emitted by the BTE tunnel into concentration of the substance being measured.

The natural spectral emission by BTE tunnel changes according to the presence and concentration of chemical substances. The far-infrared thermal radiation emitted follow Planck's Law and the predicted amount of thermal radiation can be calculated. Reference intensity is calculated by measuring thermal energy absorption outside the substance of interest band. The thermal energy absorption in the band of substance of interest can be determined via spectroscopic means by comparing the measured and predicted values at the BTE tunnel site. The signal is then converted to concentration of the substance measured according to the amount of thermal energy absorbed.

A sensor adapted to view the BTE tunnel provides means for measuring a substance of interest using natural brain far-infrared emissions emitted at the BTE tunnel site and for applying Beer-Lambert's law in-vivo. Spectral radiation of infrared energy from the surface of the BTE tunnel site corresponds to spectral information of chemical substances. These thermal emissions irradiated at 38 degrees Celsius can include the 4,000 to 14,000 nm wavelength range. For example, glucose strongly absorbs light around the 9,400 nm band. When far-infrared thermal radiation is emitted at the BTE tunnel site, glucose will absorb part of the radiation corresponding to its band of absorption. Absorption of the thermal energy by glucose bands is related in a linear fashion to blood glucose concentration in the thermally sealed and thermally stable environment present in the BTE tunnel.

The support structure includes at least one radiation source from infrared to visible light which interacts with the substance being measured at the BTE tunnel and a detector for collecting the resulting radiation.

The present invention provides method for measuring biological parameters comprising the steps of measuring infrared thermal radiation at the BTE tunnel site, producing output electrical signals representative of the intensity of the radiation, converting the resulting input, and sending the converted input to a processor. The processor is adapted to provide the necessary analysis of the signal to determine the concentration of the substance measured and for displaying the results.

The present invention includes means for directing preferably near-infrared energy into the surface of the skin at the end of the BTE tunnel, means for analyzing and converting the reflectance or back scattered spectrun into the concentration of the substance measured and support structure for positioning the light source and detector device adjacent to the surface of the skin at the BTE tunnel site.

The present invention also provides methods for determining the concentration of a substance with said methods including the steps of directing electromagnetic radiation such as near-infrared at the skin at the BTE tunnel site, detecting the near-infrared energy radiated from said skin at the BTE tunnel site, taking the resulting spectra and providing an electrical signal upon detection, processing the signal and reporting concentration of the substance of interest according to said signal. The invention also includes device and methods for positioning the light sources and detectors in stable position and with stable pressure and temperature in relation to the surface to which radiation is directed to and received from.

The present invention further includes devices for directing infrared energy through the nose using medial canthal pads, devices for positioning radiation source and detector diametrically opposed to each other, and devices for analyzing and converting the transmitted resulting spectrum into the concentration of the substance measured. The present invention also provides methods for measuring biological parameters with said methods including the steps of directing electromagnetic radiation such as near-infrared through the nose using medial canthal pads, collecting the near-infrared energy radiated from said nose, taking the resulting spectra and providing an electrical signal upon detection, processing the signal and reporting concentration of the substance measured according to said signal. The invention also includes means and methods for positioning the radiation sources and detectors in a stable position and with stable pressure and temperature in relation to the surface to which radiation is directed through.

The present invention yet includes devices for collecting natural far-infrared thermal radiation from the BTE tunnel, devices for positioning a radiation collector to receive said radiation, and devices for converting the collected radiation from the BTE tunnel into the concentration of the substance measured. The present invention also provides methods for measuring biological parameters with said methods including the steps of using the natural far-infrared thermal emission from the BTE tunnel as the resulting radiation for measuring the substance of interest, collecting the resulting radiation spectra, providing an electrical signal upon detection, processing the signal and reporting the concentration of the substance measured according to said signal.

A drug dispensing system including an infusion pump can be activated according to the level of the substance measured at the BTE tunnel, for example insulin can be injected automatically as needed to normalize glucose levels as an artificial pancreas.

Any substance present in blood which is capable of being analyzed by electromagnetic devices can be measured at the BTE tunnel. For example but not by way of limitation such substances can include exogenous chemicals such as drugs and alcohol as well as endogenous chemicals such as glucose, oxygen, lactic acid, cholesterol, bicarbonate, hormones, glutamate, urea, fatty acids, triglycerides, proteins, creatinine, aminoacids and the like. Values such as pH can also be calculated as pH can be related to light absorption using reflectance spectroscopy.

Figure 35:
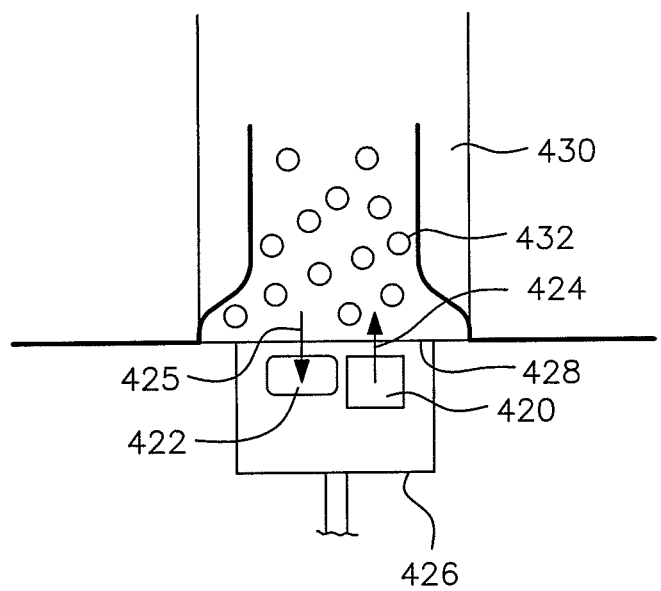
FIG. 35 is a schematic view of another preferred embodiment of the present invention using spectral reflectance.

In accordance with FIG. 35 a schematic view of one preferred reflectance measuring apparatus of the present invention is shown. FIG. 35 shows a light source 420 such as an infrared LED and a photodetector 422 located side-by-side and disposed within support structure 426 such as a medial canthal pad or modified nose pads of eyeglasses directing radiation 424 at the BTE tunnel 430 with said light source 420 laying in apposition to the skin 428 at the BTE tunnel 430. The light source 420 delivers the radiation 424 to the skin 428 at the BTE tunnel which is partially absorbed according to the interaction with the substance 432 being measured resulting in attenuated radiation 425. Part of the radiation 424 is then absorbed by the substance 432 and the resulting radiation 425 emitted from BTE tunnel 430 is collected by the photodetector 422 and converted by a processor into the blood concentration of the substance 432. Thin skin 428 is the only tissue interposed between radiation 424, 425 and the substance 432 being measured. The concentration of the substance 432 is accomplished by detecting the magnitude of light attenuation collected which is caused by the absorption signature of the substance being measured.

Infrared LEDs (wavelength-specific LEDs) are the preferred light source for this embodiment because they can emit light of known intensity and wavelength, are very small in size, low-cost, and the light can be precisely delivered to the site. The light source 420 emits preferably at least one near-infrared wavelength, but alternatively a plurality of different wavelengths can be used. The light source emits radiation 424, preferably between 750 and 3000 nm, including a wavelength typical of the absorption spectrum for the substance 432 being measured. The preferred photodetector includes a semiconductor photodiode with a 400 micron diameter photosensitive area coupled to an amplifier as an integrated circuit.

Figure 36:
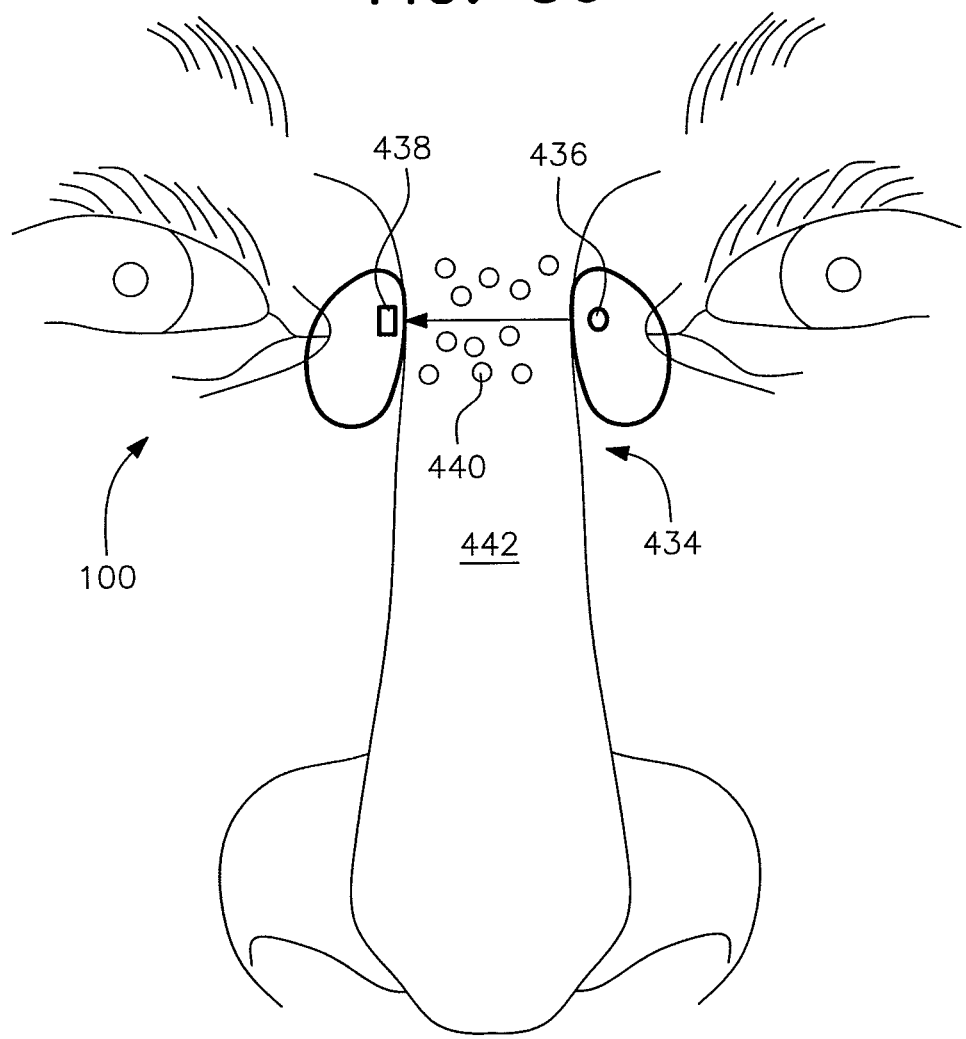
FIG. 36 is a schematic view of a person showing another preferred embodiment in accordance with the present invention using spectral transmission.

FIG. 36 shows a schematic view of a person 100 wearing a support structure 434 and light source 436 and detector 438 adapted to measure biological parameters using spectral transmission device. The light source 436 and photodetector 438 are positioned diametrically opposed to each other so that the output of the radiation source 436 goes through the nasal interface 442 containing the substance 440 being measured before being received by the detector 438. Photodetector 438 collects the resulting transmitted radiation which was directed through the nasal interface 442. A variety of LEDs and optical fibers disposed within the support structure 434 such as the medial canthal pads, nose pads and frames of eyeglasses are preferably used as a light delivery for the light source 436 and the light detector 438.

Arms of support structures 434 such as medial canthal pads are moveable and can be adjusted into different positions for creating a fixed or changeable optical path. Preferred substances measured include oxygen and glucose. The brain maintains constant blood flow, whereas flow in extremities change according to cardiac output and ambient conditions. The oxygen levels found in the physiologic tunnel reflects central oxygenation. The oxygen monitoring in a physiologic tunnel is representative of the general hemodynamic state of the body. Many critical conditions such as sepsis (disseminated infection) or heart problems which alter perfusion in most of the body can be monitored. Oxygen in the BTE tunnel can continuously monitor perfusion and detect early hemodynamic changes.

Figure 37:
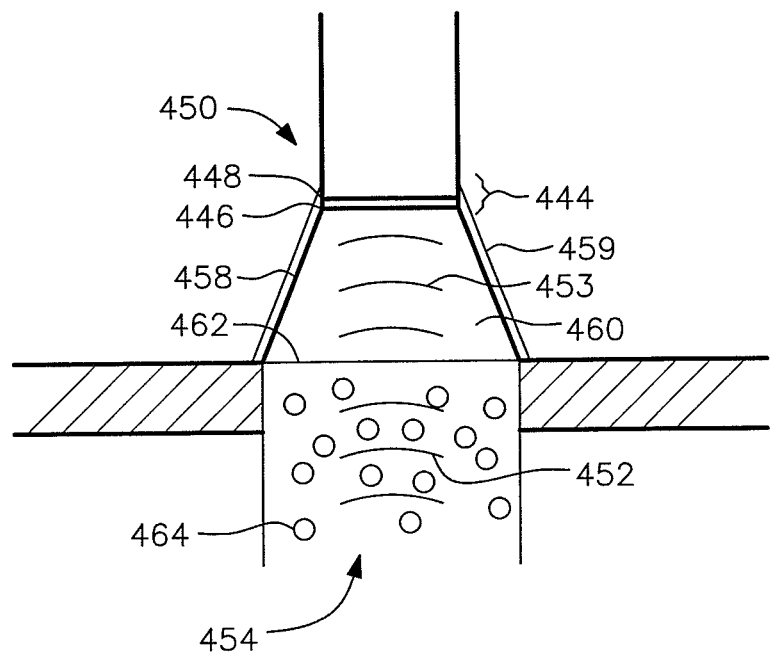
FIG. 37 is a schematic cross-sectional view of another preferred embodiment of the present invention using thermal emission.

FIG. 37 is a schematic cross-sectional view of another preferred embodiment of the present invention using thermal emission from the BTE tunnel. FIG. 37 shows a support structure 450 housing a thermal infrared detector 444 which has a filter 446 and a sensing element 448 with said sensing element 448 being preferably a thermopile and responding to thermal infrared radiation 452 naturally emitted by the BTE tunnel 454. The support structure 450 is adapted to have sensing device 448 with a field of view that corresponds to the geometry and dimension of the skin 462 at the end of the BTE tunnel 454. Support structure 450 provides walls 456, 458 which are in contact with the skin 462 with said walls creating a cavity 460 which contains thermal radiation 453 which has already passed through thin skin 462.

For example in the thermally sealed and thermally stable environment in the BTE tunnel 454, at 38° Celsius spectral radiation 453 emitted as 9,400 nm band is absorbed by glucose in a linear fashion according to the amount of the concentration of glucose due to the carbon-oxygen-carbon bond in the pyrane ring present in the glucose molecule. The resulting radiation 453 is the thermal emission 452 minus the absorbed radiation by the substance 464. The resulting radiation 453 enters the infrared detector 444 which generates an electrical signal corresponding to the spectral characteristic and intensity of said resulting radiation 453. The resulting radiation 453 is then converted into the concentration of the substance 464 according to the amount of thermal energy absorbed in relation to the reference intensity absorption outside the substance 464 band.

The same principles disclosed in the present invention can be used for near-infrared transmission measurements as well as for continuous wave tissue oximeters, evaluation of hematocrit, blood cells and other blood components. The substance measured can be endogenous such as glucose or exogenous such as alcohol and drugs including photosensitizing drugs.

Figure 38:
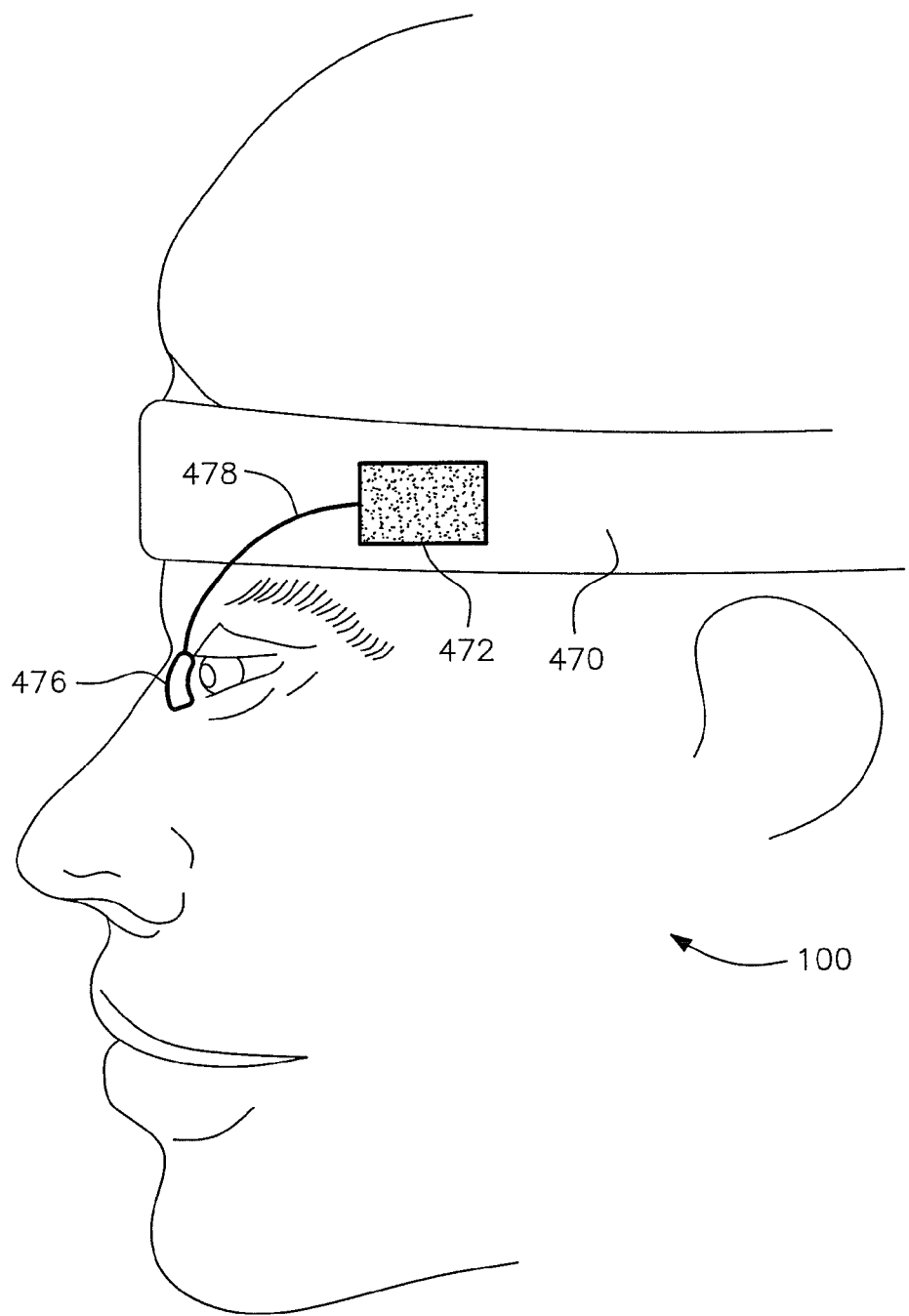
FIG. 38 is a side perspective view of an alternative embodiment using head mounted gear as a support structure.

Numerous support structures can position sensors at the BTT site for measuring biological parameters. Accordingly, FIG. 38 is a side perspective view of an alternative embodiment showing a person 100 using head mounted gear 470 as a support structure positioning with wires 478 and sensor 476 on the skin at the BTT site. A microelectronic package 472 containing transmitting means, processing means, and power source is disposed within or mounted on headband 470, with said headband 470 providing wire 478 from microelectronic package 472 for connection with sensing device 476 on the skin at the BTT site.

It is understood that the sensing device can be an integral part of the support structure or be connected to any support structures such as using conventional fasteners including screw, pins, a clip, a tongue-groove relationship, interlocking pieces, direct attachment, adhesives, mechanical joining, and the like; and said support structures include patches, clips, eyeglasses, head mounted gear, and the like.

Figure 39:
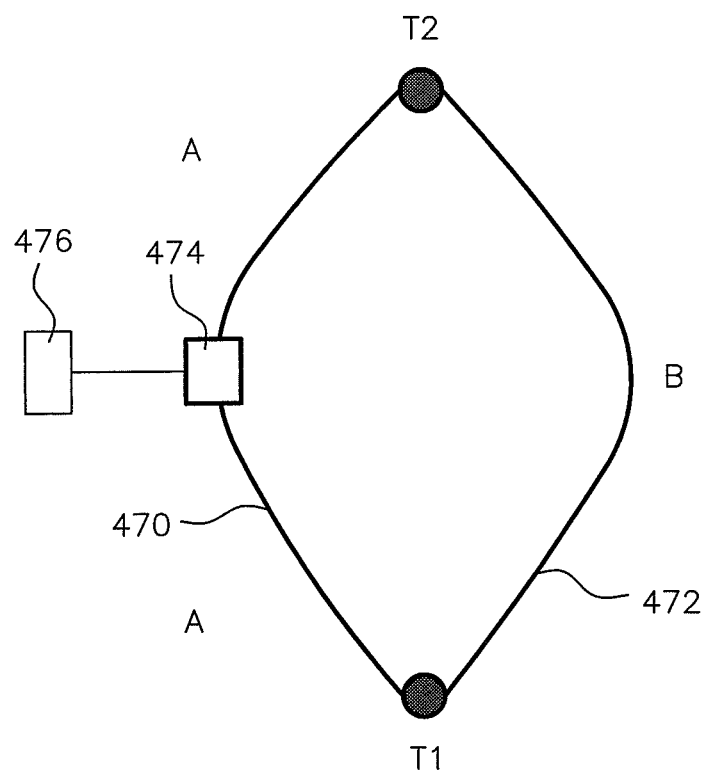
FIG. 39 is a schematic diagram of a preferred embodiment for generating thermoelectric energy to power the sensing system.

Various means to provide electrical energy to the sensing system were disclosed. The BTE tunnel offers yet a new way for natural generation of electrical energy. Accordingly, FIG. 39 is a schematic diagram of a preferred embodiment for generating thermoelectric energy from the BTE tunnel to power the sensing system. The generator of the invention converts heat from the tunnel into electricity needed to power the system. A thermoelectric module is integrated into the support structure to power the sensing system. The thermoelectric module preferably includes a thermopile or a thermocouple which comprises dissimilar metallic wires forming a junction. As heat moves from the tunnel through the thermoelectric module an electric current is generated. Since the BTE tunnel is surrounded by cold regions, the Seebeck effect can provide means for generating power by inducing electromotive force (emf) in the presence of a temperature gradient due to distribution of electric charges at the surface and interface of the thermoelectric circuit generated by the temperature at the BTE tunnel.

Accordingly, FIG. 39 shows the junctions T1 and T2 of metallic wire A 470 and metallic wire B 472 kept at different temperatures by placing junction T1 at the main entry point of the tunnel and junction T2 in a cold area such as the nose bridge (denoted in blue or purple in FIG. 1B, and referred herein as blue-purple nose). Metallic wires A 470 and B 472 are made of different materials and electric current flows from the hot to the cold region due to the thermal gradient with a magnitude given by the ratio of the thermoelectric potential. The potential U is given by $U=(Q_a-Q_b)*(T_1-T_2)$, where $Q_a$ and $Q_b$ denote the Seebeck coefficient (thermoelectric power) of metal A and metal B, and $T_1$ denotes temperature at the entry point of the BTE tunnel and $T_2$ denotes temperature at the blue-purple nose. The thermoelectric potential generated can power the sensing system and a capacitor 474 inserted into the system can be used to collect and store the energy and MCU 476 is adapted to control the delivery of energy as needed for measuring, processing and transmitting the signal.

It is understood that other means to convert thermal energy from the BTE tunnel into electricity can be used. It is also understood that the surface of the eye and carbuncle in the eye can provide a thermal gradient and Seebeck effect, however it is much less desirable than using the skin at the end of the BTE tunnel since hardware and wires touching the surface of the eye and/or coming out of the eye can be quite uncomfortable and cause infection. It is yet understood that the cold end can include any relatively cold article including the frame of the glasses as well as the air.

Contrary to that numerous support structures disclosed in the present invention including eyeglasses can easily be adapted to provide in an unobtrusive manner the power generating system of the invention, for example by using a support structure such as eyeglasses for positioning the hot junction at the BTE site using medial canthal pads and positioning the cold junction on the nose using regular nose pads of eyeglasses. It is also understood that although the power generating system using Brain Thermal Energy was designed for powering the sensing system of the present invention, any other electrical device could be adapted to be supplied with energy derived from the Brain Thermal Energy tunnel.

Additional embodiments include support structures to position the sensor at the BTT site of animals. Many useful applications can be achieved, including enhancing artificial insemination for mammalian species by detecting moment of ovulation, monitoring herd health by continuous monitoring of brain temperature, detection of parturition and the like.

Figure 40:
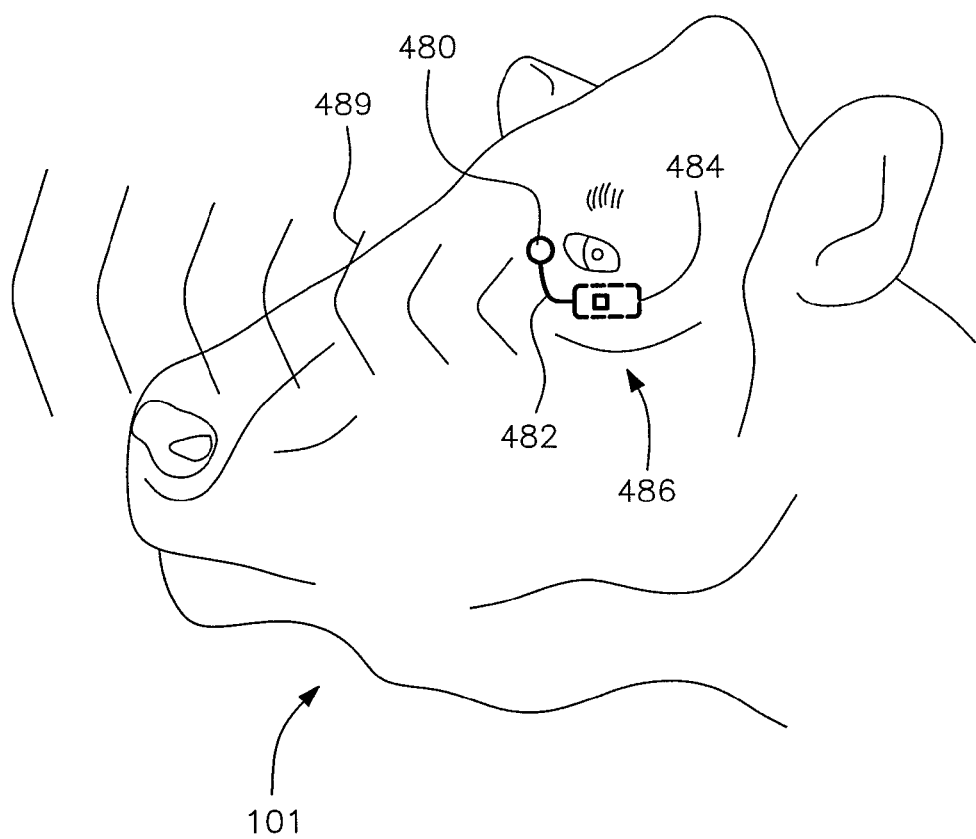
FIG. 40 is a perspective view of a preferred embodiment for animal use.

Accordingly, FIG. 40 is a perspective view of a preferred embodiment showing an animal 101 with sensor 480 positioned at the BTT site with wire 482 connecting sensor 480 with a microelectronic package 484 containing a transmitting device, a processing device, and power source in the eyelid pocket 486 of animal 101. Signal from microelectronic package 484 is preferably transmitted as radio waves 489. The signal from the transmitter in package 484 can be conveyed to a GPS collar allowing the identification of the animal having a high temperature associated with the localization of said animal by GPS means. Whenever there is an increase in brain temperature identified by the sensing device 480, the signal of high temperature activates the GPS collar to provide the localization of the affected animal. Alternatively the remote radio station receiving waves 489 activate the GPS system when the abnormal signal is received. In this case, the transmitter in package 484 only sends the signal to the remote station, but not to the GPS collar.

Figure 41A:
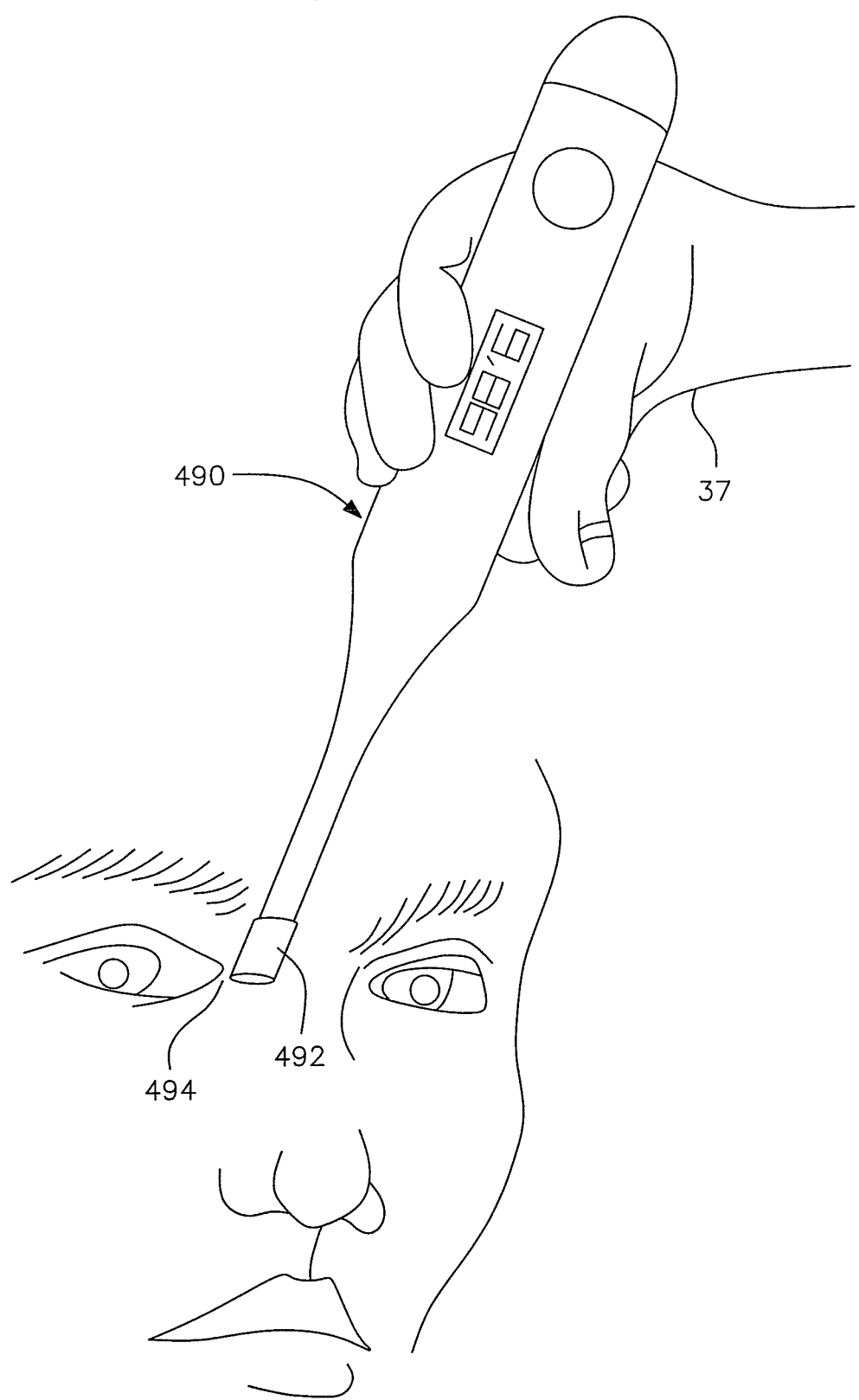
FIGS. 41A and 41B are perspective views of an alternative embodiment of a portable support structure with a sensor positioned at the tunnel.
Figure 41B:
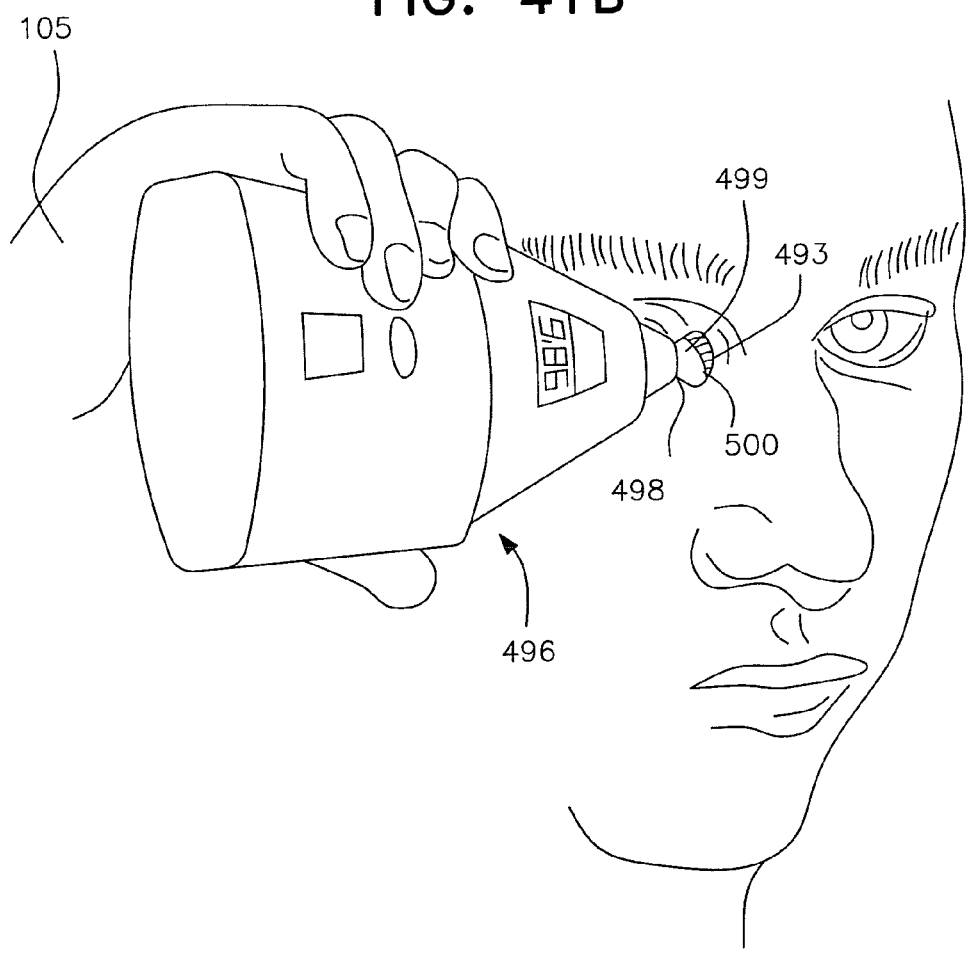

FIG. 41A is a perspective view of a portable support structure 490 positioning sensor 492 in contact with the skin 494 at the BTT site for measuring biological parameters. Support structure 490 incorporated as a thermometer with a contact sensor 492 is held by a second person 17 for positioning the sensor 492 on the skin 494 and performing the measurement. FIG. 41B is a perspective view of a portable support structure 496 with walls 500 positioning non-contact sensor 498 such as a thermopile with a field of view that matches in total or in part the geometry and dimension of the skin area at the end of the BTT. Support structure 496 incorporated as an infrared thermometer is held by a second person 105 for positioning the sensor 498 and measuring biological parameters. Although it is understood that pointing an infrared detector to the BTT site can be used in accordance with the invention, the temperature measured is not as clinically useful because of the ambient temperature. Therefore, the support structure 496 contains walls 500 that create a confined environment for thermal radiation to reach sensor 498 from the skin over the tunnel. Walls 500 of the support structure are adapted to match the geometry of the tunnel and to provide a cavity 499 with the boundaries consisting of the sensor surface 492 and the skin area 493 viewed by said sensor 498, in a similar manner as described for FIG. 37.

Figure 42A:
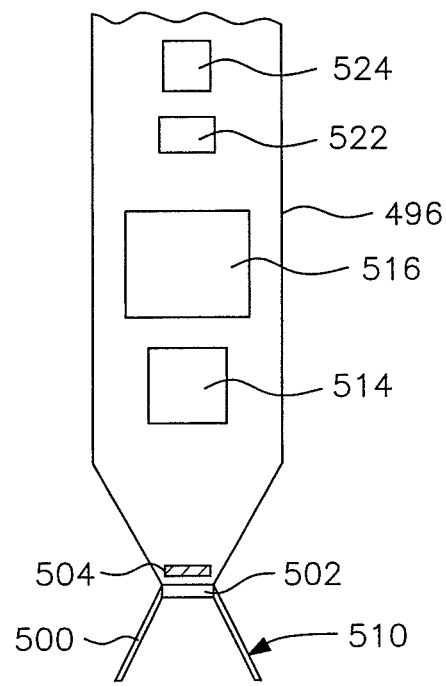
FIGS. 42A and 42B are schematic diagrams showing a non-contact sensor in accordance with the present invention.
Figure 42B:
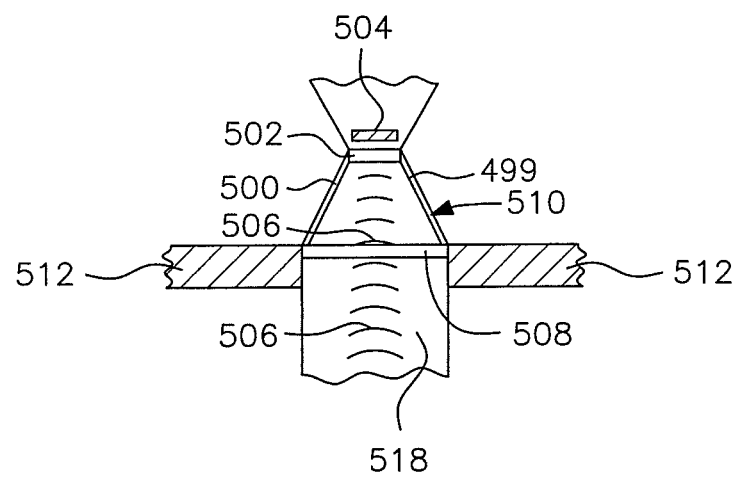

Now, with reference to FIGS. 42A and 42B, FIG. 42A is a schematic diagram showing the support structure 496, also referred to herein as a housing, a window 502 and radiation sensor 504 contained in the housing 496 and an extension 510 secured to the housing adapted for temperature measurement at the BTT area. In a preferred embodiment, the extension 510 has walls 500 and is substantially conical in shape and secured to a housing 496 adapted to be held by a hand 105 as shown in FIG. 41B. To measure the temperature, a user 105 positions the extension 510 adjacent to the BTT site such that the walls 500 of the extension 510 lie on the skin at the BTT area and the radiation sensor 504 views the BTT area. FIG. 42B is a schematic view showing the walls 500 of extension 510 creating a cavity 499 wherein thermal radiation 506 emitted from the skin 508 at the BTT area 518 is received by the radiation sensor 504. BTT area 506 is surrounded by the thick skin and fat in non-BTT areas 512. BTT temperature measurements are obtained from the output of the radiation sensor 504 contained in the housing 496. Electronics 514 within the housing 496 convert the received radiation to a temperature level which is displayed on a housing display 516 as illustratively shown in FIG. 41B.

The radiation sensor 504 views at least a portion of the BTT surface skin area 508 through an infrared radiation transparent window 502 and detect infrared radiation 506 from the BTT skin surface 508. The radiation sensor 504 is preferably a thermopile, but other radiation sensors may also be used such as pyroelectric detectors or any other radiation sensors that detect heat flux from the surface being evaluated. Exemplary window 502 materials include silicon and germanium. The sensor 504 is preferably mounted in an extension 510 which is shaped to match the dimension and geometry of the BTT area 508. The extension 510 can easily be positioned such that only the skin area 508 at the end of the BTT 518 may be viewed by the radiation sensor 504 wherein the skin area 508 is at substantially the same temperature as the brain temperature. Once in a position for the sensor 504 to view the BTT skin area 508, a button 522 is pressed to begin a measurement and the processing 514 within the housing 496 determines the brain temperature and display the value in a liquid crystal display 516 coupled to a sound device 524 for emitting an audio signal. A disposable cover may be used to cover any part of the apparatus in contact with the skin.

Although the temperature at the end of the BTT is substantially equivalent to the brain temperature based on the temperature of the cavernous sinus and cerebral blood, a variety of mathematical calculations and means can be used to determine the temperature at the BTT area including arterial heat balance, venous heat balance, and ambient temperature. It is understood that the BTT detector can contain a sensor for measuring ambient temperature and said measured ambient temperature be used for calculating temperature of the subject.

The temperature at the BTT area can be used as a reference for adjusting measurement acquired in other parts of the body outside the BTT area. The electrical equivalent of the BTT tunnel is an area of high voltage but low current, in which the voltage representing the temperature is virtually equal at the two ends of the tunnel. The high perfusion in the end of the BTT keeps a high temperature at the skin at the end of said end of the BTT.

The present invention also provides a method for detecting body temperature including the steps of providing a temperature detector positioned adjacent to the BTT during temperature detection and determining the temperature based on the radiation sensed at the BTT area. It is understood that the detector can remain in one position or move around the BTT area to identify the surface with the highest temperature.

A further method of detecting body temperature includes the steps of scanning a temperature detector across the BTT area and other areas in the head or in the contra-lateral BTT area and selecting the highest temperature, preferably selecting the highest temperature by scanning the right and the left BTT areas with the processor in the BTT detector determining and selecting the highest temperature.

Another method for identifying the highest temperature point in the BTT area can be found by scanning a radiation detector over the BTT area and having a processor adapted to select the highest reading and indicate that with an audio signal. The temperature detector 20 provides an audible beep with each peak reading.

Figure 43A:
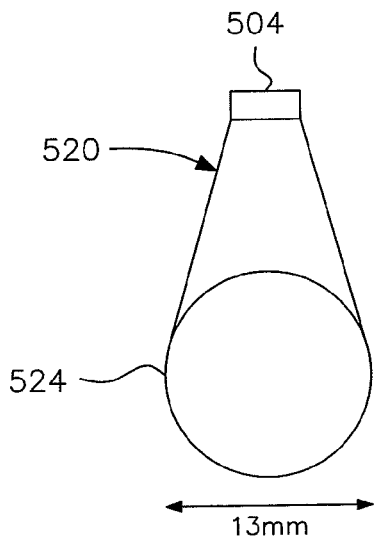
FIGS. 43A to 43C are diagrams showing preferred embodiments for the diameter of the cone extension
Figure 43B:
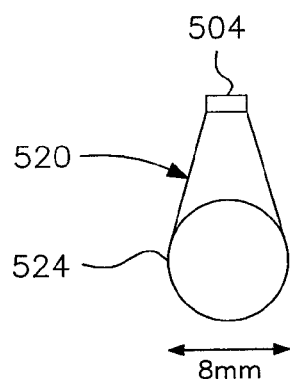
Figure 43C:
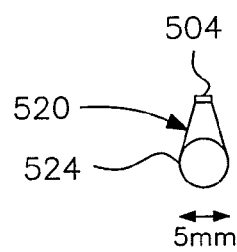

FIG. 43A to 43C are diagrams showing preferred embodiments for the diameter of the cone extension 510 at the end of the housing 496 in contact with the skin 508 at the BTT site 518. It is understood that although any shape can be used for the extension, the extension takes preferably the form of a cone with a radiation sensor positioned to view the BTT area. The cup 520 has an outer diameter at its end which is equal to or less than the BTT area. In FIG. 43A, for the radiation sensor 504 viewing the general area of the BTT site 508 the preferred outer diameter of the end 524 of the cup 520 is equal to or less than 13 mm. In FIG. 43B for the radiation sensor 504 viewing the general main entry point of the BTT site 508 the preferred outer diameter of the end 524 of the cup is equal to or less than 8 mm. In FIG. 43C, for the radiation sensor 504 viewing the main entry point the preferred outer diameter of the end 524 of the cup 520 is equal to or less than 5 mm. It is understood that although the preferred geometry of the radiation sensor and extension is round and has a substantially conical shape, any other shape of the radiation sensor and/or extension can be used including oval, square, rectangular, and the like. It is understood that the diameter and geometry is preferably chosen to match the geometry of the BTT area. It is also understood that the dimension of the sensor 504 is adapted to match the dimension of the cup 520 to the viewing area of the skin 508.

In accordance with a further aspect of the present invention, the extension is adapted to fit on top of the eyelids. The portion of the extension 510 of the housing 496 in contact with the skin 508 can also have an inner concave surface that matches the eyelid contour. Alternatively, the portion of the conical extension 510 in contact with the skin 508 can have a convex surface to match the medial canthal area and upper lid above the medial corner of the eye.

It is also understood that the dimensions for pediatric use are about two thirds of the dimension for adult size, or even half or less than half of adult size especially in small children. Accordingly, the preferred sizes of the outer diameter of the extension for children are: for the radiation sensor viewing the general area the preferred outer diameter of the extension is equal to or less than 9 mm for viewing the general area of the BTT, equal to or less than 6 mm for viewing the general main entry point of the BTT, and equal to or less than 4 mm for viewing the main entry point of the BTT.

Figure 44A:
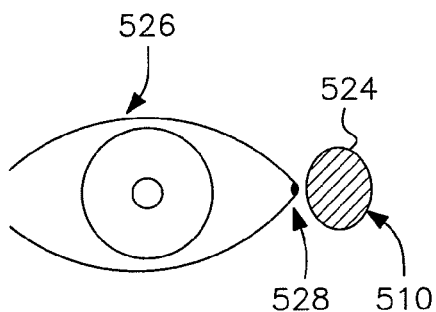
FIGS. 44A and 44B shows alternative geometries and shapes of an end of the extension.
Figure 44B:
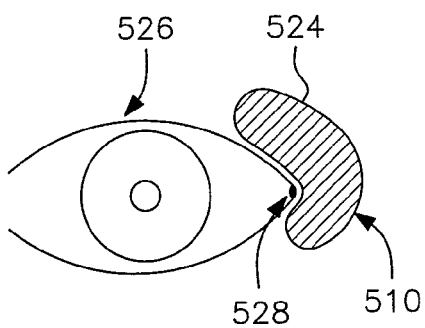

Besides the preferred round shape for the end 524 of extension 510, FIGS. 44A and 44B shows alternative geometries and shapes of end 524 extension 510 for non-contact sensor with said sensor viewing at least a portion of the BTT area next to the corner 528 of the eye 526. In FIG. 44A, the outer shape of the end 524 of extension 510 is shown as an oval shape. FIG. 44B shows an elliptical, banana or half moon shape of end 524 of extension 51D for viewing the medial canthal area and the upper eye lid area.

Figure 45A:
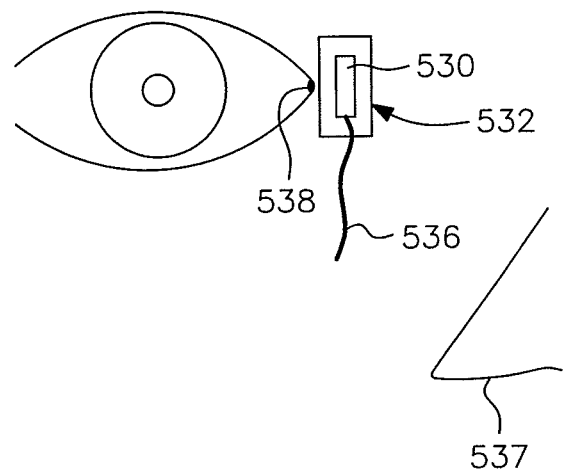
FIGS. 45A and 45B shows exemplary geometries and shapes for a support structure containing a contact sensor.
Figure 45B:
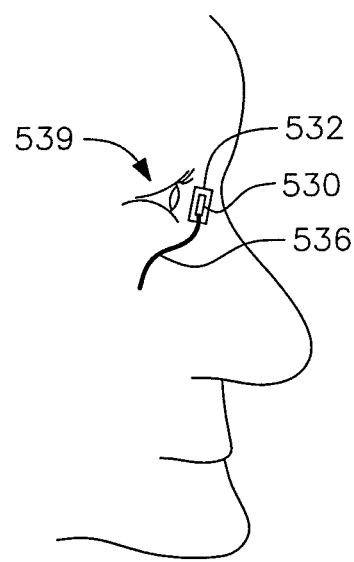

FIGS. 45A and 45B shows exemplary geometries and shapes for a support structure containing a contact sensor with said sensor positioned on the skin at the BTT area. FIG. 45 is a schematic frontal view showing a temperature sensor 530 in the shape of a rod contained in a patch 532 and positioned vertically on the BTT area 534 next to the corner of the eye 538 and nose 537 with a cord 536 extending from the distal end of the sensor 530. FIG. 45B is a side view of FIG. 45A showing sensor 530 with cord 536 contained in patch 532 next to the eye 539. A sensor is placed centrally in the patch, wherein the patch measures less than 11 mm in diameter.

Figure 46A:
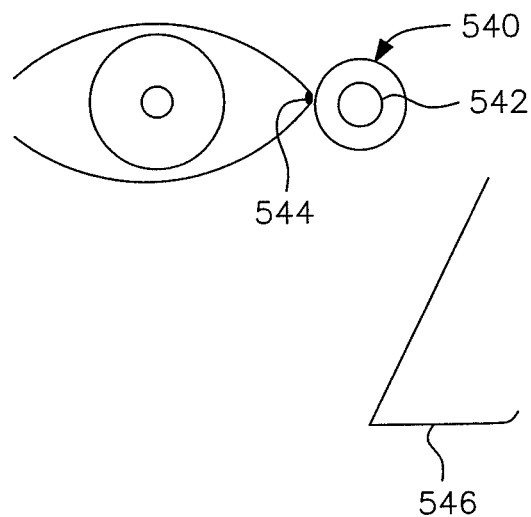
FIGS. 46A to 46D shows exemplary geometries and shapes for medial canthal pads or modified nose pads.
Figure 46B:
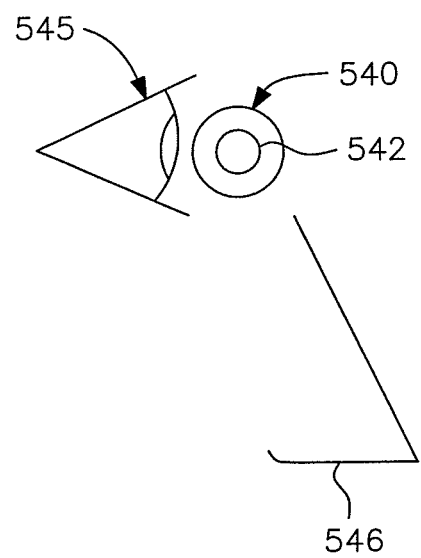
Figure 46C:
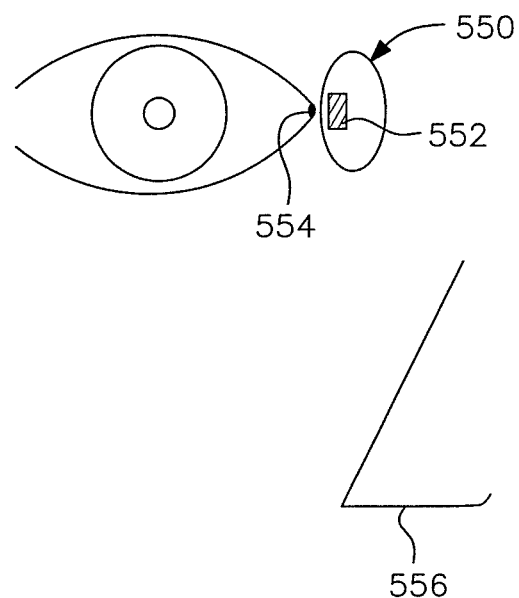
Figure 46D:
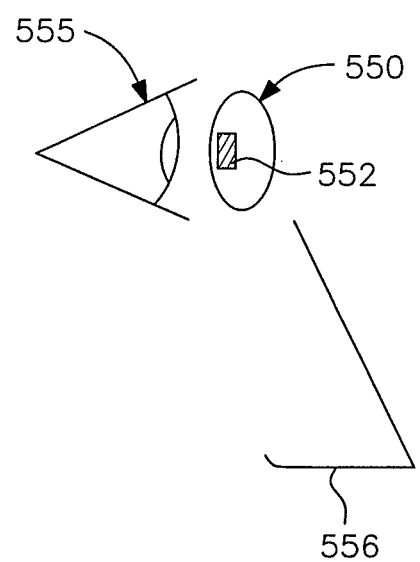

FIGS. 46A to 46D shows exemplary geometries and shapes for medial canthal pads or modified nose pads and their relation to the medial corner of the eye. FIG. 46A, shows a frontal view of a modified nose pad 540 containing a sensor 542 located centrally in said nose pad 540 wherein the sensor 542 is positioned on the skin at the BTT area next to the corner of the eye 544 and nose 546. FIG. 46B is a side view showing the eye 545 and nose 546 and the modified nose pad 540 with the sensor 542 positioned at the BTT site. FIG. 46C show a frontal view of a modified nose pad 550 having a sensor 552 located in its outer edge and positioned on the skin area at the BTT site next to the corner of the eye 554 and nose 556. FIG. 46D is a side view showing the eye 555 and nose 556 and the modified nose pad 550 with the sensor 552 positioned at the BTT site.

It is understood that although an extension is the preferred embodiment with the sensor not contacting the skin, an infrared sensor probe adapted to touch the skin at the BTT area can also be used.

Figure 47:
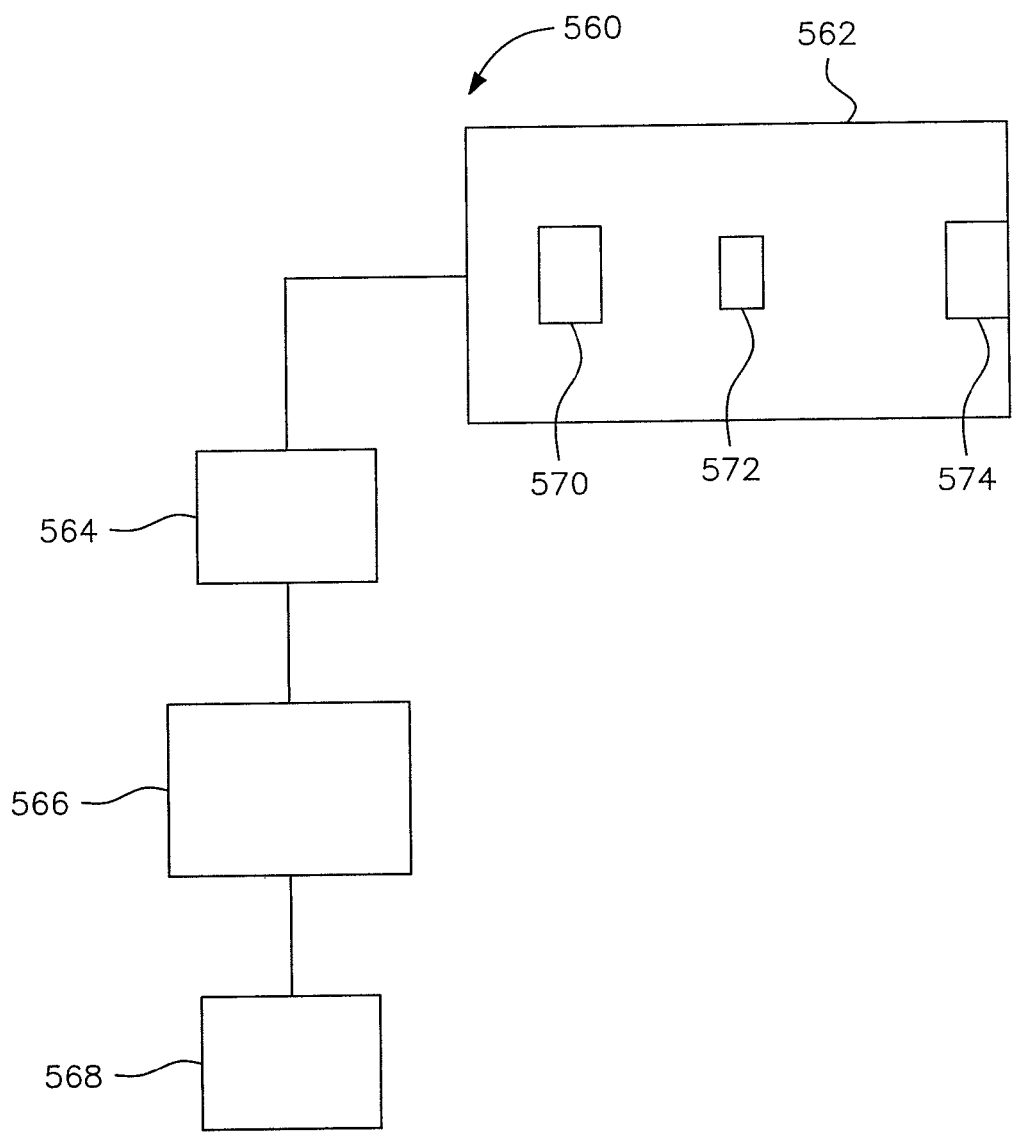
FIG. 47 is a schematic block diagram showing a preferred embodiment of the infrared imaging system of the present invention.

Now in reference to the thermal imaging systems of the present invention, FIG. 47 is a schematic block diagram showing a preferred embodiment of the infrared imaging system of the present invention. FIG. 47 shows a BTT ThermoScan 560 comprising a camera 562, a microprocessor 564, a display 566, and a power source 568. The system further includes proprietary software and software customized for the precise measurement and mapping of the BTT area. The BTT ThermoScan 560 includes a camera 562 with a lens 574, an optical system 572 that can contain mirrors, filters and lenses for optimizing image acquisition, and a photodetector 570, also referred to herein as a radiation sensor or a radiation detector, to quantify and record the energy flux in the far infrared range. The display unit 566 displays the thermal image of the BTT being viewed by the lens 574 in the camera. Radiation detector materials known in the art can be used in the photodetector 570 including alloys of indium-antimonide, mercury-cadmiun-telluride, Copper doped Germanium, Platinum Silicide, Barium Strontium Titanate, and the like.

The infrared radiation detector converts the incident radiation that includes the BTT area into electrical energy which is amplified. The detector 570 is responsive to infrared radiation to provide an output signal and discrete points (only) related to the intensity of the thermal energy received from the BTT area and the surrounding area around the BTT area.

The discrete points are imaged and each point source must have enough energy to excite the radiation detector material to release electrons. Any point size can be used, but preferably with a size between 1 and 2 mm in diameter. When using an angle of 1.3 mrads, the BTT ThermoScan can capture an instantaneous image from a point size of approximately 1 mm diameter at a distance of 1 m from the detector. It is understood that any spatial resolution for optimal capturing of the BTT image can be used, but it is preferably between 1.0 and 1.6 mrad. The camera 562 of the BTT ThermoScan 560 has a field of view adapted to view the BTT area. Discrete points are further converted into an image of the face that includes the BTT area in the medial corner of the eye and upper eyelid. The screening function of the BTT ThermoScan is based on the temperature at the BTT area, either absolute temperature or the differential temperature of the BTT area in relation to a reference.

The electrical response to the thermal radiation can be displayed on the monitor as intensity, with a strong signal producing a bright (white) point as seen in FIG. 1A with said white point being representative of the highest radiant energy from the source. In FIG. 1A the source is the human face and the highest intensity of radiation is found in the BTT area. Calibration of the display screen result in a continuum shades of gray, from black (0 isotherm) to bright white (1 isotherm). Each point is digitally stored for further processing and analysis.

It is understood that a variety of lenses, prisms, filters, Fresnel lenses, and the like known in the art can be used to change the angle of view or optimize signal acquisition and capture of thermal energy flux from the face and the BTT area. The lens of the BTT ThermoScan 560 is preferably perpendicular to the plane of the human face or of the BTT area being viewed.

The radiation detector material in the BTT ThermoScan 560 is preferably sensitive to radiation with wavelength ranging from 8 to 12 µm. The BTT ThermoScan 560 has a temperature span set between 2 to 5 degrees Celsius and is extremely sensitive and adapted to discern temperatures to within 0.008 degrees Celsius to 0.02 at a range of 1 meter. Temperature measurements can be based on radiometric means with built-in electronics or by differential using a reference such as a black body. Although the system can be uncooled, to maximize the efficiency of the detector and achieve an optimum signal to noise ratio the detector can be cooled using solid state means, liquid nitrogen, evaporation of compressed argon gas, piezoelectric components, and the like.

Many radiation detectors capable of detecting infrared waves are being developed including silicon based, solid state systems, and microbolometers, and all said systems new or to be developed in the future can be used in the apparatus of the present invention to detect thermal radiation from the BTT with the display of a corresponding image of the BTT in a monitor.

An exemplary infrared detector system includes a microbolometer which is fabricated on silicon substrates or integrated circuits containing temperature sensitive resistive material that absorbs infrared radiation, such as vanadium oxide. The incident infrared radiation from the BTT area is absorbed by the microbolometer producing a corresponding change in the resistance and temperature. Each microbolometer functions as a pixel and the changes in electrical resistance generate an electrical signal corresponding to thermal radiation from the BTT area that can be displayed in a screen of a computer.

The display of the image of the BTT is the preferred embodiment of the invention, but the present invention can be implemented without display of an image. Radiation coming from the BTT can be acquired by the radiation sensors aforementioned and the temperature of the BTT area can be calculated based on the electrical signal generated by the radiation sensor using a reference. Any means to detect thermal radiation and/or temperature from the BTT area can be used in accordance with the principles of the invention.

Besides the easy manipulation of temperature at the skin level outside the BTT area, significantly lower temperatures are found in the areas outside the BTT as shown in the image on the screen, and depicted in the photos of FIGS. 1A and 1B. The lower and more unstable temperature outside the BTT area results in generating a non-clinically significant temperature level or thermal image when said areas outside the BTT are used for sensing thermal radiation and/or measuring temperature.

It is understood that a variety of signal conditioning and processing can be used to match the temperature areas outside the BTT area to a value that corresponds to the BTT area, and those methods also fall in the scope of the invention. Image outside the BTT area as seen more like a blur compared to the BTT area and superimposition of images that include the BTT area can also be used for achieving higher level of accuracy during temperature measurements. Comparing a radiation pattern outside the BTT area with the BTT area without necessarily creating an image of the BTT area can also be used for accurate and precise temperature measurement and evaluation of the thermal status of the body in accordance with the principles of the invention. Any method or device used for temperature evaluation or evaluation of the thermal status that is based on the temperature level or thermal radiation present in the BTT area by generating or not generating an image falls within the scope of the present invention.

Figure 48:
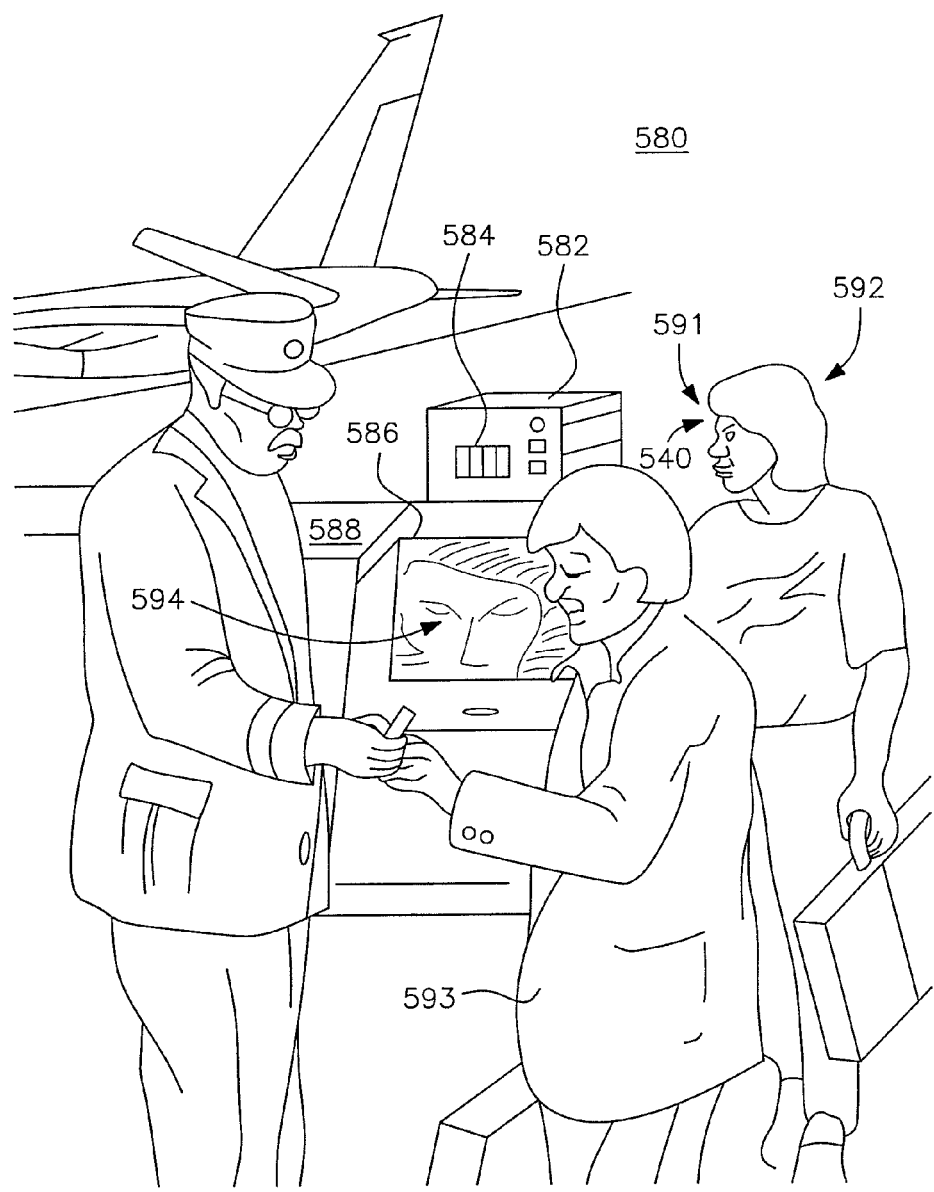
FIGS. 48 to 51 are schematic views showing the infrared imaging system of the present invention mounted in a support structure in different locations for screening people for temperature changes.

FIG. 48 is a schematic view showing the thermal imaging system 560 of the present invention adapted to be used in an airport 580 including an infrared camera 582, a processor 584, and a display 586 which are mounted in a support structure 588 at an airport 580. Camera 582 scans the BTT area present in the medial corner of the eye 590 in a human face 591 and provides an output signal to a signal processor 584. The output signal is an electronic signal which is related to the characteristic of the thermal infrared energy of the BTT 590 in the human face 591 when people 592, 593 walking by look at or are viewed by the camera 582. The processor 584 processes the output signal so that an image of the BTT area 594 can be formed by the display 586 such as a computer monitor.

Exemplarily, passenger 592 is looking at the camera 582 for sensing the thermal radiation from the BTT area 590, with said passenger 582 holding his/her eyeglasses since for the camera 582 to precisely view the BTT area 590 the eyeglasses have to be removed. If someone goes by the camera 582 without a thermal image of the BTT 590 being acquired an alarm will be activated. Likewise, if someone has a temperature disturbance an alert indicative of said temperature disturbance is activated.

Figure 49:
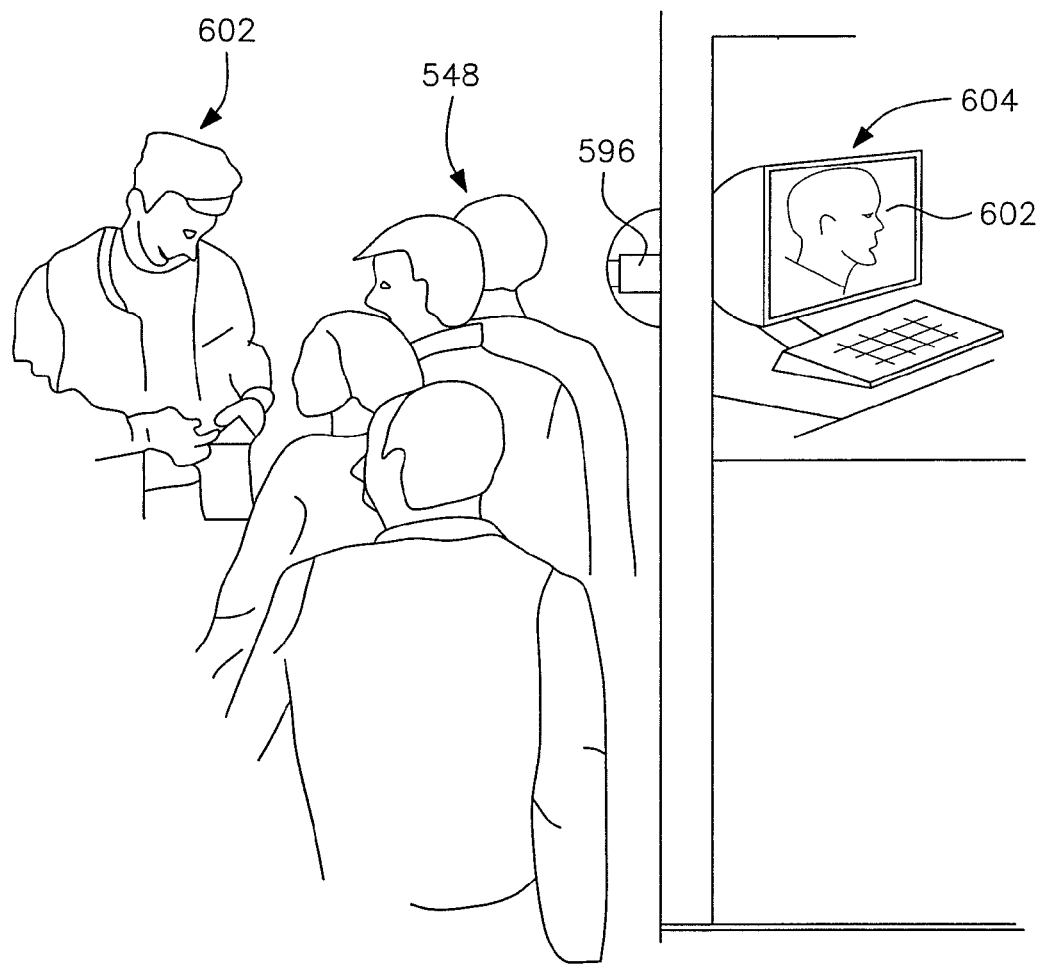

FIG. 49 is a schematic view showing the thermal imaging system 560 of the present invention adapted to be used in any facility that has a gathering of people such as a movie theater, a convention, stadium, a concert, a trade show, schools, and the like. In FIG. 49 the infrared camera 596 of the BTT Thermoscan 560 is located at the entrance of the aforementioned facilities and while people 598 show their identification or ticket to an agent 602, the BTT ThermoScan 560 scans the side of the face of the people 598 to capture a thermal image 600 and temperature at the BTT tunnel which is displayed in a remote computer display 604. The camera 596 has adjustable height and a tracking system to track the heat, and therefore said camera 596 can position itself for sensing thermal radiation from people 598 at different distances and of different height. It is also understood that the BTT Thermoscan 560 can be used in any facility including optical stores for adjusting positioning of sensors in eyeglasses.

Figure 50:
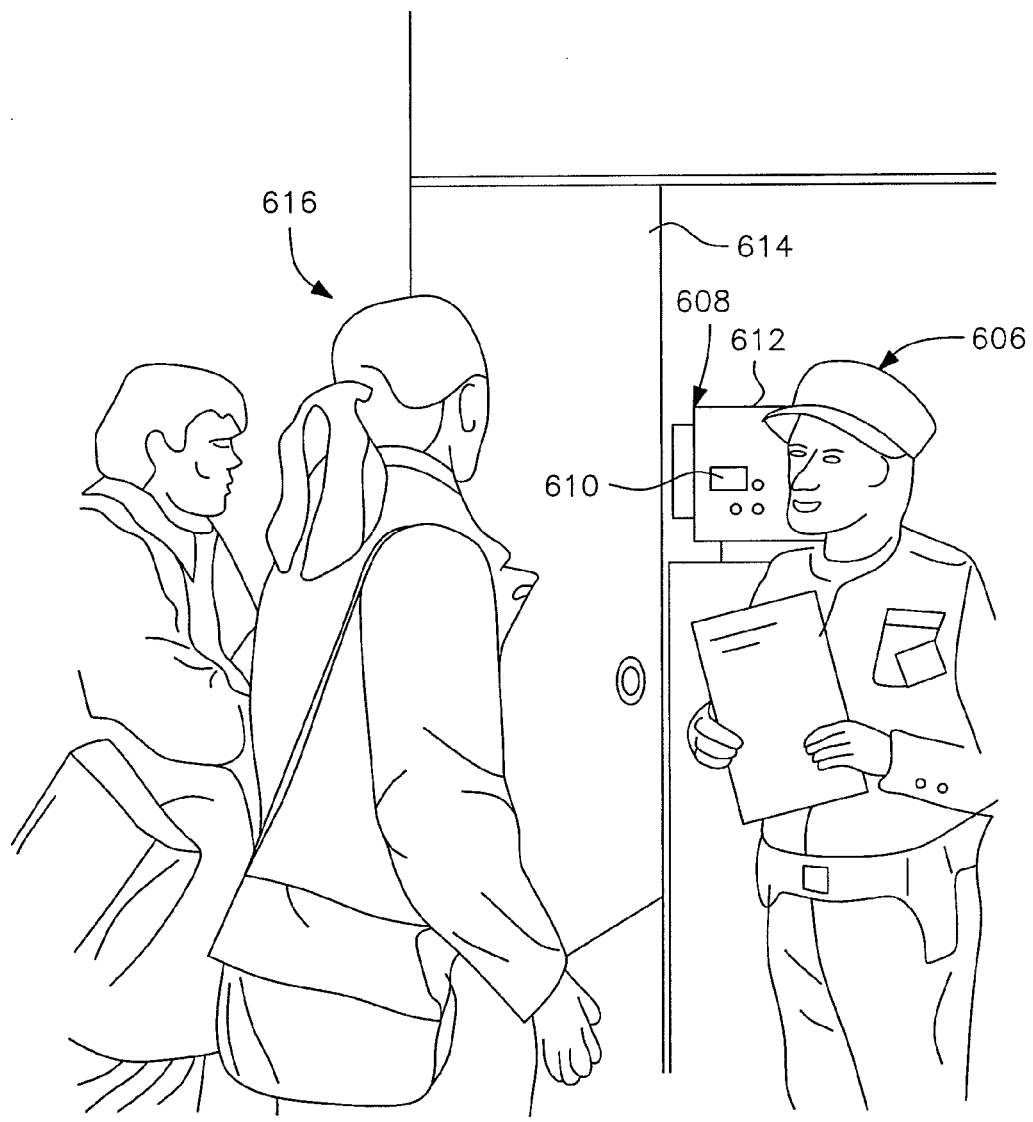

A facility that is of strategic importance such as a government building, military bases, courts, certain factories and the like can also benefit from screening for temperature disturbances. As shown in FIG. 50, a guard 606 is standing by an infrared detector camera 608 for sensing thermal radiation from the BTT area and preferably including a card slot 610 in its housing 612. Although a guard 606 is shown, the BTT ThermoScan of the present invention can work in an unguarded entrance. In this embodiment the BTT thermal image 560 works as a key to automatically open a door 614. Accordingly, employee 616 scan her Company Identification card in the slot 610 which then prompts the user to look at the camera 608 for capturing the thermal image of the BTT area. If the temperature of the BTT is within acceptable limits, the processor of the ThermoScan 608 is adapted to open the door 614. If the BTT temperature shows fever indicating a possible infection the employee is directed to a nurse. This will greatly help safety procedures in facilities dealing with food products in which one employee having a contagious disease can contaminate the whole lot of food products.

Figure 51:
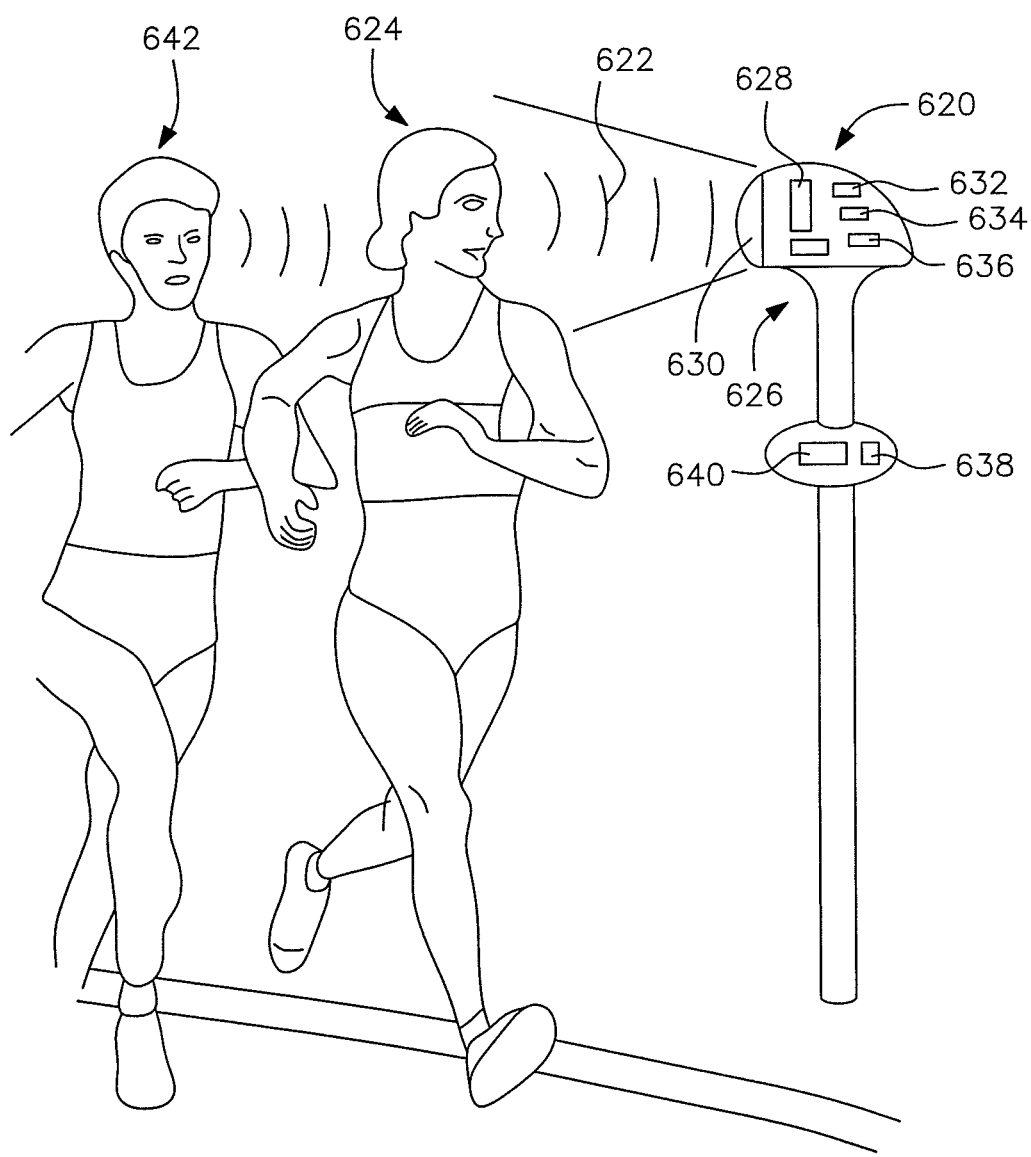

FIG. 51 is a schematic view of another embodiment of the present invention to monitor temperature disturbances during physical activity such as sports events, military training, and the like, showing infrared thermal detector 620 sensing thermal radiation 622 from an athlete 624. The infrared thermal detector 620 includes a detector head 626 which contains an infrared sensor 628, a digital camera, 630 and a set of lights, red 632, yellow 634 and green 636 indicating the thermal status of the athlete with the red light 632 indicating temperature that can reduce safety or performance of the athlete, a red light 632 flashing that indicates temperature outside safe levels, a yellow light 634 indicating borderline temperature, a green light 636 indicating safe temperature levels, and a green light 636 flashing indicating optimum thermal status for enhancing performance. The infrared sensor 628 detects the thermal radiation 622 and if the red light 632 is activated the digital camera 626 takes a picture of the scene to identify the number of the athlete at risk for heatstroke or heat illness. The infrared detector 620 further includes a processor 638 to process and a transmitter 640 to transmit the signal wired or wirelessly. It is understood that a wider field of view can be implemented with multiple BTT signals being acquired simultaneously as shown by BTT radiation from a second athlete 642 being sensed by the infrared detector head 626.

Figure 52A:
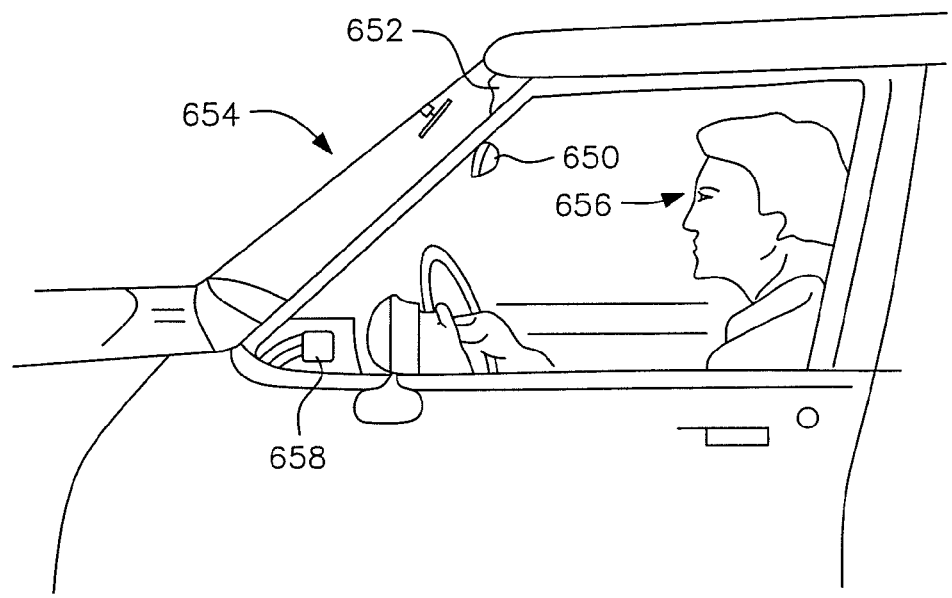
FIG. 52A is a schematic view showing the infrared imaging system of the present invention mounted in a vehicle.

Now referring to FIG. 52A, the BTT ThermoScan of this embodiment preferably includes a micro solid state infrared detector 650 which is mounted on a visor 652 of a vehicle 654 for sensing thermal radiation from the BTT of a driver 656 and of ambient radiation monitored by processor 658 mounted in the dashboard of the vehicle to determine whether the driver 656 is at risk of temperature disturbance (hyperthermia or hypothermia) which hampers mental and physical function and can lead to accidents. In addition the temperature at the BTT site of the driver 656 can be used for automated climate control and seat temperature control of vehicle 654. When the image of the BTT site indicates high body temperature the air conditioner is automatically activated.

Figure 52B:
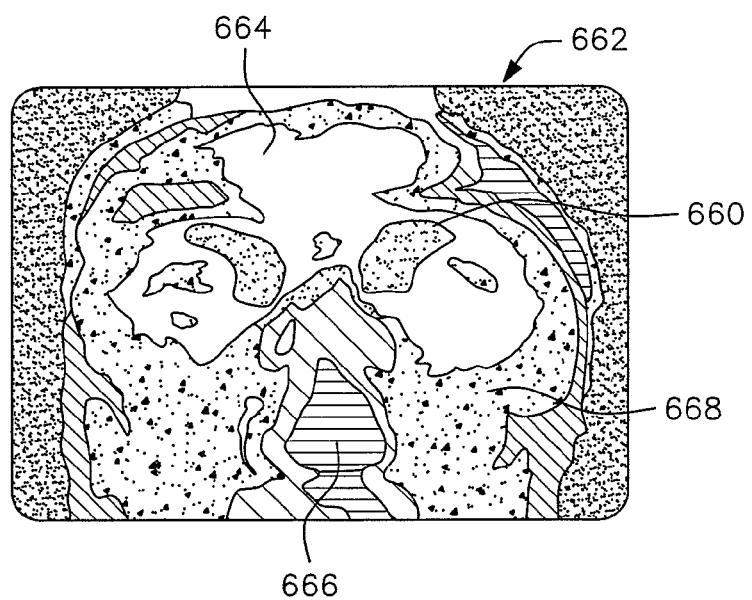
FIG. 52B is a representation of an illustrative image generated with the infrared imaging system of FIG. 52A.

FIG. 52B is a representation of an image generated by the detector 650 showing the BTT area 660 on a display 662. FIG. 48 is a representation of an illustrative image generated with the infrared imaging system of the present invention. FIG. 52B shows a frontal view of the human face and the BTT area 660 displayed on a screen 662 as well as the other areas outside the BTT area present in the human face such as forehead 664, nose 666, and cheeks 668. Please note that FIG. 1B shows an actual photo of the geometry of the general entry point of the BTT displayed on a screen and FIG. 4A shows a side view of the human face and of the BTT area displayed on a screen.

Figure 53:
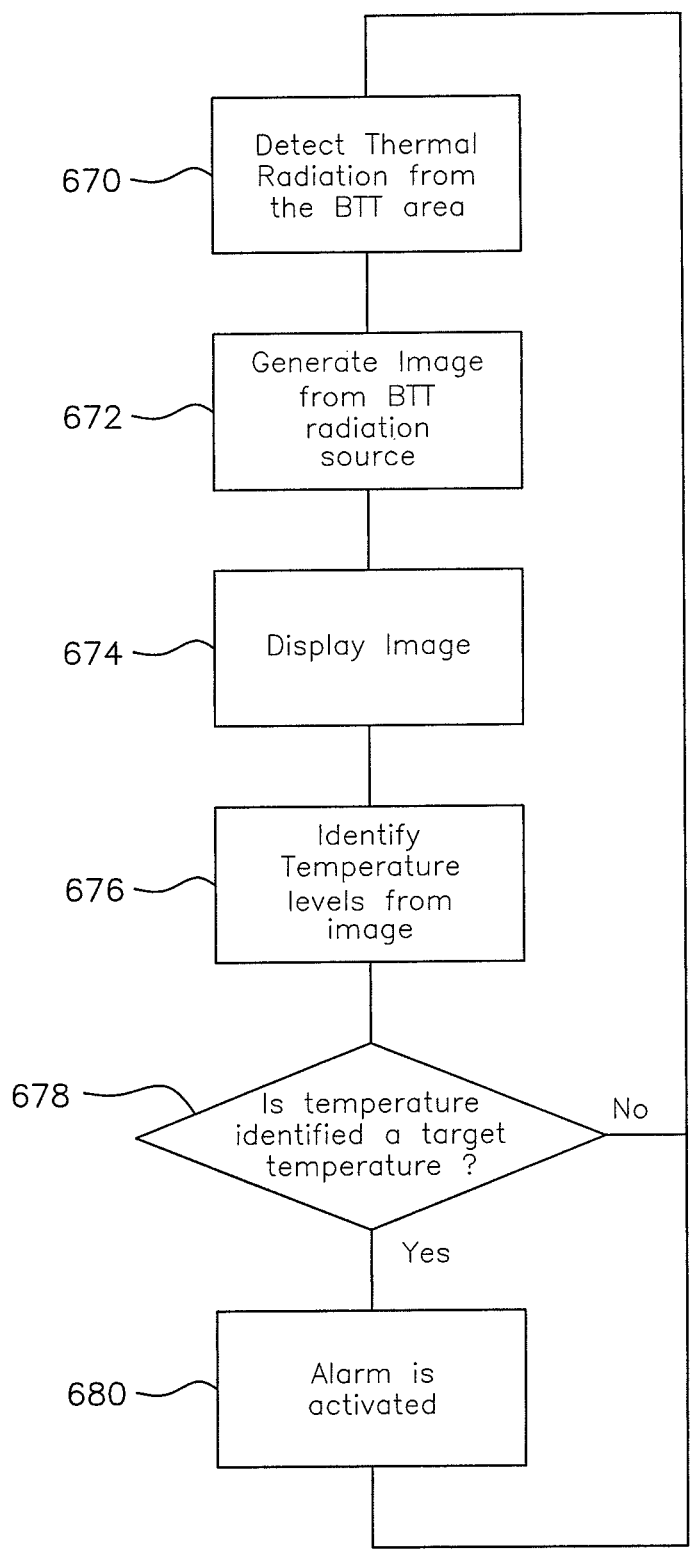
FIG. 53 shows a flowchart illustrating a method used in the present invention.

FIG. 53 shows an illustrative method of the present invention represented in a flowchart. It is to be understood that the method may be accomplished using various signal processing and conditioning with various hardware, firmware, and software configurations, so the steps described herein are by way of illustration only, and not to limit the scope of the invention. The preferred embodiment includes detecting thermal radiation from a source that includes at least a portion of the BTT area (step 670). At step 672 an image from a radiation source that includes at least a portion of the BTT area is generated. At step 674 the image generated at step 672 is displayed. Step 676 identifies temperature levels from the image displayed at step 674. Step 678 determines whether the temperature identified at step 676 matches a temperature target. The temperature target can be indicative of a temperature disturbance or indicative of the need to change the climate control level of the vehicle. Considering a temperature disturbance, if yes and there is a match between the detected temperature at the BTT and the stored target temperature, then an alarm is activated at step 680 informing the subject of the temperature disturbance (e.g., fever, hyperthermia, and hypothermia) and processing continues at step 670. If there is no match, step 678 proceeds to the next operation at step 670.

To enhance the image generated by the BTT ThermoScan, the method further includes aligning the BTT area with the field of view of the infrared detector and by removing eyeglasses during thermal detection of the BTT area.

Figure 54A:
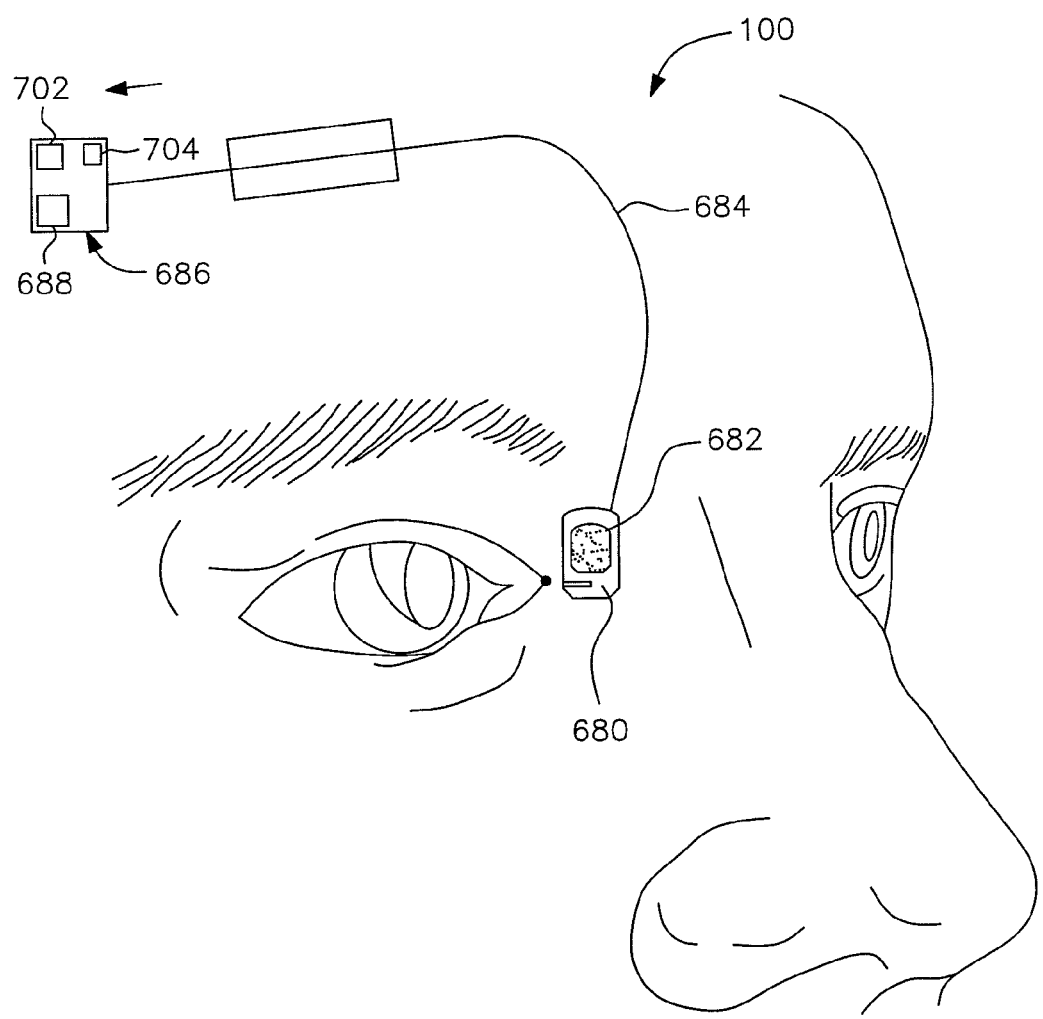
FIGS. 54A and 54B are perspective views of a preferred embodiment coupled to a head gear.
Figure 54B:
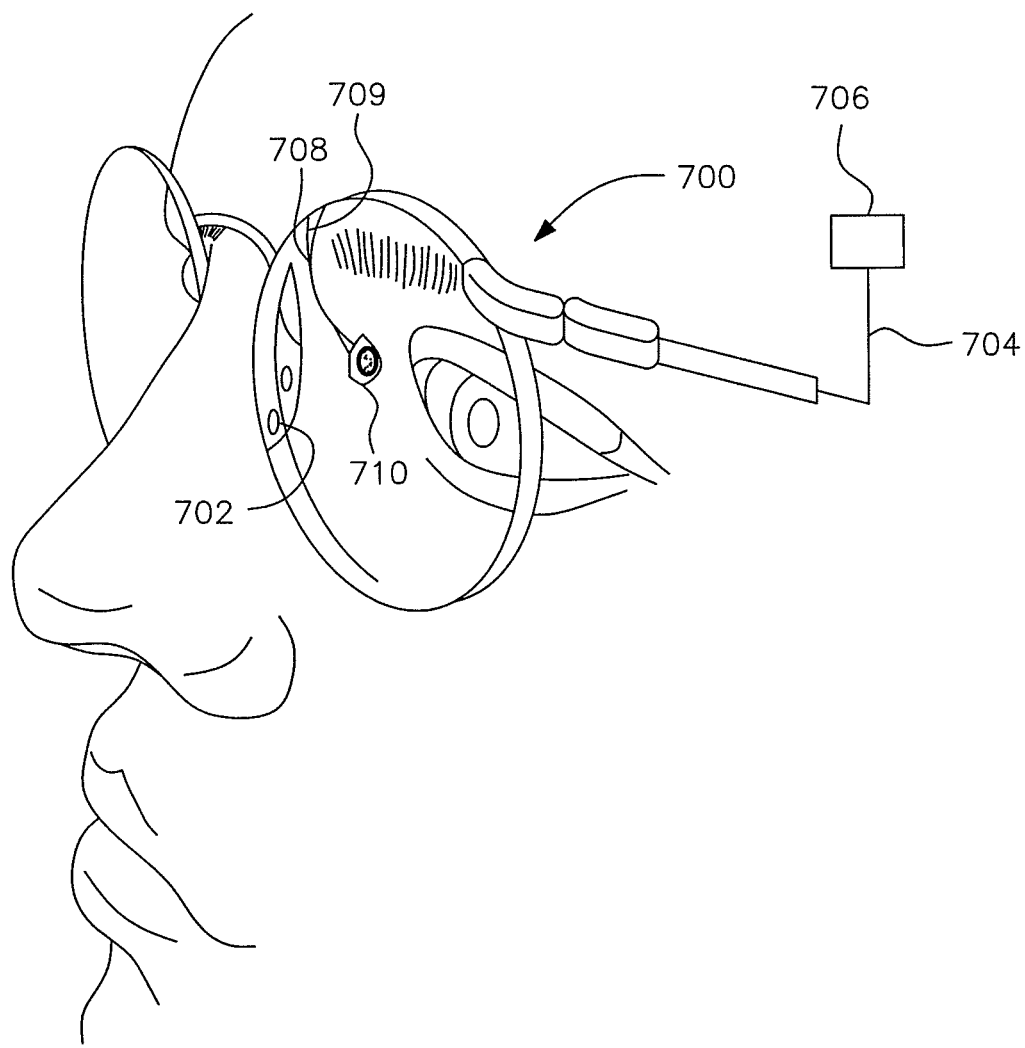

FIG. 54A is a perspective view of another preferred embodiment showing a person 100 wearing a support structure 680 comprised of a patch with sensor 682 positioned on the skin at the end of the tunnel and connected by a wire 684 to a helmet 686 which contains the decoding and processing hardware 688, transmitter 702 and display unit 704. Exemplary helmets include ones known in the art for the practice of sports, military, firefighters, and the like. Alternatively, as shown in FIG. 54B the support structure includes eyewear 700 with a warning light 702 and sensor 710 of eyewear 700 connected by wire 704 to the head mounted gear, such as a helmet 706. Sensor 710 has an arm 708 with a spring mechanism 709 for positioning and pressing the sensor 710 against the skin at the BTT area.

Figure 55:
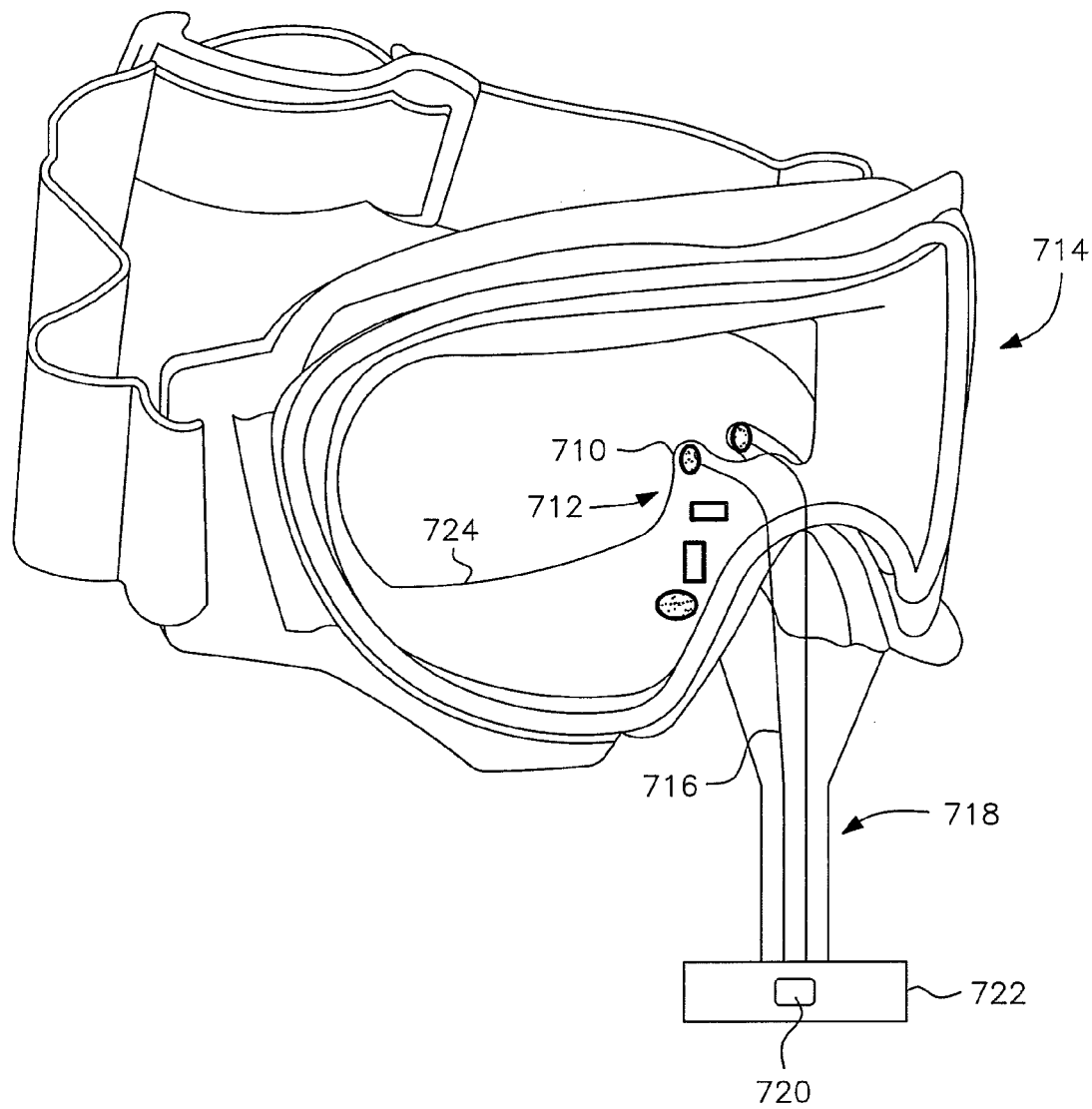
FIG. 55 is a perspective view of a preferred embodiment comprised of a mask and an air pack.

Now in reference to FIG. 55, the temperature sensor 710 can be mounted on nose pieces 712 of masks 714, for example a mask for firefighters. Wire 716 from mask 714 is mounted in an insulated manner, such as being positioned within the structure of mask 714 and air tube 718 that connects mask 714 to air pack 722. Wire 716 connects sensor 710 to radio transmitter 720 located in the air pack 722. Alternatively, wire 716 can be mounted external to the air tube 718. A warning light 724 in the mask 714 alerts the firefighter about high or low temperature.

Figure 56A:
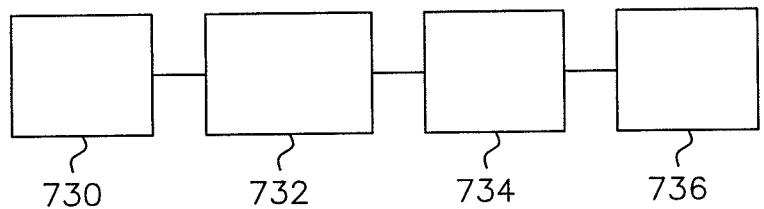
FIGS. 56A and 56B are schematic diagrams showing a BTT entry point detection system in accordance with the present invention.
Figure 56B:
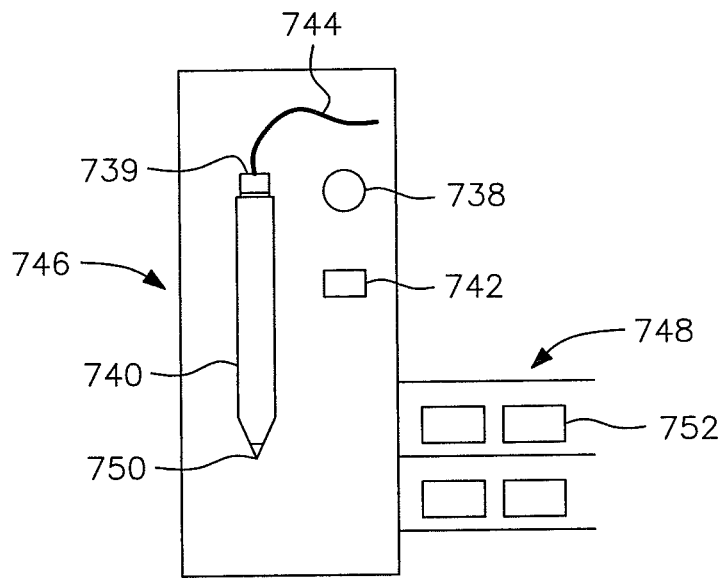

FIG. 56A is a diagram showing a BTT entry point detection system, which corresponds to the area with the highest temperature in the surface of the body, including temperature sensor 730, amplifier 732, processor 734, and pager 736. Processor 734 is adapted to drive the pager 736 to emit a high frequency tone for a high temperature and a low frequency tone for a low temperature. Scanning of the BTT area with the sensor 730 allows precise localization of the main entry point of the BTT, which corresponds to the highest frequency tone generated during the scanning. Another preferred embodiment for detection of the main entry point of the BTT includes replacing a buzzer or pager emitting sound or vibration by a light warning system. Exemplarily, FIG. 56B shows a pen 740, a LED 738 mounted on a board 746 and a LED 739 mounted on said pen 740, a sensor 750, and a processor 742. Wire 744 connects the pen 740 to board 746. The processor 742 is adapted to activate light 738, 739, when during scanning the BTT area, the highest temperature is found. By way of example, as shown in FIG. 56B, this pen 740 can be mounted on a board 746 next to a shelf 748 where TempAlert thermometers 752 are sold, allowing a customer to precisely locate the main entry point of the BTT. Sensor 750 of pen 740 can be for example a non-contact sensor (e.g., Thermopile) or a contact sensor (e.g., Thermistor).

Figure 57:
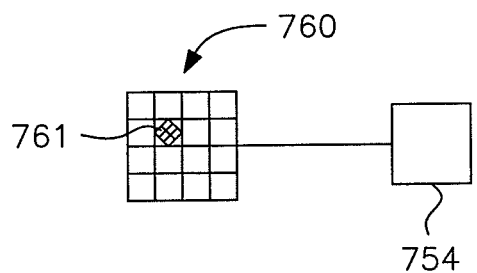
FIG. 57 is a schematic diagram showing an automated BTT entry point detection system.

The detection of the main entry point of the BTT can also be done automatically. Accordingly, FIG. 57 shows a 4 by 4 sensor array 760 placed at the BTT. The sensor array 760 contains 16 temperature sensors, which measure the temperature at the BTT site. Each temperature sensor T1 to T16 in the array 760 provides a temperature output. Sensor array 760 is connected to microprocessor 754 which is adapted to identify the sensor in sensor array 760 with the highest temperature output, which corresponds to the main entry point of the tunnel. For example temperature sensor T6 761 is identified as providing the highest temperature output, then the temperature of sensor T6 is displayed. The processor 754 continually searches for the highest temperature output of sensor array 760 in an automated manner and the highest temperature is continuously displayed.

FIG. 58A is an alternative embodiment showing support structure 758 comprised of a piece of silicone molded to fit the BTT area with said support structure 758 containing wire 769 and sensor 770 in its structure. FIG. 58B shows the support structure 758 with sensor 770 positioned at the BTT area 775 with wire 769 exiting the molded piece of silicone structure 758 toward the forehead 773. Now referring to FIG. 58C, support structure 758 can alternatively include a multilayer structure comprised of a Mylar surface 762, sensor 770 with wire 769, and silicone piece 774 in the shape of a cup that encapsulates sensor 770, allowing proper and stable positioning of sensor 770 at the BTT area.

It is also an object of the invention to provide methods and devices for treating and/or preventing temperature disturbances. As shown in FIG. 2B the brain is completely insulated on all sides with the exception at the entrance of the BTT. The BTT is a thermal energy tunnel in which thermal energy can flow in a bidirectional manner and therefore heat can be removed from the brain or delivered to the brain by externally placing a device at the entrance of the BTT that either delivers heat or removes heat. Accordingly, FIG. 59 shows the bidirectional flow of thermal energy represented by arrows 780 carrying heat to the brain and arrow 782 removing heat from the brain with the distribution of heat to and from the brain 784 occurring via the thermal storage area 786, with said thermal storage area shown in FIG. 2B in the center of the brain. From the thermal storage area 786 the thermal energy represented as hot or cold blood is distributed throughout the brain tissue 784 by the blood vessels 788, for treating and/or preventing hyperthermia (heatstroke) or hypothermia.

Accordingly, another object of this invention is to provide a new and novel BTT thermal pad for the application of cold or heat to the BTT area for cooling or heating the brain.

A further object of this invention is to provide a new and novel BTT thermal pad which covers the entrance of the BTT area, which may extend to other areas of the face. However, since the brain is insulated on all other sides but at the BTT entrance, the cooling is only external and does not reach the brain, which could be at "frying" temperature despite the external cooling sensation. Considering that, a preferred embodiment includes an extended BTT thermal pad covering the face in which only the BTT area is exposed to the cold and the remainder of the extended BTT thermal pad covering the face is insulated, preventing the warming up of the gel or ice placed inside the bag. The BTT thermal pad container can include a radiant heat-reflecting film over various portions thereof, and an insulator over the same or other portions and which together facilitate directional cooling. Thus, only heat conducted by the BTT is absorbed as the BTT is cooled.

The BTT thermal device applied to the BTT area promotes selective brain cooling or selective brain heating for treating hyperthermia and hypothermia respectively. The brain, which is the most sensitive organ to thermally induced damage, can be protected by applying heat via the BTT during hypothermia or removing heat during hyperthermia. The cooling or heating is selective since the temperature of the remaining body may not need to be changed, this is particularly important when cooling the brain for treating patients with stroke or any brain damage. The majority of the brain tissue is water and the removal or application of heat necessary to cool or heat the brain can be precisely calculated using well known formulas based on BTU (British thermal unit). A BTU is the amount of energy needed to raise the temperature of a pound of water 1 degree F., when a pound of water cools 1 F, it releases 1 BTU.

The BTT thermal pad for therapeutic treatment of excessive heat or excessive cold in the brain preferably includes a bag having a substantially comma, banana, or boomerang shape, with said bag in complete overlying relationship with the entire entrance of the BTT, said bag including an outer wall and an inner wall defining a sealed cavity to be filled with ice, gel-like material, solid material, and the like, for cooling or heating the BTT skin area overlying the entrance of the BTT.

An exemplary brain cooling or brain heating device includes hot and cold pad or pack adapted to fit and match the special geometry of the entrance of the BTT and comprising a preferably flexible and sealed pad and a gel within said pad, said gel being comprised of a mixture of water, a freezing point depressant selected from the group consisting of propylene glycol, glycerine, and mixtures thereof associated with other compounds such as sodium polyacrylate, benzoate of soda, hydroxibenzoate, and mixtures thereof and a thickening agent. Any other cooling or heating device or chemical compounds and gels including a combination of ammonium nitrate and water can be used as cooling agent as well as heating agents such as a combination of iron powder, water, activated carbon, vermiculite, salt and Purge natural mineral powder. Those compounds are commercially available from many vendors (e.g., trade name ACE from Becton-Dickson).

Figure 60A:
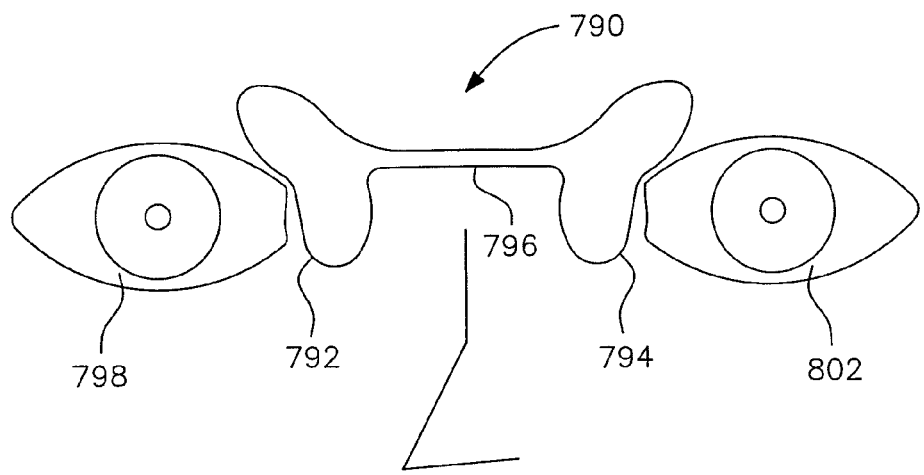
FIGS. 60A to 60C show diagrammatic views of a preferred BTT thermal pack.
Figure 60B:
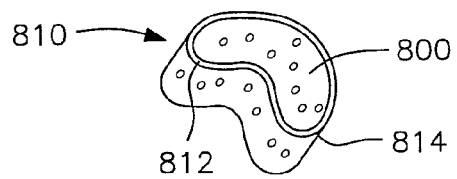
Figure 60C:
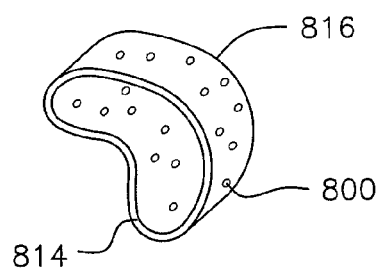

FIG. 60A shows a diagrammatic view of a preferred dual BTT thermal pad also referred to herein as BTT cold/hot pack 790 located next to eye 798, 802 including a dual bag system 792, 794 for both the right and left sides connected by connector 796. FIG. 60B shows in more detail a perspective view of the single bag BTT cold/hot pack device 810, represented by a device to be applied to the left-side, comprising preferably a generally comma-shape, boomerang-shape or banana-shape pad which is sealed in a conventional fashion at its ends 812 to enclose a quantity of a gel-like material 800 which fills the pad 814 sufficiently to enable said pad 814 to be closely conformed to the special topography of the BTT area in the recess between the eye and nose. FIG. 60C is an opposite perspective view showing an extension 816 that conforms to the recess at the BTT area of pad 814 containing gel 800. The device is referred to herein as BTT cold/hot pad or BTT cold/hot pack. Still in reference to FIG. 60C, perspective view is shown of the BTT cold/heat pack device and which is shown as being formed in a pillow-like configuration which permits the molding of the BTT cold/heat pack into the BTT area.

In use the BTT thermal pad would be put into a freezer or other chilling device for use as a cold compress or would be put into hot water to be used as a hot compress. The BTT thermal pad preferably comprises a tough flexible envelope of plastic material. The material within the BTT thermal pad is preferably a gel which will maintain its gel-like consistency over a wide range of temperatures. There exist many gels which can be cooled to freezing and which absorb heat during warmup. There are a number of different types of such gels. Some of them freeze solid, and some are flexible even at 0 degrees F. Cold packs such as a frozen water-alcohol mixture can also be used. Alternatively, a BTT thermal pad includes a bag having inner and outer walls lined interiorly with plastic which define a cavity to be filled with ice through an opening in the bag. In this instance the bag is preferably sealed with a rubber material.

Although flexible plastic is described as a preferred material for containing the gel, it is understood that any material or fabric can be used including vinyl, cotton, rayon, rubber, thermoplastic, synthetic polymers, mixtures of materials, and the like. The size and shape of the BTT pad structure is adapted to fit the special anatomy of the recess between eye and nose and for matching the special geometry of the entrance of the BTT.

Any cooling or heating device known in the art can be used in the BTT pad treatment device including hot or cold water flowing through tubes that are adapted to carry or deliver heat to the BTT area. The tubes can be mounted in any head gear or the frame of eyeglasses, pumping mechanisms can be mounted in the head gear or eyeglasses for providing a continuous flow of water through the tubes. The BTT pad can be connected to tubes which have connectors for joining to a water temperature control and circulating unit in the head gear or eyeglasses. Hot or cold liquid is circulated through tubes which are in communication with each other and which deliver or remove heat from the BTT.

Elastic band or hook and loop fastener can be used for securing the BTT pad in position. Any of the support structures mentioned herein can be used to secure the BTT pad in position including a piece of glue. For example, the BTT pad can include a clip like mechanism or the BTT thermal pad can be secured to the frame of eyeglasses. Nose pads of eyeglasses or modified nose pads of eyeglasses can include cooling or heating devices for delivering or removing heat from the BTT. A BTT thermal pad can include a stick mounted in the pad that can held by hand and manually placed in the BTT area, for example held by a player during a break in the game to reduce the temperature in the brain, or for warming up the brain of a skier during a winter competition.

An alternative embodiment includes a BTT thermal pad attached to a head gear for supplying water to evaporatively cool the BTT area. In this instance the cold water is generated by evaporative cooling in the headband and forehead and upper portion of a wearer's head.

Any cooling or heating device can be used to cool or heat the BTT area for selective brain cooling or brain heating, preferably using a moldable device that conforms to the anatomy of the region at the entrance of the BTT, with directional temperature control properties for cooling or heating the skin at the entrance of the BTT. Any of the devices for heating or overheating or for cooling, including electrical, chips, semiconductor, polymers, and the like known in the art as well as described by Abreu in U.S. Pat. No. 6,120,460; No. 6,312,393 and 6,544,193, herein incorporated in their entirety by reference, and other pending applications by Abreu can be adapted in support structures for positioning at the BTT entrance and used for cooling or heating the brain.

The present invention provides a moldable BTT thermal pad or BTT thermal pack in a packaging arrangement that can provide surfaces of differing thermal conductivities and heat reflecting properties so as to prolong the useful cooling/heating time thereof. The construction and materials of the BTT thermal pad or BTT thermal pack permits the molding of its shape and the retention thereof to the BTT site on the skin between the eye and nose. The materials disclosed herein can remain flexible plastic for temperatures in the range of −10° C. to 140° C.

Figure 61:
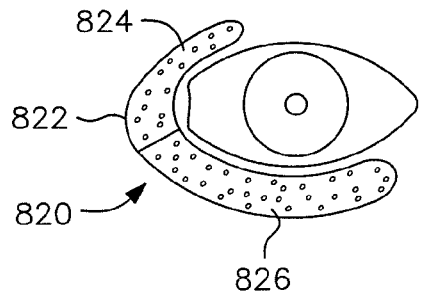
FIG. 61 is a schematic frontal view showing a preferred BTT thermal pack in accordance with the present invention.

Referring to FIG. 61, a frontal view of an alternative embodiment of BTT thermal pack 820 is shown including a bag 822 with gel 800 with said bag having two parts with the first part 824 positioned at the main portion of BTT 824 and containing the highest amount of gel 800 and a second part 826 positioned at the peripheral portion of the BTT and containing a smaller amount of gel.

Figure 62:
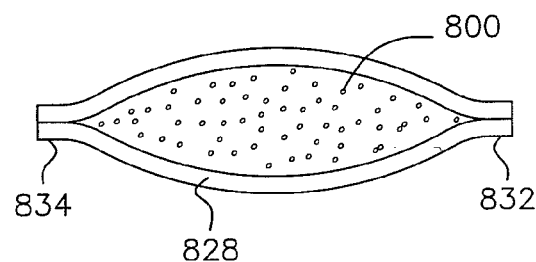
FIG. 62 is a schematic cross sectional view of a BTT thermal pack.

FIG. 62 shows a cross sectional view of the bag 828 of the BTT thermal pack containing gel 800 with said bag sealed in its ends 832, 834.

It is understood that a ring shape surrounding the eye can also be used or a shape that includes other parts of the face/forehead as long as there is conformation and apposition of part of the BTT thermal pack to the BTT area. The preferred shape and dimension matches the special geometry of the BTT area described herein.

Figure 63A:
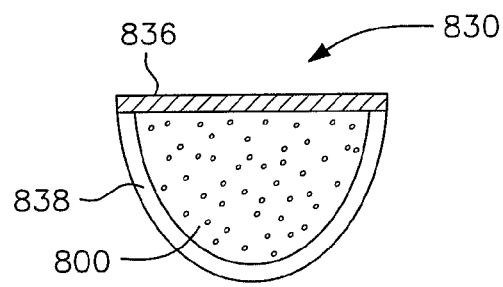
FIG. 63A is a schematic cross sectional view of a BTT thermal pack in its relaxed state.
Figure 63B:
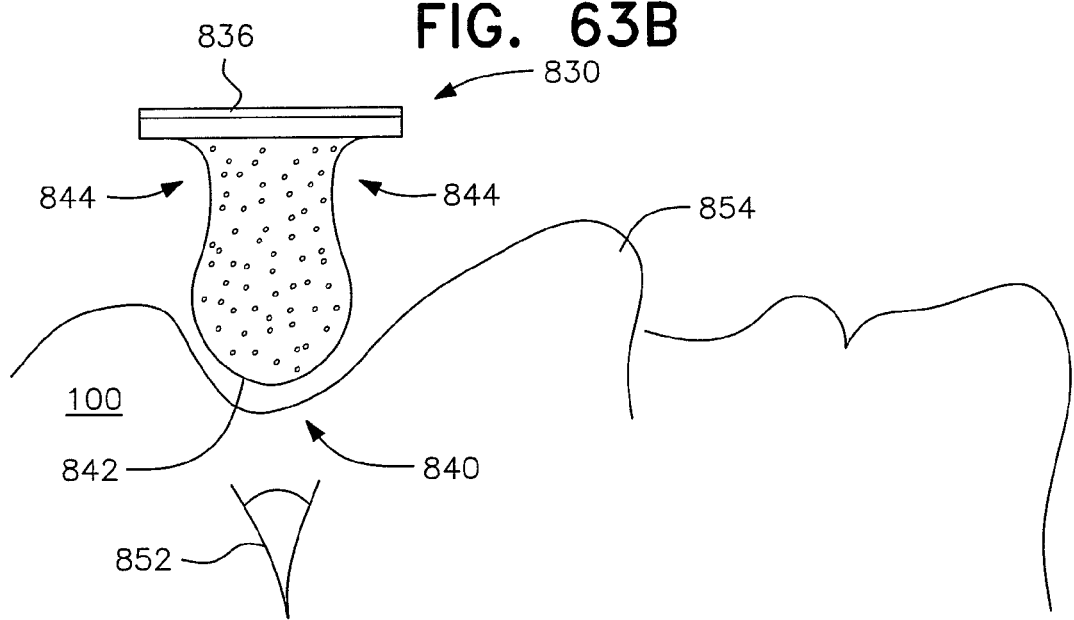
FIG. 63B is a schematic cross sectional view of a BTT thermal pack of FIG. 63A in its compressed state conforming to the BTT area.

FIG. 63A shows a preferred embodiment of the BTT thermal pack 830 in its relaxed state that includes a hard upper part 836 made preferably of hard rubber or plastic attached to a bag 838 made of soft plastic with said bag containing gel 800 and being deformable upon external pressure. As depicted in FIG. 63B, the BTT thermal pack 830 is shown with a centrally formed convex shape 842 at the opposite end of hard upper part 836 upon compression shown by arrows 844 to conform to the BTT anatomy 840 between eye 852 and nose 854 of person 100.

The BTT thermal pack is preferably moldable and the container or bag constructed with materials that are deformable and otherwise pliable over the temperature range of use so as to conform to the anatomy of the BTT area. A central convex area in the pack allows for intimate interaction and thermal energy transfer at the entrance of the BTT, but it is to be recognized that the specific shape of the convex area of the BTT cold/heat pack itself can be slightly varied according to the ethnic group.

Figure 64A:
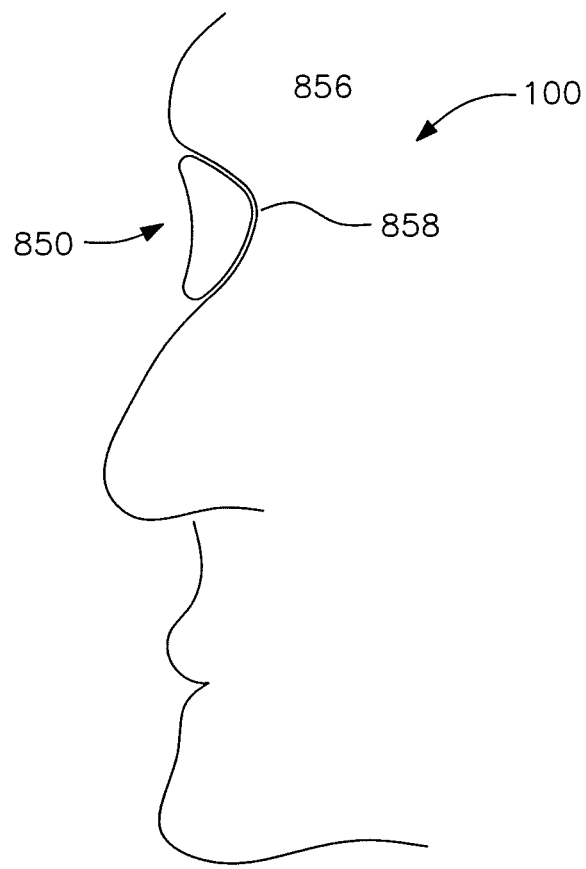
FIG. 64A is a side cross-sectional schematic view of a head of a person with a BTT thermal pack.
Figure 64B:
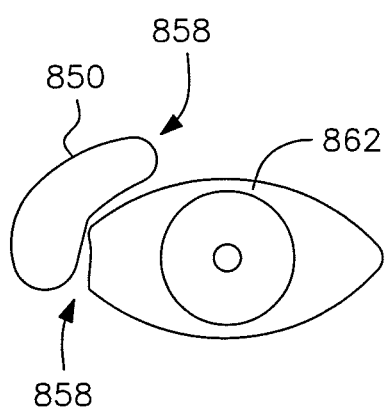
FIG. 64B is a frontal schematic view of the eye area with BTT thermal pack of FIG. 64A.

FIG. 64A shows a side cross-sectional view of a head 856 of person 100 with BTT thermal pack 850 in a pillow-like configuration located at the BTT site 858. Construction of BTT thermal pack is performed so as to maintain an intimate apposition to the BTT site. FIG. 64B is a frontal view of BTT hot/cold pack 850 shown in FIG. 64A at the BTT site 858 located next to the left eye 862.

Figure 65:
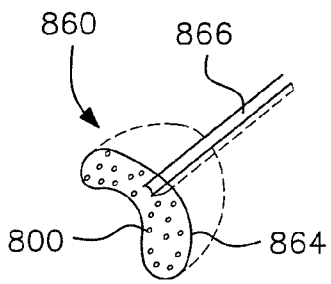
FIG. 65 shows a perspective view of a BTT thermal pack containing a rod 866.
Figure 66:
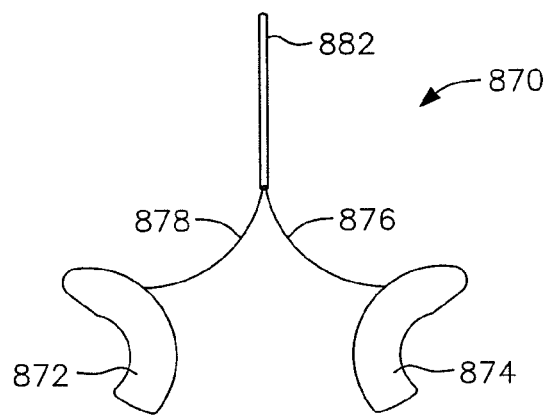
FIG. 66 shows a schematic view of another embodiment of dual bag BTT thermal pack.

FIG. 65 shows a perspective view of a BTT thermal pack 860 that includes a bag 864 containing gel 800 and a rod 866 for manually holding said BTT pack 860 at the BTT site. FIG. 66 shows a frontal view of a dual bag BTT thermal pack 870 with bags 872, 874 connected to a rod 880 by flexible wires 876, 878.

Figure 67A:
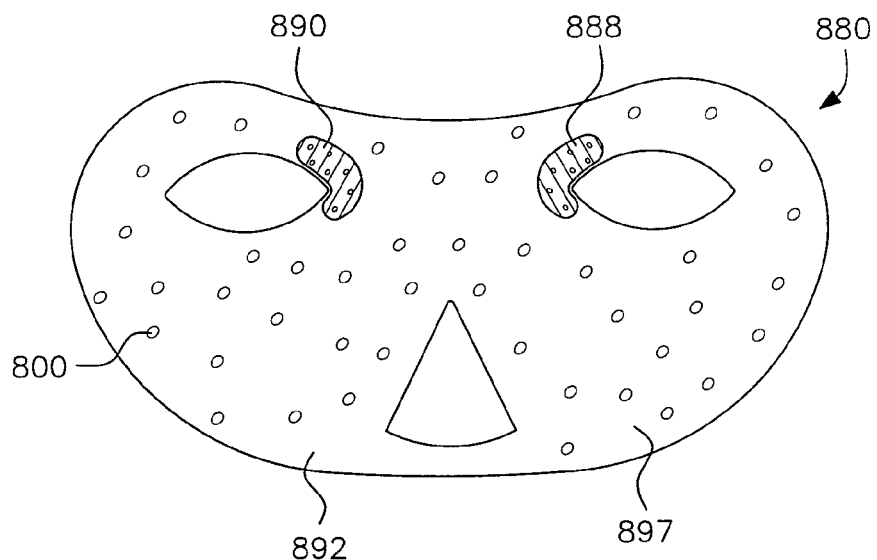
FIG. 67A shows a frontal schematic view of a BTT thermal mask.
Figure 67B:
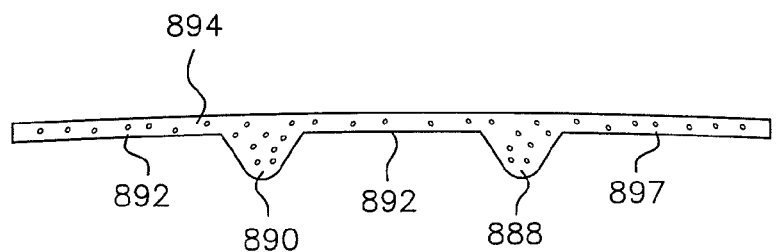
FIG. 67B shows a side cross-sectional schematic view of the BTT thermal mask of FIG. 67A.

FIG. 67A shows a BTT thermal mask 880 with openings 884 for the eyes and 886 for the nose and comprised of a pouch containing gel 800, and including bags 888, 890 for matching the anatomy of the BTT area. The remainder of the mask 880 comprises flat area 892. The flat area 892 is preferably insulated for allowing directional thermal energy flow, so the gel 800 only touches the skin at the BTT area. FIG. 67B is a cross-sectional side view of mask 880 showing pouch 894 with bags 888, 890 and the remaining flat area 892.

Figure 67C:
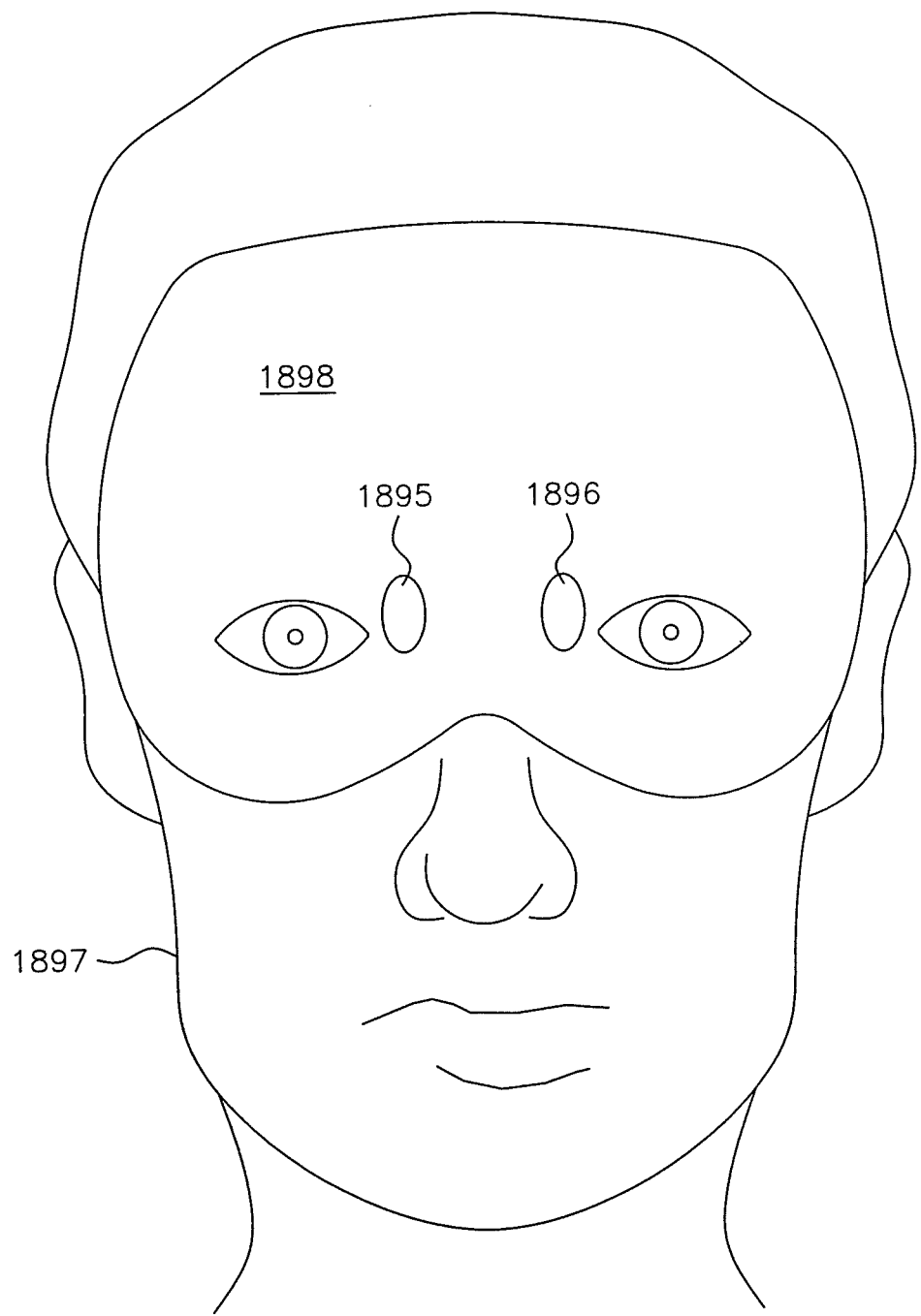
FIG. 67C shows a perspective frontal view of the BTT thermal mask of FIG. 67A on the face and on the BTT.

FIG. 67C is a schematic view of BTT thermal mask 898 with pouches 895, 896 which allow intimate apposition to the BTT area being worn by user 897.

Figure 68A:
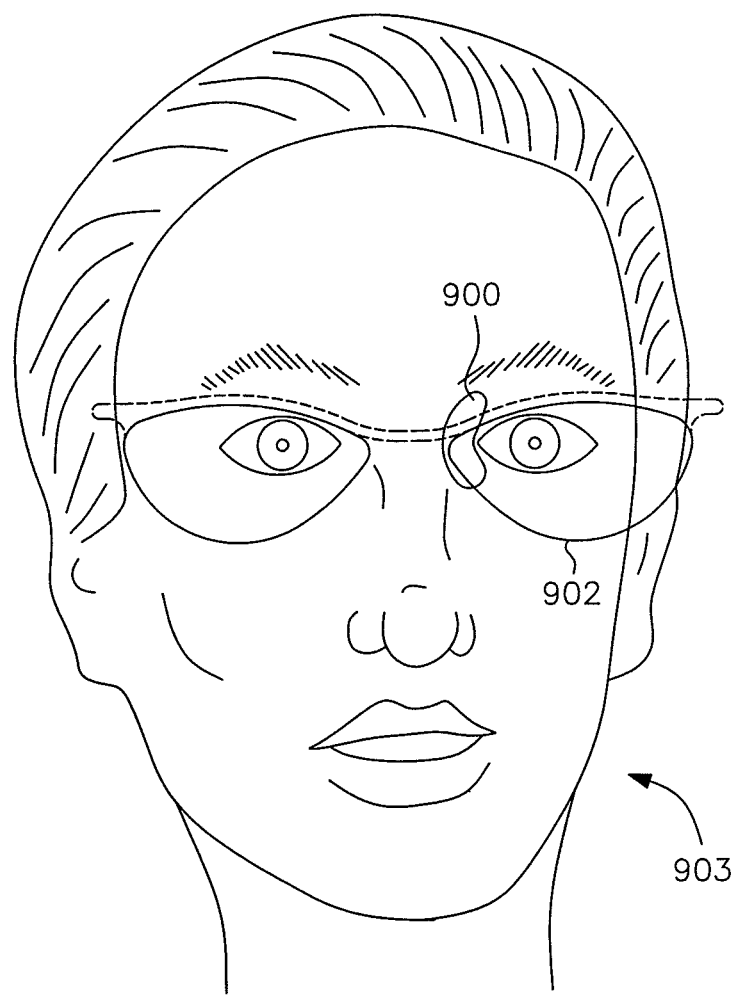
FIG. 68A shows a perspective frontal view of a BTT thermal pack supported by support structure comprised of eyewear.
Figure 68B:
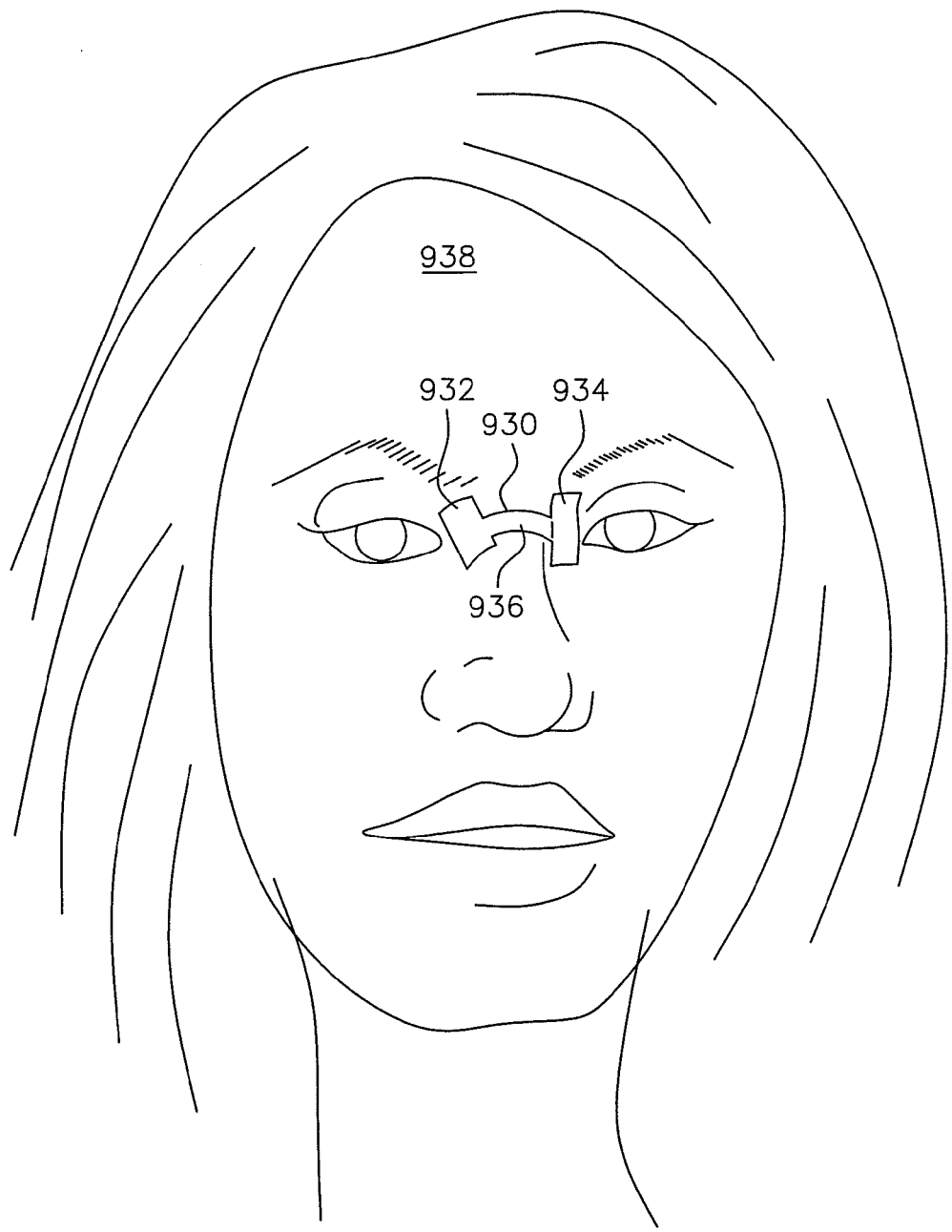
FIG. 68B shows a perspective frontal view of a BTT thermal pack supported by support structure comprised of a clip.

FIG. 68A is a perspective view showing the BTT thermal pack 900 being applied to the BTT area by support structure comprised of eyewear 902 being worn by user 903. FIG. 68B is a perspective frontal view of a BTT hot/cold pack 930 with dual bags 932, 934 for right and left BTT and connected by an arm 936 working as a clip to secure a hot/cold pack in place on the BTT of user 938.

Figure 69A:
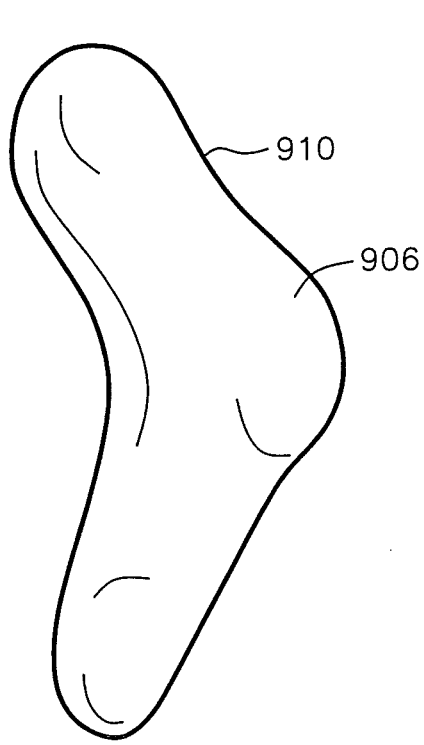
FIGS. 69A to 69C show perspective views of a preferred BTT thermal pack.
Figure 69B:
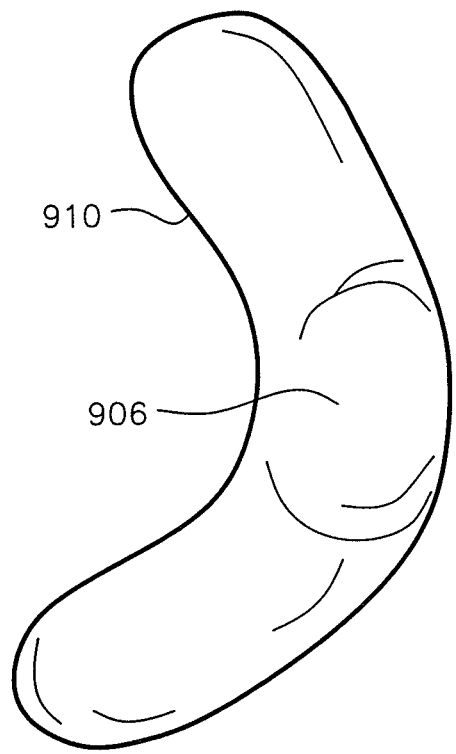
Figure 69C:
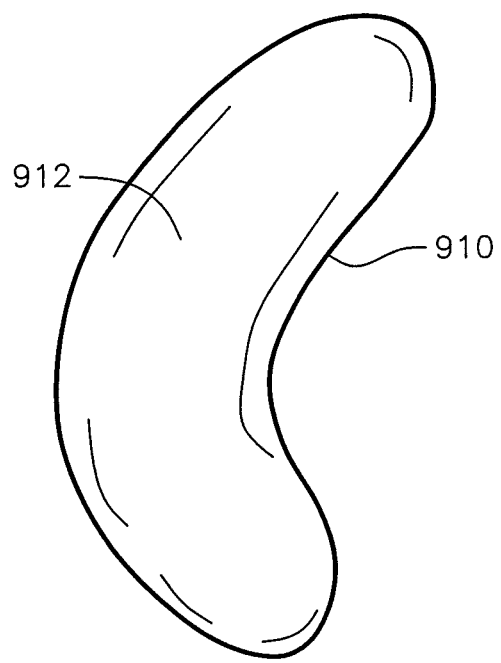
Figure 69D:
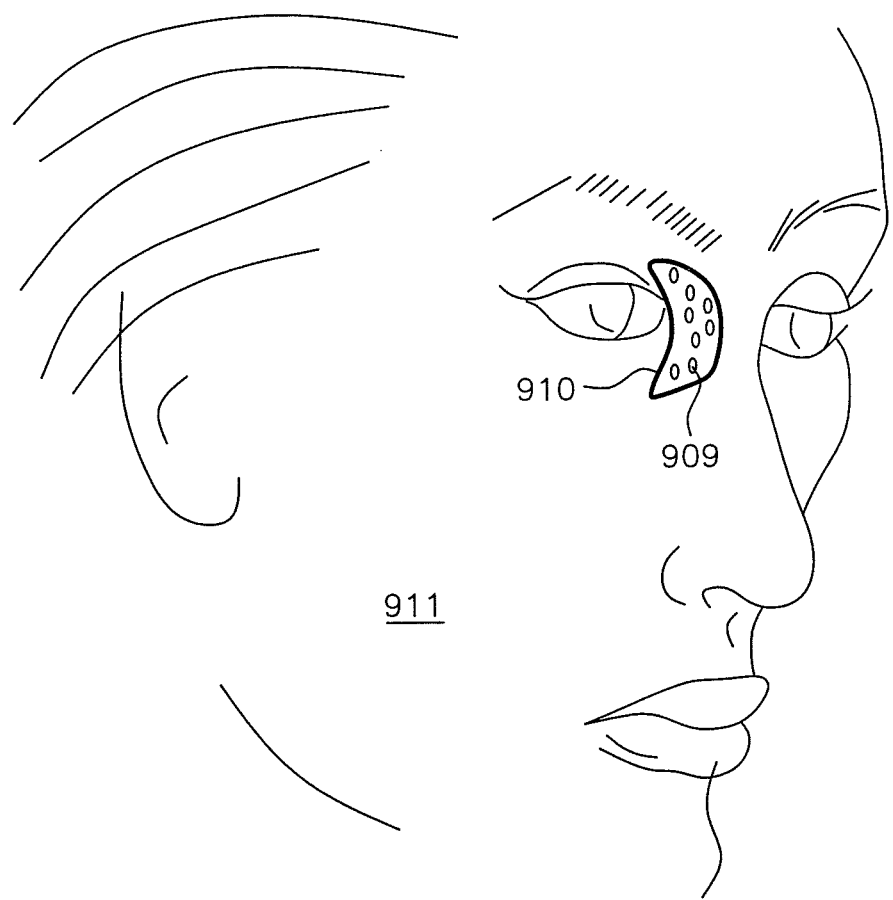
FIG. 69D is a perspective view of a BTT thermal pack of FIG. 69A positioned on the BTT.

The brain cooling or brain heating device in accordance with the principles of the invention includes hot and cold pad or pack adapted to fit and match the special geometry of the entrance of the BTT and comprising a preferably flexible and sealed pad and a gel within said pad, with the surface touching the skin having a substantially convex shape. Accordingly, FIG. 69A is a perspective side view of BTT thermal pack 910 and bulging substantially convex part 906 which rests against the skin and conforms to the anatomy of the BTT. FIG. 69B is a perspective inferior view of BTT hot/cold pack 910 and bulging substantially convex part 906 which rests against the skin and conforms to the anatomy of the BTT. FIG. 69C is a perspective planar view of BTT hot/cold pack 910 and substantially flat part 912 which faces the outside and does not touch the skin. FIG. 69D is a perspective view of hot/cold pack 910 with gel 909 being applied to the BTT area of user 911.

A tube fit to match the special geometry of the BTT site and anatomy of the region with circulating water can also be use for selectively cooling or heating the brain.

The BTT thermal pack can include a bag so as to avoid direct contact with the skin depending on the chemical compound used, such as heating agent to prevent any thermal injury to the skin.

It is understood that a combination temperature sensor and BTT cold/heat pack can be implemented and positioned in place using the support structures described herein such as eyeglasses and any head mounted gear. The nose pads of eyeglasses can have a combination of a heat flow sensor to determine how fast heat is being pulled. The gradient for instance across a thin piece of Mylar indicates the direction of heat flow. It is also understood that the right nose pad of the eyeglasses have a temperature sensor and the left side has the cooling/heating device that applies or removes heat according to the temperature measured on the opposite side.

It is also understood that many variations are evident to one of ordinary skill in the art and are within the scope of the invention. For instance, one can place a sensor on the skin at the BTT site and subsequently place an adhesive tape on top of said sensor to secure the sensor in position at the BTT site. Thus in this embodiment the sensor does not need to have an adhesive surface nor a support structure permanently connected to said sensor.

Figure 70:
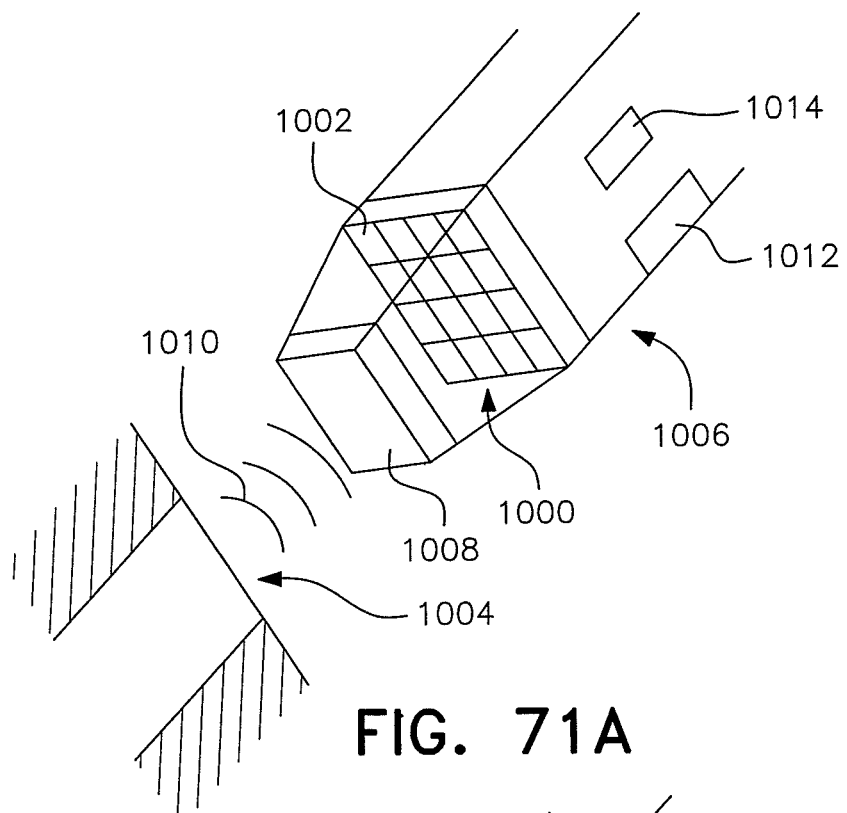
FIG. 70 is a schematic diagram showing a hand held noncontact BTT measuring device.
Figure 71A:
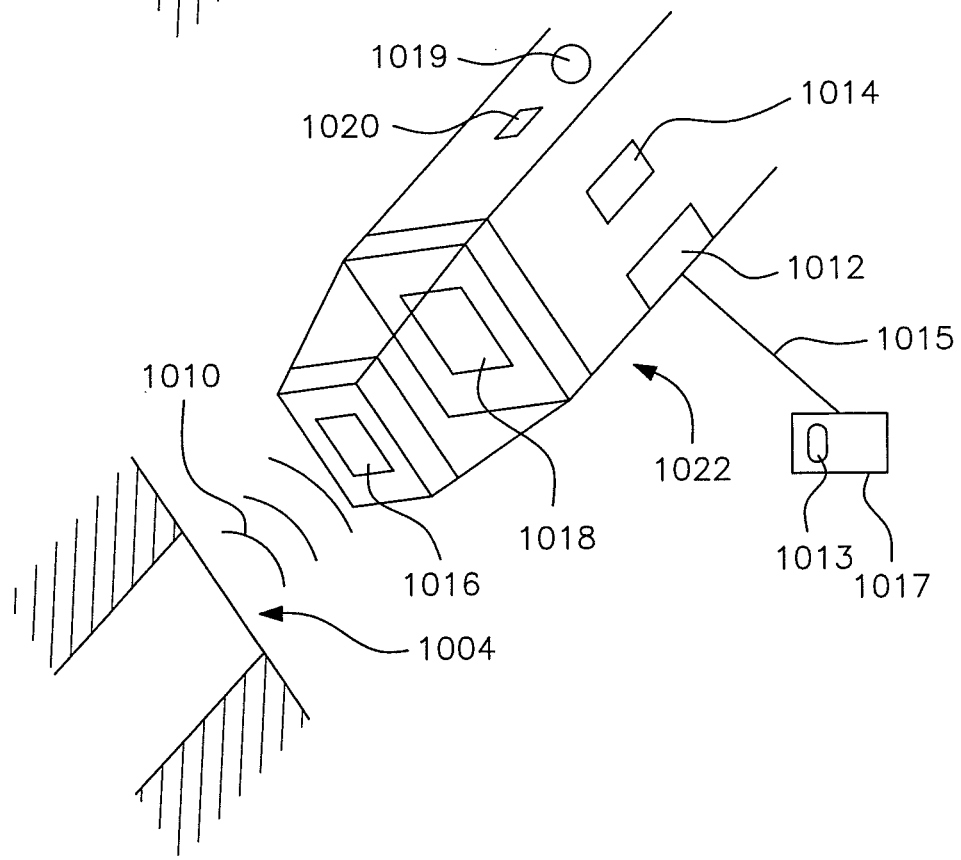
FIGS. 71A to 71C are schematic diagrams showing hand held infrared BTT measuring devices.
Figure 71B:
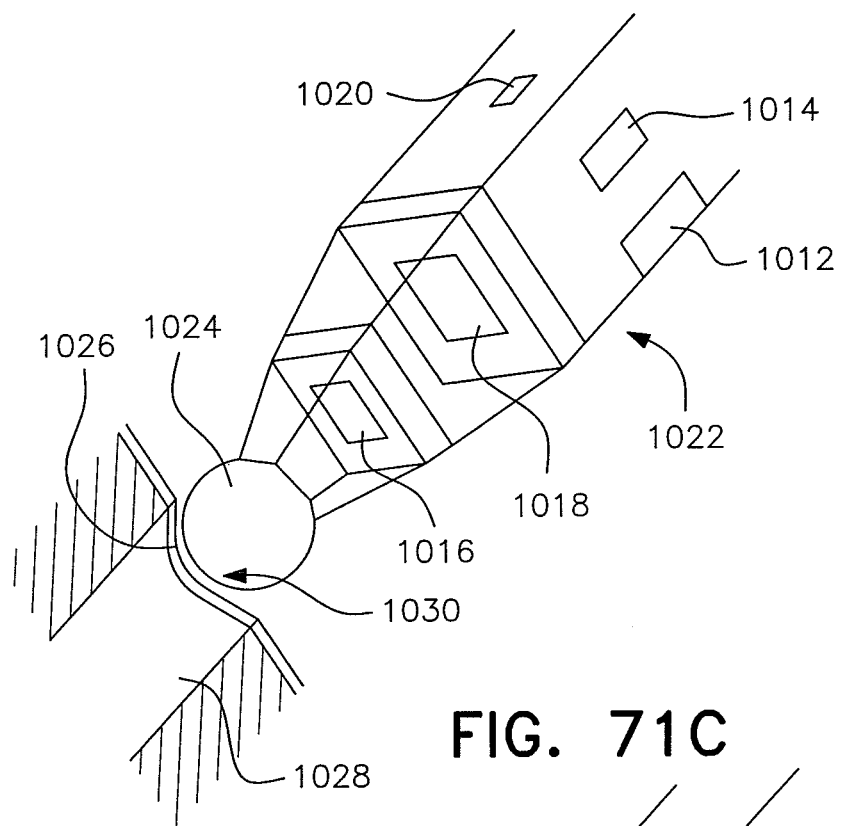

A plurality of hand held devices with non-contact or contact sensors can measure the brain temperature at the BTT for single or continuous measurement and are referred to herein as Brain Thermometers or BrainTemp devices. Accordingly, FIG. 70 shows an array 1000 of infrared sensors 1002 viewing the BTT entrance 1004 which are mounted in a housing 1006 containing a lens 1008 to focus the radiation 1010 on sensor array 1000 in a manner such as that the sensor array 1000 views only the skin at the entrance of the BTT 1004 and a microprocessor 1012 adapted to select the highest temperature value read by an infrared sensor 1002 in the array 1000 with the highest value being displayed on display 1014. Exemplary infrared sensors for the array 1000 include thermopile, thermocouples, pyroelectric sensors, and the like. Processor 1012 processes the signal and displays in display 1014 the highest temperature value measured by the sensor 1002 in the array 1000. FIG. 71A shows another embodiment comprising of a non-contact measuring system that includes a housing 1022 containing a single infrared sensor 1018 (e.g., thermopile), a lens 1016 to focus the radiation 1010 of the BTT area 1004 into the sensor 1018, a transmitter 1019, and an ambient temperature sensor 1020 used to adjust the temperature reading according to the ambient temperature, and processing 1012 and display means 1014 to process the signal and display a temperature value in addition to wire 1015 connected to an external module 1017 with said module including a processor 1013 adapted to further process the signal such as processing spectroscopic measurements, chemical measurements, and temperature measurements with said module 1017 adapted yet to display and transmit the value calculated by processor 1013 including wireless transmission and transmission over a distributed computer network such as the internet. An alternative for the pen-like systems in accordance with the invention and in accordance to FIG. 71A, as shown in FIG. 71B, includes a bulging part 1024 with a substantially convex shape at the end 1030 that touches the skin 1026 and matches the concave anatomy of the skin 1026 entrance of the BTT 1028. The bulging convex end 1024 touching the skin 1026 helps to stretch the skin 1026 and allow better emissivity of radiation in certain skin conditions, allowing the system to measure temperature in the skin of the BTT area at optimal conditions and with any type of skin.

An exemplary lens system for viewing thermal radiation coming from the BTT can include exemplarily 25 sensors for reading at 1 inch from the tip of the sensor to the skin at the BTT entrance and 100 sensor array for reading radiation coming from a distance of 3 inches between skin at the BTT and sensor tip. Preferably a five degree field of view, and most preferably a two to three degree field of view, and yet even a one degree of field view is used to see the main entry point of the BTT. The spot size (view area) of the infrared sensor is preferably between 1 and 20 mm in diameter and most preferably between 3 and 15 mm in diameter which allows the infrared sensor to receive radiation from the BTT entrance area when said sensor is aimed at the BTT entrance area which corresponds to the bright spots in FIG. 1A and the red-yellow area in FIG. 1B. It is understood that an infrared device (thermopile) can be placed at any distance and read the temperature of the BTT entrance area, as long as the sensor is positioned in a manner to view the BTT entrance area and a lens is used focus the radiation on to the temperature sensor.

Figure 73:
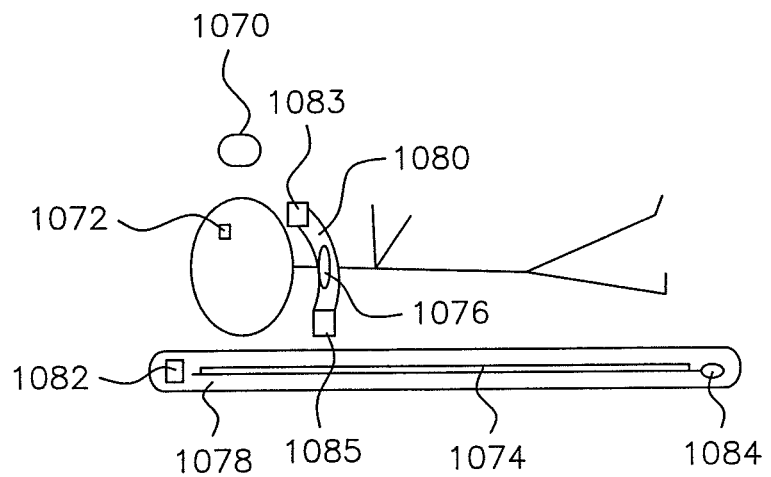
FIG. 73 is a schematic diagram showing heat transfer devices coupled to BTT measuring devices.

The array is adapted to receive the temperature of the BTT area. The temperature signal received is less than the whole face and is not the temperature of the face, nor the temperature of the forehead. The temperature signal comes from the BTT, one particular area of special geometry around the medial corner of the eye and medial aspect of the upper eyelid below the eyebrow. This said temperature signal from the BTT can be acquired by contact sensors (e.g., thermistors), non contact sensors (e.g., thermopile), and infrared thermal imaging. This said temperature signal can be fed into a processor to act upon an article of manufacturing that can remove or transfer heat as shown in FIG. 73. With said article being activated by the temperature level measured at the BTT by a hand held single measuring device, a continuous temperature measuring device, and any of the devices of the present invention. In addition, the temperature level signal can activate another device and activate a function of said device. The temperature level measured by the hand held devices can be automatically transmitted by wireless or wired transmission means to a receiver.

Figure 71C:
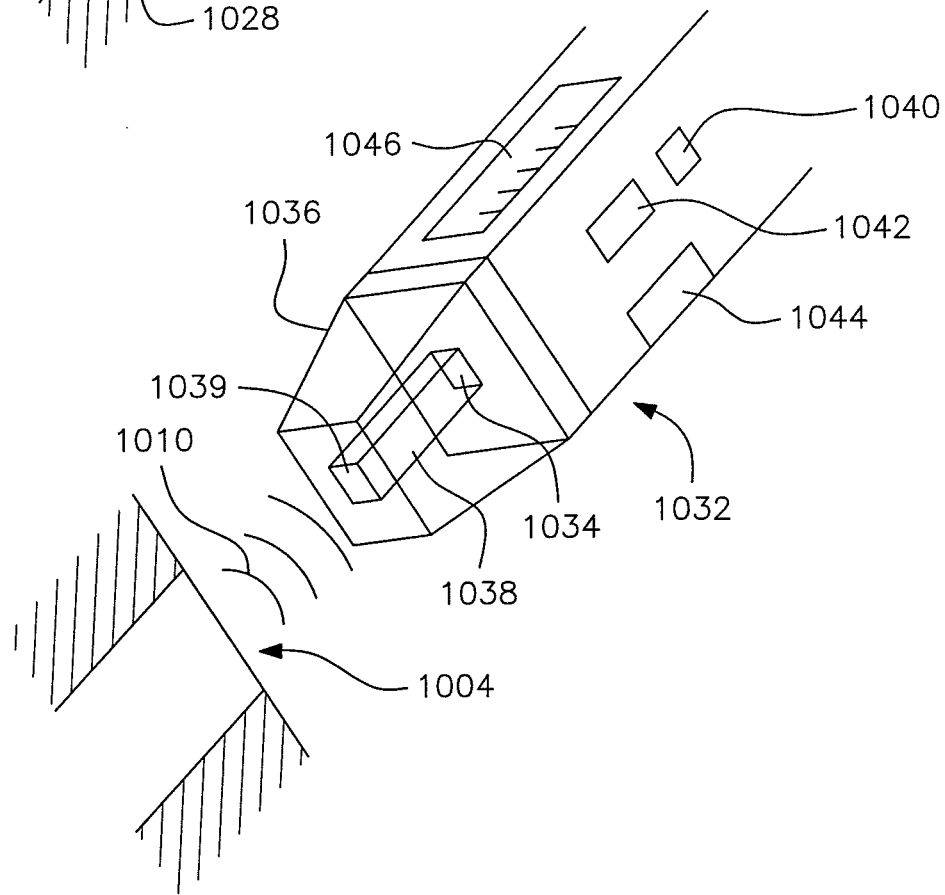

FIG. 71C shows another embodiment comprising a non-contact measuring system that includes a housing 1032 containing a single infrared sensor 1034 (e.g., thermopile), a columnar extension 1036 housing a window 1039 and cavity 1038 to focus the radiation 1010 of the BTT area 1004 into the sensor 1034 which is located about 3 cm from the window 1039 of columnar extension 1036 in addition to an amplifier 1040, processing device 1042 and display device 1044 to process the signal and display the temperature value. The columnar extension may have a widthwise dimension, either as a cylinder, rectangle, or square, of less than 3 mm, preferably less than 2.5 mm and most preferably less than 2.0 mm.

A retractable ruler 1046 is mounted in the housing 1032 and the tip of said ruler can rest on the face and used for assuring proper distance and direction of the housing in relation to the BTT for optimal view of the BTT area. It is understood that any measuring and positioning means for optimizing view of the BTT by the sensor can be used and are within the scope of the present invention. It is understood that any positioning device to establish a fixed relationship between the sensor and BTT are within the scope of the invention.

Figure 72:
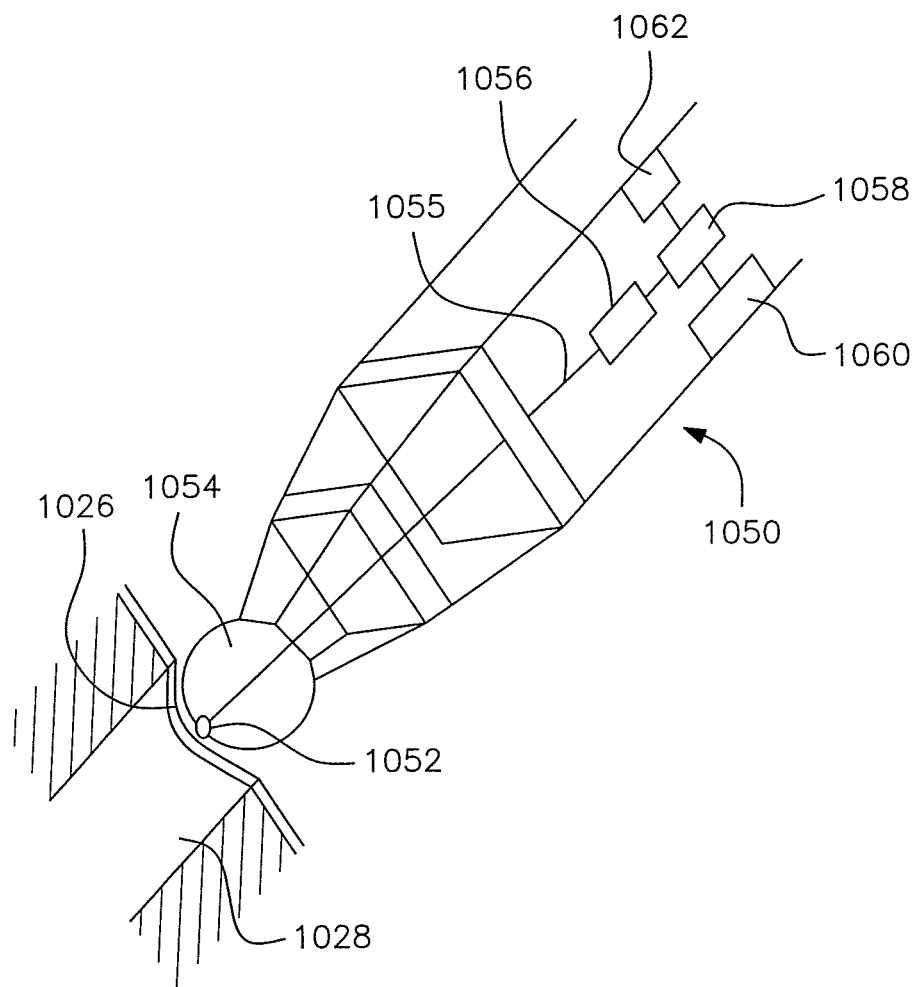
FIG. 72 is a schematic diagram showing a hand held contact sensor measuring device.

FIG. 72 is a schematic view of another embodiment preferably used as a single measurement by touching the skin at the BTT with a contact temperature sensor. Accordingly, FIG. 72 shows a pen-like housing 1050 with a sensor 1052 (e.g., thermistor) encapsulated by an insulating tip 1054 with a substantially convex external shape to conform to the BTT area and further including wire 1055 connecting sensor 1052 to processor 1056, which is in electrical connection to LCD display 1058, LED 1060, and piezoelectric device 1062. In use the sensor 1052 touches the skin at the BTT entrance area 1004 generating a voltage corresponding to the temperature, which is fed into the processor 1056 which in turn activates LED 1060 and device 1062 when the highest temperature over the time of measurement is achieved, and subsequently displays the temperature in display. The sensor 1052 and encapsulating tip 1054 can be covered by the disposable cap with a convex external surface that conforms to the convex tip 1054.

The temperature signal from sensor 1052 can be converted to an audio signal emitted by the piezoelectric device 1062 with said audio frequency proportional to the temperature level measured. In addition processor 1056 in the housing 1050 is adapted to lock in the highest frequency audio signal (which represents the highest temperature) while the user scans the BTT area. Furthermore, LED 1060 in the housing 1050 can be activated when the highest temperature level is reached, and then the value is displayed in display 1058.

It is understood that any article of manufacture that transfers heat or removes heat from the body in a direct or indirect fashion can be used in accordance with the principles of the invention. Accordingly FIG. 73 shows other exemplary embodiments including a sensing device represented by a non-contact sensing device 1070 such a thermopile housed in a hand held device or a contact sensing device 1072 such as a thermistor housed in a patch measuring temperature in the BTT area which are coupled by wires or wireless transmission means shown previously to an article of manufacture such as mattress 1078 or a collar 1080 which can alter its own temperature or the temperature in the vicinity of said articles 1078 and 1080. Exemplary embodiments include a mattress 1078 which is adapted by electrical means to change its temperature in accordance with the signal received from the temperature sensor 1070 and 1072 measuring temperature in the BTT area and an article around the neck such as a collar 1080. Articles 1078 and 1080 are provided with a serpentine tube 1074 and 1076 respectively, which run cold or hot water for removing or delivering heat to the body by mattress 1078 or to the neck and head by collar 1080, with said water system of mattress 1078 having a valve 1082 and of collar 1080 having valve 1083 which is controlled by a processor 1084 and 1085 respectively. Processor 1084 of mattress 1078 and processor 1085 of collar 1080 are adapted to open or close the valve 1082 or 1083 based on the temperature level at the BTT measured by sensor 1070 and 1072. The signal of the temperature sensor 1070 and 1072 controls the valves 1082 and 1083 that will open to allow cold fluid to fill a mattress when the signal from the sensor 1070 or 1072 indicates high body temperature (e.g., temperature equal or higher than 100.5 degrees Fahrenheit). Likewise, when the signal from the sensor 1070 or 1072 indicates low body temperature (e.g., temperature lower than 96.8 degrees Fahrenheit) the signal from said sensors 1070 and 1072 opens the valve 1082 and 1083 that allows warm fluid to fill the mattress 1078 and collar 1080. It is understood that any garment, gear, clothing, helmets, head mounted gear, eyewear, hats, and the like can function as an article of manufacture in which heat is removed or transferred to achieve thermal comfort of the wearer based on the temperature of the BTT area. It is also understood that any sensor, contact (e.g., thermistor) or non-contact (e.g., thermopile or thermal image sensing system), measuring temperature at the BTT can be used to control an article of manufacture removing or transferring heat to a body or physical matter. It is further understood that the article of manufacturing includes infusion lines capable of delivering warm or cold fluid into a vein of a patient in accordance with the temperature at the skin around the medial corner of the eye and eyelid, which corresponds to the entrance of the BTT. Other exemplary articles of manufacture include shoes, floor with heating or cooling systems, electrical draping, in-line fluid warmers, and the like.

In the embodiment in which a contact sensor touching the skin is used, the probe head can be covered with a disposable cap, such as a piece of polymer preferably with good thermal conductivity, with the shape of the disposable cap to match the shape of the various probes in accordance with the principles and disclosure of the present invention.

In addition to measuring, storing, and transmitting biological parameters, the various apparatus of the present invention such as patches, eyewear, rings, contact lens, and the like include an identification and historical record acquisition and storage device for storing the user's identification and historical data preferably using a programmable rewritable electronic module in which data can be changed, added, or deleted from the module. The identification and historical data alone or in conjunction with the biological data (such as brain temperature and chemical measurements as glucose level and presence of antibodies) are transmitted preferably by wireless transmission to a monitoring station. Accordingly FIG. 74 shows a schematic view of the apparatus and system for biological monitoring, identification, and historical data used by an animal. It is understood that the system disclosed is applicable to humans as well as animals.

FIG. 74 is the schematic of a preferred embodiment for four legged creatures showing an exemplary comprehensive system that includes: an eye ring transmitter device 1501 with said eye loop or eye ring 1501 preferably including antenna 1500, sensor 1502, microprocessing, transmitting and memory module 1504, and power source 1503 with said ring placed on the eye preferably in the periphery of the eye in the eyelid pocket 1516; a collar 1520 with said collar 1520 preferably containing power source 1506, microprocessing, transmitting, and memory module 1508, and GPS transmission system 1510 coupled by wireless waves 1512 to orbiting satellites 1514 and module 1508 in bidirectional communication by wireless waves 1522 to module 1504 of ring 1501 to power ring 1501 and collect data from ring 1501 with said module 1508 in communication by radio waves 1511 to external radio receiving station 1509 and receiving antenna 1513; an externally placed receiver 1518 and antenna 1519 which receives the signal from module 1504 of ring 1501; and an external antenna 1524 located for instance in a feed lot connected to computer 1526 with said antenna 1524 in bidirectional communication with module 1504 of ring 1501.

Each eye ring 1501 has a unique serial number permanently or temporarily embedded to identify the animal remotely. A 24 hour temperature log is sent at each transmission, most preferably 6-12 times per day. A unique one-way statistical broadcast network architecture allows all members of the herd to share one frequency and one set of data receivers. The receiver is designed to receive temperature telemetry data from a network of livestock eye ring telemetry units and forward it to a collection computer for storage, display, and monitoring.

Although various communication and power systems are shown in FIG. 74, it is understood that the system can work with only one apparatus, for instance ring 1501 sending a signal to receiver 1518 and antenna 1519 for further processing and display, or preferably ring 1501 transmitting data to module 1508 of collar 1520 which working as a booster radio transmitter transmits the signal to antenna 1513 and remote station 1509 for processing, monitoring, and displaying the data.

It is understood that besides an active system with a battery working as the power source, a passive system in which the ring 1501 is powered by an external source such as electromagnetic induction provided by collar 1520 or antenna 1524 can be used. It is further understood that a hybrid system that includes both a power source comprised of battery 1503 and a passive system in module 1504 can be used in which module 1504 contains an antenna for receiving electromagnetic energy from module 1508 of collar 1520. In this embodiment the active part of the system using the memory in module 1504 powered by battery 1503 collects data from a sensor 1502 (e.g., thermistor) and stores the data in a memory chip in module 1504. The passive system containing antenna in module 1504 can be also activated when the four legged creature passes by a coupling antenna 1524, such as for instance an antenna placed in feed lots. After there is a coupling between the passive system 1504 in the ring 1501 and the external antenna 1524 in the feedlot, the data stored in the memory chip of module 1504 of the ring 1501 is received by the external antenna 1524 and transferred to a second memory chip 1523 that is part of the module external antenna 1524. The processor of module 1504 in the ring 1501 is adapted to transfer the stored data any time that there is a coupling with the external antenna 1524. A variety of inductive coupling schemes previously mentioned can be used for powering and collecting data from eye ring 1501 by antenna 1523 and 1509.

The data from a plurality of mammals (e.g., cattle) is transmitted to a receiving system. Preferably only one animal transmits at a specific time (equivalent to having only one animal in the system) to avoid data collisions in the form of interference that prevents successful wireless transmission of the biological parameters. Two exemplary schemes can be used, polling and broadcast. The polling approach requires each animal to be equipped with a receiver which receives an individual serial number request for data from a central location and triggers that animal's transmitter to send the data log. The other approach is a broadcast system, whereby each animal independently broadcasts its data log. The problem is to avoid collisions, that is, more than one animal transmitting at a time, which could prevent successful data transfer. Each animal transmitter will preferably transmit at a certain time and the receiver is adapted to receive the signal from each animal at a time.

The ring 1501 can yet include a solar battery arranged to capture sun light, digital transmission 16 bit ID# to identify the animal and track the animal throughout life. Preferred dimensions for outer diameter of ring 1501 for use in livestock are between 40 and 45 mm, preferably between 35 and 40 mm, and most preferably between 30 and 35 mm or less than 30 mm. For large animals such as an elephant, such as to detect moment of ovulation for artificial insemination and birth in captivity, the preferred outer diameter is between 90 and 100 mm, preferably between 75 and 90 mm, and most preferably between 50 and 75 mm or less than 50 mm. Preferred largest dimension of ring including circuit board and battery for livestock is between 15 and 20 mm, preferably between 10 and 15 mm, and most preferably less than 10 mm, and for large animals a factor of 10 to 15 mm is added to achieve optimal dimensions. The preferred height of the ring 1501 for livestock is between 9 and 12 mm, preferably 6 and 9 mm, and most preferably less than 5 mm, and for large animals a factor of 5 mm is added to achieve optimal dimensions. The preferred embodiment includes hardware disposed in one quadrant of the ring which contains the sensor and is located in the inferior eyelid pocket.

An alarm is activated when certain pre-set temperature limits are reached. The system of the invention can also be used with temperature being transmitted in real time for detecting the moment of heat in animals, which starts when the body temperature of the animal starts to rise. The method includes detection of heat, and then inseminating the animals preferably between 6 to 12 hours after initial detection of heat, and most preferably between 4 and 8 hours after heat detection.

Figure 75A:
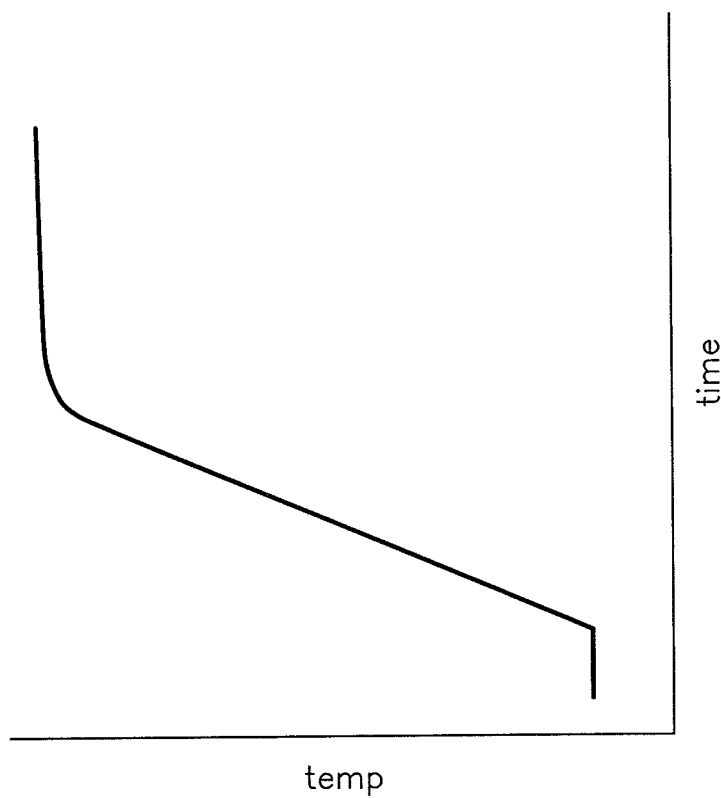
FIGS. 75A to 75E are graphs showing thermal signatures.
Figure 75B:
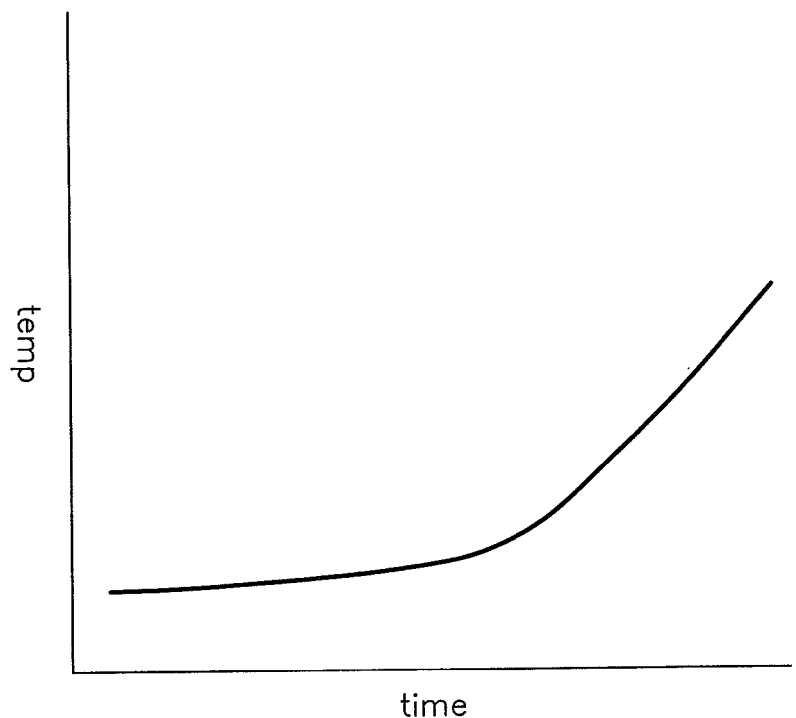
Figure 75C:
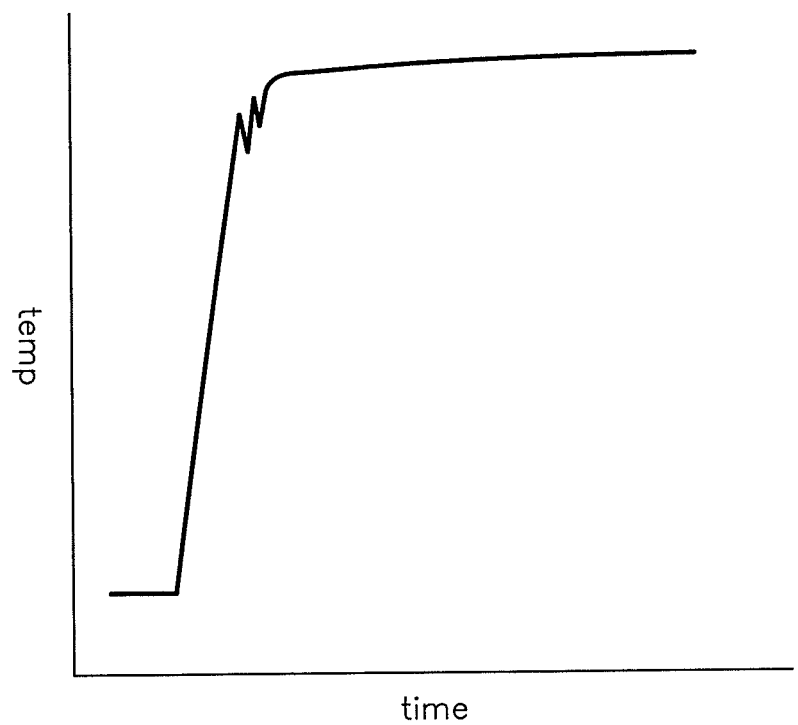
Figure 75D:
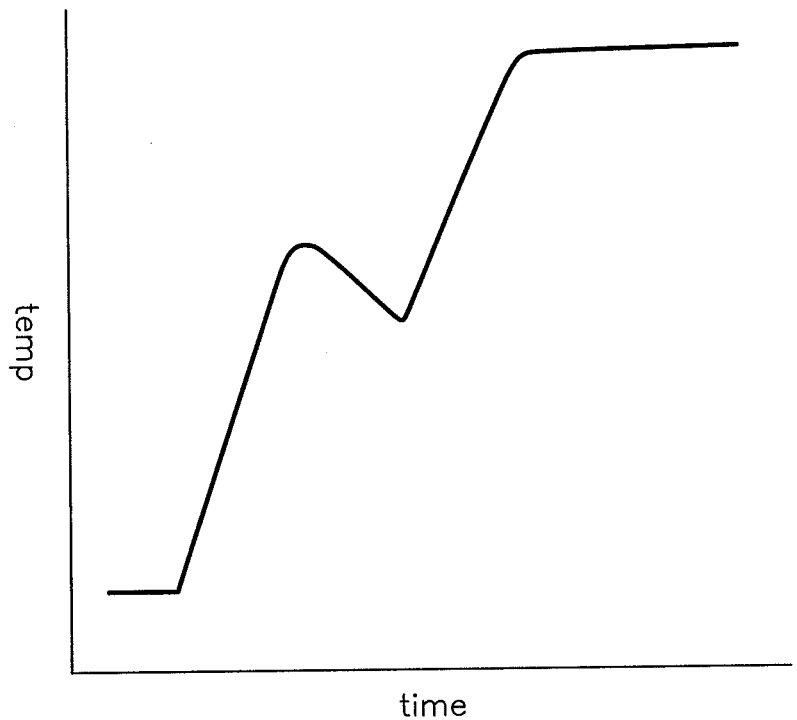
Figure 75E:
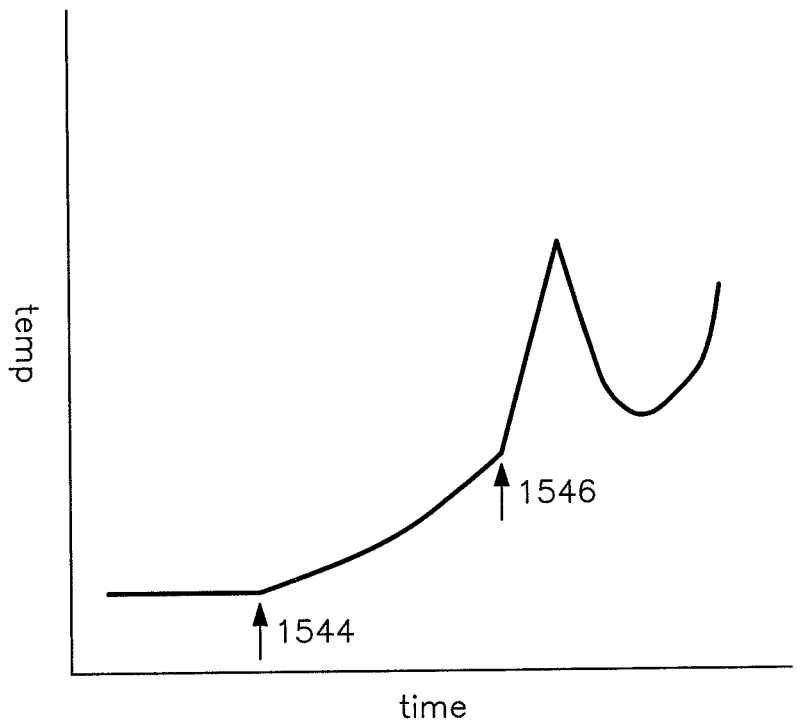

Preferably the temperature data stored over time (e.g., 24 hours) by module 1504 or 1508 is then downloaded to a computer system such as computer 1526 adapted to identify thermal signatures. Thermal signatures are representations of the temperature changes occurring over time and that reflect a particular biological condition. Exemplary thermal signatures are depicted in FIGS. 75A to 75E. FIG. 75A is a representation of a viral infection in which there is a relatively rapid increase in temperature, in this example there is a high temperature which corresponds to a pox virus infection such as foot and mouth disease. On the other hand a slow increase in temperature over 6 to 8 hours can indicate a thermal signature for hyperthermia due to hot weather, as shown in FIG. 75B. FIG. 75C shows a rapid increase in temperature reflecting bacterial infection, with spikes followed by sustained high temperature. FIG. 75D shows a thermal signature reflecting mastitis with a double hump in which there is an initial increase in temperature followed by a higher increase after the first episode. FIG. 75E shows a thermal signature indicating heat (arrow 1544) of animals, in which there is a gradual but progressive increase of the basal temperature. About 8 to 12 hours from beginning of heat there is a further increase in temperature indicating the moment of ovulation (arrow 1546), with a further sustained increase in temperature in the post-ovulation period. It is understood that a digital library of thermal signatures can be stored and used to identify the type of biological condition present based on the signal received from the ring or any other sensor measuring temperature at the BTT, for both humans and animals. The thermal signature acquired by the temperature measuring system is matched by a processing system to a thermal signature stored in the memory of a computer and associated software for matching and recognition of said thermal signatures. It is understood that the thermal signatures system of the present invention includes any temperature measuring system for both animals or humans in which a temperature disturbance is present, low or high temperature.

Figure 76A:
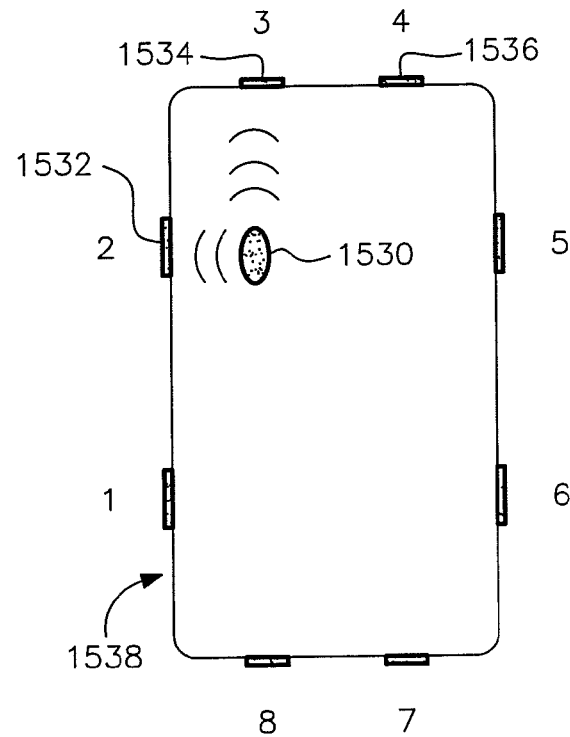
FIGS. 76A and 76B are schematic diagrams showing an antenna arrangement.
Figure 76B:
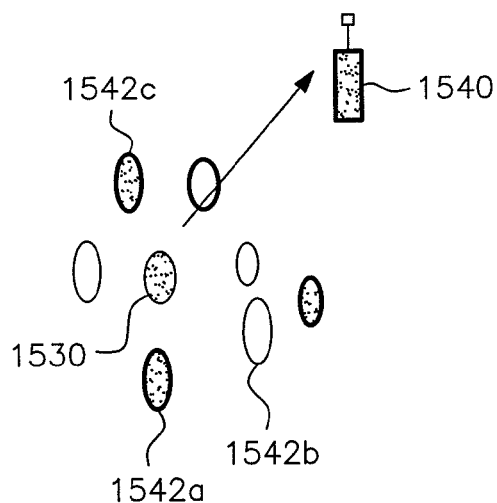

A plurality of antenna reception scheme can be used. FIG. 76A shows an exemplary antenna schemes arrangement 1538 including 8 antennas numbered 1 to 8 in a pen which can be used to cover a herd of 1000 to 2000 animals. At a particular time T1 animal 1530 transmits the data which is captured by the closest antenna, for instance antenna 1532. For animal use and to preserve power the data can be stored for 24 hours and when the animal goes by one of the antennas at time T1 the data is downloaded. When there is fever or a change in biological parameter the transmitting ring transmits the data continuously. Otherwise the ring only transmits data once a day. The antenna scheme also can be used as a locator of the animal. The pen and antenna scheme is plotted in a computer screen and depicted on the screen, and by identifying the antennas receiving the signal the animal can be located with the location highlighted in the computer screen. In FIG. 76A antennas 1534 and 1532 are receiving the signal whereas antenna 1536 is not receiving the signal since antenna 1536 is distant from the animal. Therefore animal 1530 is located in the area covered by antenna 1532 and 1534. FIG. 76B shows the precise location using a radio receiver direction finder, in which a radio receiver 1540 is carried by a farmer or located in the vicinity of the area covered by antennas 1532 and 1534 which contains animal with fever 1530 as well as healthy animals 1542a, 1542b, 1542c. Since animal 1530 is the only one emitting signal continuously, radio receiver 1540 can precisely identify sick animal 1530 among healthy animals. The ID of animal 1530 is transmitted in conjunction with the biological data for further identification of animal 1530. Alternatively, a farmer uses an electromagnetic hand held external power switch next to the animal to activate the circuit in the eye ring 1501 in order to manually initiate transmission of data to a receiver for further processing. Any lost animal could also be located with the present invention and an animal which ran from the pen could be identified as not emitting a signal within the pen.

Although a multiple antenna scheme is shown in FIG. 76A, the preferred embodiment includes an antenna 1513 or alternatively antenna 1519, and a weatherproof metal cased receiver unit with radio receiver module, computer interface, and power source such as receiver 1509 or alternatively receiver 1518.

When using a rewritable or programmable identification serial number, the eye ring 1501 can be reused and a new serial identification number programmed and written for said eye loop or eye ring 1501.

Although a ring in the eyelid pocket is shown, it is understood that another method and device includes a temperature signal coming from the BTT of cattle external to the eye which is located in the anterior corner of the eye (corner of the eye in animals is located in the most frontal part of the eye) with said signal being captured by contact or non contact temperature sensors as well as thermal imaging.

The signal from eye ring 1501 can preferably automatically activate another device. By way of illustration, a sprinkler system can be adapted to be activated by a radio signal from eye ring 1501 with said sprinkler system spraying cold water and cooling off the animal when a high body temperature signal is transmitted by eye ring 1501.

A variety of diseases can be monitored and detected by the apparatus of the invention. By way of illustration, a characteristic increase in brain temperature can detect foot-and-mouth disease, babesiosis, botulism, rabies, brucellosis, and any other disorder characterized by changes in temperature as well as detection of disorders by chemical and physical evaluation such as detection of prions in the eyelid or eye surface of an infected animal using antibodies against such prions and creating an identifiable label such as fluorescence or by generating a mechanical or electrical signal at the time of antigen-antibody interaction. Prions can cause bovine spongiform encephalopathy known also as "mad cow" disease and such prions can be present in the eye and can be detected by using an immobilized antibody contained in the eye ring against such prion or a product of such prion. By detecting mastitis (or an animal with fever) which is scheduled for milking, the present invention provides a method to prevent contaminating other animals being milked by generating a sequence for milking in which the animal with fever is milked last. This will avoid contaminating equipment with a sick animal and with said equipment being sequentially used in other healthy animals.

The present invention provides continuous monitoring of animals 24 hours a day from birth to slaughter with automatic analysis and detection of any disease that can cause a threat to human health or animal health, besides identification and location of the sick animal. Therefore with the present invention an animal with disease would not reach the consumer's table. The present invention therefore includes a method to increase food safety and to increase the value of the meat being consumed. The system of continuous disease monitoring is called DM24/7 (disease monitoring 24/7) and includes monitoring the biological variable 24 hours seven days a week from birth slaughter, feeding the information into a computer system and recording that information. Any meat coming from an animal monitored with DM24/7 receives a seal called "Monitored Meat". This seal implies that the animal was monitored throughout life for the presence of infectious diseases. Any user buying "Monitored Meat" can log on the internet, and after entering the number (ID) of the meat which can be found in the package of the meat being purchased. Said user can have access to the thermal life and biological monitoring of the animal and for the presence of fever or disease of the animal which the meat was derived from. The method and device includes a video stream associated with the ID of the animal with said video or pictures showing the farm and information on the farm where the animal came from or the meat pack facility where the animal was processed, providing therefore a complete set of information about the animal and conditions in which such animal was raised. Besides viewing over the internet, at a private location such as at home, the system may also provide information at the point of sale. Accordingly, whenever the user purchases the product and a bar code for the product for instance is scanned, a video or photos of the farm or the company packing the meat appear on a screen at the point of sale. This method can be used when purchasing any other product and preferably allows the consumer to use idle time in the cashier's station to become more familiar with the product purchased.

Preferably the ring has a temperature sensor covered by insulating material (eg. polyurethane) in one end and with an exposed surface at the other end. The preferred measuring method uses the measuring surface facing the outer part of the anatomy of the eye pocket and the insulating part facing the inner part of the eyelid pocket.

The eye ring contains memory means for storing on a permanent or temporary basis a unique identification number that identifies the animal being monitored. The ID code in the processor of the ring is transmitted to a receiver as an individual number only for identification and tracking purposes or associated with a temperature value or other biological variable value. The memory chip in the ring can also contain the life history of the animal and historical data including weight, vaccines, birth date, birth location, gender, diseases, genetic make up, and the like.

Range of the entrance of BTT area is about 30 square cm and the general main entry point is 25 square cm and encompasses the medial corner of the eye and the area of the eyelid adjacent to the eyelid margin. The correlation coefficient between temperature at the BTT area and the core temperature reflecting the thermal status of the brain is 0.9. Instead of using the whole face, the method for infrared or thermal imaging sensing as well as contact sensor includes a temperature signal which comes specifically from the BTT area, and the hottest spot in BTT area is then located and used as a source signal to activate another device or to deploy an action.

It is understood that an infrared thermal imaging camera can also be used and the point source emitting the highest amount of radiation from the entrance of the BTT is selected by the processor in the camera and the temperature level corresponding to the point source with highest thermal energy is displayed in the display. Exemplary infrared cameras include the BTT Thermoscan of the present invention.

The BTT Thermoscan of the present invention is adapted to view the entrance of the BTT around the medial corner of the eye, with the view of the sensor, by way of a lens, matching the entrance of the BTT area displayed in FIGS. 1A and 1B, and in FIGS. 3A to 9. Exemplary operational flow for measuring the temperature at the BTT with a thermal imaging system includes the first step of viewing the entrance of the BTT by radiation detector in the camera and a processor adapted to, after the first step, to search for the point source in the thermal image of the BTT with the highest emission of thermal radiation. In the following step the temperature of the point source in the thermal image of the BTT with the highest amount of radiation is calculated, with said calculated temperature value preferably displayed. In the next step, the calculated temperature value is transmitted by wire or wireless means to an article of manufacture that can remove heat or transfer heat to the body in a direct or indirect manner. In the following step, the temperature of the article of manufacture is adjusted in accordance with the signal received. Exemplary articles of manufacture that transfer or remove heat from the body in an indirect manner includes the air conditioner/heater systems of vehicles. Exemplary articles of manufacture that transfer or removes heat from the body in a direct manner includes vehicle seats. The measuring system in accordance with the present invention is adapted to seek for the hottest area around the corner of the eye and eyelid. Once the hottest spot around the medial corner of the eye and eyelid is found, a second step includes finding the hottest spot in the area identified in the first step, which means to find the hottest spot on the entrance of the BTT as shown in FIGS. 1A and 1B.

Figure 77A:
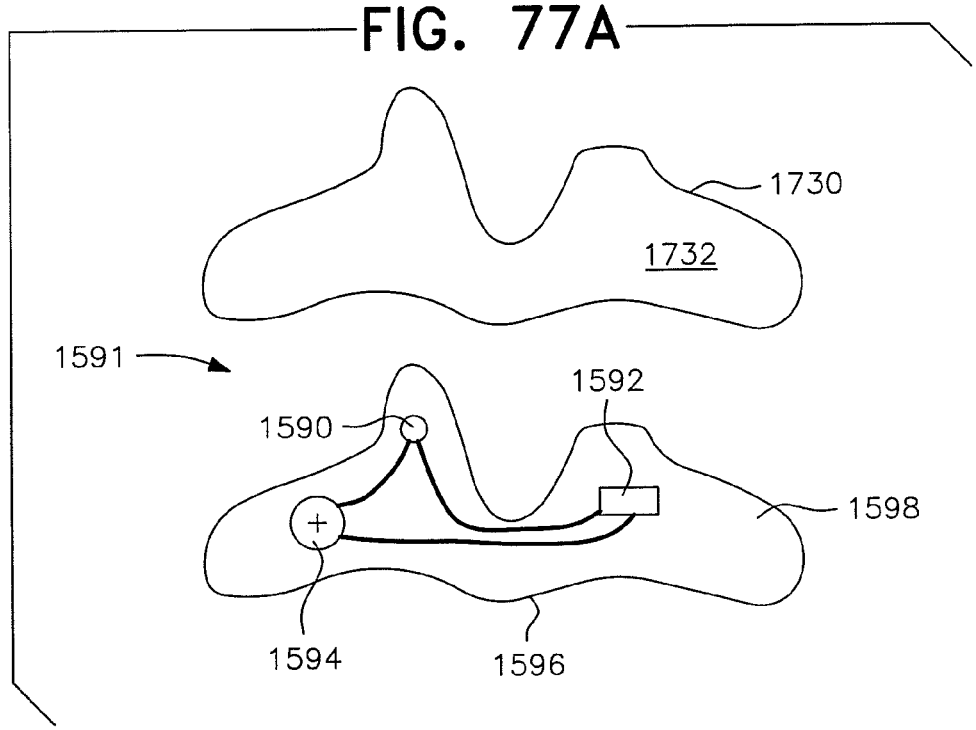
FIGS. 77A to 77C are schematic diagrams showing a support structure comprised of hook and loop fastener.
Figure 77B:
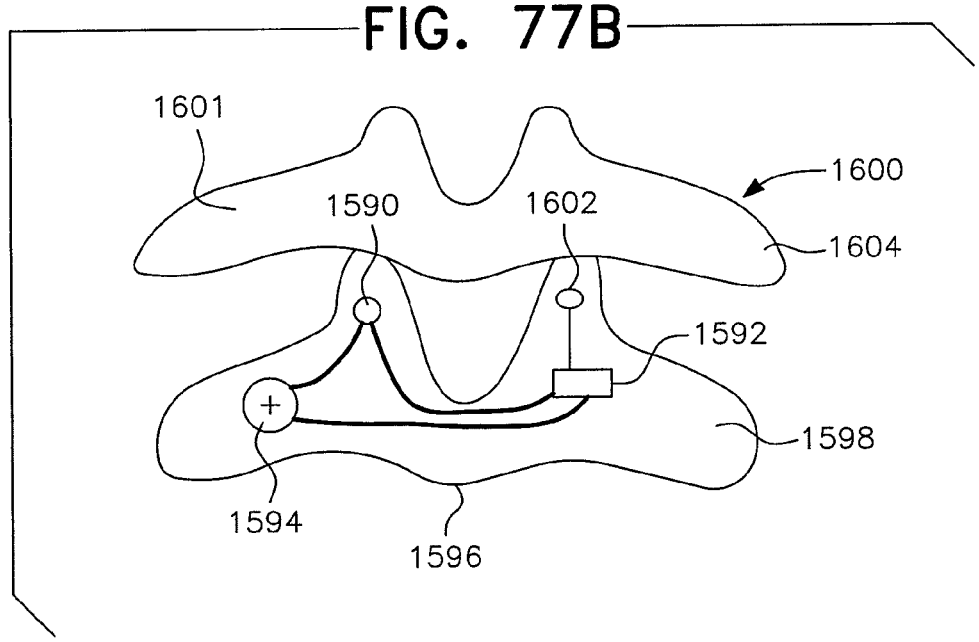
Figure 77C:
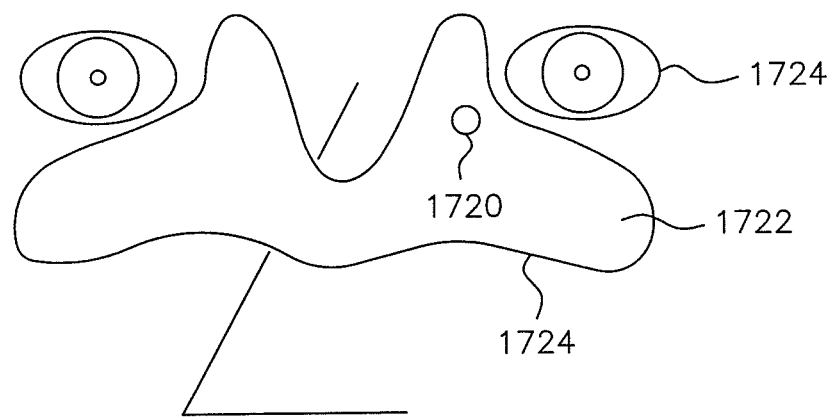

Now in accordance with another preferred embodiment of the present invention shown in FIG. 77A to 77C, an apparatus comprised of a patch for use in biological monitoring according to the invention comprises two parts: a durable part containing the sensor, electronics, and power source and a disposable part void of any hardware with said two parts durable and disposable being detachably coupled to each other preferably by a hook and loop fastener material (commercially available under the trade name VELCRO). Accordingly FIG. 77A is a schematic view showing a patch composed of two parts connected to each other by a hook and loop arrangement herein referred as VELCRO Patch with said VELCRO Patch 1591 including a disposable piece 1730 and durable piece 1596 with said durable piece 1596 housing and electrically connecting sensor 1590, power source 1594, and transmitter and processor module 1592 with VELCRO surface 1598 of durable piece 1596 detachably coupled to VELCRO surface of disposable piece 1730 and the external surface of said disposable piece 1730 covered by a liner 1732 which when peeled off exposes an adhesive surface which is applied to the skin. When in use the two parts 1730 and 1596 are connected and held in place by the hook and loop material, and liner 1732 is removed to expose the adhesive covering the external surface of disposable piece 1730 with said adhesive surface being applied to the skin in order to secure said VELCRO Patch 1591 to said skin with sensor 1590 resting adjacent to the entrance of the BTT to produce a signal representing by way of illustration the brain temperature. Although VELCRO hook and loop fastener was described as a preferred attachment between disposable and durable parts, it is understood that any other attachment device such as a disposable piece attached to a durable piece by means of glue, pins, and the like can be used or any other conventional fastening device.

FIG. 77B shows the two parts of a VELCRO Patch comprised of a disposable part 1600 which contains only VELCRO material and a durable part 1596 which contains sensor 1590, power source 1594, module 1592 which includes a transmitter, processor, piezoelectric piece, buzzer, and speaker, transmitter and processor module 1592, and LED 1602 electrically connected by wires contained in the VELCRO material with VELCRO surface 1598 of durable piece 1596 detachably coupled to VELCRO surface 1601 of disposable piece 1600 and the external surface of said disposable piece 1600 covered by a liner 1604 located on the opposite side of loop surface 1601 of disposable piece 1600 which when peeled off exposes an adhesive surface which is applied to the skin. Since the hardware housed in the durable part 1596 is relatively expensive said durable part 1596 with hardware is reusable while the disposable part 1600 can be made relatively inexpensively since it only comprises VELCRO loops and since said part is the part in contact with the skin said part 1600 may be disposed of after contacting the skin or when it is contaminated by body fluids. It is understood that the durable part can include a flexible plastic housing containing hardware and a disposable part comprised of a double coated adhesive tape. It is within the scope of the present invention to include a support structure such as a patch comprised of two parts in which a disposable part is in contact with the skin and a durable part housing hardware and electrical circuitry is not in contact with the skin. It is yet within the scope of the invention to include a support structure comprised of hook and loop material such as VELCRO comprised of two parts one disposable and durable part in which the disposable part is in contact with the skin and the durable part containing pieces in addition to the VELCRO material is durable and does not contact the skin. By way of illustration, but not by limitation, the durable part of the VELCRO can contain a spring load rod plate such as found in airway dilators (trade name BreatheRight for humans and Flair for animals) and the disposable part contains a release liner and adhesive surface which goes in contact with the skin of a human or animal. Another illustration includes a durable part housing a container with fluid or chemicals to be applied to the skin and disposable part which goes in contact with the skin by means of an adhesive surface or mechanical fasteners such as elastic bands. Yet another illustration includes a watch attached to a VELCRO material working as the durable part which contains, for instance, a sensing part for measuring glucose and a disposable part. Preferably the VELCRO part containing the hooks work as the durable part and houses pieces other than the VELCRO material while the Velcro part containing the loops work as the disposable part which preferably is in contact with the body part such as the skin.

When applied to the skin the VELCRO Patch works as one piece with durable and disposable parts connected by the hook and loop material and no hardware is visible on the surface of the durable part with the exception of a reporting device such as a LED to alert the user when the biological parameters are out of range. Accordingly FIG. 77C is a schematic view showing the VELCRO Patch of FIG. 77B, with said VELCRO Patch 1724 applied to the skin around the eyes 1726 and with an external surface of durable part 1722 containing LED 1720 which is activated by processor and driver module (not shown) housed in the durable part 1722 of VELCRO Patch 1724.

Figure 78:
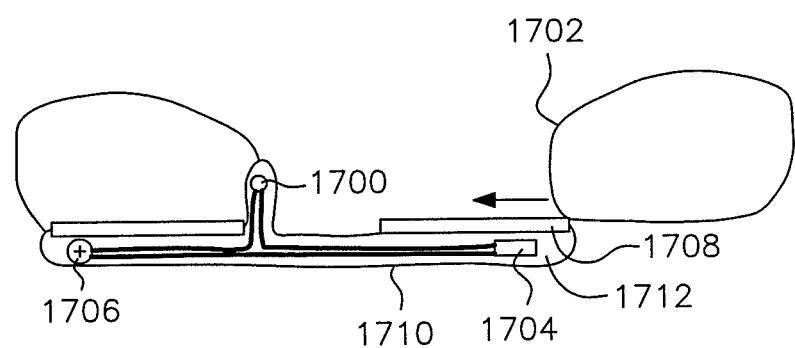
FIG. 78 is a schematic diagram showing a support structure comprised of hook and loop fastener with attached lenses.

VELCRO Patch of the present invention can further include attachment structure for attaching lenses to said VELCRO Patch, herein referred as VELCRO Eyewear. Accordingly FIG. 78 is a schematic view of VELCRO Eyewear 1710 comprised of the durable part 1712 which houses sensor 1700, power source 1706 and transmitter-processor module 1704 in addition to groove 1708 adapted to receive lens 1702 which can slide in and be secured at groove 1708. The groove mechanism of the invention allows for any type of lens to be used and replaced as needed. However it is understood that a permanent attachment of the lens 1702 to the VELCRO durable part 1712 can be used. It is also understood that the VELCRO material can be made in a way to conform to the anatomy of the face and that a variety of fastening devices previously described for attaching the lens can be used. The VELCRO Eyewear can yet have temples attached to its side for further securing to the face of the user. It is also understood that any sensor can be used including temperature, pressure, piezoelectric sensors for detecting pulse of a blood vessel, glucose sensor, and the like.

Figure 79A:
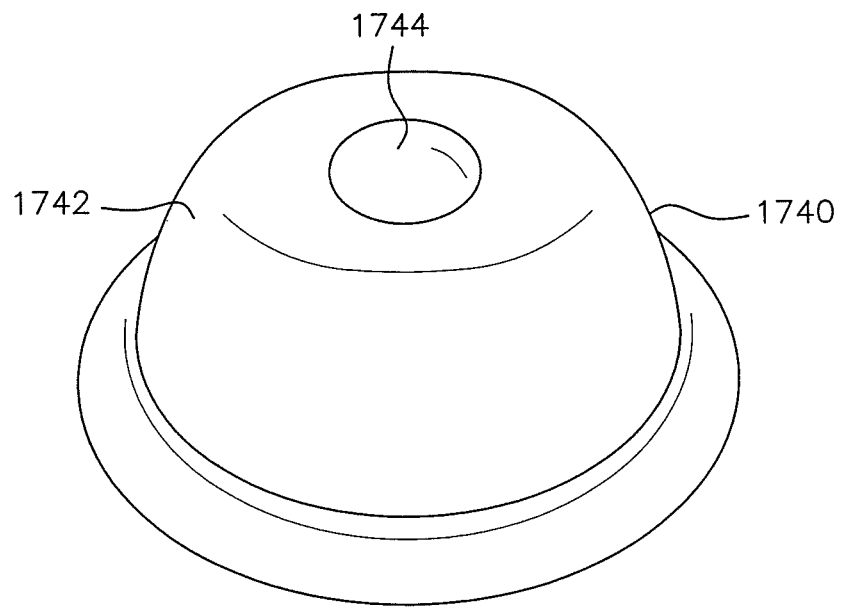
FIGS. 79A and 79B are perspective images of alternative support structures.
Figure 79B:
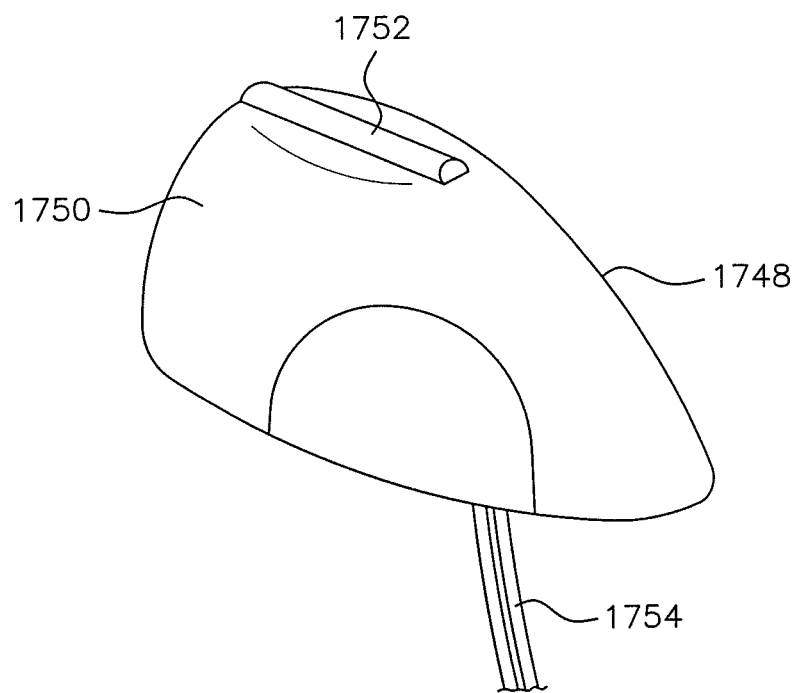

FIG. 79A is a perspective view showing another exemplary embodiment of a support structure 1740 comprised of a bowl-like structure with a substantially external convex surface 1742 to conform to the anatomy of the BTT entrance with said support structure 1740 housing sensor 1744 and electrical connection. FIG. 79B shows another embodiment of a support structure 1748 with a substantially convex outer surface 1750 to conform to the anatomy of the BTT with structure 1748 being also substantially elongated to match the geometry of the BTT entrance and further housing sensor 1752 and electrical connection 1754.

Figure 80:
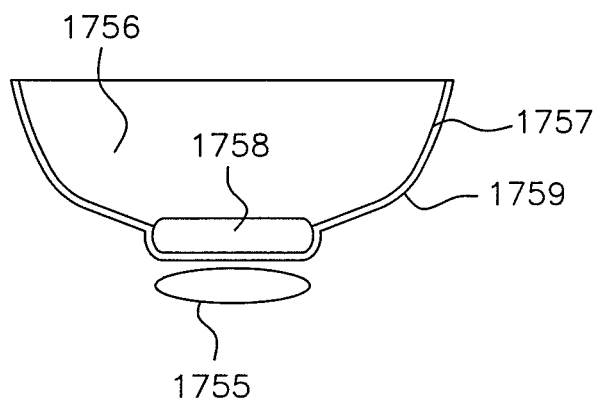
FIG. 80 is a schematic diagram showing a support structure of FIG. 79A.

FIG. 80 is a cross sectional diagram of a bowl shown in FIG. 79A including a holder 1756 in the shape of a bowl with an external convex surface 1757 and a sensor 1758 protruding through the surface of the bowl holder 1756 with said sensor being in close apposition to the skin 1759 at the BTT and its terminal blood vessel 1755.

Figure 81A:
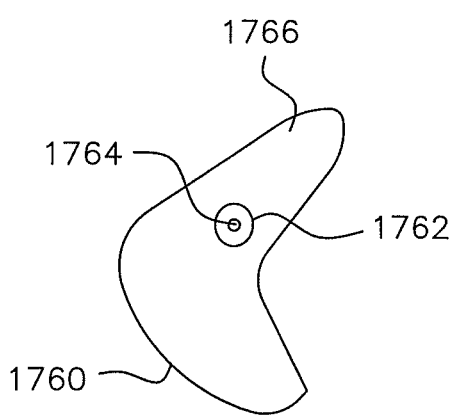
FIGS. 81A and 81D are schematic diagrams of a preferred support structure.
Figure 81B:
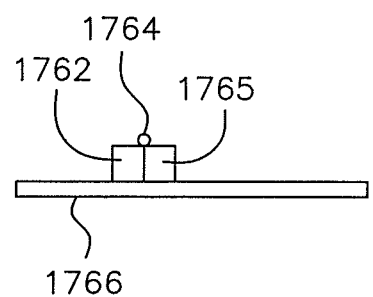
Figure 81C:
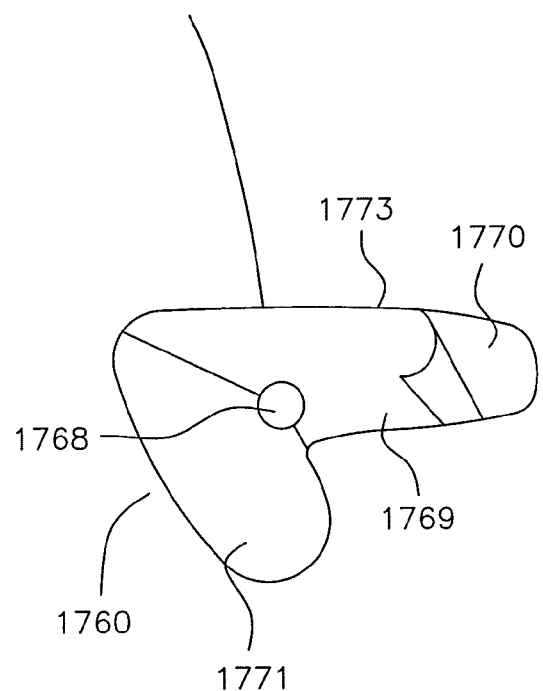
Figure 81D:
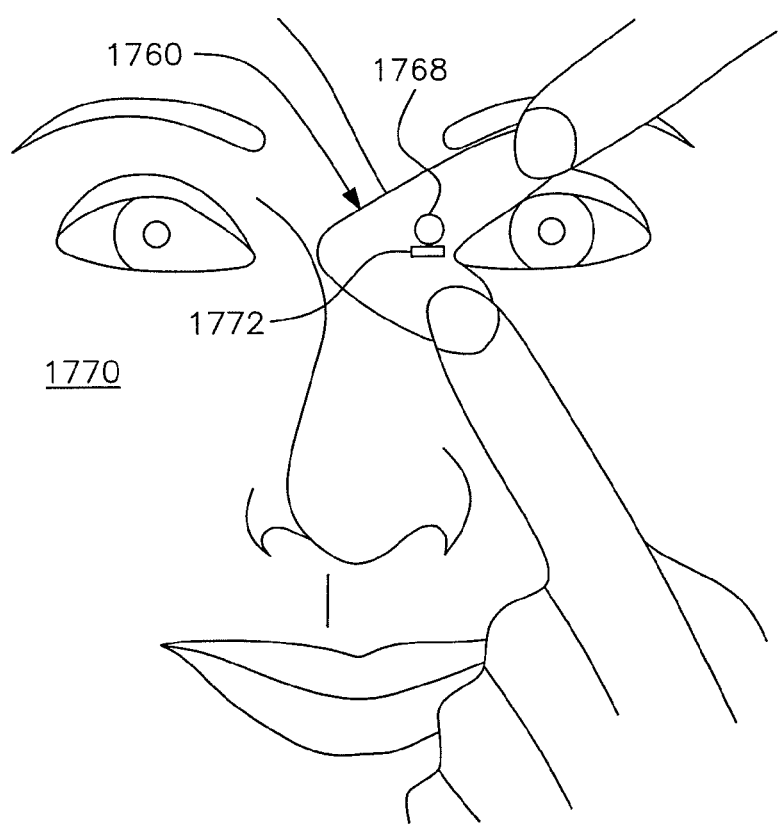

FIG. 81A is a schematic top view of another preferred embodiment for the support structure comprised of a boomerang or banana shape patch 1760 comprised of a thin insulating polyurethane layer 1766 housing a support structure 1762 which houses sensor 1764 with support structure 1762 having a different height than layer 1766 which makes sensor 1764 to protrude and be in higher position in relation to layer 1766. Surface of layer 1766 contains a pressure sensitive acrylic adhesive for securing said patch to the skin. FIG. 81B is a schematic side view of boomerang shape patch 1760 of FIG. 81A showing the different height between structure 1762, which houses sensor 1764 and wire 1765, and adhesive polyurethane layer 1766. The preferred height difference between the structures 1766 and 1762 is 5 mm, and preferably between 3 and 4 mm, and most preferably between 1 and 3 mm. FIG. 81C is a perspective view of patch 1760 with a release liner on the sensor area 1768 and a release liner 1773 comprised of two pieces, a superior piece 1769 and an inferior piece 1771. FIG. 81C shows the superior piece 1769 being peeled off to expose adhesive surface 1770. The release liner 1773 can comprise a single section or have a single or multiple slits to make a multiple section release liner. Suitable release liners for use with an adhesive layer are known in the art. According to this embodiment, when applying patch 1760 to the BTT area, sensor liner piece 1768 can be removed first and patch 1760 is then positioned with the sensor area aligned with the entrance of the BTT. Once the proper final position of the patch 1760 is determined, inferior piece liner 1771 is removed and patch 1760 applied to the nose area, and then superior piece liner 1769 can be removed and applied to the skin above the eyelid margin. FIG. 81D is a perspective view showing patch 1760 being applied to the skin of user 1770 with external markings on patch 1760 indicating sensor position 1768 and line 1772 for aligning with the corner of the eye. It is understood that the present invention includes a sensor arrangement within a support structure in which said sensor is located at a different height than the basic larger support structure comprising the patch.

Figure 82:
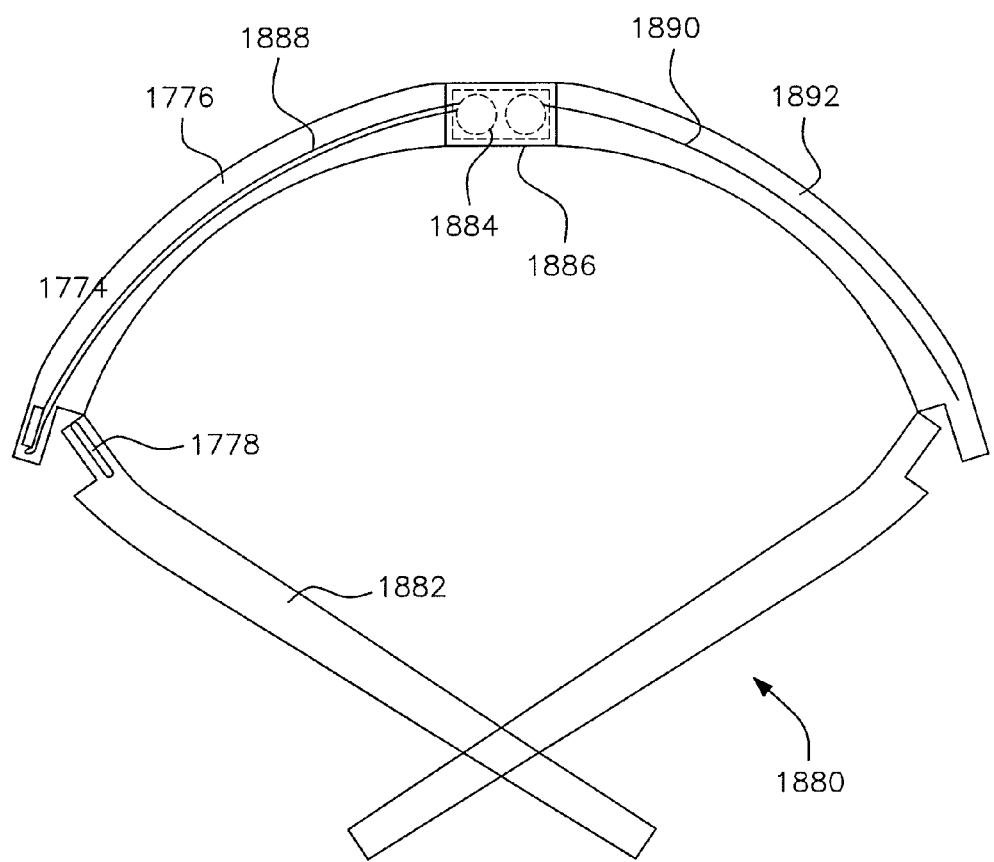
FIG. 82 is a schematic diagram showing electrical arrangement of a support structure comprised of eyewear.

FIG. 82 is a schematic top view of eyewear showing an exemplary electrical arrangement for support structure comprised of modified nose pads and frame of eyewear with said frame of eyewear 1880 including electromagnetic switch 1774 in left lens rim 1776 and magnetic rod 1778 in left temple 1882 for electrically turning the system on when in electrical contact, transmitter and power source module 1884 in nose bridge 1886 is electrically connected by wire 1888 in lens rim 1776 to switch 1774, and antenna 1890 in right lens rim 1892 connected to module 1884. When the temples are opened for using the eyewear an electrical connection is established between switch 1774 and magnetic rod 1778 which automatically activates the system. It is understood that a variety of spring mechanisms can be integrated into a shaft holding the sensors for better apposition of said sensors to the BTT area.

The present invention provides a method for optimizing fluid intake to achieve euhydration and avoid dehydration and overhydration. The present invention provides a continuous noninvasive core temperature monitoring, and when the temperature reaches certain pre-set levels such as increased temperature which reflects increased heat stored in the body, then by ingesting fluid the temperature can be lowered. Brain temperature reflects the hydration status and dehydration leads to an increase in the core (brain) temperature. The method in accordance with the present invention includes an algorithm for use in the situation of dehydrated, sedentary people exposed to heat (as illustrated by the excess mortality during heat waves), and people during physical activities. The invention showed that ingestion of 4 ounces of water every hour after body temperature reaches 100.4 degrees F. will lower the body temperature to 98.6 degrees F. and will keep the body temperature at lower than 99.5 degrees F. thus preventing the dangers of heat stroke. In case of athletes in athletic activities such as cycling, the invention showed that ingestion with fluid containing carbohydrates and minerals (e.g., trade name PowerAde of the Coca-Cola Company) can keep peak performance with ingestion of 6 to 8 ounces when the temperature at the BTT reaches 99.3 degrees Fahrenheit and performance is maintained with ingestion every 1 to 2 hours. A variety of algorithms for use in the situation of athletes at risk of overheating, can be created based on the principle of the invention. Special size containers for fluid or water can be used by an athlete who is aware of the fluid intake needed during a competition.

A method and algorithm to couple temperature (hypothermia) to nourishment (malnutrition) in elderly and in anorexia nervosa can be created, with the temperature level indicating malnutrition and further indicating what food to ingest to maintain adequate temperature. It is further understood that foods can be developed based on body temperature to achieve optimal nutritional value—fresh and frozen, or processed foods. It is yet understood that temperature changes indicating ovulation can be used as a method to create foods that increase fertility by identifying what food articles increase ovulation.

The present invention also provides methods and devices for evaluating diet such as caloric restriction in which the temperature indicates the metabolism and therefore a lower basal temperature indicates reduced metabolism and metabolic waste products including monitoring carbohydrate intake and metabolism. The present invention also provides methods for monitoring hypoglycemia in diabetes in which lowering of the temperature is a predictor of a hypoglycemic event. The invention also provides methods for detecting pulmonary infarction and cardiac events which are associated with a particular increase in temperature. Any condition which is associated with a change in temperature can be predicted and detected by the present invention from pregnancy disorders coupled to hypothermia to hyperthermia in head trauma.

The present invention provides a variety of other benefits. Other exemplary benefits include: 1. monitoring Multiple Sclerosis since increase in brain temperature can lead to worsening of the condition, and a corrective measure can be taken when the present invention identifies such increase in temperature, such as by drinking cold liquids at the appropriate time or cooling off the brain as previously described, 2. significant differences between left and right BTT can indicate a pathological central nervous system condition, 3. detecting increased brain temperature to reinforce diagnosis of meningitis or encephalitis and thus avoid excess use of lumbar tap in people without the infection, and 4. Young babies cannot regulate their body temperature in the same way that adults do and can easily become too hot. Sudden Infant Death Syndrome (SIDS) is more common in babies who have become overheated. By monitoring babies' temperature the present invention can alert parents in case the baby's temperature increases.

A receiver receiving signal from the sensor system of the present invention can be external or implantable. When implantable inside the body the receiver can be powered by magnetic induction externally or batteries recharged externally. The receiver receives the signal from a temperature sensor, glucose sensor, or the like and retransmits the signals for further display.

Any transmitter of the present invention can be integrated with Bluetooth, GRPS data transmission, and the like. The signal from the transmitter then can be captured by any Bluetooth enabled device such as cell phones, electronic organizers, computers, and the like. Software of the cell phone can be modified to receive the coded signal from a transmitter. Algorithm in the receiver will decript the signal and display the value. A cell phone can have an auto dial to call a doctor for example when fever is noted. It is understood that the signal from a cell phone or a signal directly from the transmitter of the support structure can be transmitted to a computer connected to the internet for further transmission over a distributed computer network.

The prior art used facial skin temperature as detecting means for monitoring body temperature. As seen in FIGS. 1A and 1B, temperature of the skin on the face varies significantly from area to area and is not representative of the core temperature. In addition facial skin temperature does not deliver thermal energy in a stable fashion. Any device or method that uses facial skin temperature to activate another device or monitor temperature of the body will not provide a precise nor accurate response. In addition facial skin temperature does not represent the thermal status of the body and has a poor correlation with core and brain temperature. The only skin surface of the body which is in direct and undisturbed communication with inside the body is the specialized area of special geometry located at the entrance of the BTT. Any temperature sensing device placed on or adjacent to the BTT entrance can measure core temperature in a precise and accurate manner. It is understood that any sensor including a colorimetric sticker such as with liquid crystal colorimetric thermometers can be used and placed on the skin at the entrance of the BTT area, and are within the scope of the invention.

Now referring to the previously described automated climate control system, an exemplary embodiment will be described in more detail. Although this exemplary preferred embodiment will be described for climate control in the cabin of a transportation vehicle (e.g., car) it is understood that the method, device and system can apply to any confined environment such as home, work place, a hotel room, and the like in which the temperature inside the confined environment is adjusted based on the temperature at the BTT for achieving thermal comfort for the subject inside the confined environment.

The temperature measurement at the BTT represents the thermal comfort of the body. Investigation by the present invention showed that the thermal comfort of the body is reduced as the temperature of the body increases or decreases reflected by a change in brain temperature at the BTT. Thermal comfort of a human being is reflected by the skin temperature at the BTT, with higher skin temperature at the BTT generating a hot body sensation while a lower skin temperature at the BTT generates a cold body sensation. In order to achieve thermal comfort for the occupants of a cabin the system of the invention manages cabin thermal comfort from the temperature signal generated at the BTT. The present invention preferably uses a particular specialized area in the face, and not the whole face to manage the cabin temperature and cabin thermal comfort. The present invention system preferably monitors temperature in less than the whole face which causes an optimal control of the heating and cooling of the cabin to achieve thermal comfort of the occupant of the cabin.

Figure 83:
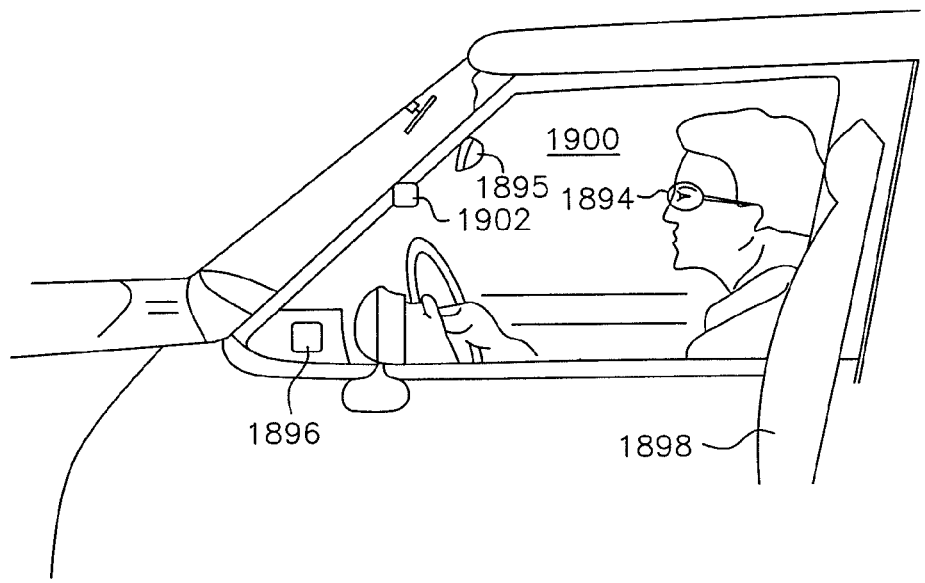
FIG. 83 is a perspective view showing an automated climate control system.

Since thermal comfort is reflected in the brain temperature adjusting the climate cabin based on the temperature of the BTT will provide a thermally comfortable environment for the occupant of the cabin. The BTT temperature is set for controlling the HVAC (heater-air conditioner) and other parts of the vehicle previously mentioned such as seats, carpets, and the like, which are adjusted to maintain the occupant's thermal sensation in a comfortable state. In particular, articles in contact or adjacent to the body are used to automatically remove or apply heat to the occupant's body based on the BTT signal. To further improve thermal comfort, the system includes a temperature sensor in the cabin for detecting cabin temperature. Accordingly, FIG. 83 shows an exemplary automated climate control system which includes BTT temperature sensing device 1894 for contact measurements (e.g., eyewear) and 1895 for non-contact measurements (e.g., infrared detector) for monitoring temperature at the BTT, control device 1896 adapted to automatically adjust articles 1898 in the cabin 1900 for removing or delivering heat based on the signal generated by BTT sensing device 1894, a cabin temperature sensor 1902 to detect the temperature in the cabin 1900, and an article 1898 inside the cabin adapted to remove heat when the signal from BTT sensor 1894 indicates high temperature or to deliver heat when the BTT sensor 1894 indicates low temperature. Although for illustration purposes a vehicle seat will be used as an article for removing/delivering heat, it is understood that other articles such as HVAC, carpet, steering wheel, and other articles previously mentioned can be used. As soon as the vehicle is started, the cabin sensor 1902 detects the cabin temperature and adjusts the article 1898 for removing or delivering heat based on the temperature signal from the cabin sensor 1902. Next or simultaneous with measurement of cabin temperature by sensor 1902, the output of BTT sensor 1894 is fed into control device 1896 which activates article 1898 to remove or deliver heat based on the signal from the BTT sensor 1894. If the BTT sensor 1894 indicates HIGH (>98.8° F.) then article 1898 will remove heat, and if LOW (<97.5° F.) is detected by BTT sensor 1894 then article 1898 will deliver heat, in order to achieve cabin thermal comfort. An exemplary embodiment for cooling includes control means 1896 connected to an air-conditioning control system for managing the amount of cool air being generated and blown in a proportional manner according to the temperature level output by BTT sensor 1894. For heating exemplarily the control device 1896 can be connected to a control system 1906 which gradually adjusts heat delivery by an electrically-based vehicle seat 1898 according to the output level by BTT sensor 1894. Control device 1896 is adapted to remain neutral and not to adjust article 1898 when temperature at the BTT is within 97.5° F. and 98.8° F. Since thermal comfort can vary from person to person, the system can be adapted for removing or delivering heat according to specific temperature thresholds in accordance with the occupant's individual needs, and not necessarily in accordance to defaults set at 97.5° F. and 98.8° F. It is understood that a combination of skin sensors placed in other parts of the body can be used in conjunction with BTT sensor 1894. It is yet understood that the rate of change in the skin temperature can be accounted for and fed into microcontroller which is adapted to adjust articles based on a large variation of skin temperature at the BTT site, with for instance a sudden cooling of the body of more than 0.6 degrees generating a corresponding decrease in the amount of cool air being generated or even shutting off an air conditioner system. It is also understood that BTT sensing devices include contact device (e.g., patches and eyewear of the present invention), non-contact devices (e.g., infrared devices of the present invention), thermal imaging (e.g., BTT Thermoscan of the present invention), and the like.

Figure 84:
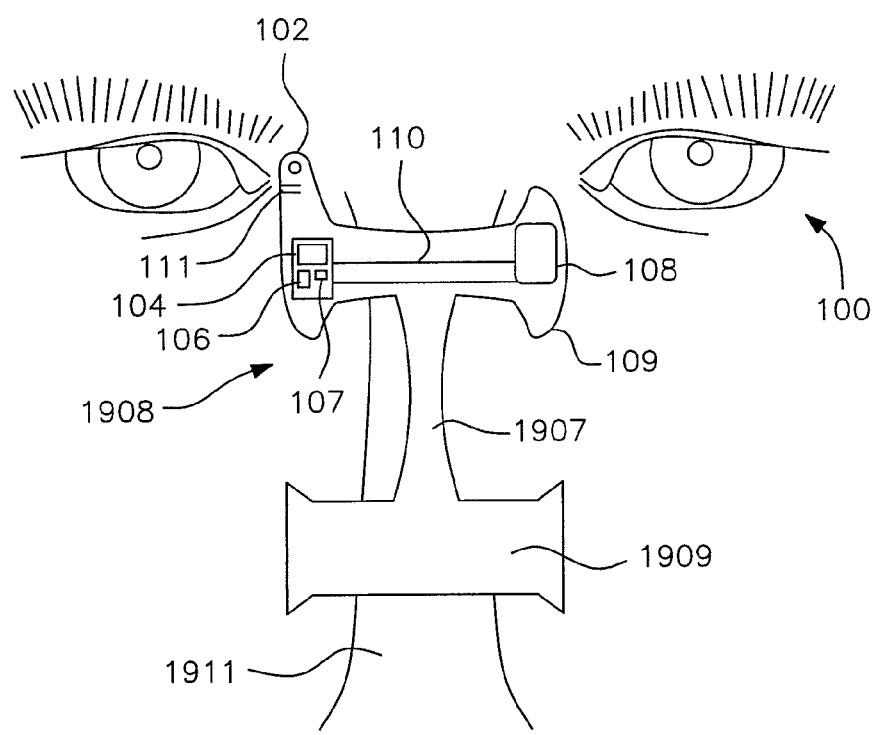
FIG. 84 is a perspective frontal view showing an nasal airway dilator as an extension of a patch of the present invention.

Yet another embodiment according to the present invention includes a support structure containing a sensor to measure biological parameters connected to a nasal strip for dilating airways of humans such as Breathe Right (commercially available under the trade name BreatheRight) and for dilating airway passages of animals (commercially available under the trade name Flair). Exemplary air dilator nasal strips were described in U.S. Pat. Nos. 5,533,503 and 5,913,873. The present invention incorporates airway dilators into patches for biological monitoring. The present invention can be an integral part of an airway dilator. The airway dilators can be an extension of the present invention. The coupling of a patch measuring biological parameters and an air dilator is convenient and beneficial since both are useful in the same activities. Nasal airway dilators are beneficial during sleeping, in athletic activities, or when suffering from a cold or respiratory infections and the patch of the present invention is used during sleeping, monitoring temperature changes in athletic activities, and monitoring fever during respiratory infections. Both nasal airway dilators and the patch of the present invention use an adhesive in its backing to secure to the skin and both are secured to the skin over the nasal bones, the patch of BTT located in the superior aspect of the nasal bone and the air dilator preferably in the inferior aspect of the nasal bone. The nasal airway dilator extension of the patch of the present invention is referred to herein as BioMonitor Dilator (BMD). Accordingly, FIG. 84 is a front perspective view of a preferred embodiment showing a person 100 wearing a BMD 1908 including a support structure comprised of a patch 109 connected by connecting arm 1907 to air dilator nasal strip 1909 with said BMD placed on the nose 1911 with patch 109 containing indicator lines 111 and containing an active sensor 102 positioned on the skin at the end of the tunnel on the upper part of the nose 1911 and air dilator nasal strip 1909 positioned on the skin of the lower part of the nose 1911 of user 100. The embodiment of the BMD 1908 shown in FIG. 84 provides transmitting device 104, processing device 106, AD converter 107 and sensing device 102 connected by flexible circuit 110 to power source 108 housed in patch 109. Although a connecting arm is shown it is understood that the BMD can be made as one piece in which the upper part houses the sensor and circuitry and the part on the lower aspect of the nose includes a spring loaded strip to act as nasal airway dilator. The present invention discloses a method of simultaneous monitoring biological parameters while dilating nasal airways.

Another embodiment includes a plurality of kits shown in FIGS. 85A to 85D. Accordingly, FIG. 85A is a schematic view of a kit 1910 containing an adhesive tape 1912 and a free sensor 1914 attached to a wire 1916. The free sensor 1914 is unattached to a support structure and when in use said sensor is preferably placed in contact with the adhesive 1912 in order for the sensor 1914 to be secured to the skin by the adhesive surface of adhesive 1912. Another embodiment shown in FIG. 85B includes a kit 1918 containing a support structure 1920 such as a patch, clip, eyewear (e.g., eyeglasses, sunglasses, goggles, and safety glasses) and the like, and receiver 1922 illustrated as a watch, but also cell phone, electronic organizer, and the like can be used as a receiver and being part of the kit. Kit 1918 can also house a magnet 1923 in its structure which acts as a switch, as previously described. It is understood that kit 1918 can include only a patch with the magnet 1923 adjacent to said patch 1922. The watch 1922 preferably has a slanted surface for better viewing during athletic activities such as during cycling with the field of view of the watch 1926 directed at an angle toward the face of the cyclist, so just by looking down and without turning the head the user can see the temperature level displayed on the watch 1926. A further embodiment shown in FIG. 85C includes a kit 1932 containing specialized BMD patch 1928 and a receiver 1930 illustrated as a watch.

Another embodiment includes shoes with temperature sensor for detecting cold and with a radio transmitter to transmit the signal to a receiver (e.g., Watch). The signal from the shoe in conjunction with the signal from the TempAlert at the BTT provides a combination of preventive device against both frostbite and hypothermia.

It is understood that the support structure such as a patch may house vapors and when the outer surface of the patch is scratched mentholated vapors can be released to help soothe and relieve nasal congestion, which can be convenient when monitoring fevers with the patch.

It is also understood that steel or cooper can be placed on top of a sensor to increase thermal conductivity as well as any other conventional means to increase heat transfer to a sensor.

It is understood that any electrochemical sensor, thermoelectric sensor, acoustic sensor, piezoelectric sensor, optical sensor, and the like can be supported by the support structure for measuring biological parameters in accordance with the principles of the invention. It is understood that sensors using amperometric, potentiometric, conductometric, gravimetric, impedimetric, and fluorescent systems, and the like can be used in the apparatus of the invention for the measurement of biological parameters. It is also understood that other forms for biosensing can be used such as changes in ionic conductance, enthalpy, and mass as well as immunobiointeractions and the like. It is also understood that new materials and thermally conductive liquid crystal polymers that produce a response in accordance to temperature can be used in the invention and positioned at the BTT site.

The foregoing description should be considered as illustrative only of the principles of the invention. Since numerous modifications and changes will readily occur to those skilled in the art, it is not desired to limit the invention to the exact construction and operation shown and described, and, accordingly, all suitable modifications and equivalents may be resorted to, falling within the scope of the invention.

FIGS. 86A to 86Z show preferred embodiments for the sensing and detecting system of the present invention. It is important to note that due to the specialized anatomic and physical configuration of the Brain Temperature Tunnel (BTT) as described in U.S. patent application Ser. No. 10/786,623, hereby incorporated by reference in its entirety, special dimensions and configurations of a sensing device are required, and will be reflected by the specialized dimensions and structure of the present invention disclosed herein. Accordingly, FIG. 86A shows the specialized support structure 2000, referred herein as sensing device 2000 which includes a specialized body 2002, which includes an essentially flexible substrate, an arm 2004, and a sensing portion such as a measuring portion 2006.

Sensing device 2000, for purposes of illustration, is shown as comprised of three parts, body 2002, arm 2004, and measuring portion 2006. Body 2002 is demarcated by line EF and line CD. Arm 2004 is demarcated by line CD and line AB. Measuring portion 2006 is demarcated by line AB, and works as the free end of sensing device 2000. Arm 2004 is connected to measuring portion 2006 and to body 2002. Body 2002 of the sensor system 2000 can preferably comprise a plate configuration, said plate preferably having essentially flexible characteristics so as to be molded and/or to conform to a body part of a human or animal. Plate 2002 can be preferably secured to a body part by adhesive or attachment means. Body part for the purpose of the description includes the body of any living creature including humans and animals of any type as well as birds and other species such as insects. Body 2002 can also include an adhesive surface or any other fastening means, clipping means, and the like which is used to secure body 2002 to an area adjacent to the BTT or on the BTT.

The present invention includes a support structure 2000 removably securable to a body part and having a sensor for measuring biological parameters from a brain tunnel. Any sensor, detector, sensing structure, molecule, moiety, element, radiation detector, a pair of light emitter-detector, fluorescent element, and the like, which can sense, analyze and/or measure an analyte or tissue can be used and disposed in or on measuring portion 2006 or at the end of arm 2004, including contact as well as non-contact detector configurations, and all fall within the scope of the invention. The sensors and/or detectors preferably are positioned on or adjacent to the upper or lower eyelid, and most preferably on or adjacent to the upper eyelid, and even more preferably on or adjacent to an area between the eye and the eyebrow.

Sensing device 2000 preferably comprises: body 2002, which has an inner surface for disposition towards the body part and preferably includes an adhesive surface to securely attach and conform the body 2002 to a body part, and an outer surface for disposition away from the body part; arm 2004 connected to body 2002, said arm 2004 being adjustably positionable and adapted to position sensor 2010 adjacent, on, or firmly against the brain tunnel; and a measuring portion 2006 connected to arm 2004, said measuring portion housing a sensor 2010. Body 2002 is physically conformable to the body part, and preferably includes an outer layer and an inner layer, the inner layer comprised of essentially soft material and including an adhesive surface, said inner layer being attached to an outer layer, said outer layer including a flexible substrate, such as a thin metal sheet, to conform to the body part and to provide stable attachment. A wire is preferably disposed on the outer layer or between the inner layer and the outer layer.

Although sensing device 2000, for purposes of illustration is shown as three parts, it is understood that sensing device 2000 can comprise an integral device fabricated as one piece. Sensing device 2000 can also comprise an integral one-piece device that is fabricated as one piece, but having three different portions. In addition, for example, arm 2004 and measuring portion 2006 can be considered as one piece. Any combination of the parts, namely body, arm, and measuring portion, described herein can be used as the support structure for a sensor, molecule, or detector.

FIG. 86B shows in more detail the sensing system 2000 of FIG. 86A including the specialized body 2002, the arm 2004, and the measuring portion 2006, said measuring portion 2006 housing a sensor 2010. Sensor system 2000 comprises preferably a plate 2002 for securing the device 2000 to a body part, and further comprises an arm 2004, said arm 2004 connecting supporting plate 2002 to a measuring portion 2006. Arm 2004 is preferably an adjustably positionable arm, which is movable in relation to plate 2002. Arm 2004 preferably comprises a shape memory alloy or any material, including plastics and polymers that have memory. Preferably, arm 2004 is deformable and has a memory. The end 2026 of arm 2004 terminates in the measuring portion 2006. Although arm 2004 comprises preferably an adjustably positionable arm, arm 2004 can also include a rigid arm. Preferred materials for the arm 2004 include a thin sheet of metal such as stainless steel, aluminum, and the like or polymers and plastics of various kinds. The material can also include rubber, silicone or other material. Sensor 2010 at the end of arm 2004 is connected to a reading and processing circuit 2012, referred to also herein as a biological parameter monitor, through wire portion 2065. Sensor 2010 is electrically coupled to the biological parameter monitor, which receives a signal from sensor 2010, and determines the value of the biological parameter, and reports the value including by visual display and audio reporting.

The present invention can employ a cantilever for sensing system 2000, in which arm 2004 is supported rigidly at plate 2002 to carry a load, such as measuring portion 2006, said measuring portion 2006 being disposed along the free end 2026 of said arm 2004. The arm 2004 is fixed at a base of body 2002, with said body 2002 being a support structure exemplarily described in embodiments as a plate; a housing secured to a head mounted gear including a headband, frame of eyewear, hats, helmets, visors, burettes for holding hair; the frame of eyewear or of a head mounted gear, clothing of any type including a shirt, a rigid structure secured to an article of manufacturing such as apparel; and the like. The free end 2026 of arm 2004 is connected to measuring portion 2006 which houses sensor 2010. Accordingly, the sensing device 2000 of the invention has an arm 2004 that distributes force and that can apply force to a body part. One of ways arm 2004 can be positioned and/or apply pressure to a body part is by virtue of a memory shape material of said arm 2004. Any means to apply pressure to a body part can be used in sensing system 2000 including a spring loaded system, in which the spring can be located at the junction 2024 of body 2002 and the arm 2004, or the spring is located at the free end 2026 of arm 2004. It is contemplated that any material with springing capabilities and any other compressible materials and materials with spring and/or compressible capabilities such as foams, sponges, gels, tension rings, high-carbon spring steels, alloy spring steels, stainless steels, copper-base alloys, nickel-base alloys, and the like can be used in sensing device 2000 to apply pressure for better apposition of measuring portion 2006 to the body part. The invention teaches apparatus and methods for creating better apposition and/or applying pressure to a body part or article by any sensor, device, detector, machine, equipment, and the like. Sensor 2010 housed in measuring portion 2006 can therefore apply pressure to a body part, such as the brain temperature tunnel area at the roof of the orbit.

The end of arm 2004 preferably terminates as a bulging part, such as measuring portion 2006, which houses sensor 2010. Arm 2004 can move in relation to plate 2002, thus allowing movement of sensor 2010 housed at the free end 2026 of arm 2004. Although the sensing system 2000 is described for a body part, it is understood that the sensing device 2000 can be applied in an industrial setting or any other setting in which a measurement of an object or article is needed. By way of illustration, sensor 2010 can include a temperature and pressure sensor while the plate 2006 is affixed to a support structure, such as a beam or wall of a machine, and the sensor 2010 is applied against a balloon or a surface, thus providing continuous measurement of the pressure and temperature inside the balloon or surface. Outside surface of body 2002 can include an adhesive surface for securing said body 2002 to a second surface such as a body part or the surface of a machine or any article of manufacturing.

In order to fit with the specialized anatomy and physical configuration of the brain tunnel, specialized sensing devices with special dimensions and configurations are necessary. The preferred dimensions and configurations described herein can be applied to any embodiments of this invention including embodiments described from FIG. 1 to FIG. 104. The preferred configuration of sensing device 2000 comprises a body 2002 that has a larger width than arm 2004. The width of body 2002 is of larger dimension than the width of arm 2004. Preferably the width of body 2002 is at least twice the width of arm 2004. Most preferably, arm 2004 has a width which is preferably one third or less than the width of body 2002. Even more preferably, arm 2004 has a width which is preferably one fourth or less than the width of body 2002.

The sensing device 2000, as exemplarily illustrated, includes an essentially curved end portion of arm 2004 and an essentially flat remaining portion of arm 2004 said flat portion connected to body 2002. During use arm 2004 is positioned in a curved configuration to fit around the bone of the eyebrow. Arm 2004 has two end portions, namely end portion 2024 which terminates in body 2002 and a free end portion 2026 which terminates in the measuring portion 2006. The preferred length of arm 2004 is equal to or no greater than 15 cm, and preferably equal to or no greater than 8 cm in length, and most preferably equal to or no greater than 5 cm in length. Depending on the size of the person other dimensions of arm 2004 are contemplated, with even more preferable length being equal to or no greater than 4 cm, and for children length equal to or no greater than 3 cm, and for babies or small children the preferred length of arm 2004 is equal to or no greater than 2 cm. Depending on the size of an animal or the support structure being used such as a burette of FIG. 100R, cap of FIG. 100*p*, or the visor of FIG. 100T other dimensions are contemplated, such as length of arm 2004 equal to or no greater than 40 cm.

The preferred width or diameter of arm 2004 is equal to or no greater than 6 cm, and preferably equal to or no greater than 3 cm, and most preferably equal to or no greater than 1.0 cm. Depending on the size of the person other dimensions for arm 2004 are contemplated, with an even more preferable width or diameter being equal to or no greater than 0.5 cm, and for children width or diameter equal to or no greater than 0.3 cm, and for babies or small children the preferred equal to or no greater than 0.2 cm. Depending on the size of a large person or size of an animal or support structure being used other dimensions for arm 2004 are contemplated, such as width or diameter equal to or no greater than 12 cm.

The preferred height (or thickness) of arm 2004 is equal to or no greater than 2.5 cm, and preferably equal to or no greater than 1.0 cm in thickness, and most preferably equal to or no greater than 0.5 cm in thickness. Depending on the size of the person other dimensions for arm 2004 are contemplated, with even more preferable thickness being equal to or no greater than 0.3 cm, and for children thickness equal to or no greater than 0.2 cm, and for babies or small children the preferred thickness is equal to or no greater than 0.1 cm. Depending on the size of a large person or size of an animal other dimensions for arm 2004 are contemplated, such as thickness equal to or no greater than 3.0 cm.

For devices, in which the preferred configuration of arm 2004 is a cylinder, the preferred diameter of arm 2004 is equal to or no greater than 2.0 cm, and preferably equal to or no greater than 1.0 cm in thickness, and most preferably equal to or no greater than 0.5 cm in thickness. Depending on the size of the person other dimensions for arm 2004 are contemplated, with even more preferable diameter being equal to or no greater than 0.25 cm, and most preferably being equal to or no greater than 0.15 cm, and for children thickness equal to or no greater than 0.2 cm, and for babies or small children the preferred thickness is equal to or no greater than 0.1 cm. Depending on the size of a large person or size of an animal or the structure being used, other dimensions for arm 2004 are contemplated, such as diameter equal to or no greater than 3.0 cm.

The preferred largest dimension of arm 2004 is equal to or no greater than 30 cm, and preferably equal to or no greater than 20 cm, and most preferably equal to or no greater than 10 cm. Preferred dimensions are based on the size of the person or animal and structure being used such as burette, visors, or cap. The preferred length of arm 2004 is no greater than 40 cm, and preferably equal to or no greater than 20 cm, and most preferably equal to or no greater than 10 cm in length. Depending on the size of the person other preferred dimensions for arm 2004 are contemplated, with an even more preferable length being equal to or no greater than 8 cm, and most preferably equal to or no greater than 6 cm, and for adults of small size length equal to or no greater than 5 cm, and for children length equal to or no greater than 4 cm and for babies or small children the preferred length is equal to or no greater than 2 cm. Arm 2004 is preferably curved at its free end 2026 for fitting with the anatomy of the brain tunnel and the facial bone.

The preferred general dimensions for human use by a person of average size for arm 2004 are: height (or thickness or diameter) equal to or less than 0.4 cm, length equal to or less than 6 cm, and width equal to or less than 0.5 cm. The preferred height (or thickness or diameter) of arm 2004 ranges between equal to or more than 0.1 cm and equal to or less than 0.5 cm. The preferred length of arm 2004 ranges between equal to or more than 1.0 cm and equal to or less than 8 cm. The preferred width of arm 2004 ranges between equal to or more than 0.1 cm and equal to or less than 1 cm.

It should be noted that for small animals such as rats, mice, chicken, birds, and other animals using the brain tunnel smaller size and different configurations are contemplated.

In one embodiment the end portions of arm 2004 terminate in plate 2002 and measuring portion 2006. Preferably, arm 2004 is made of a stainless steel type material or aluminum; however, other materials are contemplated, including other metals, plastics, polymers, rubber, wood, ceramic, and the like. The arm 2004 should be sufficiently flexible such that the relative distance between sensor 2010 and a body part may be enlarged or reduced as needed in accordance to the measurement being performed including measurement in which sensor 2010 touches the body part and measurements in which sensor 2010 is spaced away from the body part and does not touch the body part during measurement. An exemplary sensor which does not touch a body part during measurement is a thermopile. Accordingly, measuring portion 2006 can include said thermopile or any radiation detector.

Although FIG. 86B shows arm 2004 being of different size as compared to plate 2002, it is understood that arm 2004 can have the same size of plate 2002 or have larger size than plate 2002. The preferred largest dimension of end portion 2026 of arm 2004 is equal to or no greater than 3 cm, and preferably equal to or no greater than 2 cm, and most preferably equal to or no greater than 1 cm. Depending on the size of the person, it is also contemplated that end portion 2026 has an even more preferable size equal to or no greater than 0.8 cm, and even most preferably equal to or no greater 0.6 cm. For some adults of small size the end portion 2026 has an even more preferable size equal to or no greater than 0.5 cm, and for children, it is also contemplated that end portion 2026 of arm 2004 has a size equal to or no greater than 0.4 cm. and for babies the contemplated size is equal to or no greater than 0.2 cm As nanotechnology, MEMS (microelectromechanical systems), and NEMS (nanoelectromechanical systems) progresses other configurations, dimensions, and applications of the present invention are contemplated.

Although FIG. 86B shows arm 2004 being of different width (or diameter) as compared to measuring portion 2006, it is understood that arm 2004 can have the same width (or diameter) of measuring portion 2006 or have a larger width (or diameter) than measuring portion 2006. Preferably the width (or diameter) of arm 2004 is of smaller size than the dimension (or diameter) of the measuring portion 2006. Preferably the part of measuring portion 2006 connected to arm 2004 is of larger dimension than the width of arm 2004.

For the purpose of the description thickness and height are used interchangeably. The preferred configuration of sensing device 2000 comprises a body 2002 (including the body of any embodiment from FIGS. 1 to 104, and in particular the body corresponding to a housing or structure securing sensors/detector described in all figures, from FIG. 99A to FIG. 100Z) that is thicker than arm 2004. The height or thickness of body 2002 is preferably of larger size than the thickness (or height or diameter) of arm 2004. Arm 2004 has thickness (or height or diameter) which is preferably of lesser size than the thickness (or height) of body 2002. Arm 2004 has thickness (or height) which is preferably half or less than the thickness (or height) of body 2002. Arm 2004 has thickness (or height) which is most preferably one third or less than the thickness (or height) of body 2002.

The preferred configuration of sensing device 2000 comprises a measuring portion 2006 that is thicker than arm 2004. The measuring portion 2006 preferably comprises a bulging portion which is thicker than arm 2004. Arm 2004 is thinner than measuring portion 2006. Arm 2004 has thickness (or height or diameter) which is preferably half or less than the thickness (or height or diameter) of measuring portion 2006. Arm 2004 has thickness (or height or diameter) which is most preferably one third or less than the thickness (or height or diameter) of measuring portion 2006. Even more preferably arm 2004 has thickness (or height or diameter) which is one sixth or less than the thickness (or height or diameter) of measuring portion 2006. It is yet contemplated that for proper functioning in accordance with the size of the user and the principles of the invention, measuring portion 2006 has thickness (or height or diameter) which is 3 times or more larger than the thickness (or height or diameter) of arm 2004.

The preferred configuration of sensing device 2000 comprises an arm 2004 that is longer than the height (or thickness or diameter) of measuring portion 2006. The length of arm 2004 is preferably of larger dimension than the largest dimension of measuring portion 2006. In the exemplary embodiment, measuring portion 2006 is essentially cylindrical, and thus includes a circle, said circle having a diameter. For the purposes of the description, an embodiment in which the circle is replaced by a rectangle, square or other shape, the length of said rectangle, square, or other shape is considered an "equivalent dimension" to the diameter. Accordingly, measuring portion 2006 has diameter (or "equivalent dimension"), which is preferably half or less than the length of arm 2004. Measuring portion 2006 has diameter (or "equivalent dimension"), which is preferably one third or less than the length of arm 2004. It is yet contemplated that for proper functioning in accordance with the principles of the invention, arm 2004 has an even more preferred length, which is 5 times or more greater than the diameter (or "equivalent dimension") of measuring portion 2006.

The preferred configuration of sensing device 2000 comprises a measuring portion 2006, which is thicker than the body 2002, as illustrated in FIG. 86B. It is understood that in embodiments of FIG. 100A to FIG. 100Z the body as represented by the headband and housing for electronics are contemplated to be thicker than measuring portion 2006. The thickness (or height) of measuring portion 2006 is preferably of larger dimension than the thickness or height of body 2002. Body 2002 has thickness (or height) which is preferably half or less than the thickness (or height) of measuring portion 2006. Body 2002 has thickness (or height) which is preferably one third or less than the thickness (or height) of measuring portion 2006. It is yet contemplated that for proper functioning in accordance with the principles of the invention, measuring portion 2006 has thickness (or height) which is 4 times or more greater than the thickness (or height) of body 2002. When the embodiment includes body 2002 housing a wireless transmitter and/or other electronic circuit, then body 2002 can preferably have a thickness (or height) equal to or of larger dimension than thickness (or height) of measuring portion 2006.

The length of body 2002 is preferably of larger dimension than the largest dimension of measuring portion 2006. Preferably, the configuration of sensing device 2000 comprises a body 2002 which has a longer length than the length of measuring portion 2006. When measuring portion 2006 includes a circular configuration, then preferably body 2002 has larger length than the diameter of measuring portion 2006. Measuring portion 2006 has length (or diameter) which is preferably half or less than the length (or diameter) of body 2002. Measuring portion 2006 has length (or diameter) which is preferably one third or less than the length (or diameter) of body 2002. It is yet contemplated that for proper functioning in accordance to the principles of the invention, body 2002 has length (or diameter) which is 4 times or more the length (or diameter) of measuring portion 2006.

The preferred configuration of sensing device 2000 comprises an arm 2004, in which the largest dimension of said arm 2004 is larger than the largest dimension of measuring portion 2006. The preferred configuration of sensing device 2000 comprises a body 2002, in which the largest dimension of said body 2002 is larger than the largest dimension of measuring portion 2006. The preferred configuration of sensing device 2000 comprises an arm 2004, in which the smallest dimension of said arm 2004 is equal to or smaller than the smallest dimension of measuring portion 2006. The preferred configuration of sensing device 2000 comprises a body 2002, illustrated in FIG. 86B, in which the smallest dimension of said body 2002 is equal to or smaller than the smallest dimension of measuring portion 2006. The preferred configuration of sensing device 2000 comprises an arm 2004, in which the thickness of said arm 2004 has a smaller dimension than the thickness of measuring portion 2006.

It is contemplated that other geometric configurations, besides square, circle, and rectangles, can be used, such as a star, pentagon, octagon, irregular shape, or any geometric shape, and in those embodiments the largest dimension or smallest dimension of the plate 2002 (e.g., body) of sensing device 2000 is measured against the largest dimension or smallest dimension of the other part, such as arm 2004 or measuring portion 2006. The same apply when fabricating sensing device 2000 and the reference is the arm 2004, but now compared to body 2000 and/or measuring portion 2006. Yet the same apply when fabricating sensing device 2000 and the reference is the measuring portion 2006, which is now compared to body 2002 and/or arm 2004. The largest dimension of one part is compared to the largest dimension of the other part. The smallest dimension of one part is compared to the smallest dimension of the other part.

Still in reference to FIG. 86B, the end 2024 of arm 2004 connected to plate 2002 can further include a swivel or rotating mechanism 2008, allowing rotation of arm 2004, and/or the up and down movement of measuring portion 2006. The swivel or rotating mechanism 2008 can include a lock for locking arm 2004 in different angles. The different angles and positions can be based on predetermined amount of pressure by said arm 2004 applied to a body part. In addition, arm 2004 can operate as a movable arm sliding in a groove in body 2002. According to this arrangement, the movable arm 2004 works as a slidable shaft housing a measuring portion 2006 in its free end. This embodiment can comprise a larger plate 2002 which is secured to the cheek or nose, and the sliding mechanism is used to position sensor 2010 of measuring portion 2006 against the skin of the brain tunnel (BT) underneath the eyebrow, with body 2002 positioned below the eye or at the eye level. This embodiment can comprise embodiments of FIG. 90 to FIG. 100Z, including embodiments in which the arm 2004 is secured to the forehead such as using a headband, and the sliding mechanism is used to position sensor 2010 of measuring portion 2006 against the skin of the brain tunnel (BT) underneath the eyebrow, with body of the sensing device positioned above the eye or at the forehead. Other embodiments are contemplated including the slidable mechanism and swivel mechanism used as part of a headband and embodiments described in FIG. 99 to FIG. 100Z. Furthermore, another embodiment can include a dial mechanism in which the arm 2004 moves from right to left as in the hands of a clock facing the plane of the face. In this embodiment the right brain tunnel area for example of a subject with a wide nose bridge can be reached by moving the dial to the 7 o'clock or 8 o'clock position, said illustrative clock being observed from an external viewer standpoint.

Sensor 2010 at the end of measuring portion 2006 is connected to processing and display unit 2012 through wire 2014. Wire 2014 has three portions 2060, 2062, 2064. Accordingly, there is seen in FIG. 86B wire portion 2060 secured to measuring portion 2006 with the free end 2066 of said wire portion 2060 terminating in sensor 2010 and the opposite end 2068 of said wire portion 2060 terminating in arm 2004. End 2068 of wire portion 2060 preferably terminates in a 90 degree angle between the measuring portion 2006 and arm 2004. Second wire portion 2062 is secured to arm 2004 and terminates in body 2002 preferably in an essentially 180 degree angle while the opposite end of wire 2062 forms the 90 degree angle with wire portion 2068. In addition, in embodiments of FIG. 99 to FIG. 100Z, wire portion 2062 secured to arm 2004 may terminate in a housing and/or printed circuit board secured for example to a headband or any head mounted gear. Third wire portion 2064 is secured to body 2002 and remains essentially flat in body 2002. Wire portion 2064 terminates in reading and processing unit 2012 through a fourth wire portion 2065. Wire portion 2065 connects body 2002 to processing circuit and display 2012 which provides processing of the signal and may display the result. Although a 90 degree angle between measuring portion 2006 and arm 2004 comprises the preferred embodiment, it is understood that any angle including a 180 degree angle between measuring portion 2006 and arm 2004 can be used. In an alternative embodiment, the axis of measuring portion 2006 can be parallel to arm 2004 and body 2002, and all three wire portions 2060, 2062 and 2064 of wire 2014 can be disposed within the same plane of sensing device 2000. Thus wire 2014 does not need to have the 90 degree bent for functioning in this alternative embodiment.

Sensor 2010 at the end 2026 of arm 2004 comprises any sensor or detector, or any element, molecule, moiety, or element capable of measuring a substance or analyzing an analyte or tissue. Exemplary sensor 2010 includes electrochemical, optical, fluorescent, infrared, temperature, glucose sensor, chemical sensor, ultrasound sensing, acoustic sensing, radio sensing, photoacoustic, electrical, biochemical, opto-electronic, or a combination thereof in addition to a light source and detector pair, and the like, all of which for the purpose of the description will be referred herein as sensor 2010.

The preferred largest dimension of sensor 2010 is equal to or no greater than 3 cm, and preferably equal to or no greater than 1.5 cm, and most preferably equal to or no greater than 0.5 cm. Preferred dimensions are based on the size of the person or animal. Depending on the size of the person other dimensions of sensor 2010 are contemplated, such as largest dimension equal to or no greater than 0.3 cm, and for adults of small size dimension equal to or no greater than 0.2 cm, and for small children dimension equal to or no greater than 0.1 cm and for babies preferred dimension is equal to or no greater than 0.05 cm. If more than one sensor is used the dimensions are larger, and if a molecule or moiety are used as sensing element the dimensions are very small and much smaller than any of the above dimensions.

When sensor 2010 comprises a temperature sensor the preferred largest dimension of the sensor is equal to or less than 5 mm, and preferably equal to or less than 4 mm, and most preferably equal to or less than 3 mm, and even more preferably equal to or less than 2 mm. When the temperature sensor has a rectangular configuration, a preferred width is equal to or less than 1 mm, and preferably equal to or less than 500 microns. Those specialized small dimensions are necessary for proper fitting of the sensor with the thermal structure of the tunnel and the entry point of the BTT.

Sensor 2010 can also comprise a radiation source and radiation detector pair, such as a reflectance measuring system, a transmission measuring system, and/or an optoelectronic sensor. Preferably the distance from the outer edge of radiation source (e.g. light emitter) to the outer edge of detector is equal to or less than 3.5 cm, and more preferably equal to or less than 2.0 cm, and most preferably equal to or less than 1.7 cm, and even most preferably equal to or less than 1.2 cm.

In one embodiment sensor system 2010 can further comprise a temperature sensor and include a heating or a cooling element. It is understood that a variety of sensing systems such as optical sensing, fluorescent sensing, electrical sensing, electrochemical sensing, chemical sensing, enzymatic sensing and the like can be housed at the end of arm 2004 or in measuring portion 2006 in accordance to the present invention. Exemplarily, but not by way of limitation, an analyte sensing system such as a glucose sensing system and/or a pulse oximetry sensor comprised of light emitter (also referred to as light source) and light detector can be housed at the end of arm 2004 and operate as sensor system 2010. Likewise a combination light emitter and photodetector diametrically opposed and housed at the end of arm 2004 to detect oxygen saturation, glucose levels, or cholesterol levels by optical means and the like can be used and are within the scope of the present invention. Furthermore, a radiation detector can be housed at the end of arm 2004 for detecting radiation emitted naturally from the brain tunnel and/or the skin area at the brain tunnel between the eye and the eyebrow or at the roof of the orbit.

Sensor 2010 can be a contact or non-contact sensor. In the embodiment pertaining to a contact sensor, exemplarily illustrated as a thermistor, then arm 2004 is positioned in a manner such that sensor 2010 is laying against the skin at the BTT and touching the skin during measurement. When a non-contact sensor is used, two embodiments are disclosed:

Embodiment No. 1 measuring portion 2006 is spaced away from the skin and does not touch the skin, and both measuring portion 2006 and sensor 2010 housed in the measuring portion 2006 do not touch the skin during measurement. This embodiment is exemplarily illustrated as an infrared detector. This infrared detector is adapted for receiving infrared radiation naturally emitted form the brain tunnel, between the eye and the eyebrow. Exemplarily infrared radiation emitted includes near-infrared radiation, mid-infrared radiation, and far-infrared radiation. The emitted infrared can contain spectral information and/or radiation signature of analytes, said infrared radiation signature being used for noninvasive measurement of analytes, such as glucose. Alternatively, infrared radiation source, including but not limited to, near-infrared or mid-infrared can be used and the near infrared radiation and/or mid-infrared radiation directed at the brain tunnel generates a reflected radiation from the brain tunnel, which is used for non-invasive measurement of an analyte. In addition, any emitted electromagnetic radiation can contain spectral information and/or radiation signature of analytes, said infrared radiation signature being used for noninvasive measurement of analytes, such as glucose, or analyze of tissue.

Embodiment No. 2 sensor 2010 does not touch the skin but walls of a measuring portion 2006, which houses the sensor 2010, touch the skin. In this embodiment, there is a gap or space inside measuring portion 2006 and the skin at the BTT, allowing thus the sensor 2010, which is spaced away from the skin, not to be exposed to air or ambient temperature while still not touching the skin. Accordingly, the sensor 2010 is housed in a confined environment formed by essentially the walls of two structures: the wall of the measuring portion 2006 and the wall formed by the skin at the BTT. This embodiment is exemplarily illustrated as an infrared detector. This infrared detector is adapted for receiving infrared radiation naturally emitted form the brain tunnel. Exemplarily infrared radiation emitted includes near-infrared radiation, mid-infrared radiation, and far-infrared radiation. The emitted infrared can contain the radiation signature of analytes, said infrared radiation signature being used for noninvasive measurement of analytes, such as for example glucose, cholesterol, or ethanol. Alternatively, an infrared radiation source such as near-infrared, mid-infrared, and far-infrared in addition to fluorescent light can be used with said radiation directed at the brain tunnel, which generates a reflected radiation from the brain tunnel, with said reflected radiation containing a radiation signature of an analyte and being used for non-invasive measurement of an analyte. In addition, any source of electromagnetic radiation, any sound generating device, and the like can be housed in a measuring portion.

Sensor 2010 can be covered with epoxi, metal sheet, or other material, and in those embodiments the dimensions in accordance with the invention are the dimension of the material covering sensor 2010.

The preferred largest dimensions for body 2002, illustratively represented by a rectangular plate in FIG. 86B, is equal to or no greater than 18 cm, and preferably equal to or no greater than 10 cm, and most preferably equal to or no greater than 6 cm. The preferred dimensions for plate 2002 for human use are equal to or less than 8 cm in length, equal to or less than 6 cm in width, and equal to or less than 2 cm in thickness. The most preferred dimensions for plate 2002 for human use are equal to or less than 6 cm in length, equal to or less than 4 cm in width, and equal to or less than 1 cm in thickness. Most preferably, the dimensions for plate 2002 are equal to or less than 4 cm in length, equal to or less than 2 cm in width, and equal to or less than 0.5 cm in thickness. Although plate 2002 is shown in a rectangular shape, any other shape or configuration can be used including circular, oval, square, oblong, irregular, and the like. It is also contemplated that dimensions of a housing, such as a box, as described for a headband and in the embodiments of FIGS. 99 to 100Z may have different dimensions. For those embodiments the electronics can be spread along the headband making it very thin. Alternatively if a large number of components is used including Bluetooh transmitters, which are commonly of larger size, larger dimensions are contemplated.

It is understood that plate 2002 can preferably house electronics, microchips, wires, circuits, memory, processors, wireless transmitting systems, light source, buzzer, vibrator, accelerometer, LED, and any other hardware and power source necessary to perform functions according to the present invention. It is also understood that arm 2004 can also house the same hardware as does plate 2002, and preferably houses a LED or lights that are within the field of view of the user, so as to alert the user when necessary. Sensing device 2000 can be powered by a power source housed in the plate 2002. It is understood that sensing device 2000 can be powered by an external power source and that wire 2014 can be connected to said external power source. The external power source can preferably include processing circuit and display.

It is also understood that any support structure, head mounted gear, frame of eyeglasses, headband, and the like can be employed as body 2002, or be coupled to measuring portion 2006, or be connected to arm 2004. When arm 2004 and its sensor 2010 at the end of said arm 2004 is coupled to another support structure, such as frame of eyeglasses, helmet, and the like, the frame of said eyeglasses or said helmet operates as the body 2002, and it is used as the connecting point for arm 2004.

Now in reference to FIG. 86C, the measuring portion 2006, as exemplarily illustrated in FIG. 86C, comprises an essentially cylindrical shape. Measuring portion 2006 preferably comprises a body 2020 and a connecting portion 2011, which connects measuring portion 2006 to arm 2004. Body 2020 has preferably two end portions, namely top end 2016 and a bottom end 2018, said top end 2016 being connected with connecting portion 2011 and arm 2004 and said bottom end 2018 housing sensor 2010. The body 2020 houses wire 2060 for connecting sensor 2010 to a transmitting and/or processing circuit and/or display (not shown). In an embodiment for measuring temperature body 2020 includes a soft portion 2009 which is preferably made with insulating material and said body 2020 has insulating properties. The bottom end 2018 has insulating properties and is void of heat conducting elements such as metal, heat conducting ceramic, and heat conducting gel, heat conducting polymers, and the like. Contrary to the prior art which uses heat conductive material to encapsulate around a temperature sensor in order to increase heat transfer from the article or body being measured, the probe of this invention is void of heat conductive materials.

Body 2020 and connecting portion 2011 can also house electronics, chips, and/or processing circuits. In one embodiment body 2020 includes a soft portion and connecting portion 2011 comprises a hard portion.

For temperature measurement and for monitoring certain biological parameters, measuring portion 2006 preferably includes a non-metallic body 2020, said non-metallic body housing wire portion 2060. In one embodiment for measuring temperature sensor 2010 comprises a temperature sensor and body 2020 preferably comprises insulating material, said insulating material preferably being a soft material and having compressible characteristics. Although compressible characteristics are preferred, it is understood that body 2020 can also comprise rigid characteristics or a combination of rigid and soft portions. Most preferably body 2020 comprises a combination of a rigid part and a soft part, said soft part being located at the free end of body 2020, and which is in contact with a body part, such as of a mammal.

In one embodiment sensor 2010 comprises a pressure sensor or piezoelectric element and operates as a pulse and/or pressure measuring portion. In another embodiment sensor 2010 comprises an electrochemical sensor for measurement of analytes such as glucose. In another embodiment sensor 2010 comprises an ultrasound sensing system. In another embodiment sensor 2010 comprises a photoacoustic sensing system for measurement of chemical substances such as glucose. In another embodiment, sensor 2010 comprises a fluorescent element or fluorescein molecule for evaluating temperature, pressure, pulse, and chemical substances including analytes such as glucose. In another embodiment, sensor 2010 comprises an infrared detector for measuring temperature and/or concentration of chemical substances in blood from radiation naturally emitted from the brain tunnel.

The preferred diameter of measuring portion 2006, illustrated as the diameter of the body 2020, housing a temperature sensor is equal to or no greater than 4 cm, and preferably equal to or no greater than 3 cm, and most preferably equal to or no greater than 2 cm. Depending on the size of the person other even more preferable dimensions for measuring portion 2006 are contemplated, such as diameter equal to or no greater than 1.2 cm, and much more preferably equal to or less than 0.8 cm. For children preferred diameter is equal to or no greater than 0.6 cm, and for babies or small children the preferred diameter is no greater than 0.4 cm. Depending on the size of an animal or person other dimensions for measuring portion 2006 are contemplated, such as diameter equal to or no greater than 5 cm.

When a cylindrical shape is used, the preferred diameter of measuring portion 2006 for chemical or certain physical measurement is no greater than 4 cm, and preferably no greater than 3 cm, and most preferably no greater than 2 cm. The same dimensions apply to a non-cylindrical shape, such as a rectangle, and the preferred length of the rectangle is no greater than 4 cm, and preferably no greater than 3 cm, and most preferably no greater than 2 cm. Depending on the size of the person other even more preferable dimensions for measuring portion 2006 are contemplated, such as a diameter equal to or no greater than 1.2 cm, and much more preferably equal to or no greater than 0.8 cm. For children a preferred diameter is equal to or no greater than 0.7 cm, and for babies or small children the preferred diameter is equal to or no greater than 0.5 cm. Depending on the size of an animal or person other dimensions for measuring portion 2006 are contemplated, such as diameter equal to or no greater than 6 cm.

When a non-cylindrical shape is used, such as a rectangle, the preferred width of measuring portion 2006 is equal to or no greater than 2 cm, and preferably equal to or no greater than 1.5 cm, and most preferably equal to or no greater than 1 cm. Depending on the size of the person other dimensions for measuring portion 2006 are contemplated, such as width equal to or no greater than 0.8 cm and more preferably equal to or no greater than 0.5 cm, and for children width equal to or no greater than 0.4 cm, and for babies or small children the preferred width is equal to or no greater than 0.3 cm. Depending on the size of an animal or person other dimensions for measuring portion 2006 are contemplated, such as width equal to or no greater than 5 cm.

The preferred height (or thickness) of measuring portion 2006, considering a cylindrical shape, is equal to or no greater than 4 cm, and preferably equal to or no greater than 2.0 cm in thickness (or height), and most preferably equal to or no greater than 1.5 cm in thickness (or height), and much more preferably equal to or no greater than 1.3 cm. Depending on the size of the person other dimensions of measuring portion 2006 are contemplated, such as height (or thickness) equal to or no greater than 1.0 cm, and for children thickness (or height), equal to or no greater than 0.8 cm, and for babies or small children equal to or no greater than 0.5 cm. Depending on the size of an animal other dimensions of measuring portion 2006 are contemplated, such as thickness (or height) equal to or no greater than 5 cm. In the case of a measuring portion having a rectangular shape, the thickness or height referred to herein, is replaced by the length of the rectangle, and the above dimensions then are applicable.

The following preferred dimensions in this paragraph pertain to a single sensor, such as a temperature sensor or a pulse sensor or a chemical sensor. In this embodiment the preferred largest dimension of measuring portion 2006 is equal to or no greater than 6 cm, and preferably equal to or no greater than 3 cm, and most preferably equal to or no greater than 1.5 cm. The preferred general dimensions for human use for measuring portion 2006 having a cylindrical shape are height (or thickness) equal to or less than 1.2 cm and diameter equal to or less than 0.8 cm, and most preferably height equal to or less than 1.0 cm and diameter equal to or less than 0.6 cm Preferred length of a non-cylindrical measuring portion 2006 is equal to or less than 1.2 cm and width equal to or less than 0.8 cm, and most preferably length equal to or less than 1.0 cm and width equal to or less than 0.6 cm. The preferred height (or thickness) of measuring portion 2006 ranges between equal to or more than 0.4 cm and equal to or less than 2.0 cm. The preferred diameter of measuring portion 2006 ranges between equal to or more than 0.4 cm and equal to or less than 2.0 cm. Although a temperature sensor was illustrated, it is understood that any sensor can be used. For a pair sensor-detector, a pair light emitter-detector, an infrared sensor, or a sensor and combination with other elements such as a heating element other dimensions can be preferably used, and will be described below.

Measuring portion 2006 can be formed integral with arm 2004 creating a single part consisting of an arm and a measuring portion. Preferably, at least a portion of the material used for measuring portion 2006 is different from the material used for arm 2004. Arm 2004 and measuring portion 2006 preferably comprise two separate parts. In one embodiment for measuring temperature the arm 2004 is made in its majority with an adjustably positionable material such as deformable metal while measuring portion 2006 includes a portion of non-metal materials such as polymers, plastics, and/or compressible materials. The metal portion of arm 2004 can be preferably covered with rubber for comfort. Preferred materials for measuring portion 2006 include foams, rubber, polypropylene, polyurethane, plastics, polymers of all kinds, and the like. Preferably, measuring portion 2006 housing a temperature sensor comprises an insulating material, and includes a compressible material and/or a soft material. Measuring portion 2006 can include any compressible material. Measuring portion 2006 can further include a spring housed in the body 2020. Any other material with spring capabilities can be housed in body 2020 of measuring portion 2006.

Preferably, the end portion 2018 of measuring portion 2006 comprises an insulating material. Preferably the end portion 2018 comprises a non-heat conducting material including non-metallic material or non-metal material. Preferably, the end portion 2018 comprises a soft material including polymers such as polyurethane, polypropylene, Thinsulate, and the like in addition to foam, sponge, rubber, and the like.

The largest dimension of end portion 2018 of measuring portion 2006 is preferably equal to or less than 4 cm, and most preferably equal to or less than 2 cm, and even more preferably equal to or less than 1.5 cm. Accordingly, the dimensions of sensor 2010 preferably follow those dimensions of end portion 2018, said sensor 2010 being of smaller dimension than the dimension of end portion 2018. For the embodiment for measurement of temperature, the largest dimension of end portion 2018 is preferably equal to or less than 1 cm, and most preferably equal to or less than 0.8 cm, and even most preferably equal to or less than 0.6 cm.

Methods and apparatus include measuring portion 2006 touching the body part during measurements or measuring portion 2006 being spaced away from the body part and not touching the body during measurement.

In one preferred embodiment the end portion 2018 of measuring portion 2006 does not have an adhesive surface and the surface around sensor 2010 is also adhesive free. In the prior art, sensors are secured in place by adhesive surfaces, with said adhesive surrounding the sensor. Contrary to the prior art, sensors of the present invention do not have adhesive surrounding said sensors, and said sensors of the present invention are secured in place at the measuring site in the body of a mammal by another structure, such as arm 2004, with the adhesive surface being located away from the sensor surface. Accordingly, in one preferred embodiment of the present invention, the surface of the sensor and the surface of the surrounding material around the sensor is adhesive free.

Now in reference to FIG. 86D, by way of an example, FIG. 86D shows a planar diagrammatic view of an embodiment that includes a body 2002-*a* shaped as a square, an arm 2004-*a* shaped in a zig-zag configuration and a measuring portion 2006-*a* shape as a hexagon. In this embodiment, the height (or thickness) of the measuring portion 2006 (represented herein by the height or thickness of the hexagon 2006-*a*) is of larger dimension than the height or thickness of the arm 2004 (represented herein by the thickness of the zig-zag arm 2004-*a*). The thickness of square body 2002-*a* is the smallest dimension of said square body 2002-*a*, which is compared to the smallest dimension of the hexagon 2006-*a*, which is the length of said hexagon 2006-*a* from point (a) to (b). Accordingly, thickness of the square 2002-*a* (body) is smaller than the length of hexagon 2006-*a*, said hexagon 2006-*a* representing a measuring portion. The length of arm 2004-*a* is the largest dimension of arm 2004-*a*, which is compared to the largest dimension of hexagon 2006-*a*, which is the height or thickness of said hexagon 2006-*a*, from point (c) to point (d), as seen in FIG. 86E.

FIG. 86E is a diagrammatic side view of the embodiment of FIG. 86D and illustrates the thickness (or height) of the embodiment of FIG. 86D. Accordingly, as per the principles of the invention, length of the zig-zag arm 2004-*a*, represented by point (e) to (f), is of greater dimension than the thickness of hexagon 2006-*a*, represented by point (c) to (d).

To further illustrate the principles of the invention, FIG. 86F shows an embodiment that includes a body 2002-*b* shaped as an irregular geometric shape, an arm 2004-*b* shaped in a triangular configuration and a measuring portion 2006-*b* shape as a rectangle. The thickness of arm 2004-*b* is the smallest dimension of arm 2004-*b*, which is compared to the smallest dimension of rectangle 2006-*b*, which is the width of said rectangle 2006-*b* from point (g) to point (h). Accordingly, as per the principles of the invention, the thickness of the arm 2004-*b* is equal to or smaller than the width of rectangle 2006-*b*, with said rectangle 2006-*b* representing a measuring portion.

FIG. 86G is a diagrammatic perspective view of another preferred embodiment showing end portion 2018 of measuring portion 2006 having a light emitter-light detector pair assembly 2030, also referred to as radiation source-radiation detector pair. The end portion 2018 of measuring portion 2006 in this embodiment has preferably a larger dimension than the diameter (or dimension) of body 2020 of said measuring portion 2006. The radiation source-detector pair 2030 is preferably housed in a substantially rigid substrate 2024, such as a plastic plate. Although substrate 2024 can have any shape, exemplarily and preferably substrate 2024 has an essentially rectangular shape. Rectangular plate 2024 houses at least one light emitter 2032 in one side and at least one light detector 2034 on the opposite side. Light emitter 2032 is connected to at least one wire 2036 secured to the body 2020 of measuring portion 2006. Detector 2034 is connected to at least one wire 2038 secured to the body 2020 of measuring portion 2006. Wire 2036, 2038 start at the light-emitter-light detector pair 2030 in plate 2024 and run along the body 2020. Wire 2036 and wire 2038 preferably form a single multi-strand wire 2040 which exit body 2020 at the upper portion 2016 of measuring portion 2006, said wire 2040 being disposed on or within arm 2004, and further disposed on or within body 2002 for connecting light emitter-detector pair assembly 2030 to a processing circuit and display and/or a transmitter 2031. The body 2020 of measuring portion 2006 can preferably comprise a rigid material. The light emitter 2032 and detector 2034 are centrically located in plate 2024 in this illustrative embodiment. It is understood that light emitter 2032 and detector 2034 can be eccentrically located in plate 2024 depending on the anatomic configuration of the subject being measured.

FIG. 86H is a diagrammatic cross-sectional view of a preferred embodiment, and depicts a sensing device 2000 including body 2020 of measuring portion 2006 having on its free end the light source-light detector pair 2030, with light detector 2034 being adjacent to light source 2032. The radiation source-detector pair assembly 2030 is preferably mounted on a substantially rigid holder, such as plate 2024. Plate 2024 can preferably comprise a rigid or semi rigid material to allow stable reflectance measurements. Detector 2034 includes a photodetector adapted to detected radiation, including infrared radiation, received from light source 2032 and can include a printed circuit board. Light source assembly 2032 is adapted to emit radiation, including infrared radiation, directed at the brain tunnel and can include a printed circuit board. Plate 2024 can house a single or a plurality of light sources and a single or a plurality of light detectors. For example, in a pulse oximetry sensor the light source assembly may include a plurality of light sources, such as a red light emitting diode and an infrared light emitting diode. Illustratively plate 2024 is shown housing one light source 2032 in one side and one detector 2034 on the opposite side. Light emitter 2032 is connected to at least one wire 2036 secure to the body 2020 of measuring portion 2006. Detector 2034 is connected to at least one wire 2038 secured to the body 2020 of measuring portion 2006. Body 2020 is shown as an integral part with arm 2004. In this embodiment body 2020 of measuring portion 2006 forms one piece with arm 2004. Wires 2036, 2038 start at the light source-light detector pair assembly 2030 in plate 2024 and run on or within the body 2020. Wire 2036 and wire 2038 preferably form a single multi-strand wire 2040 which exits body 2020 and runs along arm 2004, and is further disposed on or within body 2002. Electric signals are carried to and from the light source and light detector assembly 2030 preferably by the multi-strand electric cable 2040, which terminates at an electrical connector for connection to a processing circuit and display and/or a transmitter (not shown). Wires 2036, 2038, and 2040 can be disposed on or within the measuring portion 2006, arm 2004, or body 2002. Plate 2024 can preferably be adapted to provide protection against light from the environment reaching emitter-detector pair 2030.

FIG. 86-I is a planar bottom view of plate 2024 showing an exemplary embodiment of said plate 2024. Plate 2024 has preferably two openings 2035, 2033 for respectively housing light emitter 2032 and light detector 2034. Light emitter 2032 and light detector 2034 are preferably disposed adjacent to each other, and in the center of plate 2024. The light source 2032 and light detector 2034 may be encased by a protective transparent material such as silicone.

Although the preferred embodiment includes an arm 2004 for support structure which works as a sensing device 2000, it is understood that arm 2004 can be replaced by a wire or cord. Accordingly, FIG. 86J shows a diagrammatic planar view of an alternative embodiment comprising an adhesive patch 2025 securing plate 2024, said adhesive patch being connected through cord 2041 to a reading and display unit 2043. The measuring portion in this embodiment comprises an adhesive patch housing a sensor assembly, said adhesive patch connected through a cord to a display unit. Illustratively the sensor or sensing portion in this embodiment is represented by light source-light detector pair 2030. Plate 2024 includes emitter 2032 and detector 2034, respectively connected to wire 2036 and wire 2038. Wire 2036 and 2038 terminates in cord 2041. Cord 2041 houses the wires 2036, 2038, and is preferably flexible in nature. In order to fit the tunnel, and in accordance with the present invention specialized dimensions are needed for functioning. The preferred longest distance between the edge of plate 2024 and adhesive patch 2025 is equal to or less than 12 mm, and preferably equal to or less than 6 mm, and most preferably equal to or less than 3 mm. The largest dimension of patch 2025 is preferably equal to or less than 3 cm and most preferably equal to or less than 2 cm, and even most preferably equal to or less than 1.5 cm. Preferably plate 2024 is located in an eccentric position on adhesive patch 2025.

FIG. 86J shows by way of illustration edge 2023 of plate 2024 and edge 2027 of patch 2025, both located at the free end of the patch 2025 opposite to the cord 2041. Edge 2023 is located preferably equal to or less than 8 mm from the edge 2027 of adhesive patch 2025, and most preferably equal to or less than 5 mm from edge 2027 of adhesive patch 2025, and even more preferably equal to or less than 3 mm from edge 2027 of adhesive patch 2025. Preferred dimensions of the plate 2024 are described in FIG. 86N. A preferred dimension of adhesive patch 2025 includes a width or diameter equal to or less than 25 mm, and preferably equal to or less than 20 mm, and most preferably equal to or less than 15 mm, and even more preferably equal to or less than 10 mm. Those dimensions are preferably used for a centrically placed single sensor, multiple sensors, light emitter-light detector pair, or for an eccentrically placed sensor. The preferred configuration of the adhesive patch is rectangular or oblong, or any configuration in which the sides of the geometric figure are not equal in size. In this embodiment there is no body for the support structure as in the embodiments of FIG. 86H and FIG. 86G. The support structure in this embodiment is comprised of a specialized adhesive patch 2025 connected to a cord 2041, said cord 2041 terminating in a processing circuit and display unit 2043. It is also contemplated that cord 2041 can exit patch 2025 from any of its sides FIG. 86K shows another embodiment when worn by a user comprised of an adhesive patch 2060 housing a light emitter-light detector pair 2062, which is housed in a holder such as plate 2064, said plate 2064 being adjacent to the edge of said adhesive patch 2060. At least one portion of adhesive patch 2060 and the light emitter-light detector pair 2062 is located between the eyebrow 2066 and eye 2068. At least a sensor such as light emitter-light detector pair 2062 is located between the eye 2066 and the eyebrow 2068. Adhesive patch 2062 can include a forehead portion 2070 located on the forehead and an upper eyelid portion 2072 located on the upper eyelid. Any sensor including a pair light emitter-light detector is preferably positioned adjacent to the junction 2074, said junction representing a junction of the end of the eyebrow 2066 with the upper portion of the nose 2075, said junction 2074 represented as a dark circle in FIG. 86K. A sensor housed in the adhesive patch is preferably located in the roof of the orbit area, right below the eyebrow. Adhesive patch 2060 further includes wire 2076 which terminates in a processing circuit and display unit 2078.

FIG. 86L shows another embodiment when worn by a user comprised of an adhesive patch 2080 housing light emitter-light detector pair 2082, said emitter and detector 2082 being located apart from each other, and adjacent to edge 2084 of said adhesive patch 2080. At least one portion of adhesive patch 2080 and a sensor such as the light emitter-light detector pair 2082 is located between the eyebrow 2086 and eye 2088. At least light emitter-light detector pair 2082 is located between the eye 2086 and the eyebrow 2088. Adhesive patch 2080 comprises a nose portion 2090 located on the nose and an upper eyelid portion 2092. Any sensor including a pair light emitter-light detector is preferably positioned adjacent to the eyebrow 2086. The sensor housed in the adhesive patch is preferably located above the eye 2088 and just below the eyebrow 2086. Adhesive patch 2080 further includes wire 2094 which terminates in a processing circuit and display unit 2096, which processes the signal in a conventional manner to detect oxygen saturation and/or concentration of analytes.

FIG. 86M shows another embodiment comprised of a clover-leaf adhesive patch 2100 housing light emitter-light detector pair 2102 housed in plate 2104, and preferably adjacent to edge 2106 of said adhesive patch 2100. Adhesive patch 2100 comprises a sensing portion 2108 housing plate 2104 and a supporting portion 2110 that includes an adhesive surface. Emitter-detector pair 2102 is preferably eccentrically positioned on patch 2100 and further includes wire 2113 from light emitter 2114 and wire 2116 from detector 2118. Wires 2113 and 2116 join at the edge of plate 2104 to form cord 2112 which terminates in unit 2120 which houses processing circuit 2124, memory 2126, and display 2122.

Light emitter 2114 preferably emits at least one infrared wavelength and a detector 2118 is adapted to receive and detect at least one infrared wavelength. Light emitter-detector pair 2102 is preferably eccentrically positioned in adhesive patch 2100, said light emitter-detector pair 2102 being located at the edge of patch 2100. Imaginary line from point (A) to point B going across plate 2104 on adhesive patch 2100 housing light emitter-detector pair 2102 measures equal to or less than 3.0 cm, and preferably measures equal to or less than 2.0 cm, and most preferably equal to or less than 1.5 cm. The preferred distance of external edge 2103 of light emitter-detector pair 2102 to the edge 2105 of patch 2100 is less than 14 mm, and preferably less than 10 mm and most preferably less than 5 mm.

Another embodiment includes an adhesive patch housing a sensor comprised of an adhesive surface intersected by a non-adhesive surface. Accordingly, FIG. 86M(1) shows the back side of adhesive patch 2131, said side being disposed toward the skin and in contact with the skin, and comprised of a first adhesive surface 2121, a second non-adhesive surface 2123, and a third adhesive surface 2125 which houses the sensor 2127. The adhesive surface is intersected by a non-adhesive surface. The non-adhesive surface 2123 is adapted to go over the eyebrow, preventing the adhesive from attaching to hair of the eyebrow.

FIG. 86N is another embodiment showing the configuration and dimensions of light emitter-detector pair 2130 and plate 2136. Light emitter 2132 and detector 2134 are disposed preferably as a pair and are positioned side-by-side for reflectance measurements. The preferred dimension of light emitter 2132 is no greater than 1.5 cm in its largest dimension and preferably no greater than 0.7 cm, and most preferably no greater than 0.5 cm, and even most preferably equal to or less than 0.4 cm. The preferred dimension of detector 2034 is equal to or no greater than 1.5 cm in its largest dimension and preferably equal to or no greater than 0.7 cm, and most preferably equal to and no greater than 0.5 cm, and even most preferably equal to or less than 0.4 cm. The preferred distance between inner edge 2138 of light emitter 2132 and the inner edge 2140 of detector 2134 is equal to or less than 0.7 cm, and preferably equal to or no greater than 0.5 cm, and most preferably equal to or no greater than 0.25 cm. It is understood that to better fit the anatomic configuration of the brain tunnel for a vast part of the population, light emitter 2132 and detector 2134 are preferably disposed side-by-side and the distance between the inner edge 2138 of light emitter 2132 and inner edge 2140 of detector 2134 is preferably equal to or no greater than 0.1 cm.

Although a pair radiation emitter-detector has been described, it is understood that another embodiment includes only a radiation detector and the measuring portion 2006 is comprised of a radiation detector for detecting radiation naturally emitted by the brain tunnel. This embodiment can include a infrared detector and is suitable for non-invasive measurement of analytes including glucose as well as temperature, with detector adapted to contact the skin or adapted as non-contact detectors, not contacting skin during measurement.

FIG. 86P shows another embodiment comprised of an essentially cylindrical measuring and sensing portion 2150. Cylindrical structure 2150 operates as the measuring portion and houses a emitter-detector pair 2152 and a wire portion 2153, with said measuring portion 2150 being connected to arm 2154. Arm 2154 comprises an adjustably positionable arm which houses wire portion 2155. Arm 2154 is preferably cylindrical contrary to arm 2004 which has preferably a flat configuration. Arm 2154 connects measuring portion 2150 to supporting portion 2151 which includes adhesive and/or attachment means. Light emitter 2156 and light detector 2158 are preferably positioned adjacent to each other within the holder 2150, represented by cone structure. Light emitter-detector pair 2152 can preferably have a bulging portion, which goes beyond the plane of the edge 2162 of cylindrical measuring portion 2150. Cylindrical measuring portion 2150 can also include a spring 2160, or any other compressible material or material with spring-like characteristics, said spring 2160 or compressible material being disposed along wire portion 2153. Light emitter-detector pair 2152 is disposed at the free end of said spring 2160. It is understood that any sensor, molecule, detector, chemical sensors, and the like can be disposed at the free end of spring 2160. Wire portion 2155 terminates in wire portion 2149 disposed on or within body 2151. Body 2151 can include any support structure, preferably a plate such as shown in FIG. 86A, as well as the frame of eyewear, a headband, the structure of a helmet, the structure of a hat, or any head mounted gear. Wire 2149 can be further connected to a processing circuit and display 2147.

Preferred diameter at the free end of measuring portion 2150 is equal to or no greater than 3.5 cm, and preferably equal to or no greater than 2.0 cm, and most preferably equal to or no greater than 1.5 cm, and even most preferably equal to or no greater than 1.0 cm. Depending on size of a subject and the type of sensor such as temperature, pressure, and the like the preferred diameter at the free end of measuring portion 2150 is equal to or no greater than 0.8 cm and preferably equal to or no greater than 0.6 cm, and more preferably equal to or no greater than 0.4 cm. Preferred length from point 2150(a) to point 2150(b) of measuring portion 2150 is equal to or no greater than 3 cm, and preferably equal to or no, greater than 1.5 cm, and most preferably equal to or no greater than 1 cm. Depending on size of a subject the preferred length from point 2150(a) to point 2150(b) of cone structure 2150 is equal to or no greater than 0.8 cm and preferably equal to or no greater than 0.6 cm, and more preferably equal to or no greater than 0.4 cm. Measuring portion 2150 can include a contact sensor in which the sensor contacts the skin at the brain tunnel or a non-contact sensor in which the sensor does not contact the skin at the brain tunnel during measurement.

FIG. 86P(1) is an exemplary sensing device 2191 for non-contact measurements at the brain tunnel 2187 and shows sensing portion 2181 housing a sensor illustrated as an infrared sensor 2183 to detect infrared radiation 2185 coming from the brain tunnel 2187. Sensing portion 2181 housing sensor 2183 is connected to body 2193 through adjustably positionable arm 2189. Wire 2195 connects sensor 2183 to body 2193. Sensor 2183 can include any infrared detector, and is adapted to receive and detect infrared radiation from the brain tunnel 2187 for determining temperature, concentration of substances including glucose, and any other measurement of analytes or tissue. Sensor 2183 can also work as a fluorescent sensor, and may include a fluorescent light source or fluorescein molecules. Furthermore, sensor 2183 can include enzymatic sensors or optical sensors.

FIG. 86P(2) is an exemplary sensing device 2197 for non-contact measurements at the brain tunnel 2187 and shows sensing portion 2199 housing a light source-light detector pair assembly 2201, such as an infrared sensor or a fluorescent element. It is contemplated that any electromagnetic radiation including radio waves can be directed at the brain tunnel for determining concentration of analytes and/or presence of analytes and/or absence of analytes and/or evaluating tissue. Light source 2203 directs radiation 2207 such as mid-infrared and/or near-infrared radiation at the brain tunnel 2187 which contains molecules 2205 (including analytes such as glucose), said radiation 2207 generating a reflected radiation that contains the radiation signature of the analyte being measured after said radiation 2207 interacts with the analyte being measured. The reflected radiation 2209 is then detected by detector 2211. The electrical signal generated by the detector 2211 is then fed to a processing circuit (not shown) housed in body 2217 through wire 2213 housed in arm 2215. Sensing portion 2199 housing pair assembly 2201 is preferably connected to body 2217 through an adjustably positionable arm. Detector 2211 can include any infrared detector, and is adapted to receive and detect infrared radiation from the brain tunnel 2187 for determining temperature, concentration of substances including glucose, and any other measurement of analytes or tissue. Detector 2211 can also work as a fluorescent detector for detecting fluorescent light generated.

FIG. 86P(3) is an exemplary hand-held sensing device 2219 for non-contact measurements at the brain tunnel 2187 and shows a light source-light detector pair assembly 2221. Light source 2223 directs radiation 2225 at the brain tunnel 2187 which contains molecules 2205 (including analytes such as glucose), said radiation 2225 generating a reflected radiation 2227 that contains the radiation signature of the analyte being measured after said radiation 2225 interacts with the analyte being measured. The reflected radiation 2227 is then detected by detector 2231. The electrical signal generated by the detector 2231 is then fed to a processing circuit 2233 which calculates the concentration of an analyte based on a calibration reference stored in memory 2235, and display said concentration on display 2237. It is understood that instead of a pair light source-light detector, a stand alone detector for detecting infrared radiation naturally emitted from the brain tunnel can also be used. It is also understood that sensing device 2219 can preferably include a mirror 2229, so as to allow the user to proper position the pair assembly 2221 in line with the skin of the BTT 2187 at the eyelid area. It is contemplated that sensing device 2219 can comprise a mirror in which electronics, display, and pair assembly 2221 are mounted in said mirror, allowing thus measurement of temperature and concentration of analytes being performed any time the user look at the mirror. It is understood that any of the embodiments of the present invention can include a mirror for accurate measurements and proper alignment of a sensor with the BTT.

FIG. 86P(4) is an exemplary sensing device 2239 for non-contact measurements at the brain tunnel 2187, said sensing device 2239 mounted on a support structure 2267, such as a wall or on an article of manufacture or an electronic device including a refrigerator, a television, a microwave, an oven, a cellular phone, a photo camera, video camera, and the like. In this embodiment just performing routine activities such as opening a refrigerator door allows the user to check core temperature, measure glucose, check for cancer markers, and the like. The spectral information contained in the radiation from the brain tunnel is captured by a sensor slidably located on those electronic devices and articles to align with different height individuals. To better align the brain tunnel area 2187 with the sensing device 2239, a light source 2241, such as LED or other confined light source is used. When the eye 2243 of the user is aligned with the light 2241 projecting from a tube or other light path confining or constricting device, the BTT area is aligned with the light source-light detector pair 2251 located at a predetermined distance from the eye. Light source 2253 directs radiation 2255 at the brain tunnel 2187 which contains molecules 2205 (including analytes such as glucose, cholesterol, ethanol, and the like), said radiation 2255 generating a reflected radiation 2257 that contains the radiation signature of the analyte being measured. The reflected radiation 2257 is then detected by detector 2259. The electrical signal generated by the detector 2259 is then fed to a processing circuit 2261 which is operatively coupled with memory 2263, and display 2265. It is understood that an iris scanner, a retinal scanner, or the like or any biometric device such as finger print detectors or camera-like device can be coupled with sensing device 2239. In this embodiment, the pair light source-light detector is preferably replaced by a detector such as for example a thermopile or array of thermopile as previously described in the present invention. Accordingly, light source 2241 can include or be replaced by an iris scanner which identifies a person while measuring the person's core body temperature. This embodiment can be useful at port of entries such as airports in order to prevent entry of people with undetected fever which could lead to entry of fatal disorders such as SARS, bird flu, influenza, and others. The temperature of the person, measured by the sensor aimed at the BTT, is coupled to the identity of the person acquired through the iris scanning, with said data temperature-iris scan being stored in a memory. The system may include a digital camera, allowing a picture of the person being coupled with the body core temperature and the iris scan. A processor identifies whether the temperature is out of range, and activates an alarm when fever is detected. The system allows measurement of temperature and concentration of analytes being performed any time the user look at the iris scanner.

It is understood that a sensor for detecting radiation or capturing a signal from the brain tunnel can be mounted on any device or article of manufacturing. Accordingly and by way of further illustration, FIG. 86P(5) shows a sensing device 2273 including a sensor 2269 mounted on a web-camera 2271 which is secured to a computer 2275 for measurements of radiation from the brain tunnel 2187, said sensing device 2273 having a cord 2277 which is connected to computer 2275 and carries an electrical signal generated by detector 2269, with the electrical signal being fed into the computer 2275. In this embodiment, the processor, display and other electronics are housed in the computer. Any time a user looks at the web-camera, measurement of body temperature and/or determination of concentration of analyte can be accomplished.

FIG. 86Q is a side cross-sectional view of sensing device 2000 showing in detail measuring portion 2006. Measuring portion 2006, as illustrated, includes two portions, external part 2162 and internal part 2164, said parts 2162, 2164 having different diameters. Measuring portion 2006 is comprised preferably of a two level (or two height structure) 2163. The external part 2162 has a larger diameter as compared to the internal part 2164. The height (or thickness) of internal part 2164 is of greater dimension than the height (or thickness) of external part 2162. Each part, external part 2162 and internal part 2164, has preferably a different thickness (or height). External part 2162 and internal part 2164 connect to free end 2165 of arm 2161, said arm 2161 terminating in body 2159.

Measuring portion 2006 has an essentially circular configuration and has a wire portion 2166 disposed in the internal part 2164. External part 2162 can comprise a washer or ring around internal part 2164. Internal part 2164 has preferably a cylindrical shape and houses wire portion 2166 inside its structure and houses sensor 2170 at its free end. Wire portion 2166 terminates in wire portion 2167 secured to arm 2161. Although a circular configuration is shown, any other shape or combination of shapes is contemplated.

FIG. 86Q(1) is a perspective diagrammatic view of measuring portion 2006 of FIG. 86Q showing two tiered external part 2162 and internal part 2164, said internal part 2164 housing wire 2166 which terminates in sensor 2170. In order to fit the brain tunnel, specialized geometry and dimensions are necessary. The preferred diameter (or length incase of a non-circular shape) of part 2162 is equal to or no greater than 3.0 cm, and preferably equal to or no greater than 1.5 cm in diameter or length, and most preferably equal to or no greater than 1.0 cm in diameter or length. For a non-circular configuration that includes a width, the preferred width of part 2162 is equal to or no greater than 3.0 cm, and preferably equal to or no greater than 2.0 cm in width, and most preferably equal to or no greater than 1.0 cm in width. The preferred height (or thickness) of part 2162 is equal to or no greater than 3.5 cm, and preferably equal to or no greater than 2.5 cm in thickness, and most preferably equal to or no greater than 1.5 cm in thickness, and much more preferably equal to or no greater than 0.5 cm in thickness. The preferred largest dimension of part 2162 is no greater than 3.5 cm, and preferably no greater than 2.0 cm, and most preferably no greater than 1.5 cm.

Part 2164 has preferably an essentially cylindrical configuration, although any other configuration or geometry is contemplated and can be used in accordance with the invention. The preferred diameter of part 2164 is equal to or no greater than 3.0 cm, and preferably equal to or no greater than 2.0 cm in diameter or length, and most preferably equal to or no greater than 1.0 cm. For a non-circular configuration that includes a width, the preferred width of part 2164 is equal to or no greater than 3.0 cm, and preferably equal to or no greater than 1.5 cm in width, and most preferably equal to or no greater than 1.0 cm in width. The preferred height (or thickness) of part 2164 is equal to or no greater than 3.5 cm, and preferably equal to or no greater than 2.5 cm, and most preferably equal to or no greater than 1.0 cm, and much more preferably equal to or no greater than 0.7 cm. The preferred largest dimension of part 2164 is no greater than 3.5 cm, and preferably no greater than 2.0 cm in diameter or length, and most preferably no greater than 1.5 cm.

For temperature monitoring, preferably, part 2162 and part 2164 are made with an insulating material such as polyurethane, polypropylene, thinsulate, and the like, however, other materials are contemplated, including other polymers, foams, and the like. Part 2162 and part 2164 preferably comprise a compressible material for certain applications.

FIG. 86R shows a diagrammatic perspective view of sensing device 2000 including plate 2180, said plate 2180 having preferably a soft and flexible portion 2172, such as a pad, for cushion, said pad including foam, silicone, polyurethane, or the like, with said soft portion 2172 having an adhesive surface 2174 which is covered by a peel back cover 2176. When in use the cover 2176 is removed by pulling tab 2175, and the adhesive surface 2174 is applied to the skin, preferably on the skin of the forehead or any other part of the face and head, but any other body part is suitable and can be used to secure securing plate 2180. Plate 2180 further comprises preferably an essentially semi-rigid portion 2281, said semi-rigid portion 2281 being connected to soft portion 2172. Semi-rigid portion 2281 can preferably comprise a thin metal sheet such as a metal with memory shape as steel. Semi-rigid portion 2281 can also include plastics and polymers. It is understood that preferably said semi-rigid portion 2281 has flexible characteristics to conform to a body part. Although semi-rigid portion 2281 is disclosed as a preferred embodiment, alternatively, plate 2180 can function only with soft portion 2172.

Rigid portion 2281 of plate 2180 continues as arm 2184, said arm 2184 having a free end 2188 which connects to measuring portion 2186. Measuring portion 2186 includes sensor 2190, said sensor 2190 is preferably disposed as a bulging portion. During use the method includes the steps of, applying plate 2180 to the skin, bending arm 2184 to fit with the particular anatomy of the user and for positioning the sensor 2190 on or adjacent to the skin of the BTT or other tunnels of the invention. Other steps include measuring an analyte or analyzing a tissue, producing a signal corresponding to the measurement and analysis, and reporting the results. Further steps can include processing the signal and displaying the result in alphanumerical format, audible format, a combination thereof and the like. A further step can include transmitting the signal to another device using a wireless or wired transmitter. The step of chemical measuring an analyte can be replaced by measuring a physical parameter such as temperature, pulse, or pressure.

FIG. 86R(1) shows a schematic view of sensing device 2289 when worn by a user 2293 and including a headband 2283 around the forehead, said headband 2283 attached to plate 2291, said plate 2291 having arm 2285 and a sensor 2287 which receives radiation from the brain tunnel 2187.

FIG. 86R(2) shows a schematic view of sensing device 2295 having a swivel mechanism 2297 at the junction of arm 2299 and body 2301, said swivel mechanism allowing rotation and motion of arm 2299 (represented by broken arrows) for positioning sensor 2303 on or adjacent to a brain tunnel. Sensor 2303 is illustrated as a light source-detector pair, with wire 2305 connecting said sensor 2303 to a processing and display unit 2307.

FIG. 86R(3) shows the embodiment of FIG. 86R(2) when worn by a user 2309, and depicting light source-detector pair 2303 positioned on the brain tunnel 2187. Body 2301 is secured to the forehead 2311 preferably by adhesive means 2313 disposed at the inner surface of body 2301, said body 2301 connected to arm 2299 by swivel mechanism 2297, which is preferably positioned over the eyebrow.

FIG. 86S(1) shows a side view of sensing device 2000 including wire 2198 which is disposed flat and without any bending, and runs from sensor 2210 in measuring portion 2196 to body 2192. Measuring portion 2196 is aligned with arm 2194 and body 2192. In this embodiment, the axis of measuring portion 2196 is in line with arm 2194, and forms a 180 degree angle. During fabrication the 180 degree angle configuration and flat shape is obtained. During use, in accordance with the method of the invention, the arm 2194 is bent. Since arm 2194 is flexible and adjustably positionable, during use arm 2194 is bent for positioning measuring portion 2196 in line with the brain tunnel.

Accordingly, FIG. 86S(2) shows sensing device 2000 worn by a user with arm 2194 bent in order to position sensor 2210 of measuring portion 2196 on or adjacent to brain tunnel area 2214 between the eyebrow 2212 and eye 2216. Wire 2198 connects sensor 2210 to body 2192, said body 2192 being preferably secured to the forehead.

Sensing device 2000 can be powered by active power including batteries secured to body 2002, solar power, or by wires connecting sensing device 2000 to a processing unit. It is also understood that any of the sensors housed in an adhesive patch or housed in support structure 2000 can operate on a passive basis, in which no power source is housed in said sensor system. In the case of passive systems, power can be provided remotely by electromagnetic waves. An exemplary embodiment includes Radio Frequency ID methodology, in which a nurse activates remotely the patch or sensor system 2000 of the present invention which then reports back the identification of the patient with the temperature being measured at the time of activation. The sensor system can also include a transponder which is powered remotely by a second device, which emits a radio signal or any suitable electromagnetic wave to power the sensor system. Besides temperature, any other biological parameter can be measured such as pulse, blood pressure, levels of chemical substances such as glucose, cholesterol, and the like in addition to blood gases, oxygen levels, oxygen saturation, and the like.

It is yet understood that arm 2004 connected to measuring portion 2006 can be detachably connected to plate 2002, with said arm 2004 and measuring portion 2006 becoming a disposable part while plate 2002, which preferably houses expensive wireless transmitter and other electronics and power source, works as the durable part of the device 2000. It is also understood that measuring portion 2006 can be detachably connected to arm 2004, said measuring portion 2006 being disposable. It is yet understood that the free end of measuring portion 2006 can be connected to a wire inside body 2020 of measuring portion 2006, said free end housing sensor 2010 being the disposable part. It is also contemplated that the present invention is directed to a method and apparatus in which the disposable part is the body 2002 and the durable reusable part is the measuring portion 2006 and arm 2004. In this embodiment an expensive sensor such as an infrared detector can be disposed in the measuring portion 2006, and is detachably connected to plate 2002, said sensor being the reusable part while the body 2002 being the disposable part. Accordingly, FIG. 86T(1) shows sensing device 2000 including arm 2004, measuring portion 2006 with sensor 2010, and plate 2002, said plate 2002 housing a circuit board 2200 including a processor 2222 operatively coupled to a memory 2228, power source 2224, and transmitter 2226. Wire 2220 connects sensor 2010 to circuit board 2200.

FIG. 86T(2) shows an exemplary embodiment of sensing device 2000 comprised of two separable pieces including a durable part 2230, represent by the body, and a disposable part 2232, represented by the arm and measuring portion. It is understood that sensing device can comprise one or more parts and a combination of durable and disposable parts. Accordingly, in FIG. 86T(2) there is seen durable part 2230 represented by plate 2002, said plate 2002 having a circuit board 2200 including processor 2222 operatively coupled to a memory 2228, power source 2224, and transmitter 2226. Disposable part 2232 comprises arm 2204 and measuring portion 2006. Plate 2002 has an electrical connector 2234 which is electrically and detachably connected to an electrical connector 2236 of arm 2004, preferably creating a male-female interface for electrical connection in which wire 2220 of arm 2004 ends as a male connector 2236 adapted to connect to a female connector 2234 of plate 2002.

FIG. 86T(3) shows an exemplary embodiment of sensing device 2000 comprised of two separable pieces including a durable part 2240 further comprised of arm 2004 and plate 2002 and a disposable part 2242 comprised of measuring portion 2006, said measuring portion 2006 including a light emitter-light detector pair 2244. Arm 2004 has an electrical connector 2246 which is electrically and detachably connected to an electrical connector 2248 of measuring portion 2006.

It is contemplated that durable part represented by plate 2002 can comprise power source and a LED for alerting changes in the biological parameter being measured or to identify that the useful life of the device has expired. Plate 2002 can also house a power source and a wireless transmitter, or a power source and a display for numerical display, or/and a combination thereof. Alternatively plate 2002 works as a passive device and comprises an antenna and other parts for electromagnetic interaction with a remote power source. Another embodiment includes a passive device or an active device comprised of a patch having a sensor and a LED, said LED being activated when certain values are detected by the sensor, allowing a nurse to identify for example a patient with fever by observing a patch in which the LED is on or flashing.

Any biological parameter and tissue can be measured and/or analyzed at the brain tunnel including temperature, concentration of chemical substances, blood pressure, pulse, and the like. Exemplarly a blood gas analyzer and a chemical analyzer will be described. The embodiment relates to a device for the transcutaneous electrochemical or optical determination of the partial pressure of oxygen and/or analytes in the blood of humans or animals at the Brain Temperature Tunnel (BTT) site, also referred to as brain tunnel (BT). The invention comprises a measuring portion 2006 which includes a measuring cell having electrodes, said cell having a surface which is to be disposed in contact with the skin at the BTT. The cell in measuring portion 2006 can include a heating or a cooling element for changing the temperature of the brain tunnel. Preferably the measuring portion 2006 includes an electrical heating element. Besides contacting the skin, the measuring surface of measuring portion 2006 can be spaced away from the skin at the brain tunnel for measuring analytes and the partial pressure of oxygen.

For measurement of oxygen the measuring portion 2006 preferably includes a Clark type sensor, but it is understood that any electrochemical or optical system can be used in accordance with the present invention and fall within the scope of the present invention. Various sensors, electrodes, devices including polarygraphic sensors, enzymatic sensors, fluorescent sensors, optical sensors, molecular imprint, radiation detectors, photodetectors, and the like can be used.

In one preferred embodiment, the measuring portion 2006 includes an element to increase blood flow, such as by way of illustration, a heating element, a suctioning element, or fluid that increases permeability of skin. Preferably a heating element is provided, whereby the sensing surface (or measuring surface) of the measuring portion 2006 is adapted to increase the temperature of the skin at the brain tunnel. This heating element increases blood flow to the entrance of the BT and accelerates the oxygen diffusion through the skin at the BT. The measuring portion 2006 is preferably located in apposition to the BT zone associated with the arterial supply and the orbital artery or any of the arterial branches located in the BT area, in order to achieve ideal measurement of the arterial oxygen and the arterial partial oxygen pressure. The transcutaneously measured oxygen pressure on the skin at the entrance of the BT is obtained by placing a specialized measuring portion 2006 of special geometry and dimensions on the skin at the BTT, in accordance with the present invention and the specialized dimensions and shape of the sensor and support structures as described herein.

In arterial blood an equilibrium exists between the percentage of oxidized hemoglobin and the partial oxygen pressure. When the blood is heated, this equilibrium is shifted so that the partial oxygen pressure increases. Therefore, when the BT method is used, the partial oxygen pressure in the peripheral blood vessels in the BT is higher than in the arteries. The oxygen coming from the arterial region of the BT diffuses through the skin at the BTT.

With exception of the skin at the BT, the skin cells in the whole body consume oxygen during diffusion of oxygen through the skin, because said skin is thick and has a thick underlying layer of subcutaneous tissue (fat tissue). Thus, the oxygen pressure at the area of the epidermis in all areas of the body, with exception of the BT area, is much lower than the actual oxygen pressure in the peripheral blood vessels. However, in the specialized skin areas of the BT the oxygen levels remain stable since the skin at the BT is the thinnest skin in the whole body and free of adipose (fat) tissue.

The specialized skin area of the BT between the eyebrow and the eye, at the roof of the orbit shown in FIG. 86U has stable levels of chemical substances including oxygen, glucose, blood gases, drugs and analytes in general. In FIG. 86U there is seen the BT area 2260 which includes the upper eyelid area 2250 and the roof of the orbit area 2252 located right below the eyebrow 2254, and above the eye 2256. The BT area 2260 is located below the eyebrow 2254, and between the eyebrow 2254 and the eye 2256, with the nose 2258 forming another boundary of the BT area. Accordingly, FIG. 86U shows a first boundary formed by the eyebrow 2254, a second boundary formed by the eye 2256, and a third boundary formed by the nose 2258, with the main entry point 2262 of the BT located at the roof of the orbit, in the junction between the nose 2258 and the eyebrow 2254. A second physiologic tunnel is located in the area adjacent to the lower eyelid extending 10 mm below from the edge of the lower eyelid, however, the most stable area for measuring biological parameters comprises the BT area 2260 with the main entry point 2262 at the roof of the orbit 2252 below the eyebrow 2254. In the BT area the blood gas, such as oxygen, and other molecules including glucose remains stable.

Since consumption of oxygen is proportional to the thickness of the skin and of subcutaneous tissue (which contains the fat tissue), and further considering that the BT, as described above and surrounding physio-anatomic tunnels disclosed in the present invention have very thin skin and no subcutaneous tissue, the amount of oxygen at the epidermis (skin) at the entrance of said tunnels is not reduced, and remains proportional to the amount present in the peripheral blood vessels. Thus, the amount of gases such as oxygen, carbon dioxide, and other gases as well as analytes present in the skin of the BTT is proportional to the amount present in blood.

Another advantage of the present invention is that the heating element does not need to reach high levels of temperature, such as 44 degrees C., since the tunnel area is extremely vascularized and associated with a unique blood vessel which is terminal (which means that the total amount of blood is delivered to the site) in addition to having the thinnest skin interface in the whole body, thereby allowing a lower temperature of a heating element to be used for increasing blood flow to the area. The preferred temperature of the heating element is equal to or less than 44 degrees Celsius, and preferably equal to or less than 41 degrees Celsius, and most preferably equal to or less than 39 degrees Celsius, and even most preferably equal to or less than 38 degrees Celsius.

The electrochemical sensor of the measuring portion 2006 for blood gas and glucose analysis has the same specialized dimensions and shape described for the other sensors of the invention, in accordance with the present invention and specialized anatomy of the BT and other surrounding tunnels. The device includes a measuring portion 2006 having a sensor, said sensor preferably being an electrochemical or optical sensor, and an associated heating element of specialized dimensions, with said measuring portion 2006 located adjacent to the BT or on the skin at the BT or other described tunnels of the invention. One of the objects of the invention includes providing a device of the described kind to be used at the BT for measurement of the arterial oxygen pressure and other blood gases such as carbon dioxide, carbon monoxide, anesthetic gases, and the like.

FIG. 87 illustrates a comparison between transcutaneous measurement of the arterial oxygen pressure in the prior art and the present invention. FIG. 87 shows the skin 2270 with its three thick layers, which is present in the whole body. Methods of the prior art use this skin 2270, which has several thick layers, namely subcutaneous tissue (fat tissue) 2272, thick dermis 2274, and thick epidermis 2276. Underneath this thick skin tissue 2270 there are small blood vessels 2278. Oxygen represented by small squares 2280 diffuses through the walls of the small blood vessels 2278, as indicated by the two small arrows in each blood vessel 2278. Contrary to the thick and multilayered skin 2270 present in other parts of the body, which comprised the method used by the prior art, the method and apparatus of the present invention uses specialized skin 2290 at the BT 2282, which has a large vascular bed 2284, no fat issue, a thin dermis 2286, and thin epidermis 2288. A large blood vessel and large vascular bed 2284 present in the brain tunnel provides more stable and more accurate level of molecules and substances such as oxygen level as well as the level of other blood substances such as glucose. Contrary to the method of the prior art which tried to measure substances in areas subject to vasoconstriction and subject to the effect of drugs, the present invention teaches device and methods using a vascular bed 2284 at the brain tunnel that is not subject to such vasoconstriction.

Skin 2270 of the prior art is thick and has a thick subcutaneous layer 2272 in comparison with the thin skin 2290 of the BT. In the method of the prior art, oxygen molecules 2280 from small blood vessel 2278, which is located deep in the body, have to cross thick layers of skin 21742 (fat tissue), 2174 (dermis), 2176 (epidermis and dead cells) present in said skin 2270 in order for said oxygen molecules 2280 to reach a conventional sensor of the prior art. Accordingly, in the method of the prior art the oxygen 2280 from vessel 2278 has a long path before reaching a sensor of the prior art. Oxygen 2280 diffuses through the wall of the small blood vessel 2278 and through the subcutaneous tissue 2272 to finally reach a thick dermis 2274 and a thick layer of dead cells 2276 at skin 2270, to only then reach conventional sensors of the prior art. As can be seen, the number of oxygen molecules 2280 drop drastically from around vessel 2278 to surface of skin 2271 as it moves along the long path of conventional thick skin 2270 present in the body.

Contrary to the prior art, the method and device of the present invention uses a specialized and extremely thin skin 2290 of the BT, in which oxygen molecules 2280 from vessel 2284 have an extremely short path to reach specialized sensor 2000 of the present invention. Oxygen molecule 2280 is right underneath the thin skin 2290 since terminal large vascular area 2284 lies just underneath the thin skin 2290, and thus oxygen 2280 rapidly and in an undisturbed fashion reaches specialized sensor 2000. This allows an undisturbed diffusion of oxygen from vessel 2284 to sensor 2000 without any drop of the partial oxygen pressure. Because the specialized skin 2290 of the BT produces a rapid and undisturbed diffusion of oxygen (and other blood gases) to the special sensor 2000 of the present invention and the area measured is characterized by a natural condition of hyperperfusion, the present invention results in more accurate measurement than previously available estimates of partial blood gas pressures.

An exemplary transcutaneous blood gas sensor of the present invention consists of a combined platinum and silver electrode covered by an oxygen-permeable hydrophobic membrane, with a reservoir of phosphate buffer and potassium chloride trapped inside the electrode. FIG. 87A shows a small heating element 2298, which is located inside the silver anode. Oxygen 2280 diffuses through the skin 2290 and reaches sensor 2292 wherein a reduction of oxygen occurs generating a current that is converted into partial pressure of oxygen. It is understood that other substances can be measured. Exemplarily, carbon dioxide can be measured with the invention, wherein carbon dioxide molecules diffuse across a permeable plastic membrane into the inner compartment of the electrode where the molecule reversibly reacts with a buffer solution altering the pH which produces a measurable signal, said signal corresponding to the amount of the substance or partial pressure of the gas. A processing circuit can be used to calculate the partial pressure of the substance based on predetermined calibration lines.

In reference to FIG. 87A, measuring portion 2006 of the sensor system is arranged on the skin 2290 at the BT 2282 and includes element 2294. The element 2294 can operate as a blood gas sensor, oxygen saturation sensor, glucose sensor, or any other sensor measuring blood substances or body tissue. Sensing element 2294 in this embodiment includes a Clark-type sensor 2292 for detecting oxygen molecule 2280 and a heating element 2298 which is adapted for periodical actuation for generating heat. Measuring portion 2006 includes a cell 2300 and a temperature sensor 2296. Cell 2300, which is the chemical sensing portion, includes sensor 2292 and heating element 2298. The maximum preferred length or diameter of cell 2300 is equal to or less than 2.5 cm, and preferably equal to or less than 1.5 cm and most preferably equal to or less than 1.0 cm as represented by line C to D. The sensing device 2000 is connected to a processing circuit 2302 and power supply circuit 2304 via a wire 2306. Measuring portion 2006 is secured onto the skin 2290 in a completely leak-free manner, to avoid oxygen from the air reaching the sensor 2292. Preferably, the surface 2308 of measuring portion 2006 is provided with an adhesive layer or other means for sealing. Surface 2310 of sensor 2292 is preferably permeable to oxygen, carbon dioxide, glucose and any other blood components depending on the analyte being measured. Measuring portion 2006 has a preferred maximum length or diameter of equal to or less than 4 cm, and preferably equal to or less than 2.5 mm and most preferably equal to or less than 1.5 cm, as represented by line A to B in FIG. 87A.

The skin 2290 at the BT 2282 is heated by heating source 2298 adjacent to the area of sensor 2292 with consequent increase in arterial blood flow. Electrodes and a voltage source in processing circuit 2302 provide a circuit in which the electrical current flow is dependent on the partial oxygen pressure at the sensor 2292.

Although a contact device and method was illustratively shown, it is understood that a non-contact method and device can be equally used in accordance with the invention. It is also understood that a variety of support structures, disclosed in the present invention, can be used for housing the elements of measuring portion 2006 including adhesive patches, head mounted gear such as eyewear and headbands, and the like. In addition to or as a substitute of wired transmission, the transmission of the signal can use a wireless transmitter and the sensor system of the invention can include a wireless transmitter.

FIG. 87B shows sensor system 2320 which includes an essentially convex sensing surface 2322. Although a convex surface is illustratively described, a flat surface can also be used. Sensor system 2320 is a reflectance sensor including a sensing portion comprised of two parts, the light emitter 2324, 2326 and the detector 2328, which receive the light emitted from light emitter 2324, 2326. Sensor system 2320 uses an infrared light source 2324, 2326 and detector 2328 in specialized pads that are fixed firmly to the skin 2290 of the BT 2282 to detect regional blood oxygen saturation. Sensing portion 2330 has a dimension from point C to point D which is preferably equal to or less than 2.1 cm, and more preferably equal to or less than 1.6 cm, and most preferably equal to or less than 1.1 cm. Sensor system 2320 includes a processing circuit 2332, said processing circuit 2332 including a processor which is coupled to a wireless transmitter 2334 for wirelessly transmitting data, preferably using Bluetooth™ technology. The light emitter can include a near-infrared emitter. Any near infrared radiation source can be used. Preferably radiation having wavelengths between 700 to 900 nm are used for measurement of oxygen and other substances. Radiation sources include near-infrared wavelength. It is understood that radiation source 2324, 2326 can also include mid-infrared wavelength. It is also understood that radiation source 2324, 2326 can also include far-infrared wavelength. It is also understood that radiation source 2324, 2326 can also include a combination of various wavelengths or any electromagnetic radiation. The region of the spectrum and wavelength used depend on the substance or analyte being measured. It is understood that a mid-infrared light source, having wavelength between 3,000 nm and 30,000 nm can also be used. The light source can further include visible light and fluorescent light depending on the analyte or tissue being evaluated.

FIG. 87C shows sensor 2340 which includes a specialized two plane surface formed by an essentially convex surface 2334 and a flat central surface 2336. The flat surface 2336 is preferably the sensing surface of sensor 2340. The two plane surface convex-flat-convex allows preferred apposition to the skin 2290 at the BT 2282. Measuring portion 2006 includes a reflectance sensor comprised of two parts, the light emitter 2338 and a detector 2342, which receive the light emitted from light emitter 2338. Measuring portion 2006 houses light emitter 2338, which uses near infrared light or mid-infrared light source, and a photodetector 2342, and a mechanical plunger 2344, which when powered through wire 2346 elicit a rhythmic motion, gently tapping the skin 2290 at the BT 2282, to increase perfusion in cases of hypoperfusion. Although a mechanical plunger is described, it is understood that any device or article that by motion compresses and decompresses the skin at the BTT will create increased perfusion and can be used in the invention as well as a suction cup and the like, all of which are within the scope of the invention. Dimensions of measuring portion 2006 from point A1 to point B1 have preferred maximum length or diameter of equal to or less than 3.1 cm, and preferably equal to or less than 2.1 cm and most preferably equal to or less than 1.6 cm.

Since the skin at the BT is highly oxygenated and has a high blood flow, the heating element or any element to cause increase blood flow is not necessary in most patients. Accordingly, another preferred embodiment of the present invention is shown in FIG. 88, and said embodiment does not include a heating element. FIG. 88 shows a face with eyes 2350 and 2352, eyebrow 2354, and nose 2356, with sensing device 2000 including body 2002, arm 2004, and measuring portion 2006 with sensor 2358 secured to the skin above eye 2350 and below eyebrow 2354. By way of illustration, sensor 2358 works as a blood gas sensor previously described, said sensor 2358 positioned on the skin at the brain tunnel or adjacent to the skin 2290 at the brain tunnel, said sensor being in contact with the skin or spaced away from the skin at the brain tunnel during measurement.

The device of the present invention is adapted to measure any component present in the blood by utilizing a plurality of sensors adjacent to or in apposition to the skin of the BT and other physiologic and anatomic tunnels of the present invention. It is understood that an electrochemical sensor or optical sensor can be used to measure other blood components such as glucose, carbon dioxide, cholesterol, pH, electrolytes, lactate, hemoglobin, and any of the blood components.

The sensor system of the invention includes skin surface oxygen pressure measurement, carbon dioxide pressure measurement and measurement of the arterial partial pressure of oxygen or carbon dioxide by locally applying a specialized device on the skin at the BTT comprised by the various new and specialized supports structures. A processing circuit uses the skin surface oxygen or carbon dioxide pressure at the BTT and other tunnels of the invention to calculate the arterial partial pressure of oxygen or carbon dioxide. The processing circuit can be operatively coupled to a memory for correlating the acquired value with a stored value. A processing circuit can be further coupled to a display for visual or audible reporting of the values.

The present invention also discloses a method comprising the steps of applying a electrochemical sensor or an optical sensor or a radiation detector on or adjacent to the skin at the entrance of the BT and other tunnels, applying electrical energy, and measuring at least one analyte including at least one of glucose, oxygen, cholesterol, oxygen, and carbon dioxide. An alternative step includes increasing blood flow to the area by using at least one of heating, creating suction, mechanically tapping the area, using sound waves such as ultrasound, increasing BT skin permeability with laser light, increasing BT skin permeability with chemical substances, and the like.

Sensor 2358 can also work as an infrared detector for measurement of analytes such as glucose. Likewise sensor 2358 can operate as a light emitter-detector pair for measuring analytes. The noninvasive measurement methods of the present invention takes advantage that the BT is an ideal emitter of infrared radiation at precisely the right spectral radiation for measuring substances such as glucose. The emission from the BT works as a black body emission. The emission from the BT contains the radiation signature of analytes. Contrary to other parts of the body in which radiation is deep inside the body, the radiation at the BT is the closest to the surface of the body. A variety of cooling or heating elements can be incorporated to enhance measurement of glucose at the BT. Besides mid-infrared radiation, it is also understood that near-infrared spectroscopy can be used of the measurement of glucose at the BTT. It is also understood that mid-infrared spectroscopy can be used of the measurement of glucose at the BTT. It is also understood that far-infrared spectroscopy can be used of the measurement of glucose at the BTT.

Furthermore, techniques such as Raman spectroscopy can also be used for measuring the concentrations of blood analytes at the BTT and other tunnels of the present invention. Raman spectroscopy has sharp spectral features, which are characteristic for each molecule. This strength is ideally suited to blood analyte measurements, where there are many interfering spectra, many of which are much stronger that that of blood analytes. Accordingly, in the present invention Raman light is generated in the tissue at the BT and collected by a mirror secured to any of the support structures of the present invention such as the frame of eyeglasses, clips, adhesive patches attached to the skin, finger like structure with a plate and an arm, and the like. A fiber bundle in any of the support structures of the present invention guides the collected Raman light to a portable spectrograph and/or to a processor and a CCD. Since there are no interfering elements at the BT, the Raman's sharp spectral features enable accurate detection of blood analyte spectra including glucose, urea, triglyceride, total protein, albumin, hemoglobin and hematocrit.

A light source can illuminate the skin at the brain tunnel area and generate a detectable Raman spectrum for detecting analytes based on said spectrum. Accordingly, another embodiment of the present invention includes an apparatus and method for the non-invasive determination of an analyte comprising a light source for generating an excitation light directed into the brain tunnel and an optical system coupled with said excitation light, said optical system configured for directing the excitation light into the brain tunnel to generate a detectable Raman spectrum thereof, a light detector coupled with said optical system and configured to detect a Raman spectrum from the brain tunnel, a processor operatively coupled with said detector said processor including a processing circuit, said processing circuit having a computer readable medium having code for a computer readable program embodied therein for comparing Raman spectrum from the brain tunnel to a reference radiation corresponding to the concentration of an analyte, and a memory operatively coupled with said processor. The electrical signal corresponding to Raman spectrum from the brain tunnel is fed into the processing circuit and compared to Raman spectrum from the brain tunnel corresponding to the analyte concentration stored in the memory.

It is also understood that glucose at the BTT can be measured with enzymatic sensors such as glucose oxidase as well as artificial glucose receptors. Fluorescence techniques can also be used and include use of engineered molecules, which exhibit altered fluorescence intensity or spectral characteristics upon binding glucose, or use of competitive binding assays that employ two fluorescent molecules in the fluorescent resonance energy transfer technique. In addition, "reverse iontophoresis", with a device held in the specialized support structures of the invention such as eyeglasses can be used, and interstitial fluid from the BT area removed for analysis. Ultrasound applied to the BT and/or a low-level electrical current on the skin of the BT, by convective transport (electro-osmosis) can also be used for moving glucose across the thin skin of the BT and other tunnels around the eye. In addition, light scattering and photoacoustic spectroscopy can be used to measure various substances such as glucose. Pulsed infrared light directed at the BT, when absorbed by molecules, produces detectable ultrasound waves from the BT, the intensity and patterns of which can be used to measure glucose levels. The apparatus and methods of the present invention then determines the concentration of an analyte using a processor that correlates signals from the brain tunnel with a reference table, said reference table having values of analytes corresponding to signals from the brain tunnel.

Furthermore, a detector having an ultrasound and a light source illuminates the skin at the rain tunnel area with a wavelength that is absorbed by the analyte being measured and generates a detectable ultrasound wave from the brain tunnel for detecting analytes based on said ultrasound wave and light absorption. Accordingly, another embodiment of the present invention includes an apparatus and method for the non-invasive determination of an analyte comprising a light source for generating light directed into the brain tunnel and an ultrasound configured to waves generated from the brain tunnel, a processor operatively coupled with said ultrasound said processor including a processing circuit, said processing circuit having a computer readable medium having code for a computer readable program embodied therein for comparing absorption of radiation from the brain tunnel based on the signal from the ultrasound to a reference radiation corresponding to the concentration of an analyte, and a memory operatively coupled with said processor. The electrical signal corresponding to the intensity of sound waves is used to determine radiation absorption of light from the brain tunnel, which is used to determine the concentration of the analyte, said signal being fed to the processing circuit and compared with the radiation absorption from the brain tunnel corresponding to the analyte concentration stored in the memory.

The present invention includes non-invasive optical methods and devices for measuring the concentration of an analyte present in the BT. A variety of optical approaches including infrared spectroscopy, fluorescent spectroscopy, and visible light can be used in the present invention to perform the measurements in the BT including transmission, reflectance, scattering measurement, frequency domain, or for example phase shift of modulated light transmitted through the substance of interest or reflected from the BT, or a combination thereof.

The present invention includes utilizing the radiation signature of the natural black-body radiation emission from the brain tunnel. Natural spectral emissions of infrared radiation from the BT and vessels of the BT include spectral information of blood components such as glucose. The radiation emitted by the BT as heat can be used as the source of infrared energy that can be correlated with the identification and measurement of the concentration of the substance of interest. Infrared emission in the BT traverses only an extremely small distance from the BT to the sensor which means no attenuation by interfering constituents. The devices and methods can include direct contact of the instrument with the skin surface at the BT or the devices of the invention can be spaced away from the BT during the measurements.

The methods, apparatus, and systems of the present invention can use spectroscopic analysis of the radiation from the BT to determine the concentration of chemical substances present in such BT while removing or reducing all actual or potential sources of errors, sources of interference, variability, and artifacts. The natural spectral emission from the BT changes according to the presence and concentration of a substance of interest. One of the methods and apparatus involves using a radiation source to direct electromagnetic radiation at the BT with said radiation interacting with the substance of interest and being collected by a detector. Another method and apparatus involves receiving electromagnetic radiation naturally emitted from the BT with said radiation interacting with the substance of interest and being collected by a detector. The data collected is then processed for obtaining a value indicative of the concentration of the substance of interest.

The infrared thermal radiation emitted from the brain tunnel follow Planck's Law, which can be used for determining the concentration of chemical substances. One embodiment includes determining the radiation signature of the substance being measured to calculate the concentration of the substance. Another embodiment includes using a reference intensity calculated by measuring thermal energy absorption outside the substance of interest band. The thermal energy absorption in the band of substance of interest can be determined via spectroscopic means by comparing the measured and predicted values at the BT. The signal is then converted to concentration of the substance of interest according to the amount of infrared energy absorbed.

The apparatus uses the steps of producing output electrical signals representative of the intensity of the radiation signature and sending the signal to a processor. The processor is adapted to provide the necessary analysis of the signal to determine the concentration of the substance of interest and is coupled to a display for displaying the concentration of the substance of interest, also referred to herein as analyte.

The analyte measured or detected can be any molecule, marker, compound, or substance that has a radiation signature. The radiation signature preferably includes a radiation signature in the infrared wavelength range including near-infrared, mid-infrared, and far-infrared. The analyte being measured can preferably have a radiation signature in the mid-infrared range or the near infrared range.

Infrared spectroscopy, as used in some embodiments of the present invention, is a technique based on the absorption of infrared radiation by substances with the identification of said substances according to its unique molecular oscillatory pattern depicted as specific resonance absorption peaks in the infrared region of the electromagnetic spectrum. Each chemical substance absorbs infrared radiation in a unique manner and has its own unique absorption spectra depending on its atomic and molecular arrangement and vibrational and rotational oscillatory pattern. This unique absorption spectra allows each chemical substance to basically have its own infrared spectrum, also referred as fingerprint or radiation signature which can be used to identify each of such substances.

In one embodiment radiation containing various infrared wavelengths is emitted at the substance or constituent to be measured, referred to herein as "substance of interest", in order to identify and quantify said substance according to its absorption spectra. The amount of absorption of radiation is dependent upon the concentration of said chemical substance being measured according to Beer-Lambert's Law.

One embodiment includes a method and apparatus for analyte measurement, such as blood glucose measurement, in the near infrared wavelength region between 750 and 3000 nm and preferably in the region where the highest absorption peaks are known to occur, such as the radiation absorption signature of the substance being measured. For glucose, for example, the near infrared region includes the region between 2080 to 2200 nm and for cholesterol the radiation signature is centered around 2300 nm. The spectral region can also include visible wavelength to detect other chemical substances including glucose or cholesterol.

The apparatus includes at least one radiation source from infrared to visible light which interacts with the substance of interest and is collected by a detector. The number and value of the interrogation wavelengths from the radiation source depends upon the chemical substance being measured and the degree of accuracy required. As the present invention provides reduction or elimination of sources of interference and errors, it is possible to reduce the number of wavelengths without sacrificing accuracy. Previously, the mid-infrared region has not been considered viable for measurement of analytes in humans because of the presence of fat tissue and the high water absorption that reduces penetration depths to microns. The present invention can use this mid-infrared region since the blood with the substance of interest is located very superficially in an area void of fat tissue which allows sufficient penetration of radiation to measure said substance of interest.

The present invention reduces variability due to tissue structure, interfering constituents, and noise contribution to the signal of the substance of interest, ultimately substantially reducing the number of variables and the complexity of data analysis, either by empirical or physical methods. The empirical methods including Partial Least Squares (PLS), principal component analysis, artificial neural networks, and the like while physical methods include chemometric techniques, mathematical models, and the like. Furthermore, algorithms were developed using in-vitro data which does not have extraneous tissue and interfering substances completely accounted for as occurs with measurement in deep tissues or with excess background noise such as in the skin with fat tissue. Conversely, standard algorithms for in-vitro testing correlates to the in vivo testing of the present invention since the structures of the brain tunnel approximates a Lambertian surface and the skin at the brain tunnel is a homogeneous structure that can fit with the light-transmission and light-scattering condition characterized by Beer-Lambert's law.

Spectral radiation of infrared energy from the brain tunnel can correspond to spectral information of the substance of interest or analyte. These thermal emissions irradiated as heat at 38 degrees Celsius can include the 3,000 nm to 30,000 nm wavelength range, and more precisely the 4,000 nm to 14,000 nm range. For example, glucose strongly absorbs light around the 9,400 nm band, which corresponds to the radiation signature of glucose. When mid-infrared heat radiation is emitted by the brain tunnel, glucose will absorb part of the radiation corresponding to its band of absorption. Absorption of the thermal energy by glucose bands is related in a linear fashion to blood glucose concentration in the brain tunnel.

The infrared radiation emitted by the BTT contains the radiation signature of the substance being measured and the determination of the analyte concentration is done by correlating the spectral characteristics of the infrared radiation emitted from the brain tunnel to the analyte concentration for that radiation signature. The analyte concentration can be calculated from the detected intensity of the infrared radiation signature, said radiation signature generating an electrical signal by a detector, with said signal being fed into a microprocessor. The microprocessor can be coupled to a memory which stores the concentration of the analyte according to the intensity of the radiation signature of the analyte being measured. The processor calculates the concentration of the substance based on the stored value in the memory. The processor is operatively coupled with said detector, said processor including a processing circuit, said processing circuit having a computer readable medium having code for a computer readable program embodied therein for comparing infrared spectrum from the brain tunnel to a reference radiation corresponding to the concentration of an analyte, and a memory operatively coupled with said processor. The electrical signal corresponding to the infrared spectrum from the brain tunnel is fed into the processing circuit and compared to infrared spectrum from the brain tunnel corresponding to the analyte concentration stored in the memory. The infrared spectrum preferably includes near-infrared or mid-infrared radiation.

One embodiment includes a device and method for measuring an analyte concentration in the blood or tissue of the BT. One embodiment includes detecting the level of infrared radiation naturally emitted from the BT. One embodiment includes detecting the level of infrared radiation emitted from the BT after directing radiation at the BTT.

One embodiment includes a device which measures the level of mid-infrared radiation from the surface of a brain tunnel and determines the concentration of an analyte based on the analyte's infrared radiation signature. The radiation signature can be preferably in the infrared region of the spectrum including near-infrared or mid-infrared. The device can include a filter, a detector, a microprocessor and a display.

A detector having a light source can illuminate the skin at the brain tunnel area and generate a detectable infrared radiation for detecting analytes based on said infrared spectrum. The detectable infrared radiation from the brain tunnel contains the radiation signature of the analyte being measured. Accordingly, another embodiment of the present invention includes an apparatus and method for the non-invasive determination of an analyte comprising a light source for generating an infrared light directed into the brain tunnel and an infrared radiation detector configured to detect infrared radiation from the brain tunnel, a processor operatively coupled with said detector, said processor including a processing circuit, said processing circuit having a computer readable medium having code for a computer readable program embodied therein for comparing infrared radiation from the brain tunnel to a reference radiation corresponding to the concentration of an analyte, and a memory operatively coupled with said processor. The electrical signal corresponding to infrared radiation signature from the brain tunnel is fed into the processing circuit and compared to infrared radiation signature from the brain tunnel corresponding to the analyte concentration stored in the memory.

A variety of radiation sources can be used in the present invention including LEDs with or without a spectral filter, a variety of lasers including diode lasers, a Nernst glower broad band light emitting diode, narrow band light emitting diodes, NiChrome wire, halogen lights a Globar, and white light sources having maximum output power in the infrared region with or without a filter, and the like. The radiation sources have preferably enough power and wavelengths required for the measurements and a high spectral correlation with the substance of interest. The range of wavelengths chosen preferably corresponds to a known range and includes the band of absorption for the substance of interest or radiation signature of the substance. The instrument comprises a light source which may be any suitable infrared light source, including mid-infrared light source, near-infrared light source, far-infrared light source, fluorescent light source, visible light source, radio waves, and the like.

A light source can provide the bandwidth of interest with said light being directed at the substance of interest in the brain tunnel. A variety of filters can be used to selectively pass one or more wavelengths which highly correlate with the substance of interest. The filter can select the wavelength and includes bandpass filter, interference filter, absorption filter, monochromator, grating monochromator, prism monochromator, linear variable filter, circular variable filter, acousto-optic tunable filter, prism, and any wavelength dispersing device The radiation can be directly emitted from a light source and directly collected by a photodetector, or the radiation can be delivered and collected using optic fiber cables. An interface lens system can be used to convert the rays to spatial parallel rays, such as from an incident divergent beam to a spatially parallel beam.

The detector can include a liquid nitrogen cooled detector, a semiconductor photodiode with a 400 µm diameter photosensitive area coupled to an amplifier as an integrated circuit, and the like. The photodetector has spectral sensitivity in the range of the light transmitted. The photodetector receives an attenuated reflected radiation and converts the radiation into an electrical signal. The detector can also include a thermocouple, a thermistor, and a microbolometer.

Analyte as used herein describes any particular substance to be measured. Infrared radiation detector refers to any detector or sensor capable of registering infrared radiation. Examples of a suitable infrared radiation detectors, include but are not limited to, a microbolometer, a thermocouple, a thermistor, and the like. The combined detected infrared radiation may be correlated with wavelengths corresponding to analyte concentrations using means such as a Fourier transform.

The BT provides the mid-infrared radiation signature and the near-infrared radiation signatures of the analytes present therein. The infrared radiation signature from the BT is affected by the concentration of analytes in the BT. One of the molecules present in the BT is glucose, and the natural mid-infrared or near-infrared radiation signature of glucose contained within the brain tunnel's natural infrared radiation allows the non-invasive measurement of glucose. Changes in the concentration of certain analytes such as glucose, cholesterol, ethanol, and others, may cause an increase or change in the brain tunnel's natural emission of infrared radiation which can be used to measure the concentration of an analyte.

The BT emits electromagnetic radiation within the infrared radiation spectrum. The spectral characteristics of the infrared radiation emitted by the BT can be correlated with the concentration of analyte. For example, glucose absorbs mid-infrared radiation at wavelengths between about 8.0 microns to about 11.0 microns. If mid-infrared radiation passes through or reflects from the brain tunnel where glucose is present, a distinct radiation signature can be detected from the attenuated radiation or the remaining radiation that is not absorbed by the analyte. The absorption of some amount of the radiation that is applied to the brain tunnel (which contains the substance of interest), may result in a measurable decrease in the amount of radiation energy, which can be utilized to determine the concentration of an analyte.

One embodiment of the present invention provides a method and device for non-invasively measuring the analyte concentration in blood or other tissues, and includes the steps of detecting mid-infrared radiation naturally emitted by the brain tunnel, and determining the concentration of said analyte by correlating the spectral characteristics or radiation signature of the detected infrared radiation with a radiation signature that corresponds to the analyte concentration. The method can also include a filtering step before detection by filtering the naturally emitted infrared radiation from the brain tunnel. In the case of glucose measurement, filtering allows only wavelengths of about 8,000 nanometers to about 11,000 nanometers to pass through the filter. The method further includes a detecting step using an infrared radiation detector, which generates an electrical signal based on the radiation received and feeds the signal into a processor. A mid-infrared radiation detector can measure the naturally emitted mid-infrared radiation from the brain tunnel. A variety of detectors can be used including thermocouples, thermistors, microbolometers, liquid nitrogen cooled MTC such as by Nicolet, and the like. A processor can be used to analyze and correlate the spectral characteristics or radiation signature of the detected mid-infrared radiation with a radiation signature of an analyte. For glucose the generated radiation signature is within the wavelength between about 8,000 nm to about 11,000 nm. The method may include an analyzing step using algorithms based on Plank's law to correlate the radiation signature with glucose concentration. The method may further include a reporting step, such as a visual display or audio reporting.

Many illustrative embodiments for chemical sensing were provided, but it is understood that any other sensing system can be used in accordance to the invention. For example a transducer that uses fluorescence to measure oxygen partial pressure, carbon dioxide, pH, nitric oxide, lactate, and anesthetic gases can also be used as well as any other optical chemical sensor including absorbance, reflectance, luminescence, birefringence, and the like.

FIG. 89 is a diagrammatic perspective view of another preferred embodiment showing measuring portion 2006 comprised of a plurality of sensors and/or detectors. There is seen measuring portion 2006 having a light emitter-light detector pair 2360 and temperature sensor 2362 housed in said measuring portion 2006. The radiation source-detector pair 2360 is preferably housed in a plate 2364. Plate 2364 can have any shape, exemplarily and preferably plate 2364 has an essentially rectangular shape. Rectangular plate 2364 houses at least one light emitter 2366 in one side and at least one detector 2368 on the opposite side. Light emitter 2366 is connected to at least one wire 2372 and detector 2368 is connected to at least one wire 2374. Wire 2372, 2374 start at the light-emitter-light detector pair 2360, and run along measuring portion 2006, and terminate in multi-strand wire 2382 of arm 2004. Wire portion 2382 terminates in wire portion 2384 of body 2002. Temperature sensing part 2370 is essentially cylindrical and houses wire portion 2375 (shown as broken lines) in its body 2380 and temperature sensor 2362 located at the free end 2378 of temperature sensing part 2370. Temperature sensing part 2370 is disposed adjacent to light emitter-detector pair 2360, preferably next to light detector 2368, to avoid heat generated by light emitter 2366 to affect body temperature measurement. Wire 2372, 2374, and 2376 preferably form a single multi-strand wire 2385 which exit measuring portion 2006. Wire portion 2382 is disposed on or within arm 2004, and further disposed on or within body 2002. The free end 2378 of temperature sensing part 2370 housing temperature sensor 2362 preferably projects beyond the bottom plane 2386 of measuring portion 2006. The temperature sensing part 2370 of measuring portion 2006 can preferably comprise a soft and compressible material. Light emitter-detector pair 2360 can also project beyond bottom plane 2386. Wire portion 2384 may be connected to a processing circuit, memory, and display and/or a transmitter. Any combination of sensors, sensing molecules, and detectors can be housed in measuring portion 2006. Another embodiment includes a pulse sensor combined with a temperature sensor and a glucose sensor. The measuring portion 2006 can also further include an oxygen sensor, including an optical sensor for measuring oxygen saturation such as pulse oximetry and an electrochemical sensor for measuring partial pressure of oxygen. Any combination of any physical measurement including temperature, pressure and pulse with any chemical measurement or optical measurement can be used and are contemplated.

FIG. 90A is a perspective planar view of another embodiment showing sensing device 2000 comprised of body 2002, arm 2004 with hole 2001 for housing a wire, and measuring portion 2006 with hole 2003 for housing a wire.

FIG. 90B is a perspective side top view of another embodiment of sensing device 2000 showing body 2002 having a tunnel structure 2005 for housing a wire, and arm 2004 with two holes 2007, 2009 for housing a wire, and an adjustably extendable neck portion 2011 such as an accordion portion for allowing better flexible bending and/or extending of arm 2004 for positioning a sensor at the BT area. Measuring portion 2006 comprises a cylinder 1999 with a wire 2013 entering said cylinder 1999 and said wire 2013 terminating in a sensor. Wire 2013 is preferably housed in a Teflon™ tube, said tube penetrating arm 2004 at hole 2007 adjacent to the accordion portion 2011 and exiting at the opposite end of arm 2004 at a second hole 2009.

FIG. 90C is a side view of another embodiment of sensing device 2000 showing body 2002 having a tunnel structure 2005 for housing a wire portion 2015, and a thin metal sheet representing arm 2004 with said arm 2004 having two holes 2007, 2009 for housing a wire portion 2017. For temperature measurement, measuring portion 2006 comprises a cylinder 1999 of insulating material with a wire 2013 entering said cylinder 1999 and running along the center of said cylinder 1999, said wire 2013 terminating in a temperature sensor 2010. Wire 2017 is preferably housed in a Teflon™ tube, said tube penetrating arm 2004 in its mid portion and exiting at the end of arm 2004 at the junction with body 2002. Body 2002 has two portions, a semi-rigid upper part 2019, preferably metal or plastic, and a soft bottom part 2021 made with rubber, polyurethane, polymers, or any other soft material. Wire portion 2015 runs inside tunnel 2005 of body 2002 and terminates in processing and reading unit 2012.

FIG. 90D is a planar view of sensing device 2000 of FIG. 90C showing body 2002, arm 2004 with holes 2007 and 2009 for housing a wire, said arm 2004 having an extendable portion 2011, and a measuring portion 2006.

FIG. 90E is a planar bottom view of sensing device 2000 showing body 2002 having two portions, a semi-rigid upper part 2019, preferably a thin sheet of metal or plastic, and a soft bottom part 2021 made with rubber, polyurethane, polymers, or any other soft material. Wire portion 2017 is secured to arm 2004, said arm 2004 having an adjustably extendable portion 2011. Measuring portion 2006 comprises a holder 1999, represented by a cylinder with a sensor 2010 disposed at the end of the cylinder 1999.

FIG. 90F is a bottom view of sensing device 2000 showing body 2002 having two portions, a semi-rigid upper part 2019, preferably a thin sheet of metal, and a soft bottom part 2021 made with rubber, polyurethane, polymers, or any other soft material. Wire portion 2017 is secured to arm 2004, said arm 2004 having an adjustably extendable portion 2011. Measuring portion 2006 comprises a holder 1999 represented as a cylinder, said cylinder 1999 having a slit 2023 for facilitating securing wire 2013 to said cylinder 1999, with a sensor 2010 disposed at the end of the cylinder 1999.

FIG. 90G is illustrative of a bottom view of sensing device 2000 which shows body 2002, arm 2004 bent for use, and measuring portion 2006 having a two level insulating material 2027 of two different heights and a wire 2025 which exits body 2002. Wire in this embodiment is not exposed and is completely covered by insulating rubber in arm 2004, and by the polyurethane cylinder in measuring portion 2006, and being sandwiched between metal plate 2019 and soft cushion pad 2021 in body 2002.

FIG. 90H shows sensing device 2000 when worn by a user 2031, with measuring portion 2006 positioned at the junction between nose and eyebrow. Body 2002 is connected to arm 2004, said body 2002 being secured to the forehead 2033 via adhesive soft surface 2021.

FIG. 90I shows sensing device 2000 when worn by a user 2035, said sensing device comprised of a plastic arm 2004 with spring capabilities, said plastic arm 2004 having a sensor 2010 at its free end positioned at the junction between the nose and the eyebrow. Body 2002 comprises a headband which may house an electronic circuit, processing circuit, power source, and transmitter, as well as a display.

FIG. 90J shows a two part, separable sensing device 2450 when worn by a user 2035, said two part, separable sensing device comprised of: (1) a holding device 2451 including plastic arm 2454 with spring capabilities, and (2) a patch 2462 housing a sensor 2460 with said plastic arm 2454 holding said patch 2462 in a stable position for measurement. To assure even better stability the patch 2462 may have an adhesive surface. Sensor 2460 can be placed centrically in patch 2462, and held in place by pressure applied by arm 2454. Arm 2454 is connected to body 2452, exemplarily shown mounted on a headband 2456, but any other structure such as a plate, frame of eyeglasses, head mounted gear, and the like as well as any support structures of the present invention can be used as body 2452 connected to arm 2454. In this embodiment sensor 2460 is located in patch 2462. Arm 2454 and body 2452 do not have any electrical parts or electronic parts, and serve as mechanical holder. Alternatively, arm 2454 and/or body 2452 may have an electrical connector for connecting with a wire from patch 2462. Dimensions of arm 2454 are similar in nature to the dimensions described for arm 2004 of sensing device 2000. Arm 2454 helps to position patch 2462 at the junction between nose and eyebrow. Body 2452 comprises a headband which may house electronic circuit, processing circuit, power source, and transmitter, as well as a display. A cushion pad 2458 can be coupled to arm 2454 for comfort.

FIG. 91 is another embodiment showing a nose bridge or clip sensing device 2500 comprised of a nose bridge piece 2502, adjustably positionable arm 2504 and measuring portion 2506. Nose bridge piece 2502 preferably includes two pads 2512 and 2514 and bridge 2520 connecting the two pads 2512, 2514, said pads preferably having an adhesive surface. Arm 2504 branches off the nose bridge piece 2502 and terminates in measuring portion 2506. Measuring portion 2506 illustratively is shown as a two level structure 2516 housing sensor 2510, such as a two level stepped "wedding cake" configuration. Arm 2504 is aimed upwards at the roof of the orbit for positioning sensor 2510 on or adjacent to the BT. A cord or strap 2518 may be secured to nose bridge piece 2502 for better stability and securing to the head.

FIG. 92A to 92F shows preferred embodiments for the sensing system 2400 of the present invention. Accordingly, in reference to FIG. 92A, the specialized support and sensing structure 2400 of the present invention includes a body 2402 (such as frame of sunglasses, a headband, a helmet, a cap, or the like), illustrated herein as the frame of eyeglasses, for securing sensing system 2400 to a body part such as the head (not shown). Sensing system 2400 includes an adjustably positionable arm 2404 preferably made with a shape memory alloy or any material that is deformable and has a memory, wherein the end of this arm 2404 terminates in a measuring portion 2406 which houses a sensor 2410 electrically connected to body 2402 via wire 2419. Wire portion 2418 in the measuring portion 2406 is surrounded by a compressible element 2422, preferably a spring. The spring 2422 is connected to sensor 2410. When in use the spring 2422 presses sensor 2410 against the skin creating a small indentation. Wire 2418 terminates in wire portion 2419, and preferably travels within arm 2404 and exits at the opposite end to connect to structure 2402, which houses circuit board 2420 including processing circuit 2422 and transmitter elements 2424 and power source 2421. Measuring portion 2406 preferably comprises an outer shell 2407, said outer shell preferably comprised of a rubber like material. Sensor 2410 can comprise a temperature sensor, said sensor preferably being covered by a metal sheet, said attachment being accomplished using a thermal transfer glue.

The eyeglasses of the present invention can include the use of a cantilever system. The present invention preferably includes an arm 2404 held rigidly at one end of the body 2402, represented by a frame of eyeglasses, said arm 2404 having a free end which includes a measuring portion 2406 with walls 2407 which houses sensor 2410. The end of arm 2404 can house any type of sensor or detector such as exemplarily a blood gas analyzer which includes not only a chemical sensor but also a temperature sensor as well as a heating element. It is understood that a variety of sensing systems such as optical sensing, fluorescent sensing, electrical sensing, ultrasound sensing, electrochemical sensing, chemical sensing, enzymatic sensing, piezoelectric, pressure sensing, pulse sensing, and the like can be housed at the end of arm 2404 in accordance to the present invention. Exemplarily, but not by way of limitation, a glucose sensing system comprised of photodetector, filters, and processor can be housed at the end of arm 2404 and operate as sensor 2410. Likewise a combination light emitter and photodetector diametrically opposed or side-by-side and housed at the end of arm 2404 to detect oxygen saturation, glucose or cholesterol by optical means and the like is within the scope of the present invention.

FIG. 92B shows the specialized support and sensing structure 2400 of FIG. 92A when worn by a user 2401, and comprises measuring portion 2406 preferably having an essentially cone like structure positioned at the brain tunnel 2409 at the junction of eyebrow and nose, and below the eyebrow and above the eye. Measuring portion 2406 is connected to an adjustably positionable arm 2404 which is flexible and shown in a bent position, said arm 2404 being connected to a headband 2405, which operates as the body of sensing structure for securing measuring portion 2406 to a body part. The center 2446 of headband 2405 has an extension 2443 which houses electronic circuits, processor, power source, and wireless transmitter. Headband 2405 can function as a frame of eyeglasses with detachable lenses.

FIG. 92C shows another embodiment of the specialized sensing eyeglasses 2430 of the present invention comprised of a dual sensing system with two arms 2434, 2444 which branch off the upper portion 2438 of frame of eyeglasses 2440, said arms 2434, 2444 extending from the middle portion 2446 of frame 2440 and being located above the nose pads 2442. Arms 2434, 2444 are located at about the middle of the frame of eyeglasses 2440. Arms 2434, 2444 may include an opening for housing rods 2438, 2439, said rods being connected to measuring portion 2436, 2437 and said rods 2438, 2439 being able to slide and move within said opening in arms 2434, 2444. Measuring portion 2436, 2437 houses sensor 2410, 2411 at its external end, exemplarily shown as a temperature measuring sensor 2410 and a pulse measuring sensor 2411. Middle portion of frame 2440 can have a receptacle area which houses power source, transmitter and processing circuit.

FIG. 92D shows another embodiment of the specialized support and sensing structure 2400-*a* of the invention and comprises frame of eyeglasses 2440-*a*, lens 2421-*a*, nose pads 2423-*a*, adjustably positionable arm 2404-*a*, and measuring portion 2406-*a* preferably having an essentially cylindrical like structure said measuring portion 2406-*a* housing a spring 2422-*a* which is connected to sensor 2410-*a*. Measuring portion 2406-*a* is connected to arm 2404-*a*, said arm 2404-*a* being connected to the frame of eyeglasses 2440-*a*. Spring 2422-*a* projects sensor 2410-*a* beyond measuring portion 2406-*a*.

FIG. 92E is a photograph of a preferred embodiment showing a bottom view of LED-based sensing eyeglasses 2480 comprised of a sensor 2470 in holder 2476 representing a measuring portion of sensing eyeglasses 2480, an adjustable arm 2474 branching off the frame 2477 of sensing eyeglasses 2480, LED 2478, said LED 2478 being disposed along the lens rim 2482 and above nose pad 2484, and said LED 2478 being operatively connected to a processor housed in frame 2477, so as to activate said LED 2478 when the value of the biological parameter being measured falls outside the normal range.

FIG. 92F is a photograph of a preferred embodiment showing a wireless-based sensing eyeglasses 2490 comprised of a sensor 2486 in holder 2488 representing a measuring portion of the wireless sensing eyeglasses 2490, an adjustable arm 2492 branching off the frame 2494 of sensing eyeglasses 2490, a housing 2496, said housing 2496 extending from frame 2494 and above nose pad 2498. A processor, power source, and transmitter may be mounted inside said housing 2496 and be electrically connected to sensor 2486. A wireless signal corresponding to the biological parameter measured is transmitted by a transmitter in the housing 2496 to a receiver.

FIG. 93A shows another embodiment of the patch sensing system of the invention. Accordingly, FIG. 93A shows a clover-leaf patch 2530 comprised of two parts: (1) a thin and large flexible part in a clover-leaf shape 2522, and (2) a thicker round shaped part 2524, represented as a button, which secures a sensor 2528, said button 2524 being thicker than the large underlying clover-leaf shape part 2522. Button 2524 securing sensor 2528 is attached to a thinner and large part 2522. The large portion of the patch 2530 comprises the thin part 2522 and the portion of the patch 2530 holding the sensor 2528 comprises a part of smaller size as compared to the thin part 2522. The portion holding the sensor 2528 is smaller and thicker than the underlying portion of the patch 2530. Large part 2522 is thinner and larger in size than said portion holding the sensor 2500. The sensor 2528 is connected to a wire 2526 which has an approximate 90 degree bend between the side portion of button 2524 and the plane of the large portion 2522. Wire 2526 runs along the button 2524 and then runs along the thin portion 2522, and exits the thin portion 2522. The button 2524 holding the sensor 2528 projects beyond the surface of the thin portion 2522, said button 2524 being preferably eccentrically positioned on the thin underlying portion 2524 of patch 2530. Both the thin portion 2522 and the thick portion 2524 of patch 2530 may have an adhesive surface on the surface of the patch 2530 facing a body part.

FIG. 94A to 94B shows an illustration of another embodiment of the support structure or sensing system 2540 of the invention, for use in animals, with sensor 2550 placed on the eyelid area 2538 of an animal 2536 at the brain tunnel 2532. The animal BTT sensing device 2540 includes a body 2542, represented by a plate, an adjustably positionable elongated arm 2544 attached to said plate 2542, and a sensor 2550 disposed at the free end of said arm 2544. Arm 2544 is secured to plate 2542, said arm 2544 preferably having a sliding mechanism and plate 2542 preferably having a groove 2552, allowing thus arm 2544 to move in relation to plate 2542 so as to position sensor 2550 on the BTT area 2532 while plate 2542 is in a fixed position on the skin of animal 2536. Grooved mechanism 2552 has a plurality of locking positions, allowing arm 2544 to be locked in different positions. Arm 2544 is connected to a processing and transmitter unit (not shown) through wire 2546. Sensor 2550 has preferably an essentially rectangular shape. Preferably sensor 2550, or the material surrounding sensor 2550 such as epoxy, has a thickness between 1 mm and 6 mm, and most preferably a thickness between 2 mm and 4 mm, and most preferably a thickness between 1 mm and 3 mm. Sensor 2550 can be covered by insulating material or any material that presses the sensor 2550 leading the sensor to enter the brain tunnel, said other materials can thus increase the overall thickness of the sensor portion.

It is understood that plate 2542 can work as a circuit board and house a processor, wireless transmitter and power source. Alternatively, plate 2542 houses a transmitter and power source with signals being transmitted to a remote receiver for further processing and display of results, or plate 2542 holds an antenna for remote electromagnetic powering including passive devices. It is understood that the electronics, transmitter, processor and power source can be housed in a box for implantation under the skin of the animal. In this embodiment the plate 2542 is replaced by this box, and the method includes the step of creating an opening on the skin, and implanting the box under the skin or on top of the skin while arm 2544 preferably remains on top of the skin, and said box is anchored under the skin. A further step may include suturing the skin around the sensor 2550 in order to provide better stability and protection of the sensor, with said suture grasping the skin 2554 on the upper part of brain tunnel 2532 and the skin 2556 in the lower part of brain tunnel 2532, and applying a stitch on edge of each said skin 2554, 2556, said stitch located right above sensor 2550.

FIG. 94B shows another embodiment for animal sensing device 2540, comprised of a multi-layer protection cover 2558 which is mounted on top of the plate 2542 and the sensor (not shown since it is covered by layer 2558), said layer 2558 preferably having insulating properties, an arm 2544, and a wire 2546. Preferably a thick support such as hard piece of material such as wood in the shape of the sensor is placed on top of said sensor for creating better apposition between sensor and the skin at the BTT.

The method includes securing plate 2542 to the head of a mammal, preferably by gluing the internal surface of the plate 2542 to the skin of the animal using glue or an adhesive surface; positioning sensor 2550 on the BTT 2532 at the eyelid area 2538, said step preferably accomplished by sliding arm 2544 in a groove 2552 in plate 2542 until the sensor 2550 is on or adjacent to the BTT area 2532. A further step may include bending the free end of arm 2544 and applying pressure at the BTT 2532 by sensor 2550 and producing a signal by said sensor 2550. Further steps include applying an electrical current, and generating a signal by sensor 2550. Other steps may include processing and analyzing said signal, and reporting a value of said signal. Similar steps can be used when applying sensing device 2000, but preferably during human medical use positioning may not include a sliding step.

Now in reference to FIG. 95A, there is seen another method and apparatus of the invention, comprised of coupling signals from a physiological tunnel, such as for example, coupling the BTT signal with alert means mounted on apparel, such as clothing, or coupled with footwear. It should be understood that any article of footwear including sneakers, cleats, sports shoes, sandals, boots, and the like is considered within the scope of this invention as well as any type of apparel or clothing.

Prior art relied on numerical values for guiding a user about exercise intensity, such as looking at a wrist watch to see the value for heart rate from a chest strap monitoring heart beat.

Looking at a number has several disadvantages including increasing stress and distraction, both of which can lead to reduced performance. In addition, the human brain is organized in a way to associate indicia such as numbers with a particular information or condition, and that may briefly reduce concentration in the exercise in order for the brain to finish the association, which in this case is for example number 100 beats per minute (bpm) means out of an optimal pulse zone for fitness or number 39.5 degrees Celsius meaning out of optimal thermal zone. Just holding the arm to look at a number may take away precious seconds of performance, since to see a number is necessary to use the ciliary muscle of the eye to focus and also to hold the display in a essentially motionless position such as holding the arm steady and aligned with the eye. In addition, a person older than 45 years of age may have presbyopia and thus have difficult seeing a numerical value unless using eyeglasses. Contrary to those disadvantages of the prior art, the present invention relies on reporting means which do not require using the ciliary muscle of the eye to focus such as in order to read a number. The present invention also is suitable for use by persons of all ages including people older than 45 years of age and with presbyopia and even cataract. In addition the present invention does not require holding a display in an essentially immobile position. Actually reporting means of the present invention are preferably in constant motion during the time of providing the information to the user. Furthermore there is no distraction as trying to read a number and associate that number with a biological condition. Furthermore there is no increased stress as occur when looking and seeing a numerical value, nor extra brain work to interpret a number. All of those advantages are accomplished by using a light source as the reporting means, as in accordance with this invention, said light source adapted to provide information according to the value of the biological parameter. In addition, a light source, such as in a shoe, is naturally present within the visual field of a human without said subject having to directly look or focus at the light. This allows the information to be naturally delivered and effortlessly received by the user. Furthermore the brain through the occipital cortex is better adapted to recognize a visual stimulus than a numerical stimulus and the brain is also better adapted to memorize visual stimuli such as a yellow LED to inform about potential danger than to memorize a number such as 147 bpm or 38.9 degrees Celsius. Furthermore, the information such as a light source is available immediately and without the need for association as occurs with numbers. In addition, the human brain is trained on a daily basis for recognizing and processing visual stimuli, such as green, yellow and red lights in a traffic light or the LED of an electronic device to indicate the device is turned on. Accordingly, the present invention couples the biological aspects related to visual stimuli with engineering and discloses such monitoring device, which preferable include LEDs mounted on or in a wearable article such as clothing, apparel accessories, or shoes as the reporting means instead of numerical values.

FIG. 95A illustrates coupling of physiological signals such as temperature and pulse with footwear, said footwear operating as a receiver for the signal and to alert the user of abnormal physiological values. This embodiment is directed to an article of footwear having one or a plurality of alert means such as light sources, represented by LEDs, vibration, buzzers, speakers and the like, which are activated according to the physiological value measured by a sensor. It is understood that any sound can be produced or any visual indicia can be used to effortlessly and naturally inform the user about the biological parameter level without the need to display any numerical value or requiring the user to look for the information such as for example looking at a watch. The information is acquired by the user in a passive and effortless manner. The visual field of a user allows receiving the visual stimulus without having to do any extra movement such as holding the arm to look at a watch. The actual numerical value during physical exercise is of secondary interest since the key aspect for evaluating exercise level is a range of values or threshold values, (such as too high or too low) which are represented by visual and sound stimuli, as per the present invention. By causing a light to be illuminated corresponding to the value of a biological parameter, the user is assisted in guiding the exercise level and remaining within safe zones, in an effortless way in which the user has immediate response without having to think about a number being displayed and then analyzing whether the number falls into a desired exercise level.

Besides temperature and pulse, any other signal can be used including oxygen level, blood pressure, glucose level, eye pressure, and the like as well as signals from other devices such as a pedometer and the like. In addition, the light-based reporting means of the invention can include activation of a light source, such as LED, to indicate the distance or in the case of speedometer to indicate the speed of the user. For example, a user can program the pedometer to activate a light every 1,000 steps or every mile for instance during a marathon. The program is also adapted to activate a LED when the user is running within a certain speed, said speed being predetermined by the user. In this embodiment for example, the pedometer has 3 LEDs blue, green, and red, which are programmed to be activated according to a predetermined speed or distance. For example, the blue LED is activated if the speed is less than 6 minutes per mile, the green LED is activated if the speed is between 6 and 7 miles per minute, and the red LED is activated if the speed is more than 7 miles per minute. The system may also include a global positioning system or other system to track speed and/or distance, with a light being activated when the desired speed or distance is achieved, or alternatively the light is activated when the programmed speed and/or distance is not achieved.

The alert means alert the user when the signals received from a sensor are within appropriate levels or alert the user when the signal is outside levels of safety. For example, alert means inform the user about said user being in an optimal thermal zone (OTZ), in which the body temperature is within ideal levels for example for stimulating formation of heat-shock proteins. The OTZ is considered an appropriate level for health and performance, such as a temperature range between 37.0 degrees C. and 39.4 degrees C., and most preferably around 38.0 degrees C., and even more preferably around 38.5 degrees, up to 39 degrees C., for stimulating formation of heat shock proteins. The OTZ indicates a range of temperature that is safe and that leads to the best performance without overheating. Different levels of OTZ can lead to burning fat efficiently, as burning generates heat which is reflected in an increase in body temperature. Likewise, an optimal pulse zone (OPZ) indicates the optimal range for improving heart fitness. A second zone OPZ-F indicates the range of pulse that can lead to burning fat. A variety of optimal zones can be used and programmed so as to activate the LEDs in accordance with the optimal zone of interest such as fitness, endurance, heart-lung exercise, improving cardiovascular fitness, burning fat, and the like.

The alert means of the footwear or clothing preferably includes a set of lights which are activated according to the level of a biological parameter, such as temperature zone or pulse of the user. One aspect of this invention includes providing an interactive footwear or apparel which helps the user maintain physical activity within an optimal range by visualizing lights and/or listening to sound from shoes and/or apparel. An array of LEDs are mounted on a portion of footwear or clothing which are easily visualized, such as for example the upper portion of a footwear or the portion of an apparel covering the chest or front part of the lower extremities. It is understood that any head mounted gear can also be used with the array of LEDs mounted on a location easily visualized during physical activity. The information about exercise level is then acquired in an effortless way and a natural way. A particular number is not necessary in the preferred embodiment, since the array of lights can indicate the level of exertion and whether the user is within an optimal zone for the planned activity. For example an array of LEDs mounted in the tongue of a shoe or upper portion of a shoe illuminates in a certain manner or flashes in a sequence to indicate the level of a biological parameter, such as pulse level, oxygen level, blood pressure level, or temperature level, or to identify the presence of a chemical substance such as drugs or any analyte present in the body.

In one embodiment an array of LEDs is mounted on the upper portion or tongue of the shoe, said LEDs being electrically connected to a processor which controls and drives the LED array based on an electrical signal, received from a transmitter coupled to a sensor monitoring a physiological parameter. The processor is operatively coupled to a receiver, said receiver receiving signals from said sensor monitoring a any parameter including physiological parameters or environmental parameters such as ambient temperature, humidity, wind and the like, said signals from said sensor preferably being wirelessly transmitted to the receiver in the footwear. In another embodiment the sensor is located in the shoe including sensors for physiological parameters such blood flow, temperature, pulse and any other physiological parameter and/or for detecting ambient conditions such as a ambient temperature, humidity, ultraviolet rays, wind, and the like. In those embodiments there is no need for signal transmission as with remotely placed sensors since the light source is also located in the shoe, and said light source can be integrated with the sensor. The processor is operative to illuminate the LED for a certain period of time preferably in accordance with the user being in the OTZ and/or OPZ, for example by illuminating a green LED. Alternatively, the processing circuit illuminates a red LED to inform the user that the temperature or pulse is too high, or a blue LED to inform that the temperature or pulse is too low, or any combination thereof involving any color or number of LEDs.

The signal from the transmitter coupled to the sensor is transmitted to the receiver in a shoe or clothing, said signal driving a LED or a speaker in said shoe or clothing. For example, when a human subject monitoring pulse and temperature with a BTT sunglasses sends a wireless signal from said BTT sunglasses to a receiver in a shoe worn by said user, and said signal corresponds to an optimal thermal zone and optimal pulse zone, then said signal causes two green LEDs to illuminate in the shoe to indicate that both temperature and pulse are within ideal levels, and causes the shoe to produce the sound "optimal zone". It is understood that any sound can be produced or any visual indicia can be used to effortlessly and naturally inform the user about the biological parameter level. Accordingly, if the signal received indicates the user is too hot or the pulse is too high, then an indicia representing a Coca-Cola™ logo or a Pepsi-Cola™ logo is illuminated indicating that the user should take some liquid and be hydrated, so as for example to avoid heat injury. Likewise, the signal indicating high temperature can cause the speaker in the shoe or apparel to produce the sound "water", "time for your Coke™", "time for your Pepsi™", and the like. Besides monitoring pulse with a BTT device, any other device for pulse detection including a conventional chest strap for pulse monitoring can be used, said monitoring devices transmitting a signal to a shoe or apparel to drive lights, speaker, and the like. It is also understood that any signal from any device monitoring physiological parameters can be used. Accordingly, a device monitoring glucose, eye pressure, drug levels, cholesterol, and the like can transmit the signal to a footwear or apparel, which cause for example a LED representing low glucose levels to illuminate, and the speaker to produce the sound "sugar low—drink a juice" or the name of a medication is illuminated in the shoe or apparel to indicate the physiological value. Thus when a diabetic is the user of the biological light-sound system of this invention and if the user is monitoring glucose and the word "insulin" is illuminated in the shoe, clothing, or accessories, then that user knows that sugar levels are too high.

It is understood that the housing, referred to herein as module or biological monitoring electronic-LED module, containing the RF receiver, power source, processor, LED, and speaker can be removably attached to the shoe or apparel or permanently mounted on the shoe or apparel. For example a pocket in the shoe or apparel such as a pocket in the tongue of the shoe can be used to house the biological monitoring electronic-LED module. Any pocket or other means to secure one or a plurality of modules to a shoe or apparel are contemplated and can be used. For example, two modules, one for monitoring temperature from a BTT sunglasses is secured by a hook and loop fastener (such as a Velcro™) to a shirt while a second module for monitoring pulse from a chest strap is placed in a pocket located in the tongue of a shoe. When the BTT sunglasses sends a temperature signal to inform the user of the temperature level the LED secured to the shirt illuminates. The same occurs with the LED in the shoe which is activated by a pulse signal from the chest strap.

Now referring to FIG. 95A, there is seen a shoe 2600 having an upper portion 2602 including a tongue 2604 having a housing 2606, such as a pocket, for housing module 2610, said module 2610 including a power source 2612, a wireless receiver circuit 2614, and at least one LED 2620 operatively coupled to the wireless receiver circuit 2614 functioning as a LED driver. Module 2610 can further include a processor 2616 and a speaker 2618. Module 2610 is preferably made of plastic or any water-proof material. Although module 2610 is shown mounted in a tongue 2604 of the shoe 2600, it is understood that module 2610 can be mounted on any part of any shoe and in any type of shoe. It is further understood that module 2610 can include electronics mounted in one location of the shoe connected to a fiber optic or LED mounted in a second location in the shoe. For example the battery, wireless receiver, and controller are housed in a cavity in the heel of the shoe, and said electronics and battery in the heel are connected through wires to a LED in the tongue of the shoe, or an electronic circuit in the sole of the shoe can be connected to fiber optics located in the front part of the shoe. Any type of light source can be used including LED, fiber optic, chemiluminescent sources such as a light stick, fluorescent light, and the like. The location of the light source and speakers include any portion of the apparel or shoe, preferably the light source is located within the natural visual field of a human. It is understood that all of the arrangements described for a shoe can be used for an apparel or clothing.

The module 2610 can include a switch 2622, which can be activated by application of pressure when the shoe is in use or the module 2610 can include a manually operated switch.

Module 2610 can include any type of inertia-based switch to allow automated activation of a receiving system of module 2610. Accordingly, when the shoe is not in use or no pressure-based switch is activating the receiving system of the shoe it automatically shuts off. In addition, if the receiving system of the shoe does not receive any signal for a certain period of time, such as for example 10 minutes, then the receiving system of the shoe also automatically shuts off. Those arrangements for automatically turning the shoe on and/or off allows saving battery power and/or making the system of this invention easier to use. If the user wants to know an actual number for the biological parameter, a switch located in the monitoring device coupled to the sensor can be activated or a second switch on the shoe or apparel can be activated and a number can be displayed in the shoe or apparel, or in the monitoring device. In this embodiment, the shoe or apparel, or monitoring device can include a numerical display. For example, it is contemplated that the BTT sunglasses can be adapted to display a numerical value on the lens if requested by the user.

In FIG. 95B-1, a schematic illustration of this invention for pulse and temperature measurement is shown and includes a heart rate monitoring device 2624, represented by a chest strap for detecting a heart beat, a thermometer 2626, represented by eyeglasses for detecting body temperature, and a shoe, 2630, said shoe 2630 having a logo 2628 comprised of LEDs. Logo 2628 is seen in a magnified view in FIG. 95B-2, which shows one first LED 2632 and a second LED 2634 corresponding to a heart zone, said first LED 2632 being coupled to a signal representing a slow heart rate, and said second LED 2634 being coupled to a signal representing a fast heart rate. Besides LEDs 2632, 2634 coupled to a heart monitoring zone, a third LED 2636 corresponds to a body temperature zone, said LED 2636 being coupled to a signal representing an unsafe temperature level, such as a high body temperature.

Several exercise programs can be implemented with the invention. In order to achieve the proper exercise intensity, the user can use keypads or buttons to enter information into the monitoring device such as the eyeglasses or the chest strap device, or alternatively the user can enter the information in the shoe, said shoe being adapted to receive information and said information including age, body weight, height, exercise goals, and the like. A processor can then calculate the optimal temperature zone and optimal pulse zone for that particular exercise goal which will activate the LEDs in accordance with the signal received and exercise goal. For example, a user 40 years of age, 1.80 m tall, and weighing 95 kg, who wants to have a long workout (more than 45 min) with the objective of burning fat (weight loss), enters the information, which is fed into a processor. The processor is operatively coupled to a memory which stores the OTZ and OPZ associated with an exercise goal and user data. For example according to the user data, OTZ is between 38.1 degrees Celsius and 38.5 degrees Celsius and the OPZ is between 117 and 135 beats per minute (bpm), meaning optimal pulse is between 117 and 135 bpm. A preferred way to calculate the OPZ includes subtracting 220 from the age, which provides 180, and then calculating a percentage of the OPZ number (180) based on the user and exercise goals, which in this example is between 65% and 75%.

The processor is operatively coupled to the LEDs, and in the exemplary embodiment if the temperature signal from the thermometer eyeglasses 2626 corresponds to a temperature higher then 38.5 degrees then LED 2636 is illuminated to indicate the high temperature, translating for example into the need for hydration or reducing exercise intensity since the user is outside his/her OTZ. Likewise, if a pulse signal from heart monitoring device 2624 corresponds to a heart rate less than 117 beats per minute, which is the target for the slowest heart rate, then the processor activates LED 2632 which is illuminated and indicating therefore a slow heart rate for the exercise goal. If the signal received from heart monitoring device 2624 corresponds to a heart rate faster than 135 bpm, which is the target for the fastest heart rate, then LED 2636 is activated and illuminated.

Considering another embodiment with four LEDs comprised of two LEDs marked T and two LEDs marked P, if the temperature falls below 38.1 degrees Celsius a "yellow LED market T" is illuminated indicating low temperature for OTZ, and if above 38.5 degrees Celsius then a "red LED marked T" is illuminated. If pulse is slower than 117 bpm then "yellow LED marked P" is illuminated and if pulse is faster than 135 a "red LED marked P" is illuminated.

An exemplary algorithm for heart monitoring in accordance with this invention is seen in FIG. 95C-1 and includes step 2640 to "acquire heart rate signal', which is preferably received wirelessly from heart monitoring device 2624. Step 2642 then determines whether "heart rate is slower than the slowest target heart rate", illustrated in the embodiment as heart rate less than 117 bpm. If yes, then step 2644 activates LED 2632 to indicate slow heart rate, and then proceed with the program at step 2640 to acquire heart rate signal. If not, then step 2646 determines whether "heart rate is faster than the fastest target heart rate" illustrated in the embodiment as a heart rate faster than 135 bpm. If yes, then step 2648 activates LED 2634 to indicate a fast heart rate and then proceed to step 2640. If not, then processing continues and program proceeds to step 2640. Likewise, FIG. 95C-2 shows an algorithm for body temperature monitoring according to this invention. Step 2650 acquires body temperature level, and step 2652 determines whether "temperature is higher than the highest target temperature", illustrated in the embodiment as temperature more than 38.5 degrees C. If yes, then step 2654 activates LED 2636 to indicate a high temperature and then proceed to step 2650. If not, then program continues to step 2650 and processing continues.

The invention includes a method for detecting and transmitting a biological parameter, receiving the transmitted signal with a receiver connected to a shoe or apparel, processing the received signal, determining the value of the biological parameter, and activating a light source based on the value. Further step may include activating a speaker. Other steps may include displaying a numerical value and transmitting the signal to another device.

It is understood that the program can be done in sequence, and include other parameters such as oxygen level and uptake, glucose level, blood pressure, acid lactic level, heat shock protein, and any other biological parameter or environmental parameter such as ambient temperature, humidity, wind speed, and the like. All of those parameters are reported using the reporting means of the invention such as the LED system of the invention. Accordingly, in yet another embodiment of this invention, a plurality of array of LEDs are provided. For example a first array of LEDs detects one parameter (e.g. pulse), said array of LEDs separate from a second array of LED measuring a second parameter (e.g. temperature), and both the first and second array of LEDs being separate from a third array of LEDs which measure a third parameter (e.g. environmental humidity). Each group of LEDs can be activated by a signal from a separate transmitter connected to each specific array of LEDs.

It is also understood that each LED can be marked with indicia indicating the physiological condition. Accordingly, an LED can have for example wording "High Temp", and/or "Fast HR" and/or "Slow HR" in order to report the physiological condition. Furthermore, a speaker or speech synthesizer can be included and concomitantly activated to produce, for example, the sound "High Temp", and/or "Fast HR" and/or "Slow HR". It is also understood that LED of different colors to indicate different levels for biological parameters can be used. For example, a green LED represents heart rate less than 130 bpm, a yellow LED represents heart rate more than 130 but less than 170 bpm, and red LED represents heart rate more than 170 bpm. A series of bars can also be used, one bar illuminated indicating heart rate less than 130 bpm, two bars illuminated indicating heart rate less than 170 bpm, and three bars illuminated indicating heart rate more than 170 bpm. The invention further includes a kit containing a device to monitor biological parameter and a shoe or an apparel. The kit can further include instructions. The illuminating device, such as LED, can be also removable to permit interchangeable selectivity of the color of the illuminating light.

Referring now to FIG. 95D, a block diagram is schematically illustrated, which includes a BTT transmitting system 2656, a heart rate transmitting system 2658, and shoe receiving system 2660. BTT transmitting system 2656 includes a BTT sensor 2662 (such as a temperature sensor), a processor and processing circuit 2664 including temperature algorithms, a transmitter 2666, an antenna 2668, and a battery 2670. Heart rate transmitting system 2658 includes a heart rate sensor 2672, a processor and processing circuit 2674 including heart rate algorithms, a transmitter 2676, an antenna 2678, and a battery 2680. Heart rate transmitting system 2658 can include a system comprised of electrodes and a transmitter attached to the body of the user, which can be housed for example in a chest strap. Heart rate monitoring system 2658 can also include a wrist band, headband, head mounted gear, or any other means to monitor pulse or gear adapted to detect a pulse of a user. Shoe receiving system 2660 includes a receiver 2682 a processor and display control circuit 2684, an antenna 2686, and LEDs 2688, 2690, 2692, said LEDs 2688, 2690, 2692, corresponding to a different physiological condition as previously described. Accordingly, LEDs 2688, 2690, 2692, can correspond to the functions of LEDs 2632, 2634, and 2636. It is understood that each of the systems 2656, 2658, 2660 can include switches, electrical connections, and other integrated circuits for performing the need functions. Sensors 2662, 2672 generate an electrical signal which is transmitted to shoe receiving system 2660. In response to the signal received from the transmitting systems 2666, 2676 the processor and display control circuit 2684 may activate one or more LEDs for a certain period of time including flashing. Essentially any combination of lighting sequences of the LEDs and flashing can be employed in response to a signal received. The system of the invention provides a novel way in which a biological parameter level is indicated through illuminating specific LEDs. By causing a light to be illuminated corresponding to the value of a biological parameter, the user is assisted in guiding the exercise level and remaining within safe zones, in an effortless way in which the user has immediate response without having to think about a number being displayed and then analyzing whether the number falls into a desired exercise level and/or safe level.

It is understood that other receiving devices are contemplated and can benefit from the present invention. For example, an exercise machine can receive the signal and an array of LEDs mounted in said machine indicate to the user the exercise condition and biological parameter values without the user having to rely on a numerical value. Other devices contemplated include a wrist band mounted with at least one LED which is activated based on the level of the biological parameter, said wrist band detecting the level and reporting the level through a least one LED. In this embodiment there is no need for wireless transmission since the wrist band can detect pulse and thus detecting and reporting function are accomplished in the same device. Likewise, a chest strap can have one or more light sources to indicate the pulse level, said chest strap preferably being part of a garment or being under a thin shirt to facilitate visualizing the flashing LEDs. In another embodiment the chest strap monitoring heart rate can include speaker for audio reporting of a numerical value or reporting an optimal zone for exercising such as OPZ or OTZ. It is also understood that a wrist watch can include a set of lights which are illuminated to indicate OPZ and OTZ, or any other optimal value of a biological parameter. Besides, a range and threshold, a mean value can also be calculated and an LED activated to indicate achieving that mean value, or being outside the mean value, such as for example a mean pulse value. It is understood that in addition to illuminating light for feedback, if the user chooses, real-time, spoken feedback can alert said user to milestones, such as number of miles, throughout a workout. It is also contemplated that the shoe or apparel may include a chip that recognizes module 2610, which can work as a removably attached module, so a user can remove module 2610 from one shoe and insert the same module 2610 in or on an apparel or in or on another shoe, so any shoe or apparel with the chip can use the module 2610.

There are basically two types of thermometer probes using contact sensors in the prior art: 1) one for measuring internal temperature such as food thermometers and body temperature such as oral thermometers, which are inserted inside the object being measured, and 2) a second one for measuring surface temperature, such as for instance measuring temperature of a grill. Contrary to the prior art this invention teaches a new method and apparatus which combines in the same thermometer probe features of both internal temperature measurement and surface temperature measurement, such arrangement being necessary for measuring temperature in the brain tunnel.

Thermometer probes for internal temperature measurement of the prior art, such as oral/rectal thermometers, have temperature sensors covered by a metal cap or by other materials which are good heat conductors. The tip of the thermometers of the prior art were made out of metal or other thermally conducting material such as ceramics and the like, including the temperature sensor on the tip being surrounded by a metallic cap. Contrary to the prior art, this invention teaches a thermometer in which the temperature sensor is surrounded by an insulating material. In distinction to the prior art, the thermometer of this invention comprises a tip in which there is no metal or any conducting material surrounding the temperature sensor. The sides of the tip of the thermometer of this invention comprise insulating material, and thus the sides of the tip have at least one insulating layer. In addition this invention couples specialized dimensions with a novel temperature sensing tip that includes an insulating tip instead of a metallic tip, said insulating tip housing the temperature sensor.

Thermometer probes measuring surface temperature are concerned only with the surface being measured and thus do not require insulation in a large area of the probe nor a metallic cover to increase heat transfer. Basically those surface thermometer probes of the prior art have a thermocouple at the end of the probe, said end being rigid and made with hard material.

The design of this invention allows both to be accomplished, measuring internal as well as surface temperature simultaneously. In order to achieve precise surface measurement the BTT sensor is completely surrounded by insulation at the end of the probe. In order to measure internal temperature, the sensor has to enter the tunnel which causes an indentation in the skin. When the probe is pushed into the tunnel because of the characteristics of the BTT area and of skin, there is a rather significant indentation, which leads the skin to encircle and surround the tip, which would lead to affecting the temperature of the thermal sensor since the skin is cold. To prevent that, the probe of the invention has a rather long area (length) of insulating material above the sensor, and no heat conducting material around the tip of the probe, besides the special dimensions previously described. In addition, to conform to the specialized geometry of the skin at the BTT, the insulating material of this invention comprises a soft and preferably compressible insulating material at the tip. Contrary to this invention, the prior art has used hard materials on the tip, since those probes are used for measuring hard and/or flat surfaces, and not irregular surfaces such as the skin at the BTT. In addition, since the BTT geometry is concave in nature, the preferred embodiment of the end of the probe of this invention is essentially convex. Furthermore, the tip of the probe may comprise one or more sensors, and preferably a plurality of sensors disposed in an essentially convex surface. Programming in the processor selects the highest temperature among all sensors facilitating reading the temperature at the main entry point of the tunnel, which has the highest temperature. Preferably, a tip of the probe or the measuring surface of the probe includes both sensor and insulating material in said surface, and said probe is essentially cylindrical. The sensor of this invention which is located at the tip of the probe is surrounded by insulating material, both on top of said sensor and around the sides of said sensor. The sensor of this invention is preferably exposed at the tip of the probe without any material covering said sensor. Contrary to hard insulating material of the prior art, the sensor of this invention is surrounded by soft insulating material. The probe preferably uses a rod and hand held configuration. Contrary to the prior art which uses hard material to support the tip of the probe, such as used in surface measuring thermometer, the present invention uses exclusively soft material around the thermal sensor in its entirety, and no metallic or hard material are adjacent to the sensor or located within 4 mm from the tip of the sensor, this material being illustratively represented in several embodiments including body 2020. The shape of the tip of the probe of this invention is designed to conform and take the shape of the area of the BTT below and adjacent to the eyebrow and the nose, and more specifically to match the roof of the orbit by the nose and eyelid area. The prior art has a very small amount of insulating material around the tip since it was not designed to measure internal temperature. Contrary to the prior art, this invention, by having the necessity of avoiding temperature of the skin that may encircle the probe during entry of the sensor into the tunnel affecting the measurement, a rather large amount of insulation is used. The preferred length of material at the tip of the probe, said insulating material facing the environment, is equal to or less than 3.5 mm, and preferably equal to or no greater than 5 mm, and most preferably equal to or no greater than 10 mm. The insulating material at the tip is preferably not covered by any other material. The thermometer probe of this invention uniquely has features of both types of thermometer, penetrating and surface measuring thermometers. The tip of the thermometer of this invention preferably uses deformable material and conforms to the surface being measured. The tip of the probe takes the contour of the area that is being measured so it seal off any ambient temperature, and prevent surrounding skin tissue around the tunnel from touching the temperature element. Preferably stand alone insulating material is what supports the tip of the probe, said material being preferably compressible material with some springing characteristics. Features mentioned herein have been described in several embodiments of this invention including measuring portion and FIG. 96V-1 to FIG. 97M-2.

In addition, the present invention discloses novel methods and apparatus for measuring biological parameters, such as temperature. Accordingly and in reference to FIG. 96, the present invention discloses an intelligent stylus 2700 associated with an electronic device 2702, such as a PDA, a hand held computerized device, a tablet computer, a notebook computer, or any electronic device which uses a rod (stylus) for touching the screen for performing a function. The device of the invention includes the intelligent stylus 2700 represented herein by a touch-screen stylus or any rod for touching the screen of the electronic device 2702. Stylus 2700 houses a sensor 2704 on one end 2706, said end being opposite to the end of the stylus adapted to touch the screen, with said end 2706 referred herein as the sensing end of stylus 2700, and further including an opposite end 2708, hereinafter referred to as the touching end of the stylus 2700. Stylus 2700 further includes wiring 2710 disposed on or inside stylus 2700, and preferably inside the body 2712 of the stylus 2700 for connecting said stylus 2700 with electronic device 2702. The free end of wire 2710 connects with sensor 2704 and the other end exits the stylus 2700, and connects with a thicker external wire portion 2714 which is connected to electronic device 2702. Wire 2710 preferably exits said stylus 2700 at the mid portion 2716. In the prior art, wires exit a rod through the end or the tip of said rod, and not through the mid-portion of the rod. This novel arrangement of the present invention which include the wire exiting in the middle portion of the rod, allows both ends, sensing end 2706 and touch screen end 2708 to be free, with the touching end 2708 for touching the screen 2718 of electronic device 2702 and sensing end 2706 housing sensor 2704 to touch the body for measurement.

The electronic device 2702 comprises a touch-screen 2718 which includes a display box 2720 for displaying the numerical value of the signal acquired by the sensor 2704, a second window 2722 to display stored values of the signal being measured, a wire 2714 for connecting the electronic device 2702 with the stylus 2700, and further preferably including a dialog box 2724 for displaying user information such as patient identification, in addition to a processor 2726, and power source 2728. If electronic device 2702 is arranged as a Personal Digital Assistant (PDA), it preferably includes a conventional key pad 2730 for PDAs.

FIG. 96A concerns Prior Art and shows a rod 2732 with a contact sensing tip 2734 for body temperature measuring device, such as internal thermometer, with said sensing tip 2734 comprised of metal or other material with high thermal conductive. Sensor 2745 in the tip 2734 of rod 2732 is covered by a high thermal conductivity material 2735. Tip 2734 of the prior art also comprises a hard material. In addition the tip of a thermometer of the prior art covered by metal or a thermally conductive material has a dimension equal to or more than 10 mm for said thermal conductive material.

In contrast to the Prior Art, FIG. 96B shows the specialized temperature measuring device 2760 of this invention, wherein a rod 2742 with a sensing tip 2740 housing a temperature sensor 2736 is surrounded by an insulating material 2738, said insulating material 2738 comprised of any material having low thermal conductivity. Rod 2742 is connected to a main body 2752, said body 2752 housing a printed circuit board with microprocessor 2754, battery 2756 and display 2758. The tip 2740 housing the temperature sensor comprises low thermal conductivity material 2738. The tip 2740 of the rod of the thermometer of this invention includes a combination of a temperature sensor 2736 and low thermal conductivity material 2738. Temperature sensor 2736 is surrounded by insulating material 2738, with only the sensing surface 2746 of said sensor 2736 not being covered by insulating material 2738. The external side surfaces 2744 of the tip 2740 comprise insulating material 2738. Temperature sensor 2736 is surrounded by the insulating material 2738. The insulating material 2738 has an external sensing surface 2748 which touches the body or skin during measurement and supports the sensor 2736, an external side surface 2744 which is essentially perpendicular to sensing surface 2748, and an internal surface 2750 which faces the inner portion of the rod 2742. FIG. 96-C is a schematic perspective view of the tip 2740 of the rod 2742 of FIG. 96-B showing sensor 2736 and the insulating material 2738, said insulating material 2738 having external sensing surface 2748 and side external face 2744. The preferred largest dimension for external sensing surface 2748 of insulating material 2738 is equal to or less than 20 mm, and preferably equal to or less than 15 mm, and most preferably equal to or less than 10 mm in its longest dimension, and even most preferably equal to or less than 8 mm. The preferred largest dimension of the temperature sensor 2736 is equal to or less than 6 mm, and preferably equal to or less than 4 mm, and most preferably equal to or less than 2 mm in its longest dimension, and even most preferably equal to or less than 1 mm, in accordance to the main entry point and general entry point, of the brain tunnel. The dimension for other sensors are similar, such as pressure, piezoelectric, and the like, and a pair light emitter-detector may include larger dimensions. Dimensions of and description of insulating material is applicable to any of the rod-like embodiments of this invention including intelligent stylus 2700, and any other rod-like sensing device such as a pen, an antenna, and any other stick-like structure. The tip housing for securing a temperature sensor of the prior art comprises an essentially hard tip. Contrary to the prior art, the tip of this invention housing or securing the temperature sensor is essentially soft. FIG. 96D shows another embodiment comprising a rod 2764 having a bulging sensor 2762 surrounded by insulating material 2766, which extends beyond the end of rod 2764.

The intelligent stylus of the invention can be used in the conventional manner with a metal cap, but contrary to the thermometers of prior art, the wire of the intelligent stylus of this invention exit said stylus in the mid-portion of the stylus. As seen in FIG. 96-E, which shows Prior Art, wire 2782 of the thermometer 2784 of the prior art exit the rod 2786 at the end 2788 of said rod 2786. Wire 2782 connect sensor 2790 to electronic device 2792. The thermometers of the Prior Art that includes a rod and a wire comprises one end having the sensor and the opposite end of the rod having the wire, such as found in Welch Allyn thermometers, Filac thermometers, and the like.

FIG. 96-F shows another embodiment according to the invention, wherein sensor 2770 is housed in the end of the stylus 2768, wherein sensor 2770 is covered with cap 2772 preferably made of metal, ceramic, or other thermally conductive material and most preferably made of a metal, said cap 2772 completely covering the end 2774 of the stylus 2768, and said sensor 2770 is connected to a wire 2778 which exits stylus 2768 in the mid-portion 2776 of said stylus 2768. The distance from the tip of the metal cap 2772 to the mid part 2776 of the stylus 2768, shown by arrow 2769, measures preferably at least 30 mm and less than 300 mm, and most preferably at least 30 mm and less than 200 mm, and even most preferably at least 20 mm and less than 40 mm. Wire 2778 which connects stylus 2768 to an electronic device 2780 uniquely exits stylus 2768 at a mid-portion 2776. Mid-portion or middle portion is referred in this invention as any portion which is located between the two ends of the stylus or any rod like structure.

FIG. 96-G1 shows another preferred embodiment, wherein a cap 2794 housing reagent 2796 such as glucose oxidase is adapted on top of the sensing end 2798 housing sensor 2800 of the stylus 2802. Cap 2794 has arms 2804 for securing cap 2794 on top of sensing end 2798. When blood containing glucose is deposited on top of cap 2794, reagent 2796 generates a reaction which is sensed by sensor 2800, such as an electrochemical or optical sensor, generating a signal that is translated into glucose level after standard processing. FIG. 96-G2 shows in more detail specialized cap 2794 of FIG. 96-G1, which is preferably essentially cylindrical, and houses reagent 2796. Cap further includes arms 2804 and extension 2806 for handling and placement purpose.

FIG. 96H shows a specialized end 2807 of the thermometer of this invention that includes a rod 2811 having a cap 2805 made of metal or thermally conductive material, said cap covering a temperature sensor 2809. Dimension "2813", represented by arrow 2813, said dimension going from the edge of the cap 2805 to the tip of the cap 2805 corresponds to the largest dimension of a metal cap of this invention. The preferred length of dimension 2813 is equal to or less than 3 mm, and preferably equal to or less than 2 mm, and more preferably equal to or less than 1.5 mm, and even more preferably equal to or less than 1 mm.

FIG. 96J is another embodiment, wherein the stylus 2810 includes a touching end 2812 and a sensing end 2814, said sensing end 2814 having a slot 2808, said slot adapted to receive a strip 2818 such as a strip reagent for a chemical reaction including glucose oxidase detection of glucose present in blood applied to said strip 2818. Stylus 2810 further includes a detecting area 2816 which is adapted to receive strip 2818 and detects the chemical reaction that occurred in said strip 2818, and produces a signal corresponding to the amount of a chemical substance or analyte present in strip 2818. Wire 2820 is connected in one to end to detecting area 2816 and exits stylus 2810 through the mid-portion 2822 of said stylus 2810. The external wire portion 2826 connects the stylus 2810 to a processing and display unit 2824. Touching end 2812 comprises an end adapted to touch a screen, or alternatively an end adapted for writing, such as a pen or pencil.

Although, a preferred embodiment includes a wired system, it is understood that the intelligent stylus of the invention also includes a wireless system. In this embodiment, as shown in FIG. 96K, stylus 2830 is connected by wireless wave 2828 with electronic wireless electronic device 2832. Stylus 2830 has three portions, sensing end 2836, touching end 2844, and middle portion 2838. The sensor 2834 is housed on the sensing end 2836 of the stylus 2830, and the mid portion 2838 of the stylus 2830 houses a printed circuit board 2840 which includes a wireless transmitter, and power source 2842. Mid-portion 2838 preferably has a larger dimension than the sensing end 2836 housing the sensor 2834 and larger than the touching end 2844. Dimension A-A1 of mid portion 2838 is preferably larger than dimension B-B1 of the touching end 2844 and larger than dimension C-C1 at the sensing end 2836.

The end opposite to sensing end 2836 preferably comprises touching end 2844, with said touching end 2844 of the stylus 2830 being preferably free of any sensors and used to touch a surface 2846 of wireless electronic device 2832. This arrangement keeps surface 2846 of wireless electronic device 2832 from being scratched or damaged if the touching end also would house a sensor. Likewise the arrangement prevents the sensor 2834 from being damaged by touching a surface, such as surface 2846.

In reference to FIG. 96-L, another preferred embodiment of the invention includes a sensing-writing instrument 2850 comprising preferably a rod-like shape article which comprises a sensing portion 2870 and a writing portion 2872. Sensing portion 2870 houses electronic parts 2864, 2866, and battery 2868 and includes a sensing end 2852 which houses a sensor 2854. Writing portion 2872 houses a writing element 2856 and includes a writing end 2874. Writing element 2856 contains ink 2858 said writing element 2856 having a distal end 2860 adapted to deliver said ink 2858. The sensing-writing device 2850 further includes a wire 2862 which connects sensor 2854 to electronics and display circuit 2864, which displays a value measured from sensor 2854, a printed circuit board/microchip 2866, which calculates the value based on signal from sensor 2854, and a power source 2868, all of which are preferably housed in the upper portion of the instrument 2850. It is understood that writing element 2856 can be mounted on a spring 2876. Sensing portion 2870 is preferably of larger diameter than the writing portion 2872. Although the preferred embodiment includes the sensor 2854 being housed in the end opposite to the writing end 2874, it is understood that the sensor 2854 can be housed in the writing end 2874, preferably having a rotating barrel and spring that includes the sensor 2854 and writing element 2856 sitting adjacent to each other in the barrel (not shown). Upon actuation the sensor end is exposed, and with further actuation the sensor end retracts and the writing end is exposed. Writing element 2856 can include a tube holding ink, and for the purposes of the description include any article that can deliver a substance that allows writing, drawing, painting, and the like and includes pens of any type, pencils of any type, wax-based writing instruments such as crayons, a paint brush, and the like.

It is understood that any electronic device such as an electronic device which recognizes alphabetical, numerical, drawing characters and the like is within the scope of the invention. An exemplary electronic device includes a device with an electronic surface that recognizes strokes by a writing instrument in which regular paper can be placed on top of said electronic surface for the purpose of writing and converting said writing into digital information by a variety of optical character recognition systems or similar systems, with said writing instrument housing a sensor in accordance with the present invention.

By way of illustration, but not of limitation, exemplary sensors and systems for the intelligent stylus will now be described. The sensor can comprise at least one of or a combination of temperature sensor, electrochemical sensor (such as a blood gas sensor for measuring oxygen), an enzymatic sensor (such as glucose oxidase sensor for measuring glucose), a fluorescent sensor, and an infrared sensing system including a light emitter and a photodetector adapted side-by-side, and using preferably reflectance for measuring the level of a substance, such as glucose or oxygen saturation.

A plurality of sensing and detecting systems are contemplated including an intelligent stylus comprising a microphone and a pressure sensor for measurement of pulse and blood pressure. The end of the stylus preferably houses a piezoelectric sensor to detect sound, and a mechanism to apply pressure, such a blood pressure cuff, in order to change the blood flow and elicit a change in sound. The blood pressure cuff has a wireless pressure transmitter that transmits the pressure information to the electronic device, such as a PDA. When the piezoelectric or microphone of the stylus detects a change in sound it sends a signal to the PDA, which then stores the pressure transmitted by the pressure cuff, creating thus a coupling between the pressure being measured by the cuff and the change in sound detected by the stylus. It is understood that the stylus can include a pressure sensor coupled to a mechanical pressure means that apply pressure in the blood vessel for detection of the mean arterial pressure, and the change in pressure corresponding to the arterial pressure. It is also understood that the end of the stylus of the invention can house a fiberoptic system or other optical system such as system for measuring fluorescent light, and for illuminating the area being measured and identifying the arterial pulse.

Another preferred embodiment includes an antenna with sensing capabilities, the sensing-antenna article comprises preferably a rod-like antenna including a whip antenna and wire antenna which houses in its free end a sensor and the opposite end is void of any sensor and connected to conventional radio electronics or communications electronics and ground plane such as antennas found in cellular phones and radios. Although the sensor is preferably located at the end of the antenna, it is understood that the sensor can be housed adjacent to the free end of the antenna. A preferred embodiment includes a cellular phone housing a temperature sensor at the free end of the antenna, with said cell phone comprising electronic means to convert the sensor signal into a temperature signal, and further means to display by visual, audio, or other indicator the temperature measured. The radio or cell phone of the present invention is adapted to generate and process the signal of a biological parameter being measured with the antenna, thus the cell phone, radio, or other device with an antenna can then function as a thermometer for measuring body temperature using a sensor housed in the antenna. Besides measuring body temperature, the antenna can be adapted to measure temperature in general such as liquids and also for measuring ambient temperature.

Accordingly, FIG. 96-M is another preferred embodiment showing a telephone 2880 including a dial pad 2888, a display 2890, electronics 2892 and a sensing antenna 2882 having a sensor 2884 in its free end 2886. Sensor 2884 is connected to ground plane and electronics 2894 through wire 2895.

FIG. 96-N and FIG. 96-P show in detail exemplary arrangements of the antenna with sensing capabilities of this invention. FIG. 96-N shows sensing antenna 2900 having two compartments, one compartment 2898 housing sensor 2896 and wire 2902, and a second compartment comprised of the antenna 2904 for transmitting and receiving electromagnetic waves. Sensor 2896 can be positioned on the top part or the side part of the compartment 2898. FIG. 96-P shows antenna 2910 having a sensor 2906 and a wire 2908 inside the antenna 2910. The method includes the step of positioning the free end of the antenna housing a sensor in apposition to the area being measured, such as the skin of the BT; generating an electrical signal based on the value of the biological parameter being measured, and reporting the value of the biological parameter such as displaying a numerical value. It is understood that any contact and non-contact sensor or detector, can be housed in or on the antenna.

The system can further include a system for measuring wind effect. In this embodiment the temperature sensor is a thermistor. Upon actuation electronics in the cell phone apply current to the thermistor in order to increase the temperature of said thermistor. Since the antenna is exposed to air, the rate of increase of temperature of the thermistor is inversely proportional to the wind speed. With higher wind speed, there is proportionally a need to increase in energy in order to maintain the temperature of the sensor constant. Software can be adapted to identify wind speed, and thus heat or cold index, based on the ambient temperature and the change in temperature of the thermistor being heated up.

It is understood that the sensor at the end of the sensing-antenna or at the end of the sensing-writing instruments can also include a probe cover to avoid cross-contamination when touching a body part, or when touching a drink to measure the temperature of such a drink. It is yet understood that software can be adapted to allow subtle changes in temperature corresponding to ovulation or pre-ovulation to be detected, with said cell phone or radio having means to identify such changes and indicators to display the information about ovulation.

It is understood that a variety of sensing and detecting arrangements are contemplated as shown from FIG. 96-Q1 to FIG. 96-Q4. FIG. 96-Q1 is a planar view of a rod-like sensing device such as a thermometer, a stylus, a writing instrument, an antenna, and the like showing the sensing surface 2912 of a rod-like sensing device having a sensor 2914. Sensing surface 2912 can comprise entirely of a sensor or detector. The preferred largest dimension of sensing surface 2912 is equal to or less than 21 mm, and preferably equal to or less than 15 mm, and most preferably equal to or less than 10 mm. Considering sensor 2914 as a single sensor, the preferred largest dimension of sensor 2914 is equal to or less than 15 mm, and preferably equal to or less than 10 mm, and most preferably equal to or less than 5 mm. FIG. 96-Q2 is a side view of another preferred embodiment showing rod-like structure 2916 having an infrared radiation detector 2918 and sensing surface 2920. FIG. 96Q-3 shows a pair light emitter-light detector 2922 mounted in a rod-like structure 2924, said sensor being disposed flush in relation to the end of said rod 2924. FIG. 96Q-4 shows a bulging light emitter-light detector pair 2926 of a rod-like sensing structure 2928.

FIG. 96R-1 is another preferred embodiment showing a spring-based measuring portion 2930 including a hollow rod 2932 that works as a tunnel, an adjustably positionable arm 2944, a spring 2936, and a sensor 2934, said sensor 2934 being secured to a sensing support structure 2940 and covered by a cap 2938. Spring 2936 is covered by an essentially cylindrical-like structure 2952 which has free end 2946 and has a second end 2942 attached to rod 2932 and/or arm 2944. Sensing support structure 2940 includes preferably two portions, a distal portion 2948 housing sensor 2934, and a proximal part 2950 comprised of a rod-like portion, said portion being adapted to secure one end of the spring 2936. The spring 2936 is connected to the proximal part 2950 of the support structure 2940 in one end and is connected to rod 2932 at the opposite end. Any attachment means such as glue, heat, and the like can be used to attach spring 2936 to support structure 2940 and rod 2932. The preferred length of the proximal part 2950, in which spring 2936 is attached to, is equal to or less than 7 mm, and preferably equal to or less than 3 mm, and most preferably equal or less than 2 mm. The preferred length of the rod 2932, in which spring 2936 is attached to, is equal to or less than 7 mm, and preferably equal to or less than 3 mm, and most preferably equal to or less than 2 mm. Rod 2932 terminates in adjustably positionable arm, 2944, which is preferably hollow and has flexible characteristics and memory, and is similar to arm 2004 which has been previously described. The preferred length from the edge of the proximal part 2950 and the edge of the rod 2932, which corresponds to the length in which spring 2936 is not in contact with any structure, is equal to or less than 9 mm, and preferably equal to or less than 4 mm, and most preferably equal to or less than 3 mm. The preferred diameter of spring 2936 is equal to or less than 10 mm, and preferably equal to or less than 4 mm, and most preferably equal to or less than 2 mm. The preferred diameter of rod 2932 is equal to or less than 10 mm, and preferably equal to or less than 4 mm, and most preferably equal to or less than 2 mm. Sensor 2934 is connected to wire 2947 which is disposed inside the spring 2936, and inside rod 2932 and arm 2944. The preferred length from the edge of cap 2938 to part 2932 is equal to or less than 14 mm, and preferably equal to or less than 11 mm, and most preferably equal to or less than 8 mm. The preferred largest dimension of sensor 2934 is equal to or less than 14 mm, and preferably equal to or less than 10 mm, and most preferably equal to or less than 5 mm, and even more preferably equal to or less than 2 mm. The embodiment of FIG. 96R-1 can be used with any support structure including those of the embodiments of FIG. 86A, FIG. 91, FIG. 92A, FIG. 92B and FIG. 92D as well as FIGS. 100A to 100Z, said FIG. 92D showing by way of example the embodiment of FIG. 96R-1 integrated into eyewear.

FIG. 96R-2 is a planar view of the spring-based measuring portion 2930 showing the surface of cap 2938 showing an exemplary sensor chip 2960 disposed under said cap 2938, said cap 2938 preferably being made of metal or other heat conducting material. A soldering joint 2962 connects sensor chip 2960 to a wire 2964, and a second wire 2966 is connected to the cap 2938 through solder joint 2968. The preferred diameter of cap 2938 is equal to or less than 14.8 mm, and preferably equal to or less than 10.8 mm, and most preferably equal to or less than 5.8 mm, and even more preferably equal to or less than 2.8 mm.

FIG. 96S-1 to 96S-4 shows an exemplary embodiment for a measuring portion of this invention. FIG. 96S-1 shows measuring portion 2970 comprised of a convex cap 2972 made preferably of copper, and includes a sensor arrangement disposed under said cap 2972, said arrangement comprised of sensor chip 2974 sandwiched between electrode 2976 and electrode 2978 and connected to wire 2982, and includes a second wire 2980 connected to cap 2972. FIG. 96S-2 shows measuring portion 2984 comprised of a convex cap 2986, and includes a sensor arrangement disposed under said cap 2986, said arrangement comprised of sensor chip 2988 sandwiched between electrode 2990 and electrode 2992. Wire 2994 is soldered with electrode 2992 and wire 2996 is disposed between electrode 2990 and cap 2986. FIG. 96S-3 shows the embodiment of FIG. 96S-1 in which convex cap 2972 is replaced by a flat cap 2998. This preferred embodiment provides the least amount of heat loss. FIG. 96S-4 shows the embodiment of FIG. 96S-1 in which flat copper cap 2998 is replaced by a solid metal cap 3000.

FIG. 96T-1 shows measuring portion 3002 including the sensor arrangement of the embodiment of FIG. 96S-3, in addition to spring 3004 seen in a cross sectional view, said spring 3004 being adjacent to wire portion 3006, which is shown in its bent position (by small arrow) after compression of spring 3004, said wire portion 3006 being adapted for bending upon compression of spring 3004, and further including rod 3008 which is attached to spring 3004 and houses wire portion 3010, said wire portion 3010 being unable to move or slide. FIG. 96T-2 shows detail of the wire portion 3006 forming a curve upon pressing of spring 3004. The curve formed by wire 3006 upon compression is limited by the diameter of the spring. It is understood that the method includes the step of positioning the sensor, compressing the spring, and generating an electrical signal from said sensor. The dimension of the wire curve is adjusted to fit within the diameter of the spring.

FIG. 96U is a cross sectional diagrammatic view of a preferred embodiment of the measuring portion or sensing assembly 3012 of this invention, and includes a flat cap 3014. Preferred thickness of cap 3014 from the edge of said cap 3014 to the tip of said cap 3014 is equal to or less than 2 mm, and the preferred diameter of said cap 3014 is equal to or less than 2 mm. Those dimensions are preferably used for measurement of temperature or pulse. Cap 3014 is attached to sensor 3016, said cap 3014 covering sensor 3016. Spring 3018 is connected in one end to cap 3014 and in the opposite end to rod 3020. A wire 3022 connected to sensor 3016 is seen in a bent position and inside an area comprised by the spring 3018. Spring 3018 is attached to cap 3014 in one end and to rod 3020 at the other end. Wire 3022 is affixed to sensor 3016 in one end and to rod 3020 in the other end in order to allow said wire 3022 to bend and extend upon compression and decompression of spring 3018. Measuring portion 3012 is covered by a structure 3024 made preferably of a soft plastic and adapted to protect the spring 3018 and associated components such as wire 3022, said structure 3024 preferably shaped as a cylinder in which the distal end 3026 is open, allowing thus unobstructed movement of cap 3014 and sensor 3016. It is understood that any material that works as a spring or which has compression and decompression capabilities can be used in a similar manner as spring 3018. Any foam, gels, or compressible material with spring capabilities can be used. It is also understood that any sensor or sensor system can be used and replace cap 3014 including enzymatic sensors, optical sensors, fluorescent light, a pair light emitter-light detector, a radiation detector including infrared radiation detector, and the like. It is also understood that preferred dimensions are chosen according to the type of sensor being used.

FIG. 96V-1 is another embodiment showing another hand-held device for measuring biological parameters, and illustratively shows the illustration of a hand held device 3030 including a body 3032 divided in two parts, one straight part 3036 and a bent part 3034, said straight part 3036 being of large diameter than bent part 3034, and said straight part 3036 terminating in a wire 3042, and further including a sensing tip 3038, which secures sensor 3044 and includes an insulating material 3040 surrounding sensor 3044. FIG. 96V-2 is a planar view of the hand held device 3030 showing sensing tip 3038 and sensor 3044 positioned on the center of sensing tip 3038 and surrounded by insulating material 3040.

FIG. 96V-3 is diagrammatic perspective view of a hand-held probe 3046 including a sensing tip 3050, said tip 3050 being essentially convex, and a sensor 3048 disposed at the end of said probe 3046. Sensing tip 3050 includes sensor 3048 and support structure 3052 which supports and insulates said sensor 3048, said structure 3052 being preferably comprised of soft insulating material. Sensor 3048 is connected to a processing and display unit 3054 through wire 3056 disposed preferably inside probe 3046. FIG. 96V-4 is a diagrammatic perspective view of a hand-held probe 3058 having a pair light emitter-detector 3060 in the sensing tip 3062, said sensing tip 3062 having support structure 3064 which preferably includes material that creates a barrier to infrared light. The radiation emitter-detector 3060 is connected to a processing and display unit 3066 through wire 3068. FIG. 96V-5 is another embodiment showing a J-shape configuration of probe 3070 of hand held measuring device 3080, said probe 3070 including two arms, 3074, 3072 said two arms 3074, 3072 being of dissimilar length. Arm 3074 terminates in sensing tip 3076, said tip 3076 securing sensor 3078. Arm 3074 is longer than the opposite arm 3072. Curve 3082 between two arms 3074 and 3072 is adapted to be positioned over the nose, with arm 3074 being positioned in a manner so as to position sensor 3078 on or adjacent to a brain tunnel. Sensor 3078 is connected through wire 3084 to a printed circuit board 3086 which houses processor 3088 and display 3090, said printed circuit board being connected to a power source 3092. Sensor 3078 includes contact and non-contact sensors and detectors such as a stand alone infrared radiation detector, said sensor being spaced from the site being measured or resting on the site being measured.

FIG. 97A to 97G shows exemplary manufacturing steps of a sensing device in accordance with this invention. FIG. 97A shows an exemplary measuring portion 3102 and a sensor 3110 connected to a wire 3108. Measuring portion 3102 includes insulating material 3104 disposed in a manner to create a two level sensing tip 3106. The first manufacturing step includes creating a passage 3116 in material 3104 to accommodate sensor 3110 and wire 3108. FIG. 97B shows material 3104 with passage 3116 and two holes 3112 and 3114 at the ends of passage 3116. Sensor 3110 and wire 3108 are inserted through material 3104. FIG. 97C shows an optional next step and includes bending the end 3109 of wire 3108 of the sensor 3110. Passage 3116 is made preferably eccentrically to allow sensor 3110 to be in the geometric center of sensing tip 3106 after being bent. This step of bending the wire of a long rectangular sensor, such as the thermistor of this invention, allows passage 3116 through material 3104 to be of small dimensions. Manufacturing may include a step of securing wire 3108 to material 3104 as shown in FIG. 97D, for example using a piece of glue 3120 or other attachment means. FIG. 97E shows plate 3118 being disposed along the lower portion 3122 of measuring portion 3102. Plate 3118 is preferably made of a thin metallic sheet, said plate 3118 having two ends 3124, 3126 and forming the arm and body of sensing device of this invention, said arm represented by portion 3134 of plate 3118 and body represented by portion 3132 of plate 3118. One end 3124 of plate 3118 is attached the lower portion 3122, sandwiching wire 3108 between end 3124 of plate 3118 and measuring portion 3102. Next step, as shown in FIG. 97F, may include inserting a rubberized sleeve 3128 including heat shrinking tube into plate 3118, but said step may also occur before attaching plate 3118 to measuring portion 3102, which is preferably used if end 3126 of plate 3118 is of larger dimension than end 3124. It is also shown in FIG. 97F the step comprised of attaching a soft plate 3130 to end 3126, said soft plate 3130 having preferably an adhesive surface 3136. FIG. 97G shows the finished sensing device 3100 including rubberized sleeve 3128 covering portion 3134 corresponding to the arm of sensing device 3100, soft plate 3130 being attached to end 3126 of plate 3118 corresponding to the body of sensing device 3100, and measuring portion 3102 with sensor 3110. It should be noted that, as in accordance to this invention, the sensor shown in FIGS. 97A to 97M-2 is supported and surrounded by the insulating material only and no other material, said insulating material being essentially soft.

FIG. 97H shows a larger sensor 3138 with wire 3142 being inserted through passage 3140. In this embodiment manufacturing step does not include bending the wire. A larger passage 3140 is made for inserting through material 3142 a sensor 3138, including a bead thermistor, a sensor covered by a cap, a thermopile, a radiation detector, and the like.

FIG. 97J shows another preferred embodiment of a measuring portion according to this invention. FIG. 97J shows support structure 3144 of a measuring portion 3148 comprised of a one level sensing tip 3146, said sensing tip 3146 securing a sensor 3150. Wire 3152 is inserted through hole 3154 into the support structure 3144 and disposed within support structure 3144 of measuring portion 3148. Wire 3152 is connected to sensor 3150 in one end and to a processing unit (not shown) at the other end. FIG. 97K-1 is another embodiment showing wire 3156 disposed on the external surface 3157 of support structure 3158 of a measuring portion. In this embodiment there is no hole in the support structure 3158 and the manufacturing step includes placing wire 3156 on the surface 3157 of structure 3158. As shown in FIG. 97K-2, manufacturing may include the step of attaching or securing wire 3156 and/or sensor 3160 to structure 3158 using glue or adhesive material represented by material 3162. FIG. 97L is another embodiment showing a slit 3164 being cut through support structure 3166, and wire 3168 being disposed along slit 3164 and secured to said slit 3164. Manufacturing may further include the steps described in FIGS. 97E and 97F.

FIG. 97M-1 is another embodiment showing a perforated plate 3170 having in one end 3182 an opening 3172 for receiving a measuring portion represented herein by structure 3174 which is adapted to secure a sensor. Perforated plate is divided in arm 3184 and body 3186, said body having a tunnel-like structure 3188. The step of a perforated plate receiving a measuring portion which holds a sensor may be followed by inserting a wire through the perforation in the plate. Accordingly, FIG. 97M-2 shows measuring portion 3176 comprised of a structure 3174, wire 3178 and sensor 3180, said measuring portion 3176 being attached to perforated plate 3170 at the end 3182. Sensor 3180 is connected by a wire 3178 which goes through structure 3174 and run on the surface of arm 3184 and then enters body 3186 through a hole 3190 and run inside tunnel 3188 of body 3186. Any of the measuring portions described in this invention can be used in a hand held device and be disposed at the end of a probe.

This embodiment of the present invention includes apparatus and methods for measuring brain temperature and detecting analytes in blood vessels directly from the brain by detecting infrared radiation from a brain tunnel. As previously taught the brain tunnel allows direct communication with the physiology and physics of the brain. Blood vessel of the brain tunnel remains open despite circulatory changes and/or vasoconstriction in other parts of the body and/or head.

The most representative and clinically significant representation of the thermal status of the body is brain temperature, and in particular the temperature of the hypothalamic thermoregulatory center. This invention identified a central thermal storage area in the brain around the hypothalamic thermoregulatory center and disclosed the pathway of least thermal resistance to the surface of the body, called Brain Temperature Tunnel because of its ability to work as a physiologic tunnel in which thermal and biological events in one end of the tunnel can be reproduced in an undisturbed manner at the other end of the tunnel. The BTT is an undisturbed and direct thermal connection between this thermal storage area in the brain and a specialized thermo-conductive peri-orbital skin.

This central thermal storage area is represented by the cavernous sinus (CS). CS is an endothelium-lined system of venous channels at the base of the skull creating a cavity working as a pool of venous blood adjacent to the hypothalamic thermoregulatory center. Venous blood in the CS is slow moving which creates a homogenous distribution of thermal energy. Venous blood is the blood type more representative of brain temperature. From a physical standpoint the slower moving blood will generate a lesser thermal gradient between the two ends of a vessel. Arterial blood, such as used in the prior art including temporal artery thermometer, is a fast moving blood which generates a significant thermal gradient and thus void the ability to reproduce accurately core temperature or brain temperature.

This invention identifies unique thermal characteristics only found in the CS. The CS collects and stores thermal energy from the various parts of the brain carried by slow moving deoxygenated blood that is in thermal equilibrium with the brain tissue, namely blood from the cerebral veins, meningeal veins, the sphenopalatine sinus, the superior petrosal sinus, the inferior petrosal sinus, and pterygoid venous plexus. By collecting blood from various parts of the brain, being located in the vicinity of the hypothalamic thermoregulatory center, and having slow moving blood, which allows thermal equilibrium with surrounding tissue and reduced heat loss, the CS functions as a central thermal storage area. While uniquely thermally communicating with various parts of the brain and being located adjacent to the thermoregulatory center, this invention identifies that the CS thermally communicates in an undisturbed manner to the surface of the body through a path of minimal thermal resistance represented by the superior ophthalmic vein (SOV).

To examine the thermal path from brain to skin and create a function for determining the temperature of brain tissue, this invention examined from a thermal standpoint each biological layer between the brain and the skin at the brain tunnel and gave a thermal resistance value to each structure. The temperature gradient between the brain and the skin at the brain tunnel is the summation of the individual temperature gradients across each structure. The lower the thermal resistance between the brain and the measuring site, the less the temperature difference.

Since according to the second law of thermodynamics heat will automatically flow from points of higher temperature to points of lower temperature, heat flow will be positive when the temperature gradient is negative. The metabolism taking place within the brain generates a considerable amount of heat, which the brain must dissipate in order to maintain a consistent and safe operating temperature within the skull. This generates a positive heat flow. When the temperature of the skin area of the brain tunnel and the temperature of the air around the skin of the brain tunnel is greater than the heat produced by the brain there will be a reduction of the positive heat flow up to a point of equilibrium between the brain and the skin area of the brain tunnel.

Most of the heat dissipation is accomplished by direct conduction through the circulatory system. However, the structure which encloses the brain providing physical protection also causes thermal isolation. As can be seen, these two requirements are in opposition to each other. Multiple layers of protection (1. thick skin, 2. subcutaneous tissue, 3. connective tissue aponeurosis (epicranium), 4. loose areolar tissue, 5. pericranium, 6. cranial bone, 7 dura matter, and 8 cerebral spinal fluid) also represent multiple layers of thermal insulation. Those insulating layers are represented by thermal resistance TR1, TR2, TR3, TR4, TR5, TR6, TR7 and TR8).

This invention identifies that with the exception of the thermal path through the BTT, heat energy flowing from within the brain to the external environment, including the forehead, must pass through about 8 insulating structures, and there is a temperature drop associated with each layer TR1 to TR8. As the heat flows in the direction of the cooler environment outside the body, we traced its path through multiple resistance layers which gives rise to a considerable temperature drop at the surface of the skin in all areas of the body including the head. The outer layer, especially, with a thick skin, fat tissue, and sweat glands (about 5 mm thick) contribute heavily to the thermal resistance equation. The variability resulting from those layers will lead to inconsistent measurements which occur in any skin area in the whole body outside the BTT, which were observed during testing and showed that skin areas outside the BTT area have 1.8 to 7.5 degrees centigrade difference between core temperature and skin temperature in skin areas outside the BTT.

Analysis of the pathway of least thermal resistance from the brain to the surface of the body was performed and the functional and anatomical architecture of the pathway characterized. A model for brain temperature and the thermal resistance pathway was done. The model includes the relationship for heat transfer by conduction proposed by the French scientist, J. J. Fourier, in 1822. It states that the rate of heat flow in a material is equal to the product of the following three quantities:

1. k, the thermal conductivity of the material.
2. A, the area of the section through which the heat flows by conduction.
3. dT/dx, the temperature gradient at the section, i.e., the rate of change of temperature T with respect to distance in the direction of heat flow x.

The fundamentals of heat transfer for conduction show that the greater the thermal conductivity, the less is the temperature drop or loss for a given quantity of heat flow. Conversely, the greater the thermal resistance in the heat flow path, the greater the temperature drop. The flow of heat through a thermal resistance is analogous to the flow of direct current through an electrical resistance because both types of flow obey similar equations.

The thermal circuit: $q = \Delta T/R$      Equation 1-1 q=thermal energy flow,
$\Delta T$=the temperature difference between two points,
R=the thermal resistance separating the two measuring points The electrical circuit: $i = \Delta E/Re$      Equation 1-2 i=the flow rate of electricity, i.e., the current
$\Delta E$=voltage difference
Re=electrical resistance The thermal resistance of the various insulating layers surrounding the brain was represented with resistors to evaluate the relative degree of resistance between different possible thermal paths from the brain to the skin. Heat flux sensors were constructed to measure true surface temperature. This is a special temperature probe with two sensors. A thin insulator is placed between the two temperature sensors. One sensor (S1) contacts the surface whose temperature is to be measured (BTT), the other sensor (S2) is on the opposite side of the insulator (facing away from the measurement site). If there is no net heat flow through the insulation layer (Q=0 in equation 1-1), there can be no temperature difference ($\Delta T$ in Equation 1-1 must=0) between the two sensors. The control circuit of the heat flux temperature probe provides just enough power to a small heating element next to sensor S2 to equalize or bring to zero the difference in temperature between S1 and S2. By eliminating the heat flow to the external environment we minimize, if not totally cancel, the heat flow from the superior ophthalmic vein to the skin surface under S1. This allows for a very accurate measurement of surface temperature (if Q=0 there is no temperature difference between the vein and skin). By comparing temperature measurements made with the heat flux temperature probe at the BTT site to those made with a miniature temperature probe (very low mass, 38 gauge connecting wires, and well insulated), it was possible to compute the temperature of the heat source (represented by the CS) within the body.

One embodiment includes acquiring radiation emitted from a brain tunnel. Preferably, radiation is acquired using the region between the eye and the eyebrow including scanning and/or positioning a radiation detector over the brain tunnel. Preferably, the brain tunnel area is scanned for about 5 to 10 seconds and the highest peak of infrared radiation from the brain tunnel is acquired, which reflects the peak temperature of the brain tunnel area. Every time a higher temperature is detected a beep or sound is produced, thus when no more beeps are produced the user knows that the peak temperature was acquired. The temperature acquired is representative of brain temperature reflected by blood from the brain. To acquire the core temperature of the brain, a specialized processing is used. The processing may take into account the thermal resistance (TR) of the path between the skin of the brain tunnel and the brain, which can be simplified by using the two main thermal resistances, namely TRB1 (representing thermal resistance due to skin) and TRB2, (representing thermal resistance due to the vascular wall and associated structures). Another factor in the calculation of core temperature may include the thermal gradient between the two ends of the tunnel. Through our experiments including using our fabricated heat flux sensors it was determined that the thermal resistance by TRB1 and TRB2 accounts for up to 0.65 degrees Celsius. Hence in order to determine the core temperature of the brain this invention includes apparatus and methods adapted to perform processing for determining internal body temperature, represented by the core temperature of the brain, illustrated by the equation:

$T_b = T_{bt} + TR$      (Equation 1-3)

where $T_b$ is the core temperature of the brain, $T_{bt}$ is the peak temperature of the skin of the brain tunnel as acquired by the radiation detector, and TR is an empirically determined factor which includes the thermal resistance between the skin of the brain tunnel and the brain.

The processing includes a sum of thermal resistances between the source of thermal energy inside the body plus the temperature of the skin area being measured. Specifically, the core temperature of the brain includes the temperature of the skin at the brain tunnel plus the sum of the thermal resistances of the structures between the skin of the brain tunnel and the brain. More specifically, the preferred processing circuit and processing includes the peak temperature of the skin area of the brain tunnel plus the sum of the thermal resistances between the skin of the brain tunnel and the brain, said thermal resistance comprised of a factor equal to or less than 0.20 degrees Celsius and equal to or more than 0.05 degrees Celsius. Preferably, processing circuit and processing includes the peak temperature of the skin area of the brain tunnel plus the sum of the thermal resistances between the skin of the brain tunnel and the brain, said thermal resistance comprised of a factor equal to or less than 0.30 degrees Celsius and more than 0.20 degrees Celsius. Most preferably, the processing circuit and processing includes the peak temperature of the skin area of the brain tunnel plus the sum of the thermal resistances between the skin of the brain tunnel and the brain, said thermal resistance comprised of a factor equal to or less than 0.65 degrees Celsius and more than 0.30 degrees Celsius. The radiation detector includes a processor and processing circuit having a computer readable medium having code for a computer readable program embodied therein for performing the calculations for determining core temperature, and may further include a memory operatively coupled with said processor, and a display, audio or visual, for reporting a value. Another embodiment includes a further step for determining the brain tissue temperature using the temperature of the skin of brain tunnel that includes a factor pertaining to heat flow and environment temperature around the brain tunnel. To acquire the temperature of the brain tissue (parenchymal temperature), a function taught by the present invention can be used and includes processing in the device to compute the brain tissue temperature based on thermal resistance and the environment temperature around the brain tunnel. The apparatus and methods includes a processing circuit that computes the brain temperature as a function of the temperature of the skin at the end of the brain tunnel and a factor related to the temperature of air within a 90 cm radius from the entrance of the brain tunnel at the skin, described herein as BT-ET300 (brain tunnel Environmental Temperature at 300 cm radius), also referred to herein as BT-300. The BT-300 factor varies with the environment temperature around the area being measured and is based on heat flow. It is understood that this function that includes a factor for each range of environment temperature can be used in other parts of the body beside the brain tunnel.

The BT-300 varies according to the environment temperature around the brain tunnel, or the skin target area being measured. If there is negative heat flow, then the value of the BT-300 is equal to zero in Equation 1-4 below, and equal to 1 (one) in Equation 1-5. If there is positive heat flow from brain to the environment of 0.1 degree Celsius, then BT-300 factor is equal to 1.003. Illustratively, if there is positive heat flow from brain to the environment with a difference of 0.2 degree Celsius, then BT-300 factor is equal to 1.006. If there is positive heat flow from brain to the environment with a difference of 0.3 degree Celsius, then BT-300 factor is equal to 1.009. If there is positive heat flow from brain to the environment with a difference of 0.5 degree Celsius, then BT-300 factor is equal to 1.012. If there is positive heat flow from brain to the environment with a difference of 0.5 degree Celsius, then BT-300 factor is equal to 1.015. If there is positive heat flow from brain to the environment with a difference of 0.6 degree Celsius, then BT-300 factor is equal to 1.018. If there is positive heat flow from brain to the environment with a difference of 0.7 degree Celsius, then BT-300 factor is equal to 1.021. If there is positive heat flow from brain to the environment with a difference of 0.8 degree Celsius, then BT-300 factor is equal to 1.024. If there is positive heat flow from brain to the environment with a difference of 0.9 degree Celsius, then BT-300 factor is equal to 1.027. If there is positive heat flow from brain to the environment with a difference of 1.0 degree Celsius, then the BT-300 factor is equal to 1.030. If there is positive heat flow from brain to the environment with a difference of equal to or more than 1.0 degree Celsius and less than 1.5 degrees Celsius, then the BT-300 factor is equal to 1.045. If there is positive heat flow from brain to the environment with a difference of equal to or more than 1.5 degrees Celsius and less than 2.0 degrees Celsius, then the BT-300 factor is equal to 1.060. If there is positive heat flow from brain to the environment with a difference of equal to or more than 2.0 degree Celsius, then the BT-300 factor is equal to 1.090. Therefore, equation 1-4 provides a method to calculate the corrected brain temperature.

$$T_{bc} = T_{bt} * BT\text{-}300 \qquad \text{(Equation 1-4)}$$

where $T_{bc}$ is the core temperature of the brain corrected for heat flow from the brain, $T_{bt}$ is the peak temperature of the skin of the brain tunnel as acquired by the radiation detector, and BT-300 is a factor based on the heat flow.

Using equation 1-4, the corrected temperature of brain tissue can be determined with the following equation:

$$T_{ct} = TR + (T_{bt} * BT\text{-}300) \qquad \text{(Equation 1-5)}$$

where $T_{ct}$ is the corrected core temperature of the brain tissue, $T_{bt}$ is again the peak temperature of the skin of the brain tunnel as acquired by the radiation detector, TR is an empirically determined factor which includes the thermal resistance between the skin of the brain tunnel and the brain, and BT-300 is a factor based on the heat flow.

FIG. 98A is another embodiment of the apparatus and method of this invention showing a hand-held radiation detector 3200 held by the hand of a subject 3202 and positioned in a preferred diagonal position in relation to the plane of the face 3204. The preferred method includes positioning the end 3208 of an infrared detector 3200, or alternatively the tip of an infrared detector, in any area below the eyebrow 3210, with the infrared sensor having a view of the brain tunnel area 3206. The preferred method includes positioning an infrared detector with an angle between 15 and 75 degrees in relation to the plane of the face, and preferably between 30 and 60 degrees, and most preferably between 40 and 50 degrees, and even most preferably at a 45 degree angle with respect to the x, y and z axes. The tip of the infrared detector is positioned in a manner that the infrared sensor has an optimal view of the brain tunnel area. The infrared detector such as a thermopile is pointed at the roof of the orbit adjacent to and below the eyebrow. Preferably the sensor is pointed to the area of the tunnel next to the nose. Preferably the sensor is pointed to an area between the eye and the eyebrow. It is understood that the plane of the face can include the plane of the forehead, surface of the face or the forehead, or similar anatomic structure. The reference point for determining angle of the method can also include the floor or similar physical structure when the head is held straight. Although the infrared detector can be positioned perpendicular to the face with the sensor viewing the brain tunnel area from this perpendicular position, the optimal position is diagonal and preferably in a tri-dimensional manner the Z axis has an angle between 15 and 75 degrees, and preferably between 30 and 60 degrees, and most preferably between 40 and 50 degrees, and even most preferably at a 45 degree angle.

The method includes the steps of positioning an infrared detector in a diagonal position aiming at the brain tunnel from below the eyebrow, receiving infrared radiation from the brain tunnel, and generating an electrical signal based on the received infrared radiation. The brain tunnel may include an area between the eye and the eyebrow. Further step may include generating radiation or directing radiation by the detector prior to the step of receiving radiation form the brain tunnel. A further step includes processing the signal and determining the body temperature or concentration of a chemical substance or analyte. The body temperature in accordance with this invention ranges preferably from 15 degrees Celsius to 45 degrees Celsius.

Another embodiment of this invention includes a device for removably mounting sensors on spectacles and more particularly to a clip for mounting a sensor on spectacles which includes a spring or a tension ring which provides the force to clamp the spectacles and an adjustably positionable sensor anchored to the clip. The mounting sensing device may further include electronics such as a processor and reporting means such as a LED and/or a wireless transmitter to report the value of a biological parameter. It is understood that a clamp for removably mounting sensors can be adapted for clamping any head mounted gear such as spectacles, headbands, caps, helmets, hats, sleeping masks, and the like.

The invention includes sensors, sensing systems, or detectors including infrared detectors adapted to removably clip onto spectacles in a manner which permits the sensors to be positioned on or adjacent to a brain tunnel. The sensor is more preferably adjustably positionable, and most preferably positioned at the roof of the orbit and between the eye and the eyebrow. The present invention is designed to removably mount sensors or detectors of any type including optical sensors, pressure sensors, pulse sensors, fluorescent elements, and the like onto spectacles or head mounted gear. It is understood that the clip of this invention can be adapted to hold any therapeutic system including drug delivery systems such as for example iontophoresis-based systems, thermal energy delivery devices such as for example thermo-voltaic systems including Peltier systems and gels which change the temperature of the area such as polypropyleneglycol. Any head mounted gear of this invention can hold or house a physical element, electrical device, substances, Peltier devices, resistors, cooling elements, heating elements in a manner so as to position those cooling or heating elements on the brain tunnel area in order to change the temperature of the brain tunnel, and consequently the temperature of the brain. Thus, this embodiment can be useful for therapy of heatstroke and hypothermia.

In accordance with this invention, a clip is provided for mounting sensors on spectacles. Preferably a spring is used to retain the front portion and back portion of the clip together and to provide the necessary force to clamp the frame of spectacles or head mounted gear. Preferably the front portion houses power source and electronics while the back portion houses the sensor. The clip includes electronic housing means, support means, sensor attaching means movably mounted relative to the support means, spectacle clamping means movably mounted relative to the support means and clamping means such as a spring or tension ring.

FIG. 99A is a frontal diagrammatic view of a sensing clip 3212 of the invention mounted on a spectacle illustrated by right lens 3244 and left lens 3246. The sensing clip 3212 comprises support means 3214, sensing means 3216, right clamping system 3218 and left clamping systems 3222, and clamping means 3220 such as pressure applying means represented herein by a spring, which is preferably housed in the centrally located support means 3214. Right and left clamping systems 3218, 3222 each comprise a front and back clamping elements, which are essentially similar and therefore only one side is illustrated. In this exemplary embodiment the left side is the sensing side and therefore the left clamping system 3222 is the side illustrated herein, said left clamping system 3222 is comprised of left front clamp element 3224 and left back clamp element 3226. Spring 3220 allows the force for right and left clamping systems 3218, 3222 to clasp a spectacle or a portion of a head mounted gear. Sensing means 3216 includes sensor 3240 and can comprise any sensor or detector mentioned or described in the present invention. The sensing means 3216 preferably branches off from the top of the support structure 3214 or alternatively sensor 3240 is built-in in the top part of the support structure 3214.

Support portion 3214 is centrally located and connects the right clamping system 3218 and left clamp system 3222, said support portion 3214 shown housing microprocessor 3236. Left front clamp element 3224 preferably houses power source 3232 and left back clamp element 3226, in the vicinity of the skin preferably houses a light source such as LED 3234. It is understood however, that the LED 3234 can be housed in the left front clamp element 3224, and in this embodiment, LED 3234 may be covering an element such as plastic, said plastic having a logo or other indicia which is illuminated upon activation of LED 3234, which allows viewing of the logo by an external observer. Wire 3242 connects electronic circuit 3236 and power source 3232 to light source 3234 and sensor 3240.

Right and left clamping systems 3218, 3222 are preferably positioned on either side of the nose of the wearer. Front clamping elements 3224 and back clamping element 3226 extend downwardly from a central support portion 3214 and are adapted for clamping a structure such as lenses and frames of spectacles and head mounted gear. Front clamping element 3224 and back clamping element 3226 may operate as legs which are aligned with each other in order to clamp a structure such as spectacles or any head mounted gear. Spring means 3220 is preferably housed in central support portion 3214 and serves to connect the right and left clamping systems 3218, 3222 and to provide the necessary forces for clamping a spectacles frame and for maintaining a stable position for the sensing clip 3212.

FIG. 99B is a side view of embodiment of FIG. 99A showing sensing clip 3212 mounted on top of left lens 3246. The sensing clip 3212 has preferably a front portion and a back portion in each side, right and left. The left front and back portion is similar to the right front and back portion, and therefore only the left side will be illustrated. The left side is illustrated herein as left back portion 3228 and left front portion 3230, said front portion 3230 and back portion 3228 being joined together by spring 3220. Back portion 3228 and front portion 3230 includes in its end the back clamping element and front clamping element respectively, illustrated herein as left front clamp element 3224 and left back clamp element 3226. The left back clamping element 3226 is located adjacent to the eye 3248. Battery 3232 is preferably housed in the left front portion clamp 3230, and more specifically in the front clamp element 3224. LED 3234 is preferably housed in the back clamp element 3226. Wire 3242 connects the components of the front portion 3230 to components of the back portion 3228 including sensor 3240. It is understood that battery, microchip, and light source can also be housed in the central support portion 3214 or in the back portion 3228.

The sensor 3240 is preferably disposed along the back portion 3228 adjacent to the skin or on the skin. Sensor 3240 preferably has an arm 3238 for adjustably positioning said sensor 3240. It is also understood that sensor 3240 may include any other structure adapted for adjustably positioning a sensor or detector such as infrared detector on or adjacent to a target area for measuring a parameter. Any of the sensors or detectors described in this invention can operate as sensor 3240. Wire 3242 connects electronics, light source and power source in the front portion 3230 to a sensing system in the back portion 3228.

Arm 3238 may house a wire and may also have a light source disposed in its surface. It is understood that sensing means 3216 does not require an arm to be operative. The sensing means of this invention can include a built-in sensor with no arm, said built-in sensor housed in support portion 3214 or any of the clamping elements of this invention. A variety of clip-on and clamping systems can have a sensor and be used to measure a parameter according to this invention including clip-on affixed with lenses which when in an operative position a lens intersect the visual axis and when in an inoperative position said lens is located away from the visual axis of the wearer.

Upon actuation and pressing the clamps, the upper end of the front portion 3230 and the upper end of the back portion 3228 are brought closed together, causing the front clamping element 3224 and back clamping element 3226 to move away from each other creating an opening for receiving a structure such as spectacles. Upon release of the upper end front portion 3230 and the upper end of the back portion 3228 spring 3220 causes front clamping element 3224 and back clamping element 3226 to be brought together causing clamping of the spectacles or any head mounted gear by virtue of the clamping elements 3224 and 3226.

In another preferred embodiment, as shown in FIG. 99C, there is seen a frontal view of a sensing clip 3250, said sensing clip including two main component parts, a clip 3252 and sensing means 3260 including sensor 3261. The clip 3252 includes the central portion 3258, which houses a spring 3262, and right and left clamping systems 3264 and 3266. Right clamping system 3264 has a front clamp and a back clamp and left clamping system 3266 has a front clamp and a back clamp, illustrated herein as left front clamp 3270 and a left back clamp 3256. The sensor 3260 is secured to a back clamp element 3256 of clip 3252 by arm 3254. The left back clamping element and right back clamping element have preferably a pad, illustrated herein as left pad 3268 for firmly clamping eyeglasses between said back clamp 3256 and a front clamp 3270.

FIG. 99D is a side view of an embodiment of a sensing clip 3272 in a resting position showing front clamp 3274 and back clamp 3276. The back clamp leg 3276 preferably has a pad 3278 and houses sensor 3280. Although an arm attached to a sensor has been described, it is understood that a sensor can be secured or be part of a sensing clip in a variety of ways. Accordingly, in this embodiment of FIG. 99D the sensor 3280 is integrally molded in unitary construction with the back clamp 3276. In the resting position front clamp 3274 rests against back clamp 3276. Preferably front clamp element 3274 is longer than back clamp element 3276, said front clamp 3274 being located on the front of a lens facing the environment and said back clamp 3276 located adjacent to the skin and/or the eye. FIG. 99E shows the sensing clip 3272 in an open position with pad 3278 of back clamp 3276 located away from front clamp 3274, for receiving a structure such as frame of eyeglasses or any head mounted gear.

It is contemplated that any other assembly for clamping, grasping, or attaching a sensing device to eyeglasses or head mounted gear can be used including clamping assembly without a spring. Accordingly, by way of example, FIG. 99F shows the frontal view of a sensing device 3280 that includes a central portion 3286 housing a right and left tension bar 3282, 3284, right and left clamping systems 3294, 3296, right and left pad 3288 and 3290 coupled to the tension bar 3282, 3284, and arm 3292 connecting sensor 3294 to back clamp element 3298, said back clamp 3298 having a LED 3300. FIG. 99G is a side view of sensing device 3280 of FIG. 99F showing tension bar 3282 in a resting position, in which left pad 3290 rests against a left back clamp element 3300. FIG. 99H is a side view of sensing device 3280 showing tension bar 3282 in an open position. In this embodiment the frame of the eyeglasses or any structure can push the pad 3290 away from back clamp 3298 and place the tension bar 3282 in an open position for securing eyeglasses.

Any attachment means with a sensor for attaching to eyeglasses or head mounted gear is contemplated or any sensing device adapted to be secured to eyeglasses or head mounted gear. Accordingly, FIG. 99J shows sensing device 3302 adapted to be secured to the frame of eyeglasses by a hook-like structure 3304 which branches off from the main support portion 3306 and includes sensor 3312. The main support portion 3306 has a U configuration with two legs 3308, 3310 which houses electronics, light source, and power source (not shown).

FIG. 99K shows a sensing device 3320 mounted on spectacles 3322 having right lens 3314 and left lens 3316. The sensing device 3320 includes a hook 3334 and is adapted to be supported by the frame of spectacles and includes right leg 3324 and left leg 3326. The right leg 3324 houses electronic processing circuit 3328 and left leg 3326 houses power source 3330 and light source 3332. The right leg 3324 and left leg 3326 face the environment and are disposed in front of the lens 3316. A sensor 3336 on the opposite side of lens 3316 is facing the face of the user.

FIG. 99L shows sensing device 3340 clipped to eyeglasses 3338 said sensing device 3340 including a dual sensing system, exemplarily illustrated as right sensing system 3342 detecting pulse and left sensing system 3344 detecting temperature. The structure of sensing device 3340 is similar to the structure described for sensing devices of FIGS. 99A to 99K. Sensing device 3340 has a dual reporting system, illustrated herein as right LED 3346 and left LED 3348.

FIG. 99M is a side view of an exemplary embodiment of sensing device 3350 having back portion 3354 and front portion 3356 and being secured to the frame of eyeglasses 3352, shown as ghost image. A sensor 3360 is secured to the back portion 3354 and a LED 3358 is positioned in alignment with the visual axis of user 3362.

In another preferred embodiment, as shown in FIG. 99N-1, there is seen a side view of a sensing device 3370, which has an opening 3364 and an inverted U shape configuration for receiving a frame of eyeglasses or a head mounted gear. Sensing device 3370 has a front portion 3374 and a back portion 3376 and is preferably made of plastic or polymer that has a memory or any shape memory alloy. Preferably internal surfaces 3382 and 3384 have a gripping surface or are rubberized for securing a structure such as frame of eyeglasses. A sensor 3380 is attached to the back portion 3376 preferably by adjustably positionable arm 3366. Back portion 3376 house LED 3378, which is operatively connected to sensor 3380. In this embodiment there is no spring, tension bar, clamping element, and the like. A stable position is achieved by virtue of the U shape configuration.

FIG. 99N-2 is a front view of the sensing clip device 3370 of FIG. 99N-1 showing front portion 3374 having a printed circuit board 3378 and memory area 3386, wireless transmitter 3388, and processor 3390. A battery 3392 is housed in front portion 3374. Battery 3392 can be permanently attached to sensing clip 3370 or be removably secured to said sensing clip 3370. Back portion 3376 houses LED 3394 and sensing means comprised of a sensor holder 3396 holding a sensor 3380, said sensor holder 3396 being connected by arm 3366 to sensing clip 3370. FIG. 99N-3 is a frontal schematic view of the sensing clip 3370 of FIG. 99N-1 mounted on eyeglasses 3398, shown as a ghost image.

FIG. 99P is a frontal view of dual sensing clip 3400, illustratively shown as a pair light emitter-light detector 3402, illustrated on the left side, including radiation emitter 3404 and radiation detector 3406, for detecting glucose, and a second pair light emitter-light detector 3408 located on the opposite side including radiation emitter 3410 and radiation detector 3412 for detecting oxygen and pulse oximetry. Besides, a temperature sensor or any other sensor can be used as a substitute or in addition to the pair light emitter-detector. Sensing clip 3400 is adapted for performing measurements and detecting analytes by touching the area being measured or by being spaced away from the area being measured. Wireless transmitter 3414 is adapted for transmitting a wireless signal to a remotely placed device including a telephone 3416, watch 3418, shoe 3420, and a digital device 3422 such as a music player or computing device.

In addition, a sensing device can have arms which wrap around or that are attached to the temples of eyeglasses or to a portion of a head mounted gear. The sensing means may branch off from the sensing device, which is adapted to position a sensor on or adjacent to a target area, such as a brain tunnel. It is also contemplated that any flip sunshades or any type of clip-on sunshades can include sensors for measuring a parameter.

The present invention teaches a modular construction of head mounted gear for measuring biological parameters. Accordingly, FIG. 100A is a perspective diagrammatic view of another support structure comprised of a specialized headband 3430 including a recess 3432 for receiving a housing 3434, said housing being preferably a module removably attached to said headband 3430 and includes right arm 3436 and left arm 3438. Arms 3436 and 3438 terminate in right and left sensing portion 3440, 3442. Housing 3434 can comprise a box housing wires from sensors 3440, 3442, and further include wire 3444 which exits box 3434 and is disposed along the surface 3446 of headband 3430, and more particularly disposed on a groove 3448. Groove 3448 is adapted for being covered by a strip 3450 attached to headband 3430. The strip 3450 is preferably made of fabric and has a hinge mechanism, said strip 3450 being positioned over the groove 3448 for securing wire 3444 to headband 3430. Edge 3456 of strip 3450 comprises preferably a hook and loop material which matches a hook and loop material 3454 secured to headband 3430. Wire 3444 terminates in connector 3452, for connecting with a processor and display unit (not shown).

FIG. 100B shows in more detail the BTT temperature module 3460 which includes a housing 3434 and a steel rod 3458 shaped as an inverted U and secured to the housing 3434. Wire 3462 runs along or in the right rod 3466, and connects sensor 3470 to PCB 3464 and processor 3478. Wire 3472 runs along or in the left rod 3474 and connects sensor 3468 to PCB 3464 and processor 3478. Processor 3478 selects the best signal, illustrated herein as selecting the highest of the two temperature signals being measured at the right and left side, illustrated herein by sensors 3470 and 3468. Processor 3478 can be operatively coupled to a memory 3476 and is connected with a display by wire 3482, said wire 3482 exiting housing 3434 and terminating in an electrical connector 3484. Sensor portion 3468 and 3470 can have any of the configurations described herein, and in particular the configuration and dimensions of measuring portion 2006. Right rod 3466 and left rod 3474 can have any of the configurations described herein, and in particular the configuration and dimensions of arm 2004. The thickness of said arm 2004 can be converted to a diameter of said arm 2004 since rods 3466, 3474 are essentially cylindrical in nature and may function as arm 2004.

FIG. 100C is a frontal perspective view of another embodiment of a sensing modular headband 3500 of this invention when worn by a user 3486 and includes a headband 3480 having an area 3488 for receiving BTT temperature module 3490, said area 3488 having an electrical connector 3492 for electrically connecting module 3490 to headband 3480. Temperature module 3490 includes processor 3494, memory 3496, and arms 3498 and 3502, said arms 3498 and 3502 terminating in measuring portion 3504 and 3506 respectively. Measuring portions 3504 and 3506 are disposed on or adjacent to the brain tunnel area 3508 and 3510, and located below the eyebrows 3512 and 3514. Electrical connector 3492 can function as an electrical pad and is connected to wire 3516 disposed along the surface or within headband 3480.

FIG. 100D is a side view of another sensing modular headband 3520 of this invention when worn by a user (as ghost image) and including four different biologic parameter modules, namely a BTT temperature module 3522, an ear temperature module 3524, an infrared detection module 3526 illustrated herein as pulse oximetry module, and a behind the ear temperature module 3528. BTT temperature module 3522 is disposed on the surface 3580 of sensing modular headband 3520 facing away from the skin 3536 and includes adjustably positionable arm 3530 and measuring portion 3532 positioned below and adjacent to the eyebrow 3534. Ear temperature module 3524 may include a removably attached module secured by a clip 3538 to the edge of headband 3520. Module 3524 may further include a retractable cord spool 3540 securing cord 3542 which terminates in sensing probe 3544 which rests in the ear canal, said probe 3544 including at least one of an infrared detector, a pair infrared emitter-infrared detector, a temperature sensor such as a thermistor, RTD, and thermocouple, and the like. Module 3524 also receives electrical input from behind the ear temperature module 3528, which measures temperature behind the ear and more specifically at the lower part of the ear 3546 and/or around the ear lobe 3548. Behind the ear temperature module 3528 can be removably attached to headband 3520 by fastening structure 3556, such as a hook or loop, and includes a C-shape housing 3550 and a sensor 3552, said sensor 3552 being connected to module 3524 by wire 3554 which is disposed on or along the C-shape housing 3550 and terminates in said ear temperature module 3524.

Pulse oximetry module 3526 is located right above the eyebrow 3534 and disposed in the internal face of headband 3520 adjacent to the skin 3536 and includes a pair light emitter-light detector 3582 housed in an adhesive patch 3558 and further includes a wire 3560 which runs on the external surface 3562 of headband 3520 after going through hole 3564 located in headband 3520. Wire 3566 of ear temperature module 3524, wire 3568 of BTT module 3522, and wire 3560 of pulse oximetry module 3526, all run along the external surface 3562 and more specifically sandwiched between a movable lip 3570 which covers the wires 3566, 3568, 3560 and the external surface 3562 of headband 3520. Wires 3566, 3568, 3560 exit headband 3520 and connect to display and processing unit 3572 through connectors 3574, 3576, and 3578.

FIG. 100E is a frontal perspective view of another sensing modular headband 3590 of this invention when worn by a user 3592 and including two different biologic parameter modules, namely a BTT temperature module 3594 and an ear monitoring module 3596, said modules 3594 and 3596 including any sensor described in this invention and any temperature sensors such as infrared radiation and thermistors. BTT temperature module 3594 is disposed on the surface 3598 of sensing modular headband 3590 and includes adjustably positionable arms 3600, 3602 and measuring portion 3604, 3608 positioned below and adjacent to the eyebrow 3606, 3610, and further including wire 3612 which exits headband 3590 and run behind the ear 3628 terminating in connector 3614 which connects to wire 3616, said wire 3616 being connected to a display and interface 3618. Ear monitoring module 3596 includes a wireless transmitter 3620 wirelessly connected to receiver and display 3622, and further including wire 3624 which terminates in ear probe 3626.

FIG. 100F is a diagrammatic view of another sensing modular headband 3630 of this invention with eyes 3674, 3678 and nose 3680 seen below, said headband 3630 including eight different biologic parameter modules, namely a Brain Tunnel module 3632 illustrated by a radiation detector 3634 on the left and a radiation emitter-detector pair 3636 on the right, an ear temperature module 3638, an infrared detection module 3640 illustrated herein as pulse oximetry module, pulse detection module 3642, a blood pressure detection module 3644, a brain monitoring module such as a digitized EEG (electroencephalogram) module illustrated herein by three electrodes 3648, 3650, 3652, a skin temperature module 3654, preferably using a sensor over the temporal artery, and a medical device holding module 3656, illustrated herein by a nasal cannula module. Brain tunnel module 3632 includes adjustably positionable arm 3660 terminating in measuring portion 3636 illustrated herein by an infrared pair emitter-detector for analyte detection such as glucose and an adjustably positionable arm 3662 terminating in measuring portion 3634 illustrated by an infrared detector positioned on or adjacent to the brain tunnel next to the bridge of the nose and/or on the eyelid.

Pulse oximetry module 3640 is disposed on cavity or recess 3666 on the internal face of headband 3630 and includes a pair light emitter-light detector 3664. Ear temperature module 3638 may include a cord 3646 that terminates in sensing probe 3658 which rests in the ear canal 3668 and receive radiation 3670 from said ear canal. Pulse detection module 3642 and a blood pressure detection module 3644 can include any pressure sensing device, piezoelectric devices, and the like. Brain monitoring module allows directly monitoring of a patient's level of consciousness to help determine and administer the precise amount of drug to meet the needs of each individual patient and to avoid intraoperative awareness. Brain monitoring module works by using a sensor that is placed on the patient's forehead to measure electrical activity in the brain from the EEG and the activity is digitized and displayed as a numerical value. Brain monitoring module allows customized amount of anesthetic and sedative medication to be delivered to the patient and therefore ensure that they are unconscious and free of pain, yet able to wake-up quickly and experience minimal side-effects from anesthesia and sedation. Brain monitoring module 3646 is illustrated herein by three electrodes 3648, 3650, and 3652. The information from the electrodes 3648, 3650, 3652 is processed and a number achieved which provides a direct measure of the patient's level of consciousness allowing clinicians to determine the most effective anesthetic and sedative mix, consequently patients have faster, more predictable wake-ups and higher-quality recoveries with less nausea and vomiting. The brain monitoring module may include an external monitor that analyzes and displays EEG signals, and then converts EEG signals to digital data, and then transfers the data to the external monitor for processing, analysis, and display. Nasal cannula module includes a cannula that goes up over the nose, and preferably not to the sides as per prior art. Modular nasal cannula 3672 is secured by fastening means such as hooks and/or VELCRO and disposed on the surface of the headband 3630. The apparatus and method for supporting the nasal cannula includes a plurality of hooks in the head mounted gear such as a headband of FIG. 100F or the frame of FIG. 100X, suspending thus the cannula and supporting the cannula along the surface of the head mounted gear, prevented from shifting during sleep and transport.

FIG. 100G is a diagrammatic cross sectional view of a sensing modular headband 3680 of this invention showing the disposition of the modules in the internal surface 3682 facing the skin 3684 and the external surface 3686 of headband 3680 facing away from the skin 3684. Strap 3688 is adapted to be secured to skin 3684 as pointed by large arrows, said strap 3688 having an area or recess 3690 on the external surface 3686 for receiving a brain tunnel module 3692, said area or recess 3690 preferably made of a thin sheet of plastic or other polymer adapted to give stability to the module; and two areas or recesses 3694, 3696 on the internal surface 3682 for receiving an infrared module 3698 and a skin temperature module 3700. The Brain Tunnel includes two areas 3702, 3704 indicating the junction of right and left adjustable arms (not shown in cross sectional view) to the housing 3730, with wires 3706, 3708 connecting wires from adjustable arms to a processor 3712. Wire 3710 connects processor 3712 with a display unit (not shown), said wire 3710 being disposed between the external surface 3686 and a lip 3714, made preferably of fabric or any pliable material. Area 3690 has preferably two plugs 3716, 3718 for fastening and securing a module such as a snap-on action to secure the module to the recess or cavity. Plugs 3716, 3718 can also work as electrical connectors.

Pulse oximetry module 3698 is disposed on cavity or recess 3696 on the internal face 3682 of strap 3688 and includes a pair light emitter-light detector 3720. Wire 3722 connects pair 3720 with a display unit (not shown), said wire 3722 being disposed between the external surface 3686 and a lip 3714 after said wire 3722 goes through a hole 3724. Skin temperature sensor module 3700 is disposed on cavity or recess 3694 on the internal face 3682 of strap 3688 and includes a sensor 3726. Wire 3728 connects sensor 3726 with a display and processing unit (not shown), said wire 3728 being disposed along the internal surface 3682 facing the skin 3684. There is also shown the flap 3714, also referred as lip, being connected to external surface 3686 by a hook and loop fastener Wire 3710 connects processor 3712 with a display unit (not shown), said wire 3710 being disposed between the external surface 3686 and a lip 3714, made preferably of fabric or any pliable material.

FIG. 100H is a diagrammatic planar view of the sensing modular headband 3680 showing the external surface 3686 of strap 3688, said external surface 3686 having area or recess 3690 for receiving a brain tunnel module 3692. Area 3690 has preferably two snap-on plugs 3716, 3718 for fastening and securing a module. There is also seen the hole 3724 and the impression of plastic sheet of area 3696 on the external surface 3686, which secures an infrared detection module. There is also shown the flap 3714, also referred as lip, being connected to external surface 3686 by a hook and loop fastener 3732.

FIG. 100J is a diagrammatic cross sectional view of a sensing modular headband 3740 of this invention showing the disposition of the modules on external surface 3742 of headband 3740 facing away from the skin 3744. Strap 3746 is adapted to be secured to skin 3744 as pointed by large arrow, said strap 3746 having an area and/or recess 3750 on the external surface 3742 for receiving a brain tunnel module 3744, said area, cavity, or recess 3750 preferably made of a thin sheet of plastic or other polymer adapted to give stability to the module; and another specialized area or recesses 3752 for receiving an infrared module 3754. Wire 3756 connects brain tunnel module 3744 with a display and processing unit (not shown), said wire 3756 being disposed between the external surface 3742 and a flap 3758. Area 3750 has preferably two plugs 3760, 3762 for fastening and securing a module.

Pulse oximetry module 3754 is disposed on the cavity or recess 3752 on the external surface 3742, said pulse oximetry module 3754 including a pair light emitter-light detector 3756. Area, recess, or cavity 3752 of strap 3746 has preferably two openings 3758, 3748 for respectively receiving light emitter 3770 and light detector 3772. Light emitter 3770 and light detector 3772 are preferably disposed in a manner to press such emitter 3770 and detector 3772 against skin 3744 and create an indentation. Openings 3758 allow light to be directed at the skin 3744 by emitter 3770 and light to be received by detector 3772 through opening 3748. Plugs 3764 and 3766 are disposed on the bottom of recess 3752 for fastening and firmly securing the module 3754 to strap 3746. Wire 3768 connects pulse oximetry module 3754 with a display and processing unit (not shown), said wire 3768 being disposed between the external surface 3742 and a flap 3758. Internal surface 3778 of strap 3746 may include a peel-back adhesive 3776, which exposes an adhesive surface for more stable securing strap 3746 to a body part. The oxymetry module is preferably located in the headband portion that is above the eye, said oximetry module being next to the module for temperature measurement.

All the modules described herein preferably physically conform to a body portion of a patient, such as a forehead, and provide a firm pressing engagement between the sensors and the living creature's body portion. The pair light emitter-detector may include a flexible structure such as a flexible patch, which is physically conformable and attachable to the subject's body portion. The pair light emitter-detector includes a light source assembly for illuminating the patient's body portion, and a light detector assembly for measuring reflected light. When the pair light emitter-detector is conformably applied to the recess or cavity of the sensing headband, preferably using the snap-on plugs of said headband, localized pressure is exerted on the body portion at the points of contact with the light source and light detector assemblies, and/or the electrodes, and/or the temperature sensors and/or the pressure sensors and pulse sensors, and any of the sensors of this invention.

As in conventional pulse oximetry sensors, the light emitter or light source may include two light-emitting diodes emitting light at red and infrared wavelengths, and the light detector assembly may include a corresponding two or more photodetectors. It is understood that a single light detector can be used to detect light at both wavelengths. The electric signals are carried to and from the light source and light detector assemblies by an electric cable which terminates at an electrical connector, said connector being connected to control and processing circuitry and display.

The present invention teaches a method and apparatus for reusing expensive parts while making the least expensive part, the only disposable part. Electronics and medical sensors are expensive and due to the arrangement of the invention, those expensive parts do not remain in contact with the skin and do not have adhesive surfaces adhering to the skin. The modular construction in which an optical sensor is the only portion touching the skin surface, allows easy cleaning of said optical sensor and reutilization, such as for pulse oximetry. For temperature measurement a very low cost disposable cover is the only disposable material, which is required for covering the sensor that rests on the BTT. Since in the arrangement of the invention, preferably, the electronics, sensors, and other expensive parts do not touch the skin, said parts can be reused. Since the arrangement is done in a manner in which only the forehead material touches the body, and the forehead material is the least expensive of the material sitting on the forehead, and actually really low cost. The device of the invention includes reusable parts and disposable parts.

FIG. 100K is a diagrammatic planar view of the external surface of the sensing modular headband 3740 showing the external surface 3742 of strap 3746, said external surface 3742 having area or recess 3750 for receiving a brain tunnel module 3744; and area or recess 3752 for receiving a pulse oximetry module 3754. Area 3750 has preferably two snap-on plugs 3760, 3762 for fastening and securing a module. Area 3752 has preferably two snap-on plugs 3764, 3766 for fastening and securing an infrared module, and openings 3758, 3748 for allowing passage of light to/from the skin to light emitter-detector pair 3756. There is also shown the flap 3758, also to referred as a lip, being connected to external surface 3742 by a hook and loop fastener 3774.

FIG. 100L is a diagrammatic planar view of the internal surface 3778 of the sensing modular headband 3740 showing the adhesive surface 3780 exposed after removing the backing 3776. Method includes using straps that have adhesive surface in different locations, allowing thus the skin to breathe more properly. Accordingly, a first strap has adhesive surface in the center, said strap is used for 3 days for example. After the 3 days, a new strap is applied, namely a second strap which has adhesive only on the side parts but not the central part as with the first strap, thus allowing area covered by adhesive to breathe since the area will not be covered consecutively with adhesives.

FIG. 100M is a diagrammatic planar view of an exemplary cavity or recess 3782 for receiving a module 3784 for monitoring biological parameters. Cavity 3782 may include an adjacent housing for housing electronic circuit and printed circuit board 3786 in addition to a processor 3788, wireless transmitter 3790, and display 3792.

FIG. 100N is a diagrammatic side view of another embodiment comprised of a head mounted gear 3800, illustrated herein by a cap worn by a user, and including arm 3796 terminating in measuring portion 3794, said arm 3796 being secured to the cap 3800 and further including a wire 3798 disposed along the cap 3800 and connected to a processing and reporting unit 3802. The reporting unit 3802 may audibly report the value of a parameter being measured, and further include an ear bud assembly 3804 connected by wire 3806 to processing and reporting unit 3802.

FIG. 100P is a diagrammatic perspective view of another embodiment comprised of a head mounted gear 3804, illustrated herein by a cap worn by a user 3822, and including arm 3806 terminating in measuring portion 3808, said arm 3806 being secured to the cap 3804, and further including a wire 3810 disposed along the cap 3804 and connected to a second measuring portion 3812, said measuring portion 3812 having a housing 3816 and a sensor 3814. The measuring portion 3812 is disposed under the brim of the cap 3804, with said measuring portion 3812 having a housing 3816 which is secured to the cap 3804. Sensor 3814 is pressed against the skin by housing 3816, said sensor comprising any of the sensors, or pair light emitter-detector, or infrared detector of this invention. Wire 3818 connects measuring portions 3808 and 3812 to processing, transmitting, and reporting unit 3820 disposed in the back of the user 3822.

FIG. 100Q is a diagrammatic perspective view of another embodiment comprised of a head mounted gear 3824, illustrated herein by a cap, and including measuring portion 3828 and 3826 housing respectively an infrared detecting system 3830 and piezoelectric system 3832 being secured to the cap 3824, and further including a groove 3826. Measuring portions 3828 and 3826 are movable and may slide on a groove shown by arrow, and illustrated herein as groove 3840 for proper positioning of sensor 3830. Wire 3834 and wire 3836 join at the back of the cap 3824 and form a single wire 3838 that connects to a processing and reporting unit (not shown). It is understood that the measuring portions can be constructed as removably attached modules as previously described for headbands.

FIG. 100R is a diagrammatic perspective view of another embodiment comprised of a head mounted gear 3842, illustrated herein by a burette worn by a user 3844, and including arm 3846 terminating in measuring portion 3848, which is disposed on or adjacent to a physiologic tunnel 3850 between the eye 3866 and the eyebrow 3868 next to the nose 3852, said arm 3846 being secured to the burette 3842, and further including a wire portion 3854 disposed along the burette 3842 and connected to a processing and transmitting unit 3856. A second arm 3858 terminates in a second measuring portion 3860, which is disposed on or adjacent to a second physiologic tunnel 3862 between the eye 3866 and the eyebrow 3868 next to the ear 3864, said arm 3858 being secured to the burette 3842, and further including a wire portion 3870 disposed along the burette 3842 and connected to a processing and transmitting unit 3856. A third arm 3872 terminates in a third measuring portion 3874, which is disposed on or adjacent to a third physiologic tunnel 3876 behind the ear 3864, said arm 3872 being secured to the burette 3842, and further including a wire portion 3878 disposed along the burette 3842 and connected to a processing and transmitting unit 3856. It is understood that any of the arms of this invention may be adjustably positionable and extendable according to the application.

FIG. 100S is a diagrammatic perspective view of another embodiment comprised of a head mounted gear 3880, illustrated herein by a light source worn by a user 3882, and including arm 3884 terminating in measuring portion 3886, which is disposed on or adjacent to a physiologic tunnel 3888 adjacent to the eyebrow 3890, said arm 3884 being secured to the sensing head light 3880, and further including a wire portion 3892 disposed on or within the head light 3880 and connected to a processing and transmitting unit 3894. Head light 3880 has an arm 3896 for securing said head light 3880 to the head 3898 of the user 3882, said arm 3896 having a housing that includes an oxygen or analyte measuring device 3900, illustrated herein by a pair radiation emitter-radiation detector 3902, which is connected by wire 3904 to a processing and transmitting unit 3894.

FIG. 100T is a diagrammatic perspective view of another embodiment comprised of a head mounted gear 3910, illustrated herein by a sensing visor worn by a user 3912, and including arm 3914 terminating in measuring portion 3916, and terminating in a second measuring portion 3918 measuring a second parameter, said arm 3914 being secured to the sensing visor 3910 by fastening means 3920 such as a loop anchored to said sensing visor 3910. Sensing visor 3910 may include a microphone 3928 disposed along the side of the face and connected to a processing, transmitting, and reporting circuit 3922 via stalk 3930, and may further include a display 3924 for visual display of data or information connected to a processing, transmitting, and reporting circuit 3922 via wire 3932. Sensing visor 3910 may include an ear bud assembly 3926 connected to a processing, transmitting, and reporting circuit 3922 via wire 3934. This embodiment includes athletic applications in which an athlete wants to report to a coach a value of biological value or other information. Accordingly, the user receives the information audibly by the ear bud assembly 3926 or visually by display 3924, and then communicates the relevant information via microphone 3928.

FIG. 100U is a diagrammatic perspective view of another embodiment comprised of apparel or clothing 3940, illustrated herein by a sensing-enabled shirt worn by a user 3942, and including a moldable wire 3944 preferably with memory for more stability and being supported by the ear or other fasteners (not shown). Wire 3944 terminates in an adjustably postionable arm 3946, which further terminates in measuring portion 3948. Arm 3946 further includes a measuring portion having a sensing system 3958 contained in an adhesive patch 3956 and applied to the forehead of user 3942. Wire 3944 terminates in a support structure 3950 secured to the collar 3952 of sensing shirt 3940, said support structure 3950 being electrically connected via wire 3960 to a reporting and display unit 3954 preferably secured to a piece of clothing.

FIG. 100V is a diagrammatic perspective view of another embodiment comprised of head mounted gear 3962, illustrated herein by a helmet, and including arm 3964 terminating in measuring portion 3966 comprised of a temperature sensor, said arm 3964 being disposed on or within helmet 3962 and being connected to a processing, transmitting, and reporting circuit 3968 via wire 3970. Sensing-enabled helmet 3962 may include an ear bud assembly 3972 connected to a processing, transmitting, and reporting circuit 3968 via wire 3976. Sensing-enabled helmet 3962 may also include a second sensor 3974 for measuring pulse and disposed along the side of the head, said sensor 3974 being connected to a processing, transmitting, and reporting unit 3974 via wire 3978. Unit 3974 may further include a music player, which adjusts to a lower volume in case the value of biological parameter is audibly transmitted.

FIG. 100X is a diagrammatic view of another sensing frame 3980 of this invention, said frame 3980 including seven different biologic parameter modules, namely a Brain Tunnel module 3982 illustrated by a radiation emitter-detector 3984 on the left and a radiation emitter-detector pair 3986 on the right; an ear monitoring module 3988, an infrared detection module 3990 illustrated herein as pulse oximetry module, pulse detection module 3992, a behind the ear detection module 3994, a skin temperature module 3996, preferably using a sensor over the temporal artery, and a medical device holding module 3998, illustrated herein by a nasal cannula module. It is understood that although removably attached modules are described, the invention includes modules being permanently attached and the frame working as an integral one piece construction, or alternatively some devices are removably attached and some are permanently affixed to the head mounted gear or eyeglasses, and those configurations apply to all devices described in this application.

Brain tunnel module 3982 includes adjustably positionable arm 3400 terminating in measuring portion 3984 illustrated herein by an infrared pair emitter-detector for analyte detection such as glucose and an adjustably positionable arm 3402 terminating in measuring portion 3986 illustrated by an infrared emitter-detector positioned on or adjacent to the brain tunnel next to the bridge of the nose and/or on the eyelid and detecting pulse and oxygen. The housing 3414 of the pulse oximetry module 3990 branches off from the frame 3980 and it is seen located on the right side of frame 3980 with the pair emitter-detector located above the eyebrow 3404. Ear monitoring module 3988 may include a cord 3406, with or without a retractable cable, from the frame 3980, said cord 3406 terminating in sensing probe 3408 which rests in the ear canal and receive radiation from said ear canal. Pulse detection module 3992 branches off the frame 3980 and is adapted to detect pulsation of a blood vessel using a sensor 3416 disposed in said module 3992, said sensor 3416 being located above the eyebrow 3410 and including any pressure sensing device, piezoelectric devices, tonometric device, and the like. Skin temperature module 3996 branches off the frame 3980 includes a temperature sensor 3412 preferably positioned over the temporal artery or in the vicinity of the temporal artery. Behind the ear monitoring module 3994 includes a sensor 3420 located in frame 3980, and more specifically at the end of the temples 3418, and even more specifically at the free end 3422 of the temples 3418. Nasal cannula module 3998 includes a cannula 3999 that goes up over the nose, and preferably not to the sides as per prior art. Modular nasal cannula 3998 is secured by fastening means such as hooks and/or loops disposed along the frame 3980 and illustrated herein by hook-loop 3424, 3426, 3428, on the left side and one hook 3430 illustrated on the right side of frame 3980. By way of illustration nasal cannula is shown on the left side as broken down lines along the frame 3980, but it is understood that said nasal cannula is disposed in the same manner on the right side. Any fastening means to secure a nasal cannula to the frame of eyeglasses can be used.

Wire 3432 connects infrared module 3390 to a processing and display circuit 3434 through electrical connector 3436. Wire 3438 connects ear monitoring module 3988 to the processing and display circuit 3434 through electrical connector 3436. Wire 3440 connects behind the ear monitoring module 3994 to the processing and display circuit 3434 through electrical connector 3436. Brain Tunnel module 3982, pulse detection module 3992, and skin temperature module 3996 connect to a processing and display circuit 3442 through wire 3446 and electrical connector 3444.

FIG. 100Y is a diagrammatic side view of another embodiment showing sensing frame 3450 worn by a user 3448, and including: a behind the ear monitoring portion 3452 comprised of a chemical sensor 3456 and temperature sensor 3458, said monitoring portion 3452 being integral with frame 3450; a skin temperature portion 3454 comprised of a temperature sensor 3460 being integral with frame 3450; an infrared emitter-detector 3462 located along the lens rim 3464; and a radiation detector 3466 held by an adjustably positionable arm 3468 for detecting radiation naturally emitted from the brain tunnel. Chemical sensor 3456 can include sensors for analyzing sweat such as glucose sensors, electrolyte sensors, protein sensors, and any analyte present in sweat or on the surface of the body.

FIG. 100Z is a diagrammatic planar view of another embodiment showing specialized sensing frame 3470 comprised of an essentially round frame for adjusting said frame 3470 to the head of a user and having temples 3472, 3474 which are adapted for securing the frame 3470 to head of the user by pressure means. Contrary to prior art the sensing frame of this invention does not have hinges. There is also seen a dual temperature sensor 3476, 3478 held by arms 3480, 3482, nose pad 3484 for nose support, and processing circuit 3488. Wire 3486 connecting sensors 3476, 3478 are disposed on or within frame 3470. Processing circuit 3488 is adapted to select the highest temperature from sensors 3476 and 3478 and report said highest value, or alternatively processing circuit 3488 is adapted to select the most stable signal from sensors 3476 and 3478, and report said value.

Another embodiment includes methods and apparatus for determining and preventing intraoperative awareness and detecting brain activity based on body temperature, more specifically temperature from the BTT.

The method and apparatus includes automated feed back control of an infusion pump based on the BTT temperature for automated and precise adjustment of infusion rate of drugs, such as anesthetics or sedatives, based on body temperature, and more particular core-brain temperature.

A first step determines the body temperature, and a second step determines if the temperature is increased. If yes then increase infusion rate by the pump. With an increased core temperature during anesthesia there will be increased drug metabolism, in which drugs are consumed faster, thus requiring increased infusion rate. With a decreased core temperature during anesthesia there will be reduced drug metabolism, in which drugs are consumed slower, thus requiring decreased infusion rate.

In the Intensive Care Unit, the apparatus and methods adjust rate of infusion of drugs, such as vasoactive drugs, based on the body temperature. With decreased core temperature patient requires warming, which may lead to vasodilation if done in excess leading to hypotension, which then requires administration of costly and dangerous drugs such as vasoconstrictors as epinephrine. Thus, with the present invention by carefully and precisely titrating the warming or cooling of the body based on the core temperature all of those issues can be avoided.

In addition, this invention provides a method and apparatus to determine brain awareness and detect risk of intraoperative awareness. If there is increased temperature during surgery, leading to increased drug metabolism, leading to a more superficial level of anesthesia and risk of intraoperative awareness, thus the method and apparatus of the invention adjusts the rate of infusion and increase the rate of infusion. With increased brain temperature there is an increase in blood flow to the brain, which increases the risk of intraoperative awareness, thus the method and apparatus of the invention adjusts the rate of infusion and increase the rate of infusion. If there is decreased temperature during surgery, leads to decreased drug metabolism, leading to more anesthetic drugs being available, which places the patient at a deeper level of anesthesia, and which can cause complications and death besides increased hospital stay and time for recovery. Thus, with the present invention, the level of anesthetic is precisely titrated and if there is lower core temperature, there is a consequent adjustment of the infusion rate with reduction of the infusion rate. With decreased temperature there is also reduced blood flow to the brain, which decreases the risk of intraoperative awareness, thus the method and apparatus of the invention adjusts the rate of infusion and decreases the rate of infusion. Integration of any pump drug with BTT signal can benefit adjustment of infusion rate of some of the most common surgical procedures including cardiac and cardiothoracic, trauma, neurosurgical, long surgeries, and high risk surgeries and surgeries in which vasodilators cannot be used, or patents with predisposition to shock or hypotension.

There are many clinical benefits due to integration of a BTT signal with a pump, including:
1) Automated and more precise adjustment of flow rate
2) To achieve better depth of anesthesia
3) To reduce risk of intraoperative awareness (increased brain temperature associated with risk of intraoperative awareness)
4) Eliminate/reduce the potential for both under- and over-dosing
5) Maintenance of drug levels within a desired range
6) Optimal administration of drugs
7) Reduced drug use
8) Reduced surgical time
9) Reduced assisted ventilation time
10) Reduced ICU time
11) Faster post-operative recovery
12) Reduced hospitalization time
13) Reduced rate of complications intraoperative
14) Reduced rate of complications postoperative
15) Improved and expedited wake-up time from surgery
16) Reduced rate of complications due to hypothermia and hyperthermia
17) Reduced health care cost
18) Improved patient outcome Integration of infusion pump with BTT continuous signal can benefit adjustment of infusion rate of some of the most common drugs including all injectable anesthetics, propofol, phentanyl, midazolam and other benzodiazepines, insulin, and vasoactive drugs such as nytric oxide and all vasodilators, phenylephrine and all vasoconstrictors. The level of core temperature can also be used to identify effect of drugs and the diagnosis and prognosis of diseases such as Parkinson's, Alzheimer's, and depression. Accordingly FIG. 101 is a diagrammatic view of an infusion pump 3500 connected to a temperature monitoring system 3502, said temperature monitoring system secured to a living creature 3504. Pump 3500 receives signal from the temperature monitoring system 3502, and said pump 3500 includes an assembly 3506 for delivering drugs to a living creature 3504.

FIG. 102 shows an exemplary portable remote powering device 3510 coupled to a BTT passive sensing device 3516. The device 3150 includes a screen 3528 and antenna 3532, seen held by the hand of a subject and positioned to power the BTT sensing device 3516 located above the eye 3522. BTT sensing device 3516 includes a sensor 3520 and an antenna 3518 for emitting electromagnetic energy. Device 3510 powers passive device 3516 with electromagnetic energy 3514, and receives a reflected energy back represented as wave 3524 which contains the identification of the subject being measured and the level of the biologic parameter being measured. By way of illustration, temperature is measured and the level is displayed on screen 3528. Device 3510 is adapted to provide feed back information based on the signal received and the level of the biological parameter. In this embodiment the temperature is elevated, causing device 3510 to display information for fever, such as antibiotics and anti-fever medications shown in dialog box 3526 of screen 3528. In addition, the signal causes the device 3510 to produce a dialogue box 3530 for names of pharmacies and doctors associated with the patient identified by the signal received.

FIG. 103A is a diagrammatic view of another embodiment of a sensing device 3540 including a measuring portion 3550 and an arm 3554. The end 3552 of arm 3554 ends in holder 3550 and the opposite end 3564 ends in a body of sensing device (not shown). The measuring portion 3550 includes a structure 3542 comprised of a soft compressible insulating material such as polyurethane. Body 3542 has an opening 3544 that houses a wire portion 3548 that terminates in wire 3556 of arm 3544. Body 3542, represented herein by material 3542, has an exposed bottom surface 3560 and an exposed side surface shown as 3562. A holder 3550 surrounds material 3542 and connects with arm 3554. The edge 3558 of the holder 3550 is preferably located at a distance equal to or no greater than 2 mm from the surface 3560, and most preferably equal to or no greater than 4 mm from the surface 3560, and even most preferably equal to or no greater than 6 mm from the surface 3560, said distance represented by a dimension shown as 3562. Surface 3560 includes sensor 3546. Thus surface 3560 has a combination of a thermistor represented herein by sensor 3546 and insulating material such as polyurethane represented by body 3542.

FIG. 103B is a diagrammatic view of a probe cover 3570 for a measuring portion and/or an arm of a sensing device of this invention, such as measuring portions and arms of the embodiments of FIG. 86A to FIG. 103A. The probe cover of this invention is essentially soft and thin and it is adapted to fit the dimensions of the sensing devices and support structures of this present invention. The probe cover 3570 has one body 3576 and two ends 3574 and 3572; one end 3574 is open and adapted to receive a measuring portion and an opposite end 3572 is closed and adapted to fit a sensor. The open end 3574 has an adhesive surface 3578 which is disposed adjacent to the open end 3574, said adhesive surface forming an extension of the distal end 3580 of body 3576. The adhesive surface may include a peel back cover in an extension of body 3576, and when in use the peel back cover is removed exposing the adhesive surface. The adhesive surface 3578 attaches the probe cover to a body of a sensing device such as body 2002, frame of eyeglasses, headband, and the like. Any means to attach or firmly secure probe cover to an arm or body of a sensing device can be used. If the measuring portion is of larger dimension than arm, the probe cover is adapted to cover and fit both parts including the measuring portion.

It is understood that any sensor system of the invention can be coupled with finger-like structure, nose bridge, and other structures described in FIGS. 86A to 91 or coupled to frames of eyeglasses and head mounted gear described in FIGS. 92 to 100. It is also understood that the eyeglasses of this invention can comprise two separate parts, preferably with a removably detachable sensor, which becomes the disposable part. The tip of a rod thermometer or rod pulse detection can also house an identification chip or Radio Frequency identification (RF ID), said tip being reusable but only for one patient who is identified by the RF ID or the ID chip, allowing thus full tracibility (of humans and animals) and portability of the sensing device. It is also understood that other embodiments include using a variety of detecting means housed in the sensing devices of this invention, including evaluating blood flow by conventional means and determining analyte concentration such as by using laser Doppler positioned at the brain tunnel for determining the concentration of analytes including glucose. It is also understood that any of the sensing devices and sensors of this invention can be powered by solar power or other renewable energy source.

Another embodiment includes stethoscope connected to a PDA, said stethoscope listening to body sounds such as heart and lung sounds and the PDA recording on digital file the heart or lung sound, and then comparing the sound captured with sounds stored in the PDA memory for determining the diagnosis of the condition.

The invention also includes methods for determining the usable life or function of a sensor based on the thickness of a coating applied to that sensor. Sensor can be covered in parylene and the thickness of the covering used for determining the life of the device. By way of example, a temperature sensor is covered with 100 microns thick layer of parylene which keeps the sensor functioning for X number of days. A 200 microns thick layer of parylene keeps then the sensor functioning for 2X number of days (twice as much) and a 50 microns layer keeps the sensor functioning for ½X (half). As the sensor continues to be used the layer of coating gradually dissolves until total dissolution of the coating exposes the sensor making said sensor inoperative. For example, a temperature sensor ceases to work properly as water and salt from the body reach the sensor and change the resistance after the parylene coating is removed.

Another embodiment includes methods and apparatus for detecting blood flow and diagnosing diseases. The embodiment further includes identifying changes in blood flow of the brain tunnel area after applying drugs locally at the brain tunnel area or systemically by oral or invasive means. The method includes applying, for example, a patch with acetylcholine to identify autonomic dysfunction and the diagnosis of diabetes, heart disease, vascular disorders and the like. Steps include measuring blood flow, applying or delivering a drug, and measuring the blood flow at the same location, such as the brain tunnel area. If there is a sustained change in blood flow at the brain tunnel area, then it is determined that function is normal. If after applying a drug the change in blood flow is not sustained it then indicates autonomic dysfunction.

Another embodiment includes therapy and/or prevention of obesity and reduction of weight through cooling the brain and monitoring the temperature at the BTT. Placing the subject under anesthesia, which reduces core temperature, lowers the temperature of the brain. A preferred step prior to anesthesia is an imaging study such as Magnetic Resonance Imaging to map and quantify the neuronal activity in the hunger center of the brain or other brain areas. Cooling of the body and of the brain is performed in order to cool the hunger center, and therefore reducing neuronal firing in the hunger center, and thus naturally reducing appetite. After the baseline activity is determined, the cooling is performed until core-brain temperature reaches 34 degrees Celsius. When the signal from the temperature sensor, such as the BTT, indicates that level of temperature or other predetermined level, an alarm sounds indicating that target temperature was achieved. Depending on the level of firing of neurons, and the baseline, the anesthesia continues on, with extended periods of anesthesia for people with severe obesity so as to shut down the hunger center and appetite, which can even last 6 months or more. The method and device can include using the area of the BTT between the eye and eyebrow and to cool this area in order to directly reduce brain activity. If a center is hyperactive, then cooling can help stabilize firing of neurons. The method and apparatus can also be used for therapy of a variety of neuro-disorders including stroke, Alzheimer, Parkinson, depression, and the like.

The invention further includes a memory chip housed in the device with a predetermined amount of memory, which correlates to the life of the device. Thus, a chip with capacity for 100 hours of measurements fills the chip memory in 100 hours, and after that occurs the sensing device does not work, and preferably a light on the device, such as body 2002 or an alarm on the screen of the reading unit informs the user that the life of the device has expired.

FIG. 104-A is another embodiment showing a diagrammatic view of a specialized noninvasive internal surface temperature measurement probe 3590. The sensor head 3594 of probe 3590 has features of both surface temperature measurement and internal temperature measurement. By being able to detect internal temperature through the sensor head 3594 penetrating into the brain tunnel through indenting the skin, the probe 3590 measures internal temperature. By touching the surface of the skin with a non-thermally conductive tip, the sensor head 3594 functions as a surface temperature measuring probe. The probe 3590 is of use only in specialized areas such as the BTT, which has a concave shape but of irregular geometry and with some anatomic variations as to the main entry point of tunnel. There is seen in FIG. 104-A probe 3590 including multi-sensor head 3594, straight handle 3600, and curved handle 3606. Sensor head 3594 for temperature measurement comprises an insulating material 3596 populated with a plurality of thermal sensors 3598, such as thermistors, thermocouples, silicone, and the like. The insulating material works as a support structure holding sensors 3598. Preferably thermal sensors 3598 comprise thermistors as per preferred embodiments of this invention. An array of thermal sensors 3598 is disposed on the surface of insulating material 3596 of the multi-sensor head 3594. The multi-sensor head has preferably a convex configuration and special dimensions. The distance from the tip 3592 of sensor head 3594 to the inferior edge 3602 of the sensor head 3594 is preferably equal to or no greater than 2.5 mm, and most preferably equal to or no greater than 4.5 mm, and even most preferably equal to or no greater than 6.5 mm, and even much more preferably is a distance equal to or no greater than 5 mm. Sensor head 3594 has one or more thermal sensors, and preferably an array of sensors 3598, each sensor connected with a respective wire represented as wire 3604. At the transition between straight handle 3600 and curved handle 3606, all wires form the sensors represented herein as wire 3604 join to from a multistrand cable which terminates in wire portion 3610, said wire portion 3610 being connected to a processing and display circuit 3612.

FIG. 104-B is a planar view of sensor head 3594 showing insulating structure 3596 populated by an array of sensors 3598. Sensor head 3594 has an essentially circular shape. Preferred diameter of sensor head 3594 is equal to or no greater than 5.0 mm, and most preferably equal to or no greater than 8.0 mm, and even most preferably equal to or no greater than 12 mm, and even much more preferably equal to or no greater than 20 mm. FIG. 104-C is a diagrammatic view of an embodiment of hand held portable sensing probe 3620 comprised of an essentially flat sensor head 3616. Probe 3620 includes three parts, a flat sensing tip 3634, also referred to as sensor head; a handle 3630 housing wires 3604 and multistrand wire 3618; and electronic and display part 3628 which houses chip 3624, battery 3626, and display 3622. Sensor head 3634 includes a sensing surface 3616, said sensing surface including an insulating material 3632 and one or more sensors 3614 disposed along the surface, and having a similar configuration as embodiment of FIG. 104-A.

As seen in FIG. 104-C handle 3630 has preferably a smaller diameter than sensor head 3634. The distance from the tip 3616 of sensor head 3634 to the inferior edge 3602 of the sensor head 3634 is preferably equal to or no greater than 2.0 mm, and most preferably equal to or no greater than 4.0 mm, and even most preferably equal to or no greater than 7.0 mm, and even much more preferably is a distance equal to or no greater than 5.0 mm.

FIG. 104-D is a side perspective view of a boomerang sensor probe 3640 including boomerang sensor head 3656 and handle 3650. It is understood that handle 3650 can be replaced by arm 2004 or other arms described in this invention, and any of the sensors heads described herein can be used in a measuring portion of other embodiments. Boomerang sensor head 3656 includes two wings 3642 and 3644, but contrary to the conventional boomerang shape which is essentially flat, the wings 3642 and 3644 have a bulging and essentially convex surface in order to fit with the anatomy of the brain tunnel entry point. Boomerang sensor head 3656 further includes a connecting portion 3658 connecting the two wings 3642 and 3644, said connecting portion having an essentially bulging and convex surface 3648, said convex surface 3648 having a much smaller radius than the radius of convex surface of wings 3642 and 3644, thus connecting portion 3658 is much more bulging than wings 3642 and 3644. Connecting portion 3658 has an essentially protruding configuration and houses at least one sensor 3646, but preferably houses a plurality of sensors along its surface, said sensors preferably having also a bulging configuration. The sensors are represented herein as small dots, but to avoid excessive repetition only one number 3646 is used for describing the plurality of sensors. Sensors 3646 are illustrated as one type of sensor, such as a thermal sensor, but it is understood that sensors measuring different parameters can be used, and any combination of sensors are contemplated, for example a sensor head comprising oxygen saturation infrared sensors, electrochemical gas sensors, thermal sensors, and pulse sensors. Each sensor 3646 connects with handle 3650, illustrated herein as wired communication, using wires 3652, which preferably become a multistrand cable 3654 in handle 3650. Handle 3650 is attached to sensor head 3656 through connecting points 3660 and 3662, located at the end of said handle 3650. Preferred dimensions of probe 3640 are consistent with the dimensions and shape of a brain tunnel area, and more particular the geometry of the area between the eye and the eyebrow on the upper eyelid and roof of the orbit.

FIG. 104-E is a planar perspective view of a boomerang sensor probe 3640 showing the sensing surface 3664 of sensor head 3656, which is the surface that touches the skin during contact measurements or the surface that is viewing the skin for non-contact measurements. The sensing surface 3664 comprises the connecting bulging portion 3658, and the wings 3642 and 3644, said sensing surface 3662 having one or more sensor 3646 on its surface. Connecting points 3660 and 3662 which connect a handle to the sensor head 3656 are seen as broken lines.

FIG. 104-F is a planar diagrammatic view of boomerang sensor head 3656, and its relation to anatomic structures such as the nose 3672, eyebrow 3666, and eye 3674. Wing 3642 which is located below the eyebrow 3666 is preferably longer than wing 3644 which rests adjacent to the nose 3672. There is also seen the essentially centrally located bulging connecting portion 3658, and its center point 3668, and the impression of the handle connecting points 3660 and 3662. The boomerang probe 3640 of this invention has preferably a tighter angle as compared to a conventional boomerang configuration. Accordingly the preferred angle 3670 between wings 3642 and 3644 is equal to or less than 45 degrees, and preferably equal to or less than 65 degrees, and most preferably equal to or less than 90 degrees. Preferred length of the wing running along the eyebrow 3666, illustrated herein as wing 3642, is equal to or less than 35 mm, and preferably equal to or less than 25 mm, and most preferably equal to or less than 20 mm, and even most preferably equal to or less than 14 mm, said length going from point 3668 to the edge 3676 of the wing 3642. Preferred width of wing 3642 is equal to or less than 30 mm, and preferably equal to or less than 20 mm, and most preferably equal to or less than 15 mm, and even most preferably equal to or less than 10 mm. Preferred thickness of wing 3642 is equal to or less than 25 mm, and preferably equal to or less than 20 mm, and most preferably equal to or less than 15 mm, and even most preferably equal to or less than 10 mm.

Preferred length of the wing running along the nose 3672, illustrated herein as wing 3644, is equal to or less than 33 mm, and preferably equal to or less than 23 mm, and most preferably equal to or less than 18 mm, and even most preferably equal to or less than 12 mm, said length going from point 3668 to the edge 3678 of the wing 3644. Preferred width of wing 3644 is equal to or less than 30 mm, and preferably equal to or less than 20 mm, and most preferably equal to or less than 15 mm, and even most preferably equal to or less than 10 mm. Preferred thickness of wing 3644 is equal to or less than 25 mm, and preferably equal to or less than 20 mm, and most preferably equal to or less than 15 mm, and even most preferably equal to or less than 10 mm.

The bulging connecting portion 3658 is the portion adapted to best fit with the main entry point of the tunnel and is located adjacent to the junction of the eyebrow 3666 with the bridge of the nose 3672. Preferred dimension or diameter of the bulging connecting portion 3658 is equal to or less than 30 mm, and preferably equal to or less than 25 mm, and most preferably equal to or less than 20 mm, and even most preferably equal to or less than 15 mm. Preferred thickness of portion 3658 is equal to or less than 30 mm, and preferably equal to or less than 20 mm, and most preferably equal to or less than 15 mm, and even most preferably equal to or less than 10 mm.

Processing circuit, such as processor 3624, screens selects the most optimal signal, depending on the application, from the plurality of signals received from the plurality of sensors. In the case of thermal sensors, processing continuously screens and then selects the highest temperature, which is then reported. One or multiple sensing points can be checked periodically and one or more signals can be selected and displayed. For temperature measurement the thermal sensors are imbedded in an insulated material shaped to fit into the anatomical and thermal characteristics of the BTT pocket for easy placement and optimal heat transfer. Thermal sensor is preferably encapsulated and surrounded with a soft thick, non-conductive, insulating material that will take the contour/shape of the irregular skin surface to completely seal off any external ambient temperature and also to prevent any skin or tissues outside the BTT entrance site from touching the sensor.

Since folds of skin can touch the tip of the sensor head when is pressed against the BTT, the sensor head has a unique and specialized dimension of insulating material surrounding the sensor, which is preferably between 3 mm and 5 mm, and most preferably between 2 mm and 7 mm, and even most preferably between 1.5 mm and 10 mm as seen in FIG. 104-G and FIG. 104-H. FIG. 104-G shows a sensor head 3680 and handle 3682. The sensor head 3680 has three thermal sensors 3684, 3686 and 3688. The sensor head 3680 comprises the insulating material 3690 and the three thermal sensors 3684, 3686 and 3688, which are disposed along the surface of the insulating material 3690. All surfaces of the sensors 3684, 3686 and 3688 are surrounded by the insulating material 3690, with the exception of the surface of the sensor exposed to the environment. The dimension of insulating material 3690 is based on the position of a thermal sensor closest to the non-insulating part 3692, illustrated as a part which is made of thermally conductive material or metal such as a handle 3682. Since sensors 3688 is lower as compared to sensors 3684 and 3686, the starting point to determine length or dimension 3694 of insulating material 3690 is based on said sensor 3688, the dimension 3694 starting at sensor 3688 and ending at non-insulating material 3692.

FIG. 104-H shows a bulging sensor 3696 on the surface of an insulating material 3690, which terminates in a thermally conductive material 3692. All surfaces of the sensor 3696 is surrounded by the insulating material 3690, with the exception of the surface of the sensor exposed to the environment or the target area being measured. The dimension of insulating material 3690 is based on the position of a thermal sensor closest to the non-insulating part 3692. Since sensors 3696 is the only thermal sensor, said sensor 3696 determines the dimension of the insulating material 3690, the dimension 3694 starting at sensor 3696 and ending at non-insulating material 3692. The dimension 3694 is the same for both embodiments, shown in FIG. 104-G and FIG. 104-H. The sensor insulation needs to have the described thickness, unlike conventional surface temperature probes of the prior art, which needs to be thin. The reason is because the BTT sensor is pushed into the BTT tunnel opening and the thicker insulation material prevents external ambient influences and tissues to come in contact with the integrity of the temperature sensor measuring the opening surface area of the BTT. Insulation material and dimension or length of insulating material as per the present invention includes any insulating material around a sensor head or measuring portion, including an insulating holder such as insulating holder 3550 as shown in FIG. 103A.

The sensing systems of this invention measures, records and/or processes feedback information for a closed loop system and controlling a second device, such as the infusion pump of FIG. 101 and thus allowing for therapeutic applications, such as cooling or heating the brain based on the signal received, or increasing oxygen delivered based on the signal of an oxygen sensor, or increasing the flow of glucose or insulin based on the signal from a glucose sensor.

It is understood that other configurations of the modular design of the invention would be apparent to one of ordinary skill in the art. Other configurations using other head mounted gear such as a cap, eyewear, and the like are contemplated. Those head mounted gear positions and secures the sensor assembly as a docking device and can measure, record, feedback multiple parameters in a modular design such as pulse oxymetry, heart rate, temperature, and the like.

FIG. 105 illustrates the maintaining of a sensor on the BTT by adhesive applied to the body of the support structure. The support structure is applied on the cheek of the user.

It should be noted that this invention provides not only measurement, recording and processing of a biological parameter such as temperature but also includes a device that will house the therapy. By way of illustration, the modular forehead docking system of this invention can include a mechanical holding and positioning structure for a cold or hot element or substance that is placed on the BTT site for cooling or heating the brain including a thermo-voltaic device such as a Peltier device, serpentine for circulating fluids, and the like. The head mounted gear such as the head band of this invention can also be an electronics structure positioning, powering, and controlling device to heat or cool the BTT site. The module of the sensing head band includes controlling/processing circuit that can work as a close loop device itself for therapy, by having one side a BTT thermometer and the other side the cold/hot device on the BTT site, providing thus an independent medical close loop monitoring, controlling and cooling/heating device.

The module of the sensing head band box is also designed to analyze a temperature signal or other biological signal and correlate it to other patient data and display other parameters either on the sensing head band device or transmit the information via wire or wireless means to another host monitor or device. The parameters that the system correlate/calculate/analyze include sleep disorder patterns, Alzheimer syndromes, obesity parameters, calorie burns for weight control, fatigue/drowsiness, ECG/EKG, brain wave patterns, and the like.

I claim:

1. A thermal imaging system comprising
    an infrared imaging system including a camera, a microprocessor and a display unit, said infrared imaging system being positioned at a checkpoint, said infrared imaging system measuring temperature by sensing thermal radiation naturally emitted by people passing the checkpoint,
    the camera having a lens, an optical system and a photodetector, the lens being only focused on discrete points of a narrow area positioned above the eye and below an eyebrow at a brain tunnel temperature of a face of the individual passing by the checkpoint,
    the photodetector quantifying energy flux in a mid infrared range naturally emitted from the brain temperature tunnel by the people passing by the checkpoint as viewed by the optical system of the camera,
    the display unit displaying a thermal image of the brain temperature tunnel area of the face of the individual as viewed by the lens of the camera as the individual passes by the checkpoint,
    the infrared imaging system measuring a specific temperature span of the brain temperature tunnel of a person passing the checkpoint of between two to five ° C. in relation to a reference compared to the narrow area located at the brain temperature tunnel.

2. The thermal imaging system as claimed in claim 1, wherein the photodetector is a radiation sensor or a radiation detector.

3. The thermal imaging system as claimed in claim 1, wherein the infrared imaging system captures an instantaneous image of the brain temperature tunnel area with a size of 1 to 2 mm.

4. The thermal imaging system as claimed in claim 3, wherein the infrared imaging system is located one meter from the brain temperature tunnel area.

5. The thermal imaging system as claimed in claim 3, wherein an angle of view of the infrared imaging system is between 1.0 and 1.6 mrad.

6. The thermal imaging system as claimed in claim 1, wherein the lens is positioned perpendicular to a plane of a human face.

7. The thermal imaging system as claimed in claim 1, wherein the infrared imaging system measures radiation with a wavelength ranging from 8 to 12 μm.

8. The thermal imaging system as claimed in claim 1, wherein the infrared imaging system is mounted in an airport.

9. The thermal imaging system as claimed in claim 1, wherein the infrared imaging system is mounted in a public space to scan multiple individuals passing by.

* * * * *